(12) United States Patent
Hegde et al.

(10) Patent No.: US 11,402,382 B2
(45) Date of Patent: Aug. 2, 2022

(54) DIAGNOSTIC AND THERAPEUTIC METHODS FOR CANCER

(71) Applicant: Genentech, Inc., South San Francisco, CA (US)

(72) Inventors: Priti Hegde, San Mateo, CA (US); Mahrukh Huseni, Union City, CA (US)

(73) Assignee: Genentech, Inc., South San Francisco, CA (US)

(*) Notice: Subject to any disclaimer, the term of this patent is extended or adjusted under 35 U.S.C. 154(b) by 28 days.

(21) Appl. No.: 16/545,177

(22) Filed: Aug. 20, 2019

(65) Prior Publication Data

US 2019/0369098 A1 Dec. 5, 2019

Related U.S. Application Data

(63) Continuation of application No. PCT/US2018/020460, filed on Mar. 1, 2018.

(60) Provisional application No. 62/572,979, filed on Oct. 16, 2017, provisional application No. 62/514,680, filed on Jun. 2, 2017, provisional application No. 62/465,547, filed on Mar. 1, 2017.

(51) Int. Cl.
| | |
|---|---|
| *C12Q 1/6886* | (2018.01) |
| *G01N 33/574* | (2006.01) |
| *A61P 35/04* | (2006.01) |
| *A61K 31/404* | (2006.01) |
| *A61K 39/395* | (2006.01) |
| *A61K 45/06* | (2006.01) |
| *C07K 16/22* | (2006.01) |
| *C07K 16/28* | (2006.01) |
| *A61K 39/00* | (2006.01) |

(52) U.S. Cl.
CPC ....... *G01N 33/5748* (2013.01); *A61K 31/404* (2013.01); *A61K 39/39558* (2013.01); *A61K 45/06* (2013.01); *A61P 35/04* (2018.01); *C07K 16/22* (2013.01); *C07K 16/2827* (2013.01); *C12Q 1/6886* (2013.01); *A61K 2039/507* (2013.01); *C07K 2317/21* (2013.01); *C07K 2317/24* (2013.01); *C07K 2317/56* (2013.01); *C07K 2317/76* (2013.01); *C12Q 2600/106* (2013.01); *C12Q 2600/158* (2013.01)

(58) Field of Classification Search
CPC combination set(s) only.
See application file for complete search history.

(56) References Cited

U.S. PATENT DOCUMENTS

| | | |
|---|---|---|
| 2002/0058041 A1 | 5/2002 | Belldegrun et al. |
| 2008/0020990 A1 | 1/2008 | Yano et al. |
| 2013/0034540 A1 | 2/2013 | Mule et al. |
| 2014/0255341 A1 | 9/2014 | Kalinski et al. |
| 2015/0071910 A1 | 3/2015 | Kowanetz et al. |
| 2015/0218650 A1 | 8/2015 | Galon et al. |
| 2016/0089366 A1 | 3/2016 | Funahashi et al. |
| 2016/0222118 A1 | 8/2016 | Chen et al. |

FOREIGN PATENT DOCUMENTS

| | | |
|---|---|---|
| CN | 102482715 A | 5/2012 |
| CN | 103059138 A | 4/2013 |
| CN | 104203268 A | 12/2014 |
| CN | 104271601 A | 1/2015 |
| CN | 105209919 A | 12/2015 |
| CN | 105246507 A | 1/2016 |
| CN | 105264380 A | 1/2016 |
| CN | 105492025 A | 4/2016 |
| JP | 2015-512612 A | 4/2015 |
| JP | 2019-521641 A | 8/2019 |
| KR | 10-2012-0059553 A | 6/2012 |
| WO | WO-2006/121168 A1 | 11/2006 |
| WO | WO-2011/008696 A2 | 1/2011 |
| WO | WO-2011/020049 A1 | 2/2011 |
| WO | WO-2012/166899 A2 | 12/2012 |

(Continued)

OTHER PUBLICATIONS

Lopez-Lago et al (Cancer Research, 2010, 70:9682-9692).*
Herbst et al (Nature, 2014, 515:563-567).*
McDermott et al (J Clinical Oncology, published online Jan. 11, 2016, 34:833-842).*

(Continued)

*Primary Examiner* — Laura B Goddard
(74) *Attorney, Agent, or Firm* — Clark & Elbing LLP; Thomas J. Takara

(57) ABSTRACT

The present invention provides diagnostic methods, therapeutic methods, and compositions for the treatment of cancer (e.g., kidney cancer (e.g., renal cell carcinoma (RCC)), lung cancer (e.g., non-small cell lung cancer (NSCLC)), bladder cancer (e.g., urothelial bladder cancer (UBC)), liver cancer (e.g., hepatocellular carcinoma (HCC)), ovarian cancer, or breast cancer (e.g., triple-negative breast cancer (TNBC))). The invention is based, at least in part, on the discovery that expression levels of one or more biomarkers described herein in a sample from an individual having cancer can be used in methods of predicting the therapeutic efficacy of treatment with a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., anti-PD-L1 antibody, e.g., atezolizumab (MPDL3280A)) or a PD-1 binding antagonist (e.g., anti-PD-1 antibody)), or with an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))).

9 Claims, 63 Drawing Sheets

Specification includes a Sequence Listing.

(56) References Cited

FOREIGN PATENT DOCUMENTS

| WO | WO-2013/106765 A1 | 7/2013 |
|---|---|---|
| WO | WO-2013/181452 A1 | 12/2013 |
| WO | WO-2014/039983 A1 | 3/2014 |
| WO | WO-2014/087156 A1 | 6/2014 |
| WO | WO-2014/151006 A2 | 9/2014 |
| WO | WO-2014/185540 A1 | 11/2014 |
| WO | WO-2015/009856 A2 | 1/2015 |
| WO | WO-2015/119930 A1 | 8/2015 |
| WO | WO-2015/134605 A1 | 9/2015 |
| WO | WO-2015/170105 A1 | 11/2015 |
| WO | WO-2016/200835 A1 | 12/2016 |
| WO | WO-2016/205277 A1 | 12/2016 |
| WO | WO-2017/181111 A2 | 10/2017 |
| WO | WO-2018/064191 A1 | 4/2018 |

OTHER PUBLICATIONS

Wallin et al (Nature Communications, 2016, 7:12624, internet pp. 1-8).*
GeneAnnot website for CD8A (published Sep. 2021).*
GeneAnnot website for EOMES (published Sep. 2021).*
GeneAnnot website for PRF1 (published Sep. 2021).*
GeneAnnot website for IFNG (published Sep. 2021).*
GeneAnnot website for PD-L1 (CD274) (published Sep. 2021).*
Giordano et al., "Cancer-related CD15/FUT4 overexpression decreases benefit to agents targeting EGFR or VEGF acting as a novel RAF-MEK-ERK kinase downstream regulator in metastatic colorectal cancer," J Exp Clin Cancer Res. 34:108 (2015).
Herbst et al., "Predictive correlates of response to the anti-PD-L1 antibody MPDL3280A in cancer patients," Nature. 515(7528):563-7 (2014) (18 pages).
Kuznar, "Adding Anti-PD-L1 Antibody to Bevacizumab Induces Responses in mRCC," retrieved on Sep. 5, 2017 from <http://www.onclive.com/conference-coverage/gu-2015/adding-anti-pd-I1-antibody-to-bevacizumab-induces-responses-in-mrcc> (2015) (2 pages).
Liu et al., "Resistance to Antiangiogenic Therapy Is Associated with an Immunosuppressive Tumor Microenvironment in Metastatic Renal Cell Carcinoma," available in PMC Sep. 1, 2016, published in final edited form as: Cancer Immunol Res. 3(9):1017-29 (2015) (21 pages).
Rodriguez-Vida et al., "Predictive and prognostic biomarkers of targeted agents and modern immunotherapy in renal cell carcinoma," ESMO Open. 1(3):e000013 (2016) (14 pages).
Wallin et al., "Atezolizumab in combination with bevacizumab enhances antigen-specific T-cell migration in metastatic renal cell carcinoma," Nat Commun. 7:12624 (2016) (8 pages).
Communication pursuant to Rules 161(1) and 162 EPC for European Patent Application No. 18712321.1, dated Oct. 11, 2019 (3 pages).
International Preliminary Report on Patentability for International Patent Application No. PCT/US2018/020460, dated Sep. 3, 2019 (11 pages).
International Search Report and Written Opinion for International Patent Application No. PCT/US2018/020460, dated Jul. 10, 2018 (21 pages).
Invitation to Pay Additional Fees for International Patent Application No. PCT/US2018/020460, dated May 9, 2018 (16 pages).
McDermott et al.,"Atezolizumab, an Anti-Programmed Death-Ligand 1 Antibody, in Metastatic Renal Cell Carcinoma: Long-Term Safety, Clinical Activity, and Immune Correlates From Phase Ia Study," J Clin Oncol. 34(8): 833-42 (2016) (18 pages).
"History of Changes for Study: NCT02420821," ClinicalTrials.gov, <https://clinicaltrials.gov/ct2/history/NCT02420821?V_39=View#StudyPageTop>, retrieved on Aug. 31, 2021 (139 pages).

"Immuno-Oncology Combinations," Thomson Reuters, Prog Pharm Sci. 39(1):73-80 (2015) (English Abstract Included).
Brawer et al., "Measurement of complexed PSA improves specificity for early detection of prostate cancer," Urology. 52(3):372-8 (1998).
Budman et al., "Biomarkers for detection and surveillance of bladder cancer," Can Urol Assoc J. 2(3):212-21 (2008).
Ciccarese et al., "Future perspectives for personalized immunotherapy in renal cell carcinoma," Expert Opin Biol Ther. 17(9):1049-1052 (2017).
Einstein et al., "Combined blockade of vascular endothelial growth factor and programmed death 1 pathways in advanced kidney cancer," Clin Adv Hematol Oncol. 15(6): 478-88 (2017).
Ghatalia et al., "Checkpoint Inhibitors for the Treatment of Renal Cell Carcinoma," Curr Treat Options Oncol. 18(1):7 (2017) (14 pages).
Golshayan et al., "Metastatic Sarcomatoid Renal Cell Carcinoma Treated With Vascular Endothelial Growth Factor-Targeted Therapy," J Clin Oncol. 27(2):235-41 (2009).
Goodman, "Atezolizumab Plus Bevacizumab Improves Progression-Free Survival in First-Line Treatment of Advanced Renal Cell Carcinoma," ASCO. (2018) (6 pages).
Joseph et al., "PD-1 and PD-L1 Expression in Renal Cell Carcinoma with Sarcomatoid Differentiation," available in PMC Dec. 1, 2016, published in final edited form as: Cancer Immunol Res. 3(12):1303-7 (2015) (12 pages).
Lebacle et al., "Epidemiology, biology and treatment of sarcomatoid RCC: current state of the art," World J Urol. 37(1):115-123 (2019).
Ludwig et al., "Biomarkers in cancer staging, prognosis and treatment selection," Nat Rev Cancer. 5(11):845-56 (2005).
Mantovani et al., "Folate binding protein distribution in normal tissues and biological fluids from ovarian carcinoma patients as detected by the monoclonal antibodies MOv18 and MOv19," Eur J Cancer. 30A(3):363-9 (1994).
Mauldin et al., "Intratumoral interferon-gamma increases chemokine production but fails to increase T cell infiltration of human melanoma metastases," Cancer Immunol Immunother. 65:1189-99 (2016).
McDermott et al., "A phase II study of atezolizumab with or without bevacizumab versus sunitinib in untreated metastatic renal cell carcinoma patients," Genitourinary Cancers Symposium (2017) (24 pages).
McDermott et al., "Clinical Activity and Molecular Correlates of Response to Atezolizumab Alone or in Combination With Bevacizumab Versus Sunitinib in Renal Cell Carcinoma," Nat Med. 24(6):749-757 (includes supplemental content) (2018) (14 pages).
Mettlin et al., "Relative Sensitivity and Specificity of Serum Prostate Specific Antigen (PSA) Level Compared with Age-Referenced PSA, PSA Density, and PSA Change," Cancer. 74(5):1615-20 (1994).
Motzer et al., "IMmotion151: A Randomized Phase III Study of Atezolizumab Plus Bevacizumab vs Sunitinib in Untreated Metastatic Renal Cell Carcinoma (mRCC)," Journal of Clinical Oncology. 36(6_suppl):578 (2018) (3 pages).
Osorio et al., "Optimizing Treatment Approaches in Advanced Renal Cancer," Oncology (Williston Park). 31(12):919-26 (12 pages).
Pepe et al., "Phases of biomarker development for early detection of cancer," J Natl Cancer Inst. 93(14):1054-61 (2001).
Rodriguez-Vida et al., "New Treatment Options for Metastatic Renal Cell Carcinoma," ESMO Open. 2(2):e000185 (2017) (11 pages).
Santoni et al., "Immunotherapy in Renal Cell Carcinoma: Latest Evidence and Clinical Implications," Drugs Context. 7:212528 (2018) (8 pages).
Shin et al., "The Association Between PD-L1 Expression and the Clinical Outcomes to Vascular Endothelial Growth Factor-Targeted Therapy in Patients With Metastatic Clear Cell Renal Cell Carcinoma," Oncologist. 20(11):1253-60 (2015).

* cited by examiner

SEQUENCE LISTING

<160> NUMBER OF SEQ ID NOS: 82

<210> SEQ ID NO 1
<211> LENGTH: 1975
<212> TYPE: RNA
<213> ORGANISM: Homo sapiens

<400> SEQUENCE: 1

| | | | | | | |
|---|---|---|---|---|---|---|
| acuuccccc | cucggcgccc | caccggcucc | cgcgcgccuc | cccucgcgcc | cgagcuucga | 60 |
| gccaagcagc | guccugggga | gcgcgucaug | gccuuaccag | ugaccgccuu | gcuccugccg | 120 |
| cuggccuugc | ugcuccacgc | cgccaggccg | agccaguucc | ggugucgcc | gcuggaucgg | 180 |
| accuggaacc | ugggcgagac | aguggagcug | aagugccagg | ugcugcuguc | caacccgacg | 240 |
| ucgggcugcu | cguggcucuu | ccagccgcgc | ggcgccgccg | ccagucccac | cuucccuccua | 300 |
| uaccucuccc | aaaacaagcc | caaggcgcc | gaggggcugg | acaccagcg | guucucgggc | 360 |
| aagagguugg | gggacaccuu | cguccucacc | cugagcgacu | uccgccgaga | gaacgagggc | 420 |
| uacuauuucu | gcucggcccu | gagcaacucc | aucauguacu | ucagcacuu | cgugccgguc | 480 |
| uuccugccag | cgaagcccac | cacgacgcca | gcgccgcgac | caccaacacc | ggcgcccacc | 540 |
| aucgcgucgc | agcccugguc | ccugcgccca | gaggcgugcc | ggccagcggc | gggggcgca | 600 |
| gugcacacga | gggggcugga | cuucgccgu | gauaucuaca | ucugggcgcc | ccuggccggg | 660 |
| acuugggggg | uccuucuccu | gucacuggu | aucacccuuu | acugcaacca | caggaaccga | 720 |
| agacguguuu | gcaaaugucc | ccggccugug | gucaaaucgg | gagacaagcc | cagccuuucg | 780 |
| gcgagauacg | ucuaacccug | ugcaacagcc | acuacauuac | uucaaacuga | gauccuuccu | 840 |
| uuugagggag | caaguccuuc | ccuuucauuu | uuccagucu | ucccccugu | guauucauuu | 900 |
| ucaugauuau | uauuuuagug | ggggcgggu | gggaaagauu | acuuuuucuu | uauguguuu | 960 |
| acgggaaaca | aaacuaggua | aaaucuacag | uacaccacaa | gggucacaau | acguugugc | 1020 |
| gcacaucgcg | guagggcgug | gaaaggggca | ggccagagcu | acccgcagag | uucucagaau | 1080 |
| caugcugaga | gagcuggagg | cacccaugcc | aucucaaccu | cuuccccgcc | cguuuuacaa | 1140 |
| agggggaggc | uaaagcccag | agacagcuug | aucaaaggca | cacagcaagu | caggguugga | 1200 |
| gcaguagcug | gagggaccuu | gucucccagc | ucagggcucu | uuccuccaca | ccauucaggu | 1260 |
| cuuucuuucc | gaggccccug | ucucagggug | aggugcuuga | gucuccaacg | gcaagggaac | 1320 |
| aaguacuucu | ugauaccugg | gauacugugc | ccagagccuc | gaggagguaa | ugaauuaaag | 1380 |
| aagagaacug | ccuuuggcag | aguucuauaa | uguaaacaau | aucagacuuu | uuuuuuuau | 1440 |
| aaucaagccu | aaaauuguau | agaccuaaaa | uaaaaugaag | uggugagcuu | aacccuggaa | 1500 |
| aaugaauccc | ucuaucucua | agaaaaaucu | cugugaaacc | ccuacgugga | ggcggaauug | 1560 |
| cucucccagc | ccuugcauug | cagagggggcc | caugaaagag | gacaggcuac | cccuuuacaa | 1620 |
| auagaauuug | agcaucagug | agguuaaacu | aaggcccucu | ugaaucucug | aauuugagau | 1680 |
| acaaacaugu | uccugggauc | acugaugacu | uuuuauacuu | uguaaagaca | auuguuggag | 1740 |
| agccccucac | acagcccugg | ccuccgcuca | acuagcagau | acagggauga | ggcagaccug | 1800 |
| acucucuuaa | ggaggcugag | agcccaaacu | gcugucccaa | acaugcacuu | ccuugcuuaa | 1860 |
| gguaugguac | aagcaaugcc | ugcccauugg | agagaaaaaa | cuuaaguaga | uaaggaaaua | 1920 |
| agaaccacuc | auaauucuuc | accuuaggaa | uaaucuccug | uuaauauggu | guaca | 1975 |

```
<210> SEQ ID NO 2
<211> LENGTH: 235
<212> TYPE: PRT
<213> ORGANISM: Homo sapiens

<400> SEQUENCE: 2

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 3
<211> LENGTH: 2061
<212> TYPE: RNA
<213> ORGANISM: Homo sapiens

<400> SEQUENCE: 3
augcaguugg gagagcagcu cuuggugagc ucagugaacc ugccuggcgc gcacuucuac      60
ccgcuggaga gugcgcgagg cggcagcggc gggagcgcug gccaccuccc cagcgcggcc    120
cccucuccuc agaaguugga cuuaggcaaa gcguccaaga aguuuuccgg cagucucuc     180 ugcgaggcgu ugagcgggga gccugcagcc gccagcgcag ggcccccgc ggccaugcuu     240 agugacaccg acgccgggga cgcauuugcc agcgcugcgg cagugccaa gccggggccc     300 ccggacggcc gcaagggcuc ccccugcggg gaggaggagc ugcccuccgc cgcugcagcc    360
gccgccgccg ccgccgccgc ggcugcggcc acugcgcgcu acuccaugga cagccugagc    420
uccgugcggu acuaccucca gucccccggu ccucagggu cggagcuggc ugcgcccugc     480
ucacucuucc cguaccaggc ggcggcuggg gcgccccacg gaccugugua cccggcuccu     540
aacggggcgc gcuacccu a cggcuccaug cugcccccg gcggcuuccc cgcggcugcg     600
```

| | |
|---|---|
| ugcccacccg ggagggcgca guucggccca ggagccggug cgggcagugg cgcgggcggu | 660 |
| aucaacggcg ggggcggcgg cccgggcacc uaucaguaca gccagggggc uccgcucuac | 720 |
| gggccguacc cuggagccgc agcggcggga ucuugcggag gacugggggg ccuggggguu | 780 |
| ccaaguucug gcuuccgugc ccacgucuac cugugcaacc ggccucugug gcucaaauuc | 840 |
| caccggcacc aaacugagau gaucaucacc aaacagggca ggcgcauguu ccuuucuug | 900 |
| agcuucaaca uaaacggacu caaccccacc gcccacuaca auguuuucgu ggaagugguu | 960 |
| cuggccgacc cuaaccacug cgcuuccag ggggcaaau gggugaccug uggcaaagcc | 1020 |
| gacaauaaca ugcagggcaa caaaauguau guucacccag agucuccuaa uacugguucc | 1080 |
| cacuggauga gacaggagau uucauucggg aaauuaaaac ucaccaauaa caaaggcgca | 1140 |
| aauaacaaca cacccagau gauagucuua caauccuuac acaaauacca acccgacug | 1200 |
| cauauuguug aaguuacaga ggauggcgug gaggacuuga augagcccuc aaagacccag | 1260 |
| acuuuuaccu ucucagaaac gcaauucauu gcagugacug ccuacaaaa caccgauauu | 1320 |
| acucaacuaa agauugauca uaaccccuuu gcaaaaggcu ucagagacaa cuaugauuca | 1380 |
| ucccaucaga uuguccugg aggucgguac ggcguucaau ccuucuuccc ggagcccuuu | 1440 |
| gucaacacuu uaccucaagc ccgcuauuau aauggcgaga gaaccgugcc acagaccaac | 1500 |
| ggccuccuuu caccccaaca gagcgaagag guggccaacc cuccccagcg guggcuuguc | 1560 |
| acgccugucc agcaaccugg gaccaacaaa cuagacauca guuccuauga aucugaauau | 1620 |
| acuucuagca cauugcuccc auauggcauu aaauccuugc cccuucagac aucccaugcc | 1680 |
| cuggguauu acccagaccc aaccuuuccu gcaauggcag ggugggggagg ucgagguucu | 1740 |
| uaccagagga agauggcagc uggacuacca uggaccucca gaacaagccc cacuguguuc | 1800 |
| ucugaagauc agcucuccaa ggagaaagug aaagaggaaa uuggcucuuc uuggauagag | 1860 |
| acaccccuu ccaucaaauc ucuagauucc aaugauucag gaguauacac cagugcuugu | 1920 |
| aagcgaaggc ggcugucucc uagcaaccuc aguaaugaaa auucacccuc cauaaagugu | 1980 |
| gggggacauua augcugaaga guauaguaaa gacaccucaa aaggcauggg agggauuau | 2040 |
| gcuuuuuaca caagucccua g | 2061 |

<210> SEQ ID NO 4
<211> LENGTH: 686
<212> TYPE: PRT
<213> ORGANISM: Homo sapiens

<400> SEQUENCE: 4

Met Gln Leu Gly Glu Gln Leu Leu Val Ser Val Asn Leu Pro Gly
1               5                   10                  15

Ala His Phe Tyr Pro Leu Glu Ser Ala Arg Gly Gly Ser Gly Gly Ser
            20                  25                  30

Ala Gly His Leu Pro Ser Ala Ala Pro Ser Pro Gln Lys Leu Asp Leu
        35                  40                  45

Asp Lys Ala Ser Lys Lys Phe Ser Gly Ser Leu Ser Cys Glu Ala Val
    50                  55                  60

Ser Gly Glu Pro Ala Ala Ala Ser Ala Gly Ala Pro Ala Ala Met Leu
65                  70                  75                  80

Ser Asp Thr Asp Ala Gly Asp Ala Phe Ala Ser Ala Ala Ala Val Ala
                85                  90                  95

Lys Pro Gly Pro Pro Asp Gly Arg Lys Gly Ser Pro Cys Gly Glu Glu
            100                 105                 110

```
Glu Leu Pro Ser Ala Ala Ala Ala Ala Ala Ala Ala Ala
        115                 120                 125
Ala Ala Thr Ala Arg Tyr Ser Met Asp Ser Leu Ser Glu Arg Tyr
130                 135                 140
Tyr Leu Gln Ser Pro Gly Pro Gln Gly Ser Glu Leu Ala Ala Pro Cys
145                 150                 155                 160
Ser Leu Phe Pro Tyr Gln Ala Ala Gly Ala Pro His Gly Pro Val
            165                 170                 175
Tyr Pro Ala Pro Asn Gly Ala Arg Tyr Pro Tyr Gly Ser Met Leu Pro
                180                 185                 190
Pro Gly Gly Phe Pro Ala Ala Val Cys Pro Pro Gly Arg Ala Gln Phe
        195                 200                 205
Gly Pro Gly Ala Gly Ala Gly Ser Gly Ala Gly Ser Ser Gly Gly
        210                 215                 220
Gly Gly Gly Pro Gly Thr Tyr Gln Tyr Ser Gln Gly Ala Pro Leu Tyr
225                 230                 235                 240
Gly Pro Tyr Pro Gly Ala Ala Ala Gly Ser Cys Gly Gly Leu Gly
                245                 250                 255
Gly Leu Gly Val Pro Gly Ser Gly Phe Arg Ala His Val Tyr Leu Cys
        260                 265                 270
Asn Arg Pro Leu Trp Leu Lys Phe His Arg His Gln Thr Glu Met Ile
275                 280                 285
Ile Thr Lys Gln Gly Arg Arg Met Phe Pro Phe Leu Ser Phe Asn Ile
        290                 295                 300
Asn Gly Leu Asn Pro Thr Ala His Tyr Asn Val Phe Val Glu Val Val
305                 310                 315                 320
Leu Ala Asp Pro Asn His Trp Arg Phe Gln Gly Gly Lys Trp Val Thr
                325                 330                 335
Cys Gly Lys Ala Asp Asn Asn Met Gln Gly Asn Lys Met Tyr Val His
            340                 345                 350
Pro Glu Ser Pro Asn Thr Gly Ser His Trp Met Arg Gln Glu Ile Ser
        355                 360                 365
Phe Gly Lys Leu Lys Leu Thr Asn Asn Lys Gly Ala Asn Asn Asn
        370                 375                 380
Thr Gln Met Ile Val Leu Gln Ser Leu His Lys Tyr Gln Pro Arg Leu
385                 390                 395                 400
His Ile Val Glu Val Thr Glu Asp Gly Val Glu Asp Leu Asn Glu Pro
                405                 410                 415
Ser Lys Thr Gln Thr Phe Thr Phe Ser Glu Thr Gln Phe Ile Ala Val
            420                 425                 430
Thr Ala Tyr Gln Asn Thr Asp Ile Thr Gln Leu Lys Ile Asp His Asn
        435                 440                 445
Pro Phe Ala Lys Gly Phe Arg Asp Asn Tyr Asp Ser Ser His Gln Ile
450                 455                 460
Val Pro Gly Gly Arg Tyr Gly Val Gln Ser Phe Phe Pro Glu Pro Phe
465                 470                 475                 480
Val Asn Thr Leu Pro Gln Ala Arg Tyr Tyr Asn Gly Glu Arg Thr Val
            485                 490                 495
Pro Gln Thr Asn Gly Leu Leu Ser Pro Gln Gln Ser Glu Glu Val Ala
        500                 505                 510
Asn Pro Pro Gln Arg Trp Leu Val Thr Pro Val Gln Gln Pro Gly Thr
        515                 520                 525
```

-continued

```
Asn Lys Leu Asp Ile Ser Ser Tyr Glu Ser Glu Tyr Thr Ser Ser Thr
    530                 535                 540

Leu Leu Pro Tyr Gly Ile Lys Ser Leu Pro Leu Gln Thr Ser His Ala
545                 550                 555                 560

Leu Gly Tyr Tyr Pro Asp Pro Thr Phe Pro Ala Met Ala Gly Trp Gly
                565                 570                 575

Gly Arg Gly Ser Tyr Gln Arg Lys Met Ala Ala Gly Leu Pro Trp Thr
            580                 585                 590

Ser Arg Thr Ser Pro Thr Val Phe Ser Glu Asp Gln Leu Ser Lys Glu
        595                 600                 605

Lys Val Lys Glu Glu Ile Gly Ser Ser Trp Ile Glu Thr Pro Pro Ser
610                 615                 620

Ile Lys Ser Leu Asp Ser Asn Asp Ser Gly Val Tyr Thr Ser Ala Cys
625                 630                 635                 640

Lys Arg Arg Arg Leu Ser Pro Ser Asn Ser Ser Asn Glu Asn Ser Pro
                645                 650                 655

Ser Ile Lys Cys Glu Asp Ile Asn Ala Glu Glu Tyr Ser Lys Asp Thr
        660                 665                 670

Ser Lys Gly Met Gly Gly Tyr Tyr Ala Phe Tyr Thr Thr Pro
    675                 680                 685
```

<210> SEQ ID NO 5
<211> LENGTH: 1668
<212> TYPE: RNA
<213> ORGANISM: Homo sapiens

<400> SEQUENCE: 5

```
auggcagccc gucugcuccu ccugggcauc cuucccugc ugcugcccu gcccgucccu      60
gccccgugcc acacagccgc acgcucagag ugcaagcgca gccacaaguu cgugccuggu    120
gcauggcugg ccggggaggg uguggacgug accagccucc gccgcucggg ucccuuccca    180
guggacacac aaagguuccu gcggcccgac ggcaccugca cccucuguga aaaugcccua    240
caggagggca cccuccagcg ccugccucug cgcgcucacca acuggcgggc cagggcucu    300
ggcugccagc gccauguaac cagggccaaa gucagcucca cugaagcugu ggcccgggau    360
gcggcucgua gcauccgcaa cgacuggaag gucgggcugg acgugacucc uaagcccacc    420
agcaaugugc augucucugu ggccggcuca cacucacagg cagccaacuu gcagcccag    480
aagacccacc aggaccagua cagcuucagc acugacacgg uggagugccg cuucuacagu    540
uccaugugg uacacacucc cccgcugcac ccugacuuca agagggcccu cggggaccug    600
ccccaccacu ucaacgccuc cacccagccc gccuaccuca ggcuuaucuc caacuacggc    660
acccacuuca uccgggcugu ggagcugggu ggccgcauau cggcccucac ugcccugcgc    720
accugcgagc uggcccugga agggcucacg acaacgagg uggaggacug ccugacuguc    780
gaggcccagg ucaacauagg cauccacggc agcaucucug ccgaagccaa ggccugugag    840
gagaagaaga agaagcacaa gaugacggcc uccuuccacc aaaccuaccg ggagcgccac    900
ucggaagugg uugcggcca ucacaccucc auuaacgacc ugcuguucgg gauccaggcc    960
gggcccgagc aguacucagc cuggguaaac uccgugcccg gcagcccugg ccugguggac   1020
uacaccugg aaccccugca cgucugcugc gacagccagg accgcggcg ggaggcacug   1080
aggagggccc ugagucagua ccugacggac agggcucgcu ggaggacugc agccggccg   1140
ugcccaccag ggcggcagaa gagcccccga gacccaugcc agugugugug ccauggcuca   1200
gcggucacca cccaggacug cugcccucgg cagagggggcc uggcccagcu ggaggugacc   1260
```

-continued

```
uucauccaag caugagccu gugggggac ugguucacug ccacggaugc cuaugugaag    1320
cucuucuuug guggccagga gcugaggacg agcaccgugu gggacaauaa caccccauc    1380 uggucagugc ggcuggauuu uggggaugug cuccuggcca cagggggcc ccugagguug    1440 caggucuggg aucaggacuc uggcagggac gaugaccucc uuggcaccug gaucaggcu    1500 cccaagucug guucccauga ggugagaugc aaccugaauc auggccaccu aaaauuccgc    1560
uaucaugcca ggugcuugcc ccaccuggga ggaggcaccu gccugacua ugucccccaa    1620 augcuucugg gggagccucc aggaaaccgg agugggccg ugugguga                 1668
```

```
<210> SEQ ID NO 6
<211> LENGTH: 555
<212> TYPE: PRT
<213> ORGANISM: Homo sapiens

<400> SEQUENCE: 6

Met Ala Ala Arg Leu Leu Leu Gly Ile Leu Leu Leu Leu Leu Pro
1               5                   10                  15

Leu Pro Val Pro Ala Pro Cys His Thr Ala Ala Arg Ser Glu Cys Lys
                20                  25                  30

Arg Ser His Lys Phe Val Pro Gly Ala Trp Leu Ala Gly Glu Gly Val
            35                  40                  45

Asp Val Thr Ser Leu Arg Arg Ser Gly Ser Phe Pro Val Asp Thr Gln
        50                  55                  60

Arg Phe Leu Arg Pro Asp Gly Thr Cys Thr Leu Cys Glu Asn Ala Leu
65                  70                  75                  80

Gln Glu Gly Thr Leu Gln Arg Leu Pro Leu Ala Leu Thr Asn Trp Arg
                85                  90                  95

Ala Gln Gly Ser Gly Cys Gln Arg His Val Thr Arg Ala Lys Val Ser
            100                 105                 110

Ser Thr Glu Ala Val Ala Arg Asp Ala Ala Arg Ser Ile Arg Asn Asp
        115                 120                 125

Trp Lys Val Gly Leu Asp Val Thr Pro Lys Pro Thr Ser Asn Val His
    130                 135                 140

Val Ser Val Ala Gly Ser His Ser Gln Ala Ala Asn Phe Ala Ala Gln
145                 150                 155                 160

Lys Thr His Gln Asp Gln Tyr Ser Phe Ser Thr Asp Thr Val Glu Cys
                165                 170                 175

Arg Phe Tyr Ser Phe His Val Val His Thr Pro Leu His Pro Asp
            180                 185                 190

Phe Lys Arg Ala Leu Gly Asp Leu Pro His His Phe Asn Ala Ser Thr
        195                 200                 205

Gln Pro Ala Tyr Leu Arg Leu Ile Ser Asn Tyr Gly Thr His Phe Ile
    210                 215                 220

Arg Ala Val Glu Leu Gly Gly Arg Ile Ser Ala Leu Thr Ala Leu Arg
225                 230                 235                 240

Thr Cys Glu Leu Ala Leu Glu Gly Leu Thr Asp Asn Glu Val Glu Asp
                245                 250                 255

Cys Leu Thr Val Glu Ala Gln Val Asn Ile Gly Ile His Gly Ser Ile
            260                 265                 270

Ser Ala Glu Ala Lys Ala Cys Glu Gly Lys Lys Lys His Lys Met
        275                 280                 285

Thr Ala Ser Phe His Gln Thr Tyr Arg Glu Arg His Ser Glu Val Val
    290                 295                 300
```

-continued

Gly Gly His His Thr Ser Ile Asn Asp Leu Leu Phe Gly Ile Gln Ala
305                 310                 315                 320

Gly Pro Glu Gln Tyr Ser Ala Trp Val Asn Ser Leu Pro Gly Ser Pro
                325                 330                 335

Gly Leu Val Asp Tyr Thr Leu Glu Pro Leu His Val Leu Leu Asp Ser
            340                 345                 350

Gln Asp Pro Arg Arg Glu Ala Leu Arg Arg Ala Leu Ser Gln Tyr Leu
        355                 360                 365

Thr Asp Arg Ala Arg Trp Arg Asp Cys Ser Arg Pro Cys Pro Pro Gly
370                 375                 380

Arg Gln Lys Ser Pro Arg Asp Pro Cys Gln Cys Val Cys His Gly Ser
385                 390                 395                 400

Ala Val Thr Thr Gln Asp Cys Cys Pro Arg Gln Arg Gly Leu Ala Gln
                405                 410                 415

Leu Glu Val Thr Phe Ile Gln Ala Trp Gly Leu Trp Gly Asp Trp Phe
            420                 425                 430

Thr Ala Thr Asp Ala Tyr Val Lys Leu Phe Phe Gly Gly Gln Glu Leu
        435                 440                 445

Arg Thr Ser Thr Val Trp Asp Asn Asn Asn Pro Ile Trp Ser Val Arg
450                 455                 460

Leu Asp Phe Gly Asp Val Leu Leu Ala Thr Gly Gly Pro Leu Arg Leu
465                 470                 475                 480

Gln Val Trp Asp Gln Asp Ser Gly Arg Asp Asp Leu Leu Gly Thr
                485                 490                 495

Cys Asp Gln Ala Pro Lys Ser Gly Ser His Glu Val Arg Cys Asn Leu
            500                 505                 510

Asn His Gly His Leu Lys Phe Arg Tyr His Ala Arg Cys Leu Pro His
        515                 520                 525

Leu Gly Gly Gly Thr Cys Leu Asp Tyr Val Pro Gln Met Leu Leu Gly
530                 535                 540

Glu Pro Pro Gly Asn Arg Ser Gly Ala Val Trp
545                 550                 555

<210> SEQ ID NO 7
<211> LENGTH: 1193
<212> TYPE: RNA
<213> ORGANISM: Homo sapiens

<400> SEQUENCE: 7
ugaagaucag cuauuagaag agaaagauca guuaaguccu uuggaccuga ucagcuugau    60
acaagaacua cugauuucaa cuucuuuggc uuaauucucu cggaaacgau gaaauauaca   120
aguuauaucu uggcuuuuca gcucugcauc guuuugggu cucuuggcug uuacugccag    180
gacccauaug uaaagaagc agaaaaccuu aagaaauauu uuaaugcagg ucauucagau   240
guagcggaua auggaacucu uuucuuaggc auuuugaaga auuggaaaga ggagagugac   300
agaaaauaa ugcagagcca aauugcuccc uuuacuuca acuuuuuaa aaacuuuaaa    360
gaugaccaga gcauccaaaa gagugugagg accaucaagg aagacaugaa ugucaaguuu   420
uucaauagca acaaaaagaa acgagaugac uucgaaaagc ugacuaauua uucgguaacu   480
gacuugaaug uccaacgcaa agcaauacau gaacucaucc aagugauggc ugaacugucg   540
ccagcagcua aaacagggaa gcgaaaaagg agucagaugc uguuucaagg ucgaagagca   600
ucccaguaau gguuguccug ccugcaauau uugaauuuua aaucuaaauc uauuuauuaa   660

| | |
|---|---:|
| uauuuaacau uauuuauaug gggaauauau uuuuagacuc aucaaucaaa uaaguauuua | 720 |
| uaauagcaac uuuuguguaa ugaaaaugaa uaucuauuaa uauauguauu auuuauaauu | 780 |
| ccuauauccu gugacugucu cacuuaaucc uuuguuuucu gacuaauuag gcaaggcuau | 840 |
| gugauuacaa ggcuuuaucu caggggccaa cuaggcagcc aaccuaagca agaucccaug | 900 |
| gguugugugu uuauuucacu ugaugauaca augaacacuu auaagugaag ugauacuauc | 960 |
| caguuacugc cgguuugaaa auaugccugc aaucugagcc agugcuuuaa uggcauguca | 1020 |
| gacagaacuu gaaugguguca ggugacccug augaaaacau agcaucucag gagauuucau | 1080 |
| gccuggugcu uccaaauauu guugacaacu gugacuguac ccaaauggaa aguaacucau | 1140 |
| uuguuaaaau uaucaauauc uaauauauau gaauaaagug uaaguucaca acu | 1193 |

<210> SEQ ID NO 8
<211> LENGTH: 166
<212> TYPE: PRT
<213> ORGANISM: Homo sapiens

<400> SEQUENCE: 8

```
Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

<210> SEQ ID NO 9
<211> LENGTH: 5830
<212> TYPE: RNA
<213> ORGANISM: Homo sapiens

<400> SEQUENCE: 9

| | |
|---|---:|
| acugagcccc gggaccccgg gagagcgguc agugguggu cgcugcguuu ccucugccug | 60 |
| cgccgggcau cacuugcgcg ccgcagaaag uccgucuggc agccggauua uccucuccua | 120 |
| ccggcacccg cagacgcccc ugcagccgcc ggucggcgcc cgggcucccu agcccugugc | 180 |
| gcucaacugu ccugcgcugc ggggugccga gaguuccacc uccgcgccuc cuucucuaga | 240 |
| caggcgcugg gagaaagaac cggcucccga guucgggca uuucgccggg ucgaggugc | 300 |
| aggaugcaga gcaaggugcu gcuggccguc gcccugugc ucugcguuga cacccgggcc | 360 |

```
gccucugugg guuugccuag uguuucucuu gaucugccca ggcucagcau acaaaaagac    420
auacuuacaa uuaaggcuaa uacaacucuu caaauuacuu gcaggggaca gagggacuug    480
gacuggcuuu ggcccaauaa ucagaguggc agugagcaaa ggguggaggu gacugagugc    540
agcgauggcc ucuucuguaa gacacucaca auuccaaaag ugaucggaaa ugacacugga    600
gccuacaagu gcuucuaccg ggaaacugac uuggccucgg ucauuuaugu cuauguucaa    660
gauuacagau cuccauuuau gcuucuguu agugaccaac auggagucgu guacauuacu    720
gagaacaaaa acaaaacugu ggugauucca ugucucgggu ccauuucaaa ucucaacgug    780
ucacuuugug caagauaccc agaaaagaga uuuguuccug augguaacag aauuuccugg    840
gacagcaaga agggcuuuac uauucccagc uacaugauca gcuaugcugg caugucuuuc    900
ugugaagcaa aaauuaauga ugaaaguuac cagucuauua guacauagu gucguugua    960 ggguauagga uuuaugaugu gguucugagu ccgucucaug gaauugaacu aucuguugga   1020
gaaaagcuug ucuuaaauug uacagcaaga acugaacuaa augugggau ugacuucaac   1080 ugggaauacc cuucuucgaa gcaucagcau aagaaacuug uaaaccgaga ccuaaaaacc   1140
cagucuggga gugagaugaa gaaauuuuug agcaccuuaa cuauagaugg guaacccgg   1200 agugaccaag gauuguacac cugugcagca uccagugggc ugaugaccaa gagaacagc   1260 acauuuguca ggguccauga aaaaccuuuu guugcuuuug gaaguggcau ggaaucucug   1320
guggaagcca cgguggggga gcgugucaga auccccgcga aguaccuugg uuaccacc    1380 ccagaaauaa aaugguauaa aaauggaaua cccuugagu ccaaucacac aauuaaagcg   1440
gggcauguac ugacgauuau ggaagugagu gaaagagaca caggaaauua cacgucauc   1500 cuuaccaauc ccauuucaaa ggagaagcag agccaugugg ucucucuggu uguguaugc   1560 ccacccccaga uuggugagaa aucucuaauc ucuccuguag auuccuacca guacggcacc   1620
acucaaacgc ugacauguac ggucuaugcc auuccucccc cgcaucacau ccacugguau   1680
uggcaguugg aggaagagug cgccaacgag cccagccaag cugucucagu gacaaaccca   1740
uacccuugug aagauggag aaguggag gacuccagg gaggaaauaa aauugaaguu   1800
aauaaaaauc aauuugcucu caauugaagga aaaaacaaa cuguaaguac ccuuguuauc   1860
caagcggcaa augucuagc uuguacaaa ugugaagcgg ucaacaaagu cgggagagga   1920
gagaggguga ucuccuucca cgugaccagg gguccugaaaa uuacuuugca accgacaug   1980 cagcccacug agcaggagag cgugucuuug uggugcacug cagacagauc uacguuugag   2040
aaccucacau gguacaagcu uggccccacag ccucugccaa uccauguggg agaguugccc   2100
acaccuguuu gcaagaacuu ggauacucuu uggaaauuga augccaccau guucucuaau   2160
agcacaaaug acauuuugau caugagccuu aagaaugcau ccuugcagga ccaaggagac   2220
uaugucugcc uugcucaaga caggaagacc aagaaaagac auugcguggu caggcagcuc   2280
acaguccuag agcgugugc acccacgauc acaggaaacc uggagaauca gacgacaagu   2340
auuggggaaa gcaucgaagu ucaugcacg gcaucuggga uccccuccc acagaucaug   2400 ugguuuaaag auaaugagac ccuuuagaa gacucaggca uuguauugaa gaugggaac   2460 cggaacccuca cuaccgcag agugaggaag gaggacgaag gccucuacac cugcaggca   2520 ugcaguguuc uuggcugugc aaaaguggag gcauuuuca uaauagaagg ugcccaggaa   2580
aagacgaacu uggaaaucau uauuucuagua ggcacggcgg ugauugccau guucuucugg   2640
cuacuucuug ucaucaaccu acggaccguu aagcgggcca auggagggga acugaagaca   2700
ggcuacuugu ccaucgucau ggauccagau gaacucccau uggaugaaca uugugaaacga   2760
```

```
cugccuuaug augccagcaa auggaauuc cccagagacc ggcugaagcu agguaagccu      2820
cuuggccgug gugccuuugg ccaagugauu gaagcagaug ccuuggaau ugacaagaca       2880
gcaacuugca ggacaguagc agucaaaaug uugaagaag gagcaacaca cagugagcau       2940
cgagcucuca ugucugaacu caagauccuc auucauauug gucaccaucu caaugugguc      3000
aaccuucuag gugccuguac caagccagga gggccacuca ugguauugu ggaauucugc       3060
aaauuuggaa accugccac uuaccugagg agcaagagaa augaauuugu ccccuacaag       3120
accaaagggg cacgauuccg ucaagggaaa gacuacguug gagcaauccc ugugaucug       3180
aaacggcgcu uggacagcau caccaguagc cagagcucag ccagcucugg auuugugag       3240
gagaaguccc ucagugaugu agaagaagag gaagcuccug aagaucugua uaggacuuc       3300
cugaccuugg agcaucucau cuguuacagc uuccaagugg cuaagggcau ggaguucuug      3360
gcaucgcgaa aguguaucca cagggaccug gcggcacgaa auaccucuuu aucggagaag      3420
aacgugguua aaaucuguga cuuuggccuu gcccgggaua uuuauaaaga uccagauuau      3480
gucagaaaag gagaugcucg ccucccuuug aaauggaugg ccccagaaac aauuuuugac      3540
agaguguaca caauccagag ugacgucugg ucuuuuggug uuuugcugug ggaauauuu        3600
uccuuaggug cuucuccaua uccuggggua agaugaug aagaauuugu uaggcgauug         3660
aaagaaggaa cuagaaugag ggccccugau uauacacac cagaaaugua ccagaccaug        3720
cuggacugcu ggcacggga ccccaguacag agacccacgu uucagaguu ggugaacau         3780
uuggaaaauc ucuugcaagc uaaugcucag caggauggca agacuacau uguucuuccg        3840
auaucagaga cuuugagcau ggaagaggau ucggacucu cucugccuac cucaccuguu       3900
uccuguaugg aggagagga aguaugugac cccaaauucc auuaugacaa cacagcagga       3960
aucagucagu aucugcagaa caguaagcga aagagccggc cugugaagu aaaaacauuu       4020
gaagauaucc cguuagaaga accagaagua aaguaauccc cagaugacaa ccagacggac      4080
aguguauggu uucuugccuc agaagagcug aaaacuuugg aagacagaac caauuuaucu      4140
ccaucuuug gugaauggu gcccagcaaa agcaggagu cuggcaucu ugaaggcuca          4200
aaccagacaa gcggcuacca guccggauau cacuccgaug acacagacac caccguguac      4260
uccagugagg aagcagaacu uuuaaagcug auagagauug gagugcaaac cgguagcaca      4320
gcccagauuc uccagccuga cucggggacc acacugagcu cuccccugu uuaaaaggaa      4380
gcauccacac cccaacuccc ggacaucaca ugagagguuc ugcagauuu ugaaguguug       4440
uucuuuccac cagcaggaag uagccgcau ugauuuucau uucgacaaca gaaaaaggac       4500
cucggacugc agggagccag ucuucuaggc auauccugga agaggcuugu gacccaagaa      4560
ugugucugug ucuucccca guuugaccu gauccucuuu uuucauucau uuaaaaagca       4620
uuaucaugcc ccugcugcgg gucucaccau gggguuaga caaagagcuu caagcaaugg      4680
ccccauccuc aaagaaguag caguaccugg ggagcugaca cuucuguaaa acuagaagau     4740
aaaccaggca acguaagugu ucgagguguu gaagaugga aggauuugca gggcugaguc     4800
uauccaagag gcuuuguuua ggacgugggu cccaagccaa gccuuaagug uggaauucgg    4860
auugauagaa aggaagacua acguuaccuu gcuuuggaga guacuggagc cugcaaaugc   4920
auuuguuug cucuggugga gguggcaug gggucuguc ugaaaguaa agggucaga          4980
cggguuucu gguuuagaa gguugcgugu cuucgaguu gggcuaaagu agaguucguu         5040
gugcuguuuc ugaucuccaa ugagaguucc uccagaccg uuagcugucu ccuugccaag      5100
ccccaggaag aaaaugaugc agcucuggcu ccuugucucc caggcugauc cuuuauucag    5160
```

-continued

```
aauaccacaa agaaaggaca uucagcucaa ggcucccugc cguguugaag aguucugacu    5220
gcacaaacca gcuucgguu ucuucuggaa ugaauacccu cauaucuguc cugaugugau    5280
augucugaga cugaaugcgg gagguucaau gugaagcugu gugugguguc aaaguuucag    5340
gaaggauuuu accccuuugu ucuucccccu gucccaacc cacucucacc ccgcaaccca    5400
ucaguauuuu aguuauuugg ccucuacucc aguaaaccug auggguuug uucacucucu    5460 gaaugauuau uagccagacu ucaaaauuau uuuauagccc aaauuauaac aucuauugua    5520
uuauuuagac uuuuaacaua uagagcuauu ucuacugauu uuugcccuug uucuguccuu    5580
uuuuucaaaa aagaaaagu guuuuugu uggugccaua gugugaaaug cugggaacaa    5640
ugacuauaag acaugcuaug gcacauauau uuauagucug uuuauguaga aacaaaugua    5700
auauauuaaa gccuuauaua uaaugaacuu uguacuauuc acauuuugua ucaguauuau    5760
guagcauaac aaaggucaua augcuuucag caauugaugu cauuuauua aagaacauug    5820 aaaaacuuga                                                          5830
```

<210> SEQ ID NO 10
<211> LENGTH: 1356
<212> TYPE: PRT
<213> ORGANISM: Homo sapiens

<400> SEQUENCE: 10

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255
```

```
Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Phe Gly Ser Gly Met
            325                 330                 335

Glu Ser Leu Val Glu Ala Thr Val Gly Glu Arg Val Arg Ile Pro Ala
        340                 345                 350

Lys Tyr Leu Gly Tyr Pro Pro Pro Glu Ile Lys Trp Tyr Lys Asn Gly
            355                 360                 365

Ile Pro Leu Glu Ser Asn His Thr Ile Lys Ala Gly His Val Leu Thr
        370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
        405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
            485                 490                 495

Ile Glu Val Asn Lys Asn Gln Phe Ala Leu Ile Glu Gly Lys Asn Lys
        500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
            565                 570                 575

Thr Phe Glu Asn Leu Thr Trp Tyr Lys Leu Gly Pro Gln Pro Leu Pro
        580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
        610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
            645                 650                 655

Arg Gln Leu Thr Val Leu Glu Arg Val Ala Pro Thr Ile Thr Gly Asn
        660                 665                 670
```

```
Leu Glu Asn Gln Thr Thr Ser Ile Gly Glu Ser Ile Glu Val Ser Cys
            675                 680                 685

Thr Ala Ser Gly Asn Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Leu
        755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Ala Pro
            980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080
```

-continued

| | | | | | | | | | | | |
|---|---|---|---|---|---|---|---|---|---|---|---|
| Ile | Gln | Ser | Asp | Val | Trp | Ser | Phe | Gly | Val | Leu | Leu | Trp | Glu | Ile |
| 1085 | | | | | 1090 | | | | | 1095 | | | | |

Phe Ser Leu Gly Ala Ser Pro Tyr Pro Gly Val Lys Ile Asp Glu
   1100                1105                1110

Glu Phe Cys Arg Arg Leu Lys Glu Gly Thr Arg Met Arg Ala Pro
   1115                1120                1125

Asp Tyr Thr Thr Pro Glu Met Tyr Gln Thr Met Leu Asp Cys Trp
   1130                1135                1140

His Gly Glu Pro Ser Gln Arg Pro Thr Phe Ser Glu Leu Val Glu
   1145                1150                1155

His Leu Gly Asn Leu Leu Gln Ala Asn Ala Gln Gln Asp Gly Lys
   1160                1165                1170

Asp Tyr Ile Val Leu Pro Ile Ser Glu Thr Leu Ser Met Glu Glu
   1175                1180                1185

Asp Ser Gly Leu Ser Leu Pro Thr Ser Pro Val Ser Cys Met Glu
   1190                1195                1200

Glu Glu Glu Val Cys Asp Pro Lys Phe His Tyr Asp Asn Thr Ala
   1205                1210                1215

Gly Ile Ser Gln Tyr Leu Gln Asn Ser Lys Arg Lys Ser Arg Pro
   1220                1225                1230

Val Ser Val Lys Thr Phe Glu Asp Ile Pro Leu Glu Glu Pro Glu
   1235                1240                1245

Val Lys Val Ile Pro Asp Asp Asn Gln Thr Asp Ser Gly Met Val
   1250                1255                1260

Leu Ala Ser Glu Glu Leu Lys Thr Leu Glu Asp Arg Thr Lys Leu
   1265                1270                1275

Ser Pro Ser Phe Gly Gly Met Val Pro Ser Lys Ser Arg Glu Ser
   1280                1285                1290

Val Ala Ser Glu Gly Ser Asn Gln Thr Ser Gly Tyr Gln Ser Gly
   1295                1300                1305

Tyr His Ser Asp Asp Thr Asp Thr Thr Val Tyr Ser Ser Glu Glu
   1310                1315                1320

Ala Glu Leu Leu Lys Leu Ile Glu Ile Gly Val Gln Thr Gly Ser
   1325                1330                1335

Thr Ala Gln Ile Leu Gln Pro Asp Ser Gly Thr Thr Leu Ser Ser
   1340                1345                1350

Pro Pro Val
   1355

<210> SEQ ID NO 11
<211> LENGTH: 2089
<212> TYPE: RNA
<213> ORGANISM: Homo sapiens

<400> SEQUENCE: 11
aguuuggacg gcugcuuccc accagcaaag accacgacug gagagccgag ccggaggcag    60
cugggaaaca ugaagagcgu cuugcugcug accacgcucc ucgugccugc acaccuggug   120
gccgccugga gcaauaauua ugcgguggac ugcccucaac acugugacag caguagugc   180 aaaagcagcc cgcgcugcaa aggacagug cucgacgacu guggcugcug ccgagugugc   240
gcugcagggc ggggagaaac uugcuaccgc acagucucag gcauggaugg caugaagugu   300
ggcccggggc ugagguguca gccuucuaau ggggaggauc cuuuuggug agaguuuggu   360 aucugcaaag acugucccua cggcaccuuc gggauggauu gcagagagac cugcaacugc   420

| | |
|---|---|
| cagucaggca ucugugacag ggggacggga aaaugcccuga aauuccccuu cuuccaauau | 480 |
| ucaguaacca agucuuccaa cagauuuguu ucucucacgg agcaugacau ggcaucugga | 540 |
| gauggcaaua uugugagaga agaaguugug aaagagaaug cugccggguc ucccguaaug | 600 |
| aggaaauggu uaaauccacg cugaucccgg cugugauuuc ugagagaagg cucuauuuuc | 660 |
| gugauuguuc aacacacagc caacauuuua ggaacuuucu agauuauagc auaaggacau | 720 |
| guaauuuuug aagaccaaau gugaugcaug guggauccag aaaacaaaaa guaggauacu | 780 |
| uacaauccau aacauccaua ugacugaaca cuuguaugug uuuguuaaau auucgaaugc | 840 |
| auguagauuu guuaaaugug uguguauagu aacacugaag aacuaaaaau gcaauuuagg | 900 |
| uaaucuuacg uggagacagg ucaaccaaag agggagcuag gcaaagcuga agaccgcagu | 960 |
| gagucaaauu aguucuuuga cuuugaugua cauuaauguu gggauaugga augaagacuu | 1020 |
| aagagcagga gaagaugggg aggggguggg agugggaaau aaaauauuua gcccuuccuu | 1080 |
| gguaggguagc uucucuagaa uuuaaugug cuuuuuuuuu uuuuuuggc uuugggaaaa | 1140 |
| gucaaaauaa aacaaccaga aaaccccuga aggaaguaag auguuugaag cuuauggaaa | 1200 |
| uuugaguaac aaacagcuuu gaacugagag caauuucaaa aggcugcuga uguaguuccc | 1260 |
| ggguuaccug uaucugaagg acgguucugg ggcauaggaa acacauacac uuccauaaau | 1320 |
| agcuuuaacg uaugccaccu cagagauaaa ucuaagaagu auuuuacccca cgguggouuu | 1380 |
| gugugoguau gaagguaaau auuuauauau uuuuauaaau aaaauguguua gugcaaguca | 1440 |
| ucuucoccuac ccauauuuau cauccucuug aggaagaaa ucuaguauua uuuguugaaa | 1500 |
| augguuagaa uaaaacuaug acucuauaag guuucaaac aucugaggca ugauaaauuu | 1560 |
| auuauccaua auuauaguaa uaauaaccuu aauaagcaua agaaaaacag agucacucug | 1620 |
| gauuucaaaa augucaaaaa augagcaaca gagggguccuu auuuaaacau aagugcugug | 1680 |
| acuuagguga auuuucaauu uaagguagaa aauaaguuuu uaggagguuu guaaaagaag | 1740 |
| aaucaauuuu cagcagaaaa caugucaacu uuaaaauaua guuuauuuc auauuuuuu | 1800 |
| cuuuuaaacu ugguugauaa guggaauuag gaguauauuu gaaagaaucu uagcacaaac | 1860 |
| aggacuguug uacuagaugu ucuuaggaaa uaucucagaa guauuuuauu ugaagugaag | 1920 |
| aacuuauuua agaauuauuu cagauauuuac cuguauuuua uucuugaagu uggccaacag | 1980 |
| aguugugaau gugugugggga aggcccuuuga auguaaagcu gcauaagcug uuaagguuuug | 2040 |
| uuuuaaaagg acauguuuau uauuguucaa uaaaaaagaa caagauaca | 2089 |

<210> SEQ ID NO 12
<211> LENGTH: 184
<212> TYPE: PRT
<213> ORGANISM: Homo sapiens

<400> SEQUENCE: 12

Met Lys Ser Val Leu Leu Leu Thr Thr Leu Leu Val Pro Ala His Leu
1               5                   10                  15

Val Ala Ala Trp Ser Asn Asn Tyr Ala Val Asp Cys Pro Gln His Cys
            20                  25                  30

Asp Ser Ser Glu Cys Lys Ser Ser Pro Arg Cys Lys Arg Thr Val Leu
        35                  40                  45

Asp Asp Cys Gly Cys Cys Arg Val Cys Ala Ala Gly Arg Gly Glu Thr
    50                  55                  60

Cys Tyr Arg Thr Val Ser Gly Met Asp Gly Met Lys Cys Gly Pro Gly
65                  70                  75                  80

Leu Arg Cys Gln Pro Ser Asn Gly Glu Asp Pro Phe Gly Glu Glu Phe
            85                  90                  95

Gly Ile Cys Lys Asp Cys Pro Tyr Gly Thr Phe Gly Met Asp Cys Arg
            100                 105                 110

Glu Thr Cys Asn Cys Gln Ser Gly Ile Cys Asp Arg Gly Thr Gly Lys
            115                 120                 125

Cys Leu Lys Phe Pro Phe Phe Gln Tyr Ser Val Thr Lys Ser Ser Asn
            130                 135                 140

Arg Phe Val Ser Leu Thr Glu His Asp Met Ala Ser Gly Asp Gly Asn
145                 150                 155                 160

Ile Val Arg Glu Glu Val Val Lys Glu Asn Ala Ala Gly Ser Pro Val
            165                 170                 175

Met Arg Lys Trp Leu Asn Pro Arg
            180

<210> SEQ ID NO 13
<211> LENGTH: 6831
<212> TYPE: RNA
<213> ORGANISM: Homo sapiens

<400> SEQUENCE: 13
ccaggcccca uuguucccgg uuccagcca uggcugccau uaccugacca gcgccacagc      60
cggucucucu gcaggcgccg ggagaaguga ccagagcaau uucugcuuuu cacagggcgg    120
guuucucaac ggugacuugu gggcagugcc uucugcugag cgaucaugg cccgaaggca    180 gaacuaacug ugccugcagu cuucacucuc aggaugcagc cgaggugggc ccaaggggcc    240 acgaugggc uuggagccu gcugacccuu cugcucuguu caagccuuga ggucaagaa      300 aacucuuuca caaucaacag uguugacaug aagagccugc cggacuggac ggugcaaaau    360
gggaagaacc ugacccugca gugcuucgcg gaugucagcc caccucuca cgucaagccu     420 cagcaccaga gcucuucua uaaggaugac gugcuguuuu acaacaucuc uccaugaag     480 agcacagaga guuauuuuau uccugaaguc cggaucuaug acucagggac auauaaaugu    540
acugugauug ugaacaacaa agagaaaacc acugcagagu accaguguu ggugaagga     600 gugcccaguc ccaggugac acuggacaag aaagaggcca uccaaggugg gaucgugagg    660
gucaacuguu cugcccaga ggaaaaggcc ccaauacacu ucacaauuga aaacuugaa     720 cuaaaugaaa aaauggucaa gcugaaaaga gagaagaauu ucgagacca gaauuuugug    780 auacuggaau ccccguuga ggaacaggac cgcguuuuau ccuuccgaug ucaagcuagg    840
aucauuucug ggauccauau gcagaccuca gaaucuacca agagugaacu ggucaccgug    900
acggaauccu ucucuacacc caaguccac aucagcccca ccggaaugau caauggaagga    960 gcucagcucc acauuaagug caccauucaa ugacucacc uggcccagga guuccagaa     1020 aucauaauuc agaaggacaa ggcgauugu gcccacaaca gacauggcaa caaggcugug    1080
uacucaguca uggccauggu ggagcacagu ggcaacuaca cgugcaaagu ggaguccagc    1140 cgcauauucca aggucagcag caucgugguc aacauaacag aacuauuuuc caagcccgaa    1200
cuggaaucuu ccuucacaca ucuggaccaa ggugaaagac ugaaccuguc cugcuccauc    1260
ccaggagcac cuccagccaa cuucaccauc cagaaggaag auacgauugu gcacagacu     1320 caagauuuca ccaagauagc cucaaagucg acagggga cguauaucug cacugcaggu    1380
auugacaaag uggucaagaa agcaacaca guccagauag ucuaugga aaugcucucc     1440 cagcccagga uuucuuauga ugcccaguuu gagguaauaa aaggacagac caucgaaguc    1500

```
cguugcgaau cgaucagugg aacuuugccu auuucuuacc aacuuuuaaa aacaaguaaa    1560
guuuuggaga auaguaccaa gaacucaaau gauccugcgg uauucaaaga caaccccacu    1620
gaagacgucg aauaccagug uguugcagau aauugccauu cccaugccaa aauguuaagu    1680
gagguucuga ggugaaggu gauagccccg guggaugagg uccagauuuc uauccuguca     1740
aguaaggugg uggagucugg agaggacauu gugcugcaau gugcugugaa ugaaggaucu    1800
ggucccauca ccuauaaguu uuacagagaa aaagagggca aacccuucua ucaaaugacc    1860
ucaaaugcca cccaggcauu uggaccaag cagaaggcua gcaaggaaca ggagggagag     1920
uauuacugca cagccuucaa cagagccaac cacgccucca gugucccag aagcaaaaua     1980 cugacaguca gagucauucu ugccccaugg aagaaaggac uuauugcagu gguuaucauc    2040
ggagugauca uugcucucuu gaucauugcg ccaaauguu auuucugag gaaagccaag      2100 gccaagcaga ugccagugga aaugccagg ccagcaguac cacuucugaa cuccaacaac     2160
gagaaaaugu cagaucccaa uaggaagcu aacagucauu acggucacaa ugacgaugu      2220 agaaaccaug caaugaaacc aauaaaugau aauaaagagc cucugaacuc agacgugcag    2280
uacacggaag uucaaguguc cucagcugag ucucacaaag aucuaggaaa gaaggacaca    2340
gagacagugu acagugaagu ccggaaagcu gucccugaug ccguggaaag cagauacucu    2400
agaacggaag gcucccuuga uggaacuuag acagcaaggc cagaugcaca ucccuggaag    2460
gacauccaug uuccgagaag aacagauaau cccuguauuu caagaccucu gugcacuuau    2520
uuaugaaccu gcccugcucc cacagaacac agcaauuccu caggcuaagc ugccgguucu    2580
uaaauccauc cugcuaaguu aauguugggu agaaagagau acagagggc uguugaauuu     2640 cccacauacc cuccuuccac caaguuggaa cauccuugga aauuggaaga gcacaagagg    2700
agauccaggg caaggccauu gggauauucu gaaacuugaa uauuuuguuu gugcagaga     2760 uaaagaccuu uuccaugcac ccucauacac agaaaccaau uuucuuuuuu auacucaauc    2820
auuucuagcg cauggccugg uuagaggcug guuuuucuc uuuuccuuug guccuucaaa     2880
ggcuuguagu uuggcuagu ccuguucuu uggaaauaca cagugcugac cagacagccu      2940
cccccugucc ccucuaugac cucgcccucc acaaaggga aaaccagacu acuugggagc     3000
accgccugug aaauaccaac cugaagacac cguucauuca ggcaacgcac aaaacagaaa    3060
augaaggugu aacaagcaca gauguucuuc aacuguuuuu gucuacacuc uuucucuuuu    3120
ccucuaccau gcugaaggcu gaaagacagg aagauggugc caucagcaaa uauuauucuu    3180
aauugaaaac uugaaaugug uauguuucuu acuaauuuuu aaaaauguau ccuugccag     3240 ggcaggcaag guggcucacg ccuguaaucc cagcacuuca ggaggcugag gugggcggau    3300
caccugaggu caggaguuug agaccagccu gaugaaaccc ugucucuacu aaaaauacaa    3360
gaauuagccg ggcguggugg cgcaugccug uaguaucagc uacucaagag gcugagguga    3420
gauuaucgcu ugaacccagg aaacggaggu uguagugagc ggagaucgcg ccacugcacu    3480
ccagccugag ugacagagug agaauccauc ucaaaaaaaa caaaaaacaa aauugcuugc    3540
uaaagaagug gucuccugag gucuuaagac auuccugaca gugucuugag ugggugggag    3600
agaggcugcu gucauugcgc ugugaauuu cacagaugag aaccacgccu agccaaaauc     3660
acuuuuccug uuugccucag ugacacagcu gcagggaccc ucguggaugu uguauuaaau    3720
aaauuugacc uuugcucuuu gcagaucugu gaaauguugu cuucgagggg ccacaugca    3780 ucuauagugc ugaggacucc uugggccucu gaagucacag agagaaccga gcaggucuau    3840
guuuuuguuu uguuguuuug agacggagau ucgcucuugu ugcccgggcu ggacugcagc    3900
```

```
ggcgcaaccu cugcucacug caaccuccgc cuccugggu caagcaguuc uccugucuca    3960
gccucccgag uagcugggau uacaggcaca ugucaccacg ccuggcuaau uuuuguauuu    4020
uuaguagaga ugggguuuca ccacguuggc caggcugauc ucgaaugccu gaccuuuggu    4080
gaucugcccg ccuugccuc augugugcuc cacaggccuu uggguuggga uugcaggcgu    4140
gagccaccau gcccagccua gacucuuuug acaauaugau gaaagcuguu gguuccuuuc    4200
cccaacacac acacaccgag uuguaucacg aaaaugucau acaauuucca gguuuucuga    4260
guggugggcu cagauugagg ucaaaggauc agacgaccuc uaacgaccuu caugucucug    4320
uugaugaucu ggggacagcc agaucccug uguccaggga guuccuuagu cccuugccac    4380
caccagagaa gggcaauugc cacgggagcu gcaaagaccc uauuccuacu ccuggugccu    4440
uacuuaugca gcacgacuga auuuuugu uuguuuuguu uuguugagac aggggcuugc    4500
ucuguugccc aggcuggagu gcaguggcac aacaauggcu caccgcagcc ucgaacccu    4560 ggcucaagc gauccccca ucucagcuuc cuggguagcu gggaccagag gcgugagccg    4620
ccauagcugg cuaauuuuua auuuuuuuu ugcagagaug gguuucacc augugccca    4680 ggcuggucuc gaacuucugg gcucaaguga uccuccucc uuggccucgc aaagugcugg    4740
gauugcaggc augagccacc gccccggcc uguggagcac acaugaguuu aaaauuacuu    4800
ucccuucugc cuauauuucc gaggaggaaa cuucaugcgc agggaucuuu cuuaguggau    4860
uuaauggcua aaaggucugu cugaauccag gacgcuggcu uuagccuucc ucggcagcug    4920
ccguaacccc ggugucuaaa ccugaagcau cccaggagca cccacuccag gaguuuucuc    4980
ggccgcggaa cucauuaguu agagcgcccu cuuguguucu caugugguaa ucggucacug    5040
aaggacuuaa aaugguccuu agccaacaca caguaaaacu uucccucuu cugacccaa    5100 gaggucagcc acccauuuca ugagcauaua cuggucgccc caucagcguu ucucgauugg    5160
cuaacugaac ccacucccg accuagacuc aagacaggcg aagugacgcu uaggucaaca    5220
uucacucacu aaagcaacga cugucgggcg auuugucuc ccgcugguuu uggaaugguug    5280 ucggagaca uuuuuggug ucacagcugg gugggugugc ucccggcauc uggugggag    5340 aaaccaagca ugcuccuaaa cauccuacag gcacagaacc gucucccacg accaagcaug    5400
aucaaguccc aaaugccaau aaugggccagg uugagaaacu cugcacagaa gcauccaguu    5460
auuugucugu uugcucaaca agcuugugcu caucaugcuc uguguuccug acgcugugcu    5520
ggguguuggc gguggaaaga uuacaagagu cacauggcag cuguccuccu ggaagguaca    5580
acccaguaga gaugcagacu aacagagagc caauuacaaa gcagugugac aagcgucaug    5640
guggaaaauu aaaagcucaa acaagggcac auggagggg cuuccaacac agacuuuggg    5700
ggauccagga aggucuaaga ggaaaguggg ucucaccaaa gccuugacca uaggcagagg    5760
guaccagugg aaaagguggg gugaagaaca uugaggacaa aaggaagaag ugcaggaagg    5820
cccugaggca aggagugggg gggugcccug gagggauggc agcagggcag ucugucagac    5880 ccaagugggcc uccagcccua gaagccaauu aguccuccuc aaaaagcugu cacugucccc    5940
uaagaauugc ugccaggcuc ccacuggccu gacucagucu uugagagucu uaaggaggag    6000
gucucugaaa gguacacacc aagaacucuc cccagcacag cuguuuuuaa gacucuccac    6060
cagcgucauu ggcguguugg gaagaaaccc ucugccacag aggccagcuu cagccuuugc    6120
cuaacaccgc aagggcaaau ggaaggguaa acgggaagga gaugucuccc cagcaggcua    6180
uuugaggaca gucuucccug cagaagaucu caaccggggg uccacagagu ggaaauguua    6240
gaguagggag cuaggcaaac augagcagga cagguagggg cccccacagg aaugucaggc    6300
```

-continued

| | |
|---|---|
| uaccaucagg ugauggucag gugguuguua aacugucucu guaaaauaau aauugguugc | 6360 |
| agccagcucc aagcaaggac agucucucaa uagauacaaa acacccugau cuggugauca | 6420 |
| gccgcuuccc gauaagaucu caggagcugg gcaagcagcc uggagcaugc gcaccaagag | 6480 |
| gcaaaauggc ggaauuuaac caguauauga ccuaccuucc ucugggaacg cacgacuggu | 6540 |
| aaggggaaaa augccucaag ugagcaugcg cgcaacuuca guaucacac ugugcaugcg | 6600 |
| accccuucca agugcuggca ggucaccaca uacgcggaca gccugcugca agggaagaau | 6660 |
| caggggagau gagacguaaa ucccagaacu augccaaaua cauaaaaccc caaguuaagg | 6720 |
| gucaggcagg gcacuuagau cucucaaguu gccugccuga cccaagugua guguacuucc | 6780 |
| uuuuguuccu gcucuaaaac uuuuuaauaa acucucacuc cugcucuaaa a | 6831 |

<210> SEQ ID NO 14
<211> LENGTH: 738
<212> TYPE: PRT
<213> ORGANISM: Homo sapiens

<400> SEQUENCE: 14

Met Gln Pro Arg Trp Ala Gln Gly Ala Thr Met Trp Leu Gly Val Leu
1               5                   10                  15

Leu Thr Leu Leu Leu Cys Ser Ser Leu Glu Gly Gln Glu Asn Ser Phe
            20                  25                  30

Thr Ile Asn Ser Val Asp Met Lys Ser Leu Pro Asp Trp Thr Val Gln
        35                  40                  45

Asn Gly Lys Asn Leu Thr Leu Gln Cys Phe Ala Asp Val Ser Thr Thr
    50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Leu Leu Val Glu
        115                 120                 125

Gly Val Pro Ser Pro Arg Val Thr Leu Asp Lys Lys Glu Ala Ile Gln
130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
                165                 170                 175

Leu Lys Arg Glu Lys Asn Ser Arg Asp Gln Asn Phe Val Ile Leu Glu
            180                 185                 190

Phe Pro Val Glu Glu Gln Asp Arg Val Leu Ser Phe Arg Cys Gln Ala
        195                 200                 205

Arg Ile Ile Ser Gly Ile His Met Gln Thr Ser Glu Ser Thr Lys Ser
    210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
            260                 265                 270

Gln Lys Asp Lys Ala Ile Val Ala His Asn Arg His Gly Asn Lys Ala
        275                 280                 285

```
Val Tyr Ser Val Met Ala Met Val Glu His Ser Gly Asn Tyr Thr Cys
    290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
                340                 345                 350

Pro Pro Ala Asn Phe Thr Ile Gln Lys Glu Asp Thr Ile Val Ser Gln
                355                 360                 365

Thr Gln Asp Phe Thr Lys Ile Ala Ser Lys Ser Asp Ser Gly Thr Tyr
    370                 375                 380

Ile Cys Thr Ala Gly Ile Asp Lys Val Val Lys Ser Asn Thr Val
385                 390                 395                 400

Gln Ile Val Val Cys Glu Met Leu Ser Gln Pro Arg Ile Ser Tyr Asp
                405                 410                 415

Ala Gln Phe Glu Val Ile Lys Gly Gln Thr Ile Glu Val Arg Cys Glu
                420                 425                 430

Ser Ile Ser Gly Thr Leu Pro Ile Ser Tyr Gln Leu Leu Lys Thr Ser
    435                 440                 445

Lys Val Leu Glu Asn Ser Thr Lys Asn Ser Asn Asp Pro Ala Val Phe
450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
                485                 490                 495

Ile Ala Pro Val Asp Glu Val Gln Ile Ser Ile Leu Ser Ser Lys Val
                500                 505                 510

Val Glu Ser Gly Glu Asp Ile Val Leu Gln Cys Ala Val Asn Glu Gly
    515                 520                 525

Ser Gly Pro Ile Thr Tyr Lys Phe Tyr Arg Glu Lys Glu Gly Lys Pro
530                 535                 540

Phe Tyr Gln Met Thr Ser Asn Ala Thr Gln Ala Phe Trp Thr Lys Gln
545                 550                 555                 560

Lys Ala Ser Lys Glu Gln Glu Gly Glu Tyr Tyr Cys Thr Ala Phe Asn
                565                 570                 575

Arg Ala Asn His Ala Ser Ser Val Pro Arg Ser Lys Ile Leu Thr Val
                580                 585                 590

Arg Val Ile Leu Ala Pro Trp Lys Lys Gly Leu Ile Ala Val Val Ile
    595                 600                 605

Ile Gly Val Ile Ile Ala Leu Leu Ile Ile Ala Ala Lys Cys Tyr Phe
    610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
                645                 650                 655

Met Glu Ala Asn Ser His Tyr Gly His Asn Asp Asp Val Arg Asn His
                660                 665                 670

Ala Met Lys Pro Ile Asn Asp Asn Lys Glu Pro Leu Asn Ser Asp Val
                675                 680                 685

Gln Tyr Thr Glu Val Gln Val Ser Ser Ala Glu Ser His Lys Asp Leu
    690                 695                 700
```

```
Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
            725                 730                 735

Gly Thr
```

<210> SEQ ID NO 15
<211> LENGTH: 1350
<212> TYPE: RNA
<213> ORGANISM: Homo sapiens

<400> SEQUENCE: 15

```
guucguugca acaaauugau gagcaaugcu uuuuauaau gccaacuuug uacaaaaaag    60
uuggcaugag cggugcuccg acggccgggg cagcccugau gcucugcgcc gccaccgccg   120
ugcuacugag cgcucagggc ggacccgugc aguccaaguc gccgcgcuuu gcguccuggg   180
acgagaugaa uguccuggcg cacggacucc ugcagcucgg ccaggggcug cgcgaacacg   240
cggagcgcac ccgcagucag cugagcgcgc uggagcggcg ccugagcgcg ugcggguccg   300
ccugucaggg aaccgagggg uccaccgacc ucccguuagc cccugagagc cggguggacc   360
cugagguccu ucagcccugc agacacaac ucaaggcuca gaacagcagg auccagcaac   420
ucuuccacaa gguggcccag cagcagcggc accuggagaa gcagccaccug cgaauucagc   480
aucugcaaag ccaguuuggc cuccuggacc acaagcaccu agaccaugag guggccaagc   540
cugcccgaag aaagaggcug cccgagaugg cccagccagu ugacccggcu cacaaugca   600
gccgccugca ccggcugccc agggauugcc aggagcuguu ccagguuggg gagaggcaga   660
guggacuauu ugaaauccag ccucaggggu uccgccauu uuuggugaac ugcaagauga   720
ccucagaugg aggcuggaca guaauucaga gcgccacga uggcucagug gacuucaacc   780
ggcccuggga agccuacaag gcggguuuug gggaucccca cggcgaguuc uggcuggguc   840
uggagaaggu gcauagcauc acgggggacc gcaacagccg ccuggccgug cagcugcggg   900
acugggaugg caacgccgag uugcugcagu ucuccgugca ccugguggca gaggacacgg   960
ccuauagccu gcagcucacu gcacccgugg ccggccagcu gggcgccacc accgucccac  1020
ccagcggccu cuccguaccc uucuccacuu gggaccagga ucacgaccuc cgcagggaca  1080
agaacugcgc caagagccuc ucuggaggcu gguggnuugg caccugcagc auuccaacc  1140
ucaacagcca guacuccgc uccauccac agcagcggca gaagcuuaag aagggaaucu  1200
ucuggaagac cuggcggggc cgcuacuacc cacugcaggc caccaccaug uugauccagc  1260
ccauggcagc agaggcagcc uccuaccacaa cuuucuugua caaguuggc auuauaagaa  1320
agcauugcuu aucaauuugu ugcaacgaac                                   1350
```

<210> SEQ ID NO 16
<211> LENGTH: 406
<212> TYPE: PRT
<213> ORGANISM: Homo sapiens

<400> SEQUENCE: 16

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45
```

```
Leu Gln Leu Gly Gln Gly Leu Arg Glu His Ala Glu Arg Thr Arg Ser
 50                  55                  60

Gln Leu Ser Ala Leu Glu Arg Arg Leu Ser Ala Cys Gly Ser Ala Cys
 65                  70                  75                  80

Gln Gly Thr Glu Gly Ser Thr Asp Leu Pro Leu Ala Pro Glu Ser Arg
                 85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
            115                 120                 125

His Leu Glu Lys Gln His Leu Arg Ile Gln His Leu Gln Ser Gln Phe
130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
            195                 200                 205

Ser Pro Pro Phe Leu Val Asn Cys Lys Met Thr Ser Asp Gly Gly Trp
            210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
            275                 280                 285

Phe Ser Val His Leu Gly Gly Glu Asp Thr Ala Tyr Ser Leu Gln Leu
290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
            355                 360                 365

Gln Gln Arg Gln Lys Leu Lys Lys Gly Ile Phe Trp Lys Thr Trp Arg
            370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 17
<211> LENGTH: 2615
<212> TYPE: RNA
<213> ORGANISM: Homo sapiens
```

<400> SEQUENCE: 17

```
ccuuuuuugg ccucgacggc ggcaacccag ccucccuccu aacgcccucc gccuuuggga    60
ccaaccaggg gagcucaagu uaguagcagc caaggagagg cgcugccuug ccaagacuaa   120
aaagggaggg gagaagagag gaaaaaagca agaauccccc accccucucc cgggcggagg   180
gggcgggaag agcgcguccu ggccaagccg aguagugucu ccacucggu gcgucucucu    240
aggagccgcg cggaaggau gcugguccgc aggggcgcgc gcgagggccc aggaugccgc   300
ggggcuggac cgcgcuuugc uugcugaguu ugcugccuuc ugggulucaug agucuugaca   360
acaacgguac ugcuacccca gaguuaccua cccagggaac auuucaaaau guuucuacaa   420
auguauccua ccaagaaacu acaacaccua guacccuugg aaguaccagc cugcacccug   480
ugucucaaca uggcaaugag gccacaacaa acaucacaga aacgacaguc aaauucacau   540
cuaccucugu gauaaccuca guuuauggaa acacaaacuc uucugccag ucacagaccu    600
cuguaaucag cacaguguuc accaccccag ccaacguuuc aacucagag acaaccuuga    660
agccuagccu gucaccugga aauguuucag accuuucaac cacuagcacu agccuugcaa   720
caucucccac uaaacccuau acaucaucuu cuccuauccu aagugacauc aaggcagaaa   780
ucaaauguuc aggcaucaga gaagugaaau ugacucaggg caucgccug gagcaaaaua    840
agaccuccag cugugcggag uuuaagaagg acaggggaga gggccuggcc cgagugcugu   900
gugggggagga gcaggcugau gcugaugcug gggcccaggu augcucccug cuccuugccc   960
agucugaggu gaggccucag ugucuacugc uggucuuggc caacagaaca gaaauuucca  1020
gcaaacucca acuuaugaaa aagcaccaau cugaccugaa aaagcugggg auccuagauu  1080
ucacugagca agauguugca agccaccaga gcuauuccca aaagacccug auugcacugg  1140
ucaccucggg agcccugcug gcugucuugg gcaucacugg cuauuccug augaaucgcc    1200
gcagcuggag ccccacagga gaaaggcugg gcgaagaccc uuauuacacg gaaaacgguaq  1260
gaggccaggu cuauagcuca ggaccuggga ccuccccuga ggcucaggga aaggccagug  1320
ugaaccgagg ggcucagaaa acgggaccg gccaggccac cuccagaaac ggccauucag  1380
caagacaaca cgugguggcu gauaccgaau ugugacucgg cuaggugggg caaggcuggg  1440
cagugucoga gagagcacc cucucugcau cugaccacgu gcuaccccca ugcuggaggu  1500
gacaucuuu acgcccaacc cuuccccacu gcacacaccu cagaggcugu ucuuggggcc  1560
cuacaccuug aggaggggc agguaaacuc cuguccuuua cacauucggc ucccuggagc   1620
cagacucugg ucuucuuugg guaaacgugu gacgggggaa agccaaggu uggagaagcu    1680
cccaggaaca aucgauggcc uugcagcacu cacacaggac ccccuucccc uaccccuccc   1740
ucucugccgc aauacaggaa cccccagggg aaagaugagc uuuucuaggc uacaauuuuc   1800
ucccaggaag cuuugauuuu uaccguuucu ucccuguauu uucuucucu acuuugagga    1860
aaccaaagua accuuuugca ccugcucucu uguaaugaua uagccagaaa aacguuugc    1920
cuugaaccac uucccucauc ucuccuccaa gacacugugg acuggucac cagcucuccc    1980
cuuguucucu aaguuccacu gagcuccaug ugccccucu accauuugca gagucuugca   2040
caguuuucug gcuggagccu agaacaggcc uccaaguuu uaggacaaac agcucaguuc   2100
uagucucucu gggccacac agaaacucuu uugggcucc uuuucucccc ucuggaucaa    2160
aguaggcagg accauggggac caggucuugg agcugagccu cucaccugua cucuccgaa    2220
aaauccucuu cccucgaggc uggauccuag ccuuauccuc ugaucccau ggcuccuc    2280
ucccuccugc cgacuccugg guugagcugu ugccucaguc ccccaacaga ugcuuuucug   2340
```

| | | |
|---|---|---|
| ucucugccuc ccucacccug agccccuucc uugcucugca cccccauaug gucauagccc | 2400 |
| agaucagcuc cuaacccuua ucaccagcug ccucuucugu ggugaccca gguccuguu | 2460 |
| ugcuguugau uucuuuccag aggguugag cagggauccu gguucaaug acgguggaa | 2520 |
| auagaaauuu ccagagaaga gaguauuggg uagauauuuu uucugaauac aaagugaugu | 2580 |
| guuuaaauac ugcaauuaaa gugauacuga aacac | 2615 |

<210> SEQ ID NO 18
<211> LENGTH: 385
<212> TYPE: PRT
<213> ORGANISM: Homo sapiens

<400> SEQUENCE: 18

```
Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110

Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
        195                 200                 205

Gly Leu Ala Arg Val Leu Cys Gly Glu Glu Gln Ala Asp Ala Asp Ala
    210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
        275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
305                 310                 315                 320
```

Gly Glu Arg Leu Gly Glu Asp Pro Tyr Tyr Thr Glu Asn Gly Gly
            325                 330                 335

Gln Gly Tyr Ser Ser Gly Pro Gly Thr Ser Pro Glu Ala Gln Gly Lys
            340                 345                 350

Ala Ser Val Asn Arg Gly Ala Gln Glu Asn Gly Thr Gly Gln Ala Thr
            355                 360                 365

Ser Arg Asn Gly His Ser Ala Arg Gln His Val Val Ala Asp Thr Glu
            370                 375                 380

Leu
385

<210> SEQ ID NO 19
<211> LENGTH: 1197
<212> TYPE: RNA
<213> ORGANISM: Homo sapiens

<400> SEQUENCE: 19
gucucaauau uagagucuca accccccaaua aauauaggac uggagauguc ugaggcucau      60
ucugcccucg agcccaccgg gaacgaaaga gaagcucuau cuccccucca ggagcccagc     120
uaugaacucc uucuccacaa gcgccuucgg uccaguugcc uucucccugg ggcugcuccu     180
gguguugccu gcugccuucc cugccccagu acccccagga gaagauucca agaugguagc     240
cgccccacac agacagccac ucaccucuuc agaacgaauu gacaaacaaa uucgguacau     300
ccucgacggc aucucagccc ugagaaagga gacauguaac aagaguaaca ugugugaaag     360
cagcaaagag gcacuggcag aaaacaaccu gaaccuucca aagauggcug aaaaagaugg     420
augcuuccaa ucuggauuca augaggagac uugccugguc aaaaucauca cuggucuuuu     480
ggaguuugag guauaccuag aguaccucca gaacagauuu gagaguagug aggaacaagc     540
cagagcugug cagaugagua caaaaguccu gauccaguuc cugcagaaaa aggcaaagaa     600
ucuagaugca auaaccaccc cugacccaac cacaaaugcc agccugcuga cgaagcugca     660
ggcacagaac caguggcugc aggacaugac aacucaucuc auucugcgca gcuuuaagga     720
guuccugcag uccagccuga ggcucuuucg gcaaaauguag cauggcaccc ucagauuguu     780
guuguuaaug ggcauuccuu cuucgggucu gaaaccuguc cacugggcac agaacuuaug     840
uuguucucua uggagaacua aaaguauagc cguuaggaca cuauuuuaau uauuuuuaau     900
uuauuaauau uuaaauaugu gaagcugagu uaauuuaugu aagucauauu uauauuuuua     960
agaaguacca cuugaaacau uuuauguauu aguuugaaa uaauaaugga aaguggcuau    1020
gcaguuugaa uauccuuugu uucagagcca gaucauuucu uggaaagugu aggcuuaccu    1080
caaauaaaug gcuaacuuau acauauuuuu aaagaaauau uuauauugua uuuauauaau    1140
guauaaaugg uuuuuauacc aauaaauggc auuuaaaaa auucagcaaa aaaaaaa        1197

<210> SEQ ID NO 20
<211> LENGTH: 212
<212> TYPE: PRT
<213> ORGANISM: Homo sapiens

<400> SEQUENCE: 20

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
            35                  40                  45

```
Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
                115                 120                 125

Leu Gln Asn Arg Phe Glu Ser Ser Glu Glu Ala Arg Ala Val Gln
            130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 21
<211> LENGTH: 1184
<212> TYPE: RNA
<213> ORGANISM: Homo sapiens

<400> SEQUENCE: 21
cacagagccc gggccgcagg caccuccucg ccagcucuuc cgcuccucuc acagccgcca      60
gacccgccug cugagcccca uggcccgcgc ugcucucucc gccgccccca gcaaucccg     120 gcuccugcga guggcacugc ugcuccugcu ccugguagcc gcuggccggc gcgcagcagg    180
agcguccgug gccacugaac ugcgcugcca gugcuugcag acccgcagg gaauucaccc     240 caagaacauc caaagugugu acgugaaguc ccccggaccc cacugcgccc aaaccgaagu    300
cauagccaca cucaagaaug ggcggaaagc uugccucaau ccugcauccc ccauaguuaa    360 gaaaucauc gaaaagaugc ugaacaguga caaauccaac ugaccagaag ggaggaggaa     420
gcucacuggu ggcuguuccu gaaggaggcc cugcccuuau aggaacagaa gaggaaagag    480
agacacagcu gcagaggcca ccuggauugu gccuaaugug uuugagcauc gcuuaggaga    540
agucuucuau uuauuuauuu auucauuagu uuugaagauu cuauguuaau auuuuaggug    600
uaaaauaauu aagggauga uuaacucuac cugcacacug uccuauuaua uucauucuuu     660
uugaaauguc aaccccaagu uaguucaauc uggauucaua uuuaauuuga agguagaaug    720
uuuucaaaug uucuccaguc auuauguuaa uauuucugag gagccugcaa caugccagcc    780
acugugauag aggcuggcgg auccaagcaa auggccaaug agaucauugu gaaggcaggg    840
gaauguaugu gcacaucugu uuuguaacug uuuagaugaa ugucaguugu auuuauuga     900 aaugauuuca cagugugugg ucaacauuuc ucauguugaa acuuuaagaa cuaaaauguu    960
cuaaauaucc cuuggacauu uuaugucuuu cuuguaggc auacugccuu guuaauggu    1020 aguuuuacag uguuucuggc uuagaacaaa ggggcuuaau uauugauguu uucauagaga   1080
```

```
atauaaaaau aaagcacuua uagaaaaaac ucguuugauu uuuggggga aacaagggcu    1140 accuuuacug gaaaaucugg ugauuuauaa aaaaaaaaaa aaaa                    1184

<210> SEQ ID NO 22
<211> LENGTH: 107
<212> TYPE: PRT
<213> ORGANISM: Homo sapiens

<400> SEQUENCE: 22

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 23
<211> LENGTH: 1234
<212> TYPE: RNA
<213> ORGANISM: Homo sapiens

<400> SEQUENCE: 23
gagcuccggg aauucccug gcccgggacu ccgggcuuuc agccccaac caugcauaaa      60 aggggucgc cguucucgga gagccacaga gcccgggcca caggcagcuc cuugccagcu   120
cuccuccucg cacagccgcu cgaaccgccu gcugagcccc auggcccgcg ccacgcucuc   180
cgccgccccc agcaaucccc ggcuccugcg gguggcgcug cugcuccugc uccuggugc   240 cgccagccgg cgcgcagcag gagcgcccc ggccacugaa cugcgcugcc agugcuugca   300
gacccugcag ggaauucacc ucaagaacau ccaaagugug aaggugaagu cccccggacc   360
ccacugcgcc caaccgaagu cauagccac acucaagaau gggcagaaag cuugucucaa   420
ccccgcaucg cccaugguua agaaaucau cgaaaagaug cugaaaaaug caaauccaa    480 cugaccagaa ggaaggagga agcuuauugg uggcuguucc ugaaggaggc ccugcccuua   540
caggaacaga gaggaaaga gagacacagc ugcagaggcc accuggauug cgccuaaugu   600
guuugagcau cacuuaggag aagucuucua uuuauuau uauuauuua uuuguuugu     660 uuagaagauu cuauguuaau auuuuagug uaaaauaagg uuaugauuga aucuacuugc   720
acacucuccc auuauauuua uuguuuauuu uaggucaaac ccaaguuagu ucaaccuga    780 uucauauuua auugaagau agaagguuug cagauauucu cuagucauuu guuaauauuu   840
cuucgugaug acauaucaca ugucagccac ugugauagag gcugaggaau ccaagaaaau   900
ggccagugag aucaauguga cggcagggaa auguaugugu gucuauuug uaacuguaaa   960 gaugaauguc aguuguuauu auugaaaug auuucacagu gugugcaa cauuucucau     1020 guugaagcuu uagaacuaa aaauguucaa uaucccuug acauuuau gucuucuug       1080 uaaggcauac ugccuuguuu aauguuaauu augcagguuu ucccucugug uuagagcaga  1140
```

```
gagguuucga uauuuauuga uguuuucaca aagaacagga aaauaaaaua uuuaaaaaua    1200
uaaaaaaaaa aaaaaaaaaa aaaaaaaaaa aaaa                                1234
```

<210> SEQ ID NO 24
<211> LENGTH: 107
<212> TYPE: PRT
<213> ORGANISM: Homo sapiens

<400> SEQUENCE: 24

```
Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly Ala Pro Leu Ala Thr Glu Leu Arg Cys Gln Cys Leu Gln Thr
        35                  40                  45

Leu Gln Gly Ile His Leu Lys Asn Ile Gln Ser Val Lys Val Lys Ser
    50                  55                  60

Pro Gly Pro His Cys Ala Gln Thr Glu Val Ile Ala Thr Leu Lys Asn
65                  70                  75                  80

Gly Gln Lys Ala Cys Leu Asn Pro Ala Ser Pro Met Val Lys Lys Ile
                85                  90                  95

Ile Glu Lys Met Leu Lys Asn Gly Lys Ser Asn
            100                 105
```

<210> SEQ ID NO 25
<211> LENGTH: 1166
<212> TYPE: RNA
<213> ORGANISM: Homo sapiens

<400> SEQUENCE: 25

```
gcuccgggaa uucccuggc ccggccgcuc cgggcuuucc agucucaacc augcauaaaa     60
agggnucgcc gaucuugggg agccacacag cccgggucgc aggcaccucc ccgccagcuc   120
ucccgcuucu cgcacagcuu cccgacgcgu cugcugagcc ccauggccca cgccacgcuc   180
uccgccgccc ccagcaaucc ccggucccug cggguggcgc ugcugcuccu gcuccuggug   240
gccgccagcc ggcgcgcagc aggagcgucc guggucacug aacugcgcug ccagugcuug   300
cagacacugc agggaauuca ccucaagaac auccaaagug ugaauguaag gucccccgga   360
ccccacugcg cccaaaccga agucauagcc acacucaaga augggaagaa agcuugucuc   420
aaccccgcau cccccauggu ucagaaaauc aucgaaaaga uacugaacaa ggggagcacc   480
aacugacagg agaaguaa gaagcuuauc agcguaucau ugcacuucc ugcagggugg     540 ucccugcccu uaccagagcu gaaaaugaaa aagagaacag cagcuuucua gggacagcug   600
gaaaggacuu aaugguguug acuauuucuu acgagggnuc uacuuauuua uguauuuauu   660
uuugaaagcu uguauuuaa uauuuuacau gcuguuauuu aaagaugugac guguguuuca   720 ucaaacauag cucaguccug auuauuuaau uggaauauga ugggnuuuaa augugucauu   780
aaacuaauau uuagugggag accauaaugu gucagccacc uugauaaaug acaggguggg   840
gaacuggagg ugggggggau ugaaaugcaa gcaauuagug gaucacuguu aggguaaggg   900
aauguaugua cacacucauu uuuuauacuu uuuuuuuaaa aaaagaaugu caguuguuau   960
uuauucaaau uaucucacau uaugugunuca acauuuuau gcugaaguuu cccuuagaca  1020
uuuuaugucu ugcuuguagg gcauaaugcc uuguuuaaug uccauucugc agcguuucuc  1080
```

```
uuucccuugg aaaagagaau uuaucauuac uguuacauuu guacaaauga caugauaaua    1140
aaaguuuuau gaaaaaaaaa aaaaaa                                         1166

<210> SEQ ID NO 26
<211> LENGTH: 107
<212> TYPE: PRT
<213> ORGANISM: Homo sapiens

<400> SEQUENCE: 26

Met Ala His Ala Thr Leu Ser Ala Ala Pro Ser Asn Pro Arg Leu Leu
1               5                   10                  15

Arg Val Ala Leu Leu Leu Leu Leu Val Ala Ser Arg Arg Ala
            20                  25                  30

Ala Gly Ala Ser Val Val Thr Glu Leu Arg Cys Gln Cys Leu Gln Thr
        35                  40                  45

Leu Gln Gly Ile His Leu Lys Asn Ile Gln Ser Val Asn Val Arg Ser
    50                  55                  60

Pro Gly Pro His Cys Ala Gln Thr Glu Val Ile Ala Thr Leu Lys Asn
65                  70                  75                  80

Gly Lys Lys Ala Cys Leu Asn Pro Ala Ser Pro Met Val Gln Lys Ile
                85                  90                  95

Ile Glu Lys Ile Leu Asn Lys Gly Ser Thr Asn
            100                 105

<210> SEQ ID NO 27
<211> LENGTH: 1718
<212> TYPE: RNA
<213> ORGANISM: Homo sapiens

<400> SEQUENCE: 27
gagggugcau aaguucucua guagggugau gauauaaaaa gccaccggag cacuccauaa     60
ggcacaaacu uucagagaca gcagagcaca caagcuucua ggacaagagc caggaagaaa    120
ccaccggaag gaaccaucuc acugugugua aacaugacuu ccaagcuggc cguggcucuc    180
uuggcagccu uccugauuuc ugcagcucug ugugaaggug caguuuugcc aaggagugcu    240
aaagaacuua gaugucagug cauaaagaca cuccaaaac cuuuccaccc caaauuuauc    300
aaagaacuga gagugauuga gaguggacca cacugcgcca acacagaaau uauuguaaag    360
cuuucugaug aagagagcu cugucuggac cccaaggaaa acugggugca gagguuugug    420
gagaaguuuu ugaagagggc ugagaauuca uaaaaaaauu cauucucugu gguauccaag    480
aaucagugaa gaugccagug aaacuucaag caaaucuacu ucaacacuuc auguauugug    540
ugggucuguu guagggpugc cagaugcaau acaagauucc agguuaaauu ugaauuucag    600
uaaacaauga auaguuuuc auuguaccau gaaauaucca gaacauacuu auauguaaag    660
uauuauuuau uugaaucuac aaaaacaac aauuaauuuu uaaauauaag gauuuuccua    720
gauauugcac gggagaauau acaaauagca aaauugaggc caagggccaa gagaauaucc    780
gaacuuuaau uucaggaauu gaaugggggu gcuagaaugu gauauuugaa gcaucacaua    840
aaaaugaugg gacaauaaau uuugccauaa agucaaauuu agcuggaaau ccuggauuuu    900
uuucuguuaa aucuggcaac ccuagucugc uagccaggau ccacaagucc uguuccacu    960 gugccuuggu uucuccuuua uuucuaagug gaaaaaguau uagccaccau cuuaccucac    1020
agugauguug ugaggacaug uggaagcacu uuaaguuuuu ucaucauaac auaaauuauu    1080
uucaagugua acuuauuaac cuauuuauua uuuauguauu uauuuaagca ucaaauauuu    1140
```

| | | | | |
|---|---|---|---|---|
| gugcaagaau | uuggaaaaau | agaagaugaa | ucauugauug | aauaguuaua | aagauguuau | 1200 |
| aguaaauuua | uuuuauuuua | gauauuaaau | gauguuuuau | uagauaaauu | ucaaucaggg | 1260 |
| uuuuuagauu | aaacaaacaa | acaauugggu | acccaguuaa | auuucauuu | cagauaaaca | 1320 |
| acaaauaauu | uuuuaguaua | aguacauuau | uguuuaucug | aaauuuuaau | ugaacuaaca | 1380 |
| auccaguuu | gauacuccca | gucuugucau | ugccagcugu | guugguagug | cuguuugaa | 1440 |
| uuacggaaua | augaguuaga | acuauuaaaa | cagccaaaac | uccacaguca | auauuaguaa | 1500 |
| uuucuugcug | guugaaacuu | guuuauuaug | ucaaauaga | uucuuauaau | auuauuuaaa | 1560 |
| ugacugcauu | uuuaaauaca | aggcuuuaua | uuuuaacuu | uaagauguuu | uuaugugcuc | 1620 |
| uccaaauuuu | uuuuacuguu | ucugauugua | uggaaauaua | aaaguaaaua | ugaaacauuu | 1680 |
| aaaauauaau | uuguugucaa | aguaaaaaaa | aaaaaaaa | | | 1718 |

<210> SEQ ID NO 28
<211> LENGTH: 99
<212> TYPE: PRT
<213> ORGANISM: Homo sapiens

<400> SEQUENCE: 28

```
Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 29
<211> LENGTH: 4507
<212> TYPE: RNA
<213> ORGANISM: Homo sapiens

<400> SEQUENCE: 29

| | | | | |
|---|---|---|---|---|
| gaccaauugu | cauacgacuu | gcagugagcg | ucaggagcac | guccaggaac | uccucagcag | 60 |
| cgccuccuuc | agcuccacag | ccagacgccc | ucagacagca | aagccuaccc | ccgcgccgcg | 120 |
| cccugcccgc | cgcugcgaug | cucgcccgcg | cccugcugcu | gugcgcgguc | cuggcgcuca | 180 |
| gccauacagc | aaauccuugc | uguucccacc | caugucaaaa | ccgaggugua | uguaugagug | 240 |
| ugggauuuga | ccaguauaag | ugcgauugua | cccggacagg | auucuaugga | gaaacugcu | 300 |
| caacaccgga | auuuugaca | agaauaaauu | uauuucugaa | acccacucca | aacacagugc | 360 |
| acuacauacu | uacccacuuc | aagggauuuu | ggaacguugu | gaauaacauu | cccuuccuuc | 420 |
| gaaaugcaau | uagaguuau | guugacauu | ccagaucaca | uuugauugac | aguccaccaa | 480 |
| cuuacaaugc | ugacuauggc | uacaaaagcu | gggaagccuu | cucuaaccuc | uccuauuaua | 540 |
| cuagagcccu | uccuccugug | ccugaugauu | gcccgacucc | cuuggguguc | aaagguaaaa | 600 |
| agcagcuucc | ugauucaaau | gagauugugg | aaaaauugcu | ucuaagaaga | aguucaucc | 660 |
| cugaucccca | gggcucaaac | augauguuug | cauucuuugc | ccagcacuuc | acgcaucagu | 720 |

```
uuuucaagac agaucauaag cgagggccag cuuucaccaa cgggcugggc caugggugug    780
acuuaaauca uauuuacggu gaaacucugg cuagacagcg uaaacugcgc cuuuucaagg    840
auggaaaaau gaaauaucag auaauugaug gagagaugua uccucccaca gucaaagaua    900
cucaggcaga gaugaucuac ccuccucaag ucccugagca ucuacgguuu gcugggggc    960 aggaggucuu uggucuggug ccuggucuga ugauguaugc cacaaucugg cugcgggaac   1020
acaacagagu augcgaugug cuuaaacagg agcauccuga aug gggugau gagcaguugu   1080 uccagacaag caggcuaaua cugauaggag agacuauuaa gauugugauu aagauuaug    1140 ugcaacacuu gaguggcuau cacuucaaac ugaaauuuga cccagaacua cuuuucaaca   1200
aacaauucca guaccaaaau cguauugcug cugaauuuua cacccucuau cacuggcauc   1260
cccuucugcc ugacaccuuu caaauucaug accagaaaua caacuaucaa caguuuaucu   1320
acaacaacuc uauauugcug gaacauggaa uacccaguu uguugaauca ucaccaggc    1380 aaauugcugg cagguugcu gguaggga auguccacc cgcaguacag aaaguaucac      1440
aggcuuccau ugaccagagc aggcagauga aauaccaguc uuuuaaugag uaccgcaaac   1500
gcuuuaugcu gaagcccuau gaaucauuug aagaacuuac aggagaaaag gaaaugucug   1560
cagaguugga agcacucuau ggugacacg augcugugga gcuguauccu gcccuucugg   1620
uagaaaagcc ucggccagau gccaucuuug gugaaaccau gguagaaguu ggagcaccau   1680
ucuccuugaa aggacuuaug gguaauguua uauguucucc ugccuacugg aagccaagca   1740
cuuuuggugg agaagugggu uucaaauca ucaacacugc cucaauucag ucucucaucu   1800
gcaauaacgu gaagggcugu cccuuuacuu cauucagugu uccagaucca gagcucauua   1860
aaacagucac caucaaugca aguucuuccc gcuccggacu agaugauauc aaucccacag   1920
uacuacuaaa agaacguucg acugaacugu agaagcuaaa ugaucauauu uauuuauuua   1980
uaugaaccau gucuauuaau uuaauuauuu aauauauuu auauuaaacu ccuuauguua   2040
cuuaacaucu ucuguaacag aagcaguac uccuguugcg gagaaaggag ucauacuugu   2100
gaagacuuuu augcacuac ucuaaagauu uugcuguugc uguuaaguuu ggaaaacagu   2160
uuuuauucug uuuuauaaac cagagagaaa ugaguuuga cgucuuuuua cuugaauuuc   2220
aacuuauauu auaagaacga aaguaaagau guuugaauac uuaaacacug ucacaagaug   2280
gcaaaaugcu gaaaguuuuu acacugucga uguuccaau gcaucuucca ugaugcauua   2340
gaaguaacua auguuugaaa uuuuaaagua cuuugguua uuuucuguc aucaaacaaa   2400 aacagguauc agugcauuau uaaaugaaua uuuuaauuag acauuaccag uaauuucaug   2460 ucuacuuuu aaaaucagca augaaacaau aauuugaaau uucaaauuc auagggcuaga   2520 auccaccugua aaagcuuguu ugauucuua aguuauuaa acuugacau auaccaaaaa    2580 gaagcugucu uggauuuaaa ucuguaaaau caguagaaau uuuacuacaa uugcuuguua   2640
aaauauuuua uaagugaugu ccuuuuuca ccaagaguau aaaccuuuuu agugugacug   2700
uuaaaacuuc cuuuuaaauc aaaaugccaa auuuauuaag guggugagc cacugcagug   2760 uuaucuuaaa auaagaauau uuguugaga uauccagaa uuuguuuaua uggcugguaa   2820
cauguaaaau cuauaucagc aaaagggucu accuuuaaaa uaagcaauaa caaagaagaa   2880
aaccaaauua uuguucaaau uuagguuuaa acuuugaag caaacuuuuu uuauccuug    2940 ugcacugcag gccugguacu cagauuuugc uaugagguua augaaguacc aagcugugcu   3000
ugaauaauga uauguuucu cagauuuucu guugucagu uuaauuuagc aguccauauc    3060
acauugcaaa aguagcaaug accucauaaa auaccucuuc aaaaugcuua aauucauuuc    3120
```

```
acacauuaau uuuaucucag ucuugaagcc aauucaguag gugcauugga aucaagccug    3180
gcuaccugca ugcuguuccu uuucuuuucu ucuuuuagcc auuuugcuaa gagacacagu    3240
cuucucauca cuucguuucu ccuauuuugu uuuacuaguu uuaagaucag aguucacuuu    3300
cuuuggacuc ugccuauauu uucuuaccug aacuuuugca aguuucagg uaaaccucag     3360 cucaggacug cuauuuagcu ccucuuaaga agauuaaaag agaaaaaaaa aggcccuuuu    3420
aaaaauagua uacacuuauu uuaagugaaa agcagagaau uuuauuuaua gcuaauuuua    3480
gcuaucugua accaagaugg augcaaagag gcuagugccu cagagagaac uguacggggu    3540
uugugacugg aaaagguuac guucccauuc uaauuaaugc ccuucuuau uuaaaaacaa     3600 aaccaaauga uaucuaagua guucucagca auaauaauaa ugacgauaau acuucuuuuc    3660
cacaucucau ugucacugac auuuaauggu acuguauauu acuuaauuua uugaagauua    3720
uuauuuaugu cuuauuagga cacuauggguu auaaacugug uuuaagccua caaucauuga   3780 uuuuuuuug uuaugucaca aucaguauau uuucuuuggg guuaccucuc ugaauauuau     3840
guaaacaauc caaagaaaug auuguauuaa gauuugugaa uaaauuuuua gaaaucugau    3900
uggcauauug agauauuuaa gguugaaugu uguccuuag gauaggccua ugugcuagcc     3960
cacaaagaau uuugucucau uagccugaau gugccauaag acugaccuuu uaaaauguuu    4020
ugagggaucu guggaugcuu cguuaauuug uucagccaca auuuauugag aaauauuucu    4080
gugucaagca cuguggguuu uaauauuuuu aaaucaaacg cugauuacag auaauagauu    4140
uuauauaaau aauugaaaaa aauuuucuuu ugggaagagg gagaaaauga aauaaauauc    4200
auuaaagaua acucaggaga aucuucuuua caauuuuacg uuuagaaugu uuaagguuaa    4260
gaaagaaaua gucaauaugc uuguauaaaa cacguucac uguuuuuuuu aaaaaaaaa      4320 cuugauuugu uauuaacauu gaucugcuga caaaaccugg gaauuugggu uguguaugcg    4380
aauguuucag ugccucagac aaauguguau uuaacuuaug uaaaagauaa gucuggaaau    4440
aaaugucugu uuauuuuugu acuauuuaaa aauugacaga ucuuuucuga agaaaaaaaa    4500
aaaaaaa                                                             4507
```

<210> SEQ ID NO 30
<211> LENGTH: 604
<212> TYPE: PRT
<213> ORGANISM: Homo sapiens

<400> SEQUENCE: 30

```
Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125
```

```
Ser Asn Leu Ser Tyr Tyr Thr Arg Ala Leu Pro Pro Val Pro Asp Asp
    130             135                 140

Cys Pro Thr Pro Leu Gly Val Lys Gly Lys Lys Gln Leu Pro Asp Ser
145             150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Phe Ala Gln His Phe Thr
                180                 185                 190

His Gln Phe Phe Lys Thr Asp His Lys Arg Gly Pro Ala Phe Thr Asn
            195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
                260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
            355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
                420                 425                 430

Val Ser Gln Ala Ser Ile Asp Gln Ser Arg Gln Met Lys Tyr Gln Ser
            435                 440                 445

Phe Asn Glu Tyr Arg Lys Arg Phe Met Leu Lys Pro Tyr Glu Ser Phe
            450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
                500                 505                 510

Ala Pro Phe Ser Leu Lys Gly Leu Met Gly Asn Val Ile Cys Ser Pro
            515                 520                 525

Ala Tyr Trp Lys Pro Ser Thr Phe Gly Gly Glu Val Gly Phe Gln Ile
            530                 535                 540
```

| Ile | Asn | Thr | Ala | Ser | Ile | Gln | Ser | Leu | Ile | Cys | Asn | Asn | Val | Lys | Gly |
|---|---|---|---|---|---|---|---|---|---|---|---|---|---|---|---|
| 545 | | | | 550 | | | | | 555 | | | | | 560 | |

| Cys | Pro | Phe | Thr | Ser | Phe | Ser | Val | Pro | Asp | Pro | Glu | Leu | Ile | Lys | Thr |
|---|---|---|---|---|---|---|---|---|---|---|---|---|---|---|---|
| | | | | 565 | | | | | 570 | | | | | 575 | |

| Val | Thr | Ile | Asn | Ala | Ser | Ser | Ser | Arg | Ser | Gly | Leu | Asp | Asp | Ile | Asn |
|---|---|---|---|---|---|---|---|---|---|---|---|---|---|---|---|
| | | | 580 | | | | | 585 | | | | | 590 | | |

| Pro | Thr | Val | Leu | Leu | Lys | Glu | Arg | Ser | Thr | Glu | Leu |
|---|---|---|---|---|---|---|---|---|---|---|---|
| | | 595 | | | | | 600 | | | | |

<210> SEQ ID NO 31
<211> LENGTH: 1204
<212> TYPE: RNA
<213> ORGANISM: Homo sapiens

<400> SEQUENCE: 31

```
ggggugcaaa gaagagacag cagcgcccag cuuggaggug cuaacuccag aggccagcau      60
cagcaacugg gcacagaaag gagccgccug ggcagggacc auggcacggc cacaucccug     120
guggcugugc guucugggga cccugguggg gcucucagcu acuccagccc caagagcugc     180
cccagagagg cacuacuggg ucagggaaa gcugugcugc cagaugugug agccaggaac      240
auccucgug aaggacugug accagcauag aaaggcugcu cagugugauc cuugcauacc      300
ggggucucc uucucuccug accaccacac ccggccccac ugugagagcu gucggcacug      360
uaacucuggu cuucucguuc gcaacugcac caucacugcc aaugcugagu gugccugucg     420
caauggcugg cagugcaggg acaaggagug caccgagugu gauccucuuc caaaccuuc      480
gcugaccgcu cggucgucuc aggcccugag cccacacccu cagcccaccc acuuaccuua     540
ugucagugag augcuggagg ccaggacagc ugggcacaug cagacucugg cugacuucag     600
gcagcugccu gccggacuc ucucuaccca cuggccaccc caaagauccc ugugcagcuc      660
cgauuuuauu cgcauccuug ugaucuucuc uggaauguuc cuuguuuuca cccuggccgg     720
ggcccuguuc cuccaucaac gaaggaaaua uagaucaaac aaaggagaaa guccugugga     780
gccugcagag ccugucguu acagcugccc cagggaggag gagggcagca ccauccccau      840
ccaggaggau uaccgaaaac cggagccgcu cugcucccc ugagccagca ccugcgguag      900
cugcacuaca gcccuggccu ccaccccac cccgccgacc auccaaggga gagugagacc     960
uggcagccac aacugcaguc ccauccucuu gucagggccc uuuccugugu acacgugaca    1020
gagugccuuu ucgagacugg cagggacgag gacaaauaug gaugaggugg agagugggaa    1080
gcaggagccc agccagcugc gccugcgcug caggagggcg ggggcucugg uuguaaaaca    1140
cacuuccugc ugcgaaagac ccacaugcua caagacgggc aaaauaaagu gacagaugac    1200
cacc                                                                1204
```

<210> SEQ ID NO 32
<211> LENGTH: 260
<212> TYPE: PRT
<213> ORGANISM: Homo sapiens

<400> SEQUENCE: 32

| Met | Ala | Arg | Pro | His | Pro | Trp | Trp | Leu | Cys | Val | Leu | Gly | Thr | Leu | Val |
|---|---|---|---|---|---|---|---|---|---|---|---|---|---|---|---|
| 1 | | | | 5 | | | | | 10 | | | | | 15 | |

| Gly | Leu | Ser | Ala | Thr | Pro | Ala | Pro | Lys | Ser | Cys | Pro | Glu | Arg | His | Tyr |
|---|---|---|---|---|---|---|---|---|---|---|---|---|---|---|---|
| | | | 20 | | | | | 25 | | | | | 30 | | |

| Trp | Ala | Gln | Gly | Lys | Leu | Cys | Cys | Gln | Met | Cys | Glu | Pro | Gly | Thr | Phe |
|---|---|---|---|---|---|---|---|---|---|---|---|---|---|---|---|
| | | 35 | | | | | 40 | | | | | 45 | | | |

```
Leu Val Lys Asp Cys Asp Gln His Arg Lys Ala Ala Gln Cys Asp Pro
 50                  55                  60

Cys Ile Pro Gly Val Ser Phe Ser Pro Asp His His Thr Arg Pro His
 65                  70                  75                  80

Cys Glu Ser Cys Arg His Cys Asn Ser Gly Leu Leu Val Arg Asn Cys
                 85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 33
<211> LENGTH: 2397
<212> TYPE: RNA
<213> ORGANISM: Homo sapiens

<400> SEQUENCE: 33
gcacacacuc aucgaaaaaa auuuggauua uuagaagaga gaggucugcg gcuuccacac      60
cguacagcgu gguuuuucuu cucgguauaa aagcaaaguu guuuugaua cgugacaguu     120 ucccacaagc caggcugauc cuuuucuguc aguccacuuc accaagccug cccuuggaca     180
aggacccgau gcccaacccc aggccuggca agcccucggc cccuccuug gcccuuggcc     240 caucccagg agccucgccc agcuggaggg cugcacccaa agccucagac cugcuggggg     300
cccggggccc aggggaacc uuccaggggcc gagaucuucg aggcggggcc caugccuccu     360
cuucuuccuu gaaccccaug ccaccaucgc agcugcagcu gcccacacug ccccuaguca     420 uggugcacc cucgggggca cggcugggcc ccuugcccca cuuacaggca cuccuccagg     480
acaggccaca uuucaugcac cagcucucaa cgguggaugc ccacgccggg acccccugugc     540 ugcaggugca ccccccuggag agcccagcca ugaucagccu cacaccaccc accaccgcca     600
cuggggucuu ucccucaag gcccggccug ccucccacc ugggaucaac guggccagcc     660
uggaaugggu guccagggag ccggcacugc ucugcaccuu cccaaauccc agugcaccca     720
ggaaggacag caccccuuucg gcugugcccc agagcuccua cccacugcug caaaugguug     780
ucugcaagug gccggaugu gagaagucu cgaagagcc agaggacuuc cucaagcacu     840
gccaggcgga ccaucuucug gaugagaagg gcagggcaca augucccuc cagagagaga     900
```

```
ugguacaguc ucuggagcag cagcuggugc uggagaagga gaagcugagu gccaugcagg      960
cccaccuggc ugggaaaaug gcacugacca aggcuucauc uguggcauca uccgacaagg     1020
gcuccugcug caucguagcu gcuggcagcc aaggcccugu cgucccagcc uggucuggcc     1080
cccgggaggc cccugacagc cuguuugcug uccggaggca ccugggggu agccauggaa      1140 acagcacauu cccagaguuc cuccacaaca uggacuacuu caaguccac aacaugcgac      1200 cccuuucac cuacgccacg cucauccgcu gggccauccu ggaggcucca gagaagcagc      1260
ggacacucaa ugagaucuac cacugguuca cacgcauguu ugccuucuuc agaaaccauc     1320
cugccaccug gaagaacgcc auccgccaca accugagucu gcacaagugc uuugugcggg     1380
uggagagcga aaggggggcu guguggaccg uggaugagcu ggaguuccgc aagaaacgga     1440
gccagaggcc cagcaggugu uccaacccua caccuggccc cugaccucaa gaucaaggaa     1500
aggaggaugg acgaacaggg gccaaacugg ugggaggcag aggugguggg ggcagggaug     1560
auaggcccug gaugugccca cagggaccaa gaagugaggu uccacugc uugccugcca      1620 gggcccucgu uccccgcug gcagccaccc ccucccccau cauauccuuu gcccaaggc      1680 ugcucagagg ggccccgguc cuggcccag ccccaccuc cgcccagac acacccca           1740 gucgagcccu gcagccaaac agagccuuca caaccagcca cacagagccu gccucagcug     1800
cucgcacaga uuacuucagg gcuggaaaag ucacacagac acacaaaaug ucacaauccu     1860
gucccucacu caacacaaac cccaaaacac agagagccug ccucaguaca cucaaacaac     1920
cucaaagcug caucaucaca caaucacaca caagcacagc ccugacaacc cacacacccc     1980
aaggcacgca cccacagcca gccucagggc cacaggggc acugcaaca caggggugug     2040 cccagaggcc uacacagaag cagcgucagu acccucagga ucugaggucc caacacgugc     2100
ucgcucacac acacggccug uuagaauuca ccuguguauc ucacgcauau gcacacgcac     2160
agccccccag ugggucucuu gagucccgug cagacacaca cagccacaca cacugccuug     2220
ccaaaaauac cccgugucuc cccugccacu caccucacuc ccauucccug agcccugauc     2280
caugccucag cuuagacugc agaggaacua ucauuuauu ugggauccaa ggcccccaac      2340
ccacaguacc gucccaaua aacugcagcc gagcucccca caaaaaaaaa aaaaaaa        2397
```

<210> SEQ ID NO 34
<211> LENGTH: 431
<212> TYPE: PRT
<213> ORGANISM: Homo sapiens

<400> SEQUENCE: 34

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110
```

Ala Arg Thr Pro Val Leu Gln Val His Pro Leu Glu Ser Pro Ala Met
115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430

<210> SEQ ID NO 35
<211> LENGTH: 2115
<212> TYPE: RNA
<213> ORGANISM: Homo sapiens

<400> SEQUENCE: 35
aguuucccuu ccgcucaccu ccgccugagc aguggagaag gcggcacucu gguggggcug      60
cuccaggcau gcagauccca caggcgcccu ggccagucgu cugggcggug cuacaacugg     120
gcuggcggcc aggaugguuc uuagacuccc cagacaggcc cuggaacccc ccaccuucu     180 ccccagcccu gcucguggug accgaagggg acaacgccac cuucaccugc agcuucucca     240
acacaucgga gagcuucgug cuaaacuggu accgcaugag ccccagcaac cagacgacga     300
agcuggccgc cuuccccgag gaccgcagcc agccggcca ggacugccgc uuccguguca     360

```
cacaacugcc caacgggcgu gacuuccaca ugagcguggu cagggcccgg cgcaaugaca      420
gcggcaccua ccucugugggg gccaucuccc uggcccccaa ggcgcagauc aaagagagcc      480
ugcgggcaga gcucagggug acagagagaa gggcagaagu gcccacagcc caccccagcc      540
ccucacccag gccagccggc caguuccaaa cccugguggu uggugucgug ggcggccugc      600
ugggcagccu ggugcugcua gucugggucc uggccgucau cugcucccgg gccgcacgag      660
ggacaauagg agccaggcgc accggccagc cccugaagga ggacccccuca gccgugccug      720 uguucucugu ggacuauggg gagcuggauu ccagguggcg agagaagacc ccggagcccc      780
ccgugcccug ugucccugag cagacggagu augccaccau ugucuuuccu agcggaaugg      840
gcaccucauc cccgcccgc aggggcucag cugacggccc ucgagugcc cagccacuga      900 ggccugagga uggacacugc ucuuggcccc ucugaccggc uuccuuggcc accaguguuc      960
ugcagacccu ccaccaugag cccggucag cgcauuuccu caggagaagc aggcagggug      1020
caggccauug caggccgucc aggggcugag cugccugggg gcgaccgggg uccagccug      1080 caccugcacc aggcacagcc ccaccacagg acucaugucu caaugccac agugagccca      1140 ggcagcaggu ucaccgucc cuacagggga gggccagaug caguccacugc uucaggucu      1200 gccagcacag agcugccgc guccagcucc cugaaucucu gcugcugcug cugcugcugc      1260
ugcugcugcc ugcggcccgg ggcugaaggc gccguggccc ugccugacgc cccggagccu      1320
ccugccugaa cuuggggggcu gguuggagau ggccuuggag cagccaaggu gcccucuggca      1380 guggcauccc gaaacgcccu ggacgcaggg cccaagacug gcacaggag ugggaggauc      1440 auggggcugg gacucccca ggaguuaucu gcucccugca ggccuagaga aguuucaggg      1500
aaggucagaa gagcuccugg cuguggguggg cagggcagga aaccccucca ccuuuacaca      1560
ugcccaggca gcaccucagg cccuuugugg ggcaggaagc ugaggcaguu aagcgggcag      1620
gcagagcugg aggccuuuca ggcccagcca gcacucuggc cuccugccgc cgcauuccac      1680
cccagccccu cacaccacuc gggagaggga cauccuacgg ucccaagguc aggagggcag      1740 ggcuggguu gacucaggcc ccucccagcu guggccaccu ggguguuggg agggcagaag      1800
ugcaggcacc uagggccccc caugugccca cccugggagc uccuuugga acccauuccu      1860 gaaauuauuu aaaggggguug gccgggcucc caccagggcc uggguggaa gguacaggcg      1920 uuccccgggg gccuaguacc cccgccgugg ccuauccacu ccucacaucc acacacugca      1980 ccccacucc ugggggcaggg ccaccagcau ccaggcggcc agcaggcacc ugagugggcug      2040 ggacaaggga uccccuuucc cugugguucu auuauauuau aauuauaauu aaauaugaga      2100
gcaugcuaag gaaaa                                                      2115
```

<210> SEQ ID NO 36
<211> LENGTH: 288
<212> TYPE: PRT
<213> ORGANISM: Homo sapiens

<400> SEQUENCE: 36

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

| | | | | | | | | | | | | | | | |
|---|---|---|---|---|---|---|---|---|---|---|---|---|---|---|---|
|Leu|Asn|Trp|Tyr|Arg|Met|Ser|Pro|Ser|Asn|Gln|Thr|Asp|Lys|Leu|Ala|
|65| | | | |70| | | |75| | | | |80| |

Ala Phe Pro Glu Asp Arg Ser Gln Pro Gly Gln Asp Cys Arg Phe Arg
                85                      90                    95

Val Thr Gln Leu Pro Asn Gly Arg Asp Phe His Met Ser Val Val Arg
        100                   105                 110

Ala Arg Arg Asn Asp Ser Gly Thr Tyr Leu Cys Gly Ala Ile Ser Leu
        115                   120                 125

Ala Pro Lys Ala Gln Ile Lys Glu Ser Leu Arg Ala Glu Leu Arg Val
        130                   135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
        180                   185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
        260                 265                 270

Ser Ala Gln Pro Leu Arg Pro Glu Asp Gly His Cys Ser Trp Pro Leu
        275                 280                 285

<210> SEQ ID NO 37
<211> LENGTH: 2033
<212> TYPE: RNA
<213> ORGANISM: Homo sapiens

<400> SEQUENCE: 37

```
cuucugugug ugcacaugug uaauacauau cugggaucaa agcuaucuau auaaaguccu    60
ugauucugug uggguucaaa cacauuucaa agcuucagga uccgaaaggu uuuugcucua   120
cuuccugaag accugaacac cgcucccaua aagccauggc uugccuugga uuucagcggc   180
acaaggcuca gcugaaccug cuaccaggac ccuggcccug cacucuccug uuuuuucuuc   240
ucuucauccc ugucuucugc aaagcaaugc acguggccca gccugcugug guacuggcca   300
gcagccgagg caucgccagc uuugugugug aguaugcauc uccaggcaaa gccacugagg   360
uccggguga c agugcuucgg caggcugaca gccaggugac ugaagucugu gcggcaaccu   420
acaugauggg gaaugaguug accuuccuag augauuccau cugcacgggc accccagug    480
gaaaucaagu gaaccucacu auccaaggac ugagggccau ggcacgggga cucuacaucu   540
gcaaggugga gcucauguac ccaccgccau acuaccuggg cauaggcaac ggaacccaga   600
uuuauguaau ugauccagaa ccgugcccag auucugacuu ccuccucugg auccuugcag   660
caguuaguuc gggguugu uu uuuuauagcu uucuccucac agcuguuucu uugagcaaaa   720
ugcuaaagaa aagaagcccu cuuacaacag gggucuaugu gaaaaugccc ccaacagagc   780
cagaauguga aaagcaauuu cagccuuauu uuauucccau caauugagaa accauugaa    840
agaagagagu ccauauuuca auuuccaaga gcugaggcaa uucuaacuuu uuugcuaucc   900
```

```
agcuauuuuu auuuguuugu gcauuuggg ggaauucauc ucucuuuaau auaaaguugg    960
augcggaacc caaauuacgu guacuacaau uuaaagcaaa ggaguagaaa gacagagcug   1020
ggauguuucu gucacaucag cuccacuuuc agugaaagca ucacuuggga uuauauggg    1080
gaugcagcau uaugaugugg gucaaggaau uaaguuaggg aauggcacag cccaaagaag   1140
gaaaaggcag ggagcgaggg agaagacuau auuguacaca ccuuauauuu acguaugaga   1200
cguuuauagc cgaaaugauc uuuucaaguu aaauuuaug ccuuuauuu cuuaaacaaa    1260
uguaugauua caucaaggcu ucaaaaauac ucacauggcu auguuuagc cagugaugcu    1320
aaagguugua uugcauauau acauauauau auauauauau auauauauau auauauauau   1380
auauauauau auauauauuu uaauuugaua guauugugca uagagccacg uauguuuug    1440
uguauuguu aaugguuuga auauaaacac uauauggcag ugucuuucca ccuuggucc    1500
cagggaaguu uuguggagga gcucaggaca cuaauacacc aggagaaca caaggucauu   1560
ugcuaacuag cuuggaaacu ggaugagguc auagcagugc uugauugcgu ggaauugugc   1620
ugaguuggug uugacaugug cuuuggggcu uuuacaccag uuccuuucaa ugguuugcaa   1680
ggaagccaca gcugguggua ucugaguuga cuugacagaa cacugucuug aagacaaugg   1740
cuuacuccag gagacccaca gguaugaccu ucuaggaagc uccaguucga ugggcccaau   1800
ucuuacaaac augugguuaa ugccauggac agaagaaggc agcagguggc agaaugggu    1860
gcaugaaggu uucugaaaau uaacacugcu uguguuuua acucaauauu uccaugaaa    1920
augcaacaac auguauaaua uuuuuaauua aauaaaauc ugguggguc guuuuaaaaa    1980
aaaaaaaaa aaaaaaaaa aaaaaaaaa aaaaaaaaa aaaaaaaaa aaa              2033
```

<210> SEQ ID NO 38
<211> LENGTH: 223
<212> TYPE: PRT
<213> ORGANISM: Homo sapiens

<400> SEQUENCE: 38

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175
```

| Tyr | Ser | Phe | Leu | Leu | Thr | Ala | Val | Ser | Leu | Ser | Lys | Met | Leu | Lys | Lys |
|---|---|---|---|---|---|---|---|---|---|---|---|---|---|---|---|
| | | | | 180 | | | | 185 | | | | 190 | | | |

| Arg | Ser | Pro | Leu | Thr | Thr | Gly | Val | Tyr | Val | Lys | Met | Pro | Pro | Thr | Glu |
|---|---|---|---|---|---|---|---|---|---|---|---|---|---|---|---|
| | 195 | | | | 200 | | | | 205 | | | | | | |

| Pro | Glu | Cys | Glu | Lys | Gln | Phe | Gln | Pro | Tyr | Phe | Ile | Pro | Ile | Asn |
|---|---|---|---|---|---|---|---|---|---|---|---|---|---|---|
| 210 | | | | | 215 | | | | | 220 | | | | |

<210> SEQ ID NO 39
<211> LENGTH: 2978
<212> TYPE: RNA
<213> ORGANISM: Homo sapiens

<400> SEQUENCE: 39

| cguccuaucu gcagucggcu acuuucagug gcagaagagg ccacaucugc uuccuguagg | 60 |
|---|---|
| cccucugggc agaagcaugc gcuggugucu ccuccugauc ugggcccagg ggcugaggca | 120 |
| ggcuccccuc gccucaggaa ugaugacagg cacaauagaa acaacgggga acauuucugc | 180 |
| agagaaaggu ggcucuauca ucuuacaaug ucaccucucc uccaccacgg cacaagugac | 240 |
| ccaggucaac ugggagcagc aggaccagcu ucuggccauu uguaaugcug acuuggggug | 300 |
| gcacaucucc ccauccuuca aggaucgagu ggccccaggu cccggccugg ccucacccu | 360 |
| ccagucgcug accgugaacg auacagggga guacuucugc aucuaucaca ccuacccuga | 420 |
| ugggacguac acuggagaa ucuuccugga ggucuagaa agcucagugg cugagcacgg | 480 |
| ugccagguuc cagauuccau ugcuuggagc cauggccgcg acgcuggugg ucaucugcac | 540 |
| agcagucauc guggugucg cguugacuag aaagaagaaa gcccucagaa uccauucugu | 600 |
| ggaaggugac cucaggagaa aaucagcugg acaggaggaa uggagcccca gugcucccuc | 660 |
| accccagga agcugugucc aggcagaagc ugcaccugcu gggcucugug agagcagcg | 720 |
| gggagaggac ugugccgagc ugcaugacua cuucaaugc cugaguuaca gaagccuggg | 780 |
| uaacugcagc uucuuacag agacugguua gcaaccagag gcaucuucug aagauacac | 840 |
| uuuugucuuu gcuauuauag augaauauau aagcagcugu acucuccauc agugcugcgu | 900 |
| gugugugugu guguguaugu gugugugugu ucaguugagu gaauaaaugu cauccucuuc | 960 |
| uccaucuuca uuuccuuggc cuuuucguuc uauccauuu ugcauuaugg caggccuagg | 1020 |
| gugaguaacg uggaucuuga ucauaaaugc aaaauuaaaa aauaucuuga ccugguuuua | 1080 |
| aaucuggcag uuugagcaga uccuaugucu cugagagaca cauuccucau aauggccagc | 1140 |
| auuuugggcu acaagguuuu guggnugaug augaggaugg caugacugca gagccauccu | 1200 |
| caucucauuu uuucacguca uuuucaguaa cuuucacuca uucaaaggca gguuauaagu | 1260 |
| aagccuggu agcagccucu augggagau uugagaguga cuaaaucuug guaucugccc | 1320 |
| ucaagaacuu acaguuaaau ggggagacaa uguugucaug aaaagguauu auaguaagga | 1380 |
| gagaaggaga cauacacagg ccuucaggaa gagacgacag uuggggguga gguaguuggc | 1440 |
| auaggcuuau cugugaugaa guggccuggg agcaccaagg ggauguugag gcuagucugg | 1500 |
| gaggagcagg aguuuugucu agggaacuug uaggaaauuc uuggagcuga aagucccaca | 1560 |
| aagaaggccc uggcaccaag ggagucagca aacuucagau uuuauucucu gggcaggcau | 1620 |
| uucaaguuuc cuuuugcugu gacauacuca uccauagac agccugauac aggccuguag | 1680 |
| ccucuuccgg ccgugugugc uggggaagcc ccaggaaacg cacaugccca cacagggagc | 1740 |
| caagucguag cauuugggcc uugaucuacc uuuucgcau caauacacuc uugagccuuu | 1800 |
| gaaaaaagaa cguuucccac uaaaaagaaa augugggauuu uuaaaauagg gacucuuccu | 1860 |

-continued

| | |
|---|---|
| aggggaaaaa gggggggcugg gagugauaga ggguuuaaaa aauaaacacc uucaaacuaa | 1920 |
| cuucuucgaa cccuuuuauu cacucccuga cgacuuugug cugggguugg gguaacugaa | 1980 |
| ccgcuuauuu cuguuuaauu gcauucaggc uggaucuuag aagacuuuua uccuuccacc | 2040 |
| aucucucuca gaggaaugag cggggagguu ggauuuacug gugacugauu uucuuucaug | 2100 |
| ggccaaggaa cugaaagaga augugaagca agguugugue uugcgcaugg uuaaaauaa | 2160 |
| agcauugucc ugcuuccuaa gacuuagacu ggguugaca auuguuuuag caacaagaca | 2220 |
| auucaacuau uucuccuagg auuuuuauua uauuauuuu uucacuuuuc uaccaaaugg | 2280 |
| guuacauagg aagaaugaac ugaaaucugu ccagagcucc aaguccuuug gaagaaagau | 2340 |
| uagaugaacg uaaaaauguu guuguuugcu guggcaguuu acagcauuuu ucuugcaaaa | 2400 |
| uuagugcaaa ucuguuggaa auagaacaca auucacaaau uggaagugaa cuaaaaugua | 2460 |
| augacgaaaa gggaguagug uuuugauuug gaggagugu auauucggca gagguuggac | 2520 |
| ugagaguugg guguuauuua acauaauuau gguaauuggg aaacauuuau aaacacuauu | 2580 |
| gggaugguga uaaauacaa aagggccuau agauguuaga aaugggucag guuacugaaa | 2640 |
| ugggauucaa uuugaaaaaa auuuuuuaa auagaacuca cugaacuaga uucuccucug | 2700 |
| agaaccagag aagaccauuu cauaguugga uccuggaga caugcgcuau ccaccacgua | 2760 |
| gccacuuucc acauguggcc aucaaccacu aagaugggg uuaguuuaaa ucaagaugug | 2820 |
| cuguuauaau ugguauaagc auaaaaucac acuagauucu ggagauuuaa uaugaauaau | 2880 |
| aagaauacua uuucaguagu uuugguauau ugugugucaa aaaugauaau auuuuggaug | 2940 |
| uauuggguga aauaaaauau uaacauuaaa aaaaaaaa | 2978 |

<210> SEQ ID NO 40
<211> LENGTH: 244
<212> TYPE: PRT
<213> ORGANISM: Homo sapiens

<400> SEQUENCE: 40

Met Arg Trp Cys Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

| | | | | | | | | | | |
|---|---|---|---|---|---|---|---|---|---|---|
|Gly|Asp|Leu|Arg|Arg|Lys|Ser|Ala|Gly|Gln|Glu|Glu|Trp|Ser|Pro|Ser|
| | | |180| | | |185| | | |190| | | | |
|Ala|Pro|Ser|Pro|Pro|Gly|Ser|Cys|Val|Gln|Ala|Glu|Ala|Ala|Pro|Ala|
| | |195| | | | |200| | | | |205| | | |
|Gly|Leu|Cys|Gly|Glu|Gln|Arg|Gly|Glu|Asp|Cys|Ala|Glu|Leu|His|Asp|
| |210| | | | |215| | | | |220| | | | |
|Tyr|Phe|Asn|Val|Leu|Ser|Tyr|Arg|Ser|Leu|Gly|Asn|Cys|Ser|Phe|Phe|
|225| | | | |230| | | | |235| | | | |240| |
|Thr|Glu|Thr|Gly| | | | | | | | | | | | |

<210> SEQ ID NO 41
<211> LENGTH: 1944
<212> TYPE: RNA
<213> ORGANISM: Homo sapiens

<400> SEQUENCE: 41

```
aauuucucac ugccccugug auaaacugug gucacuggcu guggcagcaa cuauuauaag    60
augcucugaa aacucuucag acacugaggg gcaccagagg agcagacuac aagaauggca   120
cacgcuaugg aaaacuccug acaaucagu aaagaguacc auaugauga gaagugggc     180
uuugcucugc caaauccaca ggaaaaucua ccugauuuuu auaaugacug gauguucauu   240
gcuaaacauc ugccugaucu cauagagucu ggccagcuuc gagaaagagu ugagaaguua   300
aacaugcuca gcauugauca ucucacagac acaagucac agcgccuugc acgucuaguu   360
cugggaugca ucaccauggc auaugugugg ggcaaaggu cauggagaugu ccguaaggc    420
uugccaagaa auauugcgu uccuuacugc caacucucca gaaacugga acugccuccu    480
auuuugguuu augcagacug ugucuuggca acuggaaga aaaaggaucc uaauaagccc    540
cugacuuaug agaacaugga cguuugguc ucauucgug auggagacug caguaaagga    600
uucuuccugg ucucucuauu ggaugaaaua gcagcugcuu cugcaaucaa aguaauuccu    660
acuguauuca aggcaaugca aaugcaagaa cgggacacuu ugcuaaaggc gcuguuggaa    720
auagcuucuu gcuuggagaa agcccuucaa cguguuucacc aaauccacga ucaugugaac    780
ccaaaagcau uuucagugu ucuucgcaua uauuugucug gcuggaaaga caaccccag      840
cuaucagacg gucuggugua ugaaggguuc ugggaagacc caaaggaguu ugcagggggc    900
agugcaggcc aaagcagcgu cuuucagugc uuugacgucc ugcugggcau ccagcagacu    960
gcuguggag acaugcugc ucaguccuc caggacauga aagauauau gccaccagcu       1020
cacaggaacu uccugugcuc auuagagu uaauccucag uccgugaguu uguccuuuca     1080
aaaggugaug cuggccugcg ggaagcuuau gacgccugug ugaaagcucu ggucucccug    1140
aggagcuacc aucugcaaau cgugacuaag uacauccuga uuccugcaag ccagcagcca    1200
aaggagaaua agaccucuga agacccuuca aaacuggaag ccaaaggaac uggaggcacu    1260
gauuuaauga auuccugaa acuguaaga aguacaacug agaaauccu uuugaaggaa       1320
gguuaaugua acccaacaag agcacauuuu ucauagcag agacaucugu augcauuccu    1380
gucauuaccc auuguaacag agccacaaac uaauacuaug caauguuua ccauaaugc      1440
aauacaaaag accucaaaau accugugcau ucuuguagg aaaacaacaa aagguaauua   1500
uguguaauua uacuagaagu uuuguaaucu guaucuuauc auuggaauaa aaugacauuc    1560
aauaauaaaa aaugcauaag auauauucug ucggcugggc gcgguggcuc acgccuguaa    1620
ucccagcacu uugggaggcc gaggcgggcg gaucacaagg ucaggagauc gagaccaucu    1680
uggcuaacac ggugaaaccc cgucucuacu aaaaauacaa aaauuagcc gggcgcgguc     1740
```

```
gcgggcaccu guaguccccag cuacucggga ggcugaggca ggagaauggc gugaaccugg    1800
gaggcggagc uugcagugag ccaagauugu gccacugcaa uccggccugg gcuaaagagc    1860
gggacuccgu cucaaaaaaa aaaaaaaaaa gauauauucu gucauaauaa auaaaaaugc    1920
auaagauaua aaaaaaaaaa aaaa                                            1944
```

<210> SEQ ID NO 42
<211> LENGTH: 403
<212> TYPE: PRT
<213> ORGANISM: Homo sapiens

<400> SEQUENCE: 42

```
Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335
```

```
Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
            355                 360                 365

Glu Asp Pro Ser Lys Leu Glu Ala Lys Gly Thr Gly Thr Asp Leu
370                 375                 380

Met Asn Phe Leu Lys Thr Val Arg Ser Thr Thr Glu Lys Ser Leu Leu
385                 390                 395                 400

Lys Glu Gly

<210> SEQ ID NO 43
<211> LENGTH: 1135
<212> TYPE: RNA
<213> ORGANISM: Homo sapiens

<400> SEQUENCE: 43
uuccuccucc gagagcggac agaucucugg gugcugggcg gucauggcgc uacuagaugu      60
augcggagcc ccccgagggc agcggccgga aucggcucuc ccgguugcgg aagcgggcg     120 ucgcucggac ccaggacacu acaguuucuc uaugcgaucu ccagagcucg cuuuaccccg    180
gggaaugcag cccacagaau ucuuccaguc ccuggguggg gacggagaaa ggaacguuca    240
gauugagaug gcccauggca ccaccacgcu cgccuucaag uuccagcaug gagugauugc    300
agcaguggau ucucgggccu cagcgggguc cuacauuagu gccuacggg uaacaaggu     360 gauugagauu aacccuuacc ugcuuggcac caugucuggc ugugcagcag acugucagua    420 cuggagcgc cugcuggcca aggaaugcag gcuacuau cugcgaaaug gagaacguau      480 uucaguggucg gcagccucca agcugcuguc caacaugaug ugccaguacc ggggcaugg    540 ccucucuaug ggcaguauga ucugggcug ggauaagaag gguccuggac ucuacacgu     600 ggaugaacau gggacucggc ucucaggaaa uauguucucc acgggagugu ggaacacuua    660
ugccuacggg gucauggaca guggcuaucg gccuaaucuu agcccugaag aggccuauga    720
ccuuggccgc agggcuauug cuuaugccac ucacagagac agcuauucug gaggcguugu    780
caauaugauc cacauugaagg aagaugguug ggugaaagua gaaagucag augucaguga    840 ccugcugcac caguaccggg aagccaauca uaaugguug ugguggcagc ugggcagguc    900
uccucuggga ggucuuggcc gacucaggga ccuaagccac guuaaguccca aggaagaa     960 gaggccuagc cugagccaaa gagaguac gggcucagca gccagaggag gccggugaag   1020
ugcaucuucu gcuguucuc uauuugaaca agcauuuccc ccagggaagu uucggguggc    1080
cccacuaagu agaauaaaga aaaacgguu uaaauaaaaa aaaaaaaaa aaaaa          1135

<210> SEQ ID NO 44
<211> LENGTH: 276
<212> TYPE: PRT
<213> ORGANISM: Homo sapiens

<400> SEQUENCE: 44

Met Ala Leu Leu Asp Val Cys Gly Ala Pro Arg Gly Gln Arg Pro Glu
1               5                   10                  15

Ser Ala Leu Pro Val Ala Gly Ser Gly Arg Arg Ser Asp Pro Gly His
            20                  25                  30

Tyr Ser Phe Ser Met Arg Ser Pro Glu Leu Ala Leu Pro Arg Gly Met
        35                  40                  45

Gln Pro Thr Glu Phe Phe Gln Ser Leu Gly Gly Asp Gly Glu Arg Asn
    50                  55                  60
```

Val Gln Ile Glu Met Ala His Gly Thr Thr Thr Leu Ala Phe Lys Phe
 65                  70                  75                  80

Gln His Gly Val Ile Ala Val Asp Ser Arg Ala Ser Ala Gly Ser
                 85                  90                  95

Tyr Ile Ser Ala Leu Arg Val Asn Lys Val Ile Glu Ile Asn Pro Tyr
                100                 105                 110

Leu Leu Gly Thr Met Ser Gly Cys Ala Ala Asp Cys Gln Tyr Trp Glu
                115                 120                 125

Arg Leu Leu Ala Lys Glu Cys Arg Leu Tyr Tyr Leu Arg Asn Gly Glu
        130                 135                 140

Arg Ile Ser Val Ser Ala Ala Ser Lys Leu Leu Ser Asn Met Met Cys
145                 150                 155                 160

Gln Tyr Arg Gly Met Gly Leu Ser Met Gly Ser Met Ile Cys Gly Trp
                165                 170                 175

Asp Lys Lys Gly Pro Gly Leu Tyr Tyr Val Asp Glu His Gly Thr Arg
                180                 185                 190

Leu Ser Gly Asn Met Phe Ser Thr Gly Ser Gly Asn Thr Tyr Ala Tyr
            195                 200                 205

Gly Val Met Asp Ser Gly Tyr Arg Pro Asn Leu Ser Pro Glu Glu Ala
        210                 215                 220

Tyr Asp Leu Gly Arg Arg Ala Ile Ala Tyr Ala Thr His Arg Asp Ser
225                 230                 235                 240

Tyr Ser Gly Gly Val Val Asn Met Tyr His Met Lys Glu Asp Gly Trp
                245                 250                 255

Val Lys Val Glu Ser Thr Asp Val Ser Asp Leu Leu His Gln Tyr Arg
            260                 265                 270

Glu Ala Asn Gln
        275

<210> SEQ ID NO 45
<211> LENGTH: 1048
<212> TYPE: RNA
<213> ORGANISM: Homo sapiens

<400> SEQUENCE: 45
gcgcguugug cgcuguccca gguuggaaac cagugcccca ggcggcgagg agagcggugc    60
cuugcaggga ugcugcgggc gggagcacca accggggacu uacccgggc gggagaaguc   120 cacaccggga ccaccaucau ggcaguggag uuugacgggg cguugugau ggguucugau    180 ucccgagugu cugcaggcga ggcgguggug aaccgagugu uugacaagcu guccccgcug   240
cacgagcgca ucuacugugc acucucuggu ucagcugcug augcccaagc cguggccgac   300
auggccgccu accagcugga gcccauggg auagaacugg aggaacccuc acuuguuuug   360
gcugcugcaa augggugag aaauaucagc uauaaauauc gagaggacuu gucugcacau   420
cucaugguag cuggcuggga ccaacgugaa ggaggucagg uauauggaac ccugggagga   480
augcugacuc gacagccuuu ugccauuggu ggcuccggca gccuuuau cuaugguuau     540 guggaugcag cauauaagcc aggcaugucu cccgaggagu gcaggcgcuu caccacagac   600
gcuauugcuc uggccaugag ccgggauggc ucaagcgggg gugucaucua ccuggucacu   660
auuacagcug ccggugugga ccaucgaguc aucugggca augaacugcc aaaauucuau   720 gaugaguga accuccccag acuucucuuu cuuauuuugu aauaaacucu cuagggccaa   780
aaccugguau ggcauuggg aaaugagugc uagggagau ggagcuuagg ggagugggu     840 gcuucccucc uagaugucag cauacacucu uucuucuuuu gucccagguc uaaaacaucu   900

```
uuccuagaga aaacaaaagg gacuaaacua gaaauauaaa gagcccuaua caugacaggu    960
gaucacguac ugaaugauuu ugaaguagua caaacaauaa aaauucucau uccgcaucau   1020
caugcgguuc augaugauga ggccgcaa                                     1048
```

<210> SEQ ID NO 46
<211> LENGTH: 219
<212> TYPE: PRT
<213> ORGANISM: Homo sapiens

<400> SEQUENCE: 46

```
Met Leu Arg Ala Gly Ala Pro Thr Gly Asp Leu Pro Arg Ala Gly Glu
1               5                   10                  15

Val His Thr Gly Thr Thr Ile Met Ala Val Glu Phe Asp Gly Gly Val
            20                  25                  30

Val Met Gly Ser Asp Ser Arg Val Ser Ala Gly Glu Ala Val Val Asn
        35                  40                  45

Arg Val Phe Asp Lys Leu Ser Pro Leu His Glu Arg Ile Tyr Cys Ala
    50                  55                  60

Leu Ser Gly Ser Ala Ala Asp Ala Gln Ala Val Ala Asp Met Ala Ala
65                  70                  75                  80

Tyr Gln Leu Glu Leu His Gly Ile Glu Leu Glu Glu Pro Pro Leu Val
                85                  90                  95

Leu Ala Ala Ala Asn Val Val Arg Asn Ile Ser Tyr Lys Tyr Arg Glu
            100                 105                 110

Asp Leu Ser Ala His Leu Met Val Ala Gly Trp Asp Gln Arg Glu Gly
        115                 120                 125

Gly Gln Val Tyr Gly Thr Leu Gly Gly Met Leu Thr Arg Gln Pro Phe
    130                 135                 140

Ala Ile Gly Gly Ser Gly Ser Thr Phe Ile Tyr Gly Tyr Val Asp Ala
145                 150                 155                 160

Ala Tyr Lys Pro Gly Met Ser Pro Glu Glu Cys Arg Arg Phe Thr Thr
                165                 170                 175

Asp Ala Ile Ala Leu Ala Met Ser Arg Asp Gly Ser Ser Gly Gly Val
            180                 185                 190

Ile Tyr Leu Val Thr Ile Thr Ala Ala Gly Val Asp His Arg Val Ile
        195                 200                 205

Leu Gly Asn Glu Leu Pro Lys Phe Tyr Asp Glu
    210                 215
```

<210> SEQ ID NO 47
<211> LENGTH: 2974
<212> TYPE: RNA
<213> ORGANISM: Homo sapiens

<400> SEQUENCE: 47

```
gugugcguga uggagaaaau ugggcaccag ggcugcuccc gagauucuca gaucugauuu     60
ccacgcuugc uaccaaaaua gucugggcag gccacuuuug gaaguaggcg uuaucuagug    120
agcaggcggc cgcuuucgau uucgcuuucc ccuaaauggc ugagcuucuc gccagcgcag    180
gaucagccug uuccugggac uuccgagag  ccccgcccuc guucccuccc ccagccgcca    240
guaggggagg acucggcggu acccggagcu ucaggcccca ccggggcgcg gagaguccca    300
ggcccggccg ggaccgggac ggcguccgag ugccaauggc uagcucuagg uguccgcuc     360 cccgcgggug ccgcugccuc cccggagcuu cucucgcaug gcugggggaca guacugcuac    420 uucucgccga cugggugcug cuccggaccg cgcugccccg cauauucucc cugcugguge    480
```

-continued

```
ccaccgcgcu gccacugcuc cgggucuggg cgguggggccu gagccgcugg gccgugcucu    540 ggcuggggggc cugcggggguc cucagggcaa cgguuggcuc caagagcgaa aacgcaggug    600
cccagggcug gcuggcugcu uugaagccau uagcugcggc acugggcuug gcccugccgg    660
gacuugccuu guuccgagag cugaucucau ggggagcccc cggguccgcg gauagcacca    720
ggcuacugca cugggggaagu cacccuaccg ccuucguugu caguuaugca gcggcacugc    780
ccgcagcagc ccuguggcac aaacucggga gccucugggu gccggcggu cagggcggcu    840 cuggaaaccc ugugcgucgg cuucuaggcu gccugggcuc ggagacgcgc cgccucucgc    900
uguuccuggu ccuggugguc cucuccucuc uggggggagau ggccauucca uucuuuacgg    960
gccgccucac ugacuggauu cuacaagaug gcucagccga uaccuucacu cgaaacuuaa    1020
cucucauguc cauucucacc auagccagug cagugcugga guucguggu gacgggaucu    1080 auaacaacac caugggccac gugcacagcc acuugcaggg agaggguguuu ggggcugucc    1140 ugcgccagga gacggaguuu uuccaacaga accagacagg uaacaucaug ucucggguaa    1200
cagaggacac guccacccug agugauucuc ugagugagaa ucugagccuua uuucuguggu    1260 accuggugcg aggccuaugu cucuggggga ucaugcucug gggaucagug cccucacca    1320 uggucacccu gaucacccug ccucugcuuu uccuucugcc caagaaggug ggaaaauggu    1380
accaguugcu ggaagugcag gugcgggaau cucuggcaaa guccagccag guggccauug    1440 aggcucugc ggccaugccu acaguucgaa gcuuugccaa cgaggagggc gaagcccaga    1500
aguuuaggga aaagcugcaa gaaauaaaga cacucaacca aaggaggcu guggccuaug    1560 caguccaacuc cuggaccacu aguauuucag guaugcugcu gaaagugggga auccucuaca    1620 uuggugggca gcuggugacc aguggggcug uaagcagugg gaaccuuguc acauuuguuc    1680
ucuaccagau gcaguucacc caggcugugg agguacugcu cuccaucuac cccagaguac    1740
agaaggcugu gggcuccuca gagaaaauau uugaguaccu ggaccgcacc ccucgcugcc    1800
cacccagugg ucuguugacu cccuuacacu uggaggccu uguccaguuc caagaugucu    1860
ccuuugccua cccaaaccgc ccagaugucu uagugcuaca ggggcugaca uucacccuac    1920
gcccuggcga ggugacggcg cuggugggac ccaaugggguc uggaagagc acaguggcug    1980 cccugcugca gaaucuguac cagcccaccg ggggacagcu gcuguuggau gggaagcccc    2040 uucccccaaua ugagcaccgc uaccugcaca ggcaggugggc ugcagugggga caagagccac    2100 agguauuugg aagaagucuu caagaaaaua uugccuaugg ccugacccag aagccaacua    2160
uggaggaaau cacagcugcu gcaguaaagu cuggggccca uaguuucauc ucuggacucc    2220
cucagggcua ugacacagag guagacgagg cuggagccca gcugucaggg ggucagcgac    2280
aggcaguggc guuggcccga gcauugaucc ggaaaccgug uguacuuauc cuggaugaug    2340
ccaccagugc ccuggaugca aacagccagu uacaggugga gcagcccccug uacgaaagcc    2400 cugagcggua ucccgcuca gugcuucuca ucacccagca cccagccug guggagcagg    2460 cugaccacau ccucuuucug gaaggaggcg cuauccggga gggggggaacc caccagcagc    2520 ucauggagaa aaggggggugc uacugggcca uggugcaggc uccugcagau gcuccagaau    2580
gaaagccuuc ucagaccgc gcacuccauc uccucuccuu uucuucucuc uguggggugag    2640 aaccacagcu gcagaguagg cagcugccuc caggaugagu acuugaaau uugccuugag    2700 ugguuaccu ccuuuccaag cucccucguga uaaugcagac uuccuggagu acaaacacag    2760
gauuuguaau uccuuacugu aacgaguuu agagccaggg cugaugcuuu ggugugggcca    2820 gcacucugaa acugagaaau guucagaaug uacggaaaga ugaucagcua uuucaacau    2880
```

```
aacugaaggc auaugcuggc ccauaaacac ccguaggu cuugauauuu auaauaaaau      2940 uguguuug uaaaaaaaa aaaaaaaaaa aaaa                                   2974
```

<210> SEQ ID NO 48
<211> LENGTH: 808
<212> TYPE: PRT
<213> ORGANISM: Homo sapiens

<400> SEQUENCE: 48

```
Met Ala Glu Leu Leu Ala Ser Ala Gly Ser Ala Cys Ser Trp Asp Phe
1               5                   10                  15

Pro Arg Ala Pro Pro Ser Phe Pro Pro Pro Ala Ser Arg Gly Gly
            20                  25                  30

Leu Gly Gly Thr Arg Ser Phe Arg Pro His Arg Gly Ala Glu Ser Pro
        35                  40                  45

Arg Pro Gly Arg Asp Arg Asp Gly Val Arg Val Pro Met Ala Ser Ser
    50                  55                  60

Arg Cys Pro Ala Pro Arg Gly Cys Arg Cys Leu Pro Gly Ala Ser Leu
65                  70                  75                  80

Ala Trp Leu Gly Thr Val Leu Leu Leu Ala Asp Trp Val Leu Leu
                85                  90                  95

Arg Thr Ala Leu Pro Arg Ile Phe Ser Leu Leu Val Pro Thr Ala Leu
            100                 105                 110

Pro Leu Leu Arg Val Trp Ala Val Gly Leu Ser Arg Trp Ala Val Leu
        115                 120                 125

Trp Leu Gly Ala Cys Gly Val Leu Arg Ala Thr Val Gly Ser Lys Ser
130                 135                 140

Glu Asn Ala Gly Ala Gln Gly Trp Leu Ala Ala Leu Lys Pro Leu Ala
145                 150                 155                 160

Ala Ala Leu Gly Leu Ala Leu Pro Gly Leu Ala Leu Phe Arg Glu Leu
                165                 170                 175

Ile Ser Trp Gly Ala Pro Gly Ser Ala Asp Ser Thr Arg Leu Leu His
            180                 185                 190

Trp Gly Ser His Pro Thr Ala Phe Val Val Ser Tyr Ala Ala Ala Leu
        195                 200                 205

Pro Ala Ala Ala Leu Trp His Lys Leu Gly Ser Leu Trp Val Pro Gly
    210                 215                 220

Gly Gln Gly Gly Ser Gly Asn Pro Val Arg Arg Leu Leu Gly Cys Leu
225                 230                 235                 240

Gly Ser Glu Thr Arg Arg Leu Ser Leu Phe Leu Val Leu Val Val Leu
                245                 250                 255

Ser Ser Leu Gly Glu Met Ala Ile Pro Phe Phe Thr Gly Arg Leu Thr
            260                 265                 270

Asp Trp Ile Leu Gln Asp Gly Ser Ala Asp Thr Phe Thr Arg Asn Leu
        275                 280                 285

Thr Leu Met Ser Ile Leu Thr Ile Ala Ser Ala Val Leu Glu Phe Val
    290                 295                 300

Gly Asp Gly Ile Tyr Asn Asn Thr Met Gly His Val His Ser His Leu
305                 310                 315                 320

Gln Gly Glu Val Phe Gly Ala Val Leu Arg Gln Glu Thr Glu Phe Phe
                325                 330                 335

Gln Gln Asn Gln Thr Gly Asn Ile Met Ser Arg Val Thr Glu Asp Thr
            340                 345                 350
```

```
Ser Thr Leu Ser Asp Ser Leu Ser Glu Asn Leu Ser Leu Phe Leu Trp
        355                 360                 365

Tyr Leu Val Arg Gly Leu Cys Leu Leu Gly Ile Met Leu Trp Gly Ser
    370                 375                 380

Val Ser Leu Thr Met Val Thr Leu Ile Thr Leu Pro Leu Leu Phe Leu
385                 390                 395                 400

Leu Pro Lys Lys Val Gly Lys Trp Tyr Gln Leu Leu Glu Val Gln Val
                405                 410                 415

Arg Glu Ser Leu Ala Lys Ser Ser Gln Val Ala Ile Glu Ala Leu Ser
            420                 425                 430

Ala Met Pro Thr Val Arg Ser Phe Ala Asn Glu Glu Gly Glu Ala Gln
        435                 440                 445

Lys Phe Arg Glu Lys Leu Gln Glu Ile Lys Thr Leu Asn Gln Lys Glu
    450                 455                 460

Ala Val Ala Tyr Ala Val Asn Ser Trp Thr Thr Ser Ile Ser Gly Met
465                 470                 475                 480

Leu Leu Lys Val Gly Ile Leu Tyr Ile Gly Gln Leu Val Thr Ser
                485                 490                 495

Gly Ala Val Ser Ser Gly Asn Leu Val Thr Phe Val Leu Tyr Gln Met
            500                 505                 510

Gln Phe Thr Gln Ala Val Glu Val Leu Leu Ser Ile Tyr Pro Arg Val
    515                 520                 525

Gln Lys Ala Val Gly Ser Ser Glu Lys Ile Phe Glu Tyr Leu Asp Arg
            530                 535                 540

Thr Pro Arg Cys Pro Pro Ser Gly Leu Leu Thr Pro Leu His Leu Glu
545                 550                 555                 560

Gly Leu Val Gln Phe Gln Asp Val Ser Phe Ala Tyr Pro Asn Arg Pro
                565                 570                 575

Asp Val Leu Val Leu Gln Gly Leu Thr Phe Thr Leu Arg Pro Gly Glu
            580                 585                 590

Val Thr Ala Leu Val Gly Pro Asn Gly Ser Gly Lys Ser Thr Val Ala
        595                 600                 605

Ala Leu Leu Gln Asn Leu Tyr Gln Pro Thr Gly Gly Gln Leu Leu Leu
    610                 615                 620

Asp Gly Lys Pro Leu Pro Gln Tyr Glu His Arg Tyr Leu His Arg Gln
625                 630                 635                 640

Val Ala Ala Val Gly Gln Glu Pro Gln Val Phe Gly Arg Ser Leu Gln
                645                 650                 655

Glu Asn Ile Ala Tyr Gly Leu Thr Gln Lys Pro Thr Met Glu Glu Ile
            660                 665                 670

Thr Ala Ala Ala Val Lys Ser Gly Ala His Ser Phe Ile Ser Gly Leu
        675                 680                 685

Pro Gln Gly Tyr Asp Thr Glu Val Asp Glu Ala Gly Ser Gln Leu Ser
    690                 695                 700

Gly Gly Gln Arg Gln Ala Val Ala Leu Ala Arg Ala Leu Ile Arg Lys
705                 710                 715                 720

Pro Cys Val Leu Ile Leu Asp Asp Ala Thr Ser Ala Leu Asp Ala Asn
                725                 730                 735

Ser Gln Leu Gln Val Glu Gln Leu Leu Tyr Glu Ser Pro Glu Arg Tyr
            740                 745                 750

Ser Arg Ser Val Leu Leu Ile Thr Gln His Leu Ser Leu Val Glu Gln
        755                 760                 765
```

```
Ala Asp His Ile Leu Phe Leu Glu Gly Gly Ala Ile Arg Glu Gly Gly
    770                 775                 780

Thr His Gln Gln Leu Met Glu Lys Lys Gly Cys Tyr Trp Ala Met Val
785                 790                 795                 800

Gln Ala Pro Ala Asp Ala Pro Glu
            805

<210> SEQ ID NO 49
<211> LENGTH: 5732
<212> TYPE: RNA
<213> ORGANISM: Homo sapiens

<400> SEQUENCE: 49
agaaugaagg ccuuggcugg ggaagcgaaa gcgaaagcug cccgagcccu gacgcccgcc      60
cuggccgagc guagcuggcg gaccagagcc gguagcgagg uugggagaga cggagcggac     120
cucagcgcug aagcagaagu ccccggagcu gcggucuccc cgccgcggcu gagccaugcg     180
gcucccugac cugagacccu ggaccucccu gcugcuggug gacgcggcuu acuguggcu      240 gcuucagggc ccucugggga cuuugcuucc ucaagggcug ccaggacuau ggcuggaggg     300
gacccugcgg cugggaggge ugugggggcu gcuaaagcua agagggcugc ugggauuugu     360
ggggacacug cugcucccgc ucugucuggc cacccccug acugucuccc ugagagcccu      420
ggucgcgggg gccucacgug ucccccagc cagagucgcu ucagcccuu ggagcuggcu       480 gcuggugggg uacggggcug cggggcucag cuggucacug ugggcuguuc ugagcccucc     540
uggagcccag gagaaggagc aggaccaggu gaacaacaaa gucuugaugu ggaggcugcu     600
gaagcucucc aggccggacc ugccucuccu cguugccgcc uucuucuucc uuguccuugc     660
uguuuugggu gagacauuaa ucccucacua uucggucgu ugauugaca uccugggagg       720 ugauuugac ccccaugccu uugccagugc caucuucuuc augugccucu ucuccuuugg      780
cagcucacug ucugcaggcu gccgaggagg cugcuucacc uacaccaugu ucgaaucaa     840 cuugcggauc cgggagcagc uuuucuccuc ccugcugcgc caggaccucg guucuuucca     900
ggagacuaag acaggggagc ugaacucacg gcugagcucg gauaccaccc ugaugaguaa     960
cuggcuuccu uuaaaugcca augugcucuu gcgaagccug gugaaagugg uggggcugua    1020
uggcuucaug cucagcauau cgccucgacu caccccuccu ucucugcugc acaugcccuu    1080
cacaauagca gcggagaagg uguacaacac ccgccaucag gaagugcuuc gggagaucca    1140
ggaugcagug gccagggcgg ggcagguggu gcgggaagcc guuggagggc ugcagaccgu    1200
ucgcaguuuu ggggccgagg agcaugaagu cugucgcuau aaagaggccc uugaacaaug    1260
ucggcagcug uauuggcgga gagaccugga acgcgccuug uaccugcucg uaaggagggu    1320
gcugcacuug ggggugcaga ugcugaugcu gagcuguggg cugcagcaga ugcaggaugg    1380
ggagcucacc cagggcagcc ugcuuuccuu uaugaucuac caggagagcg uggggagcua    1440
ugugcagacc cugguauaca uauaugggga uaugcucagc aacgugggag cugcagaaa     1500 gguuuucucc uacauggacc gacagccaaa ucugccuuca ccuggcacgc uugccccac      1560 cacucugcag ggguuguga aauuccaaga cgucuccuuu gcauauccca aucgcccuga    1620
caggccugug ucaagggcc ugacguuuac ccuacguccu ggugagguga cggcgcuggu    1680
gggacccaau gggucuggga gagcacagu ggcugcccug cugcagaauc uguaccagcc    1740
cacaggggga caggugcuqс uggaugaaaa gcccaucuca caguaugaac acugcuaccu    1800
gcacagccag guqguuucag uuuqggcaqqa qccuqucquq uucuccqquu cuquqaqqaa   1860
```

-continued

```
caacauugcu uaugggcugc agagcugcga agaugauaag gugauggcgg cugcccaggc    1920
ugcccacgca gaugacuuca uccaggaaau ggagcaugga auauacacag auguagggga    1980
gaagggaagc cagcuggcug cggacagaaa acaacgucug gccauugccc gggcccuugu    2040
acgagacccg cggguccuca uccuggauga ggcuacuagu gcccuagaug ugcagugcga    2100
gcaggcccug caggacugga auucccgugg ggaucgcaca gugcuggugu uugcucacag    2160
gcugcagaca guucgcgcg cccaccagau ccuggugcuc caggagggca agcugcagaa    2220
gcuugcccag cucuaggagg acaggaccu cuauucccgc cuggugcagc agcggcugau    2280
ggacugaggc cccagggaua cugggcccuc uucucagggg cgucuccagg acccagagcu    2340
guuccugcuu ugaguuuccc uagagcugug cggccagaua gcuguccug aguugcaggc    2400
acgauggaga uuuggacacu gugugcuuuu ggugggguag agaggugggg uggggugggg    2460
uggggggcugu cuguguccag gaaacuuaau ucccuggugu cuagagcuuu gccuggugau    2520
gaggaguauu uugugcauaa auacauauau uuuaaaauau uuccuucuu acaugaacug    2580
uauacauuca uauagaaaau uuagacaaua uaaaaagua caaagaagaa aaguaaaagu    2640
acccauuguu ucacuuccug gagauaacca uaguugcuau uuugcugccu gucccaucag    2700
ucguuuaucu guuguugag auagaaauua accaaaaaug acauaaauau ucaugagauu    2760
gccuuccuau auccuuccuu guccuacca gugucugcua uuuugaagaa gcuagggucu    2820
ggagggacag agaacaguuc ccugauuaac aguauuaaua cgacauugg uaacagcuac    2880
cauuauaga guuuaauugg gaguaggagc uaugcuaagu guuuucaug uauuaucguu    2940
uuuaaucauu auccccaacc cuaugagguu gguuauuauc cccauuuuac agaugaggaa    3000
acugaagcuc aaagaggcuc aaugacuuuc ccaagguggu cguaguggug gaguuggagu    3060
uugaacacag gccugacccu agaguccaca cccugaccca aucaauuaua uugcaucuug    3120
gguccauaaa cccuaaucca uaaucccauc aagaaaagcu cugcugcucu uagcucuaaa    3180
uaauucagaa ucuauucucu ucucuccagu cccguuguua uagucuucac ucauagacuu    3240
aagaugaucc caucaccaga gagguuucuc uaccauuagc uucccucuuc cggccauucu    3300
ucacaaaguc auuuuucuaa auucuguguc acauacgaug auggcauuuc uggaaauucc    3360
uucaggugcu cucaagcccu gcugcagaga uccuuuucag agcacacacu guuccagccc    3420
aucugucuca cccucuccug uuguauccag cuccacgaca aacuucugcc uuccccaaca    3480
ccuuugugcc uuugcauaug uguuuucuu gcccauuuuc ugcucgacuc gccccugauu    3540
uucaaguuca agacuuaacu cagggguucag gucuuccagg aggccuuacu uaugucguca    3600
gucuggggaa cucuccaugu gcuucuauca cugugcgguu accucuuuca cagcccuuuu    3660
aaaguucuau cuucccuuuc ccaccuuuuu ugaccuucca cuagaccaug agcaccuggg    3720
cggaaagcca uauaucuuau uaagcuuuau aucugcuacc uggccgaggg ccuaauucau    3780
aguggagaau aaauagucaa uugaauaaau gaauaaauau cuccaccauc guacuaaucu    3840
uaauccuccc ugcccacucc caccacugaa aaugcaacau guacacauc acugguuguu    3900
gggagggacu uaccuuggaa aguugcuauu cuaggaaaga gaaaccuuca uauuccugga    3960
aacagcaggu aguuuccagu gcuggcaaug aauuccccag aacugcuguu uuggauuuuu    4020
ucuugccugg cagcuguugg gagcagggug cagugaggau ggggugagag ugggcaguuu    4080
cuugugcaga uuugccuuuc uuucauccug gggcugacuu gcagcuccac acccauccau    4140
cucucaaauu ucagagaggg uaaaauaggc auuuggagag aaagaacucu ggccugauuc    4200
cuuucucucc cacaaaugcu cuuuauucau aaaacaggaa uaauaauucc uguaucsccc    4260
```

-continued

```
aacuacaugg aagcugcagc ccucacagaa gaagaugauc ugagaaauuc uuugauuucc   4320
ucaguacagu uauacccaug caucauaaua cuuuaagccu ggaaggcauc uuaaaaauaa   4380
ugcaacaguc aaaccuaauu uuacagagaa acugacauga aaucacgcag cuaaucauga   4440
uaaagcuggg uggaaaacuu aucuugaugg gcaguacagg aagaugcagu agaccuuaag   4500
auguccugaa aguucuuau cucaggggaa acucccaggu aggcuuuaug ucagggacac    4560
agaaaaaugc ucccugaaag ucaaaauauu cgggcuagac agacaaauuc cguaagugu    4620 gguuugucug ggaaccacag augucacuaa uccugguuug uccagaguu cuuuuuguuc    4680 acuccacccc cccaucacca uuugauugau cuccuuaccc uguaauuccc ccuucugu c   4740 gcuuaccugc aguaucuuuc ccacccaggc augccuuauu cuuucaaag gaaaguauga    4800 auggagaggg gaaagcuugg gaaacugaua gauuuccuug gaugccaaaa caccuccaua   4860
gccugucugc ccggcccuau guggaaacag cauugaguuu caaguccuuu augccuccac   4920
ccagggauag ccacuuguaa uccacauggc aauugugaaa caagcaggaa augcguaauu   4980
gucagaauuu gugggggaaa ggacuaggga auaaggaaaa caaagaucuu ccuuguguuu   5040
uagagcuguc agcuagagga gcaccugcuu gagucugaug ccaucuaaug ucccagaag    5100 aaacuggguu uugaaccuag aguuccaugg acucuuagga auuagacuac uacuacuacu   5160
aagcauucac uggugcuuac uaugugcuau ugcugugcca aguaucugaa accugucuuc   5220
uuaccuuauu uuucaagaua auucuaugug gcagguauua cuaucucaau ucuaagagug   5280
agaaaaugga guuuagaaaa cauuuacuaa cuugccuggg ucacauagcu aaggaagagg   5340
uggacuugcc cagcuuugca uaaaacuccu caaaagaguu gccuauacuc ccugacucca   5400
cuuaucuucc uacuauccuc uuuuuaaaau auauuauuua uuuauuuaaa uaagcaauau   5460
augaaugugg uuugaaauuc aaaagacaca aagaaguaua cagaggaaag ccucacucuc   5520
aauccuucuc aagguuugcu aauuccucuu gcauaggcaa uccguucuuc cagcuuugug   5580
uuuaucuuuc cagagaaguu uacguguauu uaagcaaaua uguauaucuu uauucuugcu   5640
caguauuuuc gcaaacagca gcugucuaag uucacuguuc ugaacuuuau uuuuuaaauu   5700
aaaaauauau ggcuauguag uauucuauuu ua                                5732
```

<210> SEQ ID NO 50
<211> LENGTH: 686
<212> TYPE: PRT
<213> ORGANISM: Homo sapiens

<400> SEQUENCE: 50

```
Met Arg Leu Pro Asp Leu Arg Pro Trp Thr Ser Leu Leu Leu Val Asp
1               5                   10                  15

Ala Ala Leu Leu Trp Leu Leu Gln Gly Pro Leu Gly Thr Leu Leu Pro
            20                  25                  30

Gln Gly Leu Pro Gly Leu Trp Leu Glu Gly Thr Leu Arg Leu Gly Gly
        35                  40                  45

Leu Trp Gly Leu Leu Lys Leu Arg Gly Leu Leu Gly Phe Val Gly Thr
    50                  55                  60

Leu Leu Leu Pro Leu Cys Leu Ala Thr Pro Leu Thr Val Ser Leu Arg
65                  70                  75                  80

Ala Leu Val Ala Gly Ala Ser Arg Ala Pro Pro Ala Arg Val Ala Ser
                85                  90                  95

Ala Pro Trp Ser Trp Leu Leu Val Gly Tyr Gly Ala Ala Gly Leu Ser
            100                 105                 110
```

```
Trp Ser Leu Trp Ala Val Leu Ser Pro Pro Gly Ala Gln Glu Lys Glu
            115                 120                 125

Gln Asp Gln Val Asn Asn Lys Val Leu Met Trp Arg Leu Leu Lys Leu
130                 135                 140

Ser Arg Pro Asp Leu Pro Leu Val Ala Ala Phe Phe Phe Leu Val
145                 150                 155                 160

Leu Ala Val Leu Gly Glu Thr Leu Ile Pro His Tyr Ser Gly Arg Val
                165                 170                 175

Ile Asp Ile Leu Gly Gly Asp Phe Asp Pro His Ala Phe Ala Ser Ala
                180                 185                 190

Ile Phe Phe Met Cys Leu Phe Ser Phe Gly Ser Ser Leu Ser Ala Gly
            195                 200                 205

Cys Arg Gly Gly Cys Phe Thr Tyr Thr Met Ser Arg Ile Asn Leu Arg
210                 215                 220

Ile Arg Glu Gln Leu Phe Ser Ser Leu Leu Arg Gln Asp Leu Gly Phe
225                 230                 235                 240

Phe Gln Glu Thr Lys Thr Gly Glu Leu Asn Ser Arg Leu Ser Ser Asp
            245                 250                 255

Thr Thr Leu Met Ser Asn Trp Leu Pro Leu Asn Ala Asn Val Leu Leu
            260                 265                 270

Arg Ser Leu Val Lys Val Val Gly Leu Tyr Gly Phe Met Leu Ser Ile
        275                 280                 285

Ser Pro Arg Leu Thr Leu Leu Ser Leu Leu His Met Pro Phe Thr Ile
            290                 295                 300

Ala Ala Glu Lys Val Tyr Asn Thr Arg His Gln Glu Val Leu Arg Glu
305                 310                 315                 320

Ile Gln Asp Ala Val Ala Arg Ala Gly Gln Val Val Arg Glu Ala Val
                325                 330                 335

Gly Gly Leu Gln Thr Val Arg Ser Phe Gly Ala Glu Glu His Glu Val
            340                 345                 350

Cys Arg Tyr Lys Glu Ala Leu Glu Gln Cys Arg Gln Leu Tyr Trp Arg
            355                 360                 365

Arg Asp Leu Glu Arg Ala Leu Tyr Leu Val Arg Arg Val Leu His
370                 375                 380

Leu Gly Val Gln Met Leu Met Leu Ser Cys Gly Leu Gln Gln Met Gln
385                 390                 395                 400

Asp Gly Glu Leu Thr Gln Gly Ser Leu Leu Ser Phe Met Ile Tyr Gln
                405                 410                 415

Glu Ser Val Gly Ser Tyr Val Gln Thr Leu Val Tyr Ile Tyr Gly Asp
            420                 425                 430

Met Leu Ser Asn Val Gly Ala Ala Glu Lys Val Phe Ser Tyr Met Asp
            435                 440                 445

Arg Gln Pro Asn Leu Pro Ser Pro Gly Thr Leu Ala Pro Thr Thr Leu
        450                 455                 460

Gln Gly Val Val Lys Phe Gln Asp Val Ser Phe Ala Tyr Pro Asn Arg
465                 470                 475                 480

Pro Asp Arg Pro Val Leu Lys Gly Leu Thr Phe Thr Leu Arg Pro Gly
                485                 490                 495

Glu Val Thr Ala Leu Val Gly Pro Asn Gly Ser Gly Lys Ser Thr Val
            500                 505                 510

Ala Ala Leu Leu Gln Asn Leu Tyr Gln Pro Thr Gly Gly Gln Val Leu
            515                 520                 525
```

| | | | | | | | | | | | |
|---|---|---|---|---|---|---|---|---|---|---|---|
|Leu|Asp|Glu|Lys|Pro|Ile|Ser|Gln|Tyr|Glu|His|Cys|Tyr|Leu|His|Ser|
| |530| | | |535| | | |540| | | | | | |
|Gln|Val|Ser|Val|Gly|Gln|Glu|Pro|Val|Leu|Phe|Ser|Gly|Ser|Val|
|545| | | |550| | | |555| | | |560| | |
|Arg|Asn|Asn|Ile|Ala|Tyr|Gly|Leu|Gln|Ser|Cys|Glu|Asp|Lys|Val|
| | | | |565| | | |570| | | |575| | |
|Met|Ala|Ala|Gln|Ala|His|Ala|Asp|Asp|Phe|Ile|Gln|Glu|Met|
| | |580| | | |585| | | |590| | | |
|Glu|His|Gly|Ile|Tyr|Thr|Asp|Val|Gly|Glu|Lys|Gly|Ser|Gln|Leu|Ala|
| | | |595| | | |600| | | |605| | | | |
|Ala|Gly|Gln|Lys|Gln|Arg|Leu|Ala|Ile|Ala|Arg|Ala|Leu|Val|Arg|Asp|
| |610| | | | |615| | | |620| | | | | |
|Pro|Arg|Val|Leu|Ile|Leu|Asp|Glu|Ala|Thr|Ser|Ala|Leu|Asp|Val|Gln|
|625| | | | |630| | | |635| | | |640| | |
|Cys|Glu|Gln|Ala|Leu|Gln|Asp|Trp|Asn|Ser|Arg|Gly|Asp|Arg|Thr|Val|
| | | | |645| | | |650| | | |655| | |
|Leu|Val|Ile|Ala|His|Arg|Leu|Gln|Thr|Val|Gln|Arg|Ala|His|Gln|Ile|
| | | |660| | | |665| | | |670| | | | |
|Leu|Val|Leu|Gln|Glu|Gly|Lys|Leu|Gln|Lys|Leu|Ala|Gln|Leu|
| |675| | | | |680| | | |685| | | | |

```
<210> SEQ ID NO 51
<211> LENGTH: 849
<212> TYPE: RNA
<213> ORGANISM: Homo sapiens

<400> SEQUENCE: 51
augaggaacu ccauagauu ucuggcaucc ucucucucag uugucguuuc ucccugcua      60 auuccugaag augucuguga aaaaauuauu ggaggaaaug aaguaacucc ucauucaaga   120
cccuacaugg uccuacuuag ucuugacaga aaaaccaucu gucugggc uuugauugca    180 aaagacuggg uguugacugc agcucacugu aacuugaaca aaaggucccca ggucauucuu   240 ggggcucacu caauaaccag gaagagcca acaaaacaga uaaugcuugu aagaaagag     300 uuucccuauc caugcuauga cccagccaca cgcgaaggug accuuaaacu uuuacagcug   360
acggaaaaag caaaaauuaa caauaugug acuauccuuc aucuaccuaa aaggggau    420 gaugugaaac caggaaccau gugccaaguu gcaggguggg ggaggacuca caauagugca   480 ucuuggucccg auacucugag agaagucauu aucaccauca uagacagaaa agucugcaau   540
gaucgaaauc acuauaauuu uaacccugug auuggaauga auaugguuug ugcuggaagc   600
cuccgaggug aagagacuc gugcaaugga gauucuggaa gcccuuuguu gugcgagggu   660 guuuccgag gggucacuuc cuuuggccuu gaaaauaaau gcggagaccc ucgugggccu   720
ggugcuauua uucuucucuc aaagaaacac cucaacugga uauuaugac uaucaaggga   780 gcaguuaaaa uaaccguuuc cuuucauuua cuguggcuuc uuaaucuuuu cacaaauaaa   840
aucaauuug                                                            849

<210> SEQ ID NO 52
<211> LENGTH: 262
<212> TYPE: PRT
<213> ORGANISM: Homo sapiens
```

<400> SEQUENCE: 52

```
Met Arg Asn Ser Tyr Arg Phe Leu Ala Ser Ser Leu Ser Val Val
1               5                   10                  15

Ser Leu Leu Leu Ile Pro Glu Asp Val Cys Glu Lys Ile Ile Gly Gly
            20                  25                  30

Asn Glu Val Thr Pro His Ser Arg Pro Tyr Met Val Leu Leu Ser Leu
                35                  40                  45

Asp Arg Lys Thr Ile Cys Ala Gly Ala Leu Ile Ala Lys Asp Trp Val
        50                  55                  60

Leu Thr Ala Ala His Cys Asn Leu Asn Lys Arg Ser Gln Val Ile Leu
65                  70                  75                  80

Gly Ala His Ser Ile Thr Arg Glu Glu Pro Thr Lys Gln Ile Met Leu
                85                  90                  95

Val Lys Lys Glu Phe Pro Tyr Pro Cys Tyr Asp Pro Ala Thr Arg Glu
            100                 105                 110

Gly Asp Leu Lys Leu Leu Gln Leu Met Glu Lys Ala Lys Ile Asn Lys
        115                 120                 125

Tyr Val Thr Ile Leu His Leu Pro Lys Lys Gly Asp Asp Val Lys Pro
130                 135                 140

Gly Thr Met Cys Gln Val Ala Gly Trp Gly Arg Thr His Asn Ser Ala
145                 150                 155                 160

Ser Trp Ser Asp Thr Leu Arg Glu Val Asn Ile Thr Ile Ile Asp Arg
                165                 170                 175

Lys Val Cys Asn Asp Arg Asn His Tyr Asn Phe Asn Pro Val Ile Gly
            180                 185                 190

Met Asn Met Val Cys Ala Gly Ser Leu Arg Gly Gly Arg Asp Ser Cys
        195                 200                 205

Asn Gly Asp Ser Gly Ser Pro Leu Leu Cys Glu Gly Val Phe Arg Gly
    210                 215                 220

Val Thr Ser Phe Gly Leu Glu Asn Lys Cys Gly Asp Pro Arg Gly Pro
225                 230                 235                 240

Gly Val Tyr Ile Leu Leu Ser Lys Lys His Leu Asn Trp Ile Ile Met
                245                 250                 255

Thr Ile Lys Gly Ala Val
            260
```

<210> SEQ ID NO 53
<211> LENGTH: 934
<212> TYPE: RNA
<213> ORGANISM: Homo sapiens

<400> SEQUENCE: 53

```
ugagaagaug caaccaaucc ugcuucugcu ggccuuccuc cugcugccca gggcagaugc    60
aggggagauc aucggggggac augaggccaa gccccacucc cgccccuaca uggcuuaucu  120
uaugaucugg gaucagaagu cucugaagag gugcggguggc uuccugauac aagacgacuu  180
cgugcugaca gcugcucacu guuggggaag cuccauaaau gucaccuugg gggcccacaa   240
uaucaaagaa caggagccga cccagcaguu uaucccugug aaaagaccca uccccccaucc  300 agccuauaau ccuaagaacu cuccaacga caucaugcua cugcagcugg agagaaaggc   360
caagcggacc agagcugugc agccccucag gcuaccuagc aacaaggccc aggugaagcc   420
agggcagaca ugcagugugg ccggcugggg gcagacggcc ccccugggaa aacacucaca   480
cacacuacaa gaggugaaga ugacagugca ggaagaucga aagugcgaau cugacuuacg   540
```

```
ccauuauuac gacaguacca uugaguugug cgugggggac ccagagauua aaaagacuuc    600
cuuuaagggg gacucuggag gcccucuugu guguaacaag guggcccagg gcauugcuc    660 cuauggacga aacaauggca ugccuccacg agccugcacc aaagucucaa gcuuuguaca    720
cuggauaaag aaaaccauga aacgcuacua acuacaggaa gcaaacuaag cccccgcugu    780
aaugaaacac cuucucugga gccaagucca gauuuacacu gggagaggug ccagcaacug    840
aauaaauacc ucucccagug uaaaucugga gccaagucca gauuuacacu gggagaggug    900
ccagcaacug aauaaauacc ucuuagcuga gugg    934
```

<210> SEQ ID NO 54
<211> LENGTH: 247
<212> TYPE: PRT
<213> ORGANISM: Homo sapiens

<400> SEQUENCE: 54

```
Met Gln Pro Ile Leu Leu Leu Ala Phe Leu Leu Pro Arg Ala
1               5                   10                  15

Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Arg Asp Asp Phe Val Leu Thr Ala Ala His
    50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245
```

<210> SEQ ID NO 55
<211> LENGTH: 7123
<212> TYPE: RNA
<213> ORGANISM: Homo sapiens

```
<400> SEQUENCE: 55
aucgaggucc gcgggaggcu cggagcgcgc caggcggaca cucccucucgg cuccuccccg      60 gcagcggcgg cggcucggag cgggcuccgg ggcucgggug cagcggccag cgggcgccug     120
gcggcgagga uuaccggggg aagugguugu cuccuggcug gagccgcgag acgggcgcuc     180
agggcgcggg gccggcggcg gcgaacgaga ggacggacuc uggcggccgg gucguuggcc     240
gcggggagcg cgggcaccgg gcgagcaggc cgcgucgcgc ucaccauggu cagcuacugg     300
gacaccgggg uccugcugug cgcgcugcuc agcugucugc uucucacagg aucuaguuca     360
gguucaaaau uaaaagaucc ugaacugagu uuaaaaggca cccagcacau caugcaagca     420
ggccagacac ugcaucucca augcaggggg gaagcagccc auaaaugguc uuugccugaa     480
auggugagua aggaaagcga aaggcugagc auaacuaaau cugccugugg aagaaauggc     540
aaacaauucu gcaguacuuu aaccuugaac acagcucaag caaaccacac uggcuucuac     600
agcugcaaau aucagcugu accuacuuca aagaagaagg aaacagaauc ugcaaucuau     660
auauuuauua gugauacagg uagaccuuuc guagagaugu acagugaaau ccccgaaauu     720
auacacauga cugaaggaag ggagcucguc auucccugcc ggguuacguc accuaacauc     780
acuguuacuu uaaaaaaguu uccacuugac acuuugaucc cugauggaaa acgcauaauc     840
ugggacagua gaaagggcuu caucauauca aaugcaacgu acaaagaaau agggcuucug     900
accugugaag caacagucaa uggguuugcuuu auaagacaa acuaucucac acaucgacaa     960
```

```
ggugucccg  agccucagau  cacuugguuu  aaaacaaacc  acaaaauaca  acaagagccu  2400
ggaauuauuu  uaggaccagg  aagcagcacg  cuguuuauug  aaagagucac  agaagaggau  2460
gaaggugucu  aucacugcaa  agccaccaac  cagaagggcu  cuguggaaag  uucagcauac  2520
cucacuguuc  aaggaaccuc  ggacaagucu  aaucuggagc  ugaucacucu  aacaugcacc  2580 ugugggcug   cgacucucuu  cuggcuccua  uuaaccccucu  uuauccgaaa  aaugaaaagg  2640 ucuucuucg   aaauaaagac  ugacuaccua  ucaauuauaa  uggacccaga  ugaaguuccu  2700
uuggaugagc  aguguagcg   gcuccuuau   gaugccagca  agugggaguu  ugcccgggag  2760
agacuuaaac  uggcaaauc   acuuggaaga  ggggcuuuug  gaaaaguggu  ucaagcauca  2820
gcauuuggca  uuaagaaauc  accacugugc  cggacugugg  cugugaaaau  gcugaaagag  2880
ggggccacgg  ccagcgagua  caaagcucug  augacgagc   uaaaaaucuu  gacccacauu  2940
ggccaccauc  ugaacguggu  uaaccugcug  ggagccugca  ccaagcaagg  agggccucug  3000
auggugauug  uugaauacug  caaauaugga  aaucucucca  acuaccucaa  gagcaaacgu  3060
gacuuauuuu  uucaacaa    ggaugcagca  cuacacaugg  agccuaagaa  agaaaaaaug  3120
gagccaggcc  uggaacaagg  caagaaacca  agacuagaua  gcgucaccag  cagcgaaagc  3180
uuugcgagcu  ccggccuuuca  ggaagauaaa  agucugagug  auguugagga  agaggaggau  3240
ucugacgguu  ucuacaagga  gcccaucacu  auggaagauc  ugauucuua   caguuuucaa  3300 guggccagag  gcauggaguu  ccugcucucc  agaaagugca  ucaucggga   ccuggcagcg  3360 agaaacauuc  uuuuaucuga  gaacaacgug  gugaagauuu  ugauuuuugg  ccugcccgg   3420 gauauuuaua  agaaccccga  uuaugugaga  aaggagauua  cucgacuucc  ucugaaaugg  3480
auggcuccug  aaucuaucuu  ugacaaaauc  uacagcacca  agagcgacgu  guggucuuac  3540
ggaguauugc  uguggaaauu  cuucuccuua  ggugggucuc  caucccagg  aguacaaaug  3600 gaugaggacu  uugcagucg   ccugagggaa  ggcaugagga  ugagagcucc  ugaguacucu  3660
acuccugaaa  ucuaucagau  caugcuggac  ugcuggcaca  gagacccaaa  agaaaggcca  3720
agauuugcag  aacuugugga  aaaacuaggu  gauuugcuuc  aagcaaaugu  acaacaggau  3780
gguaaagacu  acauccccaau  caaugccaua  cugacaggaa  auagugggguu  uacauacuca  3840 acuccugccu  ucucugagga  cuucuucaag  gaaaguauuu  cagcuccgaa  guuuaauuca  3900
ggaagcucug  augaugucag  auacguaaau  gcuuucaagu  caugagccu   ggaaagaauc  3960 aaaaccuuug  aagaacuuuu  accgaaugcc  accccaugu   uugaugacua  ccagggcgac  4020
agcagcacuc  uguuggccuc  ucccaugcug  aagcgcuuca  ccuggacuga  cagcaaaccc  4080
aaggccucgc  ucaagauuga  cuugagagua  accaguaaaa  guaaggaguc  ggggcugucu  4140
gaugucagca  ggcccaguuu  cugccauucc  agcugugggc  acgucagcga  aggcaagcgc  4200
agguucaccu  acgaccacgc  ugagcuggaa  aggaaaaucg  cgucugcuc   cccgccccca  4260 gacuacaacu  cgguggguccu  guacuccacc  ccacccaucu  agaguuugac  acgaagccuu  4320
auuucuagaa  gcacauguau  auuuauaccc  ccaggaaacu  agcuuuugcc  aguauuaugc  4380
auauauaagu  uuaaccuuuu  aucuuuccau  gggagccagc  ugcuuuugu   gauuuuuua   4440 auagugcuuu  uuuuuuuug   acuaacaaga  auguaacucc  agauagagaa  auagugacaa  4500
gugaagaaca  cuacugcuaa  auccucaugu  uacucagugu  uagagaaauc  cuuccuaaac  4560
ccaaugacuu  cccugcucca  accccgccca  ccucaggggca  cgcaggacca  guuugauuga  4620
ggagcugcac  ugaucaccca  augcaucacg  uaccccacug  ggccagcccu  gcagcccaaa  4680
acccagggca  acaagcccgu  uagccccagg  gaucacuggc  uggccugagc  aacaucucgg  4740
```

```
gaguccucua gcaggccuaa gacaugugag gaggaaaagg aaaaaaagca aaaagcaagg    4800
gagaaaagag aaaccgggag aaggcaugag aaagaauuug agacgcacca ugugggcacg    4860 gaggggacg gggcucagca augccauuuc aguggcuucc cagcucugac ccuucuacau     4920
uugagggccc agccaggagc agauggacag cgaugagggg acauuuucug gauucuggga    4980
ggcaagaaaa ggacaaauau cuuuuuugga acuaaagcaa auuuagaac uuuaccuaug     5040 gaagugguuc uauguccauu cucauucgug gcauguuuug auuuguagca cugagggugg    5100
cacucaacuc ugagcccaua cuuuuggcuc cucuaguaag augcacugaa aacuuagcca    5160
gaguuagguu gucuccaggc caugauggcc uuacacugaa aaugcacau ucuauuuugg     5220 guauuaauau auaguccaga cacuuaacuc aauuucuugg uauuauucug uuuugcacag    5280
uuaguuguga aagaaagcug agaagaauga aaaugcaguc cugaggagag gaguuuucuc    5340
cauaucaaaa cgagggcuga uggaggaaaa aggucaauaa ggucaaggga aaaccccguc    5400
ucuauaccaa ccaaaccaau ucaccaacac aguugggacc caaaacacag gaagucaguc    5460
acguuuccuu uucauuuaau ggggauucca cuaucucaca cuaacugaa aggaugugga    5520 agagcauuag cuggcgcaua uuaagcacuu uaagcccuu gaguaaaaag gugguaugua    5580
auuuaugcaa gguauuucuc caguugggac ucaggauauu aguaaugag ccaucacuag     5640 aagaaaagcc cauuucaac ugccuugaaa cuugccuggg gucugagcau gaugggaaua     5700
gggagacagg uaggaaagg cgccuacuc uucagggucu aaagaucaag ugggccuugg     5760
aucgcuaagc uggcucuguu ugaugcuauu uaugcaaguu agggucuaug uauuuaugau    5820
gucugcaccu ucugcagcca gucagaagcu ggagaggcaa caguggauug cugcuucuug    5880
gggagaagag uaugcuuccu uuuauccaug uaauuuaacu guagaaccug agcucuaagu    5940
aaccgaagaa uguaugccuc uguucuuaug ugccacaucc uuguuaaag gcucucugua    6000 ugaagagaug ggaccgucau cagcacauuc ccuagugagc cuacuggcuc cuggcagcgg    6060
cuuuugugga agacucacua gccagaagag aggagugga cagccucuc caccaagauc     6120 uaaauccaaa caaaagcagg cuagagccag aagagaggac aaaucuuugu ucuuccucuu    6180
cuuuacauac gcaaaccacc uguaacgcu ggcaauuuua uaaaucaggu aacuggaagg     6240
agguuaaaca cagaaaaag aagaccucag ucaauucucu acuuuuuuu uuuuuccaa       6300 aucagauaau agcccagcaa auagugauaa caaauaaaac cuuagcuauu caugucuuga    6360
uuucaauaau uaauucuuaa ucauuaagag accauaauaa auacuccuuu ucaagagaaa    6420
agcaaaacca uuagaauugu uacucagcuc cuucaaacuc agguuuguag cauacaugag    6480
uccauccauc agucaaagaa ugguuccauc uggagucuua auguagaaag aaaaauggag    6540
acuuguaaua augagcuagu uacaagugc uguucauua aaauagcacu gaaaauugaa      6600
acaugaauua acugauaaua uuccaaucau uugccauuua ugacaaaaau gguuggcacu    6660
aacaaagaac gagcacuucc uuucagaguu ucugagauaa uguacgugga acagucuggg    6720
uggaaugggg cugaaaccau gugcaagucu gugucuuguc agccaagaa gugacaccga    6780 gauguuaauu uagggacccc gugccuuguu uccuagccca caagaaugca aacaucaaac    6840
agauacucgc uagccucauu uaaauugauu aaaggaggag ugcaucuuug gccgacagug    6900
guguaacugu augugugugu gugugugugu gugugugugu gugugugggu guaugugugu    6960
uuugugcaua acuauuuaag gaaacuggaa uuuuaaaguu acuuuauac aaaccaagaa     7020 uauaugcuac agauauaaga cagacauggu uuggccuau auuucuaguc augaugaaug    7080
uauuuuguau accaucuuca uauaauaaac uuccaaaaac aca                     7123
```

```
<210> SEQ ID NO 56
<211> LENGTH: 1338
<212> TYPE: PRT
<213> ORGANISM: Homo sapiens

<400> SEQUENCE: 56

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380
```

```
Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
            450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
            485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
            530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
            725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
            755                 760                 765

Ala Thr Leu Phe Trp Leu Leu Leu Thr Leu Phe Ile Arg Lys Met Lys
            770                 775                 780

Arg Ser Ser Ser Glu Ile Lys Thr Asp Tyr Leu Ser Ile Ile Met Asp
785                 790                 795                 800
```

-continued

Pro Asp Glu Val Pro Leu Asp Glu Gln Cys Glu Arg Leu Pro Tyr Asp
            805                 810                 815

Ala Ser Lys Trp Glu Phe Ala Arg Glu Arg Leu Lys Leu Gly Lys Ser
        820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
            885                 890                 895

Ala Cys Thr Lys Gln Gly Gly Pro Leu Met Val Ile Val Glu Tyr Cys
        900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
            965                 970                 975

Leu Ser Asp Val Glu Glu Glu Asp Ser Asp Gly Phe Tyr Lys Glu
        980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

| | | | | | | | | | | | |
|---|---|---|---|---|---|---|---|---|---|---|---|
| Asn | Ser | Gly | Ser | Ser | Asp | Asp | Val | Arg | Tyr | Val | Asn | Ala | Phe | Lys |
| 1205 | | | | | 1210 | | | | | 1215 | | | | |
| Phe | Met | Ser | Leu | Glu | Arg | Ile | Lys | Thr | Phe | Glu | Glu | Leu | Leu | Pro |
| 1220 | | | | | 1225 | | | | | 1230 | | | | |
| Asn | Ala | Thr | Ser | Met | Phe | Asp | Asp | Tyr | Gln | Gly | Asp | Ser | Ser | Thr |
| 1235 | | | | | 1240 | | | | | 1245 | | | | |
| Leu | Leu | Ala | Ser | Pro | Met | Leu | Lys | Arg | Phe | Thr | Trp | Thr | Asp | Ser |
| 1250 | | | | | 1255 | | | | | 1260 | | | | |
| Lys | Pro | Lys | Ala | Ser | Leu | Lys | Ile | Asp | Leu | Arg | Val | Thr | Ser | Lys |
| 1265 | | | | | 1270 | | | | | 1275 | | | | |
| Ser | Lys | Glu | Ser | Gly | Leu | Ser | Asp | Val | Ser | Arg | Pro | Ser | Phe | Cys |
| 1280 | | | | | 1285 | | | | | 1290 | | | | |
| His | Ser | Ser | Cys | Gly | His | Val | Ser | Glu | Gly | Lys | Arg | Arg | Phe | Thr |
| 1295 | | | | | 1300 | | | | | 1305 | | | | |
| Tyr | Asp | His | Ala | Glu | Leu | Glu | Arg | Lys | Ile | Ala | Cys | Cys | Ser | Pro |
| 1310 | | | | | 1315 | | | | | 1320 | | | | |
| Pro | Pro | Asp | Tyr | Asn | Ser | Val | Val | Leu | Tyr | Ser | Thr | Pro | Pro | Ile |
| 1325 | | | | | 1330 | | | | | 1335 | | | | |

<210> SEQ ID NO 57
<211> LENGTH: 2545
<212> TYPE: RNA
<213> ORGANISM: Homo sapiens

<400> SEQUENCE: 57

```
auccaauaca ggagugacuu ggaacuccau ucuaucacua ugaagaaaag uggguguucuu      60
uuccucuugg gcaucaucuu gcugguucug auuggagugc aaggaacccc aguagugaga     120
aagggucgcu guccugcau cagcaccaac caagggacua uccaccuaca auccuugaaa      180
gaccuuaaac aauuugcccc aagcccuucc ugcgagaaaa uugaaaucau ugcuacacug     240
aagaauggag uucaaacaug ucuaaaccca gauucagcag augugaagga acugauuaaa     300
aaguggggaga acaggucag ccaaaagaaa aagcaaaaga augggaaaaa acaucaaaaa     360
aagaaaguuc ugaaaguucg aaaaucucaa cguucucguc aaaagaagac uacauaagag     420
accacuucac caauaaguau ucuguguuaa aaauguucua uuuuaauuau accgcuauca     480
uuccaaagga ggauggcaua uaauacaaag gcuuauuaau uugacuagaa aauuuaaaac     540
auuacucuga aauuguaacu aaaguuagaa aguugauuuu aagaauccaa acguuaagaa     600
uuguuaaagg cuaugauugu cuuuguucuu cuaccaccca ccaguugaau ucaucaugc      660
uuaaggccau gauuuuagca auacccaugu cuacacagau guucacccaa ccacauccca     720
cucacaacag cugccuggaa gagcagcccu aggcuuccac guacugcagc uccagagag      780
uaucugaggc acaugucagc aaguccuaag ccuguuagca ugcuggugag ccaagcaguu     840
ugaaauugag cuggaccuca ccaagcugcu guggccauca acccucuguau uugaaucagc     900
cuacaggccu cacacacaau ugucugaga gauucaugcu gauuguuauu ggguauucacc     960
acuggagauc accagugugu ggcuucagaa gccuccuuuc uggcuuugga agccaugauga   1020
uuccaucuug cccgcucagg cugaccacuu uauuucuuuu uguucccuu ugcuucauuc     1080
aagucagcuc uuccaauccc uaccacaaug cagcgccuuu cuucucucca gugcaccguu    1140
cauaugcucu gauuauacug agucaacucc uuucaucaucu ugccccaac accccacaga    1200
agugcuuucu ucucccaauu caucucacuu cagccagcu uaguucaagu ccugccucuu     1260
aaauaaaccu uuuuggacac acaaauuauc uuaaaacucc uguuucacuu gguucaguac   1320
```

```
cacaugggug  aacacucaau  gguuaacuaa  ucuuggguu  uuauccuau  cucuccaacc   1380 agauugucag  cuccuugagg  gcaagagcca  caguauauuu  cccuguuucu  uccacagugc   1440
cuaauaauac  ugggaacua   gguuuuaaua  auuuuuaau   ugauguuguu  augggcagga   1500
uggcaaccag  accauugucu  cagagcaggu  gcuggcucuu  uccuggcuac  uccauguugg   1560
cuagccucug  guaaccucuu  acuuauuauc  uucaggacac  ucacuacagg  gaccagggau   1620
gaugcaacau  ccuugucuuu  uuaugacagg  auguuugcuc  agcuucucca  acaauaagaa   1680
gcacguggua  aaacacuugc  ggauauucug  gacuguuuuu  aaaaauaua   caguuuaccg   1740 aaaaucauau  aaucuuacaa  ugaaaaggac  uuuauagauc  agccagugac  caaccuuuuc   1800
ccaaccauac  aaaaauuccu  uuucccgaag  gaaaagggcu  uucucaauaa  gccucagcuu   1860
ucuaagaucu  aacaagauag  ccaccgagau  ccuuaucgaa  acucauuuua  ggcaaauaug   1920
aguuuuauug  uccguuuacu  uguuucagag  uuuguauugu  gauuaucaau  uaccacacca   1980
ucucccauga  agaaagggaa  cggugaagua  cuaagcgcua  gaggaagcag  ccaagucggu   2040
uaguggaagc  augauuggug  cccaguuagc  cucugcagga  uguggaaacc  uccuuccagg   2100
ggagguucag  ugaauugugu  aggagagguu  gucuguggcc  agaauuuaaa  ccuauacuca   2160 cuuuccaaa   uugaaucacu  gcucacacug  cugaugauuu  agaugcugu   ccgguggaga   2220 ucccacccga  acgucuuauc  uaaucaugaa  acucccuagu  uccuucaugu  aacuucccug   2280
aaaaaucuaa  guguuucaua  aauuugagag  ucugugaccc  acuuaccuug  caucucacag   2340
guagacagua  uauaacuaac  aaccaaagac  uacauauugu  cacugacaca  cacguuauaa   2400
ucauuuauca  uauauauaca  uacaugcaua  cacucucaaa  gcaaauaauu  uuucacuuca   2460
aaacaguauu  gacuuguaua  ccuuguaauu  ugaauauuu   ucuuuguuaa  aauagaaugg   2520
uaucaauaaa  uagaccauua  aucag                                           2545
```

<210> SEQ ID NO 58
<211> LENGTH: 125
<212> TYPE: PRT
<213> ORGANISM: Homo sapiens

<400> SEQUENCE: 58

```
Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Val Leu Lys
            100                 105                 110

Val Arg Lys Ser Gln Arg Ser Arg Gln Lys Lys Thr Thr
        115                 120                 125
```

<210> SEQ ID NO 59
<211> LENGTH: 1172
<212> TYPE: RNA
<213> ORGANISM: Homo sapiens

<400> SEQUENCE: 59

```
gagacauucc ucaauugcuu agacauauuc ugagccuaca gcagaggaac cuccagucuc    60
agcaccauga aucaaacugc gauucugauu ugcugccuua ucuuucugac ucuaagugoc   120
auucaaggag uaccucucuc uagaaccgua cgcuguaccu gcaucagcau uaguaaucaa   180
ccuguuaauc caaggucuuu agaaaaacuu gaaauuauuc cugcaagcca auuuugucca   240
cguguugaga ucauugcuac aaugaaaaag aagggugaga agagaugucu gaauccagaa   300
ucgaaggcca ucaagaauuu acugaaagca guuagcaagg aaaugcuaaa aagaucuccu   360
uaaaaccaga ggggagcaaa aucgaugcag ugcuuccaag gauggaccac acagaggcug   420
ccucucccau cacuucccua cauggaguau augucaagcc auaauguuuc uuaguuugca   480
guuacacuaa aaggugacca augauggucca ccaaaucagc ugcuacuacu ccuguaggaa   540
gguuaauguu caucauccua agcuauucag uaauaacucu acccuggcac uauaauguaa   600
gcucuacuga ggugcuaugu ucuuaguggga uguucugacc cugcuucaaa uauuucccuc   660
accuuuccca ucuuccaagg guacuaagga aucuuucugc uuuggggoouu aucgaauuc    720
ucagaaucuc aaauaacuaa aagguaugca aucaaaucug cuuuuuaaag aaugcucuuu   780
acuucaugga cuuccacugc caucoucccca agggocccaa auucuuucag uggcuaccua   840
cauacaauuc caaacacaua caggaaggua gaaauaucug aaaaugua ug uguaaguauu   900
cuuauuuaau gaaagacugu acaaaguaua agucuuagau guauauauuu ccuauauugu   960
uuucagugua caaaggaauaa cauguaauua aguacuaugu aucaaugagu aacaggaaaa  1020
uuuuaaaaau acagauagau auaugcucug cauguuacau aagauaaaug ugcugaaugg  1080
uuuucaaaua aaaaugaggu acucuccugg aaauauuaag aaagacuauc uaaauguuga  1140
aagaucaaaa gguuaauaaa guaauuauaa cu                                1172
```

<210> SEQ ID NO 60
<211> LENGTH: 98
<212> TYPE: PRT
<213> ORGANISM: Homo sapiens

<400> SEQUENCE: 60

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 61
<211> LENGTH: 995
<212> TYPE: RNA
<213> ORGANISM: Homo sapiens

<400> SEQUENCE: 61

```
gaauucggcc aaagaggccu acuuccaaga agagcagcaa agcugaagua gcagcaacag      60
caccagcagc aacagcaaaa aacaaacaug agugugaagg gcauggcuau agccuuggcu     120
gugauauugu gugcuacagu uguucaaggc uuccccaugu ucaaagagg acgcugucuu     180
ugcauaggcc cuggguaaa agcagugaaa guggcagaua uugagaaagc cuccauaaug     240
uacccaagua acaacuguga caaaauagaa gugauuauua cccugaaaga aaauaaagga     300
caacgaugcc uaaaucccaa aucgaagcaa gcaaggcuua uaaucaaaaa aguugaaaga     360
aagaauuuuu aaaauauca aaacauauga aguccuggaa aagggcaucu gaaaaaccua     420
gaacaaguuu aacgugacu acugaaauga caagaauucu acaguaggaa acugagacuu     480
uucuauggu uugugacuuu caacuuuugu acaguuaugu gaaggaugaa aggguggua     540
aaggaccaaa aacagaaaua cagucuuccu gaaugaauga caaucagaau uccacugccc     600
aaaggagucc aacaauuaaa uggauuucua ggaaaagcua ccuuaagaaa ggcugguuac     660
caucggaguu uacaaagugc uuucacguuc uuacuguug uauuauacau ucaugcauuu     720
cuaggcuaga gaaccuucua gauuugaugc uuacaacuau ucguuguga cuaugagaac     780
auuucugucu cuagaaguua ucugucugua uugaucuuua ugcuauauua cuaucugugg     840
uuacagugga gacauugaca uuauuacugg agucaagccc uuauaaguca aaagcaccua     900
ugugucguaa agcauuccuc aaacauuuaa aaaaaaaaa aaaaaaaaa aaaaaaaaaa     960
aaaaaaaaa aaaaaaaaa aaaaaagcg gccgc                                    995
```

```
<210> SEQ ID NO 62
<211> LENGTH: 94
<212> TYPE: PRT
<213> ORGANISM: Homo sapiens

<400> SEQUENCE: 62
```

```
Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```

```
<210> SEQ ID NO 63
<211> LENGTH: 10
<212> TYPE: PRT
<213> ORGANISM: Artificial Sequence
<220> FEATURE:
<223> OTHER INFORMATION: Synthetic Construct

<400> SEQUENCE: 63
```

```
Gly Phe Thr Phe Ser Asp Ser Trp Ile His
1               5                   10
```

```
<210> SEQ ID NO 64
<211> LENGTH: 18
<212> TYPE: PRT
<213> ORGANISM: Artificial Sequence
<220> FEATURE:
<223> OTHER INFORMATION: Synthetic Construct

<400> SEQUENCE: 64

Ala Trp Ile Ser Pro Tyr Gly Gly Ser Thr Tyr Tyr Ala Asp Ser Val
1               5                   10                  15

Lys Gly

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Arg His Trp Pro Gly Gly Phe Asp Tyr
1               5

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

<400> SEQUENCE: 66

Arg Ala Ser Gln Asp Val Ser Thr Ala Val Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct

<400> SEQUENCE: 67

Ser Ala Ser Phe Leu Tyr Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Gln Gln Tyr Leu Tyr His Pro Ala Thr
1               5

<210> SEQ ID NO 69
<211> LENGTH: 118
<212> TYPE: PRT
<213> ORGANISM: Artificial Sequence
<220> FEATURE:
<223> OTHER INFORMATION: Synthetic Construct
```

-continued

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 70
<211> LENGTH: 108
<212> TYPE: PRT
<213> ORGANISM: Artificial Sequence
<220> FEATURE:
<223> OTHER INFORMATION: Synthetic Construct

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 71
<211> LENGTH: 447
<212> TYPE: PRT
<213> ORGANISM: Artificial Sequence
<220> FEATURE:
<223> OTHER INFORMATION: Synthetic Construct

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 72
<211> LENGTH: 214
<212> TYPE: PRT
<213> ORGANISM: Artificial Sequence
<220> FEATURE:
<223> OTHER INFORMATION: Synthetic Construct
```

-continued

```
<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 440
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Val Glu Ser Gly Gly Gly Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125
```

```
Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 74
<211> LENGTH: 214
<212> TYPE: PRT
<213> ORGANISM: Artificial Sequence
<220> FEATURE:
<223> OTHER INFORMATION: Synthetic Construct

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Ser Ser Asn Trp Pro Arg
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
210

<210> SEQ ID NO 75
<211> LENGTH: 2502
<212> TYPE: RNA
<213> ORGANISM: Homo sapiens

<400> SEQUENCE: 75
uauucaucaa gugcccucua gcuguuaagu cacucugauc ucgacugca gcuccuacug      60 uuggacacac cuggccggug cuucaguuag aucaaaccau ugcugaaacu gaagaggaca    120
ugucaaauau uacagaucca cagaugugggg auuuugauga ucuaaauuuc acuggcaugc   180
caccugcaga ugaagauuac agccccugua ugcuagaaac ugagacacuc aacaaguaug    240
uugugaucau cgccuaugcc cuagugauucc ugcuagccu gcugggaaac ucccugguga   300
ugcuggucau cuuauacagc agggucggcc gcuccgucac ugaugucuac cugcugaacc    360
uggccuuggc cgaccacuc uuugcccuga ccuugcccau cuggggccgcc uccaagguga    420 auggcuggau uuuggcaca uuccugugca aggugggucuc acuccugaag gaagucaacu    480
ucuacagugg cauccugcug uggccugca ucagugguga ccguuaccug gccauugucc    540
augccacacg cacacugacc cagaagcguc acuggucaa guuuguuugu cuuggcugcu    600
ggggacuguc uaugaaucug ucccugcccu ucuuccuuuu ccgccaggcu uaccauccaa    660
acaauuccag uccaguuugc uaugaggucc ugggaaauga cacagcaaaa uggcggaugg    720
uguugcggau ccugccucac accuuuggcu ucaucgugcc gcuguuuguc augcuguucu    780
gcuauggauu cacccugcgu acacuguuua aggcccacau ggggcagaag caccgagcca    840
ugagggucau cuuugcuguc guccucaucu uccugcuuug cuggcugccc uacaaccugg    900
uccugcuggc agacacccuc augaggaccc aggugaucca ggagagcugu gagcgccgca    960
acaacaucgg ccgggcccug gaugccacug agauucuggg auuucccau agcugccuca   1020 accccaucau cuacgccuuc aucggccaaa auuuucgcca uggauccuc aagauccugg   1080 cuaugcaugg ccuggucagc aaggaguucu uggcacguca ucguguuacc ccuacacuu    1140
```

| | |
|---|---|
| cuucgucugu caaugucucu uccaaccucu gaaaaccauc gaugaaggaa uaucucuucu | 1200 |
| cagaaggaaa gaauaaccaa cacccugagg uugugugugg aaggugaucu ggcucuggac | 1260 |
| aggcacuauc uggguuuugg ggggacgcua uaggaugugg ggaaguuagg aacuggaguc | 1320 |
| uucagggggcc acaccaaccu ucugaggagc uguugaggua ccuccaagga ccggccuuug | 1380 |
| caccuccaug gaaacgaagc accaucauuc ccguugaacg ucacaucuuu aacccacuaa | 1440 |
| cuggcuaauu agcauggcca caucugagcc ccgaaucuga cauuagauga gagaacaggg | 1500 |
| cugaagcugu guccucauga gggcuggaug cucucguuga cccucacagg agcaucuccu | 1560 |
| caacucugag uguuaagcgu ugagccacca agcugguggc ucugugugcu cugauccgag | 1620 |
| cucagggggg ugguuuuccc aucucaggug uguugcagug ucgcuggag acauugaggc | 1680 |
| aggcacugcc aaaacaucaa ccugccagcu ggccuuguga ggagcuggaa acacauguuc | 1740 |
| cccuugggggg uggguggauga acaaagagaa agagggguuug gaagccagau cuaugccaca | 1800 |
| agaaccccccu uuaccccccau gaccaacauc gcagacacau gugcuggcca ccugcugagc | 1860 |
| cccaagugga acgagacaag cagcccuuag cccuucccccu cugcagcuuc caggcuggcg | 1920 |
| ugcagcauca gcaucccuag aaagccaugu gcagccacca guccauuggg caggcagaug | 1980 |
| uuccuaauaa agcuucuguu ccgugcuugu cccuguggaa guaucuuggu ugugacagag | 2040 |
| ucaagggugu gugcagcauu guuggcuguu ccugcaguag aaugggggca gcaccuccua | 2100 |
| agaaggcacc ucucugggguu gaagggcagu guucccuggg gcuuuaacuc cugcuagaac | 2160 |
| agucucuuga ggcacagaaa cuccuguuca ugcccauacc ccuggccaag gaagaucccu | 2220 |
| uuguccacaa guaaaaggaa augcuccucc agggaguccuc agcuuacccc ugaggugagc | 2280 |
| aucaucuucu gggguuaggcc uugccuaggc auagcccugc cucaagcuau gugagcucac | 2340 |
| caguccccucc ccaaaugcuu uccaugaguu gcaguuuuuu ccuagucugu uucccuccu | 2400 |
| uggagacagg gcccugucgg uuuauucacu guaugucuu ggugccugga gccuacuaaa | 2460 |
| ugcucaauaa auaaugauca caggaaaaaa aaaaaaaaaa aa | 2502 |

<210> SEQ ID NO 76
<211> LENGTH: 350
<212> TYPE: PRT
<213> ORGANISM: Homo sapiens

<400> SEQUENCE: 76

```
Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125
```

```
Ala Cys Ile Ser Val Asp Arg Tyr Leu Ala Ile Val His Ala Thr Arg
            130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
            195                 200                 205

Phe Gly Phe Ile Val Pro Leu Phe Val Met Leu Phe Cys Tyr Gly Phe
210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
            275                 280                 285

Ala Thr Glu Ile Leu Gly Phe Leu His Ser Cys Leu Asn Pro Ile Ile
290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350

<210> SEQ ID NO 77
<211> LENGTH: 2880
<212> TYPE: RNA
<213> ORGANISM: Homo sapiens

<400> SEQUENCE: 77
agguucaaaa cauucagaga cagaaggugg auagacaaau cuccaccuuc agacugguag    60
gcuccuccag aagccaucag acaggaagau gugaaaaucc ccagcacuca ucccagaauc   120 acuaagugge accuguccug gccaaaguc ccaggacaga ccucauuguu ccucuggga    180 aauaccuccc caggagggca uccuggauuu cccccuugca acccagguca gaaguuucau   240
cgucaagguu guuucaucuu uuuuuuccug ucuaacagcu cugacuacca cccaaccuug   300
aggcacagug aagacaucgg uggccacucc aauaacagca ggucacagcu gcucuucugg   360
aggguccuua caggugaaaa gcccagcgac ccagucagga uuuaaguuua ccucaaaaau   420
ggaagauuuu aacauggaga gugacagcuu ugaagauuuc uggaaaggug aagaucuuag   480
uaauuacagu uacagcucua cccugccccc uuuucuacua gaugccgccc caugugaacc   540
agaaucccug gaaaucaaca aguauuuugu ggucauuauc uaugcccugg uauuccugcu   600
gagccugcug ggaaacuccc ucgugaugcu ggucaucuua acagcaggg ucggccgcuc   660 cgucacugau gucuaccugc ugaaccuagc cuuggccgac cuacucuuug cccugaccuu   720
gcccaucugg gccgccucca aggugaaugg cuggauuuuu ggcacauucc ugugcaaggu   780
ggucucacuc cugaaggaag ucaacuucua uaguggcauc cugcuacugg ccugcaucag   840 ugugaccgu uaccuggcca uguccaugc cacacgcaca cugacccaga agcgcuacuu   900
```

| | | | |
|---|---|---|---|
| ggucaaauuc auaugucuca gcaucugggg ucugaccuug cuccuggccc ugccugucuu | 960 |
| acuuuuccga aggaccgucu acucauccaa uguuagccca gccugcuaug aggacauggg | 1020 |
| caacaauaca gcaaacuggc ggaugcuguu acggauccug ccccaguccu uuggcuucau | 1080 |
| cgugccacug cugaucaugc uguucugcua cggauucacc cugcguacgc uguuuaaggc | 1140 |
| ccacauggggg cagaagcacc gggccaugcg ggucaucuuu gcugucgucc ucaucuuccu | 1200 |
| gcucugcugg cugcccuaca accugguccu gcuggcagac acccucauga ggacccaggu | 1260 |
| gauccaggag accugugagc gccgcaauca caucgaccgg gcucuggaug ccaccgagau | 1320 |
| ucugggcauc cuucacagcu gccucaaccc ccucaucuac gccuucauug ccagaaguu | 1380 |
| ucgccaugga cuccucaaga uucuagcuau acauggcuug aucagcaagg acucccugcc | 1440 |
| caaagacagc aggccuuccu uuguggcuc ucuucaggg cacacuucca cuacucucua | 1500 |
| agaccuccug ccuaagugca gccccguggg guuccuccu ucucuucaca gucacauucc | 1560 |
| aagcccaug uccacugguu cuucuuggc ucagugucaa ugcagccccc auuguggca | 1620 |
| caggaaguag aggaggccac guucuuacua guuucccuug caugguuuag aaagcuugcc | 1680 |
| cuggugccuc accccuugcc auaauuacua ugcauuugc uggagcucug cccauccugc | 1740 |
| cccugagccc auggcacucu auguucuaag aagugaaaau cuacacucca gugagacagc | 1800 |
| ucugcauacu cauuaggaug gcuaguauca aagaaagaa aaucaggcug gccaacgggg | 1860 |
| ugaaacccug ucucuacuaa aaauacaaaa aaaaaaaaaa auuagccggg cgugguggug | 1920 |
| agugccugua aucacagcua cuuggggggc ugagauggga gaaucacuug aacccgggag | 1980 |
| gcagagguug cagugagccg agauugugcc ccugcacucc agccgagcg acagugagac | 2040 |
| ucugucucag uccaugaaga uguagaggag aaacuggaac ucgagcgu gcugggggg | 2100 |
| gauuguaaaa uggugugacc acugcagaag acaguauggc agcuuccuc aaaacuucag | 2160 |
| acauagaauu aacacaugau ccugcaauuc cacuuauagg aauugaccca caagaaauga | 2220 |
| aagcagggac uugaacccau auuuguacac caauauucau agcagcuuau ucacaagacc | 2280 |
| caaaaggcag aagcaaccca aauguucauc aaugaaugaa ugaauggcua agcaaaaugu | 2340 |
| gauaugauacc uaacgaagua uccuucagcc ugaaagagga augaaguacu cauacauguu | 2400 |
| acaacacgga cgaaccuuga aaacuuuaug cuaagugaaa uaagccagac aucaacagau | 2460 |
| aaauaguuua ugauuccacc uacaugaggu acugagagug aacaaauuua cagagacaga | 2520 |
| aagcagaaca gugauuacca gggacugagg ggagggggagc augggaagug acgguuuaau | 2580 |
| gggcacaggg uuuauguuua ggauguugaa aaaguucugc agauaaacag uaguauagu | 2640 |
| uguaccgcaa ugugacuuaa ugccacuaaa uugacacuua aaaaugguuu aaauggucaa | 2700 |
| uuuuguuaug uauauuuuau aucaauuuaa aaaaaaaccu gagccccaaa agguauuuua | 2760 |
| aucaccaagg cugauuaaac caaggcuaga accaccugcc uauauuuuu guuaaaugau | 2820 |
| uucauucaau aucuuuuuuu uaauaaacca uuuuuacuug ggguguuaua aaaaaaaaaa | 2880 |

<210> SEQ ID NO 78
<211> LENGTH: 360
<212> TYPE: PRT
<213> ORGANISM: Homo sapiens

<400> SEQUENCE: 78

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

| | | | | | | | | | | | | |
|---|---|---|---|---|---|---|---|---|---|---|---|---|
|Leu|Leu|Asp|Ala|Ala|Pro|Cys|Glu|Pro|Glu|Ser|Leu|Glu|Ile|Asn|Lys|
| | |35| | | |40| | | |45| | |

Tyr Phe Val Val Ile Ile Tyr Ala Leu Val Phe Leu Leu Ser Leu Leu
    50              55              60

Gly Asn Ser Leu Val Met Leu Val Ile Leu Tyr Ser Arg Val Gly Arg
65              70              75              80

Ser Val Thr Asp Val Tyr Leu Leu Asn Leu Ala Leu Ala Asp Leu Leu
            85              90              95

Phe Ala Leu Thr Leu Pro Ile Trp Ala Ala Ser Lys Val Asn Gly Trp
            100             105             110

Ile Phe Gly Thr Phe Leu Cys Lys Val Val Ser Leu Leu Lys Glu Val
            115             120             125

Asn Phe Tyr Ser Gly Ile Leu Leu Leu Ala Cys Ile Ser Val Asp Arg
            130             135             140

Tyr Leu Ala Ile Val His Ala Thr Arg Thr Leu Thr Gln Lys Arg Tyr
145             150             155             160

Leu Val Lys Phe Ile Cys Leu Ser Ile Trp Gly Leu Ser Leu Leu Leu
                165             170             175

Ala Leu Pro Val Leu Leu Phe Arg Arg Thr Val Tyr Ser Ser Asn Val
            180             185             190

Ser Pro Ala Cys Tyr Glu Asp Met Gly Asn Asn Thr Ala Asn Trp Arg
            195             200             205

Met Leu Leu Arg Ile Leu Pro Gln Ser Phe Gly Phe Ile Val Pro Leu
            210             215             220

Leu Ile Met Leu Phe Cys Tyr Gly Phe Thr Leu Arg Thr Leu Phe Lys
225             230             235             240

Ala His Met Gly Gln Lys His Arg Ala Met Arg Val Ile Phe Ala Val
            245             250             255

Val Leu Ile Phe Leu Leu Cys Trp Leu Pro Tyr Asn Leu Val Leu Leu
            260             265             270

Ala Asp Thr Leu Met Arg Thr Gln Val Ile Gln Glu Thr Cys Glu Arg
            275             280             285

Arg Asn His Ile Asp Arg Ala Leu Asp Ala Thr Glu Ile Leu Gly Ile
            290             295             300

Leu His Ser Cys Leu Asn Pro Leu Ile Tyr Ala Phe Ile Gly Gln Lys
305             310             315             320

Phe Arg His Gly Leu Leu Lys Ile Leu Ala Ile His Gly Leu Ile Ser
            325             330             335

Lys Asp Ser Leu Pro Lys Asp Ser Arg Pro Ser Phe Val Gly Ser Ser
            340             345             350

Ser Gly His Thr Ser Thr Thr Leu
            355             360

<210> SEQ ID NO 79
<211> LENGTH: 532
<212> TYPE: RNA
<213> ORGANISM: Homo sapiens

<400> SEQUENCE: 79
gagaaaccag agacuguagc aacucuggca gggagaagcu gucucugaug gccugaagcu    60
gugggcagcu ggccaagccu aaccgcuaua aaaggagcu gccucucagc ccugcauguc    120 ucuugcagc ugucuuucag aagaccuggu ggggcaaguc cguggcauc auguugaccg    180 agcuggagaa agccuugaac ucuaucaucg acgucuacca caaguacucc cugauaaagg    240

```
ggaauuuucca ugccgucuac agggaugacc ugaagaaauu gcuagagacc gagugugccuc    300 aguauaucag gaaaaagggu gcagacgucu gguucaaaga guuggauauc aacacugaug     360
gugcaguuaa cuuccaggag uuccucauuc uggugauaaa gaugggcgug gcagcccaca     420
aaaaaagcca ugaagaaagc cacaaagagu agcugaguua cugggcccag aggcugggcc     480
ccuggacaug uaccugcaga uaauaaagu caucaauacc ucaaaaaaaa aa              532
```

<210> SEQ ID NO 80
<211> LENGTH: 93
<212> TYPE: PRT
<213> ORGANISM: Homo sapiens

<400> SEQUENCE: 80

```
Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90
```

<210> SEQ ID NO 81
<211> LENGTH: 586
<212> TYPE: RNA
<213> ORGANISM: Homo sapiens

<400> SEQUENCE: 81

```
aaacacucug uguggcuccu cggcuuugac agagugcaag acgaugacuu gcaaaaugu c    60 gcagcuggaa cgcaacauag agaccaucau caacaccuuc caccaauacu cugugaagcu   120 ggggcacccca gacacccuga accaggggga auucaaagag cuggugcgaa agaucugca   180 aaauuuucuc aagaaggaga auaagaauga aaaggucaua gaacacauca uggaggaccu   240
ggacacaaau gcagacaagc agcugagcuu cgaggaguuc aucaugcuga uggcgaggcu   300
aaccugggcc ucccacgaga agaugcacga gggugacgag ggcccuggcc accaccauaa   360
gccaggccuc ggggagggca cccccuaaga ccacaguggc caagaucaca guggccacgg   420
ccacggccac agucauggug gccacggcca cagccacuaa ucaggaggcc aggccacccu   480
gccucuaccc aaccagggcc ccggggccug uuaugucaaa cugucuuggc ugugggggcua  540 ggggcugggg ccaaauaaag ucucuuccuc caagucaaaa aaaaa                    586
```

<210> SEQ ID NO 82
<211> LENGTH: 114
<212> TYPE: PRT
<213> ORGANISM: Homo sapiens

<400> SEQUENCE: 82

```
Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30
```

```
Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
 50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                 85                  90                  95

Gly Asp Glu Gly Pro Gly His His His Lys Pro Gly Leu Gly Glu Gly
                100                 105                 110

Thr Pro
```

US 11,402,382 B2

DIAGNOSTIC AND THERAPEUTIC METHODS FOR CANCER

SEQUENCE LISTING

The instant application contains a Sequence Listing which has been submitted electronically in ASCII format and is hereby incorporated by reference in its entirety. Said ASCII copy, created on Aug. 19, 2019, is named 50474-164004_Sequence_Listing 08.19.19_ST25 and is 235,662 bytes in size.

FIELD OF THE INVENTION

The present invention is directed to diagnostic and therapeutic methods for the treatment of cancer. Also provided are related kits and assays.

BACKGROUND OF THE INVENTION

Cancer remains one of the most deadly threats to human health. In the U.S., cancer affects nearly 1.3 million new patients each year and is the second leading cause of death after heart disease, accounting for approximately 1 in 4 deaths. It is also predicted that cancer may surpass cardiovascular diseases as the number one cause of death within 5 years. Solid tumors are responsible for most of those deaths. Although there have been significant advances in the medical treatment of certain cancers, the overall 5-year survival rate for all cancers has improved only by about 10% in the past 20 years. Malignant solid tumors, in particular, metastasize and grow rapidly in an uncontrolled manner, making their timely detection and treatment extremely difficult.

Studies in humans with immune checkpoint inhibitors have demonstrated the promise of harnessing the immune system to control and eradicate tumor growth. The programmed death 1 (PD-1) receptor and its ligand programmed death-ligand 1 (PD-L1) are immune checkpoint proteins that have been implicated in the suppression of immune system responses during chronic infections, pregnancy, tissue allografts, autoimmune diseases, and cancer. PD-L1 regulates the immune response by binding to the inhibitory receptor PD-1, which is expressed on the surface of T-cells, B-cells, and monocytes. PD-L1 negatively regulates T-cell function also through interaction with another receptor, B7-1. Formation of the PD-L1/PD-1 and PD-L1/B7-1 complexes negatively regulates T-cell receptor signaling, resulting in the subsequent downregulation of T-cell activation and suppression of anti-tumor immune activity.

Despite the significant advancement in the treatment of cancer, improved diagnostic methods and cancer therapies and are still being sought.

SUMMARY OF THE INVENTION

The present invention provides diagnostic and therapeutic methods and compositions for treating an individual having a cancer (e.g., a kidney cancer (e.g., a renal cell carcinoma (RCC)), a lung cancer (e.g., a non-small cell lung cancer (NSCLC)), a bladder cancer (e.g., a urothelial bladder cancer (UBC)), a liver cancer (e.g., hepatocellular carcinoma (HCC)), an ovarian cancer, or a breast cancer (e.g., a triple-negative breast cancer (TNBC))).

In one aspect, the invention features a method of identifying an individual having a kidney cancer who may benefit from treatment with an anti-cancer therapy comprising a VEGF antagonist and a PD-L1 axis binding antagonist, the method comprising determining the expression level of one or more of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9; wherein (i) an expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample that is at or above a reference expression level of the one or more genes; or (ii) an expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample that is below a reference expression level of the one or more genes identifies the individual as one who may benefit from treatment with an anti-cancer therapy comprising a VEGF antagonist and a PD-L1 axis binding antagonist.

In another aspect, the invention features a method for selecting a therapy for an individual having a kidney cancer, the method comprising determining the expression level of one or more of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9; wherein (i) an expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample that is at or above a reference expression level of the one or more genes; or (ii) an expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample that is below a reference expression level of the one or more genes identifies the individual as one who may benefit from treatment with an anti-cancer therapy comprising a VEGF antagonist and a PD-L1 axis binding antagonist.

In some embodiments of any of the preceding aspects, the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is at or above a reference expression level of the one or more genes, and the method further comprises administering to the individual an effective amount of the anti-cancer therapy. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 is at or above a reference expression level of the one or more genes. In some embodiments, the expression level of one or more of CD8A, EOMES, PRF1, IFNG, or PD-L1 in the sample is at or above a reference expression level of the one or more genes. In some embodiments, the expression level of CD8A, EOMES, PRF1, IFNG, and PD-L1 in the sample is at or above a reference expression level of CD8A, EOMES, PRF1, IFNG, and PD-L1. In some embodiments, the expression level of one or more of IL6, CXCL1, CXCL2, CXCL3, CXCL8, PTGS2, CXCR1, CXCR2, S100A8, or S100A9 in the sample is at or above a reference expression level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is at or above a reference expression level of the one or more genes. In some embodiments, the expression level of IL6, CXCL1, CXCL2, CXCL3, CXCL8, PTGS2, CXCR1, CXCR2, S100A8, and S100A9 in the sample is at or above a reference expression level of IL6, CXCL1, CXCL2, CXCL3, CXCL8, PTGS2, CXCR1, CXCR2, S100A8, and S100A9.

In some embodiments of any of the preceding aspects, the expression level of PD-L1 in the sample is at or above a reference expression level of PD-L1, and the expression level of one or more additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, and TAP2 in the sample is at or above a reference expression level of the one or more additional genes.

In some embodiments of any of the preceding aspects, the expression level of one or more of VEGFA, KDR, ESM1, PECAM1, FLT1, ANGPTL4, or CD34 in the sample is below a reference level of the one or more genes, and the method further comprises administering to the individual an effective amount of the anti-cancer therapy. In some embodiments, the expression level of at least one, at least two, at least three, at least four, at least five, at least six, or all seven of VEGFA, KDR, ESM1, PECAM1, FLT1, ANGPTL4, or CD34 in the sample is below a reference level of the one or more genes In some embodiments, the expression level of one or more of VEGFA, KDR, ESM1, PECAM1, ANGPTL4, or CD34 in the sample is below a reference level of the one or more genes. In some embodiments, the expression level of VEGFA, KDR, ESM1, PECAM1, ANGPTL4, and CD34 in the sample is below a reference level of VEGFA, KDR, ESM1, PECAM1, ANGPTL4, and CD34. In some embodiments, the expression level of one or more of IL6, CXCL1, CXCL2, CXCL3, CXCL8, PTGS2, CXCR1, CXCR2, S100A8, or S100A9 in the sample is below a reference level of the one or more genes, and the method further comprises administering to the individual an effective amount of the anti-cancer therapy.

In some embodiments of any of the preceding aspects, the expression level of at least one, at least two, at least three, at least four, at least five, or all six of IL6, CXCL1, CXCL2, CXCL3, CXCL8, or PTGS2 in the sample is below a reference level of the one or more genes. In some embodiments, the expression level of IL6, CXCL1, CXCL2, CXCL3, CXCL8, PTGS2, CXCR1, CXCR2, S100A8, and S100A9 in the sample is below a reference level of IL6, CXCL1, CXCL2, CXCL3, CXCL8, PTGS2, CXCR1, CXCR2, S100A8, and S100A9.

In some embodiments of any of the preceding aspects, the expression level of one or more of VEGFA, KDR, ESM1, PECAM1, FLT1, ANGPTL4, or CD34 in the sample is at or above a reference level of the one or more genes, and the method further comprises administering to the individual an effective amount of an anti-cancer therapy comprising a VEGF antagonist. In some embodiments, the anti-cancer therapy further comprises a PD-L1 axis binding antagonist. In some embodiments, the expression level of at least one, at least two, at least three, at least four, at least five, at least six, or all seven of VEGFA, KDR, ESM1, PECAM1, FLT1, ANGPTL4, or CD34 is at or above a reference level of the one or more genes. In some embodiments, the expression level of one or more of VEGFA, KDR, ESM1, PECAM1, ANGPTL4, or CD34 in the sample is at or above a reference level of the one or more genes. In some embodiments, the expression level of VEGFA, KDR, ESM1, PECAM1, ANGPTL4, and CD34 in the sample is at or above a reference level of VEGFA, KDR, ESM1, PECAM1, ANGPTL4, and CD34.

In another aspect, the invention features a method of treating an individual having a kidney cancer, the method comprising: (a) determining the expression level of one or more of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9; wherein (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more genes; or (ii) the expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample is determined to be below a reference expression level of the one or more genes; and (b) administering an effective amount of an anti-cancer therapy comprising a VEGF antagonist and a PD-L1 axis binding antagonist to the individual based on the expression level of the one or more genes determined in step (a).

In some embodiments of any of the preceding aspects, the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference level of the one or more genes. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference level of the one or more genes. In some embodiments, the expression level of one or more of CD8A, EOMES, PRF1, IFNG, or PD-L1 in the sample is determined to be at or above a reference level of the one or more genes. In some embodiments, the expression level of CD8A, EOMES, PRF1, IFNG, and PD-L1 in the sample is determined to be at or above a reference level of CD8A, EOMES, PRF1, IFNG, and PD-L1. In some embodiments, the expression level of one or more of IL6, CXCL1, CXCL2, CXCL3, CXCL8, PTGS2, CXCR1, CXCR2, S100A8, or S100A9 in the sample is determined to be at or above a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is determined to be at or above a reference level of the one or more genes. In some embodiments, the expression level of IL6, CXCL1, CXCL2, CXCL3, CXCL8, PTGS2, CXCR1, CXCR2, S100A8, and S100A9 in the sample is determined to be at or above a reference level of IL6, CXCL1, CXCL2, CXCL3, CXCL8, PTGS2, CXCR1, CXCR2, S100A8, and S100A9.

In some embodiments of any of the preceding aspects, the expression level of PD-L1 in the sample is determined to be at or above a reference expression level of PD-L1, and the expression level of one or more additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more additional genes.

In some embodiments of any of the preceding aspects, the expression level of one or more of VEGFA, KDR, ESM1, PECAM1, FLT1, ANGPTL4, or CD34 in the sample is determined to be below a reference level of the one or more genes. In some embodiments, the expression level of at least one, at least two, at least three, at least four, at least five, at least six, or all seven of VEGFA, KDR, ESM1, PECAM1, FLT1, ANGPTL4, or CD34 in the sample is determined to be below a reference level of the one or more genes. In some embodiments, the expression level of one or more of VEGFA, KDR, ESM1, PECAM1, ANGPTL4, or CD34 in the sample is determined to be below a reference level of the one or more genes. In some embodiments, the expression level of VEGFA, KDR, ESM1, PECAM1, ANGPTL4, and CD34 in the sample is determined to be below a reference level of VEGFA, KDR, ESM1, PECAM1, ANGPTL4, and CD34.

In some embodiments of any of the preceding aspects, the expression level of one or more of IL6, CXCL1, CXCL2, CXCL3, CXCL8, PTGS2, CXCR1, CXCR2, S100A8, or S100A9 in the sample is determined to be below a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is determined to be below a reference level of the one or more genes. In some embodiments, the expression level of IL6, CXCL1, CXCL2, CXCL3, CXCL8, PTGS2, CXCR1, CXCR2, S100A8, and S100A9 in the sample is determined to be below a reference level of IL6, CXCL1, CXCL2, CXCL3, CXCL8, PTGS2, CXCR1, CXCR2, S100A8, and S100A9.

In another aspect, the invention provides a method of treating an individual having a kidney cancer, the method comprising administering to the individual an effective amount of an anti-cancer therapy comprising a VEGF antagonist and a PD-L1 axis binding antagonist, wherein prior to treatment (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more genes; or (ii) the expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample has been determined to be below a reference expression level of the one or more genes.

In some embodiments of any of the preceding aspects, the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference level of the one or more genes. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference level of the one or more genes. In some embodiments, the expression level of one or more of CD8A, EOMES, PRF1, IFNG, or PD-L1 in the sample has been determined to be at or above a reference level of the one or more genes. In some embodiments, the expression level of CD8A, EOMES, PRF1, IFNG, and PD-L1 in the sample has been determined to be at or above a reference level of CD8A, EOMES, PRF1, IFNG, and PD-L1. In some embodiments, the expression level of one or more of IL6, CXCL1, CXCL2, CXCL3, CXCL8, PTGS2, CXCR1, CXCR2, S100A8, or S100A9 in the sample has been determined to be at or above a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample has been determined to be at or above a reference level of the one or more genes. In some embodiments, the expression level of IL6, CXCL1, CXCL2, CXCL3, CXCL8, PTGS2, CXCR1, CXCR2, S100A8, and S100A9 has been determined to be at or above a reference level of IL6, CXCL1, CXCL2, CXCL3, CXCL8, PTGS2, CXCR1, CXCR2, S100A8, and S100A9.

In some embodiments, the expression level of PD-L1 in the sample has been determined to be at or above a reference expression level of PD-L1, and the expression level of one or more additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more additional genes.

In some embodiments of any of the preceding aspects, the expression level of one or more of VEGFA, KDR, ESM1, PECAM1, FLT1, ANGPTL4, or CD34 in the sample has been determined to be below a reference level of the one or more genes. In some embodiments, the expression level of at least one, at least two, at least three, at least four, at least five, at least six, or all seven of VEGFA, KDR, ESM1, PECAM1, FLT1, ANGPTL4, or CD34 in the sample has been determined to be below a reference level of the one or more genes. In some embodiments, the expression level of one or more of VEGFA, KDR, ESM1, PECAM1, ANGPTL4, or CD34 in the sample has been determined to be below a reference level of the one or more genes. In some embodiments, the expression level of VEGFA, KDR, ESM1, PECAM1, ANGPTL4, and CD34 in the sample has been determined to be below a reference level of VEGFA, KDR, ESM1, PECAM1, ANGPTL4, and CD34. In some embodiments, the expression level of one or more of IL6, CXCL1, CXCL2, CXCL3, PTGS2, CXCR1, CXCR2, S100A8, or S100A9 in the sample has been determined to be below a reference level of the one or more genes.

In some embodiments of any of the preceding aspects, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample has been determined to be below a reference level of the one or more genes. In some embodiments, the expression level of IL6, CXCL1, CXCL2, CXCL3, CXCL8, PTGS2, CXCR1, CXCR2, S100A8, and S100A9 in the sample has been determined to be below a reference level of IL6, CXCL1, CXCL2, CXCL3, CXCL8, PTGS2, CXCR1, CXCR2, S100A8, and S100A9.

In another aspect, the invention features a method of treating an individual having a kidney cancer, the method comprising: (a) determining the expression level of one or more of the following genes in a sample from the individual: VEGFA, KDR, ESM1, PECAM1, FLT1, ANGPTL4, or CD34, wherein the expression level of one or more of VEGFA, KDR, ESM1, PECAM1, FLT1, ANGPTL4, or CD34 in the sample is determined to be at or above a reference expression level of the one or more genes; and (b) administering an effective amount of an anti-cancer therapy comprising a VEGF antagonist to the individual based on the expression level of the one or more genes determined in step (a). In some embodiments, the anti-cancer therapy further comprises a PD-L1 axis binding antagonist.

In some embodiments, the expression level of at least one, at least two, at least three, at least four, at least five, at least six, or all seven of VEGFA, KDR, ESM1, PECAM1, FLT1, ANGPTL4, or CD34 in the sample is determined to be at or above a reference level of the one or more genes. In some embodiments, the expression level of one or more of VEGFA, KDR, ESM1, PECAM1, ANGPTL4, or CD34 in the sample is determined to be at or above a reference level of the one or more genes. In some embodiments, the expression level of VEGFA, KDR, ESM1, PECAM1, ANGPTL4, and CD34 in the sample is determined to be at or above a reference level of VEGFA, KDR, ESM1, PECAM1, ANGPTL4, and CD34.

In another aspect, the invention features a method of treating an individual having a kidney cancer, the method comprising administering to the individual an effective amount of an anti-cancer therapy comprising VEGF antagonist, wherein prior to treatment the expression level of one or more of VEGFA, KDR, ESM1, PECAM1, FLT1, ANGPTL4, or CD34 in the sample has been determined to be at or above a reference expression level of the one or more genes. In some embodiments, the anti-cancer therapy further comprises a PD-L1 axis binding antagonist. In some embodiments, the expression level of at least one, at least two, at least three, at least four, at least five, at least six, or all seven of VEGFA, KDR, ESM1, PECAM1, FLT1, ANGPTL4, or CD34 in the sample has been determined to be at or above a reference level of the one or more genes. In some embodiments, the expression level of one or more of VEGFA, KDR, ESM1, PECAM1, ANGPTL4, or CD34 in the sample has been determined to be at or above a reference level of the one or more genes. In some embodiments, the expression level of VEGFA, KDR, ESM1, PECAM1, ANGPTL4, and CD34 in the sample has been determined to be at or above a reference level of VEGFA, KDR, ESM1, PECAM1, ANGPTL4, and CD34.

In some embodiments of any of the preceding aspects, the reference level of the one or more genes is determined from a population of individuals having a kidney cancer. In some embodiments, the reference level of the one or more genes is a median expression level determined in a population of patients having a kidney cancer. In some embodiments, the reference level is a median of a Z-score of the normalized expression level of the one or more genes.

In some embodiments of any of the preceding aspects, the expression level is a nucleic acid expression level. In some embodiments, the nucleic acid expression level is an mRNA expression level. In some embodiments, the mRNA expression level is determined by RNA-seq, RT-qPCR, qPCR, multiplex qPCR or RT-qPCR, microarray analysis, SAGE, MassARRAY technique, ISH, or a combination thereof.

In other embodiments of any of the preceding aspects, the expression level is a protein expression level. In some embodiments, the protein expression level is determined by immunohistochemistry (IHC), Western blot, enzyme-linked immunosorbent assay (ELISA), immunoprecipitation, immunofluorescence, radioimmunoassay, or mass spectrometry.

In some embodiments of any of the preceding aspects, the sample is a tissue sample, a cell sample, a whole blood sample, a plasma sample, a serum sample, or a combination thereof. In some embodiments, the tissue sample is a tumor tissue sample. In some embodiments, the tumor tissue sample comprises tumor cells, tumor-infiltrating immune cells, stromal cells, or a combination thereof. In some embodiments, the tumor tissue sample is a formalin-fixed and paraffin-embedded (FFPE) sample, an archival sample, a fresh sample, or a frozen sample.

In some embodiments of any of the preceding aspects, the individual has not been previously treated for the kidney cancer. In some embodiments, the kidney cancer is renal cell carcinoma (RCC). In some embodiments, the RCC is metastatic RCC (mRCC).

In some embodiments of any of the preceding aspects, the VEGF antagonist is an anti-VEGF antibody or a VEGF receptor (VEGFR) inhibitor. In some embodiments, the VEGF antagonist is an anti-VEGF antibody. In some embodiments, the anti-VEGF antibody is bevacizumab. In some embodiments, the VEGF antagonist is a VEGFR inhibitor. In some embodiments, the VEGFR inhibitor is a multi-targeted tyrosine kinase inhibitor. In some embodiments, the multi-targeted tyrosine kinase inhibitor is sunitinib, axitinib, pazopanib, or cabozantinib. In some embodiments, the multi-targeted tyrosine kinase inhibitor is sunitinib.

In some embodiments of any of the preceding aspects, the PD-L1 axis binding antagonist is selected from the group consisting of a PD-L1 binding antagonist, a PD-1 binding antagonist, and a PD-L2 binding antagonist. In some embodiments, the PD-L1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an anti-PD-L1 antibody. In some embodiments, the anti-PD-L1 antibody is selected from the group consisting of: MPDL3280A (atezolizumab), YW243.55.570, MDX-1105, MED14736 (durvalumab), and MSB0010718C (avelumab). In some embodiments, the anti-PD-L1 antibody comprises the following hypervariable regions (HVRs): (a) an HVR-H1 sequence of GFTFSD-SWIH (SEQ ID NO: 63); (b) an HVR-H2 sequence of AWISPYGGSTYYADSVKG (SEQ ID NO: 64); (c) an HVR-H3 sequence of RHWPGGFDY (SEQ ID NO: 65); (d) an HVR-L1 sequence of RASQDVSTAVA (SEQ ID NO: 66); (e) an HVR-L2 sequence of SASFLYS (SEQ ID NO: 67); and (f) an HVR-L3 sequence of QQYLYHPAT (SEQ ID NO: 68). In some embodiments, the anti-PD-L1 antibody comprises: (a) a heavy chain variable (VH) domain comprising an amino acid sequence having at least 90% sequence identity to the amino acid sequence of EVQLVES-GGGLVQPGGSLRLSCAASGFTFSDSWIHWVRQAPG-KGLEWVAWISPYGGSTYYADSVKGRFTISADTSKNT-AYLQMNSLRAEDTAVYYCARRHWPGGFDYWGQGT-LVTVSS (SEQ ID NO: 69);

(b) a light chain variable (VL) domain comprising an amino acid sequence having at least 90% sequence identity to the amino acid sequence of DIQMTQSPSSLSAS-VGDRVTITCRASQDVSTAVAWYQQKPGKAPKLLIYS-ASFLYSGVPSRFSGSGSGTDFTLTISSLQPEDFATYYC-QQYLYHPATFGQGTKVEIKR (SEQ ID NO: 70); or (c) a VH domain as in (a) and a VL domain as in (b). In some embodiments, the anti-PD-L1 antibody comprises: (a) a VH domain comprising an amino acid sequence having at least 95% sequence identity to the amino acid sequence of SEQ ID NO: 69; (b) a VL domain comprising an amino acid sequence having at least 95% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 96% sequence identity to the amino acid sequence of SEQ ID NO: 69;

(b) a VL domain comprising an amino acid sequence having at least 96% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 97% sequence identity to the amino acid sequence of SEQ ID NO: 69; (b) a VL domain comprising an amino acid sequence having at least 97% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 98% sequence identity to the amino acid sequence of SEQ ID NO: 69; (b) a VL domain comprising an amino acid sequence having at least 98% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 99% sequence identity to the amino acid sequence of SEQ ID NO: 69; (b) a VL domain comprising an amino acid sequence having at least 99% sequence identity to the amino acid sequence of SEQ ID NO: 70; or (c) a VH domain as in (a) and a VL domain as in (b). In some embodiments, the anti-PD-L1 antibody comprises: (a) a VH domain comprising the amino acid sequence of SEQ ID NO: 69; (b) a VL domain comprising the amino acid sequence of SEQ ID NO: 70; or (c) a VH domain as in (a) and a VL domain as in (b). In some embodiments, the anti-PD-L1 antibody comprises: (a) a VH domain comprising the amino acid sequence of SEQ ID NO: 69; and (b) a VL domain comprising the amino acid sequence of SEQ ID NO: 70. In some embodiments, the anti-PD-L1 antibody is atezolizumab.

In some embodiments of any of the preceding aspects, the method further comprises administering an additional therapeutic agent to the individual. In some embodiments, the additional therapeutic agent is selected from the group consisting of an immunotherapy agent, a cytotoxic agent, a growth inhibitory agent, a radiation therapy agent, an anti-angiogenic agent, and combinations thereof.

In some embodiments of any of the preceding aspects, the individual is a human.

In another aspect, the invention features a kit for identifying an individual having a kidney cancer who may benefit from treatment with an anti-cancer therapy comprising a VEGF antagonist and a PD-L1 axis binding antagonist, the kit comprising: (a) reagents for determining the expression level of determining the expression level of one or more of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9; and, optionally, (b) instructions for using the reagents to identify an individual having a kidney cancer who may benefit from a treatment with an anti-cancer therapy comprising a VEGF antagonist and a PD-L1 axis binding antagonist.

In some embodiments of the preceding aspect, the kit comprises reagents for determining the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2. In some embodiments, the kit comprises reagents for determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2. In some embodiments, the kit comprises reagents for determining the expression level of one or more of CD8A, EOMES, PRF1, IFNG, or PD-L1. In some embodiments, the kit comprises reagents for determining the expression level of CD8A, EOMES, PRF1, IFNG, and PD-L1. In some embodiments, the kit comprises reagents for determining the expression level of one or more of IL6, CXCL1, CXCL2, CXCL3, CXCL8, PTGS2, CXCR1, CXCR2, S100A8, or S100A9. In some embodiments, the kit comprises reagents for determining the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9. In some embodiments, the kit comprises reagents for determining the expression level of IL6, CXCL1, CXCL2, CXCL3, CXCL8, PTGS2, CXCR1, CXCR2, S100A8, and S100A9. In some embodiments of the preceding aspect, the kit comprises reagents for determining the expression level of one or more of VEGFA, KDR, ESM1, PECAM1, FLT1, ANGPTL4, or CD34. In some embodiments, the kit comprises reagents for determining the expression level of at least one, at least two, at least three, at least four, at least five, at least six, or all seven of VEGFA, KDR, ESM1, PECAM1, FLT1, ANGPTL4, or CD34. In some embodiments, the kit comprises reagents for determining the expression level of one or more of VEGFA, KDR, ESM1, PECAM1, ANGPTL4, or CD34. In some embodiments, the kit comprises reagents for determining the expression level of VEGFA, KDR, ESM1, PECAM1, ANGPTL4, and CD34.

In some embodiments of the preceding aspect, the kit comprises reagents for determining the expression level of PD-L1 and one or more additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2.

In another aspect, the invention features a kit for identifying an individual having a kidney cancer who may benefit from treatment with a VEGF antagonist, the kit comprising: (a) reagents for determining the expression level of determining the expression level of one or more of the following genes in a sample from the individual: VEGFA, KDR, ESM1, PECAM1, FLT1, ANGPTL4, or CD34; and, optionally, (b) instructions for using the reagents to identify an individual having a kidney cancer who may benefit from a treatment with an anti-cancer therapy comprising a VEGF antagonist. In some embodiments, the anti-cancer therapy further comprises a PD-L1 axis binding antagonist. In some embodiments, the kit comprises reagents for determining the expression level of at least one, at least two, at least three, at least four, at least five, at least six, or all seven of VEGFA, KDR, ESM1, PECAM1, FLT1, ANGPTL4, or CD34. In some embodiments, the kit comprises reagents for determining the expression level of one or more of VEGFA, KDR, ESM1, PECAM1, ANGPTL4, or CD34. In some embodiments, the kit comprises reagents for determining the expression level of VEGFA, KDR, ESM1, PECAM1, ANGPTL4, and CD34.

In another aspect, the invention features an assay for identifying an individual having a kidney cancer who is a candidate for treatment with an anti-cancer therapy comprising a VEGF antagonist and a PD-L1 axis binding antagonist, the assay comprising determining the expression level of one or more of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9; wherein (i) an expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample that is above a reference expression level of the one or more genes; or (ii) an expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample that is below a reference expression level of the one or more genes identifies the individual as one who may benefit from treatment with an anti-cancer therapy comprising a VEGF antagonist and a PD-L1 axis binding antagonist.

In some embodiments of any of the preceding aspects, the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is at or above a reference expression level of the one or more genes. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 is at or above a reference expression level of the one or more genes. In some embodiments, the expression level of one or more of CD8A, EOMES, PRF1, IFNG, or PD-L1 in the sample is at or above a reference expression level of the one or more genes. In some embodiments, the expression level of CD8A, EOMES, PRF1, IFNG, or PD-L1 in the sample is at or above a reference expression level of CD8A, EOMES, PRF1, IFNG, or PD-L1. In some embodiments, the expression level of one or more of IL6, CXCL1, CXCL2, CXCL3, CXCL8, PTGS2, CXCR1, CXCR2, S100A8, or S100A9 in the sample is at or above a reference expression level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is at or above a reference expression level of the one or more genes. In some embodiments, the expression level of IL6, CXCL1, CXCL2, CXCL3, CXCL8, PTGS2, CXCR1, CXCR2, S100A8, and S100A9 in the sample is at or above a reference expression level of IL6, CXCL1, CXCL2, CXCL3, CXCL8, PTGS2, CXCR1, CXCR2, S100A8, and S100A9.

In some embodiments of any of the preceding aspects, the expression level of PD-L1 in the sample is at or above a reference expression level of PD-L1, and the expression level of one or more additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2 in the sample is at or above a reference expression level of the one or more additional genes.

In some embodiments of any of the preceding aspects, the expression level of one or more of VEGFA, KDR, ESM1, PECAM1, FLT1, ANGPTL4, or CD34 in the sample is below a reference level of the one or more genes. In some embodiments, the expression level of at least one, at least two, at least three, at least four, at least five, at least six, or all seven of VEGFA, KDR, ESM1, PECAM1, ANGPTL4, or CD34 in the sample is below a reference level of the one or more genes. In some embodiments, the expression level of one or more of VEGFA, KDR, ESM1, PECAM1, ANGPTL4, or CD34 in the sample is below a reference level of the one or more genes. In some embodiments, the expression level of VEGFA, KDR, ESM1, PECAM1, ANGPTL4, and CD34 in the sample is below a reference level of VEGFA, KDR, ESM1, PECAM1, ANGPTL4, and CD34.

In some embodiments of any of the preceding aspects, the expression level of one or more of IL6, CXCL1, CXCL2, CXCL3, CXCL8, PTGS2, CXCR1, CXCR2, S100A8, or S100A9 in the sample is below a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is below a reference level of the one or more genes. In some embodiments, the expression level of IL6, CXCL1, CXCL2, CXCL3, CXCL8, PTGS2, CXCR1, CXCR2, S100A8, and S100A9 in the sample is below a reference level of IL6, CXCL1, CXCL2, CXCL3, CXCL8, PTGS2, CXCR1, CXCR2, S100A8, and S100A9.

In another aspect, the invention features an assay for identifying an individual having a kidney cancer who is a candidate for treatment comprising a VEGF antagonist, the assay comprising determining the expression level of one or more of the following genes in a sample from the individual: VEGFA, KDR, ESM1, PECAM1, FLT1, ANGPTL4, or CD34, wherein an expression level of one or more of VEGFA, KDR, ESM1, PECAM1, FLT1, ANGPTL4, or CD34 in the sample that is above a reference expression level of the one or more genes identifies the individual as one who may benefit from treatment with an anti-cancer therapy comprising a VEGF antagonist. In some embodiments, the anti-cancer therapy further comprises a PD-L1 axis binding antagonist.

In some embodiments of the preceding aspect, the expression level of at least one, at least two, at least three, at least four, at least five, at least six, or all seven of VEGFA, KDR, ESM1, PECAM1, ANGPTL4, or CD34 in the sample is at or above a reference level of the one or more genes. In some embodiments, the expression level of one or more of VEGFA, KDR, ESM1, PECAM1, ANGPTL4, or CD34 in the sample is above a reference level of the one or more genes. In some embodiments, the expression level of VEGFA, KDR, ESM1, PECAM1, ANGPTL4, and CD34 in the sample is above a reference level of VEGFA, KDR, ESM1, PECAM1, ANGPTL4, and CD34.

In another aspect, the invention features an anti-cancer therapy comprising a VEGF antagonist and a PD-L1 axis binding antagonist for use in a method of treating an individual suffering from a kidney cancer, wherein prior to treatment (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in a sample from the individual has been determined to be above a reference expression level of the one or more genes; or (ii) the expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in a sample from the individual has been determined to be below a reference expression level of the one or more genes.

In another aspect, the invention provides for the use of an anti-cancer therapy comprising a VEGF antagonist and a PD-L1 axis binding antagonist in the manufacture of a medicament for treating an individual suffering from a kidney cancer, wherein prior to treatment (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in a sample from the individual has been determined to be above a reference expression level of the one or more genes; or (ii) the expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in a sample from the individual has been determined to be below a reference expression level of the one or more genes.

In some embodiments of any of the preceding aspects, the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 has been determined to be at or above a reference level of the one or more genes. In some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference level of the one or more genes. In some embodiments, the expression level of one or more of CD8A, EOMES, PRF1, IFNG, or PD-L1 has been determined to be at or above a reference level of the one or more genes. In some embodiments, the expression level of CD8A, EOMES, PRF1, IFNG, and PD-L1 has been determined to be at or above a reference level of CD8A, EOMES, PRF1, IFNG, and PD-L1. In some embodiments, the expression level of one or more of IL6, CXCL1, CXCL2, CXCL3, CXCL8, PTGS2, CXCR1, CXCR2, S100A8, or S100A9 has been determined to be at or above a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample has been determined to be at or above a reference level of the one or more genes. In some embodiments, the expression level of IL6, CXCL1, CXCL2, CXCL3, CXCL8, PTGS2, CXCR1, CXCR2, S100A8, and S100A9 has been determined to be at or above a reference level of IL6, CXCL1, CXCL2, CXCL3, CXCL8, PTGS2, CXCR1, CXCR2, S100A8, and S100A9.

In some embodiments of any of the preceding aspects, the expression level of PD-L1 in the sample has been determined to be at or above a reference expression level of PD-L1, and the expression level of one or more additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more additional genes.

In some embodiments of any of the preceding aspects, the expression level of one or more of VEGFA, KDR, ESM1, PECAM1, FLT1, ANGPTL4, or CD34 in the sample has been determined to be below a reference level of the one or more genes. In some embodiments, the expression level of at least one, at least two, at least three, at least four, at least five, at least six, or all seven of VEGFA, KDR, ESM1, PECAM1, FLT1, ANGPTL4, or CD34 in the sample has been determined to be below a reference level of the one or more genes. In some embodiments, the expression level of one or more of VEGFA, KDR, ESM1, PECAM1, ANGPTL4, or CD34 in the sample has been determined to be below a reference level of the one or more genes. In some embodiments, the expression level of VEGFA, KDR, ESM1, PECAM1, ANGPTL4, and CD34 in the sample has been determined to be below a reference level of VEGFA, KDR, ESM1, PECAM1, ANGPTL4, and CD34.

In some embodiments of any of the preceding aspects, the expression level of one or more of IL6, CXCL1, CXCL2, CXCL3, CXCL8, PTGS2, CXCR1, CXCR2, S100A8, or S100A9 in the sample has been determined to be below a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample has been determined to be below a reference level of the one or more genes. In some embodiments, the expression level of IL6, CXCL1, CXCL2, CXCL3, CXCL8, PTGS2, CXCR1, CXCR2, S100A8, and S100A9 in the sample has been determined to be below a reference level of IL6, CXCL1, CXCL2, CXCL3, CXCL8, PTGS2, CXCR1, CXCR2, S100A8, and S100A9.

In another aspect, the invention features a VEGF antagonist for use in a method of treating an individual suffering from a kidney cancer, wherein prior to treatment the expression level of one or more of VEGFA, KDR, ESM1, PECAM1, FLT1, ANGPTL4, or CD34 in a sample from the individual has been determined to be above a reference expression level of the one or more genes. In some embodiments, the VEGF antagonist is formulated for use in combination with a PD-L1 axis binding antagonist.

In another aspect, the invention provides for the use of a VEGF antagonist in the manufacture of a medicament for treating an individual suffering from a kidney cancer, wherein prior to treatment the expression level of one or more of VEGFA, KDR, ESM1, PECAM1, FLT1, ANGPTL4, or CD34 in a sample from the individual has been determined to be above a reference expression level of the one or more genes. In some embodiments, the medicament is formulated for use in combination with a PD-L1 axis binding antagonist.

In some embodiments of any of the preceding aspects, the expression level of at least one, at least two, at least three, at least four, at least five, at least six, or all seven of VEGFA, KDR, ESM1, PECAM1, FLT1, ANGPTL4, or CD34 in the sample has been determined to be at or above a reference level of the one or more genes. In some embodiments, the expression level of one or more of VEGFA, KDR, ESM1, PECAM1, ANGPTL4, or CD34 in the sample has been determined to be at or above a reference level of the one or more genes. In some embodiments, the expression level of VEGFA, KDR, ESM1, PECAM1, ANGPTL4, and CD34 in the sample has been determined to be at or above a reference level of VEGFA, KDR, ESM1, PECAM1, ANGPTL4, and CD34.

In some embodiments of any of the preceding aspects, the VEGF antagonist is an anti-VEGF antibody or a VEGF receptor (VEGFR) inhibitor. In some embodiments, the VEGF antagonist is an anti-VEGF antibody. In some embodiments, the anti-VEGF antibody is bevacizumab. In some embodiments, the VEGF antagonist is a VEGFR inhibitor. In some embodiments, the VEGFR inhibitor is a multi-targeted tyrosine kinase inhibitor. In some embodiments, the multi-targeted tyrosine kinase inhibitor is sunitinib, axitinib, pazopanib, or cabozantinib. In some embodiments, the multi-targeted tyrosine kinase inhibitor is sunitinib.

In some embodiments of any of the preceding aspects, the PD-L1 axis binding antagonist is selected from the group consisting of a PD-L1 binding antagonist, a PD-1 binding antagonist, and a PD-L2 binding antagonist. In some embodiments, the PD-L1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an anti-PD-L1 antibody. In some embodiments, the anti-PD-L1 antibody is selected from the group consisting of: MPDL3280A (atezolizumab), YW243.55.S70, MDX-1105, MEDI4736 (durvalumab), and MSB0010718C (avelumab). In some embodiments, the anti-PD-L1 antibody comprises the following hypervariable regions (HVRs): (a) an HVR-H1 sequence of GFTFSDSWIH (SEQ ID NO: 63); (b) an HVR-H2 sequence of AWISPYGGSTYYADSVKG (SEQ ID NO: 64); (c) an HVR-H3 sequence of RHWPGGFDY (SEQ ID NO: 65); (d) an HVR-L1 sequence of RASQDVSTAVA (SEQ ID NO: 66); (e) an HVR-L2 sequence of SASFLYS (SEQ ID NO: 67); and (f) an HVR-L3 sequence of QQYLYHPAT (SEQ ID NO: 68). In some embodiments, the anti-PD-L1 antibody comprises: (a) a heavy chain variable (VH) domain comprising an amino acid sequence having at least 90% sequence identity to the amino acid sequence of EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSS (SEQ ID NO: 69);

(b) a light chain variable (VL) domain comprising an amino acid sequence having at least 90% sequence identity to the amino acid sequence of DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIKR (SEQ ID NO: 70); or (c) a VH domain as in (a) and a VL domain as in (b). In some embodiments, the anti-PD-L1 antibody comprises: (a) a VH domain comprising an amino acid sequence having at least 95% sequence identity to the amino acid sequence of SEQ ID NO: 69; (b) a VL domain comprising an amino acid sequence having at least 95% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 96% sequence identity to the amino acid sequence of SEQ ID NO: 69;

(b) a VL domain comprising an amino acid sequence having at least 96% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 97% sequence identity to the amino acid sequence of SEQ ID NO: 69; (b) a VL domain comprising an amino acid sequence having at least 97% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 98% sequence identity to the amino acid sequence of SEQ ID NO: 69; (b) a VL domain comprising an amino acid sequence having at least 98% sequence identity to the amino acid sequence of SEQ ID NO: 70; or (c) a VH domain as in (a) and a VL domain as in (b). In some embodiments, the anti-PD-L1 antibody comprises: (a) a VH domain comprising an amino acid sequence having at least 99% sequence identity to the amino acid sequence of SEQ ID NO: 69; (b) a VL domain comprising an amino acid sequence having at least 99% sequence identity to the amino acid sequence of SEQ ID NO: 70; or (c) a VH domain as in (a) and a VL domain as in (b). In some embodiments, the anti-PD-L1 antibody comprises: (a) a VH domain comprising the amino acid sequence of SEQ ID NO: 69; (b) a VL domain comprising the amino acid sequence of SEQ ID NO: 70; or (c) a VH domain as in (a) and a VL domain as in (b). In some embodiments, the anti-PD-L1 antibody comprises: (a) a VH domain comprising the amino acid sequence of SEQ ID NO: 69; and (b) a VL domain comprising the amino acid sequence of SEQ ID NO: 70. In some embodiments, the anti-PD-L1 antibody is atezolizumab.

BRIEF DESCRIPTION OF THE DRAWINGS

FIG. 14A shows data for patients 1 and 2. FIG. 14B shows data for patients 3 and 4. FIG. 14C shows data for patient 5. The response of each patient is also indicated.

FIG. 15A shows data for patients 1 and 2. FIG. 15B shows data for patients 3 and 5. FIG. 15C shows data for patient 6. The response of each patient is also indicated.

FIG. 16A shows data for patients 1 and 2. FIG. 16B shows data for patients 3 and 4. FIG. 16C shows data for patients 5 and 6. The response of each patient is also indicated.

FIG. 17A shows data for patients 2 and 3. FIG. 17B shows data for patients 5 and 6.

FIG. 23A shows data for patients 2 and 3, and FIG. 23B shows data for patient 6. The top clones (up to 25) for each group are shown.

Figure 37A:
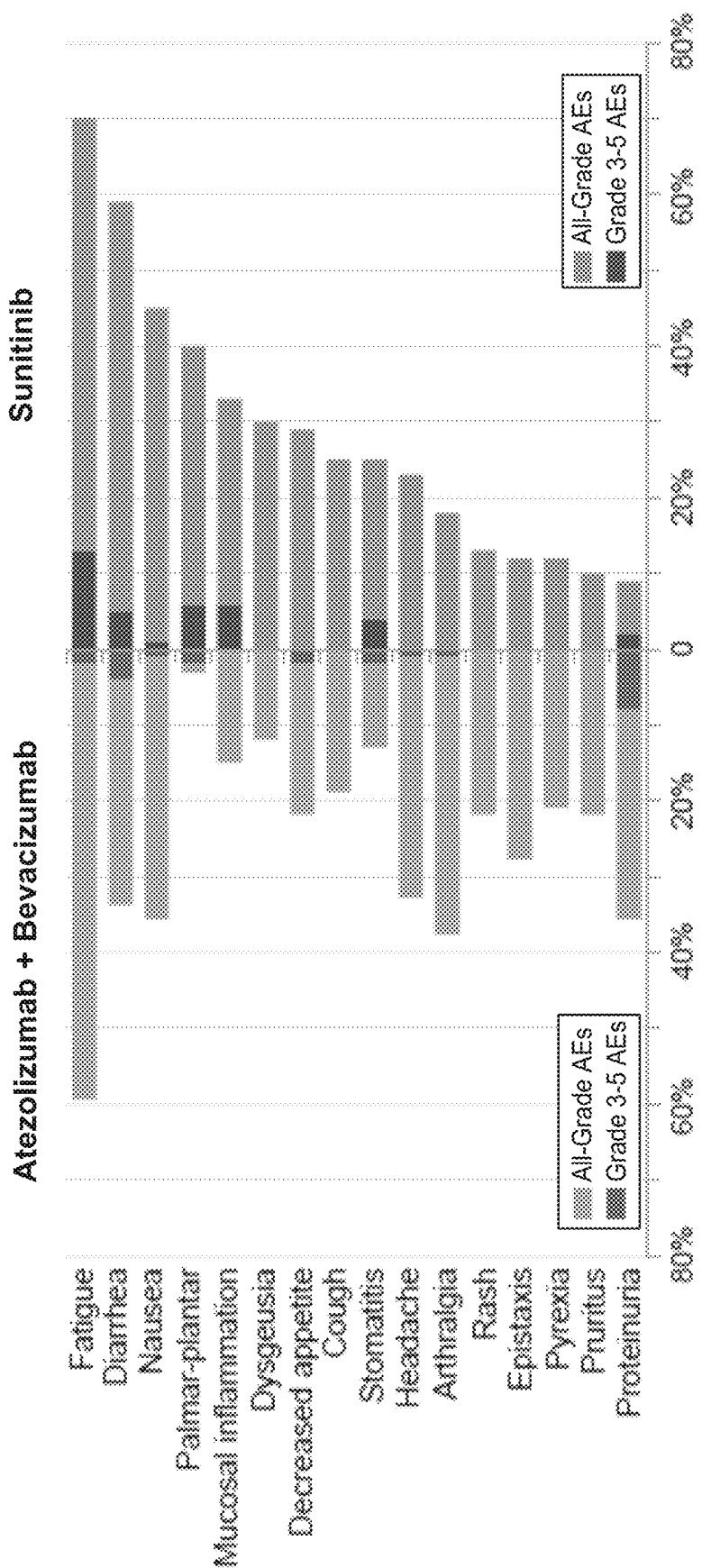
Figure 37B:
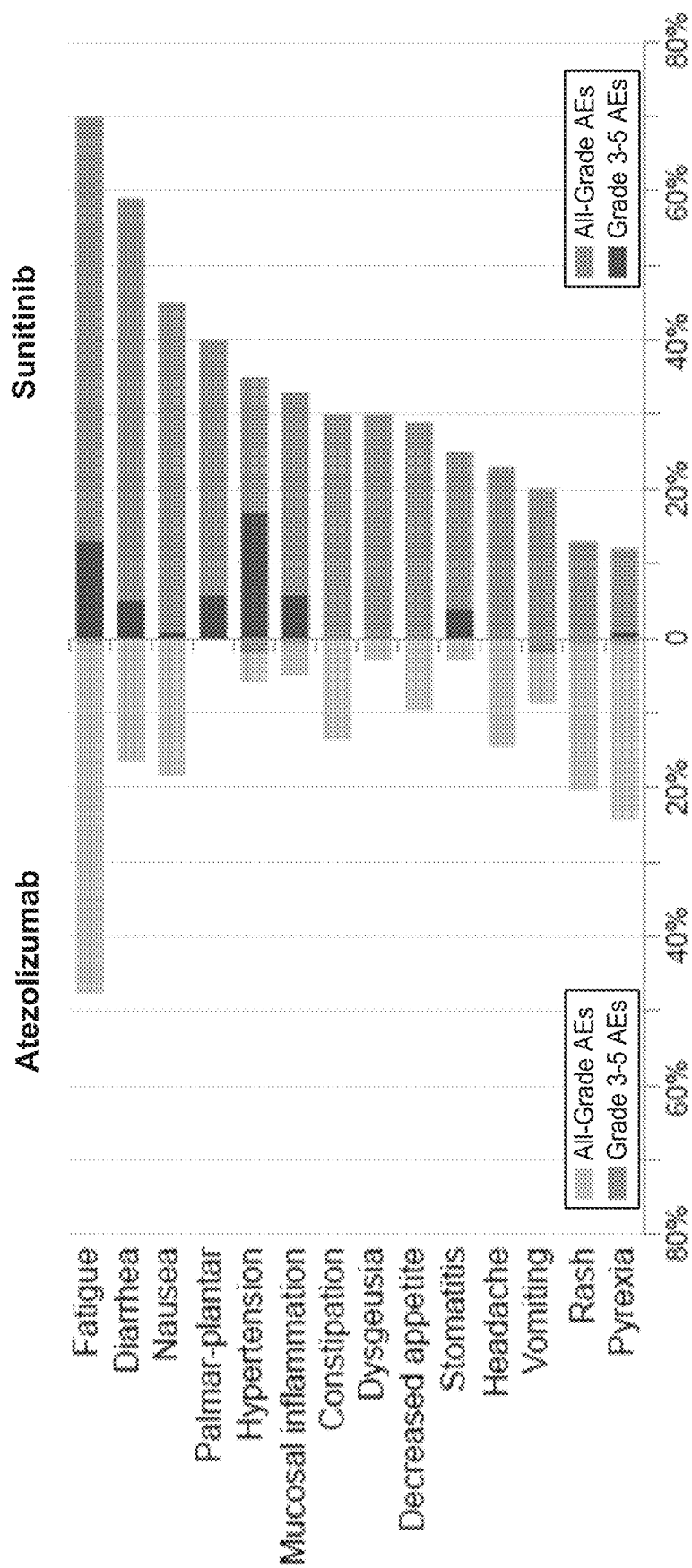

FIGS. 37A and 37B are a series of graphs showing adverse events (AEs) with >5% difference in frequency between the atezolizumab+bevacizumab versus sunitinib arms (FIG. 37A) and a ≥20% frequency within the atezolizumab versus sunitinib populations (FIG. 37B).

Figure 38A:
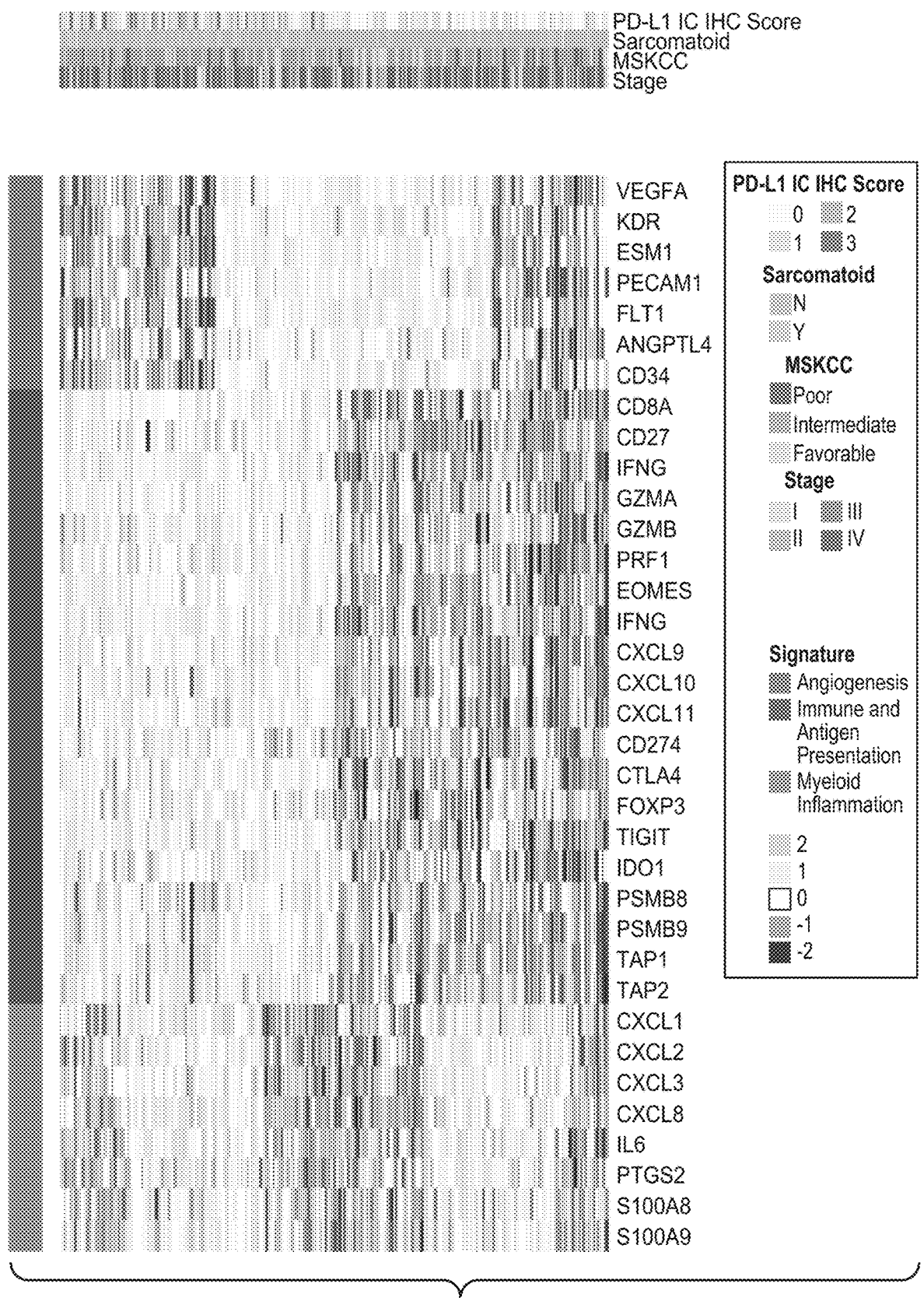

FIG. 38A is a heatmap showing expression of genes of interest (rows) in 263 pretreatment tumors (columns). Normalized counts of genes related to angiogenesis, immune and antigen presentation, and myeloid inflammation were Z-score transformed before visualization. Sample annotations include PD-L1 IHC status for tumor-infiltrating immune cells (IC), presence of sarcomatoid features, MSKCC score, and tumor stage.

Figures 38B, 38C, 38D:
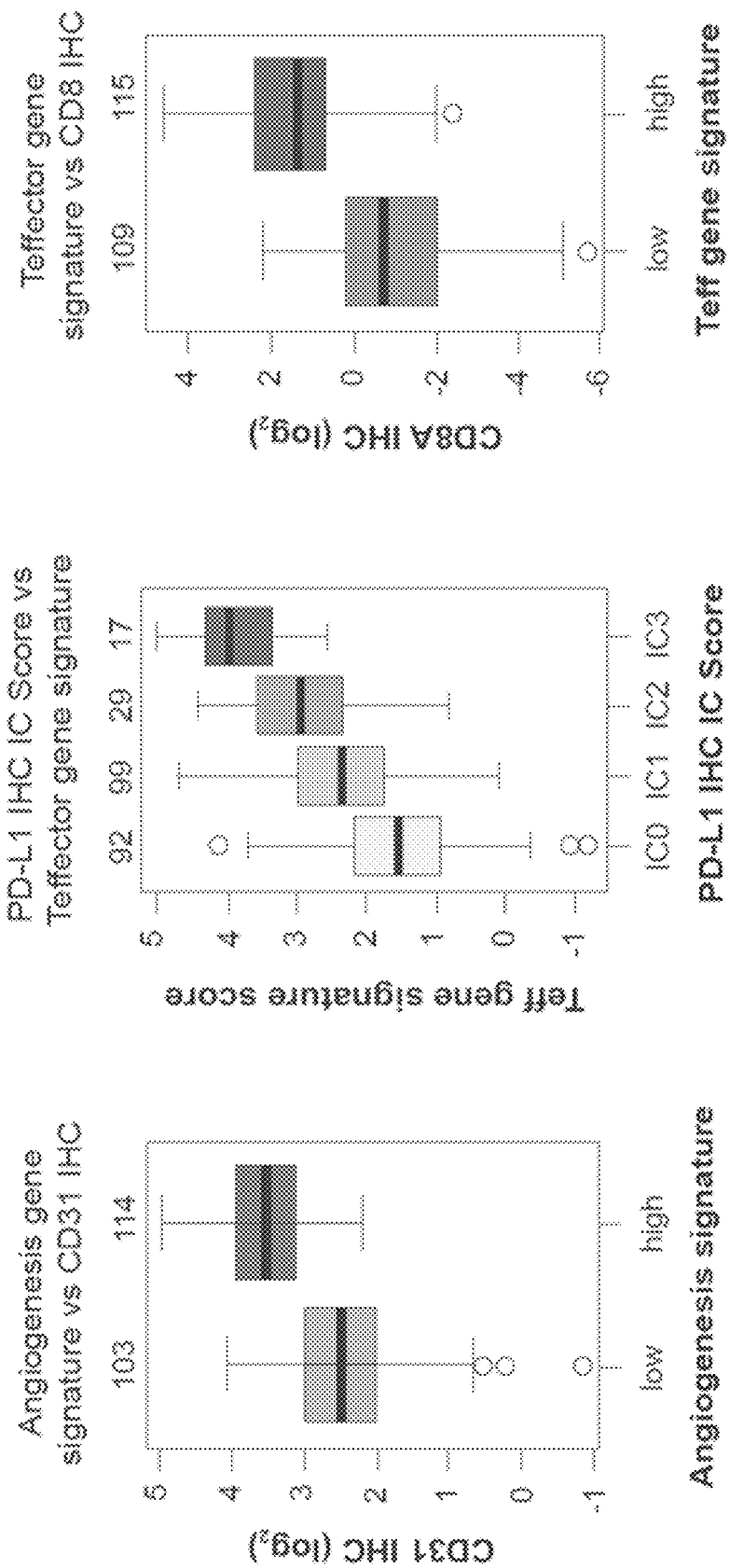

FIG. 38B is a graph showing that mean CD31 IHC staining intensity is higher in the $Angio^{High}$ population than in $Angio^{Low}$ population (two-tailed t test, $P=4.19\times10^{-21}$). Sample number per group is indicated above the graph.

FIGS. 38C and 38D are a series of graphs showing that Teff signature scores are associated with PD-L1 protein expression levels on IC by IHC (FIG. 38C; Wald test $P=3.26\times10^{-20}$) and intra-tumoral CD8A protein expression by IHC (FIG. 38D; two-tailed ttest $P=1.26\times10^{-28}$). Sample number per group is indicated above each graph.

Figure 38E:
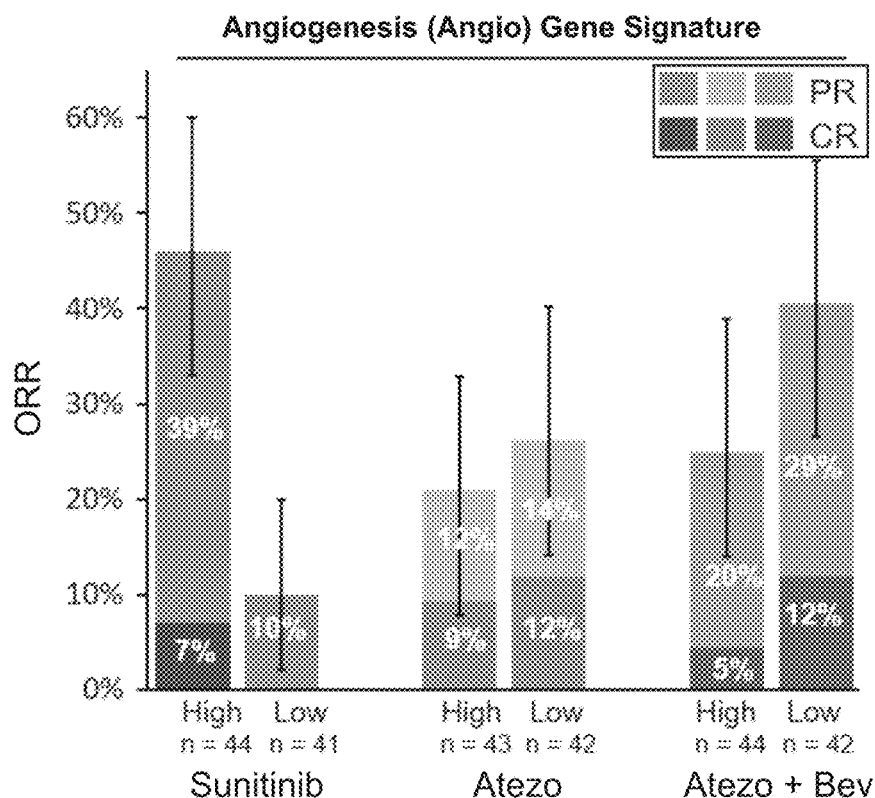

FIG. 38E is a graph showing ORR (PR+CR) in the $Angio^{High}$ and $Angio^{Low}$ populations for each treatment arm. Error bars represent 95% CI for ORR.

Figure 38F:
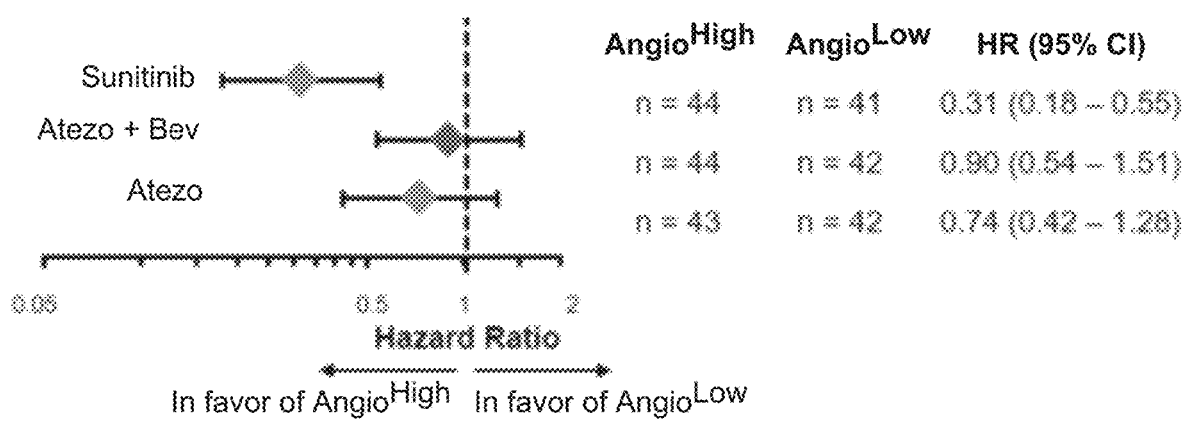

FIG. 38F is a graph showing Forest plots of PFS HRs and CIs for $Angio^{High}$ versus $Angio^{Low}$ populations within each treatment arm.

Figure 38G:
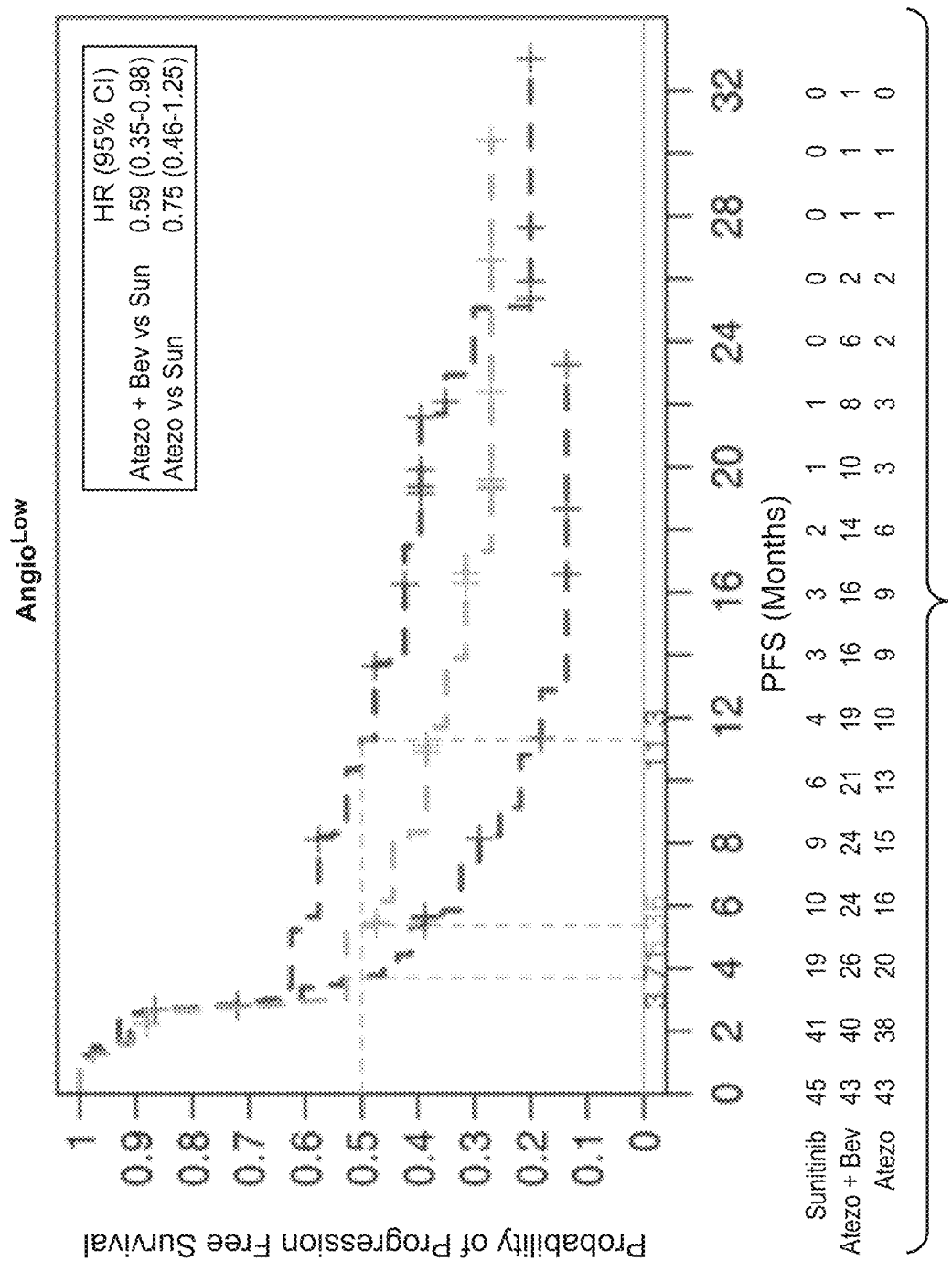
Figure 38H:
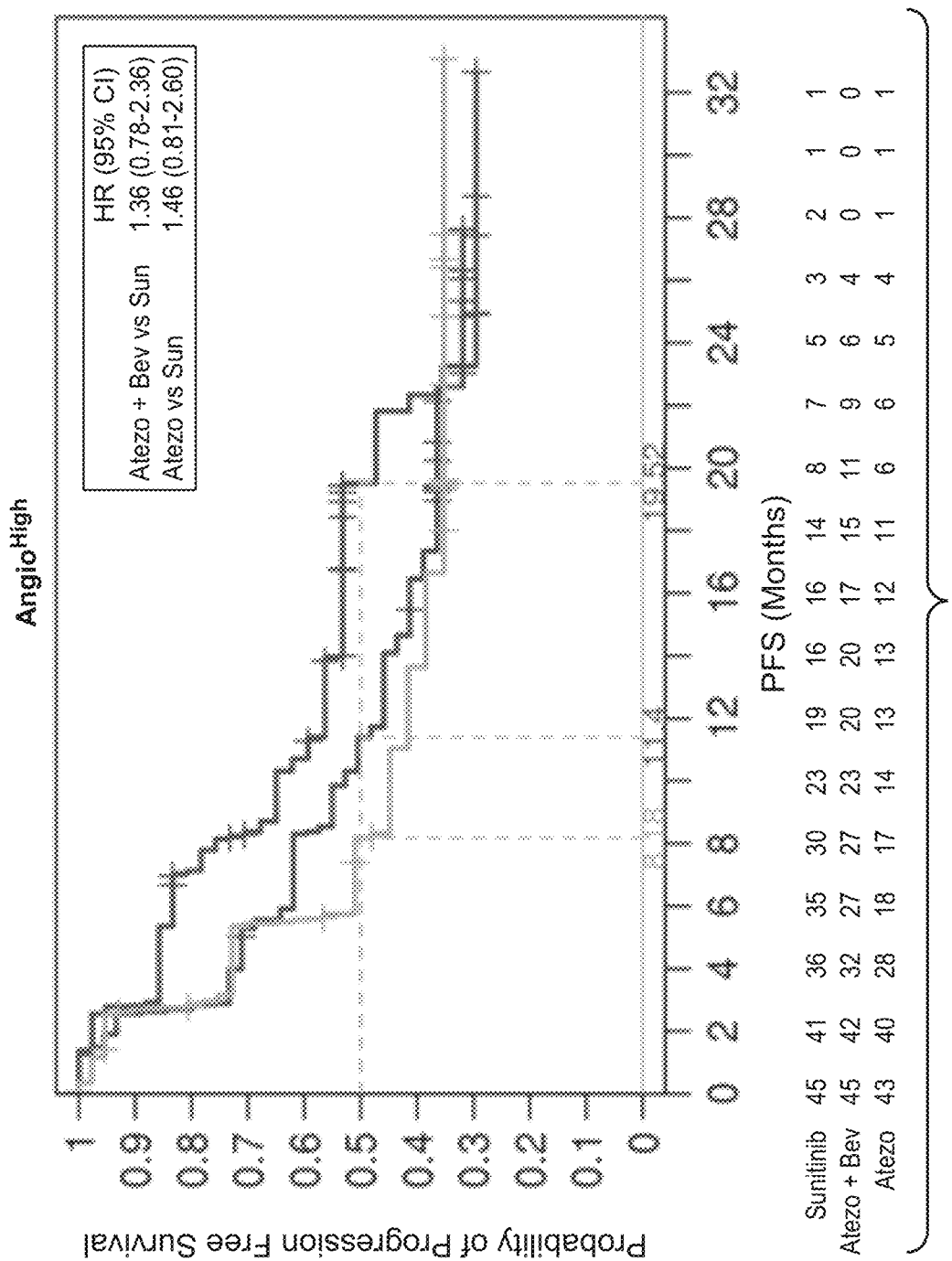

FIGS. 38G and 38H are a series of graphs showing Kaplan-Meier curves showing the probability of PFS across treatment arms in the $Angio^{Low}$ (FIG. 38G) and $Angio^{High}$ (FIG. 38H) subgroups; HR calculated versus sunitinib.

Figure 38I:
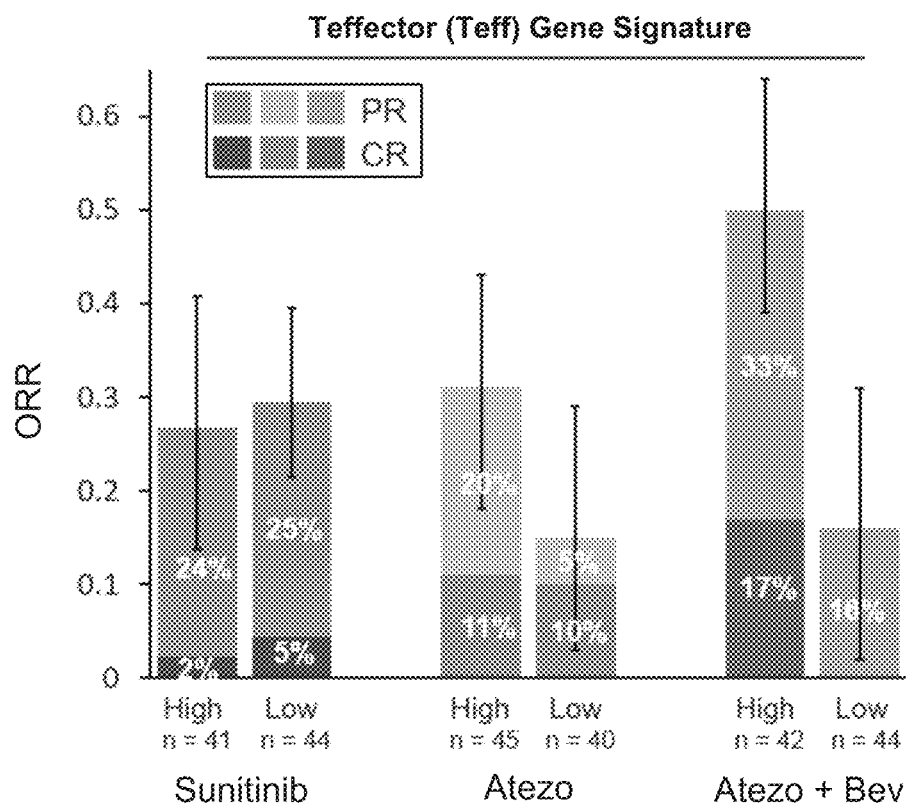

FIG. 38I is a graph showing ORR (PR+CR) in the $Teff^{High}$ and $Teff^{Low}$ populations for each treatment arm. Error bars represent 95% CIs for ORR.

Figure 38J:
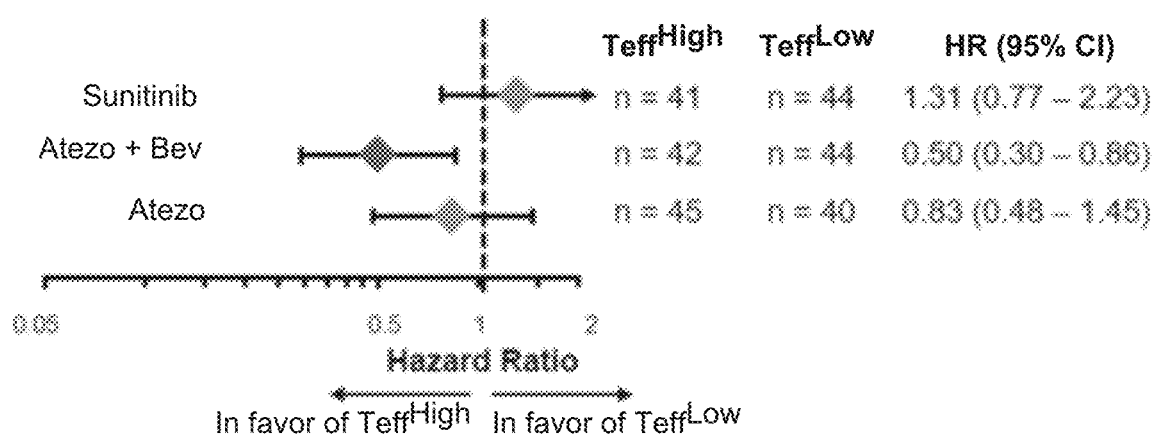

FIG. 38J is a graph showing Forest plots of PFS HRs and CIs for $Teff^{High}$ versus $Teff^{Low}$ populations within each treatment arm.

Figure 38K:
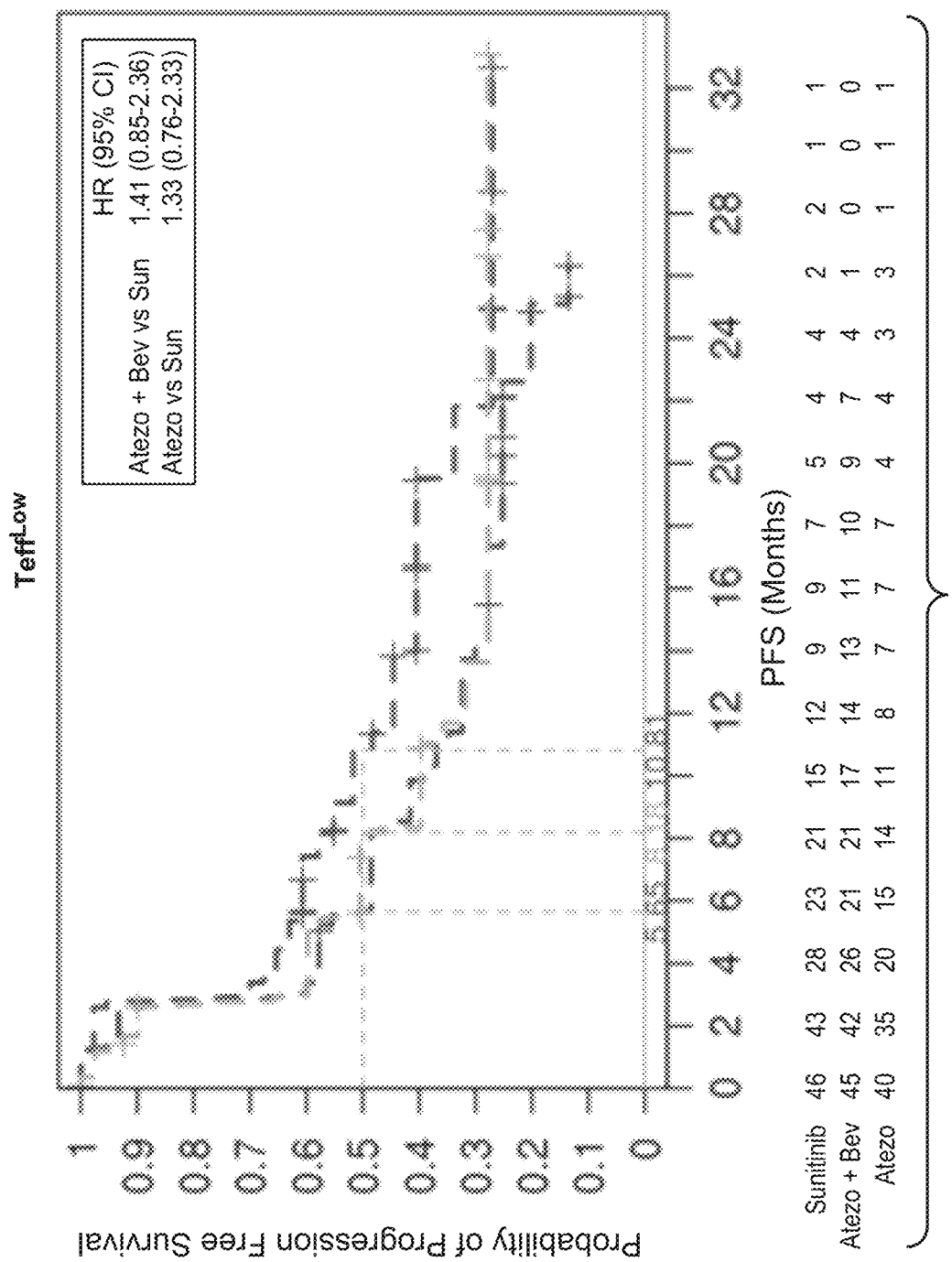
Figure 38L:
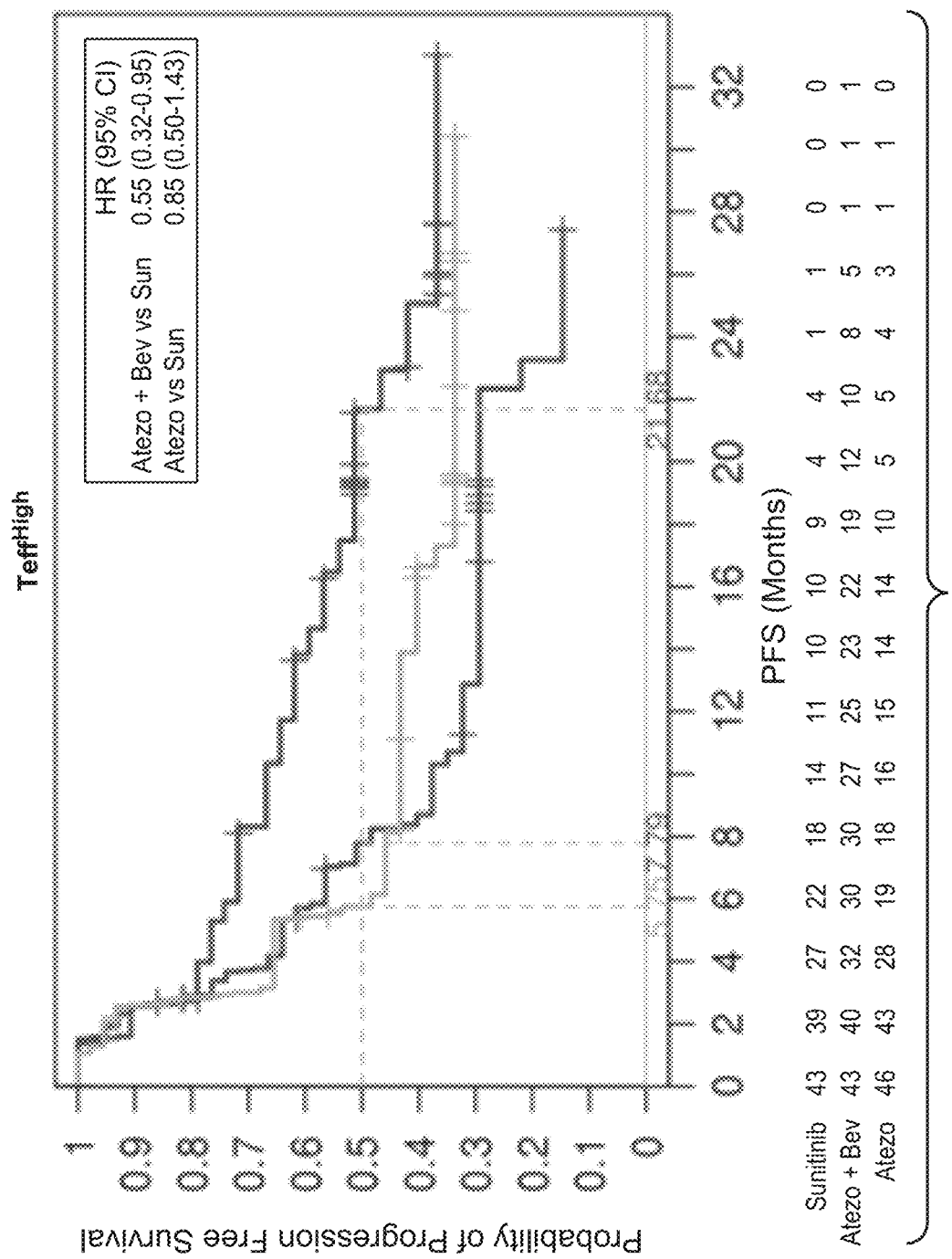

FIGS. 38K and 38L are a series of graphs showing Kaplan-Meier curves showing probability of PFS across treatment arms in $Teff^{Low}$ (FIG. 38K) and $Teff^{High}$ (FIG. 38L) subgroups; HR calculated versus sunitinib.

Figure 38M:
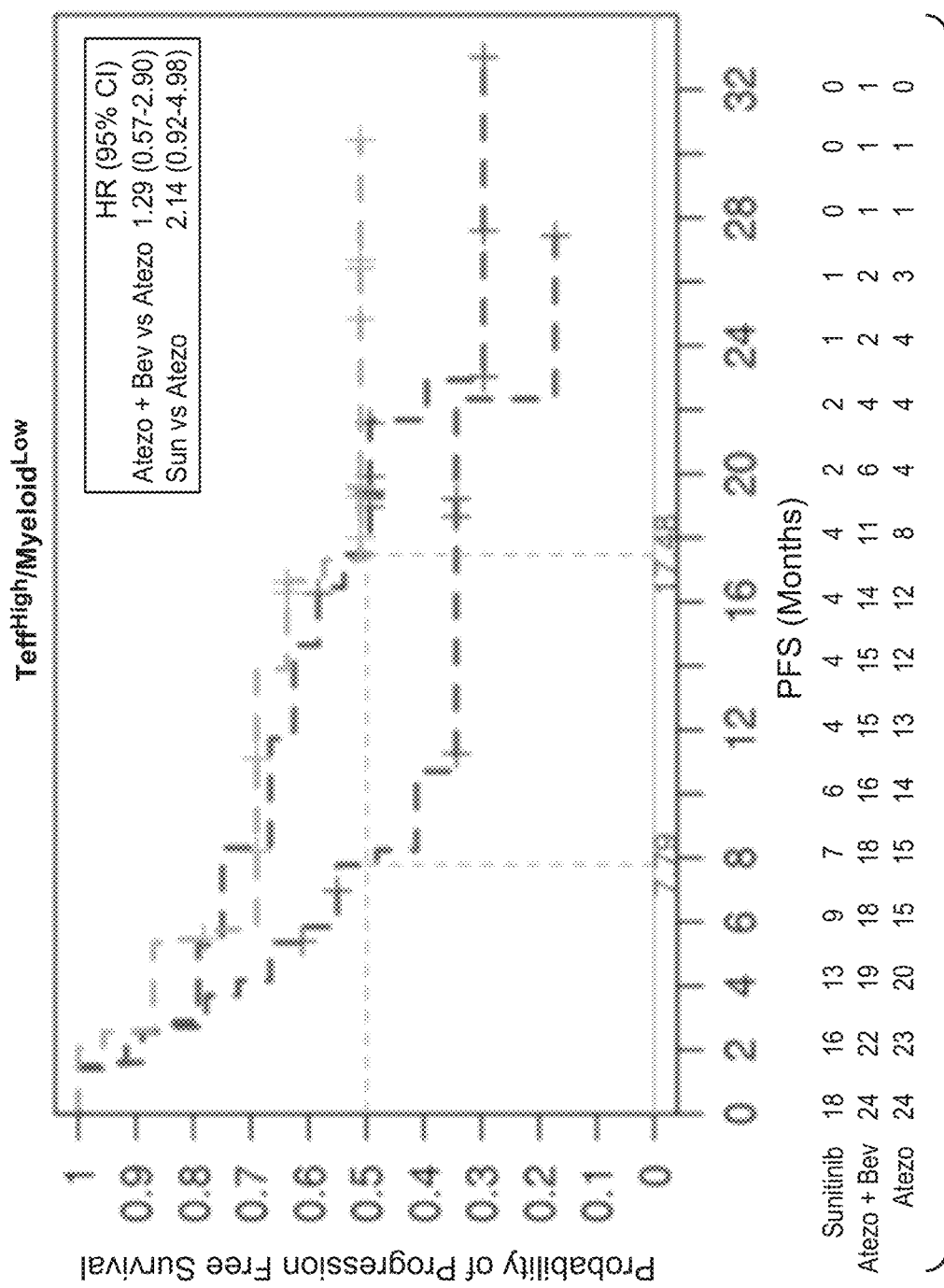
Figure 38N:
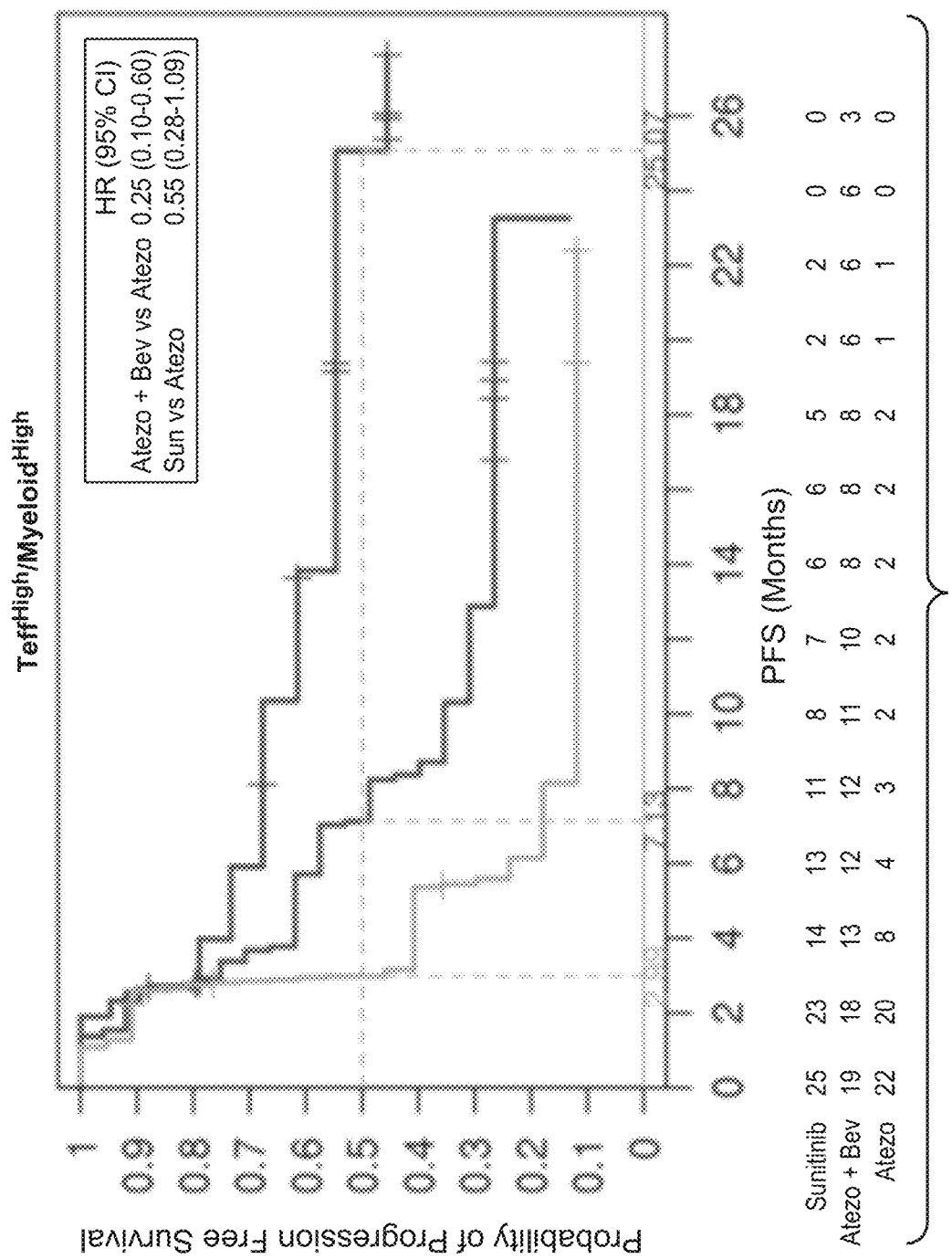

FIGS. 38M and 38N are a series of graphs showing Kaplan-Meier curves showing probability of PFS in $Teff^{High}Myeloid^{Low}$ (FIG. 38M) and $Teff^{High}Myeloid^{High}$ (FIG. 38N) subgroups; HR is calculated versus atezolizumab monotherapy. Censored data are indicated by vertical tick marks in Kaplan-Meier curves. All HR and CI values for PFS were extracted from Cox proportional hazard regression models; median survival time per group is indicated.

DETAILED DESCRIPTION OF THE INVENTION

The present invention provides diagnostic methods and assays, therapeutic methods and uses, and compositions for the treatment of cancer (e.g., a kidney cancer (e.g., a renal cell carcinoma (RCC)), a lung cancer (e.g., a non-small cell lung cancer (NSCLC)), a bladder cancer (e.g., a urothelial bladder cancer (UBC)), a liver cancer (e.g., hepatocellular carcinoma (HCC)), an ovarian cancer, or a breast cancer (e.g., a triple-negative breast cancer (TNBC))). The invention is based, at least in part, on the discovery that the expression level of one or more genes (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) in a sample obtained from an individual having a cancer e.g., a kidney cancer (e.g., a renal cell carcinoma (RCC)), a lung cancer (e.g., a non-small cell lung cancer (NSCLC)), a bladder cancer (e.g., a urothelial bladder cancer (UBC)), a liver cancer (e.g., hepatocellular carcinoma (HCC)), an ovarian cancer, or a breast cancer (e.g., a triple-negative breast cancer (TNBC))) can be used as a biomarker (e.g., a predictive biomarker) in methods of identifying whether the individual is likely to respond to treatment including a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)); selecting a therapy for treating the individual; optimizing therapeutic efficacy of a treatment that includes a VEGF antagonist and a PD-L1 axis binding antagonist; and/or monitoring the response of the individual to a treatment that includes a VEGF antagonist and a PD-L1 axis binding antagonist. The invention also provides methods for treating an individual having a cancer (e.g., a kidney cancer (e.g., a renal cell carcinoma (RCC)), a lung cancer (e.g., a non-small cell lung cancer (NSCLC)), a bladder cancer (e.g., a urothelial bladder cancer (UBC)), a liver cancer (e.g., hepatocellular carcinoma (HCC)), an ovarian cancer, or a breast cancer (e.g., a triple-negative breast cancer (TNBC))) by administering an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)).

In another aspect, the invention is based, at least in part, on the discovery that the expression level of one or more genes (e.g., VEGFA, KDR, ESM1, PECAM1, FLT1, ANGPTL4, and/or CD34) in a sample obtained from an individual having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) can be used as a biomarker (e.g., a predictive biomarker) in methods of identifying whether the individual is likely to respond to treatment with an anti-cancer therapy including an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))); selecting a therapy for treating the individual; optimizing therapeutic efficacy of a treatment with an anti-cancer therapy that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))); and/or monitoring the response of the individual to a treatment that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). The invention also provides methods for treating an individual having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) by administering an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). In some instances, the VEGF antagonist is administered as a monotherapy.

I. Defintions

It is to be understood that aspects and embodiments of the invention described herein include "comprising," "consisting," and "consisting essentially of" aspects and embodiments. As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

As used herein, the terms "individual," "patient," or "subject" are used interchangeably and refer to any single animal, more preferably a mammal (including such non-human animals as, for example, cats, dogs, horses, rabbits, zoo animals, cows, pigs, sheep, and non-human primates) for which treatment is desired. In particular embodiments, the patient herein is a human. The patient may be a "cancer patient," i.e., one who is suffering from cancer, or at risk for suffering from cancer, or suffering from one or more symptoms of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but are not limited to, kidney or renal cancer (e.g., renal cell carcinoma (RCC)); lung cancer, including small-cell lung cancer, non-small cell lung cancer, adenocarcinoma of the lung, and squamous carcinoma of the lung; bladder cancer (e.g., urothelial bladder cancer (UBC), muscle invasive bladder cancer (MIBC), and BCG-refractory non-muscle invasive bladder cancer (NMIBC)); cancer of the urinary tract; breast cancer (e.g., HER2+ breast cancer and triple-negative breast cancer (TNBC), which are estrogen receptors (ER−), progesterone receptors (PR−), and HER2 (HER2−) negative); prostate cancer, such as castration-resistant prostate cancer (CRPC); cancer of the peritoneum; hepatocellular cancer; gastric or stomach cancer, including gastrointestinal cancer and gastrointestinal stromal cancer; pancreatic cancer; glioblastoma; cervical cancer; ovarian cancer; liver cancer (e.g., hepatocellular carcinoma (HCC)); hepatoma; colon cancer; rectal cancer; colorectal cancer; endometrial or uterine carcinoma; salivary gland carcinoma; prostate cancer; vulval cancer; thyroid cancer; hepatic carcinoma; anal carcinoma; penile carcinoma; melanoma, including superficial spreading melanoma, lentigo maligna melanoma, acral lentiginous melanomas, and nodular melanomas; multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); acute myologenous leukemia (AML); hairy cell leukemia; chronic myeloblastic leukemia (CML); post-transplant lymphoproliferative disorder (PTLD); and myelodysplastic syndromes (MDS), as well as abnormal vascular proliferation associated with phakomatoses, edema (such as that associated with brain tumors), Meigs' syndrome, brain cancer, head and neck cancer, and associated metastases. In some embodiments, the cancer is kidney cancer. In particular embodiments, the kidney cancer is RCC (e.g., advanced RCC or metastatic RCC (mRCC), including previously untreated RCC).

By "early stage cancer" or "early stage tumor" is meant a cancer that is not invasive or metastatic or is classified as a Stage 0, I, or II cancer.

An "advanced" cancer is one which has spread outside the site or organ of origin, either by local invasion or metastasis.

A "refractory" cancer is one which progresses even though an anti-tumor agent, such as a chemotherapeutic agent, is being administered to the cancer patient. An example of a refractory cancer is one which is platinum refractory.

A "recurrent" cancer is one which has regrown, either at the initial site or at a distant site, after a response to initial therapy.

The terms "cell proliferative disorder" and "proliferative disorder" refer to disorders that are associated with some degree of abnormal cell proliferation. In one embodiment, the cell proliferative disorder is cancer.

The term "tumor," as used herein, refers to all neoplastic cell growth and proliferation, whether malignant or benign, and all pre-cancerous and cancerous cells and tissues.

The terms "cancer," "cancerous," "cell proliferative disorder," "proliferative disorder," and "tumor" are not mutually exclusive as referred to herein.

A "disorder" is any condition that would benefit from treatment including, but not limited to, chronic and acute disorders or diseases including those pathological conditions which predispose the mammal to the disorder in question.

The term "detection" includes any means of detecting, including direct and indirect detection.

The term "sample," as used herein, refers to a composition that is obtained or derived from a patient and/or individual of interest that contains a cellular and/or other molecular entity that is to be characterized and/or identified, for example, based on physical, biochemical, chemical, and/or physiological characteristics. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The terms "biomarker" and "marker" are used interchangeably herein to refer to a DNA, RNA, protein, carbohydrate, glycolipid, or cell-based molecular marker, the expression or presence of which in a patient's sample can be detected by standard methods (or methods disclosed herein). Such biomarkers include, but are not limited to, CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9. Expression of such a biomarker may be determined to be higher or lower in a sample obtained from a patient sensitive or responsive to a treatment (e.g., treatment with an anti-cancer therapy that includes a VEGF antagonist and a PD-L1 axis binding antagonist, or treatment with a multi-targeted tyrosine kinase inhibitor) than a reference level (including, e.g., the median expression level of the biomarker in a sample from a group/population of patients, e.g., patients having cancer, and being tested for responsiveness to a treatment; the median expression level of the biomarker in a sample from a group/population of patients, e.g., patients having cancer, and identified as not responding to a treatment; the level in a sample previously obtained from the individual at a prior time; or the level in a sample from a patient who received prior treatment (e.g., with an anti-cancer therapy that includes a VEGF antagonist and a PD-L1 axis binding antagonist, or treatment with a multi-targeted tyrosine kinase inhibitor) in a primary tumor setting, and who now may be experiencing metastasis).

The term "CD8A" as used herein, refers to any native CD8A from any vertebrate source, including mammals such as primates (e.g., humans) and rodents (e.g., mice and rats), unless otherwise indicated. The term encompasses "full-length," unprocessed CD8A as well as any form of CD8A that results from processing in the cell. The term also encompasses naturally occurring variants of CD8A, e.g., splice variants or allelic variants. The nucleic acid sequence of an exemplary human CD8A is set forth in SEQ ID NO: 1. The amino acid sequence of an exemplary protein encoded by human CD8A is shown in SEQ ID NO: 2.

The term "EOMES" as used herein, refers to any native EOMES (Eomesodermin) from any vertebrate source, including mammals such as primates (e.g., humans) and rodents (e.g., mice and rats), unless otherwise indicated. The term encompasses "full-length," unprocessed EOMES as well as any form of EOMES that results from processing in the cell. The term also encompasses naturally occurring variants of EOMES e.g., splice variants or allelic variants. The nucleic acid sequence of an exemplary human EOMES is set forth in SEQ ID NO: 3. The amino acid sequence of an exemplary protein encoded by human EOMES is shown in SEQ ID NO: 4.

The term "GZMA" as used herein, refers to any native GZMA (Granzyme A) from any vertebrate source, including mammals such as primates (e.g., humans) and rodents (e.g., mice and rats), unless otherwise indicated. The term encompasses "full-length," unprocessed GZMA as well as any form of GZMA that results from processing in the cell. The term also encompasses naturally occurring variants of GZMA, e.g., splice variants or allelic variants. The nucleic acid sequence of an exemplary human GZMA is set forth in SEQ ID NO: 51. The amino acid sequence of an exemplary protein encoded by human GZMA is shown in SEQ ID NO: 52.

The term "GZMB" as used herein, refers to any native GZMB (Granzyme B) from any vertebrate source, including mammals such as primates (e.g., humans) and rodents (e.g., mice and rats), unless otherwise indicated. The term encompasses "full-length," unprocessed GZMB as well as any form of GZMB that results from processing in the cell. The term also encompasses naturally occurring variants of GZMB, e.g., splice variants or allelic variants. The nucleic acid sequence of an exemplary human GZMB is set forth in SEQ ID NO: 53. The amino acid sequence of an exemplary protein encoded by human GZMB is shown in SEQ ID NO: 54.

The term "PRF1" as used herein, refers to any native PRF1 (Perforin 1; also known as Pore Forming Protein) from any vertebrate source, including mammals such as primates (e.g., humans) and rodents (e.g., mice and rats), unless otherwise indicated. The term encompasses "full-length," unprocessed PRF1 as well as any form of PRF1 that results from processing in the cell. The term also encompasses naturally occurring variants of PRF1, e.g., splice variants or allelic variants. The nucleic acid sequence of an exemplary human PRF1 is set forth in SEQ ID NO: 5. The amino acid sequence of an exemplary protein encoded by human PRF1 is shown in SEQ ID NO: 6.

The term "IFNG" as used herein, refers to any native IFNG (Interferon, Gamma) from any vertebrate source, including mammals such as primates (e.g., humans) and rodents (e.g., mice and rats), unless otherwise indicated. The term encompasses "full-length," unprocessed IFNG as well as any form of IFNG that results from processing in the cell. The term also encompasses naturally occurring variants of IFNG, e.g., splice variants or allelic variants. The nucleic acid sequence of an exemplary human IFNG is set forth in SEQ ID NO: 7. The amino acid sequence of an exemplary protein encoded by human IFNG is shown in SEQ ID NO: 8.

The terms "Programmed Death Ligand 1" and "PD-L1" refer herein to a native sequence PD-L1 polypeptide, polypeptide variants, and fragments of a native sequence polypeptide and polypeptide variants (which are further defined herein). The PD-L1 polypeptide described herein may be that which is isolated from a variety of sources, such as from human tissue types or from another source, or prepared by recombinant or synthetic methods.

A "native sequence PD-L1 polypeptide" comprises a polypeptide having the same amino acid sequence as the corresponding PD-L1 polypeptide derived from nature. The term encompasses "full-length," unprocessed PD-L1 as well as any form of IFNG that results from processing in the cell. The term also encompasses naturally occurring variants of IFNG, e.g., splice variants or allelic variants.

A "PD-L1 polypeptide variant," or variations thereof, means a PD-L1 polypeptide, generally an active PD-L1 polypeptide, as defined herein having at least about 80% amino acid sequence identity with any of the native sequence PD-L1 polypeptide sequences as disclosed herein. Such PD-L1 polypeptide variants include, for instance, PD-L1 polypeptides wherein one or more amino acid residues are added, or deleted, at the N- or C-terminus of a native amino acid sequence. Ordinarily, a PD-L1 polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence PD-L1 polypeptide sequence as disclosed herein. Ordinarily, PD-L1 variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 281, 282, 283, 284, 285, 286, 287, 288, or 289 amino acids in length, or more. Optionally, PD-L1 variant polypeptides will have no more than one conservative amino acid substitution as compared to a native PD-L1 polypeptide sequence, alternatively no more than 2, 3, 4, 5, 6, 7, 8, 9, or 10 conservative amino acid substitutions as compared to the native PD-L1 polypeptide sequence.

The term "vascular endothelial growth factor" or "VEGF" refers to vascular endothelial growth factor protein A (VEGFA), as exemplified by Swiss Prot Accession Number P15692, Gene ID (NCBI): 7422. The term "VEGF" encompasses the protein having the amino acid sequence of Swiss Prot Accession Number P15692, Gene ID (NCBI): 7422 as well as homologues and isoforms thereof. The term "VEGF" also encompasses the known isoforms, e.g., splice isoforms, of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110 amino acid human vascular endothelial cell growth factor generated by plasmin cleavage of $VEGF_{165}$ as described in Ferrara *Mol. Biol. Cell.* 21:687, 2010; Leung et al., *Science*, 246:1306. 1989; and Houck et al., *Mol. Endocrin.*, 5:1806, 1991. The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

The term "Kinase Insert Domain Receptor" or "KDR" as used herein, refers to any native KDR (also known in the art as Fetal Liver Kinase 1 (FLK1) or Vascular Endothelial Growth Factor Receptor 2 (VEGFR2)) from any vertebrate source, including mammals such as primates (e.g., humans) and rodents (e.g., mice and rats), unless otherwise indicated. The term encompasses "full-length," unprocessed KDR as well as any form of KDR that results from processing in the cell. The term also encompasses naturally occurring variants of KDR, e.g., splice variants or allelic variants. The nucleic acid sequence of an exemplary human KDR is set forth in SEQ ID NO: 9. The amino acid sequence of an exemplary protein encoded by human KDR is shown in SEQ ID NO: 10.

The term "Endothelial Cell Specific Molecule 1" or "ESM1" as used herein, refers to any native ESM1 (also known in the art as endocan) from any vertebrate source, including mammals such as primates (e.g., humans) and rodents (e.g., mice and rats), unless otherwise indicated. The term encompasses "full-length," unprocessed ESM1 as well as any form of ESM1 that results from processing in the cell. The term also encompasses naturally occurring variants of ESM1, e.g., splice variants or allelic variants. The nucleic acid sequence of an exemplary human ESM1 is set forth in SEQ ID NO: 11. The amino acid sequence of an exemplary protein encoded by human ESM1 is shown in SEQ ID NO: 12.

The term "Platelet And Endothelial Cell Adhesion Molecule 1" or "PECAM1" as used herein, refers to any native PECAM1 (also known in the art as CD31, endoCAM, GPIIA, or PECA1) from any vertebrate source, including mammals such as primates (e.g., humans) and rodents (e.g., mice and rats), unless otherwise indicated. The term encompasses "full-length," unprocessed PECAM1 as well as any form of PECAM1 that results from processing in the cell. The term also encompasses naturally occurring variants of PECAM1, e.g., splice variants or allelic variants. The nucleic acid sequence of an exemplary human PECAM1 is set forth in SEQ ID NO: 13. The amino acid sequence of an exemplary protein encoded by human PECAM1 is shown in SEQ ID NO: 14.

The term "FLT1" as used herein, refers to any native FLT1 (also known in the art as Vascular Endothelial Growth Factor Receptor 1 (VEGFR1) or fms related tyrosine kinase 1) from any vertebrate source, including mammals such as primates (e.g., humans) and rodents (e.g., mice and rats), unless otherwise indicated. The term encompasses "full-length," unprocessed FLT1 as well as any form of FLT1 that results from processing in the cell. The term also encompasses naturally occurring variants of FLT1, e.g., splice variants or allelic variants. The nucleic acid sequence of an exemplary human FLT1 is set forth in SEQ ID NO: 55. The amino acid sequence of an exemplary protein encoded by human FLT1 is shown in SEQ ID NO: 56.

The term "Angiopoietin Like 4" or "ANGPTL4" as used herein, refers to any native ANGPTL4 (also known in the art as Hepatic Fibrinogen/Angiopoietin-Related Protein (HFARP), Peroxisome Proliferator-Activated Receptor (PPAR) Gamma, Hepatic Angiopoietin-Related Protein (HARP), Angiopoietin-Related Protein 4 (Arp4), or Fasting-Induced Adipose Factor (FIAF)) from any vertebrate source, including mammals such as primates (e.g., humans) and rodents (e.g., mice and rats), unless otherwise indicated. The term encompasses "full-length," unprocessed ANGPTL4 as well as any form of ANGPTL4 that results from processing in the cell. The term also encompasses naturally occurring variants of ANGPTL4, e.g., splice variants or allelic variants. The nucleic acid sequence of an exemplary human ANGPTL4 is set forth in SEQ ID NO: 15. The amino acid sequence of an exemplary protein encoded by human ANGPTL4 is shown in SEQ ID NO: 16.

The term "CD34" as used herein, refers to any native CD34 (also known in the art as CD34 molecule or CD34 antigen) from any vertebrate source, including mammals such as primates (e.g., humans) and rodents (e.g., mice and rats), unless otherwise indicated. The term encompasses "full-length," unprocessed CD34 as well as any form of CD34 that results from processing in the cell. The term also encompasses naturally occurring variants of CD34, e.g., splice variants or allelic variants. The nucleic acid sequence of an exemplary human CD34 is set forth in SEQ ID NO: 17. The amino acid sequence of an exemplary protein encoded by human CD34 is shown in SEQ ID NO: 18.

The term "interleukin 6" or "IL6" as used herein, refers to any native IL6 from any vertebrate source, including mammals such as primates (e.g., humans) and rodents (e.g., mice and rats), unless otherwise indicated. The term encompasses "full-length," unprocessed IL6 as well as any form of IL6 that results from processing in the cell. The term also encompasses naturally occurring variants of IL6, e.g., splice variants or allelic variants. The nucleic acid sequence of an exemplary human IL6 is set forth in SEQ ID NO: 19. The amino acid sequence of an exemplary protein encoded by human IL6 is shown in SEQ ID NO: 20.

The term "CXCL1" as used herein, refers to any native CXCL1 (chemokine (C-X-C motif) ligand 1; also known as GRO1 or neutrophil-activating protein 3 (NAP-3)) from any vertebrate source, including mammals such as primates (e.g., humans) and rodents (e.g., mice and rats), unless otherwise indicated. The term encompasses "full-length," unprocessed CXCL1 as well as any form of CXCL1 that results from processing in the cell. The term also encompasses naturally occurring variants of CXCL1, e.g., splice variants or allelic variants. The nucleic acid sequence of an exemplary human CXCL1 is set forth in SEQ ID NO: 21. The amino acid sequence of an exemplary protein encoded by human CXCL1 is shown in SEQ ID NO: 22.

The term "CXCL2" as used herein, refers to any native CXCL2 (chemokine (C-X-C motif) ligand 2; also known as macrophage inflammatory protein 2-alpha (MIP2-alpha)) from any vertebrate source, including mammals such as primates (e.g., humans) and rodents (e.g., mice and rats), unless otherwise indicated. The term encompasses "full-length," unprocessed CXCL2 as well as any form of CXCL2 that results from processing in the cell. The term also encompasses naturally occurring variants of CXCL2, e.g., splice variants or allelic variants. The nucleic acid sequence of an exemplary human CXCL2 is set forth in SEQ ID NO: 23. The amino acid sequence of an exemplary protein encoded by human CXCL2 is shown in SEQ ID NO: 24.

The term "CXCL3" as used herein, refers to any native CXCL3 (chemokine (C-X-C motif) ligand 3; also known as macrophage inflammatory protein 2-beta (MIP2-beta)) from any vertebrate source, including mammals such as primates (e.g., humans) and rodents (e.g., mice and rats), unless otherwise indicated. The term encompasses "full-length," unprocessed CXCL3 as well as any form of CXCL3 that results from processing in the cell. The term also encompasses naturally occurring variants of CXCL3, e.g., splice variants or allelic variants. The nucleic acid sequence of an exemplary human CXCL3 is set forth in SEQ ID NO: 25. The amino acid sequence of an exemplary protein encoded by human CXCL3 is shown in SEQ ID NO: 26.

The term "CXCL8" as used herein, refers to any native CXCL8 (chemokine (C-X-C motif) ligand 8; also known as interleukin 8 (IL8)) from any vertebrate source, including mammals such as primates (e.g., humans) and rodents (e.g., mice and rats), unless otherwise indicated. The term encompasses "full-length," unprocessed CXCL8 as well as any form of CXCL8 that results from processing in the cell. The term also encompasses naturally occurring variants of CXCL8, e.g., splice variants or allelic variants. The nucleic acid sequence of an exemplary human CXCL8 is set forth in SEQ ID NO: 27. The amino acid sequence of an exemplary protein encoded by human CXCL8 is shown in SEQ ID NO: 28.

The term "PTGS2" as used herein, refers to any native PTGS2 (prostaglandin-endoperoxide synthase 2; also known as cyclooxygenase-2 (COX-2)) from any vertebrate source, including mammals such as primates (e.g., humans) and rodents (e.g., mice and rats), unless otherwise indicated. The term encompasses "full-length," unprocessed PTGS2 as well as any form of PTGS2 that results from processing in the cell. The term also encompasses naturally occurring variants of PTGS2, e.g., splice variants or allelic variants. The nucleic acid sequence of an exemplary human PTGS2 is set forth in SEQ ID NO: 29. The amino acid sequence of an exemplary protein encoded by human PTGS2 is shown in SEQ ID NO: 30.

The term "CXCR1" as used herein, refers to any native CXCR1 (C-X-C motif chemokine receptor 1; also known as interleukin 8 receptor, alpha, IL8RA, and CD181) from any vertebrate source, including mammals such as primates (e.g., humans) and rodents (e.g., mice and rats), unless otherwise indicated. The term encompasses "full-length," unprocessed CXCR1 as well as any form of CXCR1 that results from processing in the cell. The term also encompasses naturally occurring variants of CXCR1, e.g., splice variants or allelic variants. The nucleic acid sequence of an exemplary human CXCR1 is set forth in SEQ ID NO: 75. The amino acid sequence of an exemplary protein encoded by human CXCR1 is shown in SEQ ID NO: 76.

The term "CXCR2" as used herein, refers to any native CXCR2 (C-X-C motif chemokine receptor 2; also known as interleukin 8 receptor, beta, IL8RB, and CD182) from any vertebrate source, including mammals such as primates (e.g., humans) and rodents (e.g., mice and rats), unless otherwise indicated. The term encompasses "full-length," unprocessed CXCR2 as well as any form of CXCR2 that results from processing in the cell. The term also encompasses naturally occurring variants of CXCR2, e.g., splice variants or allelic variants. The nucleic acid sequence of an exemplary human CXCR2 is set forth in SEQ ID NO: 77. The amino acid sequence of an exemplary protein encoded by human CXCR2 is shown in SEQ ID NO: 78.

The term "S100A8" as used herein, refers to any native S100A8 (S100 calcium-binding protein A8; also known as calgranulin A) from any vertebrate source, including mammals such as primates (e.g., humans) and rodents (e.g., mice and rats), unless otherwise indicated. S100A8 can form a heterodimer with S100A9 called calprotectin. The term encompasses "full-length," unprocessed S100A8 as well as any form of S100A8 that results from processing in the cell. The term also encompasses naturally occurring variants of S100A8, e.g., splice variants or allelic variants. The nucleic acid sequence of an exemplary human S100A8 is set forth in SEQ ID NO: 79. The amino acid sequence of an exemplary protein encoded by human S100A8 is shown in SEQ ID NO: 80.

The term "S100A9" as used herein, refers to any native S100A9 (S100 calcium-binding protein A9; also known as calgranulin B and migration inhibitory factor-related protein 14 (MRP14)) from any vertebrate source, including mammals such as primates (e.g., humans) and rodents (e.g., mice and rats), unless otherwise indicated. The term encompasses "full-length," unprocessed S100A9 as well as any form of S100A9 that results from processing in the cell. The term also encompasses naturally occurring variants of S100A9, e.g., splice variants or allelic variants. The nucleic acid sequence of an exemplary human S100A9 is set forth in SEQ ID NO: 81. The amino acid sequence of an exemplary protein encoded by human S100A9 is shown in SEQ ID NO: 82.

The term "CXCL9" as used herein, refers to any native CXCL9 (Chemokine (C-X-C Motif) Ligand 9) from any vertebrate source, including mammals such as primates (e.g., humans) and rodents (e.g., mice and rats), unless otherwise indicated. The term encompasses "full-length," unprocessed CXCL9 as well as any form of CXCL9 that results from processing in the cell. The term also encompasses naturally occurring variants of CXCL9, e.g., splice variants or allelic variants. The nucleic acid sequence of an exemplary human CXCL9 is set forth in SEQ ID NO: 57. The amino acid sequence of an exemplary protein encoded by human CXCL9 is shown in SEQ ID NO: 58.

The term "CXCL10" as used herein, refers to any native CXCL10 (Chemokine (C-X-C Motif) Ligand 10) from any vertebrate source, including mammals such as primates (e.g., humans) and rodents (e.g., mice and rats), unless otherwise indicated. The term encompasses "full-length," unprocessed CXCL10 as well as any form of CXCL10 that results from processing in the cell. The term also encompasses naturally occurring variants of CXCL10, e.g., splice variants or allelic variants. The nucleic acid sequence of an exemplary human CXCL10 is set forth in SEQ ID NO: 59. The amino acid sequence of an exemplary protein encoded by human CXCL10 is shown in SEQ ID NO: 60.

The term "CXCL11" as used herein, refers to any native CXCL11 (Chemokine (C-X-C Motif) Ligand 11) from any vertebrate source, including mammals such as primates (e.g., humans) and rodents (e.g., mice and rats), unless otherwise indicated. The term encompasses "full-length," unprocessed CXCL11 as well as any form of CXCL11 that results from processing in the cell. The term also encompasses naturally occurring variants of CXCL11, e.g., splice variants or allelic variants. The nucleic acid sequence of an exemplary human CXCL11 is set forth in SEQ ID NO: 61. The amino acid sequence of an exemplary protein encoded by human CXCL11 is shown in SEQ ID NO: 62.

The term "CD27" as used herein, refers to any native CD27 (also known in the art as CD27L receptor or TNFRSF7) from any vertebrate source, including mammals such as primates (e.g., humans) and rodents (e.g., mice and rats), unless otherwise indicated. The term encompasses "full-length," unprocessed CD27 as well as any form of CD27 that results from processing in the cell. The term also encompasses naturally occurring variants of CD27, e.g., splice variants or allelic variants. The nucleic acid sequence of an exemplary human CD27 is listed in SEQ ID NO: 31. The amino acid sequence of an exemplary protein encoded by human CD27 is shown in SEQ ID NO: 32.

The term "FOXP3" as used herein, refers to any native FOXP3 (Forkhead Box P3, also known in the art as scurfin) from any vertebrate source, including mammals such as primates (e.g., humans) and rodents (e.g., mice and rats), unless otherwise indicated. The term encompasses "full-length," unprocessed FOXP3 as well as any form of FOXP3 that results from processing in the cell. The term also encompasses naturally occurring variants of FOXP3, e.g., splice variants or allelic variants. The nucleic acid sequence of an exemplary human FOXP3 is listed in SEQ ID NO: 33. The amino acid sequence of an exemplary protein encoded by human FOXP3 is shown in SEQ ID NO: 34.

The term "PD-1" as used herein, refers to any native PD-1 (also known as PDCD1, programmed cell death protein 1, or CD279) from any vertebrate source, including mammals such as primates (e.g., humans) and rodents (e.g., mice and rats), unless otherwise indicated. The term encompasses "full-length," unprocessed PD-1 as well as any form of PD-1 that results from processing in the cell. The term also encompasses naturally occurring variants of PD-1, e.g., splice variants or allelic variants. The nucleic acid sequence of an exemplary human PD-1 is listed in SEQ ID NO: 35. The amino acid sequence of an exemplary protein encoded by human PD-1 is shown in SEQ ID NO: 36.

The term "CTLA4" as used herein, refers to any native CTLA4 (Cytotoxic T-lymphocyte-associated protein 4, also known in the art as CD152) from any vertebrate source, including mammals such as primates (e.g., humans) and rodents (e.g., mice and rats), unless otherwise indicated. The term encompasses "full-length," unprocessed CTLA4 as well as any form of CTLA4 that results from processing in the cell. The term also encompasses naturally occurring variants of CTLA4, e.g., splice variants or allelic variants. The nucleic acid sequence of an exemplary human CTLA4 is listed in SEQ ID NO: 37. The amino acid sequence of an exemplary protein encoded by human CTLA4 is shown in SEQ ID NO: 38.

The term "TIGIT" as used herein, refers to any native TIGIT (T cell immunoreceptor with Ig and ITIM domains) from any vertebrate source, including mammals such as primates (e.g., humans) and rodents (e.g., mice and rats), unless otherwise indicated. The term encompasses "full-length," unprocessed TIGIT as well as any form of TIGIT that results from processing in the cell. The term also encompasses naturally occurring variants of TIGIT, e.g., splice variants or allelic variants. The nucleic acid sequence of an exemplary human TIGIT is listed in SEQ ID NO: 39. The amino acid sequence of an exemplary protein encoded by human TIGIT is shown in SEQ ID NO: 40.

The term "IDO1" as used herein, refers to any native IDO1 (indoleamine 2,3-dioxygenase 1) from any vertebrate source, including mammals such as primates (e.g., humans) and rodents (e.g., mice and rats), unless otherwise indicated. The term encompasses "full-length," unprocessed IDO1 as well as any form of IDO1 that results from processing in the cell. The term also encompasses naturally occurring variants of IDO1, e.g., splice variants or allelic variants. The nucleic acid sequence of an exemplary human IDO1 is listed in SEQ ID NO: 41. The amino acid sequence of an exemplary protein encoded by human IDO1 is shown in SEQ ID NO: 42.

The term "PSMB8" as used herein, refers to any native PSMB8 (Proteasome Subunit Beta Type-8) from any vertebrate source, including mammals such as primates (e.g., humans) and rodents (e.g., mice and rats), unless otherwise indicated. The term encompasses "full-length," unprocessed PSMB8 as well as any form of PSMB8 that results from processing in the cell. The term also encompasses naturally occurring variants of PSMB8, e.g., splice variants or allelic variants. The nucleic acid sequence of an exemplary human PSMB8 is listed in SEQ ID NO: 43. The amino acid sequence of an exemplary protein encoded by human PSMB8 is shown in SEQ ID NO: 44.

The term "PSMB9" as used herein, refers to any native PSMB9 (Proteasome Subunit Beta Type-9) from any vertebrate source, including mammals such as primates (e.g., humans) and rodents (e.g., mice and rats), unless otherwise indicated. The term encompasses "full-length," unprocessed PSMB9 as well as any form of PSMB9 that results from processing in the cell. The term also encompasses naturally occurring variants of PSMB9, e.g., splice variants or allelic variants. The nucleic acid sequence of an exemplary human PSMB9 is listed in SEQ ID NO: 45. The amino acid sequence of an exemplary protein encoded by human PSMB9 is shown in SEQ ID NO: 46.

The term "TAP1" as used herein, refers to any native TAP1 (Transporter Associated with Antigen Processing 1; also known in the art as antigen peptide transporter 1) from any vertebrate source, including mammals such as primates (e.g., humans) and rodents (e.g., mice and rats), unless otherwise indicated. The term encompasses "full-length," unprocessed TAP1 as well as any form of TAP1 that results from processing in the cell. The term also encompasses naturally occurring variants of TAP1, e.g., splice variants or allelic variants. The nucleic acid sequence of an exemplary human TAP1 is listed in SEQ ID NO: 47. The amino acid sequence of an exemplary protein encoded by human TAP1 is shown in SEQ ID NO: 48.

The term "TAP2" as used herein, refers to any native TAP2 (antigen peptide transporter 2) from any vertebrate source, including mammals such as primates (e.g., humans) and rodents (e.g., mice and rats), unless otherwise indicated. The term encompasses "full-length," unprocessed TAP2 as well as any form of TAP2 that results from processing in the cell. The term also encompasses naturally occurring variants of TAP2, e.g., splice variants or allelic variants. The nucleic acid sequence of an exemplary human TAP2 is listed in SEQ ID NO: 49. The amino acid sequence of an exemplary protein encoded by human TAP2 is shown in SEQ ID NO: 50.

The terms "level of expression" or "expression level" in general are used interchangeably and generally refer to the amount of a biomarker in a biological sample. "Expression" generally refers to the process by which information (e.g., gene-encoded and/or epigenetic information) is converted into the structures present and operating in the cell. Therefore, as used herein, "expression" may refer to transcription into a polynucleotide, translation into a polypeptide, or even polynucleotide and/or polypeptide modifications (e.g., post-translational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs). An expression level for more than one gene of interest may be determined by aggregation methods known to one skilled in the art and also disclosed herein, including, for example, by calculating the median or mean of all the expression levels of the genes of interest. Before aggregation, the expression level of each gene of interest may be normalized by using statistical methods known to one skilled in the art and also disclosed herein, including, for example, normalized to the expression level of one or more housekeeping genes, or normalized to a total library size, or normalized to the median or mean expression level value across all genes measured. In some instances, before aggregation across multiple genes of interest, the normalized expression level of each gene of interest may be standardized by using statistical methods known to one skilled in the art and also disclosed herein, including, for example, by calculating the Z-score of the normalized expression level of each gene of interest.

A sample or cell that "expresses" a protein of interest is one in which mRNA encoding the protein, or the protein, including fragments thereof, is determined to be present in the sample or cell.

As used herein, the term "reference expression level" refers to an expression level against which another expression level, e.g., the expression level of one or more genes described herein (e.g., any gene set forth in Table 1 or any combination thereof (e.g., any combination set forth in any one of Tables 2-12) in a sample from an individual is compared, e.g., to make a predictive, diagnostic, prognostic, and/or therapeutic determination. For example, the reference expression level may be derived from expression levels in a reference population (e.g., the median expression level in a reference population, e.g., a population of patients having a cancer), a reference sample, and/or a pre-assigned value (e.g., a cut-off value which was previously determined to significantly (e.g., statistically significantly) separate a first subset of individuals who have been treated with an anti-cancer therapy (e.g., an anti-cancer therapy including a VEGF antagonist and a PD-L1 axis binding antagonist (e.g., a PD-L1 binding antagonist (e.g., anti-PD-L1 antibody, e.g., atezolizumab (MPDL3280A)) or a PD-1 binding antagonist (e.g., anti-PD-1 antibody)), or an anti-cancer therapy including a multi-targeted tyrosine kinase inhibitor) in a reference population and a second subset of individuals who have been treated with a different anti-cancer therapy (or who have not been treated with the anti-cancer therapy) in the same reference population based on a significant difference between an individual's responsiveness to treatment with the anti-cancer therapy and an individual's responsiveness to treatment with the different anti-cancer therapy above the cut-off value and/or below the cut-off value). In some embodiments, the cut-off value may be the median or mean expression level in the reference population. In other embodiments, the reference level may be the top 40%, the top 30%, the top 20%, the top 10%, the top 5%, or the top 1% of the expression level in the reference population. In particular embodiments, the cut-off value may be the median expression level in the reference population. It will be appreciated by one skilled in the art that the numerical value for the reference expression level may vary depending on the indication (e.g., a cancer (e.g., a kidney cancer, a breast cancer, a lung cancer, or a bladder cancer), the methodology used to detect expression levels (e.g., RNA-seq or RT-qPCR), and/or the specific combinations of genes examined (e.g., any combination of the genes set forth in Table 1; or any one of the combinations of genes listed in Tables 2-12).

Expression "above" a level (e.g., above a reference level), "increased expression," "increased expression level," "increased levels," "elevated expression," "elevated expression levels," or "elevated levels" refers to an increased expression or increased levels of a biomarker in an individual relative to the expression level of the biomarker in a control (e.g., an individual or individuals who are not suffering from the disease or disorder (e.g., cancer), an internal control (e.g., a housekeeping biomarker), or the level of a biomarker in a sample obtained prior to administration of a therapy (e.g., an anti-cancer therapy that includes a VEGF antagonist and a PD-L1 antagonist)), or relative to a reference level (e.g., the median expression level of the biomarker in samples from a group/population of patients, e.g., patients having cancer who are being tested for responsiveness to a VEGF antagonist and a PD-L1 axis binding antagonist; the median expression level of the biomarker in samples from a group/population of patients, e.g., patients having cancer who have been identified as not responding to a VEGF antagonist and a PD-L1 axis binding antagonist; or the level in a sample previously obtained from the individual at a prior time).

Expression "below" a level (e.g., below a reference level), "decreased expression," "decreased expression level," "decreased levels," "reduced expression," "reduced expression levels," or "reduced levels" refers to a decrease expression or decreased levels of a biomarker in an individual relative to the expression level of the biomarker in a control (e.g., an individual or individuals who are not suffering from the disease or disorder (e.g., cancer), an internal control (e.g., a housekeeping biomarker), or the level of a biomarker in a sample obtained prior to administration of a therapy (e.g., an anti-cancer therapy that includes a VEGF antagonist and a PD-L1 antagonist)), or relative to a reference level (e.g., the median expression level of the biomarker in samples from a group/population of patients, e.g., patients having cancer who are being tested for responsiveness to a VEGF antagonist and a PD-L1 axis binding antagonist; the median expression level of the biomarker in samples from a group/population of patients, e.g., patients having cancer who have been identified as not responding to a VEGF antagonist and a PD-L1 axis binding antagonist; or the level in a sample previously obtained from the individual at a prior time). In some embodiments, reduced expression is little or no expression.

A "reference sample," "reference cell," "reference tissue," "control sample," "control cell," or "control tissue," as used herein, refers to a sample, cell, tissue, or standard that is used for comparison purposes. In one embodiment, a reference sample, reference cell, reference tissue, control sample, control cell, or control tissue is obtained from a healthy and/or non-diseased part of the body (e.g., tissue or cells) of the same patient or individual. For example, a reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same patient or individual. In yet another embodiment, a reference sample, reference cell, reference tissue, control sample, control cell, or control tissue is obtained from a healthy and/or non-diseased part of the body (e.g., tissues or cells) of an individual who is not the patient or individual. In even another embodiment, a reference sample, reference cell, reference tissue, control sample, control cell, or control tissue is obtained from an untreated tissue and/or cell of the body of an individual who is not the patient or individual. In another embodiment, a reference sample, reference cell, reference tissue, control sample, control cell, or control tissue is obtained from a patient prior to administration of a therapy (e.g., an anti-cancer therapy that includes a VEGF antagonist and/or a PD-L1 axis binding antagonist).

The phrase "based on" when used herein means that the information about one or more biomarkers is used to inform a treatment decision, information provided on a package insert, or marketing/promotional guidance, etc.

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies (e.g., anti-VEGF antibodies and anti-PD-L1 antibodies or anti-PD-1 antibodies) are used to delay development of a disease or to slow the progression of a disease or disorder.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

The technique of "polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 51:263 (1987) and Erlich, ed., *PCR Technology*, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real-time polymerase chain reaction" or "qRT-PCR" refers to a form of PCR wherein the amount of PCR product is measured at each step in a PCR reaction. This technique has been described in various publications including, for example, Cronin et al., *Am. J. Pathol.* 164(1): 35-42 (2004) and Ma et al., *Cancer Cell* 5:607-616 (2004).

The term "microarray" refers to an ordered arrangement of hybridizable array elements, preferably polynucleotide probes, on a substrate.

The term "RNA-seq," also called "Whole Transcriptome Shotgun Sequencing (WTSS)," refers to the use of highthroughput sequencing technologies to sequence and/or quantify cDNA to obtain information about a sample's RNA content. Publications describing RNA-seq include: Wang et al. *Nature Reviews Genetics* 10(1):57-63, 2009; Ryan et al. *Bio Techniques* 45(1):81-94, 2008; and Maher et al. *Nature* 458(7234):97-101, 2009.

The term "diagnosis" is used herein to refer to the identification or classification of a molecular or pathological state, disease or condition (e.g., cancer (e.g., kidney cancer)). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

A "tumor-infiltrating immune cell," as used herein, refers to any immune cell present in a tumor or a sample thereof. Tumor-infiltrating immune cells include, but are not limited to, intratumoral immune cells, peritumoral immune cells, other tumor stroma cells (e.g., fibroblasts), or any combination thereof. Such tumor-infiltrating immune cells can be, for example, T lymphocytes (such as CD8+T lymphocytes and/or CD4$^+$ T lymphocytes), B lymphocytes, or other bone marrow-lineage cells, including granulocytes (e.g., neutrophils, eosinophils, and basophils), monocytes, macrophages (e.g., CD68$^+$/CD163$^+$ macrophages), dendritic cells (e.g., interdigitating dendritic cells), histiocytes, and natural killer (NK) cells.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

As used herein, "administering" is meant a method of giving a dosage of a compound (e.g., a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))), a PD-L1 axis binding antagonist (e.g., an anti-PD-L1 antibody, e.g., atezolizumab), and/or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))) or a composition (e.g., a pharmaceutical composition, e.g., a pharmaceutical composition including a VEGF antagonist, a PD-L1 axis binding antagonist, and/or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))) to a patient. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, intravitreally (e.g., by intravitreal injection), by eye drop, orally, topically, transdermally, parenterally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

A "therapeutically effective amount" refers to an amount of a therapeutic agent to treat or prevent a disease or disorder (e.g., a cancer, e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival (e.g., overall survival or progression-free survival), time to disease progression (TTP), response rates (e.g., complete response (CR) and partial response (PR)), duration of response, and/or quality of life.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s). For example, in some embodiments, a VEGF antagonist and a PD-L1 axis binding antagonist may be administered concurrently.

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder being treated, the presence or size of metastases, or the size of the primary tumor.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose or "extended" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

"Response to a treatment," "responsiveness to treatment," or "benefit from a treatment" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival (OS HR <1) and progression free survival (PFS HR<1); and/or (9) decreased mortality at a given point of time following treatment (e.g., treatment with an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody), or treatment with an anti-cancer therapy that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))).

An "objective response" refers to a measurable response, including complete response (CR) or partial response (PR). In some embodiments, the "objective response rate (ORR)" refers to the sum of complete response (CR) rate and partial response (PR) rate.

By "complete response" or "CR" is intended the disappearance of all signs of cancer (e.g., disappearance of all target lesions) in response to treatment. This does not always mean the cancer has been cured.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration, or longer.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

The term "survival" refers to the patient remaining alive, and includes overall survival as well as progression-free survival.

As used herein, "progression-free survival" or "PFS" refers to the length of time during and after treatment during which the disease being treated (e.g., cancer, e.g., a kidney cancer (e.g., RCC), a lung cancer (e.g., NSCLC), a bladder cancer (e.g., UBC), or a breast cancer (e.g., TNBC)) does not progress or get worse. Progression-free survival may include the amount of time individuals have experienced a complete response or a partial response, as well as the amount of time individuals have experienced stable disease.

As used herein, "overall survival" or "OS" refers to the percentage of subjects in a group who are likely to be alive after a particular duration of time (e.g., 6 months, 1 year, 2 years, 3 years, 4 years, 5 years, 10 years, 15 years, 20 years, or more than 20 years from the time of diagnosis or treatment).

By "extending survival" is meant increasing overall or progression-free survival in a treated patient relative to an untreated patient (i.e. relative to a patient not treated with the medicament), or relative to a patient who does not express a biomarker at the designated level, and/or relative to a patient treated with an approved anti-tumor agent (e.g., an anti-VEGF antibody (e.g., bevacizumab), a PD-L1 axis binding antagonist (e.g., atezolizumab), and/or a multi-targeted tyrosine kinase inhibitor (e.g., sunitinib)).

As used herein, "hazard ratio" or "HR" is a statistical definition for rates of events. For the purpose of the invention, hazard ratio is defined as representing the probability of an event (e.g., PFS or OS) in the experimental (e.g., treatment) group/arm divided by the probability of an event in the control group/arm at any specific point in time. An HR with a value of 1 indicates that the relative risk of an endpoint (e.g., death) is equal in both the "treatment" and "control" groups; a value greater than 1 indicates that the risk is greater in the treatment group relative to the control group; and a value less than 1 indicates that the risk is greater in the control group relative to the treatment group. "Hazard ratio" in progression-free survival analysis (i.e., PFS HR) is a summary of the difference between two progression-free survival curves, representing the reduction in the risk of death on treatment compared to control, over a period of follow-up. "Hazard ratio" in overall survival analysis (i.e., OS HR) is a summary of the difference between two overall survival curves, representing the reduction in the risk of death on treatment compared to control, over a period of follow-up.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets: PDGFR-β, BlyS, APRIL, BCMA receptor(s), TRAIL/Apo2, other bioactive and organic chemical agents, and the like. Combinations thereof are also included in the invention.

A "VEGF antagonist" or "VEGF-specific antagonist" refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Such antagonists are also referred to herein as "VEGFR inhibitors." Included as VEGF-specific antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and VEGF$_{121}$-gelonin (Peregrine). VEGF-specific antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF-specific antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or $VEGF_{165}$.

As used herein VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGFA antibodies (e.g., bevacizumab, sevacizumab), anti-VEGFB antibodies, anti-VEGFC antibodies (e.g., VGX-100), anti-VEGFD antibodies, and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib).

An "anti-VEGF antibody" is an antibody that binds to VEGF with sufficient affinity and specificity. In certain embodiments, the antibody will have a sufficiently high binding affinity for VEGF, for example, the antibody may bind hVEGF with a Kd value of between 100 nM-1 pM. Antibody affinities may be determined, e.g., by a surface plasmon resonance based assay (such as the BIAcore® assay as described in PCT Application Publication No. WO2005/012359); enzyme-linked immunoabsorbent assay (ELISA); and competition assays (e.g. radioimmunoassays (RIAs)).

In certain embodiments, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF, or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (*Cancer Res.* 57:4593-4599, 1997), including but not limited to the antibody known as bevacizumab (BV; AVASTIN®).

The anti-VEGF antibody "Bevacizumab (BV)," also known as "rhuMAb VEGF" or "AVASTIN®," is a recombinant humanized anti-VEGF monoclonal antibody generated according to Presta et al. (*Cancer Res.* 57:4593-4599, 1997). It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879 issued Feb. 26, 2005, the entire disclosure of which is expressly incorporated herein by reference. Additional preferred antibodies include the G6 or B20 series antibodies (e.g., G6-31, B20-4.1), as described in PCT Application Publication No. WO 2005/012359. For additional preferred antibodies see U.S. Pat. Nos. 7,060,269, 6,582,959, 6,703,020; 6,054,297; WO98/45332; WO 96/30046; WO94/10202; EP 066686861; U.S. Patent Application Publication Nos. 2006009360, 20050186208, 20030206899, 20030190317, 20030203409, and 20050112126; and Popkov et al., (*Journal of Immunological Methods* 288:149-164, 2004). Other preferred antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183, and Q89.

The term "PD-L1 axis binding antagonist" refers to a molecule that inhibits the interaction of a PD-L1 axis binding partner with one or more of its binding partners, so as to remove T cell dysfunction resulting from signaling on the PD-1 signaling axis, with a result being restored or enhanced T cell function. As used herein, a PD-L1 axis binding antagonist includes a PD-L1 binding antagonist and a PD-1 binding antagonist as well as molecules that interfere with the interaction between PD-L1 and PD-1 (e.g., a PD-L2-Fc fusion).

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, for example, by a RIA. In certain embodiments, an anti-PD-L1 antibody binds to an epitope of PD-L1 that is conserved among PD-L1 from different species.

The terms "anti-PD-1 antibody" and "an antibody that binds to PD-1" refer to an antibody that is capable of binding PD-1 with sufficient affinity such that the antibody is useful as a diagnostic and/or therapeutic agent in targeting PD-1. In one embodiment, the extent of binding of an anti-PD-1 antibody to an unrelated, non-PD-1 protein is less than about 10% of the binding of the antibody to PD-1 as measured, for example, by a RIA. In certain embodiments, an anti-PD-1 antibody binds to an epitope of PD-1 that is conserved among PD-1 from different species.

The term "PD-L1 binding antagonist" refers to a molecule that decreases, blocks, inhibits, abrogates, or interferes with signal transduction resulting from the interaction of PD-L1 with either one or more of its binding partners, such as PD-1 or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen-binding fragments thereof, immunoadhesins, fusion proteins, oligopeptides, and other molecules that decrease, block, inhibit, abrogate, or interfere with signal transduction resulting from the interaction of PD-L1 with one or more of its binding partners, such as PD-1 or B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific embodiment, the anti-PD-L1 antibody is atezolizumab (CAS Registry Number: 1422185-06-5), also known as MPDL3280A, and described herein. In another specific embodiment, the anti-PD-L1 antibody is YW243.55.S70, described herein. In another specific embodiment, the anti-PD-L1 antibody is MDX-1105, described herein. In still another specific aspect, the anti-PD-L1 antibody is MED14736 (durvalumab), described herein. In still another specific aspect, the anti-PD-L1 antibody is MSB0010718C (avelumab), described herein.

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti PD-1 antibodies and antigen-binding fragments thereof, immunoadhesins, fusion proteins, oligopeptides, small molecule antagonists, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes, and other cells, mediated signaling through PD-1 or PD-L1 so as render a dysfunctional T cell less dysfunctional. In some embodiments, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is CT-011 (pidilizumab). In another specific aspect, a PD-1 binding antagonist is MEDI-0680 (AMP-514). In another specific aspect, a PD-1 binding antagonist is PDR001. In another specific aspect, a PD-1 binding antagonist is REGN2810. In another specific aspect, a PD-1 binding antagonist is BGB-108. In another specific aspect, a PD-1 binding antagonist is AMP-224.

An "angiogenesis inhibitor" or "anti-angiogenesis agent" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or the VEGF-A receptor (e.g., KDR receptor or Flt-1 receptor), anti-PDGFR inhibitors such as GLEEVEC™ (Imatinib Mesylate). Anti-angiogenesis agents also include native angiogenesis inhibitors, e.g., angiostatin, endostatin, etc. See, for example, Klagsbrun and D'Amore, *Annu. Rev. Physiol.*, 53:217-39 (1991); Streit and Detmar, *Oncogene*, 22:3172-3179 (2003) (e.g., Table 3 listing anti-angiogenic therapy in malignant melanoma); Ferrara & Alitalo, Nature Medicine 5(12):1359-1364 (1999); Tonini et al., *Oncogene*, 22:6549-6556 (2003) and, Sato *Int. J. Clin. Oncol.*, 8:200-206 (2003).

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. A tumoricidal agent causes destruction of tumor cells.

A "chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Pfizer), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride; vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlormaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1 I (*Angew. Chem. Intl. Ed. Engl.* 33:183-186, 1994); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agents also include anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); protein kinase inhibitors; lipid kinase inhibitors; antisense oligonucleotides, particularly those which inhibit expression of genes in signaling pathways implicated in aberrant cell proliferation, such as, for example, PKC-alpha, Ralf and H-Ras; ribozymes such as VEGF expression inhibitors (e.g., ANGIOZYME®) and HER2 expression inhibitors; vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and pharmaceutically acceptable salts, acids and derivatives of any of the above.

Chemotherapeutic agents also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories), which is a recombinant, exclusively human-sequence, full-length IgG1 λ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yK)]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyOmethoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396, WO 1999/09016, WO 1998/43960, WO 1997/38983, WO 1999/06378, WO 1999/06396, WO 1996/30347, WO 1996/33978, WO 1996/3397, and WO 1996/33980.

The term "multi-targeted tyrosine kinase inhibitor," as used herein, refers to a tyrosine kinase inhibitor that inhibits multiple (i.e., more than one) tyrosine kinase proteins. The tyrosine kinase proteins may be receptor tyrosine kinases and/or cellular tyrosine kinases. For example, the multi-targeted tyrosine kinase inhibitor may inhibit platelet-derived growth factor receptors (e.g., PDGFR-$\alpha\alpha$, PDGFR-$\beta\beta$, and/or PDGFR-$\alpha\beta$), VEGF receptors (e.g., VEGFR1 and/or VEGFR2), CD117 (c-Kit), RET, CD114, and/or CD135. Exemplary multi-targeted tyrosine kinase inhibitors include sunitinib (also known as N-[2-(Diethylamino)ethyl]-5-[(Z)-(5-fluoro-2-oxo-1,2-dihydro-3H-indol-3-ylidene) methyl]-2,4-dimethyl-1H-pyrrole-3-carboxamide, SUTENT® or SU11248), SU6656, motesanib, sorafenib (e.g., NEXEVAR® or BAY439006), axitinib, afatinib, bosutinib, crizotinib, cabozantinib, dasatinib, entrectinib, pazopanib, lapatinib, and vandetanib (also known as ZACTIMA® or ZD6474). It is to be understood that a multi-targeted tyrosine kinase inhibitor that inhibits a VEGF receptor may also be considered a VEGFR inhibitor.

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, all-trans retinoic acid (ATRA), valrubicin, zoledronate, and zoledronic acid, and pharmaceutically acceptable salts thereof.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "growth inhibitory agent" when used herein refers to a compound or composition which inhibits growth and/or proliferation of a cell (e.g., a cell whose growth is dependent on PD-L1 expression) either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-Iyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "*The Molecular Basis of Cancer*," Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

The term "pharmaceutical formulation" refers to a preparation which is in such form as to permit the biological activity of an active ingredient contained therein to be effective, and which contains no additional components which are unacceptably toxic to a patient to which the formulation would be administered.

A "pharmaceutically acceptable carrier" refers to an ingredient in a pharmaceutical formulation, other than an active ingredient, which is nontoxic to a patient. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications, and/or warnings concerning the use of such therapeutic products.

A "sterile" formulation is aseptic or free from all living microorganisms and their spores.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

The term "small molecule" refers to any molecule with a molecular weight of about 2000 daltons or less, preferably of about 500 daltons or less.

The word "label" when used herein refers to a compound or composition that is conjugated or fused directly or indirectly to a reagent such as a polynucleotide probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody is one which has been identified and separated and/or recovered from a component of its natural environment. Contaminant components of its natural environment are materials which would interfere with research, diagnostic, and/or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

A "blocking" antibody or an antibody "antagonist" is one which inhibits or reduces biological activity of the antigen it binds. For example, a VEGF-specific antagonist antibody binds VEGF and inhibits the ability of VEGF to induce vascular endothelial cell proliferation. Preferred blocking antibodies or antagonist antibodies completely inhibit the biological activity of the antigen.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

The "light chains" of antibodies (immunoglobulins) from any mammalian species can be assigned to one of two clearly distinct types, called kappa ("κ") and lambda ("λ"), based on the amino acid sequences of their constant domains.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2, and CH3 domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from, for example, around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al., *Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia and Lesk, *J. Mol. Biol.* 196:901-917 (1987). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the ntibody in antibody dependent cellular cytotoxicity (ADCC).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "hypervariable region," "HVR," or "HV," as used herein, refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, for example, Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, for example, Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |

| Loop | Kabat | AbM | Chothia | Contact |
|------|-------|-----|---------|---------|
| H1 | H31-H35b | H26-H35b | H26-H32 | H30-H35b (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

Unless otherwise indicated, HVR residues and other residues in the variable domain (e.g., FR residues) are numbered herein according to Kabat et al., supra.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. In some embodiments, the antibody fragment described herein is an antigen-binding fragment. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md. (1991).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down-regulation of cell surface receptors (e.g. B cell receptor); and B cell activation.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "multispecific antibody" is used in the broadest sense and specifically covers an antibody comprising a heavy chain variable domain (VH) and a light chain variable domain (VL), where the VH-VL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of antibodies are called α, δ, ε, γ, and µ, respectively.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature* 256:495-97 (1975); Hongo et al., *Hybridoma* 14 (3): 253-260 (1995), Harlow et al., *Antibodies: A Laboratory Manual* (Cold Spring Harbor Laboratory Press, 2nd ed. 1988); Hammerling et al., in: *Monoclonal Antibodies and T cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628, 1991; Marks et al., *J. Mol. Biol.* 222: 581-597, 1992; Sidhu et al., *J. Mol. Biol.* 338(2): 299-310, 2004; Lee et al., *J. Mol. Biol.* 340(5): 1073-1093, 2004; Fellouse, *Proc. Natl. Acad. Sci. USA* 101(34): 12467-12472,2004; and Lee et al., *J. Immunol Methods* 284(1-2): 119-132, 2004; and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551, 1993; Jakobovits et al., *Nature* 362: 255-258, 1993; Bruggemann et al., *Year in ImmunoL* 7:33, 1993; U.S. Pat. Nos. 5,545,807; 5,545,806; 5,569,825; 5,625,126; 5,633, 425; and 5,661,016; Marks et al., *Bio/Technology* 10: 779-783 (1992); Lonberg et al., *Nature* 368: 856-859, 1994; Morrison, *Nature* 368: 812-813, 1994; Fishwild et al., *Nature Biotechnol.* 14: 845-851, 1996; Neuberger, *Nature Biotechnol.* 14: 826, 1996; and Lonberg et al., *Intern. Rev. ImmunoL* 13: 65-93, 1995.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, FR residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525, 1986; Riechmann et al., *Nature* 332:323-329, 1988; and Presta, *Curr. Op. Struct. Biol.* 2:593-596, 1992.

A "wild-type (WT)" or "reference" sequence or the sequence of a "wild-type" or "reference" protein/polypeptide, such as an HVR or a variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

A "variant" or "mutant" of a starting or reference polypeptide (e.g., a reference antibody or its variable domain(s)/HVR(s)), is a polypeptide that (1) has an amino acid sequence different from that of the starting or reference polypeptide and (2) was derived from the starting or reference polypeptide through either natural or artificial (man-made) mutagenesis. Such variants include, for example, deletions from, and/or insertions into and/or substitutions of, residues within the amino acid sequence of the polypeptide of interest, referred to herein as "amino acid residue alterations." Thus, a variant HVR refers to a HVR comprising a variant sequence with respect to a starting or reference polypeptide sequence (such as that of a source antibody or antigen binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described herein.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of $10^{-4}$M or lower, alternatively $10^{-5}$M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a Kd in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and Kd values are inversely related. A high affinity for an antigen is measured by a low Kd value. In one embodiment, the term "specific binding" refers to binding where a molecule binds to a particular polypeptide or epitope on a particular polypeptide without substantially binding to any other polypeptide or polypeptide epitope.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

An "immunoconjugate" is an antibody conjugated to one or more heterologous molecule(s), including but not limited to a cytotoxic agent.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG1, IgG2 (including IgG2A and IgG2B), IgG3, or IgG4 subtypes, IgA (including IgA1 and IgA2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130. For example, useful immunoadhesins as medicaments useful for therapy herein include polypeptides that comprise the extracellular domain (ECD) or PD-1-binding portions of PD-L1 or PD-L2, or the extracellular or PD-L1- or PD-L2-binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, and the like. The two portions may be linked directly by a single peptide bond or through a peptide linker but are in reading frame with each other.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs.

A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally-occurring nucleotides with an analog, internucleotide modifications such as, for example, those with uncharged linkages (e.g., methyl phosphonates, phosphotriesters, phosphoamidates, carbamates, and the like) and with charged linkages (e.g., phosphorothioates, phosphorodithioates, and the like), those containing pendant moieties, such as, for example, proteins (e.g., nucleases, toxins, antibodies, signal peptides, poly-L-lysine, and the like), those with intercalators (e.g., acridine, psoralen, and the like), those containing chelators (e.g., metals, radioactive metals, boron, oxidative metals, and the like), those containing alkylators, those with modified linkages (e.g., alpha anomeric nucleic acids), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro-, or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, single stranded, polynucleotides that are, but not necessarily, less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single-stranded polynucleotide that is capable of hybridizing to a nucleic acid and allowing polymerization of a complementary nucleic acid, generally by providing a free 3'-OH group.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

II. Diagnostic Methods and Assays

Provided herein are methods and assays for identifying an individual having a cancer (e.g., a kidney cancer (e.g., a renal cell carcinoma (RCC)), a lung cancer (e.g., a non-small cell lung cancer (NSCLC)), a bladder cancer (e.g., a urothelial bladder cancer (UBC)), a liver cancer (e.g., HCC), an ovarian cancer, or a breast cancer (e.g., a triple-negative breast cancer (TNBC))) who may benefit from a treatment with an anti-cancer therapy including a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)). Also provided herein are methods and assays for identifying an individual having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) who may benefit from a treatment with an anti-cancer therapy including an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). In particular embodiments, the angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) therapy may be a monotherapy (e.g., a sunitinib monotherapy).

The methods and assays described herein are based on the finding that the expression level of one or more genes (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) in a sample from the individual may be used to predict the therapeutic efficacy of an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)). In another aspect, methods and assays described herein are based on the finding that the expression level of one or more genes (e.g., VEGFA, KDR, ESM1, PECAM1, FLT1, ANGPTL4, and/or CD34) in a sample from the individual may be used to predict the therapeutic efficacy of a treatment including an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))).

Further provided herein are methods and assays for selecting a therapy for an individual having a cancer (e.g., kidney cancer (e.g., RCC), lung cancer (e.g., NSCLC), bladder cancer (e.g., UBC), a liver cancer (e.g., hepatocellular carcinoma (HCC)), an ovarian cancer, or breast cancer (e.g., TNBC)); methods for determining whether an individual having a cancer is likely to respond to treatment including a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)); methods for determining whether an individual having a cancer is likely to respond to treatment including an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))); methods for predicting the responsiveness of an individual having a cancer to treatment comprising a VEGF antagonist and a PD-L1 axis binding antagonist; methods for predicting the responsiveness of an individual having a cancer to treatment comprising an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))); methods for monitoring the response of an individual having a cancer to treatment including a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)); and methods for monitoring the response of an individual having a cancer to treatment including an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). Any of the methods provided herein may further include administering to the individual a VEGF antagonist and a PD-L1 axis binding antagonist (e.g., as described below in Section III) to the individual.

Provided herein is a method of identifying an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) who may benefit from treatment with an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) that involves determining the expression level of one or more of the genes set forth in Table 1 in a sample from the individual, wherein a change in the expression level of one or more of the genes set forth in Table 1 identifies the individual as one who may benefit from treatment with an anti-cancer therapy (e.g., an anti-cancer therapy comprising a VEGF antagonist and a PD-L1 axis binding antagonist or a angiogenesis inhibitor). In some instances, the change is an increase. In other instances, the change is a decrease.

TABLE 1

| Exemplary Biomarkers |
| --- |
| Biomarkers |
| CD8A |
| EOMES |
| GZMA |
| GZMB |
| PRF1 |
| IFNG |
| PD-L1 |
| CXCL9 |

TABLE 1-continued

| Exemplary Biomarkers |
| --- |
| Biomarkers |
| CXCL10 |
| CXCL11 |
| CD27 |
| FOXP3 |
| PD-1 |
| CTLA4 |
| TIGIT |
| IDO1 |
| PSMB8 |
| PSMB9 |
| TAP1 |
| TAP2 |
| VEGFA |
| KDR |
| ESM1 |
| PECAM1 |
| FLT1 |
| ANGPTL4 |
| CD34 |
| IL6 |
| CXCL1 |
| CXCL2 |
| CXCL3 |
| CXCL8 |
| PTGS2 |
| CXCR1 |
| CXCR2 |
| S100A8 |
| S100A9 |

The invention also provides for selecting a therapy for an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) that includes determining the expression level of one or more of the genes set forth in Table 1 in a sample from the individual, wherein a change in the expression level of one or more of the genes set forth in Table 1 identifies the individual as one who may benefit from treatment with an anti-cancer therapy (e.g., an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)), or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). In some instances, the change is an increase. In other instances, the change is a decrease.

In another embodiment, the invention provides a method of diagnosing or prognosing a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) that includes determining the expression level of one or more biomarkers in a sample from an individual and comparing the expression level of the one or more biomarkers in the sample with a reference level, thereby diagnosing or prognosing the cancer. In some embodiments, a change in the expression level (e.g., an increase or a decrease) of the one or more biomarkers in the sample relative to the reference level diagnoses or prognoses the individual. In some embodiments, the biomarker is set forth in Table 1.

In yet another embodiment, the invention provides a method of determining whether a patient having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) is likely to respond to treatment with an anti-cancer therapy (e.g., an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)), or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) that includes determining the expression level of one or more biomarkers in a sample from the individual and comparing the expression level of the one or more biomarkers in the sample with a reference level, thereby identifying the individual as one who is likely to respond to the anti-cancer therapy. In some embodiments, a change in the expression level (e.g., an increase or a decrease) of the one or more biomarkers in the biological sample relative to the reference level identifies the patient as likely to respond to treatment with the anti-cancer therapy. In some embodiments, the biomarker is set forth in Table 1.

In other embodiments, the invention provides a method of optimizing therapeutic efficacy of an anti-cancer therapy (e.g., an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)), or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))) that includes determining the expression level of one or more biomarkers in a biological sample obtained from the patient and comparing the expression level of the one or more biomarkers in the sample with a reference level, wherein a change (e.g., an increase or decrease) in the expression level of the one or more biomarkers in the biological sample relative to the reference level identifies a patient who is likely to respond to the anti-cancer therapy. In some embodiments, the biomarker is set forth in Table 1.

In another embodiment, provided herein is a method of identifying an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) who may benefit from treatment with an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) that includes determining the expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9, wherein (i) an expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample that is at or above a reference expression level of the one or more genes; or (ii) an expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample that is below a reference expression level of the one or more genes identifies the individual as one who may benefit from treatment with an anti-cancer therapy that includes a VEGF antagonist and a PD-L1 axis binding antagonist.

In yet another embodiment, provided herein is a method for selecting a therapy for an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) that includes determining the expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9, wherein (i) an expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample that is at or above a reference expression level of the one or more genes; or (ii) an expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample that is below a reference expression level of the one or more genes identifies the individual as one who may benefit from treatment with an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)).

In any of the preceding methods, the method may include determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2. In some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2.

For example, any of the preceding methods may include determining the expression level of one or more (e.g., 1, 2, 3, 4, or 5) of CD8A, EOMES, PRF1, IFNG, or PD-L1. In some embodiments, the method includes determining the expression level of at least two, at least three, at least four, or all five of CD8A, EOMES, PRF1, IFNG, and PD-L1. In some embodiments, the method includes determining the expression level of two of CD8A, EOMES, PRF1, IFNG, and PD-L1, for example, any of the exemplary combinations shown in Table 2. In some embodiments, the method includes determining the expression level of three of CD8A, EOMES, PRF1, IFNG, and PD-L1, for example, any of the exemplary combinations shown in Table 3. In some embodiments, the method includes determining the expression level of four of CD8A, EOMES, PRF1, IFNG, and PD-L1, for example, any of the exemplary combinations shown in Table 4. In some embodiments, the method involves determining the expression level of CD8A, EOMES, PRF1, IFNG, and PD-L1.

TABLE 2

Two-Gene Combinations of CD8A, EOMES, PRF1, IFNG, and PD-L1

CD8A and EOMES
CD8A and PRF1
CD8A and IFNG
CD8A and PD-L1
EOMES and PRF1
EOMES and IFNG
EOMES and PD-L1
PRF1 and IFNG
PRF1 and PD-L1
IFNG and PD-L1

TABLE 3

Three-Gene Combinations of CD8A, EOMES, PRF1, IFNG, and PD-L1

CD8A, EOMES, and PRF1
CD8A, EOMES, and IFNG
CD8A, EOMES, and PD-L1
CD8A, PRF1, and IFNG
CD8A, PRF1, and PD-L1
CD8A, IFNG, and PD-L1
EOMES, PRF1, and IFNG
EOMES, PRF1, and PD-L1
EOMES, IFNG, and PD-L1
PRF1, IFNG, and PD-L1

TABLE 4

Four-Gene Combinations of CD8A, EOMES, PRF1, IFNG, and PD-L1

CD8A, EOMES, PRF1, and IFNG
CD8A, EOMES, PRF1, and PD-L1
CD8A, EOMES, IFNG, and PD-L1
CD8A, PRF1, IFNG, and PD-L1
EOMES, PRF1, IFNG, and PD-L1

In some embodiments, any of the preceding methods may include determining the expression level of PD-L1 and one or more additional genes, wherein the one or more additional genes is other than PD-L1. For example, in some embodiments, the method may include determining the expression level of PD-L1 and one or more additional genes (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) selected from the group consisting of: CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and S100A9. In some embodiments, the method includes determining the expression level of PD-L1 and one or more (e.g., 1, 2, 3, 4, 5, 6, 7, 8, 9, 10, 11, 12, 13, 14, 15, 16, 17, 18, or 19) additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, and TAP2. In other embodiments, the method includes determining the expression level of PD-L1 and one or more (e.g., 1, 2, 3, 4, 5, 6, or 7) of VEGFA, KDR, ESM1, PECAM1, FLT1, ANGPTL4, or CD34. In other embodiments, the method includes determining the expression level of PD-L1 and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9.

Any of the preceding methods may include determining the expression level of one or more (e.g., 1, 2, 3, 4, 5, 6, or 7) of VEGFA, KDR, ESM1, PECAM1, FLT1, ANGPTL4, or CD34. In some embodiments, the method includes determining the expression level of at least two, at least three, at least four, at least five, at least six, or all seven of VEGFA, KDR, ESM1, PECAM1, FLT1, ANGPTL4, or CD34. For example, in some embodiments, the method includes determining the expression level of one or more (e.g., 1, 2, 3, 4, 5, or 6) of VEGFA, KDR, ESM1, PECAM1, ANGPTL4, or CD34. In some embodiments, the method includes determining the expression level of at least two, at least three, at least four, at least five, or all six of VEGFA, KDR, ESM1, PECAM1, ANGPTL4, and CD34. In some embodiments, the method includes determining the expression level of two of VEGFA, KDR, ESM1, PECAM1, ANGPTL4, and CD34, for example, any of the exemplary combinations shown in Table 5. In some embodiments, the method includes determining the expression level of three of VEGFA, KDR, ESM1, PECAM1, ANGPTL4, and CD34, for example, any of the exemplary combinations shown in Table 6. In some embodiments, the method includes determining the expression level of four of VEGFA, KDR, ESM1, PECAM1, ANGPTL4, and CD34, for example, any of the exemplary combinations shown in Table 7. In some embodiments, the method includes determining the expression level of five of VEGFA, KDR, ESM1, PECAM1, ANGPTL4, and CD34, for example, any of the exemplary combinations shown in Table 8. In some embodiments, the method includes determining the expression level of VEGFA, KDR, ESM1, PECAM1, ANGPTL4, and CD34.

TABLE 5

Two-Gene Combinations of VEGFA, KDR, ESM1, PECAM1, ANGPTL4, and CD34

VEGFA and KDR
VEGFA and ESM1
VEGFA and PECAM1
VEGFA and ANGPTL4
VEGFA and CD34
KDR and ESM1
KDR and PECAM1

TABLE 5-continued

Two-Gene Combinations of VEGFA, KDR, ESM1,
PECAM1, ANGPTL4, and CD34

KDR and ANGPTL4
KDR and CD34
ESM1 and PECAM1
ESM1 and ANGPTL4
ESM1 and CD34
PECAM1 and ANGPTL4
PECAM1 and CD34
ANGPTL4 and CD34

TABLE 6

Three-Gene Combinations of VEGFA, KDR,
ESM1, PECAM1, ANGPTL4, and CD34

VEGFA, KDR, and ESM1
VEGFA, KDR, and PECAM1
VEGFA, KDR, and ANGPTL4
VEGFA, KDR, and CD34
VEGFA, ESM1, and PECAM1
VEGFA, ESM1, and ANGPTL4
VEGFA, ESM1, and CD34
VEGFA, PECAM1, and ANGPTL4
VEGFA, PECAM1, and CD34
VEGFA, ANGPTL4, and CD34
KDR, ESM1, and PECAM1
KDR, ESM1, and ANGPTL4
KDR, ESM1, and CD34
KDR, PECAM1, and ANGPTL4
KDR, PECAM1, and CD34
KDR, ANGPTL4, and CD34
ESM1, PECAM1, and ANGPTL4
ESM1, PECAM1, and CD34
ESM1, ANGPTL4, and CD34
PECAM1, ANGPTL4, and CD34

TABLE 7

Four-Gene Combinations of VEGFA, KDR, ESM1,
PECAM1, ANGPTL4, and CD34

VEGFA, KDR, ESM1, and PECAM1
VEGFA, KDR, ESM1, and ANGPTL4
VEGFA, KDR, ESM1, and CD34
VEGFA, KDR, PECAM1, and ANGPTL4
VEGFA, KDR, PECAM1, and CD34
VEGFA, KDR, ANGPTL4, and CD34
VEGFA, ESM1, PECAM1, and ANGPTL4
VEGFA, ESM1, PECAM1, and CD34
VEGFA, ESM1, ANGPTL4, and CD34
VEGFA, PECAM1, ANGPTL4, and CD34
KDR, ESM1, PECAM1, and ANGPTL4
KDR, ESM1, PECAM1, and CD34
KDR, ESM1, ANGPTL4, and CD34
KDR, PECAM1, ANGPTL4, and CD34
ESM1, PECAM1, ANGPTL4, and CD34

TABLE 8

Five-Gene Combinations of VEGFA, KDR, ESM1, PECAM1,
ANGPTL4, and CD34

VEGFA, KDR, ESM1, PECAM1, and ANGPTL4
VEGFA, KDR, ESM1, PECAM1, and CD34
VEGFA, KDR, ESM1, ANGPTL4, and CD34
VEGFA, KDR, PECAM1, ANGPTL4, and CD34
VEGFA, ESM1, PECAM1, ANGPTL4, and CD34
KDR, ESM1, PECAM1, ANGPTL4, and CD34

Any of the preceding methods may include determining the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. In some embodiments, the method includes determining the expression level of at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9. In some embodiments, the method includes determining the expression level of two of IL6, CXCL1, CXCL2, CXCL3, CXCL8, PTGS2, CXCR1, CXCR2, S100A8, and S100A9, for example, any of the exemplary combinations shown in Table 9. In some embodiments, the method includes determining the expression level of three of IL6, CXCL1, CXCL2, CXCL3, CXCL8, PTGS2, CXCR1, CXCR2, S100A8, and S100A9, for example, any of the exemplary combinations shown in Table 10. In some embodiments, the method includes determining the expression level of four of IL6, CXCL1, CXCL2, CXCL3, CXCL8, PTGS2, CXCR1, CXCR2, S100A8, and S100A9, for example, any of the exemplary combinations shown in Table 11. In some embodiments, the method includes determining the expression level of five of IL6, CXCL1, CXCL2, CXCL3, CXCL8, PTGS2, CXCR1, CXCR2, S100A8, and S100A9, for example, any of the exemplary combinations shown in Table 12. In some embodiments, the method includes determining the expression level of six of IL6, CXCL1, CXCL2, CXCL3, CXCL8, PTGS2, CXCR1, CXCR2, S100A8, and S100A9, for example, any of the exemplary combinations shown in Table 13. In some embodiments, the method includes determining the expression level of seven of IL6, CXCL1, CXCL2, CXCL3, CXCL8, PTGS2, CXCR1, CXCR2, S100A8, and S100A9, for example, any of the exemplary combinations shown in Table 14. In some embodiments, the method includes determining the expression level of eight of IL6, CXCL1, CXCL2, CXCL3, CXCL8, PTGS2, CXCR1, CXCR2, S100A8, and S100A9, for example, any of the exemplary combinations shown in Table 15. In some embodiments, the method includes determining the expression level of nine of IL6, CXCL1, CXCL2, CXCL3, CXCL8, PTGS2, CXCR1, CXCR2, S100A8, and S100A9, for example, any of the exemplary combinations shown in Table 16. In some embodiments, the method includes determining the expression level of IL6, CXCL1, CXCL2, CXCL3, CXCL8, PTGS2, CXCR1, CXCR2, S100A8, and S100A9.

TABLE 9

Two-Gene Combinations of IL6, CXCL1, CXCL2,
CXCL3, CXCL8, PTGS2, CXCR1,
CXCR2, S100A8, and S100A9

IL6 and CXCL1
IL6 and CXCL2
IL6 and CXCL3
IL6 and CXCL8
IL6 and PTGS2
IL6 and CXCR1
IL6 and CXCR2
IL6 and S100A8
IL6 and S100A9
CXCL1 and CXCL2
CXCL1 and CXCL3
CXCL1 and CXCL8
CXCL1 and PTGS2
CXCL1 and CXCR1
CXCL1 and CXCR2
CXCL1 and S100A8
CXCL1 and S100A9
CXCL2 and CXCL3
CXCL2 and CXCL8
CXCL2 and PTGS2
CXCL2 and CXCR1

TABLE 9-continued

Two-Gene Combinations of IL6, CXCL1, CXCL2, CXCL3, CXCL8, PTGS2, CXCR1, CXCR2, S100A8, and S100A9

CXCL2 and CXCR2
CXCL2 and S100A8
CXCL2 and S100A9
CXCL3 and CXCL8
CXCL3 and PTGS2
CXCL3 and CXCR1
CXCL3 and CXCR2
CXCL3 and S100A8
CXCL3 and S100A9
CXCL8 and PTGS2
CXCL8 and CXCR1
CXCL8 and CXCR2
CXCL8 and S100A8
CXCL8 and S100A9
PTGS2 and CXCR1
PTGS2 and CXCR2
PTGS2 and S100A8
PTGS2 and S100A9
CXCR1 and CXCR2
CXCR1 and S100A8
CXCR1 and S100A9
CXCR2 and S100A8
CXCR2 and S100A9
S100A8 and S100A9

TABLE 10

Three-Gene Combinations of IL6, CXCL1, CXCL2, CXCL3, CXCL8, PTGS2, CXCR1, CXCR2, S100A8, and S100A9

IL6, CXCL1, and CXCL2
IL6, CXCL1, and CXCL3
IL6, CXCL1, and CXCL8
IL6, CXCL1, and PTGS2
IL6, CXCL1, and CXCR1
IL6, CXCL1, and CXCR2
IL6, CXCL1, and S100A8
IL6, CXCL1, and S100A9
IL6, CXCL2, and CXCL3
IL6, CXCL2, and CXCL8
IL6, CXCL2, and PTGS2
IL6, CXCL2, and CXCR1
IL6, CXCL2, and CXCR2
IL6, CXCL2, and S100A8
IL6, CXCL2, and S100A9
IL6, CXCL3, and CXCL8
IL6, CXCL3, and PTGS2
IL6, CXCL3, and CXCR1
IL6, CXCL3, and CXCR2
IL6, CXCL3, and S100A8
IL6, CXCL3, and S100A9
IL6, CXCL8, and PTGS2
IL6, CXCL8, and CXCR1
IL6, CXCL8, and CXCR2
IL6, CXCL8, and S100A8
IL6, CXCL8, and S100A9
IL6, PTGS2, and CXCR1
IL6, PTGS2, and CXCR2
IL6, PTGS2, and S100A8
IL6, PTGS2, and S100A9
IL6, CXCR1, and CXCR2
IL6, CXCR1, and S100A8
IL6, CXCR1, and S100A9
IL6, CXCR2, and S100A8
IL6, CXCR2, and S100A9
IL6, S100A8, and S100A9
CXCL1, CXCL2, and CXCL3
CXCL1, CXCL2, and CXCL8
CXCL1, CXCL2, and PTGS2
CXCL1, CXCL2, and CXCR1
CXCL1, CXCL2, and CXCR2
CXCL1, CXCL2, and S100A8
CXCL1, CXCL2, and S100A9
CXCL1, CXCL3, and CXCL8

TABLE 10-continued

Three-Gene Combinations of IL6, CXCL1, CXCL2, CXCL3, CXCL8, PTGS2, CXCR1, CXCR2, S100A8, and S100A9

CXCL1, CXCL3, and PTGS2
CXCL1, CXCL3, and CXCR1
CXCL1, CXCL3, and CXCR2
CXCL1, CXCL3, and S100A8
CXCL1, CXCL3, and S100A9
CXCL1, CXCL8, and PTGS2
CXCL1, CXCL8, and CXCR1
CXCL1, CXCL8, and CXCR2
CXCL1, CXCL8, and S100A8
CXCL1, CXCL8, and S100A9
CXCL1, PTGS2, and CXCR1
CXCL1, PTGS2, and CXCR2
CXCL1, PTGS2, and S100A8
CXCL1, PTGS2, and S100A9
CXCL1, CXCR1, and CXCR2
CXCL1, CXCR1, and S100A8
CXCL1, CXCR1, and S100A9
CXCL1, CXCR2, and S100A8
CXCL1, CXCR2, and S100A9
CXCL1, S100A8, and S100A9
CXCL2, CXCL3, and CXCL8
CXCL2, CXCL3, and PTGS2
CXCL2, CXCL3, and CXCR1
CXCL2, CXCL3, and CXCR2
CXCL2, CXCL3, and S100A8
CXCL2, CXCL3, and S100A9
CXCL2, CXCL8, and PTGS2
CXCL2, CXCL8, and CXCR1
CXCL2, CXCL8, and CXCR2
CXCL2, CXCL8, and S100A8
CXCL2, CXCL8, and S100A9
CXCL2, PTGS2, and CXCR1
CXCL2, PTGS2, and CXCR2
CXCL2, PTGS2, and S100A8
CXCL2, PTGS2, and S100A9
CXCL2, CXCR1, and CXCR2
CXCL2, CXCR1, and S100A8
CXCL2, CXCR1, and S100A9
CXCL2, CXCR2, and S100A8
CXCL2, CXCR2, and S100A9
CXCL2, S100A8, and S100A9
CXCL3, CXCL8, and PTGS2
CXCL3, CXCL8, and CXCR1
CXCL3, CXCL8, and CXCR2
CXCL3, CXCL8, and S100A8
CXCL3, CXCL8, and S100A9
CXCL3, PTGS2, and CXCR1
CXCL3, PTGS2, and CXCR2
CXCL3, PTGS2, and S100A8
CXCL3, PTGS2, and S100A9
CXCL3, CXCR1, and CXCR2
CXCL3, CXCR1, and S100A8
CXCL3, CXCR1, and S100A9
CXCL3, CXCR2, and S100A8
CXCL3, CXCR2, and S100A9
CXCL3, S100A8, and S100A9
CXCL8, PTGS2, and CXCR1
CXCL8, PTGS2, and CXCR2
CXCL8, PTGS2, and S100A8
CXCL8, PTGS2, and S100A9
CXCL8, CXCR1, and CXCR2
CXCL8, CXCR1, and S100A8
CXCL8, CXCR1, and S100A9
CXCL8, CXCR2, and S100A8
CXCL8, CXCR2, and S100A9
CXCL8, S100A8, and S100A9
PTGS2, CXCR1, and CXCR2
PTGS2, CXCR1, and S100A8
PTGS2, CXCR1, and S100A9
PTGS2, CXCR2, and S100A8
PTGS2, CXCR2, and S100A9
PTGS2, S100A8, and S100A9
CXCR1, CXCR2, and S100A8
CXCR1, CXCR2, and S100A9
CXCR1, S100A8, and S100A9
CXCR2, S100A8, and S100A9

TABLE 11

Four-Gene Combinations of IL6, CXCL1, CXCL2, CXCL3, CXCL8, PTGS2, CXCR1, CXCR2, S100A8, and S100A9

IL6, CXCL1, CXCL2, and CXCL3
IL6, CXCL1, CXCL2, and CXCL8
IL6, CXCL1, CXCL2, and PTGS2
IL6, CXCL1, CXCL2, and CXCR1
IL6, CXCL1, CXCL2, and CXCR2
IL6, CXCL1, CXCL2, and S100A8
IL6, CXCL1, CXCL2, and S100A9
IL6, CXCL1, CXCL3, and CXCL8
IL6, CXCL1, CXCL3, and PTGS2
IL6, CXCL1, CXCL3, and CXCR1
IL6, CXCL1, CXCL3, and CXCR2
IL6, CXCL1, CXCL3, and S100A8
IL6, CXCL1, CXCL3, and S100A9
IL6, CXCL1, CXCL8, and PTGS2
IL6, CXCL1, CXCL8, and CXCR1
IL6, CXCL1, CXCL8, and CXCR2
IL6, CXCL1, CXCL8, and S100A8
IL6, CXCL1, CXCL8, and S100A9
IL6, CXCL1, PTGS2, and CXCR1
IL6, CXCL1, PTGS2, and CXCR2
IL6, CXCL1, PTGS2, and S100A8
IL6, CXCL1, PTGS2, and S100A9
IL6, CXCL1, CXCR1, and CXCR2
IL6, CXCL1, CXCR1, and S100A8
IL6, CXCL1, CXCR1, and S100A9
IL6, CXCL1, CXCR2, and S100A8
IL6, CXCL1, CXCR2, and S100A9
IL6, CXCL1, S100A8, and S100A9
IL6, CXCL2, CXCL3, and CXCL8
IL6, CXCL2, CXCL3, and PTGS2
IL6, CXCL2, CXCL3, and CXCR1
IL6, CXCL2, CXCL3, and CXCR2
IL6, CXCL2, CXCL3, and S100A8
IL6, CXCL2, CXCL3, and S100A9
IL6, CXCL2, CXCL8, and PTGS2
IL6, CXCL2, CXCL8, and CXCR1
IL6, CXCL2, CXCL8, and CXCR2
IL6, CXCL2, CXCL8, and S100A8
IL6, CXCL2, CXCL8, and S100A9
IL6, CXCL2, PTGS2, and CXCR1
IL6, CXCL2, PTGS2, and CXCR2
IL6, CXCL2, PTGS2, and S100A8
IL6, CXCL2, PTGS2, and S100A9
IL6, CXCL2, CXCR1, and CXCR2
IL6, CXCL2, CXCR1, and S100A8
IL6, CXCL2, CXCR1, and S100A9
IL6, CXCL2, CXCR2, and S100A8
IL6, CXCL2, CXCR2, and S100A9
IL6, CXCL2, S100A8, and S100A9
IL6, CXCL3, CXCL8, and PTGS2
IL6, CXCL3, CXCL8, and CXCR1
IL6, CXCL3, CXCL8, and CXCR2
IL6, CXCL3, CXCL8, and S100A8
IL6, CXCL3, CXCL8, and S100A9
IL6, CXCL3, PTGS2, and CXCR1
IL6, CXCL3, PTGS2, and CXCR2
IL6, CXCL3, PTGS2, and S100A8
IL6, CXCL3, PTGS2, and S100A9
IL6, CXCL3, CXCR1, and CXCR2
IL6, CXCL3, CXCR1, and S100A8
IL6, CXCL3, CXCR1, and S100A9
IL6, CXCL3, CXCR2, and S100A8
IL6, CXCL3, CXCR2, and S100A9
IL6, CXCL3, S100A8, and S100A9
IL6, CXCL8, PTGS2, and CXCR1
IL6, CXCL8, PTGS2, and CXCR2
IL6, CXCL8, PTGS2, and S100A8
IL6, CXCL8, PTGS2, and S100A9
IL6, CXCL8, CXCR1, and CXCR2
IL6, CXCL8, CXCR1, and S100A8
IL6, CXCL8, CXCR1, and S100A9
IL6, CXCL8, CXCR2, and S100A8
IL6, CXCL8, CXCR2, and S100A9
IL6, CXCL8, S100A8, and S100A9
IL6, PTGS2, CXCR1, and CXCR2
IL6, PTGS2, CXCR1, and S100A8
IL6, PTGS2, CXCR1, and S100A9
IL6, PTGS2, CXCR2, and S100A8
IL6, PTGS2, CXCR2, and S100A9
IL6, PTGS2, S100A8, and S100A9
IL6, CXCR1, CXCR2, and S100A8
IL6, CXCR1, CXCR2, and S100A9
IL6, CXCR1, S100A8, and S100A9
IL6, CXCR2, S100A8, and S100A9
CXCL1, CXCL2, CXCL3, and CXCL8
CXCL1, CXCL2, CXCL3, and PTGS2
CXCL1, CXCL2, CXCL3, and CXCR1
CXCL1, CXCL2, CXCL3, and CXCR2
CXCL1, CXCL2, CXCL3, and S100A8
CXCL1, CXCL2, CXCL3, and S100A9
CXCL1, CXCL2, CXCL8, and PTGS2
CXCL1, CXCL2, CXCL8, and CXCR1
CXCL1, CXCL2, CXCL8, and CXCR2
CXCL1, CXCL2, CXCL8, and S100A8
CXCL1, CXCL2, CXCL8, and S100A9
CXCL1, CXCL2, PTGS2, and CXCR1
CXCL1, CXCL2, PTGS2, and CXCR2
CXCL1, CXCL2, PTGS2, and S100A8
CXCL1, CXCL2, PTGS2, and S100A9
CXCL1, CXCL2, CXCR1, and CXCR2
CXCL1, CXCL2, CXCR1, and S100A8
CXCL1, CXCL2, CXCR1, and S100A9
CXCL1, CXCL2, CXCR2, and S100A8
CXCL1, CXCL2, CXCR2, and S100A9
CXCL1, CXCL2, S100A8, and S100A9
CXCL1, CXCL3, CXCL8, and PTGS2
CXCL1, CXCL3, CXCL8, and CXCR1
CXCL1, CXCL3, CXCL8, and CXCR2
CXCL1, CXCL3, CXCL8, and S100A8
CXCL1, CXCL3, CXCL8, and S100A9
CXCL1, CXCL3, PTGS2, and CXCR1
CXCL1, CXCL3, PTGS2, and CXCR2
CXCL1, CXCL3, PTGS2, and S100A8
CXCL1, CXCL3, PTGS2, and S100A9
CXCL1, CXCL3, CXCR1, and CXCR2
CXCL1, CXCL3, CXCR1, and S100A8
CXCL1, CXCL3, CXCR1, and S100A9
CXCL1, CXCL3, CXCR2, and S100A8
CXCL1, CXCL3, CXCR2, and S100A9
CXCL1, CXCL3, S100A8, and S100A9
CXCL1, CXCL8, PTGS2, and CXCR1
CXCL1, CXCL8, PTGS2, and CXCR2
CXCL1, CXCL8, PTGS2, and S100A8
CXCL1, CXCL8, PTGS2, and S100A9
CXCL1, CXCL8, CXCR1, and CXCR2
CXCL1, CXCL8, CXCR1, and S100A8
CXCL1, CXCL8, CXCR1, and S100A9
CXCL1, CXCL8, CXCR2, and S100A8
CXCL1, CXCL8, CXCR2, and S100A9
CXCL1, CXCL8, S100A8, and S100A9
CXCL1, PTGS2, CXCR1, and CXCR2
CXCL1, PTGS2, CXCR1, and S100A8
CXCL1, PTGS2, CXCR1, and S100A9
CXCL1, PTGS2, CXCR2, and S100A8
CXCL1, PTGS2, CXCR2, and S100A9
CXCL1, PTGS2, S100A8, and S100A9
CXCL1, CXCR1, CXCR2, and S100A8
CXCL1, CXCR1, CXCR2, and S100A9
CXCL1, CXCR1, S100A8, and S100A9
CXCL1, CXCR2, S100A8, and S100A9
CXCL2, CXCL3, CXCL8, and PTGS2
CXCL2, CXCL3, CXCL8, and CXCR1
CXCL2, CXCL3, CXCL8, and CXCR2
CXCL2, CXCL3, CXCL8, and S100A8
CXCL2, CXCL3, CXCL8, and S100A9
CXCL2, CXCL3, PTGS2, and CXCR1
CXCL2, CXCL3, PTGS2, and CXCR2
CXCL2, CXCL3, PTGS2, and S100A8
CXCL2, CXCL3, PTGS2, and S100A9
CXCL2, CXCL3, CXCR1, and CXCR2
CXCL2, CXCL3, CXCR1, and S100A8
CXCL2, CXCL3, CXCR1, and S100A9
CXCL2, CXCL3, CXCR2, and S100A8
CXCL2, CXCL3, CXCR2, and S100A9

TABLE 11-continued

Four-Gene Combinations of IL6, CXCL1, CXCL2, CXCL3, CXCL8, PTGS2, CXCR1, CXCR2, S100A8, and S100A9

CXCL2, CXCL3, S100A8, and S100A9
CXCL2, CXCL8, PTGS2, and CXCR1
CXCL2, CXCL8, PTGS2, and CXCR2
CXCL2, CXCL8, PTGS2, and S100A8
CXCL2, CXCL8, PTGS2, and S100A9
CXCL2, CXCL8, CXCR1, and CXCR2
CXCL2, CXCL8, CXCR1, and S100A8
CXCL2, CXCL8, CXCR1, and S100A9
CXCL2, CXCL8, CXCR2, and S100A8
CXCL2, CXCL8, CXCR2, and S100A9
CXCL2, CXCL8, S100A8, and S100A9
CXCL2, PTGS2, CXCR1, and CXCR2
CXCL2, PTGS2, CXCR1, and S100A8
CXCL2, PTGS2, CXCR1, and S100A9
CXCL2, PTGS2, CXCR2, and S100A8
CXCL2, PTGS2, CXCR2, and S100A9
CXCL2, PTGS2, S100A8, and S100A9
CXCL2, CXCR1, CXCR2, and S100A8
CXCL2, CXCR1, CXCR2, and S100A9
CXCL2, CXCR1, S100A8, and S100A9
CXCL2, CXCR2, S100A8, and S100A9
CXCL3, CXCL8, PTGS2, and CXCR1
CXCL3, CXCL8, PTGS2, and CXCR2
CXCL3, CXCL8, PTGS2, and S100A8
CXCL3, CXCL8, PTGS2, and S100A9
CXCL3, CXCL8, CXCR1, and CXCR2
CXCL3, CXCL8, CXCR1, and S100A8
CXCL3, CXCL8, CXCR1, and S100A9
CXCL3, CXCL8, CXCR2, and S100A8
CXCL3, CXCL8, CXCR2, and S100A9
CXCL3, CXCL8, S100A8, and S100A9
CXCL3, PTGS2, CXCR1, and CXCR2
CXCL3, PTGS2, CXCR1, and S100A8
CXCL3, PTGS2, CXCR1, and S100A9
CXCL3, PTGS2, CXCR2, and S100A8
CXCL3, PTGS2, CXCR2, and S100A9
CXCL3, PTGS2, S100A8, and S100A9
CXCL3, CXCR1, CXCR2, and S100A8
CXCL3, CXCR1, CXCR2, and S100A9
CXCL3, CXCR1, S100A8, and S100A9
CXCL3, CXCR2, S100A8, and S100A9
CXCL8, PTGS2, CXCR1, and CXCR2
CXCL8, PTGS2, CXCR1, and S100A8
CXCL8, PTGS2, CXCR1, and S100A9
CXCL8, PTGS2, CXCR2, and S100A8
CXCL8, PTGS2, CXCR2, and S100A9
CXCL8, PTGS2, S100A8, and S100A9
CXCL8, CXCR1, CXCR2, and S100A8
CXCL8, CXCR1, CXCR2, and S100A9
CXCL8, CXCR1, S100A8, and S100A9
CXCL8, CXCR2, S100A8, and S100A9
PTGS2, CXCR1, CXCR2, and S100A8
PTGS2, CXCR1, CXCR2, and S100A9
PTGS2, CXCR1, S100A8, and S100A9
PTGS2, CXCR2, S100A8, and S100A9
CXCR1, CXCR2, S100A8, and S100A9

TABLE 12

Five-Gene Combinations of IL6, CXCL1, CXCL2, CXCL3, CXCL8, PTGS2, CXCR1, CXCR2, S100A8, and S100A9

IL6, CXCL1, CXCL2, CXCL3, and CXCL8
IL6, CXCL1, CXCL2, CXCL3, and PTGS2
IL6, CXCL1, CXCL2, CXCL3, and CXCR1
IL6, CXCL1, CXCL2, CXCL3, and CXCR2
IL6, CXCL1, CXCL2, CXCL3, and S100A8
IL6, CXCL1, CXCL2, CXCL3, and S100A9
IL6, CXCL1, CXCL2, CXCL8, and PTGS2
IL6, CXCL1, CXCL2, CXCL8, and CXCR1
IL6, CXCL1, CXCL2, CXCL8, and CXCR2
IL6, CXCL1, CXCL2, CXCL8, and S100A8
IL6, CXCL1, CXCL2, CXCL8, and S100A9
IL6, CXCL1, CXCL2, PTGS2, and CXCR1

TABLE 12-continued

Five-Gene Combinations of IL6, CXCL1, CXCL2, CXCL3, CXCL8, PTGS2, CXCR1, CXCR2, S100A8, and S100A9

IL6, CXCL1, CXCL2, PTGS2, and CXCR2
IL6, CXCL1, CXCL2, PTGS2, and S100A8
IL6, CXCL1, CXCL2, PTGS2, and S100A9
IL6, CXCL1, CXCL2, CXCR1, and CXCR2
IL6, CXCL1, CXCL2, CXCR1, and S100A8
IL6, CXCL1, CXCL2, CXCR1, and S100A9
IL6, CXCL1, CXCL2, CXCR2, and S100A8
IL6, CXCL1, CXCL2, CXCR2, and S100A9
IL6, CXCL1, CXCL2, S100A8, and S100A9
IL6, CXCL1, CXCL3, CXCL8, and PTGS2
IL6, CXCL1, CXCL3, CXCL8, and CXCR1
IL6, CXCL1, CXCL3, CXCL8, and CXCR2
IL6, CXCL1, CXCL3, CXCL8, and S100A8
IL6, CXCL1, CXCL3, CXCL8, and S100A9
IL6, CXCL1, CXCL3, PTGS2, and CXCR1
IL6, CXCL1, CXCL3, PTGS2, and CXCR2
IL6, CXCL1, CXCL3, PTGS2, and S100A8
IL6, CXCL1, CXCL3, PTGS2, and S100A9
IL6, CXCL1, CXCL3, CXCR1, and CXCR2
IL6, CXCL1, CXCL3, CXCR1, and S100A8
IL6, CXCL1, CXCL3, CXCR1, and S100A9
IL6, CXCL1, CXCL3, CXCR2, and S100A8
IL6, CXCL1, CXCL3, CXCR2, and S100A9
IL6, CXCL1, CXCL3, S100A8, and S100A9
IL6, CXCL1, CXCL8, PTGS2, and CXCR1
IL6, CXCL1, CXCL8, PTGS2, and CXCR2
IL6, CXCL1, CXCL8, PTGS2, and S100A8
IL6, CXCL1, CXCL8, PTGS2, and S100A9
IL6, CXCL1, CXCL8, CXCR1, and CXCR2
IL6, CXCL1, CXCL8, CXCR1, and S100A8
IL6, CXCL1, CXCL8, CXCR1, and S100A9
IL6, CXCL1, CXCL8, CXCR2, and S100A8
IL6, CXCL1, CXCL8, CXCR2, and S100A9
IL6, CXCL1, CXCL8, S100A8, and S100A9
IL6, CXCL1, PTGS2, CXCR1, and CXCR2
IL6, CXCL1, PTGS2, CXCR1, and S100A8
IL6, CXCL1, PTGS2, CXCR1, and S100A9
IL6, CXCL1, PTGS2, CXCR2, and S100A8
IL6, CXCL1, PTGS2, CXCR2, and S100A9
IL6, CXCL1, PTGS2, S100A8, and S100A9
IL6, CXCL1, CXCR1, CXCR2, and S100A8
IL6, CXCL1, CXCR1, CXCR2, and S100A9
IL6, CXCL1, CXCR1, S100A8, and S100A9
IL6, CXCL1, CXCR2, S100A8, and S100A9
IL6, CXCL2, CXCL3, CXCL8, and PTGS2
IL6, CXCL2, CXCL3, CXCL8, and CXCR1
IL6, CXCL2, CXCL3, CXCL8, and CXCR2
IL6, CXCL2, CXCL3, CXCL8, and S100A8
IL6, CXCL2, CXCL3, CXCL8, and S100A9
IL6, CXCL2, CXCL3, PTGS2, and CXCR1
IL6, CXCL2, CXCL3, PTGS2, and CXCR2
IL6, CXCL2, CXCL3, PTGS2, and S100A8
IL6, CXCL2, CXCL3, PTGS2, and S100A9
IL6, CXCL2, CXCL3, CXCR1, and CXCR2
IL6, CXCL2, CXCL3, CXCR1, and S100A8
IL6, CXCL2, CXCL3, CXCR1, and S100A9
IL6, CXCL2, CXCL3, CXCR2, and S100A8
IL6, CXCL2, CXCL3, CXCR2, and S100A9
IL6, CXCL2, CXCL3, S100A8, and S100A9
IL6, CXCL2, CXCL8, PTGS2, and CXCR1
IL6, CXCL2, CXCL8, PTGS2, and CXCR2
IL6, CXCL2, CXCL8, PTGS2, and S100A8
IL6, CXCL2, CXCL8, PTGS2, and S100A9
IL6, CXCL2, CXCL8, CXCR1, and CXCR2
IL6, CXCL2, CXCL8, CXCR1, and S100A8
IL6, CXCL2, CXCL8, CXCR1, and S100A9
IL6, CXCL2, CXCL8, CXCR2, and S100A8
IL6, CXCL2, CXCL8, CXCR2, and S100A9
IL6, CXCL2, CXCL8, S100A8, and S100A9
IL6, CXCL2, PTGS2, CXCR1, and CXCR2
IL6, CXCL2, PTGS2, CXCR1, and S100A8
IL6, CXCL2, PTGS2, CXCR1, and S100A9
IL6, CXCL2, PTGS2, CXCR2, and S100A8
IL6, CXCL2, PTGS2, CXCR2, and S100A9
IL6, CXCL2, PTGS2, S100A8, and S100A9
IL6, CXCL2, CXCR1, CXCR2, and S100A8
IL6, CXCL2, CXCR1, CXCR2, and S100A9

TABLE 12-continued

Five-Gene Combinations of IL6, CXCL1, CXCL2, CXCL3, CXCL8, PTGS2, CXCR1, CXCR2, S100A8, and S100A9

IL6, CXCL2, CXCR1, S100A8, and S100A9
IL6, CXCL2, CXCR2, S100A8, and S100A9
IL6, CXCL3, CXCL8, PTGS2, and CXCR1
IL6, CXCL3, CXCL8, PTGS2, and CXCR2
IL6, CXCL3, CXCL8, PTGS2, and S100A8
IL6, CXCL3, CXCL8, PTGS2, and S100A9
IL6, CXCL3, CXCL8, CXCR1, and CXCR2
IL6, CXCL3, CXCL8, CXCR1, and S100A8
IL6, CXCL3, CXCL8, CXCR1, and S100A9
IL6, CXCL3, CXCL8, CXCR2, and S100A8
IL6, CXCL3, CXCL8, CXCR2, and S100A9
IL6, CXCL3, CXCL8, S100A8, and S100A9
IL6, CXCL3, PTGS2, CXCR1, and CXCR2
IL6, CXCL3, PTGS2, CXCR1, and S100A8
IL6, CXCL3, PTGS2, CXCR1, and S100A9
IL6, CXCL3, PTGS2, CXCR2, and S100A8
IL6, CXCL3, PTGS2, CXCR2, and S100A9
IL6, CXCL3, PTGS2, S100A8, and S100A9
IL6, CXCL3, CXCR1, CXCR2, and S100A8
IL6, CXCL3, CXCR1, CXCR2, and S100A9
IL6, CXCL3, CXCR1, S100A8, and S100A9
IL6, CXCL3, CXCR2, S100A8, and S100A9
IL6, CXCL8, PTGS2, CXCR1, and CXCR2
IL6, CXCL8, PTGS2, CXCR1, and S100A8
IL6, CXCL8, PTGS2, CXCR1, and S100A9
IL6, CXCL8, PTGS2, CXCR2, and S100A8
IL6, CXCL8, PTGS2, CXCR2, and S100A9
IL6, CXCL8, PTGS2, S100A8, and S100A9
IL6, CXCL8, CXCR1, CXCR2, and S100A8
IL6, CXCL8, CXCR1, CXCR2, and S100A9
IL6, CXCL8, CXCR1, S100A8, and S100A9
IL6, CXCL8, CXCR2, S100A8, and S100A9
IL6, PTGS2, CXCR1, CXCR2, and S100A8
IL6, PTGS2, CXCR1, CXCR2, and S100A9
IL6, PTGS2, CXCR1, S100A8, and S100A9
IL6, PTGS2, CXCR2, S100A8, and S100A9
IL6, CXCR1, CXCR2, S100A8, and S100A9
CXCL1, CXCL2, CXCL3, CXCL8, and PTGS2
CXCL1, CXCL2, CXCL3, CXCL8, and CXCR1
CXCL1, CXCL2, CXCL3, CXCL8, and CXCR2
CXCL1, CXCL2, CXCL3, CXCL8, and S100A8
CXCL1, CXCL2, CXCL3, CXCL8, and S100A9
CXCL1, CXCL2, CXCL3, PTGS2, and CXCR1
CXCL1, CXCL2, CXCL3, PTGS2, and CXCR2
CXCL1, CXCL2, CXCL3, PTGS2, and S100A8
CXCL1, CXCL2, CXCL3, PTGS2, and S100A9
CXCL1, CXCL2, CXCL3, CXCR1, and CXCR2
CXCL1, CXCL2, CXCL3, CXCR1, and S100A8
CXCL1, CXCL2, CXCL3, CXCR1, and S100A9
CXCL1, CXCL2, CXCL3, CXCR2, and S100A8
CXCL1, CXCL2, CXCL3, CXCR2, and S100A9
CXCL1, CXCL2, CXCL3, S100A8, and S100A9
CXCL1, CXCL2, CXCL8, PTGS2, and CXCR1
CXCL1, CXCL2, CXCL8, PTGS2, and CXCR2
CXCL1, CXCL2, CXCL8, PTGS2, and S100A8
CXCL1, CXCL2, CXCL8, PTGS2, and S100A9
CXCL1, CXCL2, CXCL8, CXCR1, and CXCR2
CXCL1, CXCL2, CXCL8, CXCR1, and S100A8
CXCL1, CXCL2, CXCL8, CXCR1, and S100A9
CXCL1, CXCL2, CXCL8, CXCR2, and S100A8
CXCL1, CXCL2, CXCL8, CXCR2, and S100A9
CXCL1, CXCL2, CXCL8, S100A8, and S100A9
CXCL1, CXCL2, PTGS2, CXCR1, and CXCR2
CXCL1, CXCL2, PTGS2, CXCR1, and S100A8
CXCL1, CXCL2, PTGS2, CXCR1, and S100A9
CXCL1, CXCL2, PTGS2, CXCR2, and S100A8
CXCL1, CXCL2, PTGS2, CXCR2, and S100A9
CXCL1, CXCL2, PTGS2, S100A8, and S100A9
CXCL1, CXCL2, CXCR1, CXCR2, and S100A8
CXCL1, CXCL2, CXCR1, CXCR2, and S100A9
CXCL1, CXCL2, CXCR1, S100A8, and S100A9
CXCL1, CXCL2, CXCR2, S100A8, and S100A9
CXCL1, CXCL3, CXCL8, PTGS2, and CXCR1
CXCL1, CXCL3, CXCL8, PTGS2, and CXCR2
CXCL1, CXCL3, CXCL8, PTGS2, and S100A8
CXCL1, CXCL3, CXCL8, PTGS2, and S100A9
CXCL1, CXCL3, CXCL8, CXCR1, and CXCR2
CXCL1, CXCL3, CXCL8, CXCR1, and S100A8
CXCL1, CXCL3, CXCL8, CXCR1, and S100A9
CXCL1, CXCL3, CXCL8, CXCR2, and S100A8
CXCL1, CXCL3, CXCL8, CXCR2, and S100A9
CXCL1, CXCL3, CXCL8, S100A8, and S100A9
CXCL1, CXCL3, PTGS2, CXCR1, and CXCR2
CXCL1, CXCL3, PTGS2, CXCR1, and S100A8
CXCL1, CXCL3, PTGS2, CXCR1, and S100A9
CXCL1, CXCL3, PTGS2, CXCR2, and S100A8
CXCL1, CXCL3, PTGS2, CXCR2, and S100A9
CXCL1, CXCL3, PTGS2, S100A8, and S100A9
CXCL1, CXCL3, CXCR1, CXCR2, and S100A8
CXCL1, CXCL3, CXCR1, CXCR2, and S100A9
CXCL1, CXCL3, CXCR1, S100A8, and S100A9
CXCL1, CXCL3, CXCR2, S100A8, and S100A9
CXCL1, CXCL8, PTGS2, CXCR1, and CXCR2
CXCL1, CXCL8, PTGS2, CXCR1, and S100A8
CXCL1, CXCL8, PTGS2, CXCR2, and S100A8
CXCL1, CXCL8, PTGS2, CXCR2, and S100A9
CXCL1, CXCL8, PTGS2, S100A8, and S100A9
CXCL1, CXCL8, CXCR1, CXCR2, and S100A8
CXCL1, CXCL8, CXCR1, CXCR2, and S100A9
CXCL1, CXCL8, CXCR1, S100A8, and S100A9
CXCL1, CXCL8, CXCR2, S100A8, and S100A9
CXCL1, PTGS2, CXCR1, CXCR2, and S100A8
CXCL1, PTGS2, CXCR1, CXCR2, and S100A9
CXCL1, PTGS2, CXCR1, S100A8, and S100A9
CXCL1, PTGS2, CXCR2, S100A8, and S100A9
CXCL1, CXCR1, CXCR2, S100A8, and S100A9
CXCL2, CXCL3, CXCL8, PTGS2, and CXCR1
CXCL2, CXCL3, CXCL8, PTGS2, and CXCR2
CXCL2, CXCL3, CXCL8, PTGS2, and S100A8
CXCL2, CXCL3, CXCL8, PTGS2, and S100A9
CXCL2, CXCL3, CXCL8, CXCR1, and CXCR2
CXCL2, CXCL3, CXCL8, CXCR1, and S100A8
CXCL2, CXCL3, CXCL8, CXCR1, and S100A9
CXCL2, CXCL3, CXCL8, CXCR2, and S100A8
CXCL2, CXCL3, CXCL8, CXCR2, and S100A9
CXCL2, CXCL3, CXCL8, S100A8, and S100A9
CXCL2, CXCL3, PTGS2, CXCR1, and CXCR2
CXCL2, CXCL3, PTGS2, CXCR1, and S100A8
CXCL2, CXCL3, PTGS2, CXCR1, and S100A9
CXCL2, CXCL3, PTGS2, CXCR2, and S100A8
CXCL2, CXCL3, PTGS2, CXCR2, and S100A9
CXCL2, CXCL3, PTGS2, S100A8, and S100A9
CXCL2, CXCL3, CXCR1, CXCR2, and S100A8
CXCL2, CXCL3, CXCR1, CXCR2, and S100A9
CXCL2, CXCL3, CXCR1, S100A8, and S100A9
CXCL2, CXCL3, CXCR2, S100A8, and S100A9
CXCL2, CXCL8, PTGS2, CXCR1, and CXCR2
CXCL2, CXCL8, PTGS2, CXCR1, and S100A8
CXCL2, CXCL8, PTGS2, CXCR1, and S100A9
CXCL2, CXCL8, PTGS2, CXCR2, and S100A8
CXCL2, CXCL8, PTGS2, CXCR2, and S100A9
CXCL2, CXCL8, PTGS2, S100A8, and S100A9
CXCL2, CXCL8, CXCR1, CXCR2, and S100A8
CXCL2, CXCL8, CXCR1, CXCR2, and S100A9
CXCL2, CXCL8, CXCR1, S100A8, and S100A9
CXCL2, CXCL8, CXCR2, S100A8, and S100A9
CXCL2, PTGS2, CXCR1, CXCR2, and S100A8
CXCL2, PTGS2, CXCR1, CXCR2, and S100A9
CXCL2, PTGS2, CXCR1, S100A8, and S100A9
CXCL2, PTGS2, CXCR2, S100A8, and S100A9
CXCL2, CXCR1, CXCR2, S100A8, and S100A9
CXCL3, CXCL8, PTGS2, CXCR1, and CXCR2
CXCL3, CXCL8, PTGS2, CXCR1, and S100A8
CXCL3, CXCL8, PTGS2, CXCR1, and S100A9
CXCL3, CXCL8, PTGS2, CXCR2, and S100A8
CXCL3, CXCL8, PTGS2, CXCR2, and S100A9
CXCL3, CXCL8, PTGS2, S100A8, and S100A9
CXCL3, CXCL8, CXCR1, CXCR2, and S100A8
CXCL3, CXCL8, CXCR1, S100A8, and S100A9
CXCL3, CXCL8, CXCR2, S100A8, and S100A9
CXCL3, PTGS2, CXCR1, CXCR2, and S100A8
CXCL3, PTGS2, CXCR1, CXCR2, and S100A9

TABLE 12-continued

Five-Gene Combinations of IL6, CXCL1, CXCL2, CXCL3, CXCL8, PTGS2, CXCR1, CXCR2, S100A8, and S100A9

CXCL3, PTGS2, CXCR1, S100A8, and S100A9
CXCL3, PTGS2, CXCR2, S100A8, and S100A9
CXCL3, CXCR1, CXCR2, S100A8, and S100A9
CXCL8, PTGS2, CXCR1, CXCR2, and S100A8
CXCL8, PTGS2, CXCR1, CXCR2, and S100A9
CXCL8, PTGS2, CXCR1, S100A8, and S100A9
CXCL8, PTGS2, CXCR2, S100A8, and S100A9
CXCL8, CXCR1, CXCR2, S100A8, and S100A9
PTGS2, CXCR1, CXCR2, S100A8, and S100A9

TABLE 13

Six-Gene Combinations of IL6, CXCL1, CXCL2, CXCL3, CXCL8, PTGS2, CXCR1, CXCR2, S100A8, and S100A9

IL6, CXCL1, CXCL2, CXCL3, CXCL8, and PTGS2
IL6, CXCL1, CXCL2, CXCL3, CXCL8, and CXCR1
IL6, CXCL1, CXCL2, CXCL3, CXCL8, and CXCR2
IL6, CXCL1, CXCL2, CXCL3, CXCL8, and S100A8
IL6, CXCL1, CXCL2, CXCL3, CXCL8, and S100A9
IL6, CXCL1, CXCL2, CXCL3, PTGS2, and CXCR1
IL6, CXCL1, CXCL2, CXCL3, PTGS2, and CXCR2
IL6, CXCL1, CXCL2, CXCL3, PTGS2, and S100A8
IL6, CXCL1, CXCL2, CXCL3, PTGS2, and S100A9
IL6, CXCL1, CXCL2, CXCL3, CXCR1, and CXCR2
IL6, CXCL1, CXCL2, CXCL3, CXCR1, and S100A8
IL6, CXCL1, CXCL2, CXCL3, CXCR1, and S100A9
IL6, CXCL1, CXCL2, CXCL3, CXCR2, and S100A8
IL6, CXCL1, CXCL2, CXCL3, CXCR2, and S100A9
IL6, CXCL1, CXCL2, CXCL3, S100A8, and S100A9
IL6, CXCL1, CXCL2, CXCL8, PTGS2, and CXCR1
IL6, CXCL1, CXCL2, CXCL8, PTGS2, and CXCR2
IL6, CXCL1, CXCL2, CXCL8, PTGS2, and S100A8
IL6, CXCL1, CXCL2, CXCL8, PTGS2, and S100A9
IL6, CXCL1, CXCL2, CXCL8, CXCR1, and CXCR2
IL6, CXCL1, CXCL2, CXCL8, CXCR1, and S100A8
IL6, CXCL1, CXCL2, CXCL8, CXCR1, and S100A9
IL6, CXCL1, CXCL2, CXCL8, CXCR2, and S100A8
IL6, CXCL1, CXCL2, CXCL8, CXCR2, and S100A9
IL6, CXCL1, CXCL2, CXCL8, S100A8, and S100A9
IL6, CXCL1, CXCL2, PTGS2, CXCR1, and CXCR2
IL6, CXCL1, CXCL2, PTGS2, CXCR1, and S100A8
IL6, CXCL1, CXCL2, PTGS2, CXCR1, and S100A9
IL6, CXCL1, CXCL2, PTGS2, CXCR2, and S100A8
IL6, CXCL1, CXCL2, PTGS2, CXCR2, and S100A9
IL6, CXCL1, CXCL2, PTGS2, S100A8, and S100A9
IL6, CXCL1, CXCL2, CXCR1, CXCR2, and S100A8
IL6, CXCL1, CXCL2, CXCR1, CXCR2, and S100A9
IL6, CXCL1, CXCL2, CXCR1, S100A8, and S100A9
IL6, CXCL1, CXCL2, CXCR2, S100A8, and S100A9
IL6, CXCL1, CXCL3, CXCL8, PTGS2, and CXCR1
IL6, CXCL1, CXCL3, CXCL8, PTGS2, and CXCR2
IL6, CXCL1, CXCL3, CXCL8, PTGS2, and S100A8
IL6, CXCL1, CXCL3, CXCL8, PTGS2, and S100A9
IL6, CXCL1, CXCL3, CXCL8, CXCR1, and CXCR2
IL6, CXCL1, CXCL3, CXCL8, CXCR1, and S100A8
IL6, CXCL1, CXCL3, CXCL8, CXCR1, and S100A9
IL6, CXCL1, CXCL3, CXCL8, CXCR2, and S100A8
IL6, CXCL1, CXCL3, CXCL8, CXCR2, and S100A9
IL6, CXCL1, CXCL3, CXCL8, S100A8, and S100A9
IL6, CXCL1, CXCL3, PTGS2, CXCR1, and CXCR2
IL6, CXCL1, CXCL3, PTGS2, CXCR1, and S100A8
IL6, CXCL1, CXCL3, PTGS2, CXCR1, and S100A9
IL6, CXCL1, CXCL3, PTGS2, CXCR2, and S100A8
IL6, CXCL1, CXCL3, PTGS2, CXCR2, and S100A9
IL6, CXCL1, CXCL3, PTGS2, S100A8, and S100A9
IL6, CXCL1, CXCL3, CXCR1, CXCR2, and S100A8
IL6, CXCL1, CXCL3, CXCR1, CXCR2, and S100A9
IL6, CXCL1, CXCL3, CXCR1, S100A8, and S100A9
IL6, CXCL1, CXCL3, CXCR2, S100A8, and S100A9
IL6, CXCL1, CXCL8, PTGS2, CXCR1, and CXCR2
IL6, CXCL1, CXCL8, PTGS2, CXCR1, and S100A8
IL6, CXCL1, CXCL8, PTGS2, CXCR1, and S100A9
IL6, CXCL1, CXCL8, PTGS2, CXCR2, and S100A8

TABLE 13-continued

Six-Gene Combinations of IL6, CXCL1, CXCL2, CXCL3, CXCL8, PTGS2, CXCR1, CXCR2, S100A8, and S100A9

IL6, CXCL1, CXCL8, PTGS2, CXCR2, and S100A9
IL6, CXCL1, CXCL8, PTGS2, S100A8, and S100A9
IL6, CXCL1, CXCL8, CXCR1, CXCR2, and S100A8
IL6, CXCL1, CXCL8, CXCR1, CXCR2, and S100A9
IL6, CXCL1, CXCL8, CXCR1, S100A8, and S100A9
IL6, CXCL1, CXCL8, CXCR2, S100A8, and S100A9
IL6, CXCL1, PTGS2, CXCR1, CXCR2, and S100A8
IL6, CXCL1, PTGS2, CXCR1, CXCR2, and S100A9
IL6, CXCL1, PTGS2, CXCR1, S100A8, and S100A9
IL6, CXCL1, PTGS2, CXCR2, S100A8, and S100A9
IL6, CXCL1, CXCR1, CXCR2, S100A8, and S100A9
IL6, CXCL2, CXCL3, CXCL8, PTGS2, and CXCR1
IL6, CXCL2, CXCL3, CXCL8, PTGS2, and CXCR2
IL6, CXCL2, CXCL3, CXCL8, PTGS2, and S100A8
IL6, CXCL2, CXCL3, CXCL8, PTGS2, and S100A9
IL6, CXCL2, CXCL3, CXCL8, CXCR1, and CXCR2
IL6, CXCL2, CXCL3, CXCL8, CXCR1, and S100A8
IL6, CXCL2, CXCL3, CXCL8, CXCR1, and S100A9
IL6, CXCL2, CXCL3, CXCL8, CXCR2, and S100A8
IL6, CXCL2, CXCL3, CXCL8, CXCR2, and S100A9
IL6, CXCL2, CXCL3, CXCL8, S100A8, and S100A9
IL6, CXCL2, CXCL3, PTGS2, CXCR1, and CXCR2
IL6, CXCL2, CXCL3, PTGS2, CXCR1, and S100A8
IL6, CXCL2, CXCL3, PTGS2, CXCR1, and S100A9
IL6, CXCL2, CXCL3, PTGS2, CXCR2, and S100A8
IL6, CXCL2, CXCL3, PTGS2, CXCR2, and S100A9
IL6, CXCL2, CXCL3, PTGS2, S100A8, and S100A9
IL6, CXCL2, CXCL3, CXCR1, CXCR2, and S100A8
IL6, CXCL2, CXCL3, CXCR1, CXCR2, and S100A9
IL6, CXCL2, CXCL3, CXCR1, S100A8, and S100A9
IL6, CXCL2, CXCL3, CXCR2, S100A8, and S100A9
IL6, CXCL2, CXCL8, PTGS2, CXCR1, and CXCR2
IL6, CXCL2, CXCL8, PTGS2, CXCR1, and S100A8
IL6, CXCL2, CXCL8, PTGS2, CXCR1, and S100A9
IL6, CXCL2, CXCL8, PTGS2, CXCR2, and S100A8
IL6, CXCL2, CXCL8, PTGS2, CXCR2, and S100A9
IL6, CXCL2, CXCL8, PTGS2, S100A8, and S100A9
IL6, CXCL2, CXCL8, CXCR1, CXCR2, and S100A8
IL6, CXCL2, CXCL8, CXCR1, CXCR2, and S100A9
IL6, CXCL2, CXCL8, CXCR1, S100A8, and S100A9
IL6, CXCL2, CXCL8, CXCR2, S100A8, and S100A9
IL6, CXCL2, PTGS2, CXCR1, CXCR2, and S100A8
IL6, CXCL2, PTGS2, CXCR1, CXCR2, and S100A9
IL6, CXCL2, PTGS2, CXCR1, S100A8, and S100A9
IL6, CXCL2, PTGS2, CXCR2, S100A8, and S100A9
IL6, CXCL2, CXCR1, CXCR2, S100A8, and S100A9
IL6, CXCL3, CXCL8, PTGS2, CXCR1, and CXCR2
IL6, CXCL3, CXCL8, PTGS2, CXCR1, and 100A8
IL6, CXCL3, CXCL8, PTGS2, CXCR1, and S100A9
IL6, CXCL3, CXCL8, PTGS2, CXCR2, and S100A8
IL6, CXCL3, CXCL8, PTGS2, CXCR2, and S100A9
IL6, CXCL3, CXCL8, PTGS2, S100A8, and S100A9
IL6, CXCL3, CXCL8, CXCR1, CXCR2, and S100A8
IL6, CXCL3, CXCL8, CXCR1, CXCR2, and S100A9
IL6, CXCL3, CXCL8, CXCR1, S100A8, and S100A9
IL6, CXCL3, CXCL8, CXCR2, S100A8, and S100A9
IL6, CXCL3, PTGS2, CXCR1, CXCR2, and S100A8
IL6, CXCL3, PTGS2, CXCR1, CXCR2, and S100A9
IL6, CXCL3, PTGS2, CXCR1, S100A8, and S100A9
IL6, CXCL3, PTGS2, CXCR2, S100A8, and S100A9
IL6, CXCL3, CXCR1, CXCR2, S100A8, and S100A9
IL6, CXCL8, PTGS2, CXCR1, CXCR2, and S100A8
IL6, CXCL8, PTGS2, CXCR1, CXCR2, and S100A9
IL6, CXCL8, PTGS2, CXCR1, S100A8, and S100A9
IL6, CXCL8, PTGS2, CXCR2, S100A8, and S100A9
IL6, CXCL8, CXCR1, CXCR2, S100A8, and S100A9
IL6, PTGS2, CXCR1, CXCR2, S100A8, and S100A9
CXCL1, CXCL2, CXCL3, CXCL8, PTGS2, and CXCR1
CXCL1, CXCL2, CXCL3, CXCL8, PTGS2, and CXCR2
CXCL1, CXCL2, CXCL3, CXCL8, PTGS2, and S100A8
CXCL1, CXCL2, CXCL3, CXCL8, PTGS2, and S100A9
CXCL1, CXCL2, CXCL3, CXCL8, CXCR1, and CXCR2
CXCL1, CXCL2, CXCL3, CXCL8, CXCR1, and S100A8
CXCL1, CXCL2, CXCL3, CXCL8, CXCR1, and S100A9
CXCL1, CXCL2, CXCL3, CXCL8, CXCR2, and S100A8
CXCL1, CXCL2, CXCL3, CXCL8, CXCR2, and S100A9
CXCL1, CXCL2, CXCL3, CXCL8, S100A8, and S100A9

TABLE 13-continued

Six-Gene Combinations of IL6, CXCL1, CXCL2, CXCL3, CXCL8, PTGS2, CXCR1, CXCR2, S100A8, and S100A9

CXCL1, CXCL2, CXCL3, PTGS2, CXCR1, and CXCR2
CXCL1, CXCL2, CXCL3, PTGS2, CXCR1, and S100A8
CXCL1, CXCL2, CXCL3, PTGS2, CXCR1, and S100A9
CXCL1, CXCL2, CXCL3, PTGS2, CXCR2, and S100A8
CXCL1, CXCL2, CXCL3, PTGS2, CXCR2, and S100A9
CXCL1, CXCL2, CXCL3, PTGS2, S100A8, and S100A9
CXCL1, CXCL2, CXCL3, CXCR1, CXCR2, and S100A8
CXCL1, CXCL2, CXCL3, CXCR1, CXCR2, and S100A9
CXCL1, CXCL2, CXCL3, CXCR1, S100A8, and S100A9
CXCL1, CXCL2, CXCL3, CXCR2, S100A8, and S100A9
CXCL1, CXCL2, CXCL8, PTGS2, CXCR1, and CXCR2
CXCL1, CXCL2, CXCL8, PTGS2, CXCR1, and S100A8
CXCL1, CXCL2, CXCL8, PTGS2, CXCR1, and S100A9
CXCL1, CXCL2, CXCL8, PTGS2, CXCR2, and S100A8
CXCL1, CXCL2, CXCL8, PTGS2, CXCR2, and S100A9
CXCL1, CXCL2, CXCL8, PTGS2, S100A8, and S100A9
CXCL1, CXCL2, CXCL8, CXCR1, CXCR2, and S100A8
CXCL1, CXCL2, CXCL8, CXCR1, CXCR2, and S100A9
CXCL1, CXCL2, CXCL8, CXCR1, S100A8, and S100A9
CXCL1, CXCL2, CXCL8, CXCR2, S100A8, and S100A9
CXCL1, CXCL2, PTGS2, CXCR1, CXCR2, and S100A8
CXCL1, CXCL2, PTGS2, CXCR1, CXCR2, and S100A9
CXCL1, CXCL2, PTGS2, CXCR1, S100A8, and S100A9
CXCL1, CXCL2, PTGS2, CXCR2, S100A8, and S100A9
CXCL1, CXCL2, CXCR1, CXCR2, S100A8, and S100A9
CXCL1, CXCL3, CXCL8, PTGS2, CXCR1, and CXCR2
CXCL1, CXCL3, CXCL8, PTGS2, CXCR1, and S100A8
CXCL1, CXCL3, CXCL8, PTGS2, CXCR1, and S100A9
CXCL1, CXCL3, CXCL8, PTGS2, CXCR2, and S100A8
CXCL1, CXCL3, CXCL8, PTGS2, CXCR2, and S100A9
CXCL1, CXCL3, CXCL8, PTGS2, S100A8, and S100A9
CXCL1, CXCL3, CXCL8, CXCR1, CXCR2, and S100A8
CXCL1, CXCL3, CXCL8, CXCR1, CXCR2, and S100A9
CXCL1, CXCL3, CXCL8, CXCR1, S100A8, and S100A9
CXCL1, CXCL3, CXCL8, CXCR2, S100A8, and S100A9
CXCL1, CXCL3, PTGS2, CXCR1, CXCR2, and S100A8
CXCL1, CXCL3, PTGS2, CXCR1, CXCR2, and S100A9
CXCL1, CXCL3, PTGS2, CXCR1, S100A8, and S100A9
CXCL1, CXCL3, PTGS2, CXCR2, S100A8, and S100A9
CXCL1, CXCL3, CXCR1, CXCR2, S100A8, and S100A9
CXCL1, CXCL8, PTGS2, CXCR1, CXCR2, and S100A8
CXCL1, CXCL8, PTGS2, CXCR1, CXCR2, and S100A9
CXCL1, CXCL8, PTGS2, CXCR1, S100A8, and S100A9
CXCL1, CXCL8, PTGS2, CXCR2, S100A8, and S100A9
CXCL1, CXCL8, CXCR1, CXCR2, S100A8, and S100A9
CXCL1, PTGS2, CXCR1, CXCR2, S100A8, and S100A9
CXCL2, CXCL3, CXCL8, PTGS2, CXCR1, and CXCR2
CXCL2, CXCL3, CXCL8, PTGS2, CXCR1, and S100A8
CXCL2, CXCL3, CXCL8, PTGS2, CXCR1, and S100A9
CXCL2, CXCL3, CXCL8, PTGS2, CXCR2, and S100A8
CXCL2, CXCL3, CXCL8, PTGS2, CXCR2, and S100A9
CXCL2, CXCL3, CXCL8, PTGS2, S100A8, and S100A9
CXCL2, CXCL3, CXCL8, CXCR1, CXCR2, and S100A8
CXCL2, CXCL3, CXCL8, CXCR1, CXCR2, and S100A9
CXCL2, CXCL3, CXCL8, CXCR1, S100A8, and S100A9
CXCL2, CXCL3, CXCL8, CXCR2, S100A8, and S100A9
CXCL2, CXCL3, PTGS2, CXCR1, CXCR2, and S100A8
CXCL2, CXCL3, PTGS2, CXCR1, CXCR2, and S100A9
CXCL2, CXCL3, PTGS2, CXCR1, S100A8, and S100A9
CXCL2, CXCL3, PTGS2, CXCR2, S100A8, and S100A9
CXCL2, CXCL3, CXCR1, CXCR2, S100A8, and S100A9
CXCL2, CXCL8, PTGS2, CXCR1, CXCR2, and S100A8
CXCL2, CXCL8, PTGS2, CXCR1, CXCR2, and S100A9
CXCL2, CXCL8, PTGS2, CXCR1, S100A8, and S100A9
CXCL2, CXCL8, PTGS2, CXCR2, S100A8, and S100A9
CXCL2, CXCL8, CXCR1, CXCR2, S100A8, and S100A9
CXCL2, PTGS2, CXCR1, CXCR2, S100A8, and S100A9
CXCL3, CXCL8, PTGS2, CXCR1, CXCR2, and S100A8
CXCL3, CXCL8, PTGS2, CXCR1, CXCR2, and S100A9
CXCL3, CXCL8, PTGS2, CXCR1, S100A8, and S100A9
CXCL3, CXCL8, PTGS2, CXCR2, S100A8, and S100A9
CXCL3, CXCL8, CXCR1, CXCR2, S100A8, and S100A9
CXCL3, PTGS2, CXCR1, CXCR2, S100A8, and S100A9
CXCL8, PTGS2, CXCR1, CXCR2, S100A8, and S100A9

TABLE 14

Seven-Gene Combinations of IL6, CXCL1, CXCL2, CXCL3, CXCL8, PTGS2, CXCR1, CXCR2, S100A8, and S100A9

IL6, CXCL1, CXCL2, CXCL3, CXCL8, PTGS2, and CXCR1
IL6, CXCL1, CXCL2, CXCL3, CXCL8, PTGS2, and CXCR2
IL6, CXCL1, CXCL2, CXCL3, CXCL8, PTGS2, and S100A8
IL6, CXCL1, CXCL2, CXCL3, CXCL8, PTGS2, and S100A9
IL6, CXCL1, CXCL2, CXCL3, CXCL8, CXCR1, and CXCR2
IL6, CXCL1, CXCL2, CXCL3, CXCL8, CXCR1, and S100A8
IL6, CXCL1, CXCL2, CXCL3, CXCL8, CXCR1, and S100A9
IL6, CXCL1, CXCL2, CXCL3, CXCL8, CXCR2, and S100A8
IL6, CXCL1, CXCL2, CXCL3, CXCL8, CXCR2, and S100A9
IL6, CXCL1, CXCL2, CXCL3, CXCL8, S100A8, and S100A9
IL6, CXCL1, CXCL2, CXCL3, PTGS2, CXCR1, and CXCR2
IL6, CXCL1, CXCL2, CXCL3, PTGS2, CXCR1, and S100A8
IL6, CXCL1, CXCL2, CXCL3, PTGS2, CXCR1, and S100A9
IL6, CXCL1, CXCL2, CXCL3, PTGS2, CXCR2, and S100A8
IL6, CXCL1, CXCL2, CXCL3, PTGS2, CXCR2, and S100A9
IL6, CXCL1, CXCL2, CXCL3, PTGS2, S100A8, and S100A9
IL6, CXCL1, CXCL2, CXCL3, CXCR1, CXCR2, and S100A8
IL6, CXCL1, CXCL2, CXCL3, CXCR1, CXCR2, and S100A9
IL6, CXCL1, CXCL2, CXCL3, CXCR1, S100A8, and S100A9
IL6, CXCL1, CXCL2, CXCL3, CXCR2, S100A8, and S100A9
IL6, CXCL1, CXCL2, CXCL8, PTGS2, CXCR1, and CXCR2
IL6, CXCL1, CXCL2, CXCL8, PTGS2, CXCR1, and S100A8
IL6, CXCL1, CXCL2, CXCL8, PTGS2, CXCR1, and S100A9
IL6, CXCL1, CXCL2, CXCL8, PTGS2, CXCR2, and S100A8
IL6, CXCL1, CXCL2, CXCL8, PTGS2, CXCR2, and S100A9
IL6, CXCL1, CXCL2, CXCL8, PTGS2, S100A8, and S100A9
IL6, CXCL1, CXCL2, CXCL8, CXCR1, CXCR2, and S100A8
IL6, CXCL1, CXCL2, CXCL8, CXCR1, CXCR2, and S100A9
IL6, CXCL1, CXCL2, CXCL8, CXCR1, S100A8, and S100A9
IL6, CXCL1, CXCL2, CXCL8, CXCR2, S100A8, and S100A9
IL6, CXCL1, CXCL2, PTGS2, CXCR1, CXCR2, and S100A8
IL6, CXCL1, CXCL2, PTGS2, CXCR1, CXCR2, and S100A9
IL6, CXCL1, CXCL2, PTGS2, CXCR1, S100A8, and S100A9
IL6, CXCL1, CXCL2, PTGS2, CXCR2, S100A8, and S100A9
IL6, CXCL1, CXCL2, CXCR1, CXCR2, S100A8, and S100A9
IL6, CXCL1, CXCL3, CXCL8, PTGS2, CXCR1, and CXCR2
IL6, CXCL1, CXCL3, CXCL8, PTGS2, CXCR1, and S100A8
IL6, CXCL1, CXCL3, CXCL8, PTGS2, CXCR1, and S100A9
IL6, CXCL1, CXCL3, CXCL8, PTGS2, CXCR2, and S100A8
IL6, CXCL1, CXCL3, CXCL8, PTGS2, CXCR2, and S100A9
IL6, CXCL1, CXCL3, CXCL8, PTGS2, S100A8, and S100A9
IL6, CXCL1, CXCL3, CXCL8, CXCR1, CXCR2, and S100A8
IL6, CXCL1, CXCL3, CXCL8, CXCR1, CXCR2, and S100A9
IL6, CXCL1, CXCL3, CXCL8, CXCR1, S100A8, and S100A9
IL6, CXCL1, CXCL3, CXCL8, CXCR2, S100A8, and S100A9
IL6, CXCL1, CXCL3, PTGS2, CXCR1, CXCR2, and S100A8
IL6, CXCL1, CXCL3, PTGS2, CXCR1, CXCR2, and S100A9
IL6, CXCL1, CXCL3, PTGS2, CXCR1, S100A8, and S100A9
IL6, CXCL1, CXCL3, PTGS2, CXCR2, S100A8, and S100A9
IL6, CXCL1, CXCL3, CXCR1, CXCR2, S100A8, and S100A9
IL6, CXCL1, CXCL8, PTGS2, CXCR1, CXCR2, and S100A8
IL6, CXCL1, CXCL8, PTGS2, CXCR1, CXCR2, and S100A9
IL6, CXCL1, CXCL8, PTGS2, CXCR1, S100A8, and S100A9
IL6, CXCL1, CXCL8, PTGS2, CXCR2, S100A8, and S100A9
IL6, CXCL1, CXCL8, CXCR1, CXCR2, S100A8, and S100A9
IL6, CXCL1, PTGS2, CXCR1, CXCR2, S100A8, and S100A9
IL6, CXCL2, CXCL3, CXCL8, PTGS2, CXCR1, and CXCR2
IL6, CXCL2, CXCL3, CXCL8, PTGS2, CXCR1, and S100A8
IL6, CXCL2, CXCL3, CXCL8, PTGS2, CXCR1, and S100A9
IL6, CXCL2, CXCL3, CXCL8, PTGS2, CXCR2, and S100A8
IL6, CXCL2, CXCL3, CXCL8, PTGS2, CXCR2, and S100A9
IL6, CXCL2, CXCL3, CXCL8, PTGS2, S100A8, and S100A9
IL6, CXCL2, CXCL3, CXCL8, CXCR1, CXCR2, and S100A8
IL6, CXCL2, CXCL3, CXCL8, CXCR1, CXCR2, and S100A9
IL6, CXCL2, CXCL3, CXCL8, CXCR1, S100A8, and S100A9
IL6, CXCL2, CXCL3, CXCL8, CXCR2, S100A8, and S100A9
IL6, CXCL2, CXCL3, PTGS2, CXCR1, CXCR2, and S100A8
IL6, CXCL2, CXCL3, PTGS2, CXCR1, CXCR2, and S100A9
IL6, CXCL2, CXCL3, PTGS2, CXCR1, S100A8, and S100A9
IL6, CXCL2, CXCL3, PTGS2, CXCR2, S100A8, and S100A9
IL6, CXCL2, CXCL3, CXCR1, CXCR2, S100A8, and S100A9
IL6, CXCL2, CXCL8, PTGS2, CXCR1, CXCR2, and S100A8
IL6, CXCL2, CXCL8, PTGS2, CXCR1, CXCR2, and S100A9
IL6, CXCL2, CXCL8, PTGS2, CXCR1, S100A8, and S100A9
IL6, CXCL2, CXCL8, PTGS2, CXCR2, S100A8, and S100A9
IL6, CXCL2, CXCL8, CXCR1, CXCR2, S100A8, and S100A9
IL6, CXCL2, PTGS2, CXCR1, CXCR2, S100A8, and S100A9

TABLE 14-continued

Seven-Gene Combinations of IL6, CXCL1, CXCL2, CXCL3, CXCL8, PTGS2, CXCR1, CXCR2, S100A8, and S100A9

IL6, CXCL3, CXCL8, PTGS2, CXCR1, CXCR2, and S100A8
IL6, CXCL3, CXCL8, PTGS2, CXCR1, CXCR2, and S100A9
IL6, CXCL3, CXCL8, PTGS2, CXCR1, S100A8, and S100A9
IL6, CXCL3, CXCL8, PTGS2, CXCR2, S100A8, and S100A9
IL6, CXCL3, CXCL8, CXCR1, CXCR2, S100A8, and S100A9
IL6, CXCL3, PTGS2, CXCR1, CXCR2, S100A8, and S100A9
IL6, CXCL8, PTGS2, CXCR1, CXCR2, S100A8, and S100A9
CXCL1, CXCL2, CXCL3, CXCL8, PTGS2, CXCR1, and CXCR2
CXCL1, CXCL2, CXCL3, CXCL8, PTGS2, CXCR1, and S100A8
CXCL1, CXCL2, CXCL3, CXCL8, PTGS2, CXCR1, and S100A9
CXCL1, CXCL2, CXCL3, CXCL8, PTGS2, CXCR2, and S100A8
CXCL1, CXCL2, CXCL3, CXCL8, PTGS2, CXCR2, and S100A9
CXCL1, CXCL2, CXCL3, CXCL8, PTGS2, S100A8, and S100A9
CXCL1, CXCL2, CXCL3, CXCL8, CXCR1, CXCR2, and S100A8
CXCL1, CXCL2, CXCL3, CXCL8, CXCR1, CXCR2, and S100A9
CXCL1, CXCL2, CXCL3, CXCL8, CXCR1, S100A8, and S100A9
CXCL1, CXCL2, CXCL3, CXCL8, CXCR2, S100A8, and S100A9
CXCL1, CXCL2, CXCL3, PTGS2, CXCR1, CXCR2, and S100A8
CXCL1, CXCL2, CXCL3, PTGS2, CXCR1, CXCR2, and S100A9
CXCL1, CXCL2, CXCL3, PTGS2, CXCR1, S100A8, and S100A9
CXCL1, CXCL2, CXCL3, PTGS2, CXCR2, S100A8, and S100A9
CXCL1, CXCL2, CXCL3, CXCR1, CXCR2, S100A8, and S100A9
CXCL1, CXCL2, CXCL8, PTGS2, CXCR1, CXCR2, and S100A8
CXCL1, CXCL2, CXCL8, PTGS2, CXCR1, CXCR2, and S100A9
CXCL1, CXCL2, CXCL8, PTGS2, CXCR1, S100A8, and S100A9
CXCL1, CXCL2, CXCL8, PTGS2, CXCR2, S100A8, and S100A9
CXCL1, CXCL2, CXCL8, CXCR1, CXCR2, S100A8, and S100A9
CXCL1, CXCL2, PTGS2, CXCR1, CXCR2, S100A8, and S100A9
CXCL1, CXCL3, CXCL8, PTGS2, CXCR1, CXCR2, and S100A8
CXCL1, CXCL3, CXCL8, PTGS2, CXCR1, CXCR2, and S100A9
CXCL1, CXCL3, CXCL8, PTGS2, CXCR1, S100A8, and S100A9
CXCL1, CXCL3, CXCL8, PTGS2, CXCR2, S100A8, and S100A9
CXCL1, CXCL3, CXCL8, CXCR1, CXCR2, S100A8, and S100A9
CXCL1, CXCL3, PTGS2, CXCR1, CXCR2, S100A8, and S100A9
CXCL1, CXCL8, PTGS2, CXCR1, CXCR2, S100A8, and S100A9
CXCL2, CXCL3, CXCL8, PTGS2, CXCR1, CXCR2, and S100A8
CXCL2, CXCL3, CXCL8, PTGS2, CXCR1, CXCR2, and S100A9
CXCL2, CXCL3, CXCL8, PTGS2, CXCR1, S100A8, and S100A9
CXCL2, CXCL3, CXCL8, PTGS2, CXCR2, S100A8, and S100A9
CXCL2, CXCL3, CXCL8, CXCR1, CXCR2, S100A8, and S100A9
CXCL2, CXCL3, PTGS2, CXCR1, CXCR2, S100A8, and S100A9
CXCL2, CXCL8, PTGS2, CXCR1, CXCR2, S100A8, and S100A9
CXCL3, CXCL8, PTGS2, CXCR1, CXCR2, S100A8, and S100A9

TABLE 15

Eight-Gene Combinations of IL6, CXCL1, CXCL2, CXCL3, CXCL8, PTGS2, CXCR1, CXCR2, S100A8, and S100A9

IL6, CXCL1, CXCL2, CXCL3, CXCL8, PTGS2, CXCR1, and CXCR2
IL6, CXCL1, CXCL2, CXCL3, CXCL8, PTGS2, CXCR1, and S100A8
IL6, CXCL1, CXCL2, CXCL3, CXCL8, PTGS2, CXCR1, and S100A9
IL6, CXCL1, CXCL2, CXCL3, CXCL8, PTGS2, CXCR2, and S100A8
IL6, CXCL1, CXCL2, CXCL3, CXCL8, PTGS2, CXCR2, and S100A9
IL6, CXCL1, CXCL2, CXCL3, CXCL8, PTGS2, S100A8, and S100A9
IL6, CXCL1, CXCL2, CXCL3, CXCL8, CXCR1, CXCR2, and S100A8
IL6, CXCL1, CXCL2, CXCL3, CXCL8, CXCR1, CXCR2, and S100A9
IL6, CXCL1, CXCL2, CXCL3, CXCL8, CXCR1, S100A8, and S100A9
IL6, CXCL1, CXCL2, CXCL3, CXCL8, CXCR2, S100A8, and S100A9
IL6, CXCL1, CXCL2, CXCL3, PTGS2, CXCR1, CXCR2, and S100A8
IL6, CXCL1, CXCL2, CXCL3, PTGS2, CXCR1, CXCR2, and S100A9
IL6, CXCL1, CXCL2, CXCL3, PTGS2, CXCR1, S100A8, and S100A9
IL6, CXCL1, CXCL2, CXCL3, PTGS2, CXCR2, S100A8, and S100A9
IL6, CXCL1, CXCL2, CXCL3, CXCR1, CXCR2, S100A8, and S100A9
IL6, CXCL1, CXCL2, CXCL8, PTGS2, CXCR1, CXCR2, and S100A8
IL6, CXCL1, CXCL2, CXCL8, PTGS2, CXCR1, CXCR2, and S100A9
IL6, CXCL1, CXCL2, CXCL8, PTGS2, CXCR1, S100A8, and S100A9
IL6, CXCL1, CXCL2, CXCL8, PTGS2, CXCR2, S100A8, and S100A9
IL6, CXCL1, CXCL2, CXCL8, CXCR1, CXCR2, S100A8, and S100A9
IL6, CXCL1, CXCL2, PTGS2, CXCR1, CXCR2, S100A8, and S100A9
IL6, CXCL1, CXCL3, CXCL8, PTGS2, CXCR1, CXCR2, and S100A8
IL6, CXCL1, CXCL3, CXCL8, PTGS2, CXCR1, CXCR2, and S100A9
IL6, CXCL1, CXCL3, CXCL8, PTGS2, CXCR1, S100A8, and S100A9
IL6, CXCL1, CXCL3, CXCL8, PTGS2, CXCR2, S100A8, and S100A9

TABLE 15-continued

Eight-Gene Combinations of IL6, CXCL1, CXCL2, CXCL3, CXCL8, PTGS2, CXCR1, CXCR2, S100A8, and S100A9

IL6, CXCL1, CXCL3, CXCL8, CXCR1, CXCR2, S100A8, and S100A9
IL6, CXCL1, CXCL3, PTGS2, CXCR1, CXCR2, S100A8, and S100A9
IL6, CXCL1, CXCL8, PTGS2, CXCR1, CXCR2, S100A8, and S100A9
IL6, CXCL2, CXCL3, CXCL8, PTGS2, CXCR1, CXCR2, and S100A8
IL6, CXCL2, CXCL3, CXCL8, PTGS2, CXCR1, CXCR2, and S100A9
IL6, CXCL2, CXCL3, CXCL8, PTGS2, CXCR1, S100A8, and S100A9
IL6, CXCL2, CXCL3, CXCL8, PTGS2, CXCR2, S100A8, and S100A9
IL6, CXCL2, CXCL3, CXCL8, CXCR1, CXCR2, S100A8, and S100A9
IL6, CXCL2, CXCL3, PTGS2, CXCR1, CXCR2, S100A8, and S100A9
IL6, CXCL2, CXCL8, PTGS2, CXCR1, CXCR2, S100A8, and S100A9
IL6, CXCL3, CXCL8, PTGS2, CXCR1, CXCR2, S100A8, and S100A9
CXCL1, CXCL2, CXCL3, CXCL8, PTGS2, CXCR1, CXCR2, and S100A8
CXCL1, CXCL2, CXCL3, CXCL8, PTGS2, CXCR1, CXCR2, and S100A9
CXCL1, CXCL2, CXCL3, CXCL8, PTGS2, CXCR1, S100A8, and S100A9
CXCL1, CXCL2, CXCL3, CXCL8, PTGS2, CXCR2, S100A8, and S100A9
CXCL1, CXCL2, CXCL3, CXCL8, CXCR1, CXCR2, S100A8, and S100A9
CXCL1, CXCL2, CXCL3, PTGS2, CXCR1, CXCR2, S100A8, and S100A9
CXCL1, CXCL2, CXCL8, PTGS2, CXCR1, CXCR2, S100A8, and S100A9
CXCL1, CXCL3, CXCL8, PTGS2, CXCR1, CXCR2, S100A8, and S100A9
CXCL2, CXCL3, CXCL8, PTGS2, CXCR1, CXCR2, S100A8, and S100A9

TABLE 16

Nine-Gene Combinations of IL6, CXCL1, CXCL2, CXCL3, CXCL8, PTGS2, CXCR1, CXCR2, S100A8, and S100A9

IL6, CXCL1, CXCL2, CXCL3, CXCL8, PTGS2, CXCR1, CXCR2, and S100A8
IL6, CXCL1, CXCL2, CXCL3, CXCL8, PTGS2, CXCR1, CXCR2, and S100A9
IL6, CXCL1, CXCL2, CXCL3, CXCL8, PTGS2, CXCR1, S100A8, and S100A9
IL6, CXCL1, CXCL2, CXCL3, CXCL8, PTGS2, CXCR2, S100A8, and S100A9
IL6, CXCL1, CXCL2, CXCL3, CXCL8, CXCR1, CXCR2, S100A8, and S100A9
IL6, CXCL1, CXCL2, CXCL3, PTGS2, CXCR1, CXCR2, S100A8, and S100A9
IL6, CXCL1, CXCL2, CXCL8, PTGS2, CXCR1, CXCR2, S100A8, and S100A9
IL6, CXCL1, CXCL3, CXCL8, PTGS2, CXCR1, CXCR2, S100A8, and S100A9
IL6, CXCL2, CXCL3, CXCL8, PTGS2, CXCR1, CXCR2, S100A8, and S100A9
CXCL1, CXCL2, CXCL3, CXCL8, PTGS2, CXCR1, CXCR2, S100A8, and S100A9

In any of the preceding methods, the method may include determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2, and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. For example, in some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2, and at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9.

For example, any of the preceding methods may include determining the expression level of one or more (e.g., 1, 2, 3, 4, or 5) of CD8A, EOMES, PRF1, IFNG, or PD-L1, and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. In some embodiments, the method includes determining the expression level of at least two, at least three, at least four, or all five of CD8A, EOMES, PRF1, IFNG, and PD-L1, and at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9. In some embodiments, the method comprises determining the expression level of any one of the combinations set forth in Tables 2-4 and any one of the combinations set forth in Tables 9-16. For example, in some embodiments, the method includes determining the expression level of two of CD8A, EOMES, PRF1, IFNG, and PD-L1, for example, any of the exemplary combinations shown in Table 2, and two of IL6, CXCL1, CXCL2, CXCL3, CXCL8, PTGS2, CXCR1, CXCR2, S100A8, and S100A9, for example, any of the exemplary combinations shown in Table 9. In some embodiments, the method includes determining the expression level of three of CD8A, EOMES, PRF1, IFNG, and PD-L1, for example, any of the exemplary combinations shown in Table 3, and three of IL6, CXCL1, CXCL2, CXCL3, CXCL8, PTGS2, CXCR1, CXCR2, S100A8, and S100A9, for example, any of the exemplary combinations shown in Table 10. In some embodiments, the method includes determining the expression level of four of CD8A, EOMES, PRF1, IFNG, and PD-L1, for example, any of the exemplary combinations shown in Table 4, and four of IL6, CXCL1, CXCL2, CXCL3, CXCL8, PTGS2, CXCR1, CXCR2, S100A8, and S100A9, for example, any of the exemplary combinations shown in Table 11. In some embodiments, the method involves determining the expression level of CD8A, EOMES, PRF1, IFNG, and PD-L1, and five of IL6, CXCL1, CXCL2, CXCL3, CXCL8, PTGS2, CXCR1, CXCR2, S100A8, and S100A9, for example, any of the exemplary combinations shown in Table 12. In some embodiments, the method involves determining the expression level of CD8A, EOMES, PRF1, IFNG, and PD-L1, and six of IL6, CXCL1, CXCL2, CXCL3, CXCL8, PTGS2, CXCR1, CXCR2, S100A8, and S100A9, for example, any of the exemplary combinations shown in Table 13. In some embodiments, the method involves determining the expression level of CD8A, EOMES, PRF1, IFNG, and PD-L1, and seven of IL6, CXCL1, CXCL2, CXCL3, CXCL8, PTGS2, CXCR1, CXCR2, S100A8, and S100A9, for example, any of the exemplary combinations shown in Table 14. In some embodiments, the method involves determining the expression level of CD8A, EOMES, PRF1, IFNG, and PD-L1, and eight of IL6, CXCL1, CXCL2, CXCL3, CXCL8, PTGS2, CXCR1, CXCR2, S100A8, and S100A9, for example, any of the exemplary combinations shown in Table 15. In some embodiments, the method involves determining the expression level of CD8A, EOMES, PRF1, IFNG, and PD-L1, and nine of IL6, CXCL1, CXCL2, CXCL3, CXCL8, PTGS2, CXCR1, CXCR2, S100A8, and S100A9, for example, any of the exemplary combinations shown in Table 16. In some embodiments, the method involves determining the expression level of CD8A, EOMES, PRF1, IFNG, PD-L1, IL6, CXCL1, CXCL2, CXCL3, CXCL8, PTGS2, CXCR1, CXCR2, S100A8, and S100A9.

In other embodiments, in any of the preceding methods, the method may include determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2, and one or more (e.g., 1, 2, 3, 4, 5, 6, or 7) of VEGFA, KDR, ESM1, PECAM1, FLT1, ANGPTL4, or CD34. For example, in some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2, and at least two, at least three, at least four, at least five, at least six, or all seven of VEGFA, KDR, ESM1, PECAM1, FLT1, ANGPTL4, or CD34.

For example, any of the preceding methods may include determining the expression level of one or more (e.g., 1, 2, 3, 4, or 5) of CD8A, EOMES, PRF1, IFNG, or PD-L1, and one or more (e.g., 1, 2, 3, 4, 5, or 6) of VEGFA, KDR, ESM1, PECAM1, ANGPTL4, or CD34. In some embodiments, the method includes determining the expression level of at least two, at least three, at least four, or all five of CD8A, EOMES, PRF1, IFNG, and PD-L1, and at least one, at least two, at least three, at least four, at least five, or all six of VEGFA, KDR, ESM1, PECAM1, ANGPTL4, and CD34. In some embodiments, the method comprises determining the expression level of any one of the combinations set forth in Tables 2-4 and any one of the combinations set forth in Tables 5-8. For example, in some embodiments, the method includes determining the expression level of two of CD8A, EOMES, PRF1, IFNG, and PD-L1, for example, any of the exemplary combinations shown in Table 2, and two of VEGFA, KDR, ESM1, PECAM1, ANGPTL4, and CD34, for example, any of the exemplary combinations shown in Table 5. In some embodiments, the method includes determining the expression level of three of CD8A, EOMES, PRF1, IFNG, and PD-L1, for example, any of the exemplary combinations shown in Table 3, and three of three of VEGFA, KDR, ESM1, PECAM1, ANGPTL4, and CD34, for example, any of the exemplary combinations shown in Table 6. In some embodiments, the method includes determining the expression level of four of CD8A, EOMES, PRF1, IFNG, and PD-L1, for example, any of the exemplary combinations shown in Table 4, and four of VEGFA, KDR, ESM1, PECAM1, ANGPTL4, and CD34, for example, any of the exemplary combinations shown in Table 7. In some embodiments, the method involves determining the expression level of CD8A, EOMES, PRF1, IFNG, and PD-L1, and five of VEGFA, KDR, ESM1, PECAM1, ANGPTL4, and CD34, for example, any of the exemplary combinations shown in Table 8. In some embodiments, the method involves determining the expression level of CD8A, EOMES, PRF1, IFNG, PD-L1, VEGFA, KDR, ESM1, PECAM1, ANGPTL4, and CD34.

In a further embodiment, in any of the preceding methods, the method may include determining the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9, and one or more (e.g., 1, 2, 3, 4, 5, 6, or 7) of VEGFA, KDR, ESM1, PECAM1, FLT1, ANGPTL4, or CD34. For example, in some embodiments, the method includes determining the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9, and at least two, at least three, at least four, at least five, at least six, or all seven of VEGFA, KDR, ESM1, PECAM1, FLT1, ANGPTL4, or CD34.

For example, any of the preceding methods may include determining the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9, and one or more (e.g., 1, 2, 3, 4, 5, or 6) of VEGFA, KDR, ESM1, PECAM1, ANGPTL4, or CD34. In some embodiments, the method includes determining the expression level of at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9, and at least two, at least three, at least four, at least five, or all six of VEGFA, KDR, ESM1, PECAM1, ANGPTL4, and CD34. In some embodiments, the method comprises determining the expression level of any one of the combinations set forth in Tables 9-16 and any one of the combinations set forth in Tables 5-8. For example, in some embodiments, the method includes determining the expression level of two of IL6, CXCL1, CXCL2, CXCL3, CXCL8, PTGS2, CXCR1, CXCR2, S100A8, and S100A9, for example, any of the exemplary combinations shown in Table 9, and two of VEGFA, KDR, ESM1, PECAM1, ANGPTL4, and CD34, for example, any of the exemplary combinations shown in Table 5. In some embodiments, the method includes determining the expression level of three of IL6, CXCL1, CXCL2, CXCL3, CXCL8, PTGS2, CXCR1, CXCR2, S100A8, and S100A9, for example, any of the exemplary combinations shown in Table 10, and three of three of VEGFA, KDR, ESM1, PECAM1, ANGPTL4, and CD34, for example, any of the exemplary combinations shown in Table 6. In some embodiments, the method includes determining the expression level of four of IL6, CXCL1, CXCL2, CXCL3, CXCL8, PTGS2, CXCR1, CXCR2, S100A8, and S100A9, for example, any of the exemplary combinations shown in Table 11, and four of VEGFA, KDR, ESM1, PECAM1, ANGPTL4, and CD34, for example, any of the exemplary combinations shown in Table 7. In some embodiments, the method involves determining the expression level of five of IL6, CXCL1, CXCL2, CXCL3, CXCL8, PTGS2, CXCR1, CXCR2, S100A8, and S100A9, for example, any of the exemplary combinations shown in Table 12, and five of VEGFA, KDR, ESM1, PECAM1, ANGPTL4, and CD34, for example, any of the exemplary combinations shown in Table 8. In some embodiments, the method involves determining the expression level of six of IL6, CXCL1, CXCL2, CXCL3, CXCL8, PTGS2, CXCR1, CXCR2, S100A8, and S100A9, for example, any of the exemplary combinations shown in Table 13, and VEGFA, KDR, ESM1, PECAM1, ANGPTL4, and CD34. In some embodiments, the method involves determining the expression level of seven of IL6, CXCL1, CXCL2, CXCL3, CXCL8, PTGS2, CXCR1, CXCR2, S100A8, and S100A9, for example, any of exemplary combinations shown in Table 14, and VEGFA, KDR, ESM1, PECAM1, ANGPTL4, and CD34. In some embodiments, the method involves determining the expression level of eight of IL6, CXCL1, CXCL2, CXCL3, CXCL8, PTGS2, CXCR1, CXCR2, S100A8, and S100A9, for example, any of the exemplary combinations shown in Table 15, and VEGFA, KDR, ESM1, PECAM1, ANGPTL4, and CD34. In some embodiments, the method involves determining the expression level of nine of IL6, CXCL1, CXCL2, CXCL3, CXCL8, PTGS2, CXCR1, CXCR2, S100A8, and S100A9, for example, any of the exemplary combinations shown in Table 16, and VEGFA, KDR, ESM1, PECAM1, ANGPTL4, and CD34. In some embodiments, the method involves determining the expression level of IL6, CXCL1, CXCL2, CXCL3, CXCL8, PTGS2, CXCR1, CXCR2, S100A8, S100A9, VEGFA, KDR, ESM1, PECAM1, ANGPTL4, and CD34.

In some embodiments of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is at or above a reference expression level of the one or more genes, and the method further includes administering to the individual an effective amount of the anti-cancer therapy. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 is at or above a reference expression level of the one or more genes. In some instances, the expression level of one or more (e.g., 1, 2, 3, 4, or 5) of CD8A, EOMES, PRF1, IFNG, or PD-L1 in the sample is at or above a reference expression level of the one or more genes. In some embodiments, the expression level of one or more of the exemplary combinations set forth in Tables 2-4 in the sample is at or above a reference expression level of the one or more genes. In some embodiments, the expression level of CD8A, EOMES, PRF1, IFNG, and PD-L1 in the sample is at or above a reference expression level of CD8A, EOMES, PRF1, IFNG, and PD-L1.

In some embodiments of any of the preceding methods, the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 in the sample is at or above a reference expression level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is at or above a reference expression level of the one or more genes. In some embodiments, the expression level of one or more of the exemplary combinations set forth in Tables 9-16 in the sample is at or above a reference expression level of the one or more genes. In some embodiments, the expression level of IL6, CXCL1, CXCL2, CXCL3, CXCL8, PTGS2, CXCR1, CXCR2, S100A8, and S100A9 in the sample is at or above a reference expression level of IL6, CXCL1, CXCL2, CXCL3, CXCL8, PTGS2, CXCR1, CXCR2, S100A8, and S100A9.

In some embodiments of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is at or above a reference expression level of the one or more genes, and the method further includes administering to the individual an effective amount of the anti-cancer therapy. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 is at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is at or above a reference expression level of the one or more genes. In some embodiments, an expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 at or above a reference expression level of the one or more genes identifies the presence of myeloid inflammation in a tumor.

For example, in some embodiments, the expression level of one or more (e.g., 1, 2, 3, 4, or 5) of CD8A, EOMES, PRF1, IFNG, or PD-L1 is at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is at or above a reference expression level of the one or more genes. In some embodiments, the expression level of at least two, at least three, at least four, or all five of CD8A, EOMES, PRF1, IFNG, and PD-L1 is at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is at or above a reference expression level of the one or more genes. In some embodiments, the expression level of any one of the combinations set forth in Tables 2-4 is at or above a reference expression level of the one or more genes and the expression level of any one of the combinations set forth in Tables 9-16 is at or above a reference expression level of the one or more genes. For example, in some embodiments, the expression level of two of CD8A, EOMES, PRF1, IFNG, and PD-L1, for example, any of the exemplary combinations shown in Table 2, is at or above a reference expression level of the one or more genes, and the expression level of two of IL6, CXCL1, CXCL2, CXCL3, CXCL8, PTGS2, CXCR1, CXCR2, S100A8, and S100A9, for example, any of the exemplary combinations shown in Table 9, is at or above a reference expression level of the one or more genes. In some embodiments, the expression level of three of CD8A, EOMES, PRF1, IFNG, and PD-L1, for example, any of the exemplary combinations shown in Table 3, is at or above a reference expression level of the one or more genes, and the expression level of three of IL6, CXCL1, CXCL2, CXCL3, CXCL8, PTGS2, CXCR1, CXCR2, S100A8, and S100A9, for example, any of the exemplary combinations shown in Table 10, is at or above a reference expression level of the one or more genes. In some embodiments, the expression level of four of CD8A, EOMES, PRF1, IFNG, and PD-L1, for example, any of the exemplary combinations shown in Table 4, is at or above a reference expression level of the one or more genes, and the expression level of four of IL6, CXCL1, CXCL2, CXCL3, CXCL8, PTGS2, CXCR1, CXCR2, S100A8, and S100A9, for example, any of the exemplary combinations shown in Table 11, is at or above a reference expression level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of five of IL6, CXCL1, CXCL2, CXCL3, CXCL8, PTGS2, CXCR1, CXCR2, S100A8, and S100A9, for example, any of the exemplary combinations shown in Table 12, is at or above a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of six of IL6, CXCL1, CXCL2, CXCL3, CXCL8, PTGS2, CXCR1, CXCR2, S100A8, and S100A9, for example, any of the exemplary combinations shown in Table 13, is at or above a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of seven of IL6, CXCL1, CXCL2, CXCL3, CXCL8, PTGS2, CXCR1, CXCR2, S100A8, and S100A9, for example, any of the exemplary combinations shown in Table 14, is at or above a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of eight of IL6, CXCL1, CXCL2, CXCL3, CXCL8, PTGS2, CXCR1, CXCR2, S100A8, and S100A9, for example, any of the exemplary combinations shown in Table 15, is at or above a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of nine of IL6, CXCL1, CXCL2, CXCL3, CXCL8, PTGS2, CXCR1, CXCR2, S100A8, and S100A9, for example, any of the exemplary combinations shown in Table 16, is at or above a reference level of the one or more genes. In some embodiments, the expression level of CD8A, EOMES, PRF1, IFNG, PD-L1, IL6, CXCL1, CXCL2, CXCL3, CXCL8, PTGS2, CXCR1, CXCR2, S100A8, and S100A9 is at or above a reference expression level of CD8A, EOMES, PRF1, IFNG, PD-L1, IL6, CXCL1, CXCL2, CXCL3, CXCL8, PTGS2, CXCR1, CXCR2, S100A8, and S100A9. In some embodiments, an expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 at or above a reference expression level of the one or more genes identifies the presence of myeloid inflammation in a tumor. In some embodiments, an expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample at or above a reference expression level of the one or more genes, and an expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 at or above a reference expression level of the one or more genes indicates that the individual is less likely to benefit (e.g., is resistant to) a PD-L1 axis binding antagonist (e.g., an anti-PD-L1 antibody, e.g., atezolizumab) monotherapy.

In other embodiments of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is below a reference expression level of the one or more genes, and the method further includes administering to the individual an effective amount of a PD-L1 axis binding antagonist (e.g., an anti-PD-L1 antibody (e.g., atezolizumab) or an anti-PD-1 antibody) monotherapy. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 is at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is below a reference expression level of the one or more genes.

For example, in some embodiments, the expression level of one or more (e.g., 1, 2, 3, 4, or 5) of CD8A, EOMES, PRF1, IFNG, or PD-L1 is at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is below a reference expression level of the one or more genes. In some embodiments, the expression level of at least two, at least three, at least four, or all five of CD8A, EOMES, PRF1, IFNG, and PD-L1 is at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is below a reference expression level of the one or more genes. In some embodiments, the expression level of any one of the combinations set forth in Tables 2-4 is at or above a reference expression level of the one or more genes and the expression level of any one of the combinations set forth in Tables 9-16 is below a reference expression level of the one or more genes. For example, in some embodiments, the expression level of two of CD8A, EOMES, PRF1, and PD-L1, for example, any of the exemplary combinations shown in Table 2, is at or above a reference expression level of the one or more genes, and the expression level of two of IL6, CXCL1, CXCL2, CXCL3, CXCL8, PTGS2, CXCR1, CXCR2, S100A8, and S100A9, for example, any of the exemplary combinations shown in Table 9, is below a reference expression level of the one or more genes. In some embodiments, the expression level of three of CD8A, EOMES, PRF1, IFNG, and PD-L1, for example, any of the exemplary combinations shown in Table 3, is at or above a reference expression level of the one or more genes, and the expression level of three of IL6, CXCL1, CXCL2, CXCL3, CXCL8, PTGS2, CXCR1, CXCR2, S100A8, and S100A9, for example, any of the exemplary combinations shown in Table 10, is below a reference expression level of the one or more genes. In some embodiments, the expression level of four of CD8A, EOMES, PRF1, IFNG, and PD-L1, for example, any of the exemplary combinations shown in Table 4, is at or above a reference expression level of the one or more genes, and the expression level of four of IL6, CXCL1, CXCL2, CXCL3, CXCL8, PTGS2, CXCR1, CXCR2, S100A8, and S100A9, for example, any of the exemplary combinations shown in Table 11, is below a reference expression level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of five of IL6, CXCL1, CXCL2, CXCL3, CXCL8, PTGS2, CXCR1, CXCR2, S100A8, and S100A9, for example, any of the exemplary combinations shown in Table 12, is below a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of six of IL6, CXCL1, CXCL2, CXCL3, CXCL8, PTGS2, CXCR1, CXCR2, S100A8, and S100A9, for example, any of the exemplary combinations shown in Table 13, is below a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of seven of IL6, CXCL1, CXCL2, CXCL3, CXCL8, PTGS2, CXCR1, CXCR2, S100A8, and S100A9, for example, any of the exemplary combinations shown in Table 14, is below a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of eight of IL6, CXCL1, CXCL2, CXCL3, CXCL8, PTGS2, CXCR1, CXCR2, S100A8, and S100A9, for example, any of the exemplary combinations shown in Table 15, is below a reference level of the one or more genes. In some embodiments, the expression level of CD8A, EOMES, PRF1, IFNG, and PD-L1 is at or above a reference expression level of CD8A, EOMES, PRF1, IFNG, and PD-L1, and the expression level of nine of IL6, CXCL1, CXCL2, CXCL3, CXCL8, PTGS2, CXCR1, CXCR2, S100A8, and S100A9, for example, any of the exemplary combinations shown in Table 16, is below a reference level of the one or more genes. In some embodiments, the expression level of CD8A, EOMES, PRF1, IFNG, and PD-L1 is at or above a reference level of CD8A, EOMES, PRF1, IFNG, and PD-L1, and the expression level of IL6, CXCL1, CXCL2, CXCL3, CXCL8, PTGS2, CXCR1, CXCR2, S100A8, and S100A9 is below a reference expression level of IL6, CXCL1, CXCL2, CXCL3, CXCL8, PTGS2, CXCR1, CXCR2, S100A8, and S100A9.

In some embodiments of any of the preceding methods, the expression level of PD-L1 in the sample is at or above a reference expression level of PD-L1, and the expression level of one or more (e.g., 1, 2, 3, 4, 5, 6, 7, 8, 9, 10, 11, 12, 13, 14, 15, 16, 17, 18, or 19) additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2 in the sample is at or above a reference expression level of the one or more additional genes.

In some embodiments of any of the preceding methods, the expression level of one or more (e.g., 1, 2, 3, 4, 5, 6, or 7) of VEGFA, KDR, ESM1, PECAM1, FLT1, ANGPTL4, or CD34 in the sample is below a reference level of the one or more genes, and the method further comprises administering to the individual an effective amount of the anti-cancer therapy. For example, in some embodiments, the expression level of at least one, at least two, at least three, at least four, at least five, at least six, or all seven of VEGFA, KDR, ESM1, PECAM1, FLT1, ANGPTL4, or CD34 in the sample is below a reference level of the one or more genes. In some embodiments, the expression level of one or more of the exemplary combinations set forth in Tables 5-8 in the sample is below a reference expression level of the one or more genes. In some embodiments, the expression level of one or more of VEGFA, KDR, ESM1, PECAM1, ANGPTL4, or CD34 in the sample is below a reference level of the one or more genes. For example, in some embodiments, the expression level of VEGFA, KDR, ESM1, PECAM1, ANGPTL4, and CD34 in the sample is below a reference level of VEGFA, KDR, ESM1, PECAM1, ANGPTL4, and CD34.

In other embodiments, in any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 is at or above a reference level of the one or more genes, and the expression level of one or more (e.g., 1, 2, 3, 4, 5, 6, or 7) of VEGFA, KDR, ESM1, PECAM1, FLT1, ANGPTL4, or CD34 is below a reference level of the one or more genes, and the method further comprises administering to the individual an effective amount of the anti-cancer therapy. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 is at or above a reference level of the one or more genes, and the expression level of at least two, at least three, at least four, at least five, at least six, or all seven of VEGFA, KDR, ESM1, PECAM1, FLT1, ANGPTL4, or CD34 is below a reference level of the one or more genes.

For example, in some embodiments, the expression level of one or more (e.g., 1, 2, 3, 4, or 5) of CD8A, EOMES, PRF1, IFNG, or PD-L1 is at or above a reference level of the one or more genes, and the expression level of one or more (e.g., 1, 2, 3, 4, 5, or 6) of VEGFA, KDR, ESM1, PECAM1, ANGPTL4, or CD34 is below a reference level of the one or more genes. In some embodiments, the expression level of at least two, at least three, at least four, or all five of CD8A, EOMES, PRF1, IFNG, and PD-L1 is at or above a reference level of the one or more genes, and the expression level of at least one, at least two, at least three, at least four, at least five, or all six of VEGFA, KDR, ESM1, PECAM1, ANGPTL4, and CD34 is below a reference level fo the one or more genes. In some embodiments, the expression level of any one of the combinations set forth in Tables 2-4 is at or above a reference level of the one or more genes, and the expression level of any one of the combinations set forth in Tables 5-8 is below a reference level of the one or more genes. For example, in some embodiments, the expression level of two of CD8A, EOMES, PRF1, IFNG, and PD-L1, for example, any of the exemplary combinations shown in Table 2, is at or above a reference level of the one or more genes, and the expression level of two of VEGFA, KDR, ESM1, PECAM1, ANGPTL4, and CD34, for example, any of the exemplary combinations shown in Table 5, is below a reference level of the one or more genes. In some embodiments, the expression level of three of CD8A, EOMES, PRF1, IFNG, and PD-L1, for example, any of the exemplary combinations shown in Table 3, is at or above a reference level of the one or more genes, and the expression level of three of three of VEGFA, KDR, ESM1, PECAM1, ANGPTL4, and CD34, for example, any of the exemplary combinations shown in Table 6, is below a reference level of the one or more genes. In some embodiments, the expression level of four of CD8A, EOMES, PRF1, IFNG, and PD-L1, for example, any of the exemplary combinations shown in Table 4, is at or above a reference level of the one or more genes, and the expression level of four of VEGFA, KDR, ESM1, PECAM1, ANGPTL4, and CD34, for example, any of the exemplary combinations shown in Table 7, is below a reference level of the one or more genes. In some embodiments, the expression level of CD8A, EOMES, PRF1, IFNG, and PD-L1 is at or above a reference level of CD8A, EOMES, PRF1, IFNG, and PD-L1, and the expression level of five of VEGFA, KDR, ESM1, PECAM1, ANGPTL4, and CD34, for example, any of the exemplary combinations shown in Table 8, is below a reference level of the one or more genes. In some embodiments, the expression level of CD8A, EOMES, PRF1, IFNG, and PD-L1 is at or above a reference level of CD8A, EOMES, PRF1, IFNG, and PD-L1, and the expression level of VEGFA, KDR, ESM1, PECAM1, ANGPTL4, and CD34 is below a reference level of VEGFA, KDR, ESM1, PECAM1, ANGPTL4, and CD34.

In some embodiments of any of the preceding methods, the expression level of one or more (e.g., 1, 2, 3, 4, 5, or 6) of IL6, CXCL1, CXCL2, CXCL3, CXCL8, PTGS2, CXCR1, CXCR2, S100A8, or S100A9 in the sample is below a reference level of the one or more genes, and the method further comprises administering to the individual an effective amount of the anti-cancer therapy. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is below a reference level of the one or more genes. For example, in some embodiments, the expression level of one or more of the exemplary combinations set forth in Tables 9-16 in the sample is below a reference expression level of the one or more genes. In some embodiments, the expression level of IL6, CXCL1, CXCL2, CXCL3, CXCL8, PTGS2, CXCR1, CXCR2, S100A8, and S100A9 in the sample is below a reference level of IL6, CXCL1, CXCL2, CXCL3, CXCL8, PTGS2, CXCR1, CXCR2, S100A8, and S100A9.

In other embodiments of any of the preceding methods, the expression level of one or more (e.g., 1, 2, 3, 4, 5, 6, or 7) of VEGFA, KDR, ESM1, PECAM1, FLT1, ANGPTL4, or CD34 in the sample is at or above a reference level of the one or more genes, and the method further includes administering to the individual an effective amount of an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). In some embodiments, the expression level of at least one, at least two, at least three, at least four, at least five, at least six, or all seven of VEGFA, KDR, ESM1, PECAM1, FLT1, ANGPTL4, or CD34 is at or above a reference level of the one or more genes. In some embodiments, the expression level of one or more (e.g., 1, 2, 3, 4, 5, or 6) of VEGFA, KDR, ESM1, PECAM1, ANGPTL4, or CD34 in the sample is at or above a reference level of the one or more genes. In some embodiments, the expression level of one or more of the exemplary combinations set forth in Tables 5-8 in the sample is at or above a reference expression level of the one or more genes. In some embodiments, the expression level of VEGFA, KDR, ESM1, PECAM1, ANGPTL4, and CD34 in the sample is at or above a reference level of VEGFA, KDR, ESM1, PECAM1, ANGPTL4, and CD34.

In certain embodiments of any of the preceding methods, a reference level is the expression level of the one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) genes (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9) in a reference population, for example, a population of individuals having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)). In particular embodiments, the cancer is a kidney cancer (e.g., RCC, e.g., mRCC). In certain embodiments, a reference level is the median expression level of the one or more genes in a reference population, for example, a population of individuals having a cancer. In other embodiments, the reference level may be the top 40%, the top 30%, the top 20%, the top 10%, the top 5%, or the top 1% of the expression level in the reference population. In certain embodiments, the reference level is a pre-assigned expression level for the one or more genes. In some embodiments, the reference level is the expression level of the one or more genes in a biological sample obtained from the patient at a previous time point, wherein the previous time point is following administration of the anti-cancer therapy. In some embodiments of any of the preceding methods, a reference level is the expression level of the one or more genes (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9) in a biological sample from the patient obtained prior to (e.g., minutes, hours, days, weeks (e.g., 1, 2, 3, 4, 5, 6, or 7 weeks), months, or years prior to) administration of the anti-cancer therapy. In other embodiments, the reference level is the expression level of the one or more genes in a biological sample obtained from the patient at a subsequent time point (e.g., minutes, hours, days, weeks, months, or years after administration of an anti-cancer therapy).

The presence and/or expression level of any of the biomarkers described above may be assessed qualitatively and/or quantitatively based on any suitable criterion known in the art, including but not limited to DNA, mRNA, cDNA, proteins, protein fragments, and/or gene copy number. Methodologies for measuring such biomarkers are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (e.g., Serum ELISA), biochemical enzymatic activity assays, in situ hybridization (ISH), fluorescence in situ hybridization (FISH), Southern analysis, Northern analysis, whole genome sequencing, polymerase chain reaction (PCR) including quantitative real time PCR (qRT-PCR) and other amplification type detection methods, such as, for example, branched DNA, SISBA, TMA and the like, RNA-Seq, microarray analysis, gene expression profiling, whole-genome sequencing (WGS), and/or serial analysis of gene expression ("SAGE"), as well as any one of the wide variety of assays that can be performed by protein, gene, and/or tissue array analysis. Typical protocols for evaluating the status of genes and gene products are found, for example, in Ausubel et al. eds. (*Current Protocols In Molecular Biology,* 1995), Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments of any of the preceding methods, the expression level of a biomarker may be a nucleic acid expression level (e.g., a DNA expression level or an RNA expression level (e.g., an mRNA expression level)). Any suitable method of determining a nucleic acid expression level may be used. In some embodiments, the nucleic acid expression level is determined using RNA-seq, RT-qPCR, qPCR, multiplex qPCR or RT-qPCR, microarray analysis, SAGE, MassARRAY technique, ISH, or a combination thereof.

Methods for the evaluation of mRNAs in cells are well known and include, for example, serial analysis of gene expression (SAGE), whole genome sequencing (WGS), hybridization assays using complementary DNA probes (such as in situ hybridization using labeled riboprobes specific for the one or more genes, Northern blot and related techniques) and various nucleic acid amplification assays (such as RT-PCR (e.g., qRT-PCR) using complementary primers specific for one or more of the genes, and other amplification type detection methods, such as, for example, branched DNA, SISBA, TMA and the like). In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of treatment comprising a VEGF antagonist and a PD-L1 axis binding antagonist may be arrayed on a solid support. Hybridization of a labeled probe with a particular array member indicates that the sample from which the probe was derived expresses that gene.

In other embodiments of any of the preceding methods, the expression level of a biomarker may be a protein expression level. In certain embodiments, the method comprises contacting the sample with antibodies that specifically bind to a biomarker described herein under conditions permissive for binding of the biomarker, and detecting whether a complex is formed between the antibodies and biomarker. Such method may be an in vitro or in vivo method. In some instances, an antibody is used to select patients eligible for therapy with a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)), e.g., a biomarker for selection of individuals. In other instances, an antibody is used to select patients eligible for therapy with an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))), e.g., a biomarker for selection of individuals. Any method of measuring protein expression levels known in the art or provided herein may be used. For example, in some embodiments, a protein expression level of a biomarker is determined using a method selected from the group consisting of flow cytometry (e.g., fluorescence-activated cell sorting (FACS™)), Western blot, enzyme-linked immunosorbent assay (ELISA), immunoprecipitation, immunohistochemistry (IHC), immunofluorescence, radioimmunoassay, dot blotting, immunodetection methods, HPLC, surface plasmon resonance, optical spectroscopy, mass spectrometry, and HPLC. In some embodiments, the protein expression level of the biomarker is determined in tumor-infiltrating immune cells. In some embodiments, the protein expression level of the biomarker is determined in tumor cells. In some embodiments, the protein expression level of the biomarker is determined in tumor-infiltrating immune cells and/or in tumor cells. In some embodiments, the protein expression level of the biomarker is determined in peripheral blood mononuclear cells (PBMCs).

In certain embodiments, the presence and/or expression level/amount of a biomarker protein in a sample is examined using IHC and staining protocols. IHC staining of tissue sections has been shown to be a reliable method of determining or detecting the presence of proteins in a sample. In some embodiments of any of the methods, assays and/or kits, the biomarker is one or more of the protein expression products of the following genes: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9. In one embodiment, an expression level of biomarker is determined using a method comprising: (a) performing IHC analysis of a sample (such as a tumor sample obtained from a patient) with an antibody; and (b) determining expression level of a biomarker in the sample. In some embodiments, IHC staining intensity is determined relative to a reference. In some embodiments, the reference is a reference value. In some embodiments, the reference is a reference sample (e.g., a control cell line staining sample, a tissue sample from non-cancerous patient, or a tumor sample that is determined to be negative for the biomarker of interest).

IHC may be performed in combination with additional techniques such as morphological staining and/or in situ hybridization (e.g., ISH). Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for IHC typically will be labeled with a detectable moiety. Numerous labels are available which can be generally grouped into the following categories: (a) radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, lissamine, umbelliferone, phycocrytherin, phycocyanin, or commercially-available fluorophores such as SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase ((β-D-Gal) with a chromogenic substrate (e.g., p-nitrophenyl-β-D-galactosidase) or fluorogenic substrate (e.g., 4-methylumbelliferyl-β-D-galactosidase). For a general review of these, see, for example, U.S. Pat. Nos. 4,275,149 and 4,318,980.

Specimens may be prepared, for example, manually, or using an automated staining instrument (e.g., a Ventana BenchMark XT or Benchmark ULTRA instrument). Specimens thus prepared may be mounted and coverslipped. Slide evaluation is then determined, for example, using a microscope, and staining intensity criteria, routinely used in the art, may be employed. In one embodiment, it is to be understood that when cells and/or tissue from a tumor is examined using IHC, staining is generally determined or assessed in tumor cell(s) and/or tissue (as opposed to stromal or surrounding tissue that may be present in the sample). In some embodiments, it is understood that when cells and/or tissue from a tumor is examined using IHC, staining includes determining or assessing in tumor-infiltrating immune cells, including intratumoral or peritumoral immune cells. In some embodiments, the presence of a biomarker is detected by IHC in >0% of the sample, in at least 1% of the sample, in at least 5% of the sample, in at least 10% of the sample, in at least 15% of the sample, in at least 15% of the sample, in at least 20% of the sample, in at least 25% of the sample, in at least 30% of the sample, in at least 35% of the sample, in at least 40% of the sample, in at least 45% of the sample, in at least 50% of the sample, in at least 55% of the sample, in at least 60% of the sample, in at least 65% of the sample, in at least 70% of the sample, in at least 75% of the sample, in at least 80% of the sample, in at least 85% of the sample, in at least 90% of the sample, in at least 95% of the sample, or more. Samples may be scored using any method known in the art, for example, by a pathologist or automated image analysis.

In some embodiments of any of the methods, the biomarker is detected by immunohistochemistry using a diagnostic antibody (i.e., primary antibody). In some embodiments, the diagnostic antibody specifically binds human antigen. In some embodiments, the diagnostic antibody is a non-human antibody. In some embodiments, the diagnostic antibody is a rat, mouse, or rabbit antibody. In some embodiments, the diagnostic antibody is a rabbit antibody. In some embodiments, the diagnostic antibody is a monoclonal antibody. In some embodiments, the diagnostic antibody is directly labeled. In other embodiments, the diagnostic antibody is indirectly labeled.

In some embodiments of any of the preceding embodiments, the sample is obtained from the individual prior to (e.g., minutes, hours, days, weeks (e.g., 1, 2, 3, 4, 5, 6, or 7 weeks), months, or years prior to) administration of the anti-cancer therapy. In some embodiments of any of the preceding methods, the sample from the individual is obtained about 2 to about 10 weeks (e.g., 2, 3, 4, 5, 6, 7, 8, 9, or 10 weeks) following administration of the anti-cancer therapy. In some embodiments, the sample from the individual is obtained about 4 to about 6 weeks following administration of the anti-cancer therapy.

In some embodiments of any of the preceding methods, the expression level or number of a biomarker is detected in a tissue sample, a primary or cultured cells or cell line, a cell supernatant, a cell lysate, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, or any combination thereof. In some embodiments, the sample is a tissue sample (e.g., a tumor tissue sample), a cell sample, a whole blood sample, a plasma sample, a serum sample, or a combination thereof. In some embodiments, the tumor tissue sample wherein the tumor tissue sample includes tumor cells, tumor-infiltrating immune cells, stromal cells, or a combination thereof. In some embodiments, the tumor tissue sample is a formalin-fixed and paraffin-embedded (FFPE) sample, an archival sample, a fresh sample, or a frozen sample.

For example, in some embodiments of any of the preceding methods, the expression level of a biomarker is detected in tumor-infiltrating immune cells, tumor cells, PBMCs, or combinations thereof using known techniques (e.g., flow cytometry or IHC). Tumor-infiltrating immune cells include, but are not limited to, intratumoral immune cells, peritumoral immune cells or any combinations thereof, and other tumor stroma cells (e.g., fibroblasts). Such tumor infiltrating immune cells may be T lymphocytes (such as CD8+ T lymphocytes (e.g., CD8+T effector (Ten) cells) and/or CD4+T lymphocytes (e.g., CD4+ $T_{eff}$ cells), B lymphocytes, or other bone marrow-lineage cells including granulocytes (neutrophils, eosinophils, basophils), monocytes, macrophages, dendritic cells (e.g., interdigitating dendritic cells), histiocytes, and natural killer (NK) cells. In some embodiments, the staining for a biomarker is detected as membrane staining, cytoplasmic staining, or combinations thereof. In other embodiments, the absence of a biomarker is detected as absent or no staining in the sample, relative to a reference sample.

In particular embodiments of any of the preceding methods, the expression level of a biomarker is assessed in a sample that contains or is suspected to contain cancer cells. The sample may be, for example, a tissue biopsy or a metastatic lesion obtained from a patient suffering from, suspected to suffer from, or diagnosed with cancer (e.g., a kidney cancer, in particular renal cell carcinoma (RCC), such as advanced RCC or metastatic RCC (mRCC)). In some embodiments, the sample is a sample of kidney tissue, a biopsy of an kidney tumor, a known or suspected metastatic kidney cancer lesion or section, or a blood sample, e.g., a peripheral blood sample, known or suspected to comprise circulating cancer cells, e.g., kidney cancer cells. The sample may comprise both cancer cells, i.e., tumor cells, and non-cancerous cells (e.g., lymphocytes, such as T cells or NK cells), and, in certain embodiments, comprises both cancerous and non-cancerous cells. Methods of obtaining biological samples including tissue resections, biopsies, and body fluids, e.g., blood samples comprising cancer/tumor cells, are well known in the art.

In some embodiments of any of the preceding methods, the patient has carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. In some embodiments, the cancer is kidney cancer (e.g., renal cell carcinoma (RCC), e.g., advanced RCC or metastatic RCC (mRCC)), squamous cell cancer (e.g., epithelial squamous cell cancer), lung cancer (including small-cell lung cancer (SCLC), non-small cell lung cancer (NSCLC), adenocarcinoma of the lung, and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer (e.g., HCC), hepatoma, breast cancer (including metastatic breast cancer), bladder cancer, colon cancer, rectal cancer, colorectal cancer, endometrial or uterine carcinoma, salivary gland carcinoma, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, head and neck cancer, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), abnormal vascular proliferation associated with phakomatoses, edema (such as that associated with brain tumors), or Meigs' syndrome. In some embodiments, the cancer is a kidney cancer (e.g., RCC), a lung cancer (e.g., NSCLC), a bladder cancer (e.g., UBC), a liver cancer (e.g., HCC), an ovarian cancer, or a breast cancer (e.g., TNBC). In preferred embodiments, the patient has a kidney cancer (e.g., RCC, e.g., advanced RCC or mRCC, e.g., previously untreated advanced RCC or mRCC). The patient may optionally have an advanced, refractory, recurrent, chemotherapy-resistant, and/or platinum-resistant form of the cancer.

In certain embodiments, the presence and/or expression levels/amount of a biomarker in a first sample is increased or elevated as compared to presence/absence and/or expression levels/amount in a second sample. In certain embodiments, the presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue.

In certain embodiments, a reference sample, reference cell, reference tissue, control sample, control cell, or control tissue is a single sample or combined multiple samples from the same patient or individual that are obtained at one or more different time points than when the test sample is obtained. For example, a reference sample, reference cell, reference tissue, control sample, control cell, or control tissue is obtained at an earlier time point from the same patient or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the patient. In certain embodiments, a reference sample, reference cell, reference tissue, control sample, control cell, or control tissue is a combined multiple samples from one or more individuals with a disease or disorder (e.g., cancer) who are not the patient or individual. In certain embodiments, a reference sample, reference cell, reference tissue, control sample, control cell, or control tissue is pooled RNA samples from normal tissues or pooled plasma or serum samples from one or more individuals who are not the patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

In some embodiments of any of the preceding methods, an expression level above a reference level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference level, reference sample, reference cell, reference tissue, control sample, control cell, or control tissue. In certain embodiments, the elevated expression or number refers to the increase in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2 CXCR1, CXCR2, S100A8, and/or S100A9) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference level, reference sample, reference cell, reference tissue, control sample, control cell, or control tissue. In some embodiments, elevated expression or number refers to an overall increase in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2 CXCR1, CXCR2, S100A8, and/or S100A9) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference level, reference sample, reference cell, reference tissue, control sample, control cell, control tissue, or internal control (e.g., housekeeping gene).

In some embodiments of any of the preceding methods, an expression level below a reference level, or a reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference level, reference sample, reference cell, reference tissue, control sample, control cell, or control tissue. In certain embodiments, reduced expression or number refers to the decrease in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference level, reference sample, reference cell, reference tissue, control sample, control cell, or control tissue. In some embodiments, reduced (decreased) expression or number refers to an overall decrease in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5- fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference level, reference sample, reference cell, reference tissue, control sample, control cell, control tissue, or internal control (e.g., housekeeping gene).

III. Therapeuctic Methods and Uses

Provided herein are methods for treating an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., a TNBC)). In particular embodiments, the cancer is a kidney cancer, such as RCC, e.g., advanced RCC or mRCC, e.g., previously untreated advanced RCC or mRCC. In some instances, the methods of the invention include administering to the individual an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) based on the expression level of a biomarker of the invention. In other embodiments, the methods of the invention include administering to the individual an anti-cancer therapy that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). Any of the VEGF antagonists, PD-L1 axis binding antagonists, angiogenesis inhibitors (e.g., multi-targeted tyrosine kinase inhibitors), or other anti-cancer agents described herein (e.g., as described below in Section IV and/or the Examples) or known in the art may be used in the methods. The invention further relates to methods for improving progression-free survival (PFS) and/or overall survival (OS) of a patient suffering from a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., a TNBC)) by administration of an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)). The invention further relates to methods for improving progression-free survival (PFS) and/or overall survival (OS) of a patient suffering from a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., a TNBC)) by administration of an anti-cancer therapy that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). The expression level or number of any of the biomarkers described herein may be determined using any method known in the art and/or described herein, for example, in Section II above and/or in the working Examples.

Provided herein is a method of treating an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) that includes (a) determining the expression level of one or more of the genes set forth in Table 1 in a sample from the individual, wherein the expression level of one or more of the genes set forth in Table 1 is determined to be changed relative to a reference level; and (b) administering an effective amount of an anti-cancer therapy (e.g., an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)), or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))) to the individual based on the expression level of the one or more genes determined in step (a). In some instances, the change is an increase. In other instances, the change is a decrease.

Also provided herein is a method of treating an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) that includes administering an effective amount of an anti-cancer therapy (e.g., an anti-cancer therapy comprising a VEGF antagonist and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)), or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))) to the individual, wherein the expression level of one or more of the genes set forth in Table 1 in a sample from the individual has been determined to be changed relative to a reference level, wherein a change in the expression level of one or more of the genes set forth in Table 1 identifies the individual as one who may benefit from treatment with an anti-cancer therapy. In some instances, the change is an increase. In other instances, the change is a decrease.

In another aspect, provided herein is a method of treating an individual having a cancer (e.g., a kidney cancer (e.g., RCC), a lung cancer (e.g., NSCLC), a bladder cancer (e.g., UBC), a liver cancer (e.g., hepatocellular carcinoma (HCC)), an ovarian cancer, or a breast cancer (e.g., TNBC)) that includes (a) determining the expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9, wherein (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more genes; or (ii) the expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample is determined to be below a reference expression level of the one or more genes; and (b) administering an effective amount of an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)) to the individual based on the expression level of the one or more genes determined in step (a).

Any of the preceding methods may include determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2. In some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2.

For example, any of the preceding methods may include determining the expression level of one or more (e.g., 1, 2, 3, 4, or 5) of CD8A, EOMES, PRF1, IFNG, or PD-L1. In some embodiments, the method includes determining the expression level of at least two, at least three, at least four, or all five of CD8A, EOMES, PRF1, IFNG, and PD-L1. In some embodiments, the method includes determining the expression level of two of CD8A, EOMES, PRF1, IFNG, and PD-L1, for example, any of the exemplary combinations shown in Table 2. In some embodiments, the method includes determining the expression level of three of CD8A, EOMES, PRF1, IFNG, and PD-L1, for example, any of the exemplary combinations shown in Table 3. In some embodiments, the method includes determining the expression level of four of CD8A, EOMES, PRF1, IFNG, and PD-L1, for example, any of the exemplary combinations shown in Table 4. In some embodiments, the method involves determining the expression level of CD8A, EOMES, PRF1, IFNG, and PD-L1.

In some embodiments, any of the preceding methods may include determining the expression level of PD-L1 and one or more additional genes, wherein the one or more additional genes is other than PD-L1. For example, in some embodiments, the method may include determining the expression level of PD-L1 and one or more additional genes (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) selected from the group consisting of: CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and S100A9. In some embodiments, the method includes determining the expression level of PD-L1 and one or more (e.g., 1, 2, 3, 4, 5, 6, 7, 8, 9, 10, 11, 12, 13, 14, 15, 16, 17, 18, or 19) additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, and TAP2. In other embodiments, the method includes determining the expression level of PD-L1 and one or more (e.g., 1, 2, 3, 4, 5, 6, or 7) of VEGFA, KDR, ESM1, PECAM1, FLT1, ANGPTL4, or CD34. In other embodiments, the method includes determining the expression level of PD-L1 and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9.

Any of the preceding methods may include determining the expression level of one or more (e.g., 1, 2, 3, 4, 5, 6, or 7) of VEGFA, KDR, ESM1, PECAM1, FLT1, ANGPTL4, or CD34. In some embodiments, the method includes determining the expression level of at least two, at least three, at least four, at least five, at least six, or all seven of VEGFA, KDR, ESM1, PECAM1, FLT1, ANGPTL4, or CD34. For example, in some embodiments, the method includes determining the expression level of one or more of VEGFA, KDR, ESM1, PECAM1, ANGPTL4, or CD34. In some embodiments, the method includes determining the expression level of at least two, at least three, at least four, at least five, or all six of VEGFA, KDR, ESM1, PECAM1, ANGPTL4, and CD34. In some embodiments, the method includes determining the expression level of two of VEGFA, KDR, ESM1, PECAM1, ANGPTL4, and CD34, for example, any of the exemplary combinations shown in Table 5. In some embodiments, the method includes determining the expression level of three of VEGFA, KDR, ESM1, PECAM1, ANGPTL4, and CD34, for example, any of the exemplary combinations shown in Table 6. In some embodiments, the method includes determining the expression level of four of VEGFA, KDR, ESM1, PECAM1, ANGPTL4, and CD34, for example, any of the exemplary combinations shown in Table 7. In some embodiments, the method includes determining the expression level of five of VEGFA, KDR, ESM1, PECAM1, ANGPTL4, and CD34, for example, any of the exemplary combinations shown in Table 8. In some embodiments, the method includes determining the expression level of VEGFA, KDR, ESM1, PECAM1, ANGPTL4, and CD34.

Any of the preceding methods may include determining the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. In some embodiments, the method includes determining the expression level of at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9. In some embodiments, the method includes determining the expression level of two of IL6, CXCL1, CXCL2, CXCL3, CXCL8, PTGS2, CXCR1, CXCR2, S100A8, and S100A9, for example, any of the exemplary combinations shown in Table 9. In some embodiments, the method includes determining the expression level of three of IL6, CXCL1, CXCL2, CXCL3, CXCL8, PTGS2, CXCR1, CXCR2, S100A8, and S100A9, for example, any of the exemplary combinations shown in Table 10. In some embodiments, the method includes determining the expression level of four of IL6, CXCL1, CXCL2, CXCL3, CXCL8, PTGS2, CXCR1, CXCR2, S100A8, and S100A9, for example, any of the exemplary combinations shown in Table 11. In some embodiments, the method includes determining the expression level of five of IL6, CXCL1, CXCL2, CXCL3, CXCL8, PTGS2, CXCR1, CXCR2, S100A8, and S100A9, for example, any of the exemplary combinations shown in Table 12. In some embodiments, the method includes determining the expression level of six of IL6, CXCL1, CXCL2, CXCL3, CXCL8, PTGS2, CXCR1, CXCR2, S100A8, and S100A9, for example, any of the exemplary combinations shown in Table 13. In some embodiments, the method includes determining the expression level of seven of IL6, CXCL1, CXCL2, CXCL3, CXCL8, PTGS2, CXCR1, CXCR2, S100A8, and S100A9, for example, any of the exemplary combinations shown in Table 14. In some embodiments, the method includes determining the expression level of eight of IL6, CXCL1, CXCL2, CXCL3, CXCL8, PTGS2, CXCR1, CXCR2, S100A8, and S100A9, for example, any of the exemplary combinations shown in Table 15. In some embodiments, the method includes determining the expression level of nine of IL6, CXCL1, CXCL2, CXCL3, CXCL8, PTGS2, CXCR1, CXCR2, S100A8, and S100A9, for example, any of the exemplary combinations shown in Table 16. In some embodiments, the method includes determining the expression level of IL6, CXCL1, CXCL2, CXCL3, CXCL8, PTGS2, CXCR1, CXCR2, S100A8, and S100A9.

In any of the preceding methods, the method may include determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2, and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. For example, in some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2, and at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9.

For example, any of the preceding methods may include determining the expression level of one or more (e.g., 1, 2, 3, 4, or 5) of CD8A, EOMES, PRF1, IFNG, or PD-L1, and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. In some embodiments, the method includes determining the expression level of at least two, at least three, at least four, or all five of CD8A, EOMES, PRF1, IFNG, and PD-L1, and at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9. In some embodiments, the method comprises determining the expression level of any one of the combinations set forth in Tables 2-4 and any one of the combinations set forth in Tables 9-16. For example, in some embodiments, the method includes determining the expression level of two of CD8A, EOMES, PRF1, IFNG, and PD-L1, for example, any of the exemplary combinations shown in Table 2, and two of IL6, CXCL1, CXCL2, CXCL3, CXCL8, PTGS2, CXCR1, CXCR2, S100A8, and S100A9, for example, any of the exemplary combinations shown in Table 9. In some embodiments, the method includes determining the expression level of three of CD8A, EOMES, PRF1, IFNG, and PD-L1, for example, any of the exemplary combinations shown in Table 3, and three of IL6, CXCL1, CXCL2, CXCL3, CXCL8, PTGS2, CXCR1, CXCR2, S100A8, and S100A9, for example, any of the exemplary combinations shown in Table 10. In some embodiments, the method includes determining the expression level of four of CD8A, EOMES, PRF1, IFNG, and PD-L1, for example, any of the exemplary combinations shown in Table 4, and four of IL6, CXCL1, CXCL2, CXCL3, CXCL8, PTGS2, CXCR1, CXCR2, S100A8, and S100A9, for example, any of the exemplary combinations shown in Table 11. In some embodiments, the method involves determining the expression level of CD8A, EOMES, PRF1, IFNG, and PD-L1, and five of IL6, CXCL1, CXCL2, CXCL3, CXCL8, PTGS2, CXCR1, CXCR2, S100A8, and S100A9, for example, any of the exemplary combinations shown in Table 12. In some embodiments, the method involves determining the expression level of CD8A, EOMES, PRF1, IFNG, and PD-L1, and six of IL6, CXCL1, CXCL2, CXCL3, CXCL8, PTGS2, CXCR1, CXCR2, S100A8, and S100A9, for example, any of the exemplary combinations shown in Table 13. In some embodiments, the method involves determining the expression level of CD8A, EOMES, PRF1, IFNG, and PD-L1, and seven of IL6, CXCL1, CXCL2, CXCL3, CXCL8, PTGS2, CXCR1, CXCR2, S100A8, and S100A9, for example, any of the exemplary combinations shown in Table 14. In some embodiments, the method involves determining the expression level of CD8A, EOMES, PRF1, IFNG, and PD-L1, and eight of IL6, CXCL1, CXCL2, CXCL3, CXCL8, PTGS2, CXCR1, CXCR2, S100A8, and S100A9, for example, any of the exemplary combinations shown in Table 15. In some embodiments, the method involves determining the expression level of CD8A, EOMES, PRF1, IFNG, and PD-L1, and nine of IL6, CXCL1, CXCL2, CXCL3, CXCL8, PTGS2, CXCR1, CXCR2, S100A8, and S100A9, for example, any of the exemplary combinations shown in Table 16. In some embodiments, the method involves determining the expression level of CD8A, EOMES, PRF1, IFNG, PD-L1, IL6, CXCL1, CXCL2, CXCL3, CXCL8, PTGS2, CXCR1, CXCR2, S100A8, and S100A9.

In other embodiments, in any of the preceding methods, the method may include determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2, and one or more (e.g., 1, 2, 3, 4, 5, 6, or 7) of VEGFA, KDR, ESM1, PECAM1, FLT1, ANGPTL4, or CD34. For example, in some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2, and at least two, at least three, at least four, at least five, at least six, or all seven of VEGFA, KDR, ESM1, PECAM1, FLT1, ANGPTL4, or CD34.

For example, any of the preceding methods may include determining the expression level of one or more (e.g., 1, 2, 3, 4, or 5) of CD8A, EOMES, PRF1, IFNG, or PD-L1, and one or more (e.g., 1, 2, 3, 4, 5, or 6) of VEGFA, KDR, ESM1, PECAM1, ANGPTL4, or CD34. In some embodiments, the method includes determining the expression level of at least two, at least three, at least four, or all five of CD8A, EOMES, PRF1, IFNG, and PD-L1, and at least one, at least two, at least three, at least four, at least five, or all six of VEGFA, KDR, ESM1, PECAM1, ANGPTL4, and CD34. In some embodiments, the method comprises determining the expression level of any one of the combinations set forth in Tables 2-4 and any one of the combinations set forth in Tables 5-8. For example, in some embodiments, the method includes determining the expression level of two of CD8A, EOMES, PRF1, IFNG, and PD-L1, for example, any of the exemplary combinations shown in Table 2, and two of VEGFA, KDR, ESM1, PECAM1, ANGPTL4, and CD34, for example, any of the exemplary combinations shown in Table 5. In some embodiments, the method includes determining the expression level of three of CD8A, EOMES, PRF1, IFNG, and PD-L1, for example, any of the exemplary combinations shown in Table 3, and three of three of VEGFA, KDR, ESM1, PECAM1, ANGPTL4, and CD34, for example, any of the exemplary combinations shown in Table 6. In some embodiments, the method includes determining the expression level of four of CD8A, EOMES, PRF1, IFNG, and PD-L1, for example, any of the exemplary combinations shown in Table 4, and four of VEGFA, KDR, ESM1, PECAM1, ANGPTL4, and CD34, for example, any of the exemplary combinations shown in Table 7. In some embodiments, the method involves determining the expression level of CD8A, EOMES, PRF1, IFNG, and PD-L1, and five of VEGFA, KDR, ESM1, PECAM1, ANGPTL4, and CD34, for example, any of the exemplary combinations shown in Table 8. In some embodiments, the method involves determining the expression level of CD8A, EOMES, PRF1, IFNG, PD-L1, VEGFA, KDR, ESM1, PECAM1, ANGPTL4, and CD34.

In a further embodiment, in any of the preceding methods, the method may include determining the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9, and one or more (e.g., 1, 2, 3, 4, 5, 6, or 7) of VEGFA, KDR, ESM1, PECAM1, FLT1, ANGPTL4, or CD34. For example, in some embodiments, the method includes determining the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9, and at least two, at least three, at least four, at least five, at least six, or all seven of VEGFA, KDR, ESM1, PECAM1, FLT1, ANGPTL4, or CD34.

For example, any of the preceding methods may include determining the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9, and one or more (e.g., 1, 2, 3, 4, 5, or 6) of VEGFA, KDR, ESM1, PECAM1, ANGPTL4, or CD34. In some embodiments, the method includes determining the expression level of at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9, and at least two, at least three, at least four, at least five, or all six of VEGFA, KDR, ESM1, PECAM1, ANGPTL4, and CD34. In some embodiments, the method comprises determining the expression level of any one of the combinations set forth in Tables 9-16 and any one of the combinations set forth in Tables 5-8. For example, in some embodiments, the method includes determining the expression level of two of IL6, CXCL1, CXCL2, CXCL3, CXCL8, PTGS2, CXCR1, CXCR2, S100A8, and S100A9, for example, any of the exemplary combinations shown in Table 9, and two of VEGFA, KDR, ESM1, PECAM1, ANGPTL4, and CD34, for example, any of the exemplary combinations shown in Table 5. In some embodiments, the method includes determining the expression level of three of IL6, CXCL1, CXCL2, CXCL3, CXCL8, PTGS2, CXCR1, CXCR2, S100A8, and S100A9, for example, any of the exemplary combinations shown in Table 10, and three of VEGFA, KDR, ESM1, PECAM1, ANGPTL4, and CD34, for example, any of the exemplary combinations shown in Table 6. In some embodiments, the method includes determining the expression level of four of IL6, CXCL1, CXCL2, CXCL3, CXCL8, PTGS2, CXCR1, CXCR2, S100A8, and S100A9 for example, any of the exemplary combinations shown in Table 11, and four of VEGFA, KDR, ESM1, PECAM1, ANGPTL4, and CD34, for example, any of the exemplary combinations shown in Table 7. In some embodiments, the method involves determining the expression level of five of IL6, CXCL1, CXCL2, CXCL3, CXCL8, PTGS2, CXCR1, CXCR2, S100A8, and S100A9, for example, any of the exemplary combinations shown in Table 12, and five of VEGFA, KDR, ESM1, PECAM1, ANGPTL4, and CD34, for example, any of the exemplary combinations shown in Table 8. In some embodiments, the method involves determining the expression level of six of IL6, CXCL1, CXCL2, CXCL3, CXCL8, PTGS2, CXCR1, CXCR2, S100A8, and S100A9, for example, any of the exemplary combinations shown in Table 13, and and at least two, at least three, at least four, at least five, or all six of VEGFA, KDR, ESM1, PECAM1, ANGPTL4, and CD34. In some embodiments, the method involves determining the expression level of seven of IL6, CXCL1, CXCL2, CXCL3, CXCL8, PTGS2, CXCR1, CXCR2, S100A8, and S100A9, for example, any of the exemplary combinations shown in Table 14, and and at least two, at least three, at least four, at least five, or all six of VEGFA, KDR, ESM1, PECAM1, ANGPTL4, and CD34. In some embodiments, the method involves determining the expression level of eight of IL6, CXCL1, CXCL2, CXCL3, CXCL8, PTGS2, CXCR1, CXCR2, S100A8, and S100A9, for example, any of the exemplary combinations shown in Table 15, and and at least two, at least three, at least four, at least five, or all six of VEGFA, KDR, ESM1, PECAM1, ANGPTL4, and CD34. In some embodiments, the method involves determining the expression level of nine of IL6, CXCL1, CXCL2, CXCL3, CXCL8, PTGS2, CXCR1, CXCR2, S100A8, and S100A9, for example, any of the exemplary combinations shown in Table 16, and and at least two, at least three, at least four, at least five, or all six of VEGFA, KDR, ESM1, PECAM1, ANGPTL4, and CD34. In some embodiments, the method involves determining the expression level of IL6, CXCL1, CXCL2, CXCL3, CXCL8, PTGS2, CXCR1, CXCR2, S100A8, S100A9, VEGFA, KDR, ESM1, PECAM1, ANGPTL4, and CD34.

In some embodiments of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 is determined to be at or above a reference expression level of the one or more genes. In some instances, the expression level of one or more (e.g., 1, 2, 3, 4, or 5) of CD8A, EOMES, PRF1, IFNG, or PD-L1 in the sample is determined to be at or above a reference expression level of the one or more genes. In some embodiments, the expression level of one or more of the exemplary combinations set forth in Tables 2-4 in the sample is determined to be at or above a reference expression level of the one or more genes. In some embodiments, the expression level of CD8A, EOMES, PRF1, IFNG, and PD-L1 in the sample is determined to be at or above a reference expression level of CD8A, EOMES, PRF1, IFNG, and PD-L1.

In some embodiments of any of the preceding methods, the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 in the sample is determined to be at or above a reference expression level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is determined to be at or above a reference expression level of the one or more genes. In some embodiments, the expression level of one or more of the exemplary combinations set forth in Tables 9-16 in the sample is determined to be at or above a reference expression level of the one or more genes. In some embodiments, the expression level of IL6, CXCL1, CXCL2, CXCL3, CXCL8, PTGS2, CXCR1, CXCR2, S100A8, and S100A9 in the sample is determined to be at or above a reference expression level of IL6, CXCL1, CXCL2, CXCL3, CXCL8, PTGS2, CXCR1, CXCR2, S100A8, and S100A9.

In some embodiments of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is determined to be at or above a reference expression level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 is determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is determined to be at or above a reference expression level of the one or more genes.

For example, in some embodiments, the expression level of one or more (e.g., 1, 2, 3, 4, or 5) of CD8A, EOMES, PRF1, IFNG, or PD-L1 is determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is determined to be at or above a reference expression level of the one or more genes. In some embodiments, the expression level of at least two, at least three, at least four, or all five of CD8A, EOMES, PRF1, IFNG, and PD-L1 is determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is determined to be at or above a reference expression level of the one or more genes. In some embodiments, the expression level of any one of the combinations set forth in Tables 2-4 is determined to be at or above a reference expression level of the one or more genes and the expression level of any one of the combinations set forth in Tables 9-16 is determined to be at or above a reference expression level of the one or more genes. For example, in some embodiments, the expression level of two of CD8A, EOMES, PRF1, IFNG, and PD-L1, for example, any of the exemplary combinations shown in Table 2, is determined to be at or above a reference expression level of the one or more genes, and the expression level of two of IL6, CXCL1, CXCL2, CXCL3, CXCL8, PTGS2, CXCR1, CXCR2, S100A8, and S100A9, for example, any of the exemplary combinations shown in Table 9, is determined to be at or above a reference expression level of the one or more genes. In some embodiments, the expression level of three of CD8A, EOMES, PRF1, IFNG, and PD-L1, for example, any of the exemplary combinations shown in Table 3, is determined to be at or above a reference expression level of the one or more genes, and the expression level of three of IL6, CXCL1, CXCL2, CXCL3, CXCL8, PTGS2, CXCR1, CXCR2, S100A8, and S100A9, for example, any of the exemplary combinations shown in Table 10, is determined to be at or above a reference expression level of the one or more genes. In some embodiments, the expression level of four of CD8A, EOMES, PRF1, IFNG, and PD-L1, for example, any of the exemplary combinations shown in Table 4, is determined to be at or above a reference expression level of the one or more genes, and the expression level of four of IL6, CXCL1, CXCL2, CXCL3, CXCL8, PTGS2, CXCR1, CXCR2, S100A8, and S100A9, for example, any of the exemplary combinations shown in Table 11, is determined to be at or above a reference expression level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of five of IL6, CXCL1, CXCL2, CXCL3, CXCL8, PTGS2, CXCR1, CXCR2, S100A8, and S100A9, for example, any of the exemplary combinations shown in Table 12, is determined to be at or above a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of six of IL6, CXCL1, CXCL2, CXCL3, CXCL8, PTGS2, CXCR1, CXCR2, S100A8, and S100A9, for example, any of the exemplary combinations shown in Table 13, is determined to be at or above a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of seven of IL6, CXCL1, CXCL2, CXCL3, CXCL8, PTGS2, CXCR1, CXCR2, S100A8, and S100A9, for example, any of the exemplary combinations shown in Table 14, is determined to be at or above a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of eight of IL6, CXCL1, CXCL2, CXCL3, CXCL8, PTGS2, CXCR1, CXCR2, S100A8, and S100A9, for example, any of the exemplary combinations shown in Table 15, is determined to be at or above a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of nine of IL6, CXCL1, CXCL2, CXCL3, CXCL8, PTGS2, CXCR1, CXCR2, S100A8, and S100A9, for example, any of the exemplary combinations shown in Table 16, is determined to be at or above a reference level of the one or more genes. In some embodiments, the expression level of CD8A, EOMES, PRF1, IFNG, PD-L1, IL6, CXCL1, CXCL2, CXCL3, CXCL8, PTGS2, CXCR1, CXCR2, S100A8, and S100A9 is determined to be at or above a reference expression level of CD8A, EOMES, PRF1, IFNG, PD-L1, IL6, CXCL1, CXCL2, CXCL3, CXCL8, PTGS2, CXCR1, CXCR2, S100A8, and S100A9.

In some embodiments of any of the preceding methods, the expression level of PD-L1 in the sample is determined to be at or above a reference expression level of PD-L1, and the expression level of one or more (e.g., 1, 2, 3, 4, 5, 6, 7, 8, 9, 10, 11, 12, 13, 14, 15, 16, 17, 18, or 19) additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more additional genes.

In some embodiments of any of the preceding methods, the expression level of one or more (e.g., 1, 2, 3, 4, 5, 6, or 7) of VEGFA, KDR, ESM1, PECAM1, FLT1, ANGPTL4, or CD34 in the sample is determined to be below a reference level of the one or more genes. For example, in some embodiments, the expression level of at least one, at least two, at least three, at least four, at least five, at least six, or all seven of VEGFA, KDR, ESM1, PECAM1, FLT1, ANGPTL4, or CD34 in the sample is determined to be below a reference level of the one or more genes. In some embodiments, the expression level of one or more of the exemplary combinations set forth in Tables 5-8 in the sample is determined to be below a reference expression level of the one or more genes. In some embodiments, the expression level of one or more of VEGFA, KDR, ESM1, PECAM1, ANGPTL4, or CD34 in the sample is determined to be below a reference level of the one or more genes. For example, in some embodiments, the expression level of VEGFA, KDR, ESM1, PECAM1, ANGPTL4, and CD34 in the sample is determined to be below a reference level of VEGFA, KDR, ESM1, PECAM1, ANGPTL4, and CD34.

In other embodiments, in any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 is determined to be at or above a reference level of the one or more genes, and the expression level of one or more (e.g., 1, 2, 3, 4, 5, 6, or 7) of VEGFA, KDR, ESM1, PECAM1, FLT1, ANGPTL4, or CD34 is determined to be below a reference level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 is determined to be at or above a reference level of the one or more genes, and the expression level of at least two, at least three, at least four, at least five, at least six, or all seven of VEGFA, KDR, ESM1, PECAM1, FLT1, ANGPTL4, or CD34 is determined to be below a reference level of the one or more genes.

For example, in some embodiments, the expression level of one or more (e.g., 1, 2, 3, 4, or 5) of CD8A, EOMES, PRF1, IFNG, or PD-L1 is determined to be at or above a reference level of the one or more genes, and the expression level of one or more (e.g., 1, 2, 3, 4, 5, or 6) of VEGFA, KDR, ESM1, PECAM1, ANGPTL4, or CD34 is determined to be below a reference level of the one or more genes. In some embodiments, the expression level of at least two, at least three, at least four, or all five of CD8A, EOMES, PRF1, IFNG, and PD-L1 is determined to be at or above a reference level of the one or more genes, and the expression level of at least one, at least two, at least three, at least four, at least five, or all six of VEGFA, KDR, ESM1, PECAM1, ANGPTL4, and CD34 is determined to be below a reference level fo the one or more genes. In some embodiments, the expression level of any one of the combinations set forth in Tables 2-4 is determined to be at or above a reference level of the one or more genes, and the expression level of any one of the combinations set forth in Tables 5-8 is determined to be below a reference level of the one or more genes. For example, in some embodiments, the expression level of two of CD8A, EOMES, PRF1, IFNG, and PD-L1, for example, any of the exemplary combinations shown in Table 2, is determined to be at or above a reference level of the one or more genes, and the expression level of two of VEGFA, KDR, ESM1, PECAM1, ANGPTL4, and CD34, for example, any of the exemplary combinations shown in Table 5, is determined to be below a reference level of the one or more genes. In some embodiments, the expression level of three of CD8A, EOMES, PRF1, IFNG, and PD-L1, for example, any of the exemplary combinations shown in Table 3, is determined to be at or above a reference level of the one or more genes, and the expression level of three of three of VEGFA, KDR, ESM1, PECAM1, ANGPTL4, and CD34, for example, any of the exemplary combinations shown in Table 6, is determined to be below a reference level of the one or more genes. In some embodiments, the expression level of four of CD8A, EOMES, PRF1, IFNG, and PD-L1, for example, any of the exemplary combinations shown in Table 4, is determined to be at or above a reference level of the one or more genes, and the expression level of four of VEGFA, KDR, ESM1, PECAM1, ANGPTL4, and CD34, for example, any of the exemplary combinations shown in Table 7, is determined to be below a reference level of the one or more genes. In some embodiments, the expression level of CD8A, EOMES, PRF1, IFNG, and PD-L1 is determined to be at or above a reference level of CD8A, EOMES, PRF1, IFNG, and PD-L1, and the expression level of five of VEGFA, KDR, ESM1, PECAM1, ANGPTL4, and CD34, for example, any of the exemplary combinations shown in Table 8, is determined to be below a reference level of the one or more genes. In some embodiments, the expression level of CD8A, EOMES, PRF1, IFNG, and PD-L1 is determined to be at or above a reference level of CD8A, EOMES, PRF1, IFNG, and PD-L1, and the expression level of VEGFA, KDR, ESM1, PECAM1, ANGPTL4, and CD34 is determined to be below a reference level of VEGFA, KDR, ESM1, PECAM1, ANGPTL4, and CD34.

In some embodiments of any of the preceding methods, the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 in the sample is determined to be below a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample is determined to be below a reference level of the one or more genes. For example, in some embodiments, the expression level of one or more of the exemplary combinations set forth in Tables 9-16 in the sample is determined to be below a reference expression level of the one or more genes. In some embodiments, the expression level of IL6, CXCL1, CXCL2, CXCL3, CXCL8, PTGS2, CXCR1, CXCR2, S100A8, and S100A9 in the sample is determined to be below a reference level of IL6, CXCL1, CXCL2, CXCL3, CXCL8, PTGS2, CXCR1, CXCR2, S100A8, and S100A9.

In another aspect, provided herein is a method of treating an individual having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) that includes (a) determining the expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; or IL6, CXCL1, CXCL2, CXCL3, CXCL8, PTGS2, CXCR1, CXCR2, S100A8, or S100A9, wherein (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more genes; and (ii) the expression level of one or more of IL6, CXCL1, CXCL2, CXCL3, CXCL8, PTGS2, CXCR1, CXCR2, S100A8, or S100A9 in the sample is determined to be below a reference expression level of the one or more genes; and (b) administering an effective amount of a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)) monotherapy to the individual based on the expression level of the one or more genes determined in step (a).

In any of the preceding methods, the method may include determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2, and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. For example, in some embodiments, the method includes determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2, and at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9.

For example, any of the preceding methods may include determining the expression level of one or more (e.g., 1, 2, 3, 4, or 5) of CD8A, EOMES, PRF1, IFNG, or PD-L1, and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. In some embodiments, the method includes determining the expression level of at least two, at least three, at least four, or all five of CD8A, EOMES, PRF1, IFNG, and PD-L1, and at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9. In some embodiments, the method comprises determining the expression level of any one of the combinations set forth in Tables 2-4 and any one of the combinations set forth in Tables 9-16. For example, in some embodiments, the method includes determining the expression level of two of CD8A, EOMES, PRF1, IFNG, and PD-L1, for example, any of the exemplary combinations shown in Table 2, and two of IL6, CXCL1, CXCL2, CXCL3, CXCL8, PTGS2, CXCR1, CXCR2, S100A8, and S100A9, for example, any of the exemplary combinations shown in Table 9. In some embodiments, the method includes determining the expression level of three of CD8A, EOMES, PRF1, IFNG, and PD-L1, for example, any of the exemplary combinations shown in Table 3, and three of IL6, CXCL1, CXCL2, CXCL3, CXCL8, PTGS2, CXCR1, CXCR2, S100A8, and S100A9, for example, any of the exemplary combinations shown in Table 10. In some embodiments, the method includes determining the expression level of four of CD8A, EOMES, PRF1, IFNG, and PD-L1, for example, any of the exemplary combinations shown in Table 4, and four of IL6, CXCL1, CXCL2, CXCL3, CXCL8, PTGS2, CXCR1, CXCR2, S100A8, and S100A9, for example, any of the exemplary combinations shown in Table 11. In some embodiments, the method involves determining the expression level of CD8A, EOMES, PRF1, IFNG, and PD-L1, and five of IL6, CXCL1, CXCL2, CXCL3, CXCL8, and PTGS2, for example, any of the exemplary combinations shown in Table 12. In some embodiments, the method involves determining the expression level of CD8A, EOMES, PRF1, IFNG, and PD-L1, and six of IL6, CXCL1, CXCL2, CXCL3, CXCL8, and PTGS2, for example, any of the exemplary combinations shown in Table 13. In some embodiments, the method involves determining the expression level of CD8A, EOMES, PRF1, IFNG, and PD-L1, and seven of IL6, CXCL1, CXCL2, CXCL3, CXCL8, and PTGS2, for example, any of the exemplary combinations shown in Table 14. In some embodiments, the method involves determining the expression level of CD8A, EOMES, PRF1, IFNG, and PD-L1, and eight of IL6, CXCL1, CXCL2, CXCL3, CXCL8, and PTGS2, for example, any of the exemplary combinations shown in Table 15. In some embodiments, the method involves determining the expression level of CD8A, EOMES, PRF1, IFNG, and PD-L1, and nine of IL6, CXCL1, CXCL2, CXCL3, CXCL8, and PTGS2, for example, any of the exemplary combinations shown in Table 16. In some embodiments, the method involves determining the expression level of CD8A, EOMES, PRF1, IFNG, PD-L1, IL6, CXCL1, CXCL2, CXCL3, CXCL8, PTGS2, CXCR1, CXCR2, S100A8, and S100A9.

In some of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample is determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is determined to be below a reference expression level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 is determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is determined to be below a reference expression level of the one or more genes.

For example, in some embodiments, the expression level of one or more (e.g., 1, 2, 3, 4, or 5) of CD8A, EOMES, PRF1, IFNG, or PD-L1 is determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 is determined to be below a reference expression level of the one or more genes. In some embodiments, the expression level of at least two, at least three, at least four, or all five of CD8A, EOMES, PRF1, IFNG, and PD-L1 is determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 is determined to be below a reference expression level of the one or more genes. In some embodiments, the expression level of any one of the combinations set forth in Tables 2-4 is determined to be at or above a reference expression level of the one or more genes and the expression level of any one of the combinations set forth in Tables 9-16 is determined to be below a reference expression level of the one or more genes. For example, in some embodiments, the expression level of two of CD8A, EOMES, PRF1, IFNG, and PD-L1, for example, any of the exemplary combinations shown in Table 2, is determined to be at or above a reference expression level of the one or more genes, and the expression level of two of IL6, CXCL1, CXCL2, CXCL3, CXCL8, PTGS2, CXCR1, CXCR2, S100A8, and S100A9, for example, any of the exemplary combinations shown in Table 9, is determined to be below a reference expression level of the one or more genes. In some embodiments, the expression level of three of CD8A, EOMES, PRF1, IFNG, and PD-L1, for example, any of the exemplary combinations shown in Table 3, is determined to be at or above a reference expression level of the one or more genes, and the expression level of three of IL6, CXCL1, CXCL2, CXCL3, CXCL8, PTGS2, CXCR1, CXCR2, S100A8, and S100A9, for example, any of the exemplary combinations shown in Table 10, is determined to be below a reference expression level of the one or more genes. In some embodiments, the expression level of four of CD8A, EOMES, PRF1, IFNG, and PD-L1, for example, any of the exemplary combinations shown in Table 4, is determined to be at or above a reference expression level of the one or more genes, and the expression level of four of IL6, CXCL1, CXCL2, CXCL3, CXCL8, PTGS2, CXCR1, CXCR2, S100A8, and S100A9, for example, any of the exemplary combinations shown in Table 11, is determined to be below a reference expression level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of five of IL6, CXCL1, CXCL2, CXCL3, CXCL8, PTGS2, CXCR1, CXCR2, S100A8, and S100A9, for example, any of the exemplary combinations shown in Table 12, is determined to be below a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of six of IL6, CXCL1, CXCL2, CXCL3, CXCL8, PTGS2, CXCR1, CXCR2, S100A8, and S100A9, for example, any of the exemplary combinations shown in Table 13, is determined to be below a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of seven of IL6, CXCL1, CXCL2, CXCL3, CXCL8, PTGS2, CXCR1, CXCR2, S100A8, and S100A9, for example, any of the exemplary combinations shown in Table 14, is determined to be below a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of eight of IL6, CXCL1, CXCL2, CXCL3, CXCL8, PTGS2, CXCR1, CXCR2, S100A8, and S100A9, for example, any of the exemplary combinations shown in Table 15, is determined to be below a reference level of the one or more genes. In some embodiments, the expression level of CD8A, EOMES, PRF1, IFNG, and PD-L1 is determined to be at or above a reference expression level of CD8A, EOMES, PRF1, IFNG, and PD-L1, and the expression level of nine of IL6, CXCL1, CXCL2, CXCL3, CXCL8, PTGS2, CXCR1, CXCR2, S100A8, and S100A9, for example, any of the exemplary combinations shown in Table 16, is determined to be below a reference level of the one or more genes. In some embodiments, the expression level of CD8A, EOMES, PRF1, IFNG, and PD-L1 is determined to be at or above a reference level of CD8A, EOMES, PRF1, IFNG, and PD-L1, and the expression level of IL6, CXCL1, CXCL2, CXCL3, CXCL8, PTGS2, CXCR1, CXCR2, S100A8, and S100A9 is determined to be below a reference expression level of IL6, CXCL1, CXCL2, CXCL3, CXCL8, PTGS2, CXCR1, CXCR2, S100A8, and S100A9.

In another aspect, provided herein is a method of treating an individual having (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)), the method including administering to the individual an effective amount of an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist, wherein (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more genes; or (ii) the expression level of one or more of VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9 in the sample has been determined to be below a reference expression level of the one or more genes. In some embodiments, the expression level of one or more of the genes has been determined prior to treatment with the anti-cancer therapy. In other embodiments, the expression level of one or more of the genes has been determined after treatment with the anti-cancer therapy.

In some embodiments of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 has been determined to be at or above a reference expression level of the one or more genes. In some instances, the expression level of one or more (e.g., 1, 2, 3, 4, or 5) of CD8A, EOMES, PRF1, IFNG, or PD-L1 in the sample has been determined to be at or above a reference expression level of the one or more genes. In some embodiments, the expression level of one or more of the exemplary combinations set forth in Tables 2-4 in the sample has been determined to be at or above a reference expression level of the one or more genes. In some embodiments, the expression level of CD8A, EOMES, PRF1, IFNG, and PD-L1 in the sample has been determined to be at or above a reference expression level of CD8A, EOMES, PRF1, IFNG, and PD-L1.

In some embodiments of any of the preceding methods, the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 in the sample has been determined to be at or above a reference expression level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample has been determined to be at or above a reference expression level of the one or more genes. In some embodiments, the expression level of one or more of the exemplary combinations set forth in Tables 9-16 in the sample has been determined to be at or above a reference expression level of the one or more genes. In some embodiments, the expression level of IL6, CXCL1, CXCL2, CXCL3, CXCL8, PTGS2, CXCR1, CXCR2, S100A8, and S100A9 in the sample has been determined to be at or above a reference expression level of IL6, CXCL1, CXCL2, CXCL3, CXCL8, PTGS2, CXCR1, CXCR2, S100A8, and S100A9.

In some embodiments of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 has been determined to be at or above a reference expression level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 has been determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 has been determined to be at or above a reference expression level of the one or more genes.

For example, in some embodiments, the expression level of one or more (e.g., 1, 2, 3, 4, or 5) of CD8A, EOMES, PRF1, IFNG, or PD-L1 has been determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 has been determined to be at or above a reference expression level of the one or more genes. In some embodiments, the expression level of at least two, at least three, at least four, or all five of CD8A, EOMES, PRF1, IFNG, and PD-L1 has been determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 has been determined to be at or above a reference expression level of the one or more genes. In some embodiments, the expression level of any one of the combinations set forth in Tables 2-4 has been determined to be at or above a reference expression level of the one or more genes and the expression level of any one of the combinations set forth in Tables 9-16 has been determined to be at or above a reference expression level of the one or more genes. For example, in some embodiments, the expression level of two of CD8A, EOMES, PRF1, IFNG, and PD-L1, for example, any of the exemplary combinations shown in Table 2, has been determined to be at or above a reference expression level of the one or more genes, and the expression level of two of IL6, CXCL1, CXCL2, CXCL3, CXCL8, PTGS2, CXCR1, CXCR2, S100A8, and S100A9, for example, any of the exemplary combinations shown in Table 9, has been determined to be at or above a reference expression level of the one or more genes. In some embodiments, the expression level of three of CD8A, EOMES, PRF1, IFNG, and PD-L1, for example, any of the exemplary combinations shown in Table 3, has been determined to be at or above a reference expression level of the one or more genes, and the expression level of three of IL6, CXCL1, CXCL2, CXCL3, CXCL8, PTGS2, CXCR1, CXCR2, S100A8, and S100A9, for example, any of the exemplary combinations shown in Table 10, has been determined to be at or above a reference expression level of the one or more genes. In some embodiments, the expression level of four of CD8A, EOMES, PRF1, IFNG, and PD-L1, for example, any of the exemplary combinations shown in Table 4, has been determined to be at or above a reference expression level of the one or more genes, and the expression level of four of IL6, CXCL1, CXCL2, CXCL3, CXCL8, PTGS2, CXCR1, CXCR2, S100A8, and S100A9, for example, any of the exemplary combinations shown in Table 11, has been determined to be at or above a reference expression level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of five of IL6, CXCL1, CXCL2, CXCL3, CXCL8, PTGS2, CXCR1, CXCR2, S100A8, and S100A9, for example, any of the exemplary combinations shown in Table 12, has been determined to be at or above a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of six of IL6, CXCL1, CXCL2, CXCL3, CXCL8, PTGS2, CXCR1, CXCR2, S100A8, and S100A9, for example, any of the exemplary combinations shown in Table 13, has been determined to be at or above a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of seven of IL6, CXCL1, CXCL2, CXCL3, CXCL8, PTGS2, CXCR1, CXCR2, S100A8, and S100A9, for example, any of the exemplary combinations shown in Table 14, has been determined to be at or above a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of eight of IL6, CXCL1, CXCL2, CXCL3, CXCL8, PTGS2, CXCR1, CXCR2, S100A8, and S100A9, for example, any of the exemplary combinations shown in Table 15, has been determined to be at or above a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of nine of IL6, CXCL1, CXCL2, CXCL3, CXCL8, PTGS2, CXCR1, CXCR2, S100A8, and S100A9, for example, any of the exemplary combinations shown in Table 16, has been determined to be at or above a reference expression level of the one or more genes. In some embodiments, the expression level of CD8A, EOMES, PRF1, IFNG, PD-L1, IL6, CXCL1, CXCL2, CXCL3, CXCL8, PTGS2, CXCR1, CXCR2, S100A8, and S100A9 has been determined to be at or above a reference expression level of CD8A, EOMES, PRF1, IFNG, PD-L1, IL6, CXCL1, CXCL2, CXCL3, CXCL8, PTGS2, CXCR1, CXCR2, S100A8, and S100A9.

In some embodiments of any of the preceding methods, the expression level of PD-L1 in the sample has been determined to be at or above a reference expression level of PD-L1, and the expression level of one or more (e.g., 1, 2, 3, 4, 5, 6, 7, 8, 9, 10, 11, 12, 13, 14, 15, 16, 17, 18, or 19) additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more additional genes.

In some embodiments of any of the preceding methods, the expression level of one or more (e.g., 1, 2, 3, 4, 5, 6, or 7) of VEGFA, KDR, ESM1, PECAM1, FLT1, ANGPTL4, or CD34 in the sample has been determined to be below a reference level of the one or more genes. For example, in some embodiments, the expression level of at least one, at least two, at least three, at least four, at least five, at least six, or all seven of VEGFA, KDR, ESM1, PECAM1, FLT1, ANGPTL4, or CD34 in the sample has been determined to be below a reference level of the one or more genes. In some embodiments, the expression level of one or more of the exemplary combinations set forth in Tables 5-8 in the sample has been determined to be below a reference expression level of the one or more genes. In some embodiments, the expression level of one or more of VEGFA, KDR, ESM1, PECAM1, ANGPTL4, or CD34 in the sample has been determined to be below a reference level of the one or more genes. For example, in some embodiments, the expression level of VEGFA, KDR, ESM1, PECAM1, ANGPTL4, and CD34 in the sample has been determined to be below a reference level of VEGFA, KDR, ESM1, PECAM1, ANGPTL4, and CD34.

In other embodiments, in any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 has been determined to be at or above a reference level of the one or more genes, and the expression level of one or more (e.g., 1, 2, 3, 4, 5, 6, or 7) of VEGFA, KDR, ESM1, PECAM1, FLT1, ANGPTL4, or CD34 has been determined to be below a reference level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 has been determined to be at or above a reference level of the one or more genes, and the expression level of at least two, at least three, at least four, at least five, at least six, or all seven of VEGFA, KDR, ESM1, PECAM1, FLT1, ANGPTL4, or CD34 has been determined to be below a reference level of the one or more genes.

For example, in some embodiments, the expression level of one or more (e.g., 1, 2, 3, 4, or 5) of CD8A, EOMES, PRF1, IFNG, or PD-L1 has been determined to be at or above a reference level of the one or more genes, and the expression level of one or more (e.g., 1, 2, 3, 4, 5, or 6) of VEGFA, KDR, ESM1, PECAM1, ANGPTL4, or CD34 has been determined to be below a reference level of the one or more genes. In some embodiments, the expression level of at least two, at least three, at least four, or all five of CD8A, EOMES, PRF1, IFNG, and PD-L1 has been determined to be at or above a reference level of the one or more genes, and the expression level of at least one, at least two, at least three, at least four, at least five, or all six of VEGFA, KDR, ESM1, PECAM1, ANGPTL4, and CD34 has been determined to be below a reference level fo the one or more genes. In some embodiments, the expression level of any one of the combinations set forth in Tables 2-4 has been determined to be at or above a reference level of the one or more genes, and the expression level of any one of the combinations set forth in Tables 5-8 has been determined to be below a reference level of the one or more genes. For example, in some embodiments, the expression level of two of CD8A, EOMES, PRF1, IFNG, and PD-L1, for example, any of the exemplary combinations shown in Table 2, has been determined to be at or above a reference level of the one or more genes, and the expression level of two of VEGFA, KDR, ESM1, PECAM1, ANGPTL4, and CD34, for example, any of the exemplary combinations shown in Table 5, has been determined to be below a reference level of the one or more genes. In some embodiments, the expression level of three of CD8A, EOMES, PRF1, IFNG, and PD-L1, for example, any of the exemplary combinations shown in Table 3, has been determined to be at or above a reference level of the one or more genes, and the expression level of three of three of VEGFA, KDR, ESM1, PECAM1, ANGPTL4, and CD34, for example, any of the exemplary combinations shown in Table 6, has been determined to be below a reference level of the one or more genes. In some embodiments, the expression level of four of CD8A, EOMES, PRF1, IFNG, and PD-L1, for example, any of the exemplary combinations shown in Table 4, has been determined to be at or above a reference level of the one or more genes, and the expression level of four of VEGFA, KDR, ESM1, PECAM1, ANGPTL4, and CD34, for example, any of the exemplary combinations shown in Table 7, has been determined to be below a reference level of the one or more genes. In some embodiments, the expression level of CD8A, EOMES, PRF1, IFNG, and PD-L1 has been determined to be at or above a reference level of CD8A, EOMES, PRF1, IFNG, and PD-L1, and the expression level of five of VEGFA, KDR, ESM1, PECAM1, ANGPTL4, and CD34, for example, any of the exemplary combinations shown in Table 8, has been determined to be below a reference level of the one or more genes. In some embodiments, the expression level of CD8A, EOMES, PRF1, IFNG, and PD-L1 has been determined to be at or above a reference level of CD8A, EOMES, PRF1, IFNG, and PD-L1, and the expression level of VEGFA, KDR, ESM1, PECAM1, ANGPTL4, and CD34 has been determined to be below a reference level of VEGFA, KDR, ESM1, PECAM1, ANGPTL4, and CD34.

In some embodiments of any of the preceding methods, the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 in the sample has been determined to be below a reference level of the one or more genes. In some embodiments, the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, or S100A9 in the sample has been determined to be below a reference level of the one or more genes. For example, in some embodiments, the expression level of one or more of the exemplary combinations set forth in Tables 9-16 in the sample has been determined to be below a reference expression level of the one or more genes. In some embodiments, the expression level of IL6, CXCL1, CXCL2, CXCL3, CXCL8, PTGS2, CXCR1, CXCR2, S100A8, and S100A9 in the sample has been determined to be below a reference level of IL6, CXCL1, CXCL2, CXCL3, CXCL8, PTGS2, CXCR1, CXCR2, S100A8, and S100A9.

In another aspect, provided herein is a method of treating an individual having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) that includes (a) determining the expression level of one or more (e.g., 1, 2, 3, 4, 5, 6, or 7) of the following genes in a sample from the individual: VEGFA, KDR, ESM1, PECAM1, FLT1, ANGPTL4, or CD34, wherein the expression level of one or more of VEGFA, KDR, ESM1, PECAM1, FLT1, ANGPTL4, or CD34 in the sample is determined to be at or above a reference expression level of the one or more genes; and (b) administering an effective amount of an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) to the individual based on the expression level of the one or more genes determined in step (a).

In some embodiments, the method includes determining the expression level of at least two, at least three, at least four, at least five, at least six, or all seven of VEGFA, KDR, ESM1, PECAM1, FLT1, ANGPTL4, or CD34. For example, in some embodiments, the method includes determining the expression level of one or more of VEGFA, KDR, ESM1, PECAM1, ANGPTL4, or CD34. In some embodiments, the method includes determining the expression level of at least two, at least three, at least four, at least five, or all six of VEGFA, KDR, ESM1, PECAM1, ANGPTL4, and CD34. In some embodiments, the method includes determining the expression level of two of VEGFA, KDR, ESM1, PECAM1, ANGPTL4, and CD34, for example, any of the exemplary combinations shown in Table 5. In some embodiments, the method includes determining the expression level of three of VEGFA, KDR, ESM1, PECAM1, ANGPTL4, and CD34, for example, any of the exemplary combinations shown in Table 6. In some embodiments, the method includes determining the expression level of four of VEGFA, KDR, ESM1, PECAM1, ANGPTL4, and CD34, for example, any of the exemplary combinations shown in Table 7. In some embodiments, the method includes determining the expression level of five of VEGFA, KDR, ESM1, PECAM1, ANGPTL4, and CD34, for example, any of the exemplary combinations shown in Table 8. In some embodiments, the method includes determining the expression level of VEGFA, KDR, ESM1, PECAM1, ANGPTL4, and CD34.

In some embodiments, the expression level of one or more (e.g., 1, 2, 3, 4, 5, 6, or 7) of VEGFA, KDR, ESM1, PECAM1, FLT1, ANGPTL4, or CD34 in the sample is determined to be at or above a reference level of the one or more genes. For example, in some embodiments, the expression level of at least one, at least two, at least three, at least four, at least five, at least six, or all seven of VEGFA, KDR, ESM1, PECAM1, FLT1, ANGPTL4, or CD34 in the sample is determined to be at or above a reference level of the one or more genes. In some embodiments, the expression level of one or more of the exemplary combinations set forth in Tables 5-8 in the sample is determined to be at or above a reference expression level of the one or more genes. In some embodiments, the expression level of one or more of VEGFA, KDR, ESM1, PECAM1, ANGPTL4, or CD34 in the sample is determined to be at or above a reference level of the one or more genes. For example, in some embodiments, the expression level of VEGFA, KDR, ESM1, PECAM1, ANGPTL4, and CD34 in the sample is determined to be at or above a reference level of VEGFA, KDR, ESM1, PECAM1, ANGPTL4, and CD34.

In another aspect, provided herein is a method of treating an individual having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) that includes administering to the individual an effective amount of an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))), wherein the expression level of one or more (e.g., 1, 2, 3, 4, 5, 6, or 7) of VEGFA, KDR, ESM1, PECAM1, FLT1, ANGPTL4, or CD34 in the sample has been determined to be at or above a reference expression level of the one or more genes.

In some embodiments, the expression level of one or more (e.g., 1, 2, 3, 4, 5, 6, or 7) of VEGFA, KDR, ESM1, PECAM1, FLT1, ANGPTL4, or CD34 in the sample has been determined to be at or above a reference level of the one or more genes. For example, in some embodiments, the expression level of at least one, at least two, at least three, at least four, at least five, at least six, or all seven of VEGFA, KDR, ESM1, PECAM1, FLT1, ANGPTL4, or CD34 in the sample has been determined to be at or above a reference level of the one or more genes. In some embodiments, the expression level of one or more of the exemplary combinations set forth in Tables 5-8 in the sample has been determined to be at or above a reference expression level of the one or more genes. In some embodiments, the expression level of one or more of VEGFA, KDR, ESM1, PECAM1, ANGPTL4, or CD34 in the sample has been determined to be at or above a reference level of the one or more genes. For example, in some embodiments, the expression level of VEGFA, KDR, ESM1, PECAM1, ANGPTL4, and CD34 in the sample has been determined to be at or above a reference level of VEGFA, KDR, ESM1, PECAM1, ANGPTL4, and CD34.

In another aspect, provided herein is a method of treating an individual having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)), the method including administering to the individual an effective amount of a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., an anti-PD-1 antibody)) monotherapy, wherein (i) the expression level of one or more of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more genes; or (ii) the expression level of one or more of IL6, CXCL1, CXCL2, CXCL3, CXCL8, PTGS2, CXCR1, CXCR2, S100A8, or S100A9 in the sample has been determined to be below a reference expression level of the one or more genes. In some embodiments, the expression level of one or more of the genes has been determined prior to treatment with the PD-L1 axis binding antagonist monotherapy. In other embodiments, the expression level of one or more of the genes has been determined after treatment with the PD-L1 axis binding antagonist monotherapy.

In some of any of the preceding methods, the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2 in the sample has been determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 has been determined to be below a reference expression level of the one or more genes. For example, in some embodiments, the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2 has been determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 has been determined to be below a reference expression level of the one or more genes.

For example, in some embodiments, the expression level of one or more (e.g., 1, 2, 3, 4, or 5) of CD8A, EOMES, PRF1, IFNG, or PD-L1 has been determined to be at or above a reference expression level of the one or more genes, and the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9 has been determined to be below a reference expression level of the one or more genes. In some embodiments, the expression level of at least two, at least three, at least four, or all five of CD8A, EOMES, PRF1, IFNG, and PD-L1 has been determined to be at or above a reference expression level of the one or more genes, and the expression level of at least one, at least two, at least three, at least four, at least five, at least six, at least seven, at least eight, at least nine, or all ten of IL6, CXCL1, CXCL2, CXCL3, CXCL8, PTGS2, CXCR1, CXCR2, S100A8, and S100A9 has been determined to be below a reference expression level of the one or more genes. In some embodiments, the expression level of any one of the combinations set forth in Tables 2-4 has been determined to be at or above a reference expression level of the one or more genes and the expression level of any one of the combinations set forth in Tables 9-12 has been determined to be below a reference expression level of the one or more genes. For example, in some embodiments, the expression level of two of CD8A, EOMES, PRF1, IFNG, and PD-L1, for example, any of the exemplary combinations shown in Table 2, has been determined to be at or above a reference expression level of the one or more genes, and the expression level of two of IL6, CXCL1, CXCL2, CXCL3, CXCL8, PTGS2, CXCR1, CXCR2, S100A8, and S100A9, for example, any of the exemplary combinations shown in Table 9, has been determined to be below a reference expression level of the one or more genes. In some embodiments, the expression level of three of CD8A, EOMES, PRF1, IFNG, and PD-L1, for example, any of the exemplary combinations shown in Table 3, has been determined to be at or above a reference expression level of the one or more genes, and the expression level of three of IL6, CXCL1, CXCL2, CXCL3, CXCL8, PTGS2, CXCR1, CXCR2, S100A8, and S100A9, for example, any of the exemplary combinations shown in Table 10, has been determined to be below a reference expression level of the one or more genes. In some embodiments, the expression level of four of CD8A, EOMES, PRF1, IFNG, and PD-L1, for example, any of the exemplary combinations shown in Table 4, has been determined to be at or above a reference expression level of the one or more genes, and the expression level of four of IL6, CXCL1, CXCL2, CXCL3, CXCL8, PTGS2, CXCR1, CXCR2, S100A8, and S100A9, for example, any of the exemplary combinations shown in Table 11, has been determined to be below a reference expression level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of five of IL6, CXCL1, CXCL2, CXCL3, CXCL8, PTGS2, CXCR1, CXCR2, S100A8, and S100A9, for example, any of the exemplary combinations shown in Table 12, has been determined to be below a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of six of IL6, CXCL1, CXCL2, CXCL3, CXCL8, PTGS2, CXCR1, CXCR2, S100A8, and S100A9, for example, any of the exemplary combinations shown in Table 13, has been determined to be below a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of seven of IL6, CXCL1, CXCL2, CXCL3, CXCL8, PTGS2, CXCR1, CXCR2, S100A8, and S100A9, for example, any of the exemplary combinations shown in Table 14, has been determined to be below a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of eight of IL6, CXCL1, CXCL2, CXCL3, CXCL8, PTGS2, CXCR1, CXCR2, S100A8, and S100A9, for example, any of the exemplary combinations shown in Table 15, has been determined to be below a reference level of the one or more genes. In some embodiments, the expression level of CD8A, EOMES, PRF1, IFNG, and PD-L1 has been determined to be at or above a reference expression level of CD8A, EOMES, PRF1, IFNG, and PD-L1, and the expression level of nine of IL6, CXCL1, CXCL2, CXCL3, CXCL8, PTGS2, CXCR1, CXCR2, S100A8, and S100A9, for example, any of the exemplary combinations shown in Table 16, has been determined to be below a reference level of the one or more genes. In some embodiments, the expression level of CD8A, EOMES, PRF1, IFNG, and PD-L1 has been determined to be at or above a reference level of CD8A, EOMES, PRF1, IFNG, and PD-L1, and the expression level of IL6, CXCL1, CXCL2, CXCL3, CXCL8, PTGS2, CXCR1, CXCR2, S100A8, and S100A9 has been determined to be below a reference expression level of IL6, CXCL1, CXCL2, CXCL3, CXCL8, PTGS2, CXCR1, CXCR2, S100A8, and S100A9.

In some embodiments of any of the preceding methods, therapy with a VEGF antagonist (e.g., an anti-VEGF antibody, such as bevacizumab) in combination with a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) preferably extends and/or improves survival, including progression free survival (PFS) and/or overall survival (OS). In one embodiment, therapy with the VEGF antagonist (e.g., an anti-VEGF antibody, such as bevacizumab) in combination with a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) extends survival by at least about 10%, 20%, 30%, 40%, 50%, 60%, 70%, 80%, 90%, 100%, 200%, or more, relative to the survival achieved by administering an approved anti-tumor agent, or standard of care, for the cancer being treated.

In other embodiments of any of the preceding methods, therapy with the angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) preferably extends and/or improves survival, including progression free survival (PFS) and/or overall survival (OS). In one embodiment, therapy with the angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) extends survival by at least about 10%, 20%, 30%, 40%, 50%, 60%, 70%, 80%, 90%, 100%, 200%, or more, relative to the survival achieved by administering an approved anti-tumor agent, or standard of care, for the cancer being treated.

In certain embodiments of any of the preceding methods, a reference level is the expression level of the one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) genes (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9) in a reference population, for example, a population of individuals having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)). In particular embodiments, the cancer is a kidney cancer (e.g., RCC, e.g., mRCC). In certain embodiments, a reference level is the median expression level of the one or more genes in a reference population, for example, a population of individuals having a cancer. In other embodiments, the reference level may be the top 40%, the top 30%, the top 20%, the top 10%, the top 5%, or the top 1% of the expression level in the reference population. In certain embodiments, the reference level is a pre-assigned expression level for the one or more genes. In some embodiments, the reference level is the expression level of the one or more genes in a biological sample obtained from the patient at a previous time point, wherein the previous time point is following administration of the anti-cancer therapy. In some embodiments of any of the preceding methods, a reference level is the expression level of the one or more genes (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9) in a biological sample from the patient obtained prior to (e.g., minutes, hours, days, weeks (e.g., 1, 2, 3, 4, 5, 6, or 7 weeks), months, or years prior to) administration of the anti-cancer therapy. In other embodiments, the reference level is the expression level of the one or more genes in a biological sample obtained from the patient at a subsequent time point (e.g., minutes, hours, days, weeks, months, or years after administration of an anti-cancer therapy).

In some embodiments of any of the preceding embodiments, the sample is obtained from the individual prior to (e.g., minutes, hours, days, weeks (e.g., 1, 2, 3, 4, 5, 6, or 7 weeks), months, or years prior to) administration of the anti-cancer therapy. In some embodiments of any of the preceding methods, the sample from the individual is obtained about 2 to about 10 weeks (e.g., 2, 3, 4, 5, 6, 7, 8, 9, or 10 weeks) following administration of the anti-cancer therapy. In some embodiments, the sample from the individual is obtained about 4 to about 6 weeks following administration of the anti-cancer therapy.

In some embodiments of any of the preceding methods, the expression level or number of a biomarker is detected in a tissue sample, a primary or cultured cells or cell line, a cell supernatant, a cell lysate, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, or any combination thereof. In some embodiments, the sample is a tissue sample (e.g., a tumor tissue sample), a cell sample, a whole blood sample, a plasma sample, a serum sample, or a combination thereof. In some embodiments, the tumor tissue sample wherein the tumor tissue sample includes tumor cells, tumor-infiltrating immune cells, stromal cells, or a combination thereof. In some embodiments, the tumor tissue sample is a formalin-fixed and paraffin-embedded (FFPE) sample, an archival sample, a fresh sample, or a frozen sample.

For example, in some embodiments of any of the preceding methods, the expression level of a biomarker is detected in tumor-infiltrating immune cells, tumor cells, PBMCs, or combinations thereof using known techniques (e.g., flow cytometry or IHC). Tumor-infiltrating immune cells include, but are not limited to, intratumoral immune cells, peritumoral immune cells or any combinations thereof, and other tumor stroma cells (e.g., fibroblasts). Such tumor infiltrating immune cells may be T lymphocytes (such as CD8+ T lymphocytes (e.g., CD8+ T effector (Ten) cells) and/or CD4+ T lymphocytes (e.g., CD4+ $T_{eff}$ cells), B lymphocytes, or other bone marrow-lineage cells including granulocytes (neutrophils, eosinophils, basophils), monocytes, macrophages, dendritic cells (e.g., interdigitating dendritic cells), histiocytes, and natural killer (NK) cells. In some embodiments, the staining for a biomarker is detected as membrane staining, cytoplasmic staining, or combinations thereof. In other embodiments, the absence of a biomarker is detected as absent or no staining in the sample, relative to a reference sample.

In particular embodiments of any of the preceding methods, the expression level of a biomarker is assessed in a sample that contains or is suspected to contain cancer cells. The sample may be, for example, a tissue biopsy or a metastatic lesion obtained from a patient suffering from, suspected to suffer from, or diagnosed with cancer (e.g., a kidney cancer, in particular renal cell carcinoma (RCC), such as advanced RCC or metastatic RCC (mRCC)). In some embodiments, the sample is a sample of kidney tissue, a biopsy of an kidney tumor, a known or suspected metastatic kidney cancer lesion or section, or a blood sample, e.g., a peripheral blood sample, known or suspected to comprise circulating cancer cells, e.g., kidney cancer cells. The sample may comprise both cancer cells, i.e., tumor cells, and non-cancerous cells (e.g., lymphocytes, such as T cells or NK cells), and, in certain embodiments, comprises both cancerous and non-cancerous cells. Methods of obtaining biological samples including tissue resections, biopsies, and body fluids, e.g., blood samples comprising cancer/tumor cells, are well known in the art.

In some embodiments of any of the preceding methods, the individual has carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. In some embodiments, the cancer is kidney cancer (e.g., renal cell carcinoma (RCC), e.g., advanced RCC or metastatic RCC (mRCC)), squamous cell cancer (e.g., epithelial squamous cell cancer), lung cancer (including small-cell lung cancer (SCLC), non-small cell lung cancer (NSCLC), adenocarcinoma of the lung, and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer (e.g., HCC), hepatoma, breast cancer (including TNBC and metastatic breast cancer), bladder cancer, colon cancer, rectal cancer, colorectal cancer, endometrial or uterine carcinoma, salivary gland carcinoma, prostate cancer, vulval cancer, thyroid cancer, hepatic carcinoma, anal carcinoma, penile carcinoma, Merkel cell cancer, mycoses fungoids, testicular cancer, esophageal cancer, tumors of the biliary tract, head and neck cancer, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), abnormal vascular proliferation associated with phakomatoses, edema (such as that associated with brain tumors), or Meigs' syndrome. In some embodiments, the cancer is a kidney cancer (e.g., RCC), a lung cancer (e.g., NSCLC), a bladder cancer (e.g., UBC), a liver cancer (e.g., HCC), an ovarian cancer, or a breast cancer (e.g., TNBC). In preferred embodiments, the patient has a kidney cancer (e.g., RCC, e.g., advanced RCC or mRCC, e.g., previously untreated advanced RCC or mRCC). The patient may optionally have an advanced, refractory, recurrent, chemotherapy-resistant, and/or platinum-resistant form of the cancer.

In certain embodiments, the presence and/or expression levels/amount of a biomarker in a first sample is increased or elevated as compared to presence/absence and/or expression levels/amount in a second sample. In certain embodiments, the presence/absence and/or expression levels/amount of a biomarker in a first sample is decreased or reduced as compared to presence and/or expression levels/amount in a second sample. In certain embodiments, the second sample is a reference sample, reference cell, reference tissue, control sample, control cell, or control tissue.

In certain embodiments, a reference sample, reference cell, reference tissue, control sample, control cell, or control tissue is a single sample or combined multiple samples from the same patient or individual that are obtained at one or more different time points than when the test sample is obtained. For example, a reference sample, reference cell, reference tissue, control sample, control cell, or control tissue is obtained at an earlier time point from the same patient or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combined multiple samples from one or more healthy individuals who are not the patient. In certain embodiments, a reference sample, reference cell, reference tissue, control sample, control cell, or control tissue is a combined multiple samples from one or more individuals with a disease or disorder (e.g., cancer) who are not the patient or individual. In certain embodiments, a reference sample, reference cell, reference tissue, control sample, control cell, or control tissue is pooled RNA samples from normal tissues or pooled plasma or serum samples from one or more individuals who are not the patient. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the patient.

In some embodiments of any of the preceding methods, an expression level above a reference level, or an elevated or increased expression or number, refers to an overall increase of about any of 10%, 20%, 30%, 40%, 50%, 60%, 70%, 80%, 90%, 95%, 96%, 97%, 98%, 99% or greater, in the level or number of a biomarker (e.g., protein, nucleic acid (e.g., gene or mRNA), or cell), detected by methods such as those described herein and/or known in the art, as compared to a reference level, reference sample, reference cell, reference tissue, control sample, control cell, or control tissue. In certain embodiments, the elevated expression or number refers to the increase in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) in the sample wherein the increase is at least about any of 1.1×, 1.2×, 1.3×, 1.4×, 1.5×, 1.6×, 1.7×, 1.8×, 1.9×, 2×, 2.1×, 2.2×, 2.3×, 2.4×, 2.5×, 2.6×, 2.7×, 2.8×, 2.9×, 3×, 3.5×, 4×, 4.5×, 5×, 6×, 7×, 8×, 9×, 10×, 15×, 20×, 30×, 40×, 50×, 100×, 500×, or 1000× the expression level/amount of the respective biomarker in a reference level, reference sample, reference cell, reference tissue, control sample, control cell, or control tissue. In some embodiments, elevated expression or number refers to an overall increase in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference level, reference sample, reference cell, reference tissue, control sample, control cell, control tissue, or internal control (e.g., housekeeping gene).

In some embodiments of any of the preceding methods, an expression level below a reference level, or reduced (decreased) expression or number, refers to an overall reduction of about any of 10%, 20%, 30%, 40%, 50%, 60%, 70%, 80%, 90%, 95%, 96%, 97%, 98%, 99% or greater, in the level of biomarker (e.g., protein, nucleic acid (e.g., gene or mRNA), or cell), detected by standard art known methods such as those described herein, as compared to a reference level, reference sample, reference cell, reference tissue, control sample, control cell, or control tissue. In certain embodiments, reduced expression or number refers to the decrease in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) in the sample wherein the decrease is at least about any of 0.9×, 0.8×, 0.7×, 0.6×, 0.5×, 0.4×, 0.3×, 0.2×, 0.1×, 0.05×, or 0.01× the expression level/amount of the respective biomarker in a reference level, reference sample, reference cell, reference tissue, control sample, control cell, or control tissue. In some embodiments, reduced (decreased) expression or number refers to an overall decrease in expression level/amount of a biomarker (e.g., CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and/or S100A9) of greater than about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, about 2.8-fold, about 2.9-fold, about 3-fold, about 3.5-fold, about 4-fold, about 4.5-fold, about 5-fold, about 6-fold, about 7-fold, about 8-fold, about 9-fold, about 10-fold, about 15-fold, about 20-fold, about 30-fold, about 40-fold, about 50-fold, about 100-fold, about 500-fold, about 1,000-fold or greater as compared to a reference level, reference sample, reference cell, reference tissue, control sample, control cell, control tissue, or internal control (e.g., housekeeping gene).

For the prevention or treatment of cancer, the dose of an anti-cancer therapy (e.g., a VEGF antagonist (e.g., an anti- VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)), or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))) will depend on the type of cancer to be treated, as defined above, the severity and course of the cancer, whether the anti-cancer therapy is administered for preventive or therapeutic purposes, previous therapy, the patient's clinical history and response to the drug, and the discretion of the attending physician.

In some embodiments, the anti-cancer therapy (e.g., a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)), or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib))))) may be suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the anti-cancer therapy). An initial higher loading dose, followed by one or more lower doses may be administered. However, other dosage regimens may be useful. The progress of this therapy is easily monitored by conventional techniques and assays.

For example, as a general proposition, the therapeutically effective amount of a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and/or PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) administered to human will be in the range of about 0.01 to about 50 mg/kg of patient body weight, whether by one or more administrations. In some embodiments, the therapeutic agent (e.g., antibody) used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg administered daily, weekly, every two weeks, every three weeks, or monthly, for example. In some embodiments, the antibody is administered at 15 mg/kg. However, other dosage regimens may be useful. In one embodiment, an VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and/or PD-L1 axis binding antagonist (e.g., a PD-L1 binding antagonist, such as atezolizumab) is administered to a human at a dose of about 50 mg, about 100 mg, about 200 mg, about 300 mg, about 400 mg, about 420 mg, about 500 mg, about 525 mg, about 600 mg, about 700 mg, about 800 mg, about 840 mg, about 900 mg, about 1000 mg, about 1050 mg, about 1100 mg, about 1200 mg, about 1300 mg, about 1400 mg, about 1500 mg, about 1600 mg, about 1700 mg, or about 1800 mg on day 1 of 21-day cycles (every three weeks, q3w).

In some embodiments, atezolizumab is administered at 1200 mg intravenously every three weeks (q3w). In some embodiments, bevacizumab is administered at a fixed dose at one time or over a series of treatments. Where a fixed dose is administered, preferably it is in the range from about 5 mg to about 2000 mg. For example, the fixed dose may be approximately 420 mg, approximately 525 mg, approximately 840 mg, or approximately 1050 mg. In some embodiments, bevacizumab is administered at 10 mg/kg intravenously every two weeks. In some embodiments, bevacizumab is administered at 15 mg/kg intravenously every three weeks. The dose of VEGF antagonist and/or PD-L1 axis binding antagonist may be administered as a single dose or as multiple doses (e.g., 2, 3, 4, 5, 6, 7, 8, 9, or 10 or more doses). Where a series of doses are administered, these may, for example, be administered approximately every week, approximately every 2 weeks, approximately every 3 weeks, or approximately every 4 weeks. The dose of the antibody administered in a combination treatment may be reduced as compared to a single treatment. The progress of this therapy is easily monitored by conventional techniques.

Any suitable dose of a VEGFR inhibitor (e.g., a multi-targeted tyrosine kinase inhibitor (e.g., sunitinib, axitinib, pazopanib, or cabozantinib))) may be used in the methods described herein. Suitable dosages are well known in the art. For example, with respect to sunitib, capsules of 12.5 mg, 25 mg, and 50 mg of sunitinib are commercially available. For example, for treatment of metastatic renal cell carcinoma or gastrointestinal stromal tumor, sunitinib may be administered at 50 mg by mouth (PO) once a day (qDay) for 4 weeks, followed by 2 weeks drug-free, with further repeats of the cycle. For treatment of pancreatic neuroendocrine tumors, a standard dose is 37.5 mg PO qDay continuously without a scheduled off-treatment period.

VEGF antagonists (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and PD-L1 axis binding antagonists (e.g., an antibody (e.g., an anti-PD-L1 antibody, e.g., atezolizumab), binding polypeptide, and/or small molecule) described herein (any additional therapeutic agent) may be formulated, dosed, and administered in a fashion consistent with good medical practice. Likewise, angiogenesis inhibitors (e.g., a VEGF antagonist (e.g., a VEGFR inhibitor, (e.g., a multi-targeted tyrosine kinase inhibitor (e.g., sunitinib, axitinib, pazopanib, or cabozantinib)))) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The VEGF antagonist and PD-L1 antagonist, or the angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))), need not be, but is optionally formulated with and/or administered concurrently with one or more agents currently used to prevent or treat the disorder in question. The effective amount of such other agents depends on the amount of the VEGF antagonist, PD-L1 antagonist, and/or angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) is administered concurrently with a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)). In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) are administered as part of the same formulation. In other embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) is administered separately from a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)).

In some embodiments, any of the preceding methods may further include administering an additional therapeutic agent. In some embodiments, the additional therapeutic agent is selected from the group consisting of an immunotherapy agent, a cytotoxic agent, a growth inhibitory agent, a radiation therapy agent, an anti-angiogenic agent, and combinations thereof.

In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) is administered concurrently with an agonist directed against an activating co-stimulatory molecule. In some embodiments, an activating co-stimulatory molecule may include CD40, CD226, CD28, OX40, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an antagonist directed against an inhibitory co-stimulatory molecule. In some embodiments, an inhibitory co-stimulatory molecule may include CTLA-4 (also known as CD152), TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, TIM-3, BTLA, VISTA, LAG-3, B7-H3, B7-H4, IDO, TIGIT, MICA/B, or arginase.

In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an antagonist directed against CTLA-4 (also known as CD152), e.g., a blocking antibody. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with ipilimumab (also known as MDX-010, MDX-101, or YERVOY®). In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with tremelimumab (also known as ticilimumab or CP-675,206). In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an antagonist directed against B7-H3 (also known as CD276), e.g., a blocking antibody. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with MGA271. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an antagonist directed against a TGF-beta, e.g., metelimumab (also known as CAT-192), fresolimumab (also known as GC1008), or LY2157299.

In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an agonist directed against CD137 (also known as TNFRSF9, 4-1 BB, or ILA), e.g., an activating antibody. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with urelumab (also known as BMS-663513). In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an agonist directed against CD40, e.g., an activating antibody. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with CP-870893. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an agonist directed against OX40 (also known as CD134), e.g., an activating antibody. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an anti-OX40 antibody (e.g., AgonOX). In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an agonist directed against CD27, e.g., an activating antibody. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with CDX-1127. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an antagonist directed against TIGIT, for example, an anti-TIGIT antibody. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an antagonist directed against indoleamine-2,3-dioxygenase (IDO). In some embodiments, the IDO antagonist is 1-methyl-D-tryptophan (also known as 1-D-MT).

In some embodiments, VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., *Cancer Sci.* 104:14-21, 2013). In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an adjuvant. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD_1 antibody)) may be administered in conjunction with a treatment comprising a TLR agonist, e.g., Poly-ICLC (also known as HILTONOL®), LPS, MPL, or CpG ODN. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with tumor necrosis factor (TNF) alpha. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with IL-1. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with HMGB1. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an IL-10 antagonist. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an IL-4 antagonist. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an IL-13 antagonist. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an HVEM antagonist. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an ICOS agonist, e.g., by administration of ICOS-L, or an agonistic antibody directed against ICOS. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with a treatment targeting CX3CL1. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with a treatment targeting CXCL9. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with a treatment targeting CXCL10. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with a treatment targeting CCL5. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with an LFA-1 or ICAM1 agonist. In some embodiments, a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A) or a PD-1 binding antagonist (e.g., an anti-PD-1 antibody)) may be administered in conjunction with a Selectin agonist.

A chemotherapeutic agent, if administered, is usually administered at dosages known therefore, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Where the chemotherapeutic agent is paclitaxel, preferably, it is administered at a dose between about 130 mg/m$^2$ to 200 mg/m$^2$ (e.g., approximately 175 mg/m$^2$), for instance, over 3 hours, once every 3 weeks. Where the chemotherapeutic agent is carboplatin, preferably it is administered by calculating the dose of carboplatin using the Calvert formula which is based on a patient's preexisting renal function or renal function and desired platelet nadir. Renal excretion is the major route of elimination for carboplatin. The use of this dosing formula, as compared to empirical dose calculation based on body surface area, allows compensation for patient variations in pretreatment renal function that might otherwise result in either underdosing (in patients with above average renal function) or overdosing (in patients with impaired renal function). The target AUC of 4-6 mg/mL/min using single agent carboplatin appears to provide the most appropriate dose range in previously treated patients.

In addition to the above therapeutic regimes, the patient may be subjected to surgical removal of tumors and/or cancer cells.

Such combination therapies noted above encompass combined administration (where two or more therapeutic agents are included in the same or separate formulations), and separate administration, in which case, administration of a VEGF antagonist and/or a PD-L1 axis binding antagonist, or an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))), can occur prior to, simultaneously, and/or following, administration of the additional therapeutic agent or agents. In one embodiment, administration of VEGF antagonist and/or a PD-L1 axis binding antagonist, or a an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))), and administration of an additional therapeutic agent occur within about one month, or within about one, two or three weeks, or within about one, two, three, four, five, or six days, of each other.

In embodiments where either the VEGF antagonist or the PD-L1 axis binding antagonist is an antibody (e.g., bevacizumab or atezolizumab), the administered antibody may be a naked antibody. The VEGF antagonist (e.g., an anti-VEGF antibody, such as bevacizumab) and/or the PD-L1 axis binding antagonist (e.g., a PD-L1 binding antagonist, such as atezolizumab) administered may be conjugated with a cytotoxic agent. Preferably, the conjugated and/or antigen to which it is bound is/are internalized by the cell, resulting in increased therapeutic efficacy of the conjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases, and DNA endonucleases.

The compositions utilized in the methods described herein can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), parenterally, by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some embodiments, the PD-L1 axis binding antagonist is administered intravenously, intramuscularly, subcutaneously, topically, orally, transdermally, intraperitoneally, intraorbitally, by implantation, by inhalation, intrathecally, intraventricularly, or intranasally. In some embodiments, the multi-targeted tyrosine kinase inhibitor is administered orally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

IV. Compositions and Pharmaceutical Formulations

In one aspect, the invention is based, in part, on the discovery that biomarkers of the invention can be used to identify individuals having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) who may benefit from anti-cancer therapies that include VEGF antagonists and PD-L1 axis binding antagonists. In another aspect, the invention is based, in part, on the discovery that biomarkers of the invention can be used to identify individuals having a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) who may benefit from anti-cancer therapies that include an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). These agents, and combinations thereof, are useful for the treatment of cancer, e.g., as part of any of the methods described herein, for example, in Sections II and III above. Any suitable VEGF antagonist, PD-L1 axis binding antagonist, and/or angiogenesis inhibitor can be used in the methods and assays described herein. Non-limiting examples suitable for use in the methods and assays of the invention are described further below.

A. Exemplary VEGF Antagonists

VEGF antagonists include any molecule capable of binding VEGF, reducing VEGF expression levels, or neutralizing, blocking, inhibiting, abrogating, reducing, or interfering with VEGF biological activities. An exemplary human VEGF is shown under UniProtKB/Swiss-Prot Accession No. P15692, Gene ID (NCBI): 7422.

In some instances, the VEGF antagonist is an anti-VEGF antibody. In some embodiments, the anti-VEGF antibody is bevacizumab, also known as "rhuMab VEGF" or "AVASTIN®." Bevacizumab is a recombinant humanized anti-VEGF monoclonal antibody generated according to Presta et al. (*Cancer Res.* 57:4593-4599, 1997). It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879 issued Feb. 26, 2005, the entire disclosure of which is expressly incorporated herein by reference. Additional preferred antibodies include the G6 or B20 series antibodies (e.g., G6-31, B20-4.1), as described in PCT Application Publication No. WO 2005/012359. For additional preferred antibodies see U.S. Pat. Nos. 7,060,269, 6,582,959, 6,703,020; 6,054,297; WO98/45332; WO 96/30046; WO94/10202; EP 066686861; U.S. Patent Application Publication Nos. 2006009360, 20050186208, 20030206899, 20030190317, 20030203409, and 20050112126; and Popkov et al. (*Journal of Immunological Methods* 288:149-164, 2004). Other preferred antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183, and Q89.

In other instances, the VEGF antagonist is an anti-VEGFR2 antibody or related molecule (e.g., ramucirumab, tanibirumab, aflibercept); an anti-VEGFR1 antibody or related molecules (e.g., icrucumab, aflibercept (VEGF Trap-Eye; EYLEA®), or ziv-aflibercept (VEGF Trap; ZAL-TRAP®)); a bispecific VEGF antibody (e.g., MP-0250, vanucizumab (VEGF-ANG2), or bispecific antibodies disclosed in US 2001/0236388); a bispecific antibody including a combination of two of anti-VEGF, anti-VEGFR1, and anti-VEGFR2 arms; an anti-VEGFA antibody (e.g., bevacizumab, sevacizumab); an anti-VEGFB antibody; an anti-VEGFC antibody (e.g., VGX-100), an anti-VEGFD antibody; or a nonpeptide small molecule VEGF antagonist (e.g., pazopanib, axitinib, vandetanib, stivarga, cabozantinib, lenvatinib, nintedanib, orantinib, telatinib, dovitinib, cediranib, motesanib, sulfatinib, apatinib, foretinib, famitinib, or tivozanib).

It is expressly contemplated that such VEGF antagonist antibodies or other antibodies described herein (e.g., anti-VEGF antibodies for detection of VEGF expression levels) for use in any of the embodiments enumerated above may have any of the features, singly or in combination, described in Sections i-vii of Subsection C below.

B. Exemplary PD-L1 Axis Binding Antagonists

PD-L1 axis binding antagonists include PD-1 binding antagonists, PD-L1 binding antagonists, and PD-L2 binding antagonists. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1 LG2," "CD273," "B7-DC," "Btdc," and "PDL2." An exemplary human PD-L2 is shown in UniProtKB/Swiss-Prot Accession No. Q9BQ51. In some embodiments, PD-1, PD-L1, and PD-L2 are human PD-1, PD-L1, and PD-L2. The PD-1 axis binding antagonist may, in some instances, be a PD-1 binding antagonist, a PD-L1 binding antagonist, or a PD-L2 binding antagonist.

(i) PD-L1 Binding Antagonists

In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some instances, the antibody is selected from the group consisting of: MPDL3280A (atezolizumab), YW243.55.S70, MDX-1105, MED14736 (durvalumab), and MSB0010718C (avelumab).

In some instances, the anti-PD-L1 antibody is a monoclonal antibody. In some instances, the anti-PD-L1 antibody is an antibody fragment selected from the group consisting of Fab, Fab'-SH, Fv, scFv, and (Fab')₂ fragments. In some instances, the anti-PD-L1 antibody is a humanized antibody. In some instances, the anti-PD-L1 antibody is a human antibody. In some instances, the anti-PD-L1 antibody described herein binds to human PD-L1. In some particular instances, the anti-PD-L1 antibody is atezolizumab (CAS Registry Number: 1422185-06-5). Atezolizumab (Genentech) is also known as MPDL3280A.

In some instances, the anti-PD-L1 antibody comprises a heavy chain variable region (HVR-H) comprising an HVR-H1, HVR-H2, and HVR-H3 sequence, wherein:
(a) the HVR-H1 sequence is GFTFSDSWIH (SEQ ID NO: 62);
(b) the HVR-H2 sequence is AWISPYGGSTYYADSVKG (SEQ ID NO: 63); and
(c) the HVR-H3 sequence is RHWPGGFDY (SEQ ID NO: 64).

In some instances, the anti-PD-L1 antibody further comprises a light chain variable region (HVR-L) comprising an HVR-L1, HVR-L2, and HVR-L3 sequence, wherein:
(a) the HVR-L1 sequence is RASQDVSTAVA (SEQ ID NO: 65);
(b) the HVR-L2 sequence is SASFLYS (SEQ ID NO: 66); and
(c) the HVR-L3 sequence is QQYLYHPAT (SEQ ID NO: 67).

In some instances, the anti-PD-L1 antibody comprises a heavy chain and a light chain sequence, wherein:
(a) the heavy chain variable (VH) region sequence comprises the amino acid sequence: EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSS (SEQ ID NO: 69); and
(b) the light chain variable (VL) region sequence comprises the amino acid sequence:

```
                                  (SEQ ID NO: 70)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In some instances, the anti-PD-L1 antibody comprises a heavy chain and a light chain sequence, wherein:
(a) the heavy chain comprises the amino acid sequence: EVQLVESGGGLVQPGGSLRLSCAASGFTFSDSWIHWVRQAPGKGLEWVAWISPYGGSTYYADSVKGRFTIS ADTSKNTAYLQMNSLRAEDTAVYYCARRHW PGGFDYWGQGTLVTVSSASTKGPSVFPLAPSSKSTSGGTA ALGCLVKDYFPEPVTVSWNSGALTSGVHTFPAVLQSSGLYS-LSSVVTVPSSSLGTQTYICNVNHKPSNTKVD KKVEPKSCDKTHTCPPCPAPELLGG PSVFLFPPKPKDTLMISRTPEVTCVVVDVSHEDPE-VKFNWYVDGVEV HNAKTKPRE-EQYASTYRVVSVLTVLHQDWLNGKEYKCKVSNKA-LPAPI EKTISKAKGQPREPQVYTLPPSRE EMTKNQVSLTCLVKGFYPSDIAVEW ESNGQPEN-NYKTTPPVLDSDGSFFLYSK-LTVDKSRWQQGNVFSCSV MHEALHNHYTQKSLSL-SPG (SEQ ID NO: 71); and
(b) the light chain comprises the amino acid sequence:

```
                                  (SEQ ID NO: 72)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In some instances, the anti-PD-L1 antibody comprises (a) a VH domain comprising an amino acid sequence comprising having at least 95% sequence identity (e.g., at least 95%, 96%, 97%, 98%, or 99% sequence identity) to, or the sequence of (SEQ ID NO: 69); (b) a VL domain comprising an amino acid sequence comprising having at least 95% sequence identity (e.g., at least 95%, 96%, 97%, 98%, or 99% sequence identity) to, or the sequence of (SEQ ID NO: 70); or (c) a VH domain as in (a) and a VL domain as in (b). In other instances, the anti-PD-L1 antibody is selected from the group consisting of YVV243.55.570, MDX-1105, MED14736 (durvalumab), and MSB0010718C (avelumab). Antibody YW243.55.570 is an anti-PD-L1 described in PCT Pub. No. WO 2010/077634. MDX-1105, also known as BMS-936559, is an anti-PD-L1 antibody described in PCT Pub. No. WO 2007/005874. MED14736 (durvalumab) is an anti-PD-L1 monoclonal antibody described in PCT Pub. No. WO 2011/066389 and U.S. Pub. No. 2013/034559. Examples of anti-PD-L1 antibodies useful for the methods of this invention, and methods for making thereof are described in PCT Pub. Nos. WO 2010/077634, WO 2007/005874, and WO 2011/066389, and also in U.S. Pat. No. 8,217,149, and U.S. Pub. No. 2013/034559, which are incorporated herein by reference.

(ii) PD-1 Binding Antagonists

In some instances, the PD-L1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In a further aspect, the invention provides for the use of a PD-L1 axis binding antagonist in the manufacture or preparation of a medicament. In one embodiment, the medicament is for treatment of a cancer. In a further embodiment, the medicament is for use in a method of treating a cancer (e.g., a kidney cancer (e.g., RCC), a lung cancer (e.g., NSCLC), a bladder cancer (e.g., UBC), a liver cancer (e.g., HCC), an ovarian cancer, or a breast cancer (e.g., TNBC)) comprising administering to a patient suffering from cancer an effective amount of the medicament. In one such embodiment, the method further comprises administering to the individual an effective amount of at least one additional therapeutic agent, e.g., as described below.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding ligands. In a specific aspect, PD-L1 binding partners are PD-1 and/or B7-1. In another embodiment, the PD-L2 binding antagonist is a molecule that inhibits the binding of PD-L2 to its ligand binding partners. In a specific aspect, the PD-L2 binding ligand partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody), for example, as described below. In some embodiments, the anti-PD-1 antibody is selected from the group consisting of MDX-1106 (nivolumab), MK-3475 (pembrolizumab), CT-011 (pidilizumab), MEDI-0680 (AMP-514), PDR001, REGN2810, and BGB-108. MDX-1106, also known as MDX-1106-04, ONO-4538, BMS-936558, or nivolumab, is an anti-PD-1 antibody described in WO2006/121168. MK-3475, also known as pembrolizumab or lambrolizumab, is an anti-PD-1 antibody described in WO 2009/114335. CT-011, also known as hBAT, hBAT-1 or pidilizumab, is an anti-PD-1 antibody described in WO 2009/101611. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. AMP-224, also known as B7-DCIg, is a PD-L2-Fc fusion soluble receptor described in WO 2010/027827 and WO 2011/066342.

In some embodiments, the anti-PD-1 antibody is MDX-1106. Alternative names for "MDX-1106" include MDX-1106-04, ONO-4538, BMS-936558, and nivolumab. In some embodiments, the anti-PD-1 antibody is nivolumab (CAS Registry Number: 946414-94-4). In a still further embodiment, provided is an isolated anti-PD-1 antibody comprising a heavy chain variable region comprising the heavy chain variable region amino acid sequence from SEQ ID NO: 73 and/or a light chain variable region comprising the light chain variable region amino acid sequence from SEQ ID NO: 74.

In a still further embodiment, provided is an isolated anti-PD-1 antibody comprising a heavy chain and/or a light chain sequence, wherein: (a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence: QVQLVESGGGVVQP-GRSLRLDCKASGITFSNSGMHWVRQAPGKGLEWVA-VIWYDGSKRYYADSVKGRFTISRDNSKNTLFLQMNS-LRAEDTAVYYCATNDDYWGQGTLVTVSSASTKGPS-VFPLAPCSRSTSESTAALGCLVKDYFPEPVTVSWNS-GALTSGVHTFPAVLQSSGLYSLSSVVTVPSSSLGTKT-YTCNVDHKPSNTKVDKRVESKYGPPCPPCPAPEFLG-GPSVFLFPPKPKDTLMISRTPEVTCVVVDVSQEDPEV-QFNWYVDGVEVHNAKTKPREEQFNSTYRVVSVLTV-LHQDWLNGKEYKCKVSNKGLPSSIEKTISKAKGQP-REPQVYTLPPSQEEMTKNQVSLTCLVKGFYPSDIAVE-WESNGQPENNYKTTPPVLDSDGSFFLYSRLTVDKSR-WQEGNVFSCSVMHEALHNHYTQKSLSLSLGK (SEQ ID NO: 73), and (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 74)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

It is expressly contemplated that such PD-L1 axis binding antagonist antibodies (e.g., anti-PD-L1 antibodies, anti- PD-1 antibodies, and anti-PD-L2 antibodies), or other antibodies described herein (e.g., anti-PD-L1 antibodies for detection of PD-L1 expression levels) for use in any of the embodiments enumerated above may have any of the features, singly or in combination, described in Sections i-vii of Subsection C below.

C. Antibodies i. Antibody Affinity

In certain embodiments, an antibody provided herein (e.g., an anti-VEGF antibody, an anti-PD-L1 antibody or an anti-PD-1 antibody) has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881, 1999). To establish conditions for the assay, MICROTITER® multiwell plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$L]I-antigen are mixed with serial dilutions of a Fab of interest (e.g., consistent with assessment of the anti-VEGF antibody, Fab-12, in Presta et al., *Cancer Res.* 57:4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., (*J. Mol. Biol.* 293:865-881, 1999). If the on-rate exceeds $10^6$ M$^{-1}$s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

ii. Antibody Fragments

In certain embodiments, an antibody (e.g., an anti-PD-L1 antibody or an anti-PD-1 antibody) provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. (*Nat. Med.* 9:129-134, 2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994). See also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097, WO 1993/01161, Hudson et al. *Nat. Med.* 9:129-134, 2003, and Hollinger et al. *Proc. Natl. Acad. Sci. USA* 90: 6444-6448, 1993. Triabodies and tetrabodies are also described in Hudson et al. (*Nat. Med.* 9:129-134, 2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), according to known methods.

iii. Chimeric and Humanized Antibodies

In certain embodiments, an antibody (e.g., an anti-VEGF antibody, an anti-PD-L1 antibody or an anti-PD-1 antibody) provided herein is a chimeric antibody. Certain chimeric antibodies are described, e.g., in U.S. Pat. No. 4,816,567; and Morrison et al. (*Proc. Natl. Acad. Sci. USA,* 81:6851-6855, 1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, (*Front. Biosci.* 13:1619-1633, 2008), and are further described, e.g., in Riechmann et al. (*Nature* 332:323-329, 1988); Queen et al. (*Proc. Natl. Acad. Sci. USA* 86:10029-10033, 1989); U.S. Pat. Nos. 5,821,337, 7,527,791, 6,982,321, and 7,087,409; Kashmiri et al. (*Methods* 36:25-34, 2005) (describing specificity determining region (SDR) grafting); Padlan, (*Mol. Immunol.* 28:489-498, 1991) (describing "resurfacing"); Dall'Acqua et al. (*Methods* 36:43-60, 2005) (describing "FR shuffling"); Osbourn et al. (*Methods* 36:61-68, 2005), and Klimka et al. (*Br. J. Cancer,* 83:252-260, 2000) (describing the "guided selection" approach to FR shuffling).

Human framework regions that may be used for humanization include but are not limited to: framework regions selected using the "best-fit" method (see, e.g., Sims et al. *J. Immunol.* 151:2296, 1993); framework regions derived from the consensus sequence of human antibodies of a particular subgroup of light or heavy chain variable regions (see, e.g., Carter et al. *Proc. Natl. Acad. Sci. USA,* 89:4285, 1992; and Presta et al. *J. Immunol.,* 151:2623, 1993); human mature (somatically mutated) framework regions or human germline framework regions (see, e.g., Almagro and Fransson, *Front. Biosci.* 13:1619-1633, 2008); and framework regions derived from screening FR libraries (see, e.g., Baca et al., *J. Biol. Chem.* 272:10678-10684, 1997; and Rosok et al. *J. Biol. Chem.* 271:22611-22618, 1996).

iv. Human Antibodies

In certain embodiments, an antibody (e.g., an anti-VEGF antibody, an anti-PD-L1 antibody or an anti-PD-1 antibody) provided herein is a human antibody. Human antibodies can be produced using various techniques known in the art. Human antibodies are described generally in van Dijk and van de Winkel, (*Curr. Opin. Pharmacol.* 5: 368-74, 2001) and Lonberg (*Curr. Opin. Immunol.* 20:450-459, 2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, (*Nat. Biotech.* 23:1117-1125, 2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor, (*J. Immunol* 133: 3001, 1984); Brodeur et al. (*Monoclonal Antibody Production Techniques and Applications,* pp. 51-63, Marcel Dekker, Inc., New York, 1987); and Boerner et al. (*J. Immunol.,* 147: 86, 1991). Human antibodies generated via human B-cell hybridoma technology are also described in Li et al., *Proc. Natl. Acad. Sci. USA,* 103:3557-3562, 2006. Additional methods include those described, for example, in U.S. Pat. No. 7,189,826 (describing production of monoclonal human IgM antibodies from hybridoma cell lines) and Ni, (*Xiandai Mianyixue,* 26(4):265-268, 2006) (describing human-human hybridomas). Human hybridoma technology (Trioma technology) is also described in Vollmers and Brandlein, (*Histology and Histopathology,* 20(3):927-937, 2005) and Vollmers and Brandlein, (*Methods and Findings in Experimental and Clinical Pharmacology,* 27(3):185-91, 2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

v. Library-Derived Antibodies

Antibodies of the invention (e.g., anti-VEGF antibodies, anti-PD-L1 antibodies, or anti-PD-1 antibodies) may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. (*Methods in Molecular Biology* 178:1-37, O'Brien et al., ed., *Human Press,* Totowa, N.J., 2001) and further described, e.g., in McCafferty et al. (*Nature* 348:552-554, 1990); Clackson et al. (*Nature* 352: 624-628, 1991); Marks et al. (*J. Mol. Biol.* 222: 581-597, 1992); Marks and Bradbury, (*Methods in Molecular Biology* 248:161-175, Lo, ed., Human Press, Totowa, N.J., 2003); Sidhu et al. (*J. Mol. Biol.* 338(2): 299-310, 2004); Lee et al. (*J. Mol. Biol.* 340(5): 1073-1093, 2004); Fellouse, (*Proc. Natl. Acad. Sci. USA* 101(34): 12467-12472, 2004); and Lee et al. (*J. Immunol. Methods* 284(1-2): 119-132, 2004).

In certain phage display methods, repertoires of VH and VL genes are separately cloned by polymerase chain reaction (PCR) and recombined randomly in phage libraries, which can then be screened for antigen-binding phage as described in Winter et al. (*Ann. Rev. Immunol.,* 12: 433-455, 1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and self antigens without any immunization as described by Griffiths et al. (*EMBO J,* 12: 725-734, 1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, (*J. Mol. Biol.,* 227: 381-388, 1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

vi. Multispecific Antibodies

In any one of the above aspects, an antibody (e.g., an anti-VEGF antibody, an anti-PD-L1 antibody, or an anti-PD-1 antibody) provided herein may be a multispecific antibody, for example, a bispecific antibody. Multispecific antibodies are monoclonal antibodies that have binding specificities for at least two different sites. In certain embodiments, an antibody provided herein is a multispecific antibody, e.g., a bispecific antibody. In certain embodiments, one of the binding specificities is for PD-L1 and the other is for any other antigen. In certain embodiments, one of the binding specificities is for VEGF and the other is for any other antigen. In certain embodiments, bispecific antibodies may bind to two different epitopes of PD-L1. In certain embodiments, bispecific antibodies may bind to two different epitopes of VEGF. Bispecific antibodies may also be used to localize cytotoxic agents to cells which express PD-L1 or VEGF. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537, 1983), WO 93/08829 and Traunecker et al. *EMBO J.* 10: 3655, 1991) and "knob-in-hole" engineering (see, e.g., U.S. Pat. No. 5,731,168). Multi-specific antibodies may also be made by engineering electrostatic steering effects for making antibody Fc-heterodimeric molecules (see, e.g., WO 2009/089004A1); cross-linking two or more antibodies or fragments (see, e.g., U.S. Pat. No. 4,676,980, and Brennan et al. *Science* 229: 81, 1985); using leucine zippers to produce bi-specific antibodies (see, e.g., Kostelny et al. *J. Immunol.* 148(5): 1547-1553, 1992); using "diabody" technology for making bispecific antibody fragments (see, e.g., Hollinger et al. *Proc. Natl. Acad. Sci. USA* 90:6444-6448, 1993); and using single-chain Fv (sFv) dimers (see, e.g., Gruber et al. *J. ImmunoL* 152:5368, 1994); and preparing trispecific antibodies as described, e.g., in Tutt et al. *J. ImmunoL* 147: 60, 1991).

Engineered antibodies with three or more functional antigen binding sites, including "Octopus antibodies," are also included herein (see, e.g., US 2006/0025576A1).

The antibody or fragment herein includes a "Dual Acting FAb" or "DAF" comprising an antigen binding site that binds to PD-L1 and another, different antigen. The antibody or fragment herein also includes a DAF comprising an antigen binding site that binds to VEGF and another, different antigen.

vii. Antibody Variants

In certain embodiments, amino acid sequence variants of the antibodies of the invention (e.g., anti-VEGF antibodies, anti-PD-L1 antibodies, and anti-PD-1 antibodies) are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 17 under the heading of "preferred substitutions." More substantial changes are provided in Table 17 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 17

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196, 2008), and/or residues that contact antigen, with the resulting variant VH or VL being tested for binding affinity. Affinity maturation by constructing and reselecting from secondary libraries has been described, e.g., in Hoogenboom et al. (*Methods in Molecular Biology* 178: 1-37, O'Brien et al., ed., Human Press, Totowa, N.J., 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen-contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (*Science*, 244:1081-1085, 1989). In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain embodiments, antibodies of the invention can be altered to increase or decrease the extent to which the antibody is glycosylated. Addition or deletion of glycosylation sites to an antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, U.S. Patent Publication Nos. US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. (*J. Mol. Biol.* 336:1239-1249, 2004); and Yamane-Ohnuki et al. (*Biotech. Bioeng.* 87: 614, 2004). Examples of cell lines capable of producing defucosylated antibodies include Lec13 CHO cells deficient in protein fucosylation (Ripka et al. *Arch. Biochem. Biophys.* 249:533-545, 1986); U.S. Pat. Appl. No. US 2003/0157108 A1; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda, Y. et al. *Biotechnol. Bioeng.* 94(4):680-688, 2006; and WO 2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c. Fc Region Variants

In certain embodiments, one or more amino acid modifications may be introduced into the Fc region of an antibody of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, (*Annu. Rev. Immunol.* 9:457-492, 1991). Non-limiting examples of in vitro assays to assess ADCC activity of a molecule of interest is described in U.S. Pat. No. 5,500,362 (see, e.g., Hellstrom, I. et al. Proc. *Natl. Acad. Sci. USA* 83:7059-7063, 1986) and Hellstrom, I et al. *Proc. Natl. Acad. Sci. USA* 82:1499-1502, 1985; U.S. Pat. No. 5,821,337; Bruggemann et al. *J. Exp. Med.* 166:1351-1361, 1987). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (*Proc. Natl. Acad. Sci. USA* 95:652-656, 1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods* 202:163, 1996; Cragg et al. *Blood.* 101:1045-1052, 2003; and Cragg et al. *Blood.* 103:2738-2743, 2004). FcRn binding and in vivo clearance/half-life determinations can also be performed using methods known in the art (see, e.g., Petkova et al. *Int'l Immunol.* 18(12):1759-1769, 2006).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

Certain antibody variants with improved or diminished binding to FcRs are described (see, e.g., U.S. Pat. No. 6,737,056; WO 2004/056312, and Shields et al., *J. Biol. Chem.* 9(2): 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. (*J. Immunol.* 164: 4178-4184, 2000).

Antibodies with increased half-lives and improved binding to the neonatal Fc receptor (FcRn), which is responsible for the transfer of maternal IgGs to the fetus (Guyer et al., *J. Immunol.* 117:587, 1976; and Kim et al. *J. Immunol.* 24:249, 1994), are described in U.S. Pub. No. 2005/0014934A1. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan and Winter, (*Nature* 322:738-40, 1988); U.S. Pat. Nos. 5,648,260; 5,624,821; and WO 94/29351, concerning other examples of Fc region variants.

d. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

f. Immunoconjugates

The invention also provides immunoconjugates comprising an antibody herein (e.g., an anti-VEGF antibody, an anti-PD-L1 antibody, or an anti-PD-1 antibody) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020 and 5,416,064 and European Patent EP 0 425 235 B1); an auristatin such as monomethylauristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al. *Cancer Res.* 53:3336-3342, 1993; and Lode et al. *Cancer Res.* 58:2925-2928, 1998); an anthracycline such as daunomycin or doxorubicin (see Kratz et al. *Current Med. Chem.* 13:477-523, 2006; Jeffrey et al. *Bioorganic & Med. Chem. Letters* 16:358-362, 2006; Torgov et al., *Bioconj. Chem.* 16:717-721 (2005); Nagy et al., *Proc. Natl. Acad. Sci. USA* 97:829-834 (2000); Dubowchik et al., Bioorg. & Med. Chem. Letters 12:1529-1532, 2002; King et al., J. Med. Chem. 45:4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At_{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron. Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. (Science 238:1098, 1987). Carbon-14-labeled 1-isothiocyanatobenzyl-3-methyldiethylene triamine-pentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al. *Cancer Res.* 52:127-131, 1992; and U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

D. Multi-targeted Tyrosine Kinase Inhibitors

Any suitable multi-targeted tyrosine kinase inhibitor can be used in the methods described herein. For example, the multi-targeted tyrosine kinase inhibitor may inhibit platelet-derived growth factor receptors (e.g., PDGFR-αα, PDGFR-ββ, and PDGFR-αβ), VEGF receptors (e.g., VEGFR1 and VEGFR2), CD117 (c-Kit), RET, CD114, and/or CD135. Exemplary multi-targeted tyrosine kinase inhibitors include sunitinib (also known as N-[2-(Diethylamino)ethyl]-5-[(Z)-(5-fluoro-2-oxo-1,2-dihydro-3H-indol-3-ylidene)methyl]-2,4-dimethyl-1H-pyrrole-3-carboxamide, SUTENT®, or SU11248), SU6656, motesanib, sorafenib (e.g., NEXEVAR® or BAY439006), axitinib, afatinib, bosutinib, crizotinib, cabozantinib, dasatinib, entrectinib, pazopanib, lapatinib, and vandetanib (also known as ZACTIMA® or ZD6474). In some embodiments, the multi-targeted tyrosine kinase inhibitor is a VEGFR inhibitor.

E. Pharmaceutical Formulations

Therapeutic formulations of the VEGF antagonists and the PD-L1 axis binding antagonists used in accordance with the present invention (e.g., an anti-VEGF antibody, such as bevacizumab, and an anti-PD-L1 antibody, such as atezolizumab) are prepared for storage by mixing the antagonist having the desired degree of purity with optional pharmaceutically acceptable carriers, excipients, or stabilizers in the form of lyophilized formulations or aqueous solutions. Therapeutic formulations of the multi-targeted tyrosine kinase inhibitors used in accordance with the present invention (e.g., sunitinib) are also prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics,* 8th Ed., Pergamon Press, 1990; A. Gennaro (ed.), *Remington's Pharmaceutical Sciences,* 18th Edition, Mack Publishing Co., Pennsylvania, 1990; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of antagonist present in the formulation, and clinical parameters of the patients.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

V. Arcticles of Manufacture and Kits

In another aspect of the invention, a kit or an article of manufacture containing materials useful for the treatment, prevention, and/or diagnosis of individuals is provided.

In some instances, such kits or articles of manufacture can be used to identify an individual having a cancer (e.g., kidney cancer (e.g., RCC), lung cancer (e.g., NSCLC), bladder cancer (e.g., UBC), liver cancer (e.g., HCC), ovarian cancer, or breast cancer (e.g., TNBC)) who may benefit from an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., anti-PD-1 antibody)). In other instances, such articles of manufacture or kits can be used to identify an individual having a cancer (e.g., kidney cancer (e.g., RCC), lung cancer (e.g., NSCLC), bladder cancer (e.g., UBC), or breast cancer (e.g., TNBC)) who may benefit from an anti-cancer therapy that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). Such articles of manufacture or kits may include (a) reagents for determining the expression level of one or more genes set forth in Table 1, or any combination thereof (e.g., any combination set forth in any one of Tables 2-12) in a sample from the individual and (b) instructions for using the reagents to identify an individual having a cancer (e.g., lung cancer (e.g., NSCLC), bladder cancer (e.g., UBC), kidney cancer (e.g., RCC), liver cancer (e.g., HCC), ovarian cancer, or breast cancer (e.g., TNBC)) who may benefit from a treatment including a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab (MPDL3280A)) or a PD-1 binding antagonist (e.g., anti-PD-1 antibody)), or with an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))).

In one aspect, provided herein is a kit for identifying an individual having a cancer (e.g., a kidney cancer (e.g., RCC), a lung cancer (e.g., NSCLC), a bladder cancer (e.g., UBC), liver cancer (e.g., HCC), ovarian cancer, or a breast cancer (e.g., TNBC)) who may benefit from treatment with an anti-cancer therapy comprising a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., an anti-PD-L1 antibody, e.g., atezolizumab (MPDL3280A)) or a PD-1 binding antagonist (e.g., anti-PD-1 antibody)) that includes (a) reagents for determining the expression level of determining the expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the following genes in a sample from the individual: CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2; VEGFA, KDR, ESM1, PECAM1, FLT1, ANGPTL4, or CD34; or IL6, CXCL1, CXCL2, CXCL3, CXCL8, PTGS2, CXCR1, CXCR2, S100A8, or S100A9; and, optionally, (b) instructions for using the reagents to identify an individual having a cancer who may benefit from a treatment with an anti-cancer therapy comprising a VEGF antagonist and a PD-L1 axis binding antagonist.

Any of the preceding kits may include reagents for determining the expression level of one or more (e.g., 1, 2, 3, 4, 5, 6, 7, 8, 9, 10, 11, 12, 13, 14, 15, 16, 17, 18, 19, or 20) of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, or TAP2. In some embodiments, the kit includes reagents for determining the expression level of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or all twenty of CD8A, EOMES, GZMA, GZMB, PRF1, IFNG, PD-L1, CXCL9, CXCL10, CXCL11, CD27, FOXP3, PD-1, CTLA4, TIGIT, IDO1, PSMB8, PSMB9, TAP1, and TAP2.

For example, any of the preceding kits may include reagents for determining the expression level of one or more (e.g., 1, 2, 3, 4, or 5) of CD8A, EOMES, PRF1, IFNG, or PD-L1. In some embodiments, the kit includes determining the expression level of at least two, at least three, at least four, or all five of CD8A, EOMES, PRF1, IFNG, and PD-L1. In some embodiments, the kit includes reagents for determining the expression level of two of CD8A, EOMES, PRF1, IFNG, and PD-L1, for example, any of the exemplary combinations shown in Table 2. In some embodiments, the kit includes reagents for determining the expression level of three of CD8A, EOMES, PRF1, IFNG, and PD-L1, for example, any of the exemplary combinations shown in Table 3. In some embodiments, the kit includes reagents for determining the expression level of four of CD8A, EOMES, PRF1, IFNG, and PD-L1, for example, any of the exemplary combinations shown in Table 4. In some embodiments, the kit includes reagents for determining the expression level of CD8A, EOMES, PRF1, IFNG, and PD-L1.

In some embodiments, any of the preceding kits may include reagents for determining the expression level of PD-L1 and one or more additional genes, wherein the one or more additional genes is other than PD-L1. For example, in some embodiments, the kit may include reagents for determining the expression level of PD-L1 and one or more additional genes (e.g., 1,2,3,4,5,6,7,8,9,10,11,12,13,14,15, 16,17,18,19, 20, 21, 22, 23, 24, 25, 26, 27, 28, 29, 30, 31, 32, 33, 34, 35, or 36) selected from the group consisting of: CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, TAP2, VEGFA, KDR, ESM1, PECAM1, FLT1, ANGPTL4, CD34, IL6, CXCL1, CXCL2, CXCL3, CXCL8, PTGS2, CXCR1, CXCR2, S100A8, and S100A9. In some embodiments, the kit includes reagents for determining the expression level of PD-L1 and one or more (e.g., 1, 2, 3, 4, 5, 6, 7, 8, 9, 10, 11, 12, 13, 14, 15, 16, 17, 18, or 19) additional genes selected from the group consisting of CD8A, EOMES, GZMA, GZMB, PRF1, IFNG, CXCL9, CXCL10, CXCL11, CD27, FOXP3, PD-1, CTLA4, TIGIT, IDO1, PSMB8, PSMB9, TAP1, and TAP2. In other embodiments, the kit includes reagents for determining the expression level of PD-L1 and one or more (e.g., 1, 2, 3, 4, 5, 6, or 7) of VEGFA, KDR, ESM1, PECAM1, FLT1, ANGPTL4, or CD34. In other embodiments, the kit includes determining the expression level of PD-L1 and one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9.

Any of the preceding kits may include reagents for determining the expression level of one or more (e.g., 1, 2, 3, 4, 5, 6, or 7) of VEGFA, KDR, ESM1, PECAM1, FLT1, ANGPTL4, or CD34. In some embodiments, the kit includes reagents for determining the expression level of at least two, at least three, at least four, at least five, at least six, or all seven of VEGFA, KDR, ESM1, PECAM1, FLT1, ANGPTL4, or CD34. For example, in some embodiments, the kit includes reagents for determining the expression level of one or more of VEGFA, KDR, ESM1, PECAM1, ANGPTL4, or CD34. In some embodiments, the kit includes reagents for determining the expression level of at least two, at least three, at least four, at least five, or all six of VEGFA, KDR, ESM1, PECAM1, ANGPTL4, and CD34. In some embodiments, the kit includes reagents for determining the expression level of two of VEGFA, KDR, ESM1, PECAM1, ANGPTL4, and CD34, for example, any of the exemplary combinations shown in Table 5. In some embodiments, the kit includes reagents for determining the expression level of three of VEGFA, KDR, ESM1, PECAM1, ANGPTL4, and CD34, for example, any of the exemplary combinations shown in Table 6. In some embodiments, the kit includes reagents for determining the expression level of four of VEGFA, KDR, ESM1, PECAM1, ANGPTL4, and CD34, for example, any of the exemplary combinations shown in Table 7. In some embodiments, the kit includes reagents for determining the expression level of five of VEGFA, KDR, ESM1, PECAM1, ANGPTL4, and CD34, for example, any of the exemplary combinations shown in Table 8. In some embodiments, the kit includes reagents for determining the expression level of VEGFA, KDR, ESM1, PECAM1, ANGPTL4, and CD34.

Any of the preceding kits may include reagents for determining the expression level of one or more (e.g., 1, 2, 3, 4, 5, 6, 7, 8, 9, or 10) of IL6, CXCL1, CXCL2, CXCL3, CXCL8, PTGS2, CXCR1, CXCR2, S100A8, or S100A9. In some embodiments, the kit includes reagents for determining the expression level of at least two, at least three, at least four, at least five, or all six of IL6, CXCL1, CXCL2, CXCL3, CXCL8, PTGS2, CXCR1, CXCR2, S100A8, and S100A9. In some embodiments, the kit includes reagents for determining the expression level of two of IL6, CXCL1, CXCL2, CXCL3, CXCL8, PTGS2, CXCR1, CXCR2, S100A8, and S100A9, for example, any of the exemplary combinations shown in Table 9. In some embodiments, the kit includes reagents for determining the expression level of three of IL6, CXCL1, CXCL2, CXCL3, CXCL8, PTGS2, CXCR1, CXCR2, S100A8, and S100A9, for example, any of the exemplary combinations shown in Table 10. In some embodiments, the kit includes reagents for determining the expression level of four of IL6, CXCL1, CXCL2, CXCL3, CXCL8, PTGS2, CXCR1, CXCR2, S100A8, and S100A9, for example, any of the exemplary combinations shown in Table 11. In some embodiments, the kit includes reagents for determining the expression level of five of IL6, CXCL1, CXCL2, CXCL3, CXCL8, PTGS2, CXCR1, CXCR2, S100A8, and S100A9, for example, any of the exemplary combinations shown in Table 12. In some embodiments, the kit includes reagents for determining the expression level of six of IL6, CXCL1, CXCL2, CXCL3, CXCL8, PTGS2, CXCR1, CXCR2, S100A8, and S100A9, for example, any of the exemplary combinations shown in Table 13. In some embodiments, the kit includes reagents for determining the expression level of seven of IL6, CXCL1, CXCL2, CXCL3, CXCL8, PTGS2, CXCR1, CXCR2, S100A8, and S100A9, for example, any of the exemplary combinations shown in Table 14. In some embodiments, the kit includes reagents for determining the expression level of eight of IL6, CXCL1, CXCL2, CXCL3, CXCL8, PTGS2, CXCR1, CXCR2, S100A8, and S100A9, for example, any of the exemplary combinations shown in Table 15. In some embodiments, the kit includes reagents for determining the expression level of nine of IL6, CXCL1, CXCL2, CXCL3, CXCL8, PTGS2, CXCR1, CXCR2, S100A8, and S100A9, for example, any of the exemplary combinations shown in Table 16. In some embodiments, the kit includes reagents for determining the expression level of IL6, CXCL1, CXCL2, CXCL3, CXCL8, PTGS2, CXCR1, CXCR2, S100A8, and S100A9.

In one aspect, provided herein is a kit for identifying an individual having a cancer (e.g., a kidney cancer (e.g., RCC), a lung cancer (e.g., NSCLC), a bladder cancer (e.g., UBC), liver cancer (e.g., HCC), ovarian cancer, or a breast cancer (e.g., TNBC)) who may benefit from treatment with an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) that includes (a) reagents for determining the expression level of determining the expression level of one or more (e.g., 1, 2, 3, 4, 5, 6, or 7) of the following genes in a sample from the individual: VEGFA, KDR, ESM1, PECAM1, FLT1, ANGPTL4, or CD34; and, optionally, (b) instructions for using the reagents to identify an individual having a cancer who may benefit from a treatment with an anti-cancer therapy comprising an angiogenesis inhibitor.

In some embodiments, the kit includes reagents for determining the expression level of at least two, at least three, at least four, at least five, at least six, or all seven of VEGFA, KDR, ESM1, PECAM1, FLT1, ANGPTL4, or CD34. For example, in some embodiments, the kit includes reagents for determining the expression level of one or more of VEGFA, KDR, ESM1, PECAM1, ANGPTL4, or CD34. In some embodiments, the kit includes reagents for determining the expression level of at least two, at least three, at least four, at least five, or all six of VEGFA, KDR, ESM1, PECAM1, ANGPTL4, and CD34. In some embodiments, the kit includes reagents for determining the expression level of two of VEGFA, KDR, ESM1, PECAM1, ANGPTL4, and CD34, for example, any of the exemplary combinations shown in Table 5. In some embodiments, the kit includes reagents for determining the expression level of three of VEGFA, KDR, ESM1, PECAM1, ANGPTL4, and CD34, for example, any of the exemplary combinations shown in Table 6. In some embodiments, the kit includes reagents for determining the expression level of four of VEGFA, KDR, ESM1, PECAM1, ANGPTL4, and CD34, for example, any of the exemplary combinations shown in Table 7. In some embodiments, the kit includes reagents for determining the expression level of five of VEGFA, KDR, ESM1, PECAM1, ANGPTL4, and CD34, for example, any of the exemplary combinations shown in Table 8. In some embodiments, the kit includes reagents for determining the expression level of VEGFA, KDR, ESM1, PECAM1, ANGPTL4, and CD34.

In some instances, such kits or articles of manufacture include a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist, e.g., an anti-PD-L1 antibody, e.g., atezolizumab (MPDL3280A)) for treating an individual with a cancer (e.g., lung cancer (e.g., NSCLC), bladder cancer (e.g., UBC), kidney cancer (e.g., RCC), liver cancer (e.g., HCC), ovarian cancer, or breast cancer (e.g., TNBC)). In some instances, such articles of manufacture or kits further include a package insert including instructions for administration of an anti-cancer therapy comprising the VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and the PD-L1 axis binding antagonist (e.g., a PD-L1 binding antagonist, e.g., an anti-PD-L1 antibody, e.g., atezolizumab (MPDL3280A)) to an individual having a cancer (e.g., lung cancer (e.g., NSCLC), bladder cancer (e.g., UBC), kidney cancer (e.g., RCC), liver cancer (e.g., HCC), ovarian cancer, or breast cancer (e.g., TNBC)), wherein the patient is identified as one who may benefit from the anti-cancer therapy by any of the methods and/or kits described herein.

In other instances, such kits or articles of manufacture include an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))) for treating an individual with a cancer (e.g., lung cancer (e.g., NSCLC), bladder cancer (e.g., UBC), kidney cancer (e.g., RCC), liver cancer (e.g., HCC), ovarian cancer, or breast cancer (e.g., TNBC)) for treating an individual with a cancer (e.g., lung cancer (e.g., NSCLC), bladder cancer (e.g., UBC), kidney cancer (e.g., RCC), liver cancer (e.g., HCC), ovarian cancer, or breast cancer (e.g., TNBC)). In some instances, such articles of manufacture or kits further include a package insert including instructions for administration of an anti-cancer therapy comprising the an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))), wherein the patient is identified as one who may benefit from the anti-cancer therapy by any of the methods and/or kits described herein.

In other instances, such kits or articles of manufacture include a PD-L1 axis binding antagonist (e.g., a PD-L1 binding antagonist, e.g., an anti-PD-L1 antibody, e.g., atezolizumab (MPDL3280A), or a PD-1 binding antagonist, e.g., an anti-PD-1 antibody) monotherapy for treating an individual with a cancer (e.g., lung cancer (e.g., NSCLC), bladder cancer (e.g., UBC), kidney cancer (e.g., RCC), liver cancer (e.g., HCC), ovarian cancer, or breast cancer (e.g., TNBC)) for treating an individual with a cancer (e.g., lung cancer (e.g., NSCLC), bladder cancer (e.g., UBC), kidney cancer (e.g., RCC), liver cancer (e.g., HCC), ovarian cancer, or breast cancer (e.g., TNBC)). In some instances, such articles of manufacture or kits further include a package insert including instructions for administration of the PD-L1 axis binding antagonist monotherapy, wherein the patient is identified as one who may benefit from the anti-cancer therapy by any of the methods and/or kits described herein.

Any of the kits or articles of manufacture described may include a carrier means being compartmentalized to receive in close confinement one or more container means such as vials, tubes, and the like, each of the container means comprising one of the separate elements to be used in the method. Where the article of manufacture or kit utilizes nucleic acid hybridization to detect the target nucleic acid, the kit may also have containers containing nucleotide(s) for amplification of the target nucleic acid sequence and/or a container comprising a reporter-means, such as an enzymatic, florescent, or radioisotope label.

In some instances, the article of manufacture or kit includes the container described above and one or more other containers including materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above. For example, the article of manufacture or kit may further include a container including a pharmaceutically-acceptable buffer, such as bacteriostatic water for injection (BWFI), phosphate-buffered saline, Ringer's solution, and dextrose solution.

The kits or articles of manufacture described herein may have a number of embodiments. In one instance, the kits or articles of manufacture includes a container, a label on said container, and a composition contained within said container, wherein the composition includes one or more polynucleotides that hybridize to a complement of a gene listed herein (e.g., a gene set forth in Table 1, or any combination of genes set forth in Tables 2-12) under stringent conditions, and the label on said container indicates that the composition can be used to evaluate the presence of a gene listed herein (e.g., a gene set forth in Table 1, or any combination of genes set forth in Tables 2-12) in a sample, and wherein the kit includes instructions for using the polynucleotide(s) for evaluating the presence of the gene RNA or DNA in a particular sample type.

For oligonucleotide-based articles of manufacture or kits, the article of manufacture or kit can include, for example: (1) an oligonucleotide, e.g., a detectably labeled oligonucleotide, which hybridizes to a nucleic acid sequence encoding a protein or (2) a pair of primers useful for amplifying a nucleic acid molecule. The article of manufacture or kit can also include, e.g., a buffering agent, a preservative, or a protein stabilizing agent. The article of manufacture or kit can further include components necessary for detecting the detectable label (e.g., an enzyme or a substrate). The article of manufacture or kit can also contain a control sample or a series of control samples that can be assayed and compared to the test sample. Each component of the article of manufacture or kit can be enclosed within an individual container and all of the various containers can be within a single package, along with instructions for interpreting the results of the assays performed using the kit.

VI. Examples

The following is an example of the methods of the invention. It is understood that various other embodiments may be practiced, given the general description provided above.

Example 1

Materials and Experimental Methods

A. Study Design

The goal of the phase Ib study described in Examples 1-4 was to evaluate the safety and tolerability of the anti-PD-L1 antibody atezolizumab, in combination with bevacizumab, a human, monoclonal, engineered anti-VEGF antibody concurrently administered by intravenous infusion every 3 weeks (q3w) to patients with previously untreated advanced metastatic renal cell carcinoma (mRCC). Treatment was continued as long as patients were experiencing clinical benefit in the opinion of the investigator (i.e. in the absence of unacceptable toxicity or symptomatic deterioration attributed to disease progression). Patients were allowed to continue to receive study treatment at the discretion of the investigator if pseudoprogression was suspected or if there was evidence of a mixed response. Study objectives included an evaluation of tumor and circulating pharmacodynamic markers associated with the administration of bevacizumab and atezolizumab and preliminary assessment of the antitumor activity of the treatment combination.

Safety evaluations (clinical and laboratory) were performed at screening and throughout the trial. A final evaluation occurred by 30 days after the last dose. The incidence, nature and severity of adverse events (AEs) were graded according to National Cancer Institute Common Terminology Criteria for Adverse Events (CTCAE), version 4.0.

Any evaluable or measurable disease was documented at screening and reassessed at each tumor evaluation. Tumor evaluations were performed at the ends of cycles 2, 4, 6, 8, 12 and 16 or as clinically indicated. Assessments were performed during the last week of the drug administration cycle and before the start of treatment in the next cycle. Patients who discontinued study treatment for reasons other than disease progression continued to have tumor assessments every 12 weeks until the patient experienced disease progression, initiated further systemic cancer therapy, or died.

Protocol-defined dose-limiting toxicity (DLT) criteria included standard Grade 3 or 4 hematologic and non-hematologic toxicities. Dosing commenced with the recommended Phase 2 dose of atezolizumab administered in combination with the labeled q3w dose of bevacizumab, and no DLTs were reported.

B. Patients

Patients were eligible to participate in this cohort of the phase Ib study if they had advanced or metastatic RCC for which they had not received prior systemic therapy. Patients were required to be at least 18 years old; have adequate hematological and end-organ function; and have an Eastern Cooperative Oncology Group performance status of 0 or 1. Disease had to be measurable per Response Evaluation Criteria in Solid Tumors (RECIST). Patients with known primary central nervous system (CNS) malignancy or symptomatic CNS metastases, history or risk of autoimmune disease, or history of human immunodeficiency virus, hepatitis B, or hepatitis C infection were excluded. Also excluded were patients who received prior treatment with anti-CTLA-4, anti-PD-1, or anti-PD-L1 therapeutic antibodies or pathway-targeting agents as well as patients who were treated with systemic immunostimulatory agents or systemic immunosuppressive medications within a specified period before study start.

Of the ten patients on study, six yielded biopsies with sufficient viable tumor cells at both post treatment time points. Of the six pairs (i.e., biopsies from the same patient at both on-treatment time points), seven were derived from kidney lesions, four from the abdominal/chest wall, one from a lung lesion, one from lymph node, and five were from undisclosed lesions.

C. Immunohistochemical Analysis for PD-L1, CD8, and MHC-I

Formalin-fixed, paraffin-embedded (FFPE) tissue sections of 4 μm thickness were stained for PD-L1 with an anti-human PD-L1 rabbit monoclonal antibody (clone SP142; Ventana, Tucson, Ariz.) on an automated staining platform (BenchMark; Ventana) using a concentration of 4.3 mg/ml, with signal visualization by diaminobenzidine; sections were counter-stained with haematoxylin. PD-L1 expression was evaluated on tumor cells and tumor-infiltrating immune cells. For tumor cells, the proportion of PD-L1-positive tumor cells was estimated as a percentage of the total number of tumor cells; tumor cells typically showed membranous staining with a variably strong component of cytoplasmic staining. The distribution of PD-L1-positive tumor cells within a given tumor sample was typically very focal; in tumors growing as solid aggregates, PD-L1-positive tumor cells were more commonly observed at the interface between malignant cells and stroma containing tumor-infiltrating immune cells. For tumor-infiltrating immune cells, the percentage of PD-L1-positive tumor-infiltrating immune cells occupying the tumor was determined. Tumor-infiltrating immune cells with clearly discernible cytoplasm, such as macrophages and dendritic cells, showed a membranous staining pattern for PD-L1. This was more difficult to determine for cells of small lymphoid morphology with scant amounts of cytoplasm. PD-L1-positive tumor-infiltrating immune cells were typically seen as variably-sized aggregates towards the periphery of the tumor mass, in stromal bands dissecting the tumor mass, as single cells scattered in stroma, or within tumor-infiltrating immune cell aggregates. Specimens were scored as IHC 0, 1, 2, or 3 if <1%, ≥1% but <5%, ≥5% but <10%, or ≥10% of cells per area were PD-L1 positive, respectively. PD-L1 IHC scores in patients with multiple specimens were based on the highest score. CD8 (clone SP16 (Epitomics)) IHC was performed on a Discovery XT autostainer (Ventana) using CC1 antigen retrieval and OMNIMAP™ (Ventana) detection technology.

All MHC-I IHC steps were carried out on the Ventana Discovery XT automated platform (Ventana Medical Systems; Tucson, Ariz.). Sections were treated with Cell Conditioner 1, standard time, and then incubated in primary antibody, MHC Class I (EP1395Y, Novus, cat. # NB110-57201) at a 1:5000 dilution for 60 min at 37° C. Bound primary antibody was detected by the OMNIMAP™ anti-rabbit HRP detection kit, followed by DAB (Ventana Medical Systems; Tucson, Ariz.). Sections were counterstained with Hematoxylin II (Ventana Medical Systems; Tucson, Ariz.) for 4 min, bluing solution for 4 min, then dehydrated and cover-slipped. Human cell pellets endogenously expressing low, medium, and high MHC-I were used in parallel as positive controls. Negative controls were performed using rabbit monoclonal (Clone DA1 E, Cell Signaling Technology, Cat #39005) isotype antibody. MHC-I staining in tumor cells was scored using an H-score system. Briefly, staining intensity of tumor cell membranes was assigned a numerical value of 0, 1, 2, or 3 corresponding to no, low, medium, or high 3,3'-diaminobenzidine (DAB) signal intensity, respectively. Relative to the overall tumor area, the percentage of cells at different staining intensities was determined by visual assessment. A final score was calculated by multiplying the membrane intensity score by the area percentage for each population present in a given tumor sample as follows: 1×(% of 1+cells)+2×(% of 2+cells)+3×(% of 3+cells)=H score. Cases were scored by two independent pathologists. Scoring brackets were defined as scores of ≤00, 101-200, and 201-300, and concordance was defined as independent scores falling within the same bracket. Any discordance was resolved upon mutual review of the cases.

D. Dual- and Triple-Color Immunohistochemistry and a Whole Slide Digital Analysis Consecutive 4 μm thickness sections of FFPE tumor tissues were stained with the following in-house developed IHC assays using Ventana Benchmark XT or Benchmark Ultra automated platforms (Ventana Medical Systems; Tucson, Ariz.): Ki67/CD8, PDPN/CD34/ASMA, and CD163/CD68.

For the Ki67/CD8 assay, sections were treated with Cell Conditioner 1 for 64 min. Sections were then incubated in primary antibody, Ki67 (30-9, RTU, Ventana) for 4 min at 37° C. Bound primary antibody was detected by the OptiView DAB IHC detection kit (Ventana Medical Systems; Tucson, Ariz.). Subsequently, slides were incubated in primary antibody anti-CD8 (SP239, Spring Biosciences) at a 1:100 dilution for 60 min at 37° C. Bound primary antibody was detected by the UltraView Universal AP Red detection kit (Ventana Medical Systems; Tucson, Ariz.). Sections were counterstained with Hematoxylin II (Ventana Medical Systems; Tucson, Ariz.) for 4 min, bluing solution for 4 min, then dehydrated and cover-slipped.

For the PDPN/CD34/ASMA assay, sections were treated with Cell Conditioner 1 for 32 min. Sections were then incubated in the primary antibody anti-Podoplanin (D2-40, RTU, Ventana) for 16 min at 37° C. Bound primary antibody was detected by the OptiView DAB IHC detection kit (Ventana Medical Systems; Tucson, Ariz.). Subsequently, slides were incubated in primary antibody anti-CD34 (QBEnd/10; RTU, Ventana) for 16 min at 37° C. Bound primary antibody was detected by the iView Blue Plus detection kit (Ventana Medical Systems; Tucson, Ariz.). Finally, slides were incubated in primary antibody anti-smooth muscle actin ("SMActin") (1A4; RTU, Ventana) for 16 min at 37° C. Bound primary antibody was detected by the UltraView Universal AP Red detection kit (Ventana Medical Systems; Tucson, Ariz.). Sections were counterstained with Hematoxylin II (Ventana Medical Systems; Tucson, Ariz.) for 4 min, bluing solution for 4 min, then dehydrated and cover-slipped.

For the CD163/CD68 assay, sections were treated with Cell Conditioner 1 for 32 min and incubated in primary antibody anti-CD163 (MRQ-26, RTU, Ventana), for 8 min at 37° C. Bound primary antibody was detected by the OptiView DAB IHC detection kit (Ventana Medical Systems; Tucson, Ariz.). Subsequently, slides were incubated in primary antibody anti-CD68 (KP-1, RTU, Ventana) for 8 min at 37° C. Bound primary antibody was detected by the UltraView Universal AP Red detection kit (Ventana Medical Systems; Tucson, Ariz.). Sections were counterstained with Hematoxylin II (Ventana Medical Systems; Tucson, Ariz.) for 4 min, bluing solution for 4 min, then dehydrated and cover-slipped. Appropriate negative and positive controls were performed according to known methods.

Algorithms for the detection and classification of IHC-stained objects on a whole slide basis were written in Matlab. Following brightfield stain unmixing, IHC-stained objects were detected as cell candidates. For all cell candidates, quantitative features were extracted. Candidates were then classified into the various cell classes (e.g. $CD8^+/Ki67^-$ cells) using supervised machine learning. The classification method was trained using a ground truth gallery of true and false stained objects (provided by a pathologist). Finally, classified cells and tumor areas (provided by a pathologist through digital slide annotation) were reported and quality control (QC) images were generated for pathology review. The results of automated digital slide analysis were reported for tumor areas as follows: $Ki67^-/CD8^+$ and $Ki67^+/CD8^+$ cell densities (number of cell counts per $mm^2$), $CD68^+/CD163^+$ and $CD68^+/CD163^-$ percent of area coverage (area coverage in relation to the whole tumor area), $CD34^+/\alpha SMA^-$ and $CD34^+/\alpha SMA^+$ vessel densities (vessel count per $mm^2$).

E. RNA Isolation from FFPE Tumor Tissue

RNA isolation was performed as described by Schleifman et al. (*PLoS One* 8:e74231, 2014). Briefly, tumor FFPE sections were macro dissected to enrich for neoplastic tissue, and tissue was lysed using tumor lysis buffer and Proteinase K to allow for complete digestion and release of nucleic acids. RNA was isolated using the High Pure FFPE RNA Micro Kit (Roche Applied Sciences, Indianapolis, Ind.) according to the manufacturer's protocol. DNA was isolated using the QIAAMP® DNA FFPE Tissue Kit (Qiagen, Hilden, Germany) according to the manufacturer's protocol. RNA and DNA were stored at 280 uC until the analyses were performed.

F. Fluidigm and Nanostring Expression Analysis

Gene-expression analysis was performed using the BioMark HD™ real-time PCR Platform (Fluidigm) as described by Schleifman et al. (*PLoS One* 8:e74231, 2014). All TAQMAN® assays in the expression panel used FAM™ dye-labeled TAQMAN® minor groove binder (MGB) probes and ordered through Life Technologies either made-to-order or custom-designed, including four reference genes: SP2, GUSB, TMEM55B and VPS33B. A geometric median of the Ct values for the four reference genes (SP2, GUSB, TMEM55B and VPS33B) was calculated for each sample, and expression levels were determined using the delta Ct ($\Delta$Ct) method as follows: Ct (target Gene)2GeoMedian Ct (reference genes). Median mRNA expression levels (as measured by immunochip (iChip)) across patients on study were used as cutoffs to derive high- versus low-expression categorization. P values were determined by t test.

NanoString gene expression data were processed using the R/Bioconductor package "NanoStringQCPro." Raw counts were adjusted by positive control counts before probe- and lane-specific background was calculated based on both negative controls and blank measurements. After background correction, counts were $\log_2$ transformed and normalized by housekeeping gene expression (TMEM55B, VPS33B, TBP, and TUBB).

G. TCR Sequencing

The amplification and sequencing of TCR6 repertoire were performed at Adaptive Biotechnologies as described by Klinger et al. (*PLoS One* 8:e74231, 2013).

H. Flow Cytometry

Whole blood flow cytometry for CD3, CD8, HLA-DR, and Ki-67 expression was performed at LabCorp central laboratory according to established protocols. Peripheral blood mononuclear cells (PBMCs) were isolated at Precision Bioservices and cryopreserved samples were shipped to Genentech for analysis of fractalkine receptor expression and detection of tumor-specific T cells. PBMCs were thawed and rested overnight, and a small aliquot of cells were stained with anti-HLA-A2-FITC (BB7.2, BD) and anti-CD45-APC-H7 (2D1, BD) to determine HLA-A2 status. The remaining cells were stained with a mixture of HLA-A*0201/peptide dextramers and pentamers (Immudex and Proimmune, see Table 18) for 10 min at room temperature followed by staining with anti-CD3-BV510 (UCHT1, Biolegend), anti-CD8-A700 (RPA-T8, BD), anti-CD4-PE-Cy7 (RPA-T4, eBioscience), anti-CD45RA-eVolve605 (HI100, eBioscience), anti-CCR7-BV421 (G043H7, Biolegend), anti-CX3CR1-PerCP-eFluor710 (2A9-1, eBioscience), and Fixable Viability Dye eFluor780 (eBioscience) for 30 minutes on ice. Samples were washed twice prior to data acquisition and sorting on a BD FACSARIA™ running FACSDIVA™ v8 software. A minimum of 10 dextramer-positive events out of 50,000 CD8$^+$ T cells is considered a tumor-specific response. Table 18 shows a list of dextramers used for flow cytometry.

TABLE 18

| Dextramers for flow cytometry RCC-specific/associated antigens | | |
|---|---|---|
| Dex-FITC | Dex-PE | Dex-APC |
| APOL1 | MAGE-A1 | G250 217-225 |
| APOL1 | PRAME-1 | NY-ESO-1 |
| MUC-1 12-20 | PRAME-2 | PRAME-4 |
| MUC-1 13-21 | PRAME-3 | PRAME-5 |
| SSX-2 | Survivin | PRAME-6 |

TABLE 18-continued

| Dextramers for flow cytometry RCC-specific/associated antigens | | |
|---|---|---|
| Dex-FITC | Dex-PE | Dex-APC |
| SSX-2 | CCND1 | Survivin |
| DLK1 | Hsp70-2 | MET |
| EphA2 | IDO | PLIN |
| NRP1 | FLT1 | PRUNE2 |
| TEM1 | KDR | |

I. Statistical Analysis

Data from all ten patients with RCC who received more than one dose of atezolizumab and bevacizumab intravenously every 21 days were used to determine baseline characteristics and rates of adverse events. Efficacy was assessed according to RECIST v1.1. The best confirmed overall objective response rate was derived from investigator-reported assessments. Objective response rate (ORR) was defined as the number of patients with a best overall objective response of complete or partial response divided by the total number of patients with a baseline tumor assessment.

Patients who were alive and did not experience disease progression at the cutoff date were censored at the time of last tumor assessment. Duration of response was obtained by Kaplan Meier method. Summaries of all AEs, AEs related to treatment, and grade 3-4 AEs are provided from all ten patients.

Example 2

Figure 1:
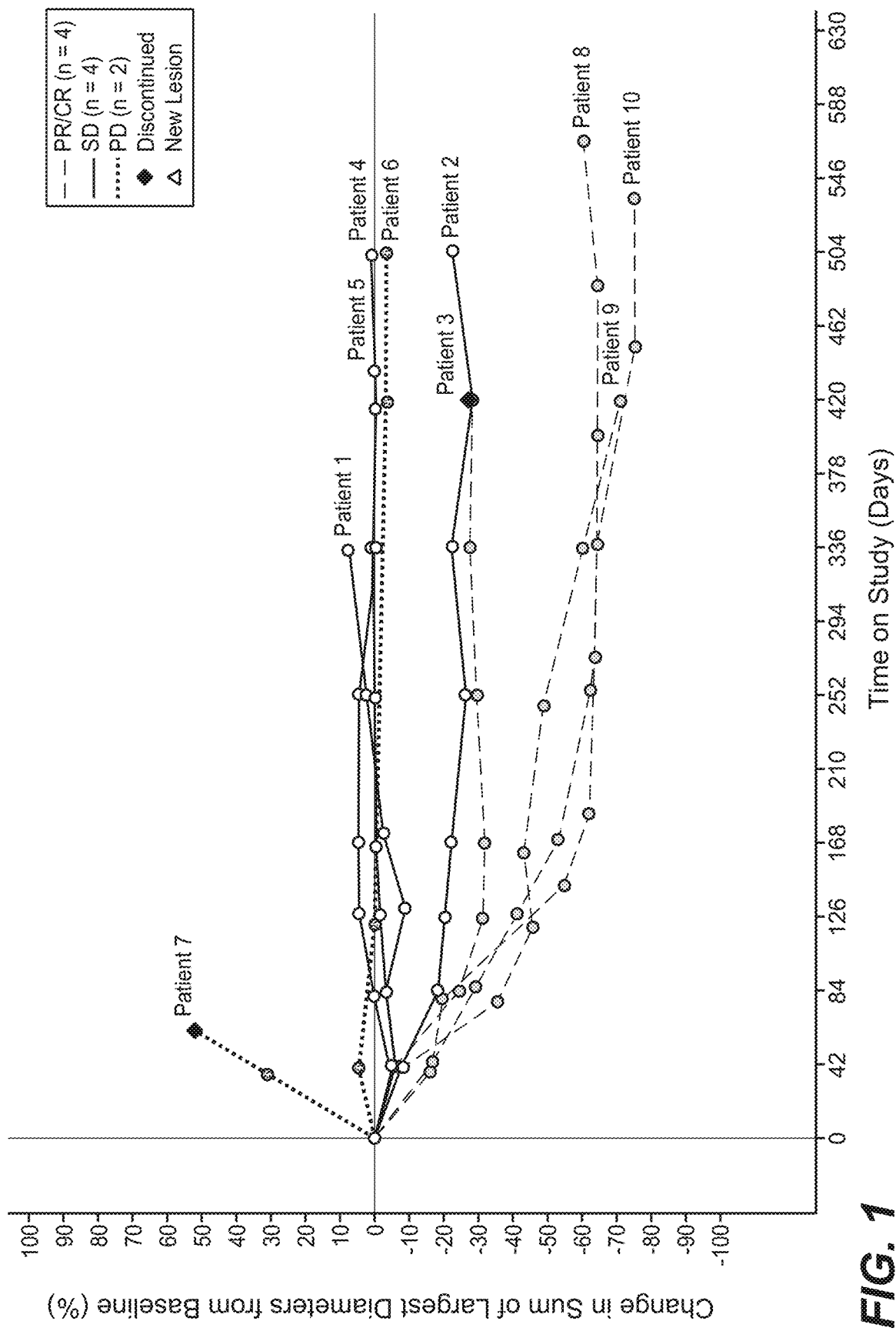
FIG. 1 is a graph showing the tumor burden over time among renal cell carcinoma (RCC) patients receiving atezolizumab and bevacizumab combination treatment. Points on the graph show the maximum reduction from baseline in the sum of the longest diameter (SLD) for target lesions. PR, partial response; PD, progressive disease; SD, stable disease.
Figure 2:
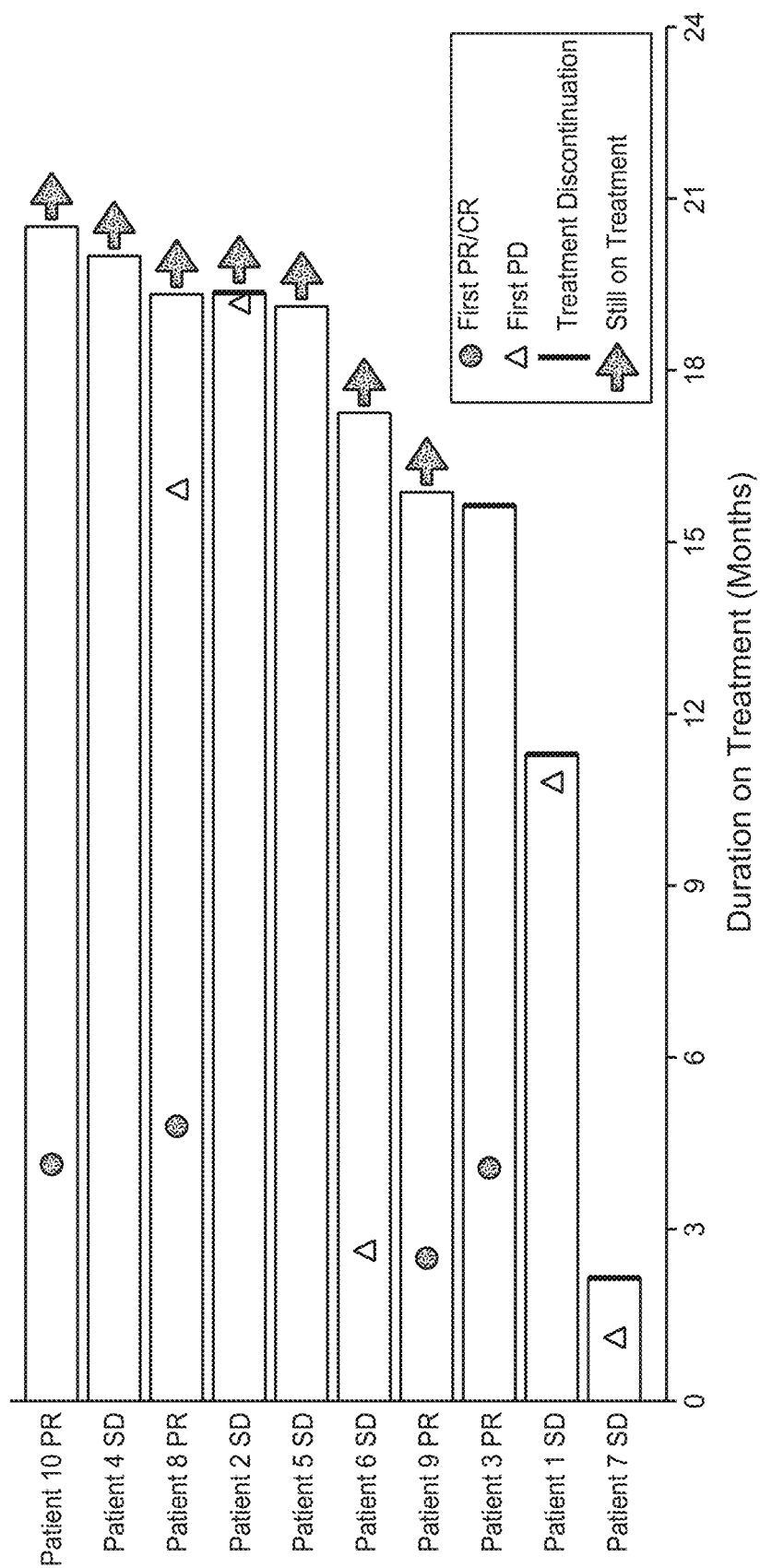
FIG. 2 is a graph showing the duration of study treatment for each RCC patient. Time of first PR or CR is indicated with a circle; time of first PD is indicated with a triangle; treatment discontinuation is indicated with a black bar; and patients still on treatment as of the time of analysis are identified with an arrow.

Gene Expression Analysis Identifies Biomarkers Associated with Bevacizumab Monotherapy and Bevacizumab and Atezolizumab Combination Therapy A phase 1 b clinical study was performed in which 10 patients with previously untreated mRCC received a single dose of bevacizumab on C1D1, followed by combined administration of atezolizumab and bevacizumab every three weeks beginning on C2D1. Baseline demographics of the patient cohort are shown in Table 19. Partial responses (PR) were observed in four out of ten patients using RECIST v1.1, while an additional five patients had prolonged stable disease (SD) (FIGS. 1 and 2). The clinical activity observed in this small cohort was higher than previously obtained with either monotherapy. The duration of response has not been reached and the median time to response was 4.2 months.

TABLE 19

| Baseline Demographics | |
|---|---|
| Characteristics | N = 10 |
| Median age (range), y | 62 (42-74) |
| Male, n (%) | 7 (70%) |
| Patients with metastatic disease, n (%) | 8 (80%) |
| Liver or lung | 5 (50%) |
| Other than liver | 6 (60%) |

In addition to safety, tolerability, and clinical activity, one key objective of the phase Ib study described above was to evaluate the mechanism of combination activity. The trial design included a run-in period with bevacizumab to specifically interrogate the effects of bevacizumab on the local tumor immune microenvironment, followed by combination therapy with immune checkpoint blockade using atezolizumab. Tumor biopsies and blood were collected prior to treatment, 15-18 days following bevacizumab, and 4-6 weeks after the atezolizumab and bevacizumab combination treatment had been initiated.

Figure 3:
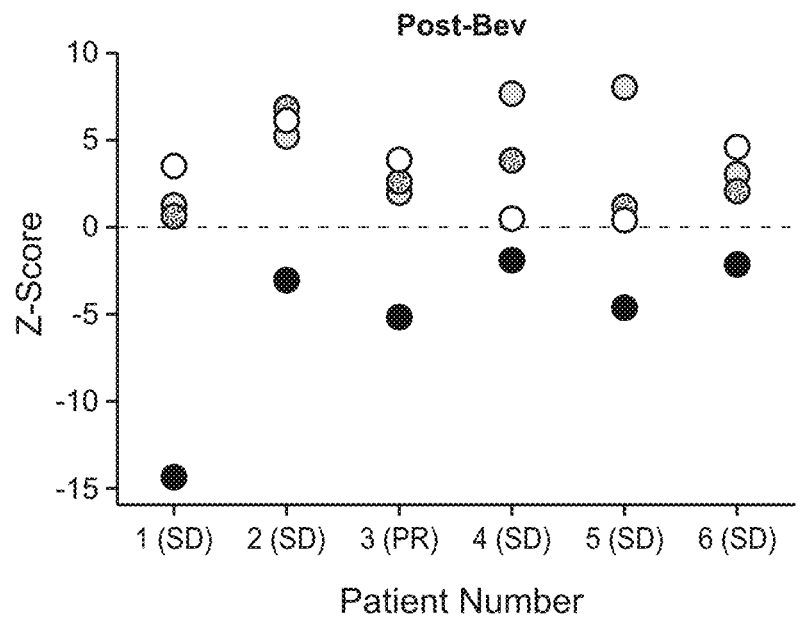
FIG. 3 is a graph showing gene expression levels of tumor biomarkers following bevacizumab ("Bev") treatment. The expression levels of on-treatment tumor samples are shown relative to the baseline expression levels (pre-treatment). Vascular signature genes (ANGPT2, CD34, DLL4, EGFL7, and ESM1) are shown in black, CD8 T cell effector genes (CD8A, CD8B, EOMES, GZMA, IFNG, and PRF1) are shown in patterned gray, Th1 chemokines (CXCL10, CXCL11, CXCL13, and CXCL9) are shown in white, and natural killer (NK) cell genes (GZMB, KLRK1, and SLAMF7) are shown in solid gray.

To identify tumor markers associated with bevacizumab monotherapy or combination therapy, gene expression analysis was performed using both a 90 gene PCR-based Fluidigm panel and an 800 gene custom NanoString panel. Genes associated with the neo-vasculature, which reflect VEGF downstream signaling activity, were significantly decreased at both on-treatment time points in all patients (FIG. 3), confirming anti-angiogenic activity of bevacizumab. Surprisingly, comparison of the pre-treatment time point and the bevacizumab treatment alone time point revealed that there was increased gene expression of Th1 chemokines (CXCL9, CXLC10, CXCL11, and CXCL13) (ranging from about 0.7-fold to 6.9-fold relative to pre-treatment levels), CD8 T-effector markers (CD8A, CD8B, EOMES, GZMA, GZMB, IFNG, and PRF1) (ranging from about 0.4-fold to 6.2-fold relative to pre-treatment levels), as well as NK cell markers (GZMB, KLRK1, and SLAMF7) (ranging from about 0.7-fold to 8.2-fold relative to pre-treatment levels) (FIG. 3). Bevacizumab treatment resulted in four of the six patients showing a significant increase in gene signatures related to Th1 signaling. Importantly, at the individual patient level, these signatures were delinked from the degree of reduction of the VEGF dependent signature. FasL expression by IHC has been described as a potential barrier to immune cells in several cancers including RCC (Motz et al. *Nat. Med.* 20:607-615, 2014). In this study, consistent changes in FasL gene expression with bevacizumab or combination treatment were not observed. Overall, these differences indicate that bevacizumab treatment alone results in modulation of tumor immune microenvironment with Th1-related signatures reflecting the most significant treatment-induced alterations in the tumor microenvironment.

Figure 4:
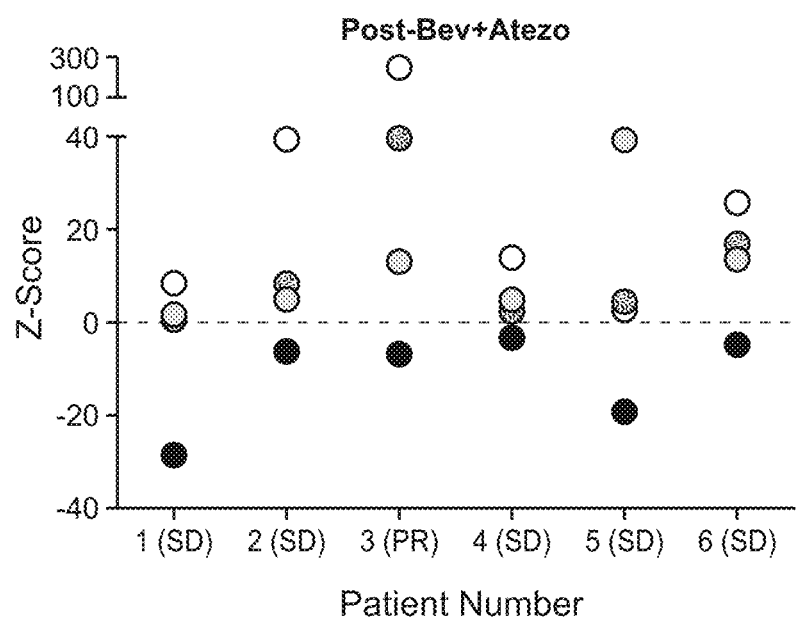
FIG. 4 is a graph showing gene expression levels of tumor biomarkers following atezolizumab and bevacizumab combination ("Bev+Atezo") treatment. The expression levels of on-treatment tumor samples are shown relative to the baseline expression levels (pre-treatment). Vascular signature genes (ANGPT2, CD34, DLL4, EGFL7, and ESM1) are shown in black, CD8 T cell effector genes (CD8A, CD8B, EOMES, GZMA, IFNG, and PRF1) are shown in patterned gray, Th1 chemokines (CXCL10, CXCL11, CXCL13, and CXCL9) are shown in white, and NK cell genes (GZMB, KLRK1, and SLAMF7) are shown in solid gray.

The increased expression of Th1 chemokines (CXCL9, CXLC10, CXCL11, and CXCL13), CD8 T-effector markers (CD8A, CD8B, EOMES, GZMA, GZMB, IFNG, and PRF1), and NK cell markers (GZMB, KLRK1, and SLAMF7) were enhanced upon administration of atezolizumab in combination with bevacizumab (FIG. 4). The expression level of the Th1 chemokine signature was increased 2.9- to 250.4-fold at the bevacizumab+atezolizumab time point relative to pre-treatment, and increased 0.9- to 81.8-fold compared to the bevacizumab alone time point. The expression level of the CD8 Teff signature was increased 0.8- to 51.8-fold at the bevacizumab+atezolizumab time point relative to pre-treatment, and increased 0.3- to 17.6-fold compared to the bevacizumab alone time point. The expression level of the NK cell signature was increased 0.7- to 7.8-fold at the bevacizumab+atezolizumab time point relative to pre-treatment, and increased 0.4- to 13.1-fold compared to the bevacizumab alone time point.

Example 3

Figure 5:
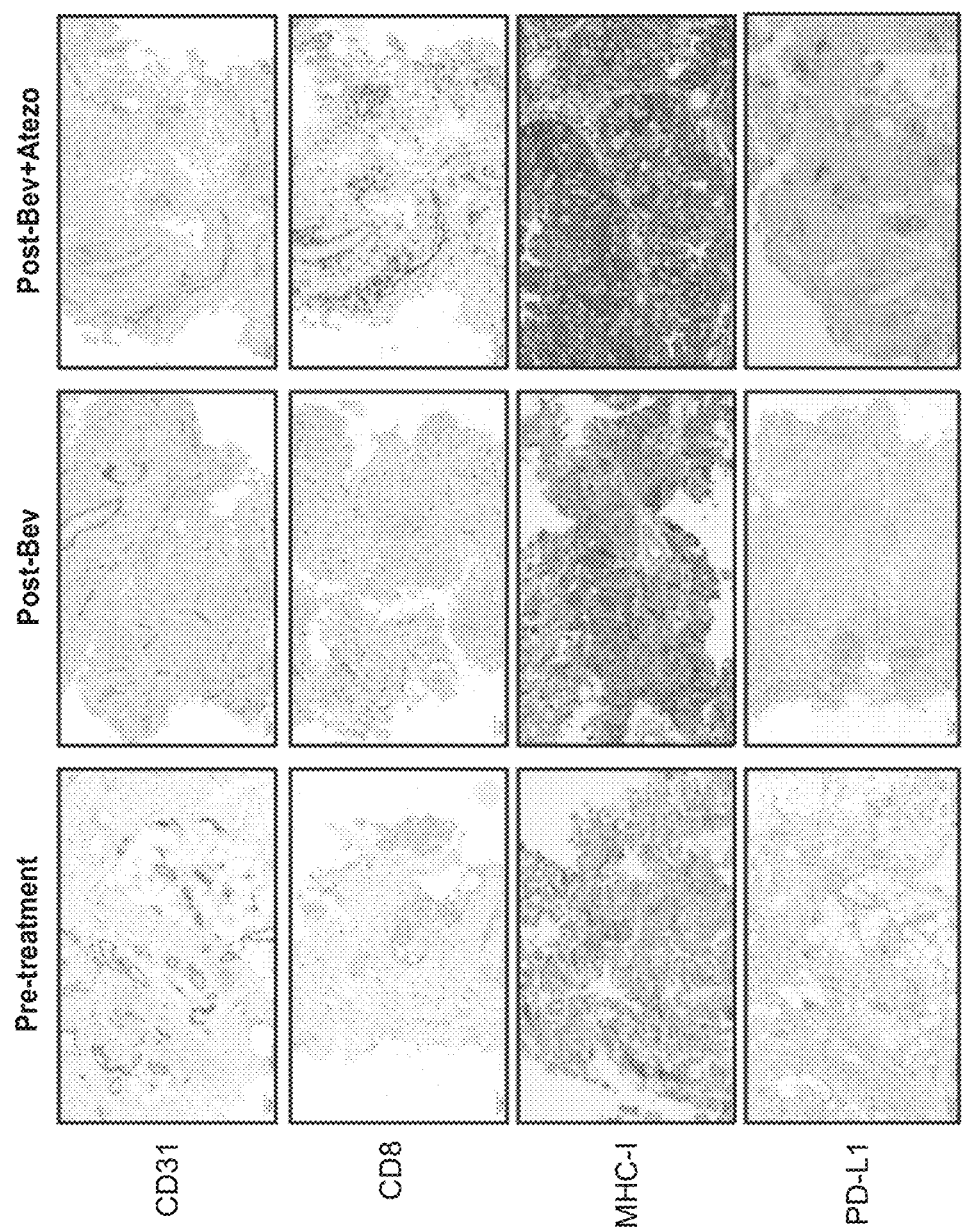
FIG. 5 is a series of representative images showing protein expression of immune and vasculature markers in tumor samples from patient 3, as assessed by immunohistochemistry (IHC). CD31 is stained dark gray (first row), CD8 is stained dark gray (second row), MHC-I is stained dark gray (third row), and PD-L1 is stained dark gray (fourth row). Pre-treatment samples are shown in the left-hand column, post-bevacizumab samples are shown in the middle column, and post-bevacizumab+atezolizumab samples are shown in the right-hand column.
Figure 6:
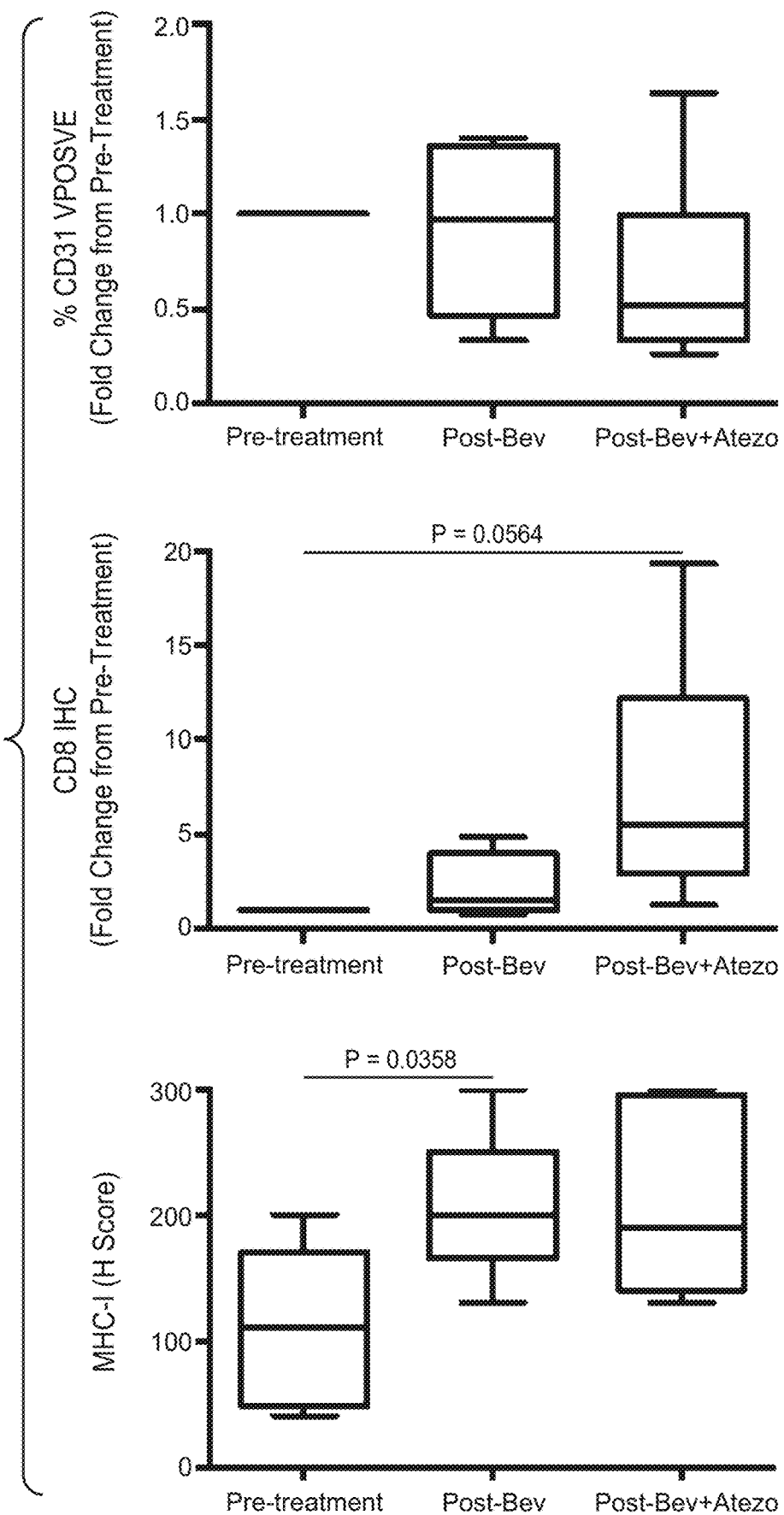
FIG. 6 is a series of graphs showing quantification of immune and vasculature markers at the indicated time points, as assessed by IHC. CD31 expression is shown in the top panel, CD8 expression is shown in the middle panel, and MHC-I expression is shown in the bottom panel. P values were determined by paired t-test. "VPOSVE" is a measure of vessel density.
Figure 7:
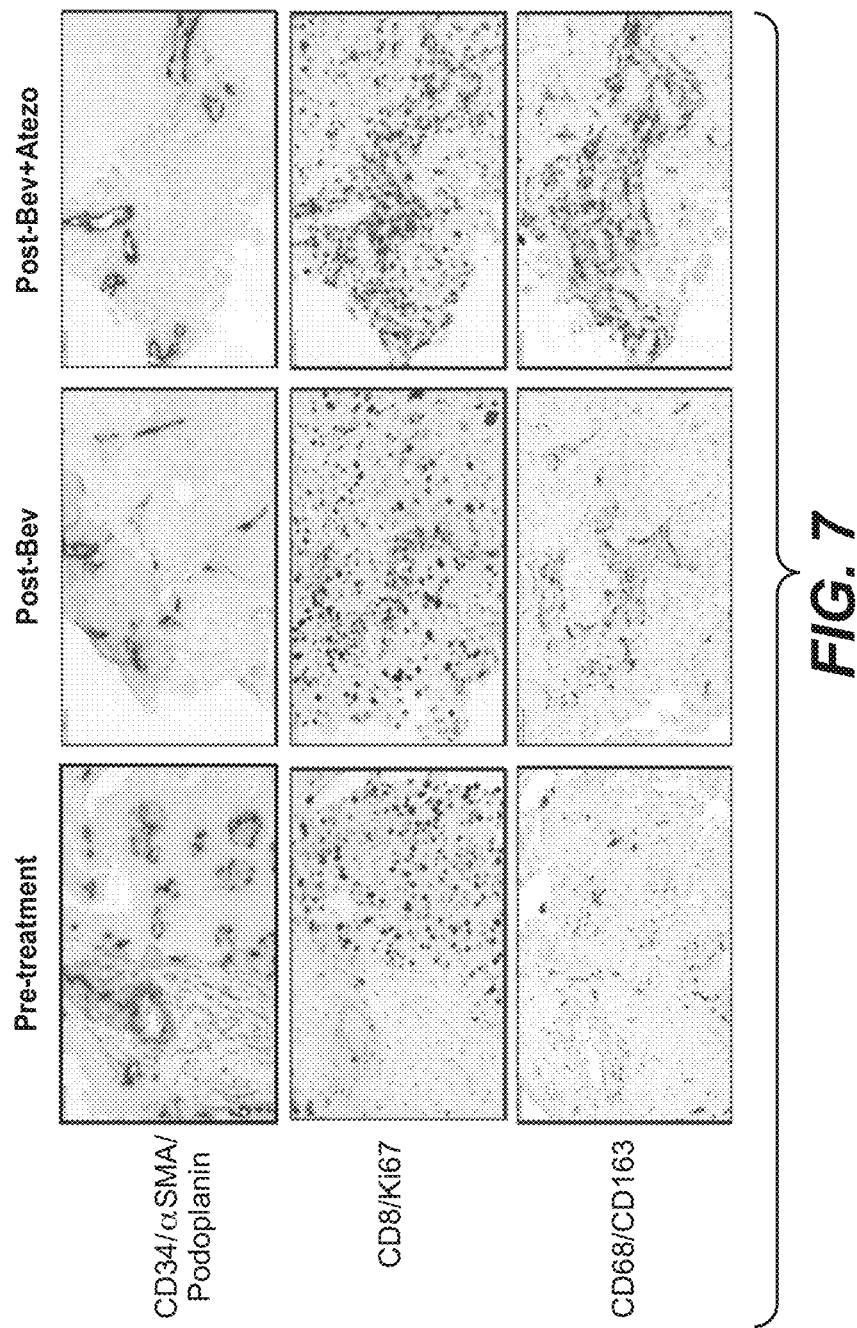
FIG. 7 is a series of representative images showing protein expression of immune and vasculature markers from serial sections of tumor samples from Patient 3, as assessed by IHC. The first row shows expression of CD34, alpha smooth muscle actin (αSMA), and podoplanin. The second row shows expression of CD8 and Ki67. The third row shows expression of CD68 and CD163. Pre-treatment samples are shown in the left-hand column, post-bevacizumab samples are shown in the middle column, and post-bevacizumab+atezolizumab samples are shown in the right-hand column.
Figure 8:
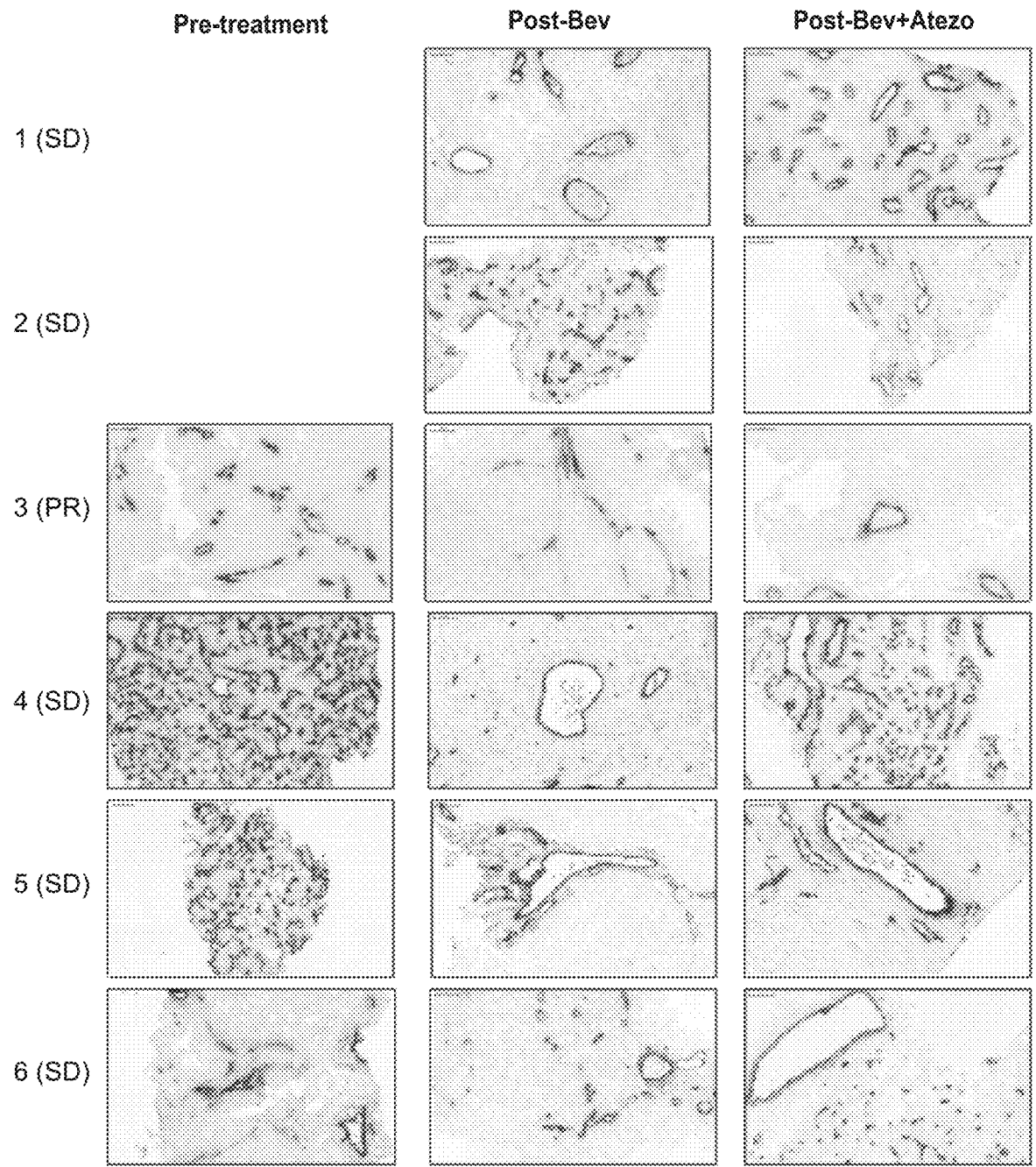
FIG. 8 is a series of representative images showing protein expression of CD34 and αSMA in tumor samples, as assessed by IHC. Pre-treatment samples are shown in the left-hand column, post-bevacizumab samples are shown in the middle column, and post-bevacizumab+atezolizumab samples are shown in the right-hand column. Sections of individual patients 1-6 are arranged on each row. The response of each patient is also indicated.
Figure 9:
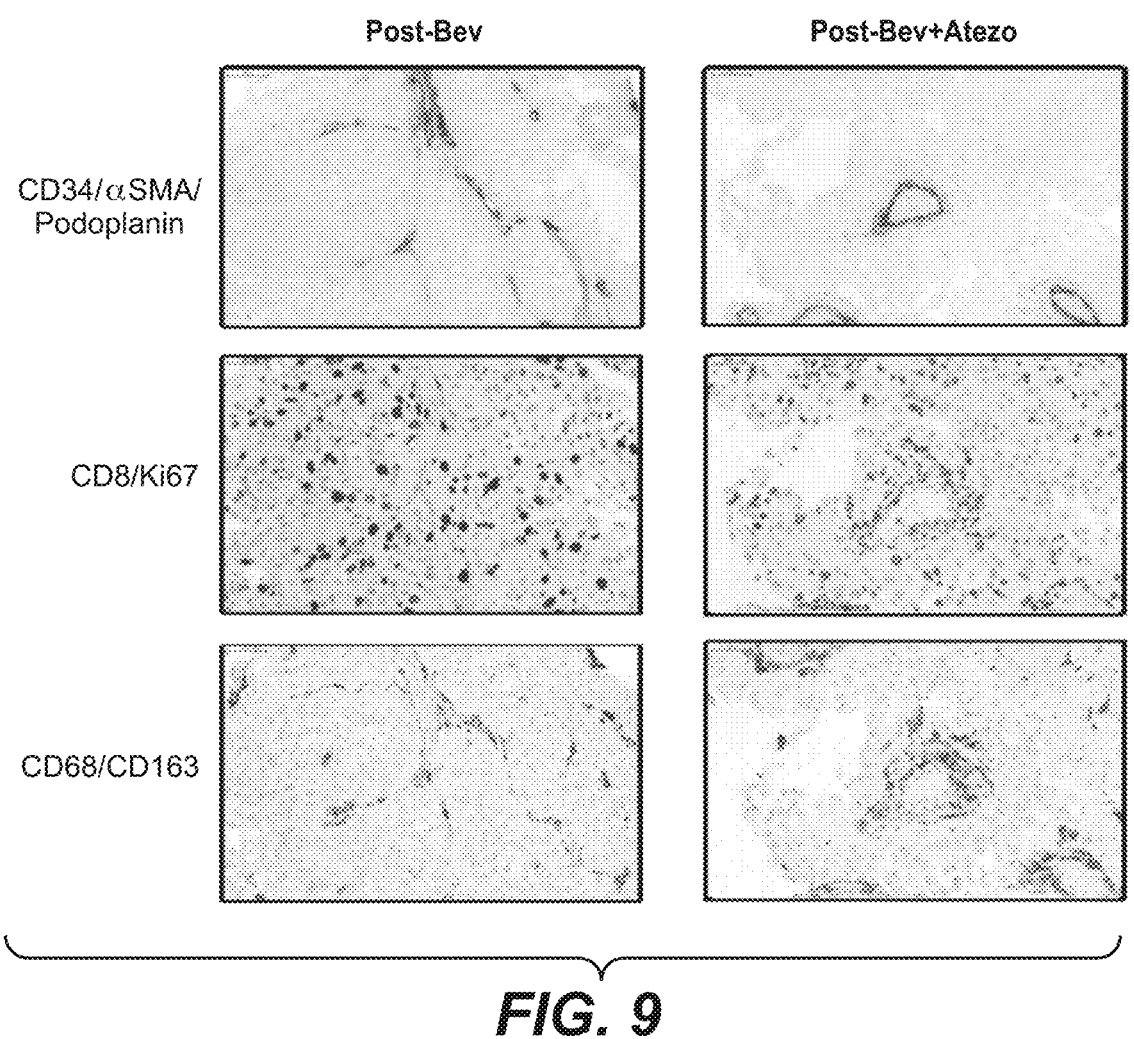
FIG. 9 is a series of representative images showing protein expression of immune and vasculature markers from serial sections of tumors, as assessed by IHC. The first row shows expression of CD34, αSMA, and podoplanin. The second row shows expression of CD8 and Ki67. The third row shows expression of CD68 and CD163. Post-bevacizumab samples are shown in the left-hand column, and post-bevacizumab+atezolizumab samples are shown in the right-hand column.
Figure 10:
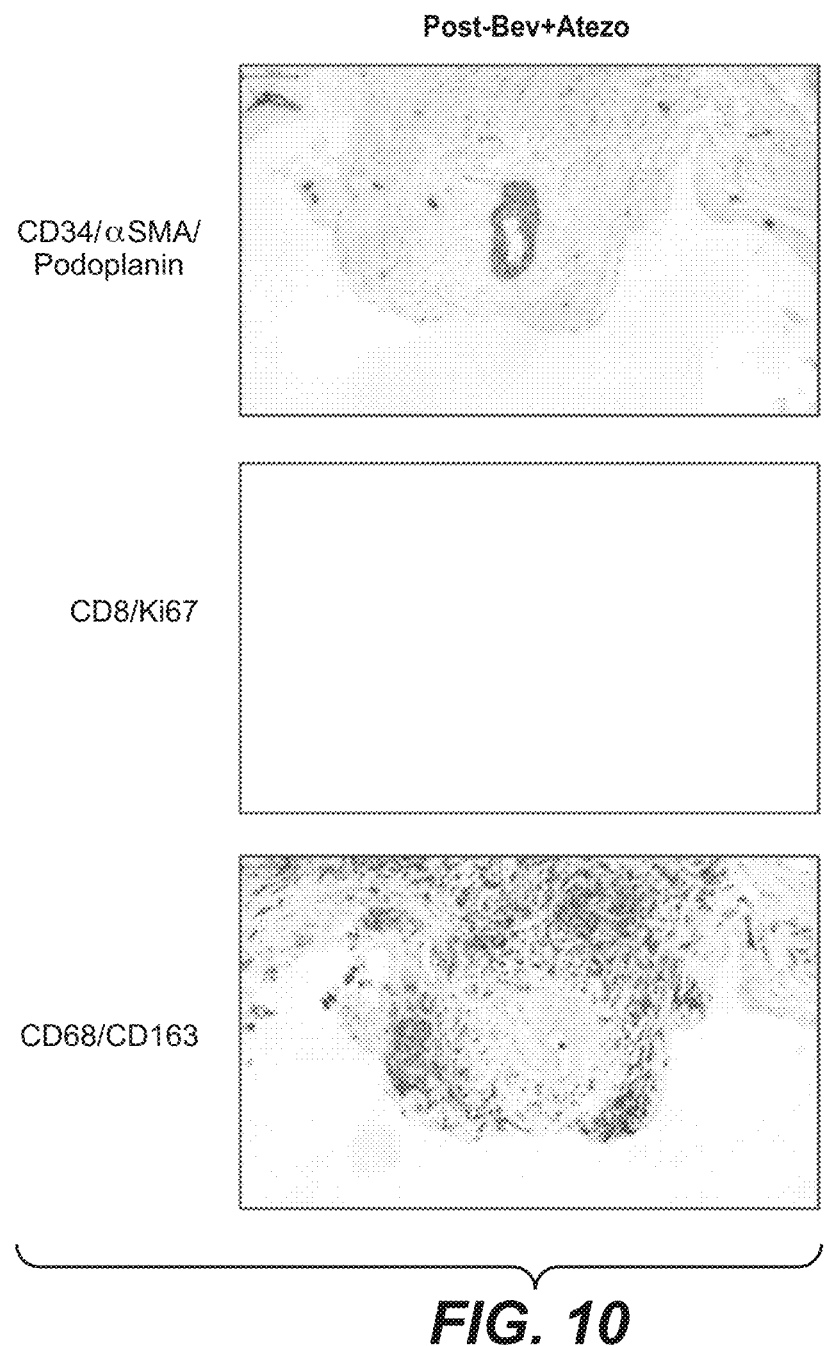
FIG. 10 is a series of representative images showing protein expression of immune and vasculature markers from serial sections of tumors post-bevacizumab+atezolizumab, as assessed by IHC. The top image shows expression of CD34, αSMA, and podoplanin. The middle image shows expression of CD8 and Ki67. The bottom image shows expression of CD68 and CD163.
Figure 11:
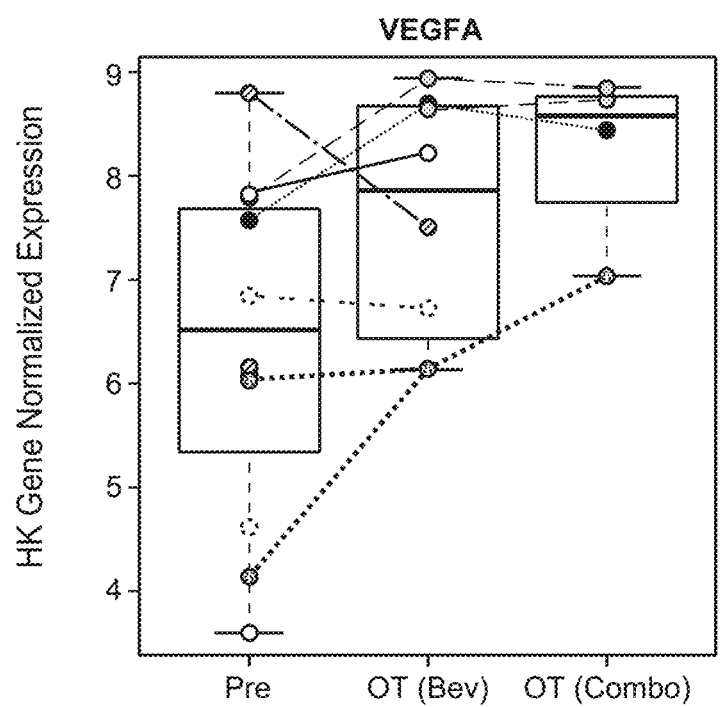
FIG. 11 is a graph showing the upregulation of VEGF transcript expression in tumors in response to bevacizumab and bevacizumab+atezolizumab treatment. Expression is normalized to housekeeping (HK) gene expression. Each line represents an individual patient.

Characterization of Biomarkers of Vascular and Immune Responses Following Bevacizumab Monotherapy or Combination Therapy in Both On-Treatment Time Points To confirm the immune and vascular gene expression changes observed in the tumor, immune and vascular protein expression changes in pre-treatment and on-treatment tissue were evaluated by immunohistochemistry. A decrease in CD31, a marker of vessel-lining endothelial cells, was observed (FIGS. 5 and 6). Dual staining of CD34, another marker of endothelial cells, with alpha-smooth muscle actin ($\alpha$SMA) showed that immature or unstable vessels (CD34$^+$/$\alpha$SMA$^-$) were primarily affected with bevacizumab treatment (FIGS. 7 and 8), consistent with other published reports (see, e.g., Gasparini et al. *Nat. Clin. Pract. Oncol.* 2:562-577, 2005). Morphological changes in endothelial cells were also evident for the combination treatment, consistent with findings in metastatic melanoma following ipilumimab and bevacizumab treatment (see, e.g., Hodi et al. *Cancer Immunol. Res.* 2:632-642, 2014). In addition, contextual localization of CD68$^+$/CD163$^+$ but not CD68$^+$/CD163$^-$ macrophages was observed in four patients on-treatment adjacent to the immature vessels but not the mature vessels, which were largely unaffected by bevacizumab therapy (FIGS. 7, 9, and 10). Without wishing to be bound by theory, one potential explanation is that the macrophages localized to unstable vessels could be responding to the inflammation and vascular-induced changes caused by bevacizumab. Macrophages have been shown to promote vascularization by secreting VEGF (Lamagna et al. *J. Leukoc. Biol.* 80:705-713, 2006), and VEGF transcript expression was upregulated in the tumors on-treatment (FIG. 11).

Figure 12:
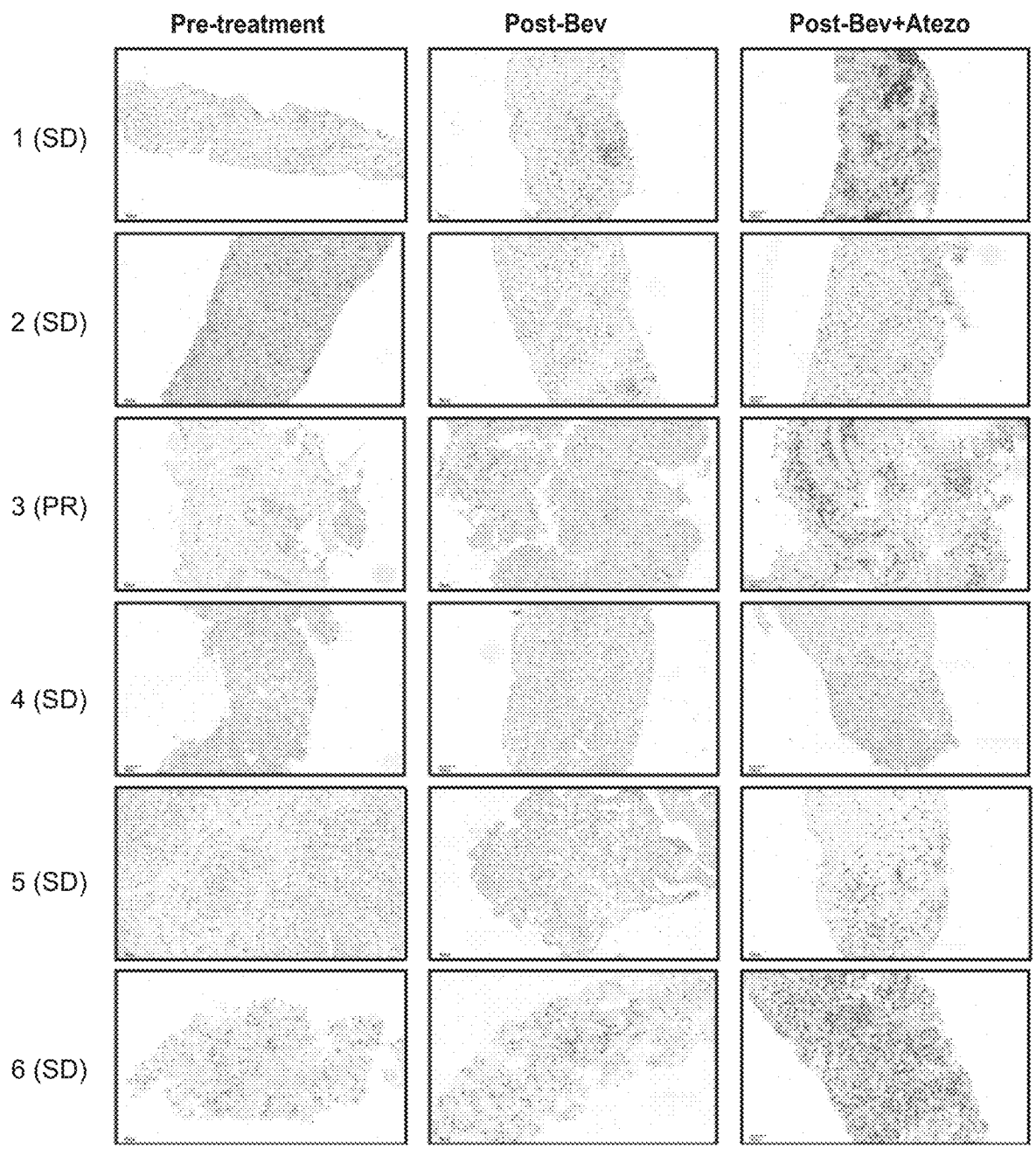
FIG. 12 is a series of representative images showing protein expression of CD8 (stained dark gray) from tumor sections, as assessed by IHC. Pre-treatment samples are shown in the left-hand column, post-bevacizumab samples are shown in the middle column, and post-bevacizumab+atezolizumab samples are shown in the right-hand column. Sections of individual patients 1-6 are arranged on each row. The response of each patient is also indicated.

Intratumoral CD8$^+$ T cell increases were pronounced following combination treatment in all but one of the patients (FIGS. 5, 6, and 12). However, upregulation of PD-L1, which is an IFN-$\gamma$ response gene, was only detected by immunohistochemistry in one patient, who demonstrated a PR (FIG. 5). Conversely and unexpectedly, a concomitant increase in MHC-I staining was observed following both bevacizumab and combination treatment (FIGS. 5 and 6). The modulation of MHC-I by anti-VEGF antibody therapy has not been previously described and was not consistently associated with an increase in CD8$^+$ T cells. Previous studies have found that hypoxia is linked to increased MHC-I expression through HIF-1$\alpha$ (Ghosh et al. *Mol. Cell. Biol.* 33: 2718-2731, 2013).

To address if the increase in CD8$^+$ T cell densities upon combination therapy were attributed to enhanced intratumoral proliferation or increased trafficking, dual immunohistochemistry staining of CD8 with the proliferation marker Ki67 was employed. The ratio of Ki67$^+$/CD8$^+$ cells to Ki67$^-$/CD8$^+$ cells remained unchanged on-treatment (FIGS. 7, 13, 14A-14C, 15A-15C, and 16A-16C), suggesting that the CD8$^+$ T cell increase was not due to enhanced intratumoral proliferation but rather due to increased trafficking and infiltration of proliferating CD8$^+$ T cells.

Example 4

Figure 19:
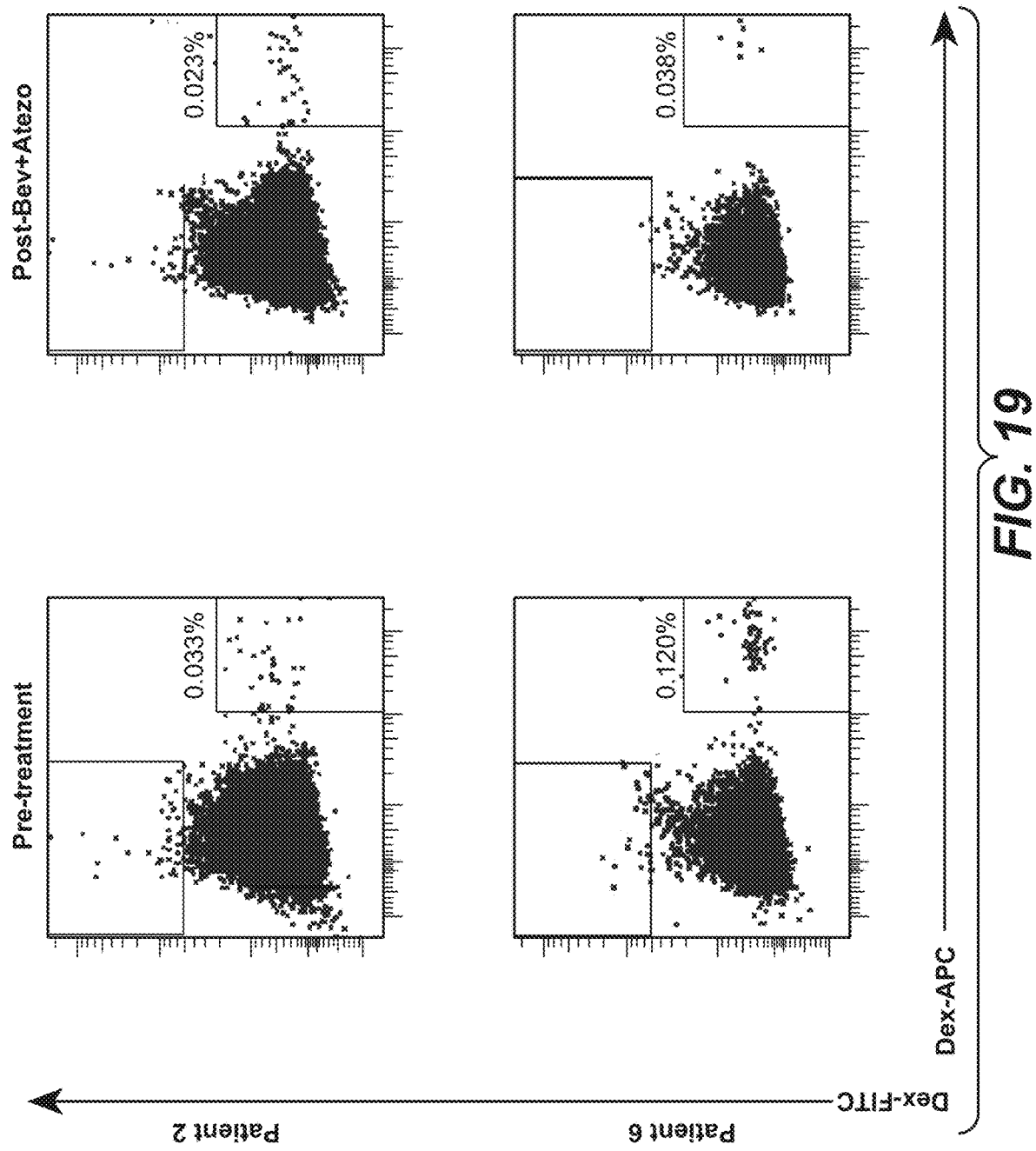
FIG. 19 is a series of flow cytometry plots showing representative frequencies of antigen-specific T cells in the blood. Representative data from two HLA-A2-positive patients with blood draws matched to tumor biopsy time points are shown.

Characterization of Antigen-Specific T Cell Response Following Combination Therapy To confirm whether the elevation in intratumoral CD8$^+$ T cells was due to increased trafficking, cell populations in the periphery were phenotyped by flow cytometry. HLA-A2 dextramers containing previously described RCC tumor antigen peptides (Table 18) were used to determine if antigen-specific T cells were present in patient blood and if these cell populations changed with treatment. Of the 10 patients, in only two HLA-A2 positive patients were positive for cells in the Dex-APC channel at the pre-treatment timepoint (FIG. 19). Of these two patients, only patient 6 demonstrated an increase in intratumoral CD8+ T cells. Interestingly, Dex-APC-positive staining decreased at least 3-fold by the post combination treatment timepoint for patient 6 but not for patient 2, who did not show an increase in intratumoral CD8+ T cells. These changes may suggest that RCC antigen-specific T cells traffic from the periphery into tumors.

Figure 20:
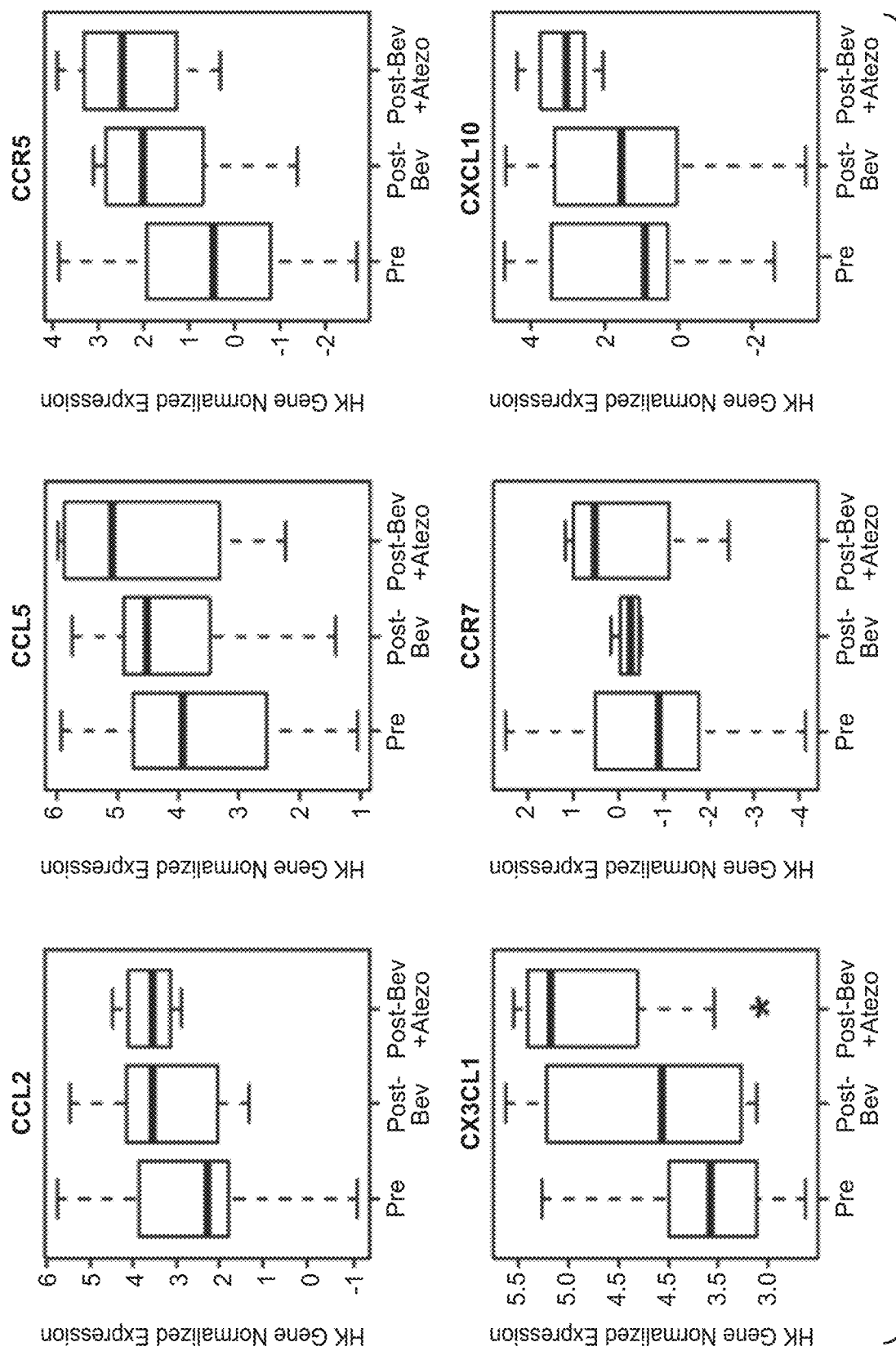
FIG. 20 is a series of graphs showing the change in chemokine expression (CCL2, CCL5, CCR5, CX3CL1, CCR7, and CXCL10) in tumors at the indicated treatment time points. Expression was normalized to housekeeping (HK) gene expression.
Figure 21A:
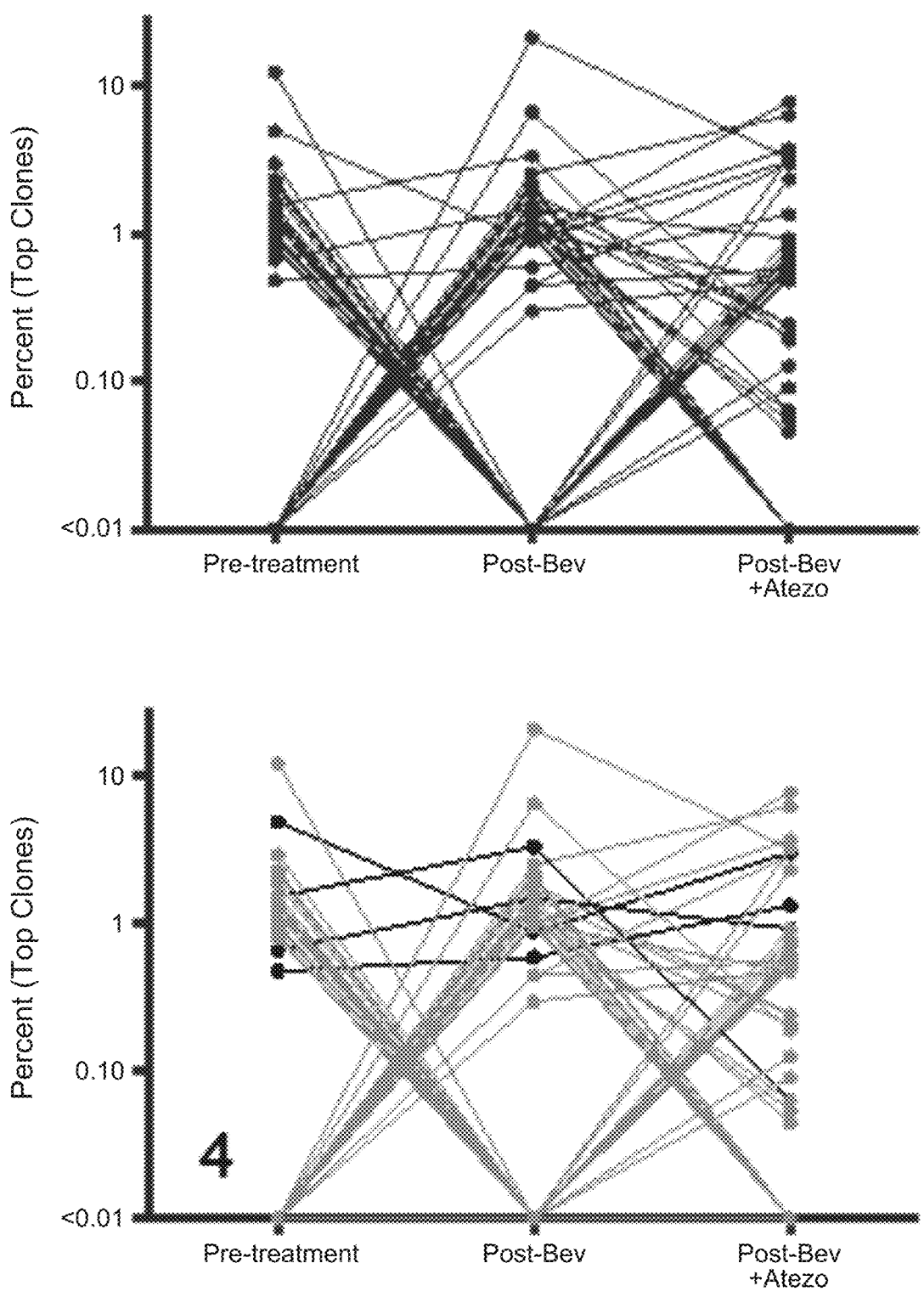
FIGS. 21A-21C are a series of graphs showing the results of TCRβ sequencing of infiltrating lymphocytes (TILs) before and after treatment in tumor samples from patient 6. The top clones (up to 25) for each group are shown. The prevalence of trending TCRβ clone populations are shown in the darker lines in FIGS. 21A (bottom panel), 21B, and 21C.
Figure 21B:
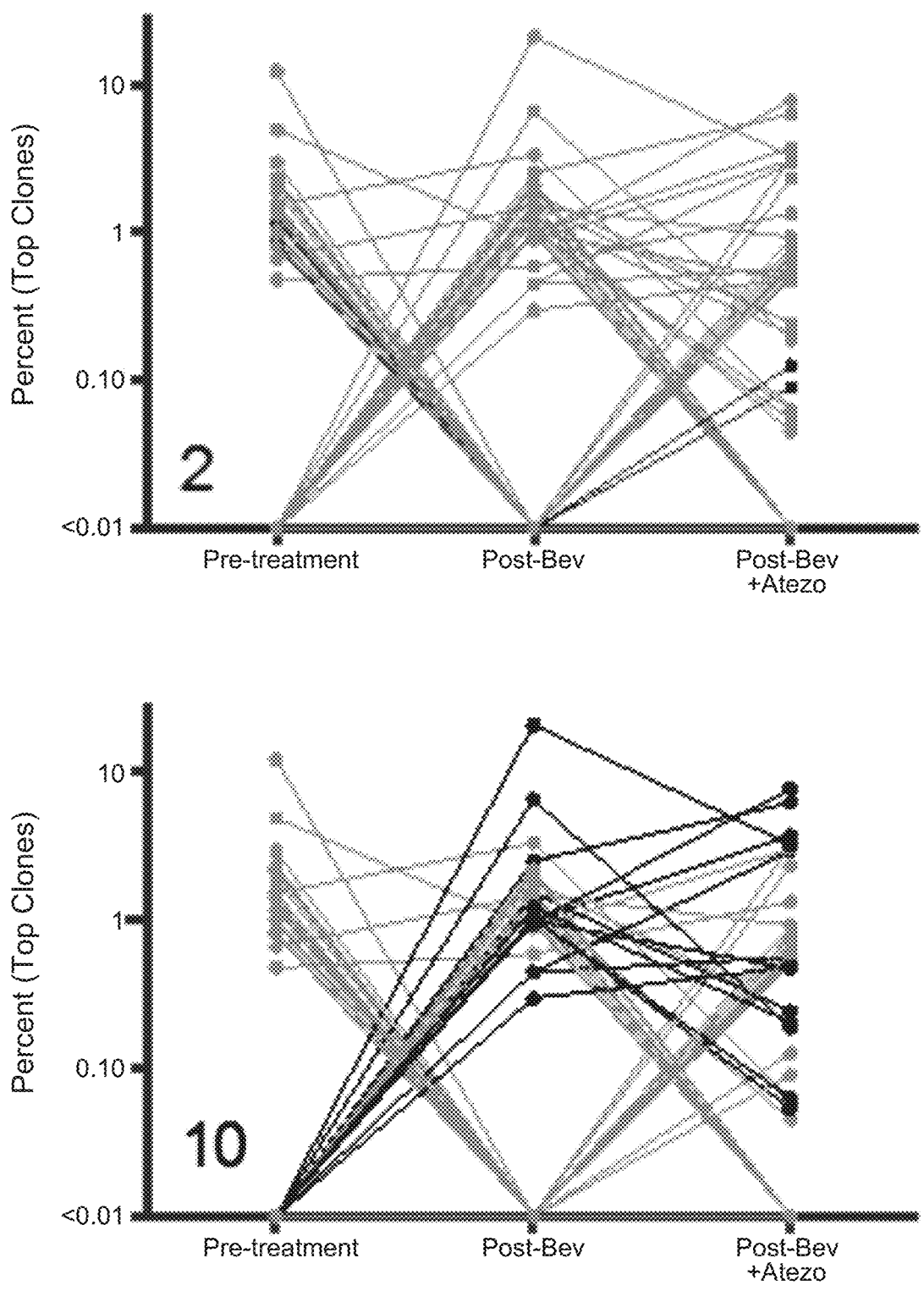
Figure 21C:
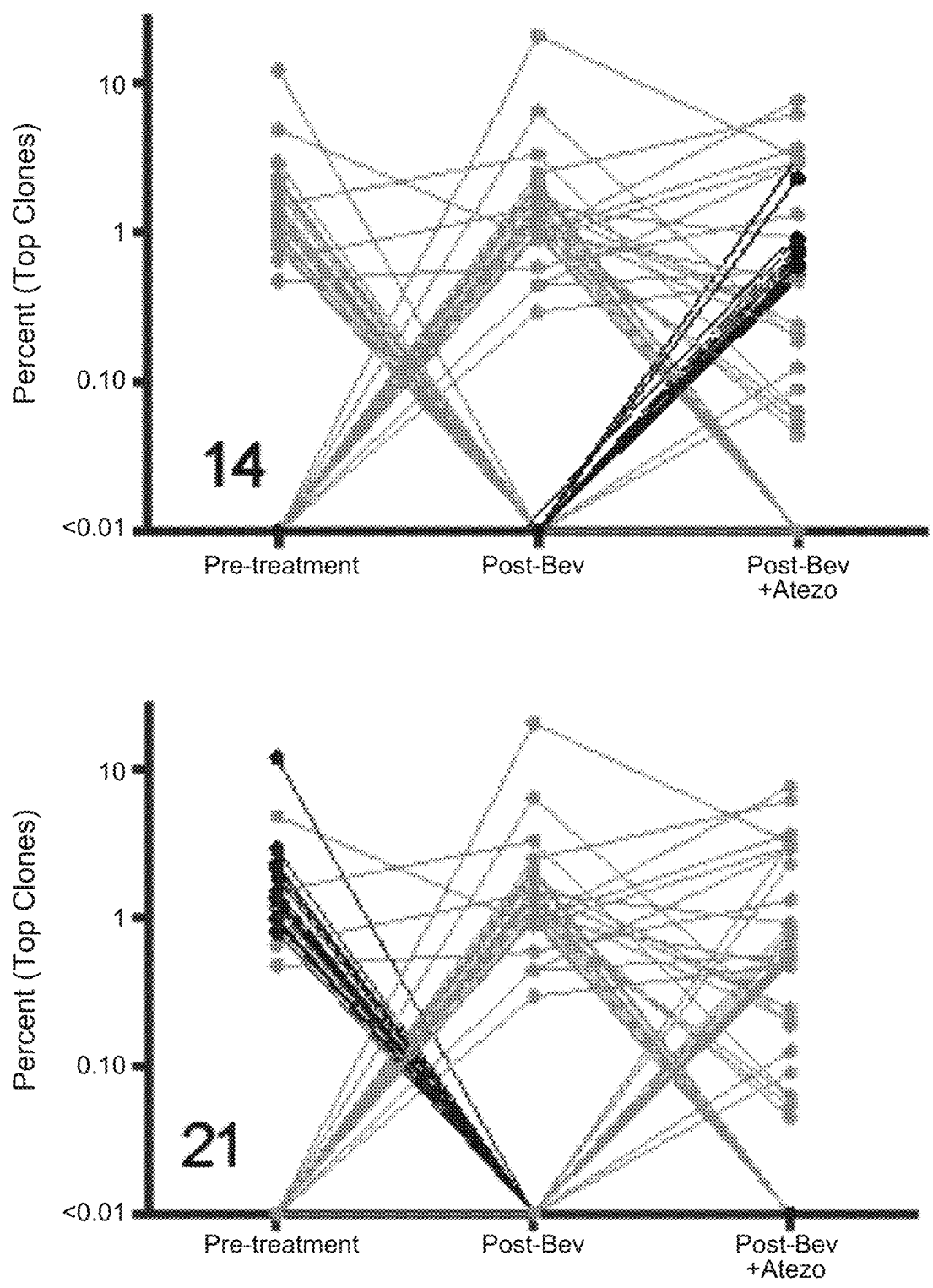
Figure 22:
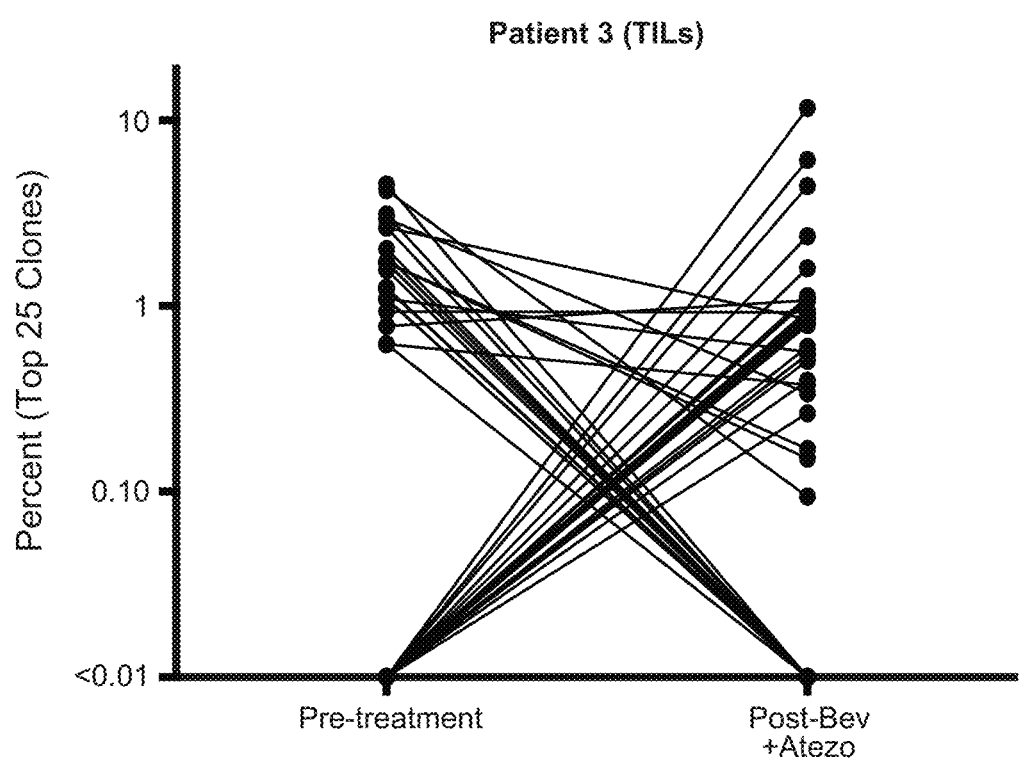
FIG. 22 is a graph showing the results of TCRβ sequencing from Patient 3 TILs before and after bevacizumab+atezolizumab treatment.

Gene expression data also indicated that several other chemokines and chemokine receptors increased in patient tumors on-treatment (FIG. 20). The most significant change occurred with fractalkine (CX3CL1), which is known to be expressed on the membrane of activated endothelial cells in inflammatory or hypoxic environments (Szukiewicz et al. *Mediators Inflamm.* 2013:437576, 2013; Umehara et al. *Arterioscler. Thromb. Vasc. Biol.* 24:34-40, 2004).

Figure 13:
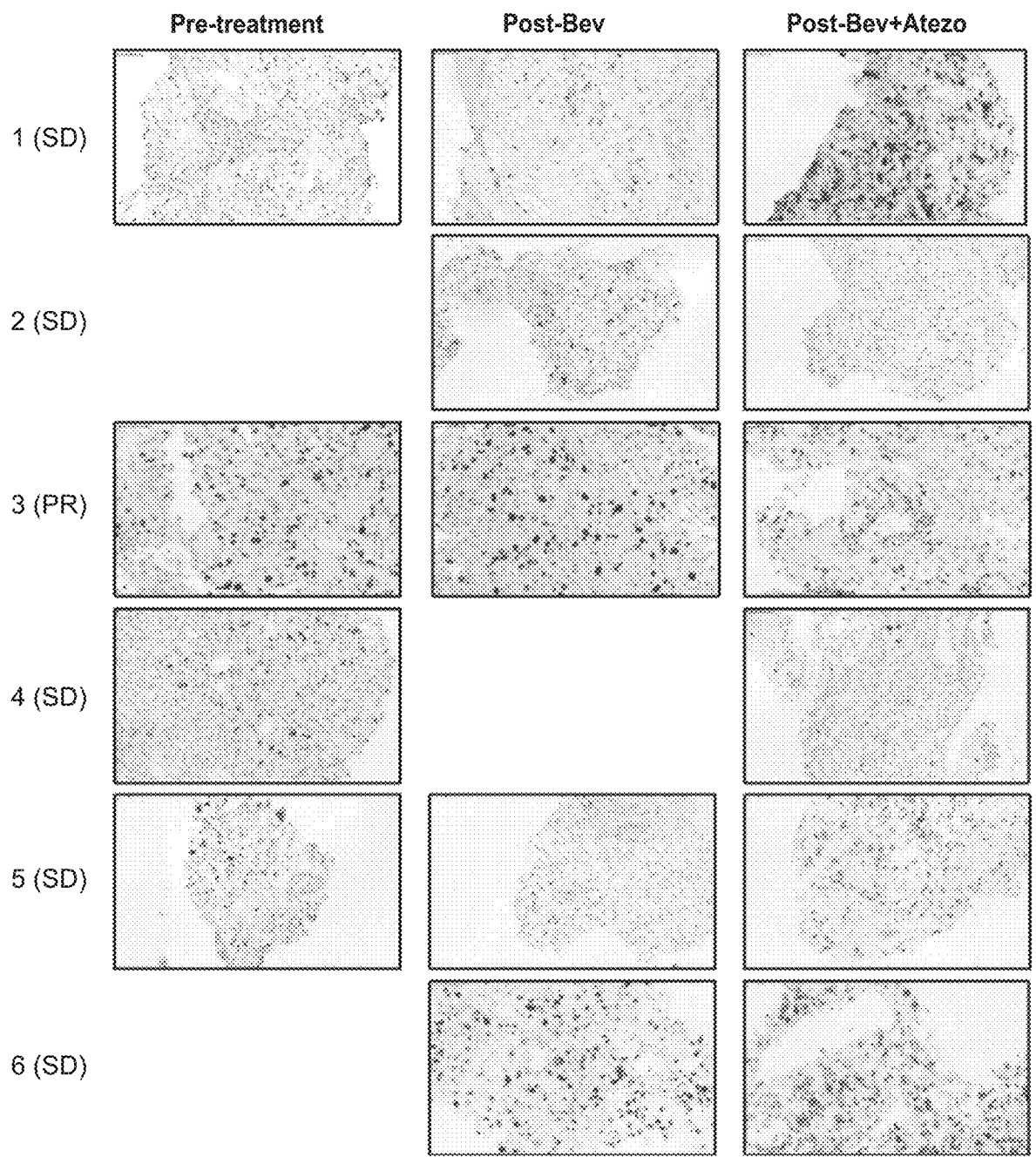
FIG. 13 is a series of representative images showing protein expression of CD8 and Ki67 from tumor sections, as assessed by IHC. Pre-treatment samples are shown in the left-hand column, post-bevacizumab samples are shown in the middle column, and post-bevacizumab+atezolizumab samples are shown in the right-hand column. Sections of individual patients 1-6 are arranged on each row.
Figure 14A:
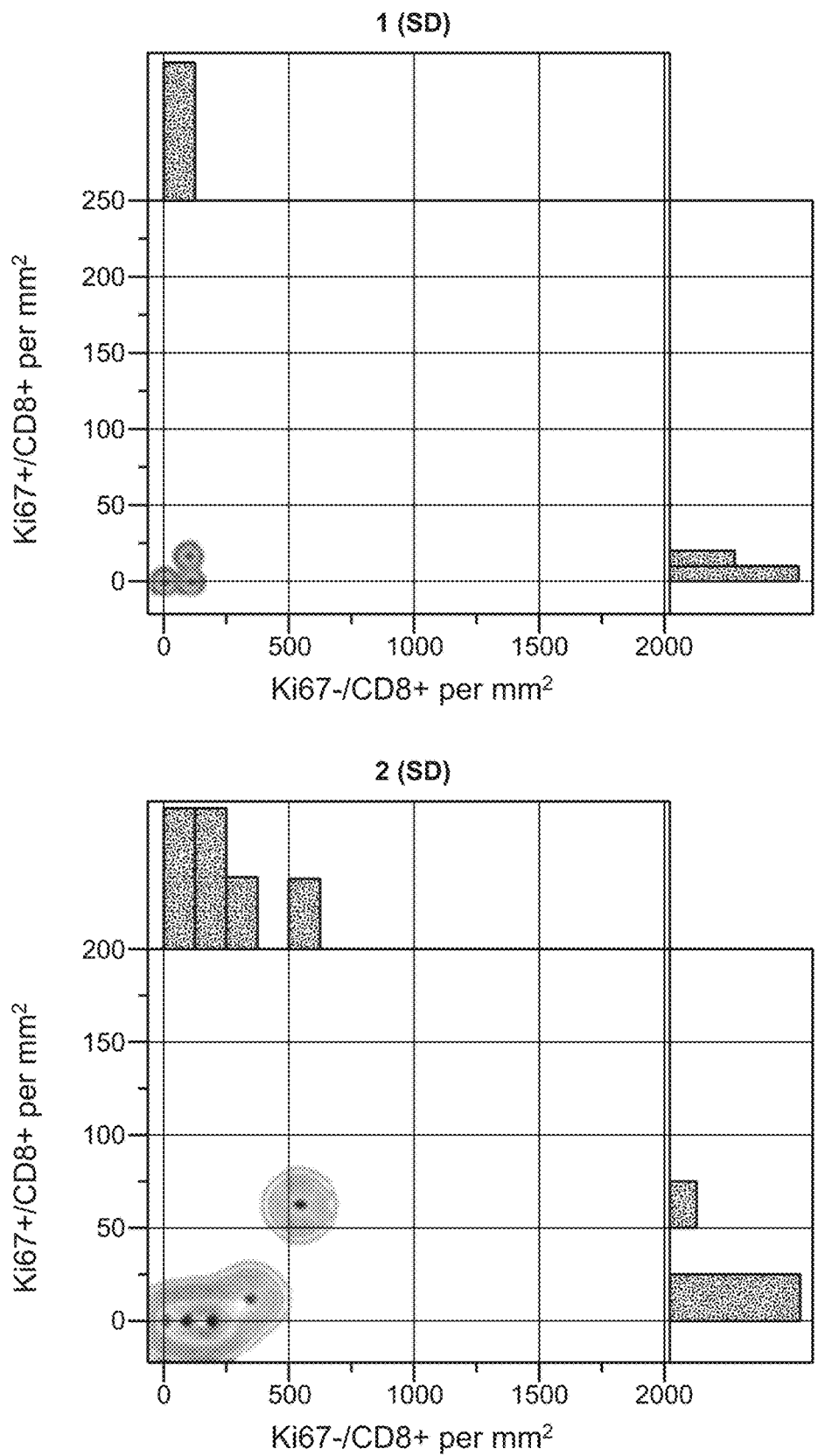
FIGS. 14A-14C are a series of graphs showing the number of cells expressing CD8 or both Ki67 and CD8 per square millimeter ($mm^2$) tumor area for each patient at the pre-treatment time point.
Figure 14B:
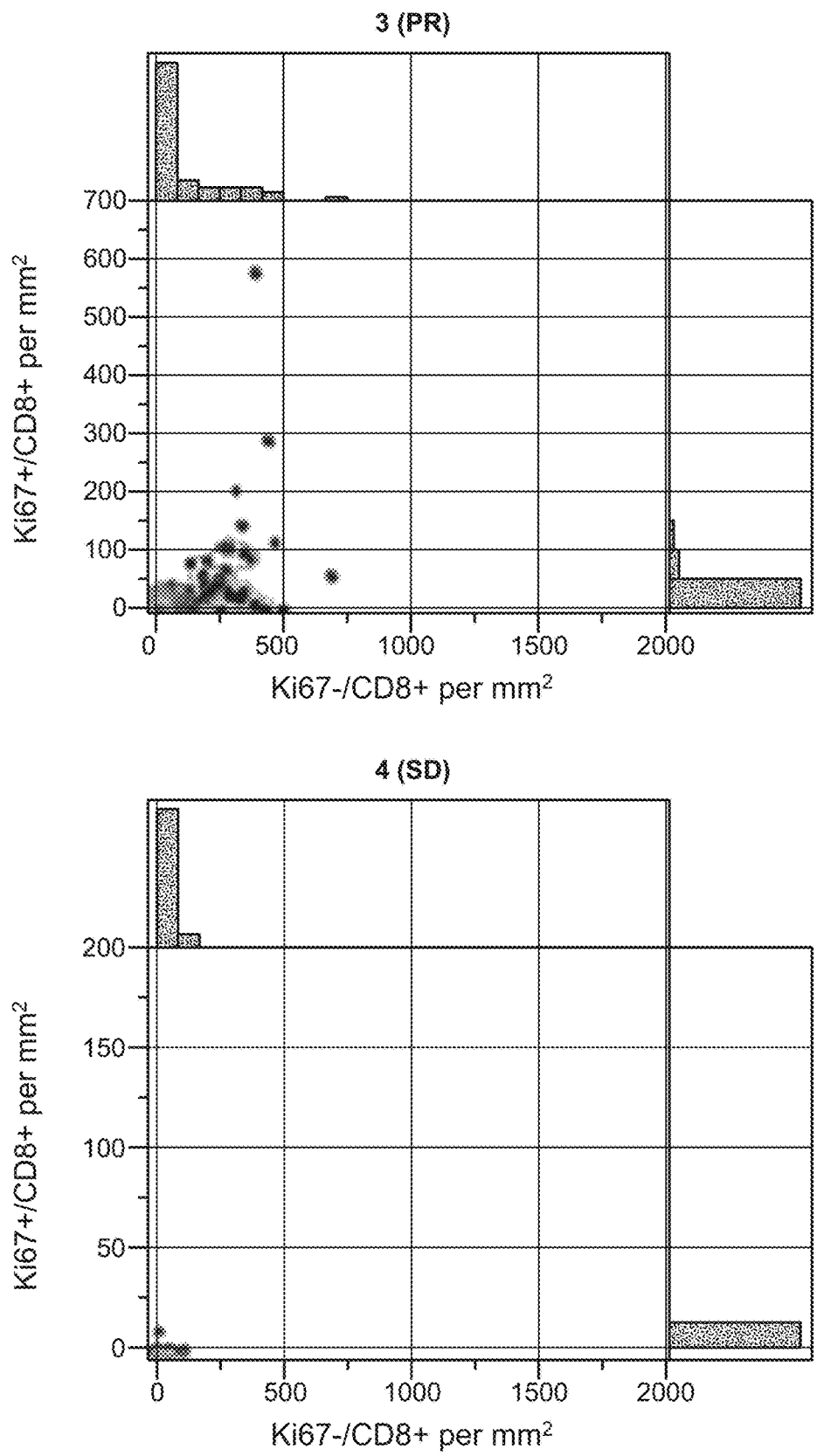
Figure 14C:
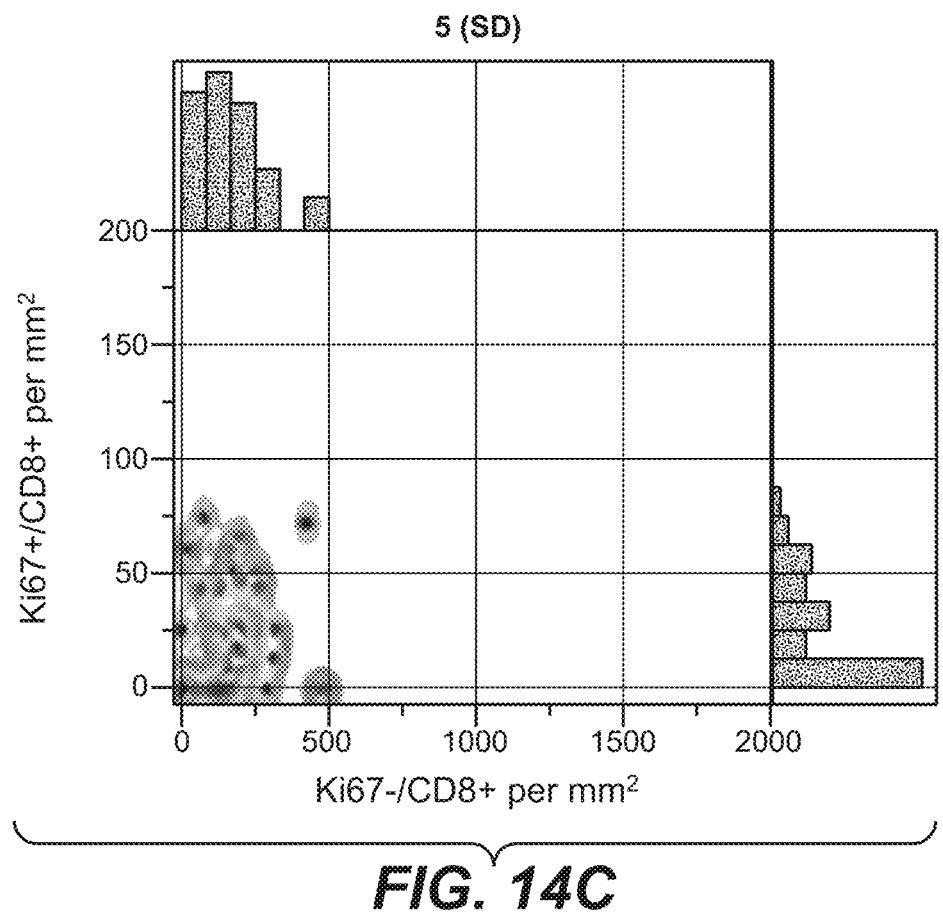
Figure 15A:
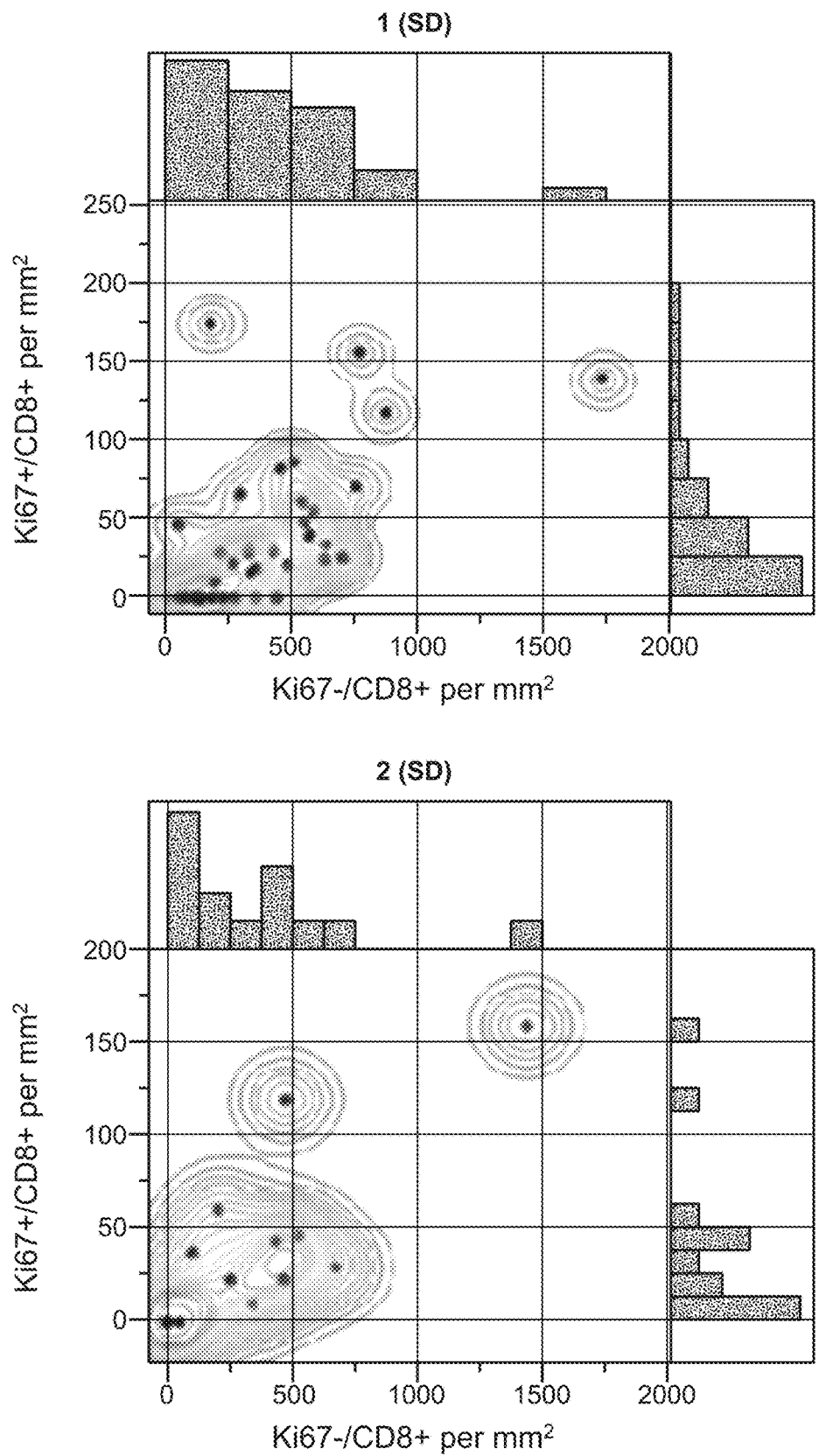
FIGS. 15A-15C are a series of graphs showing the number of cells expressing CD8 or both Ki67 and CD8 per $mm^2$ tumor area for each patient at the post-bevacizumab time point.
Figure 15B:
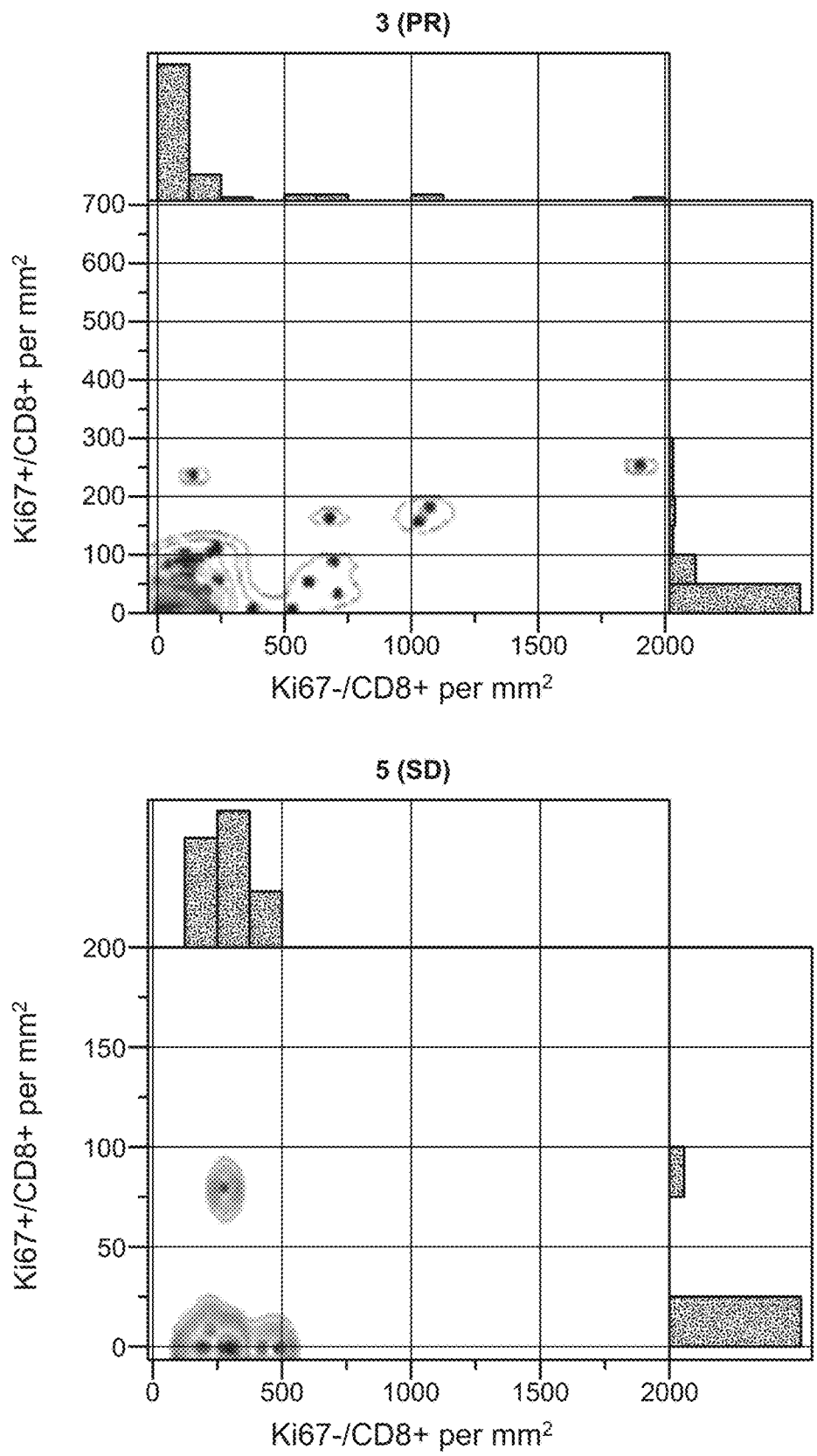
Figure 15C:
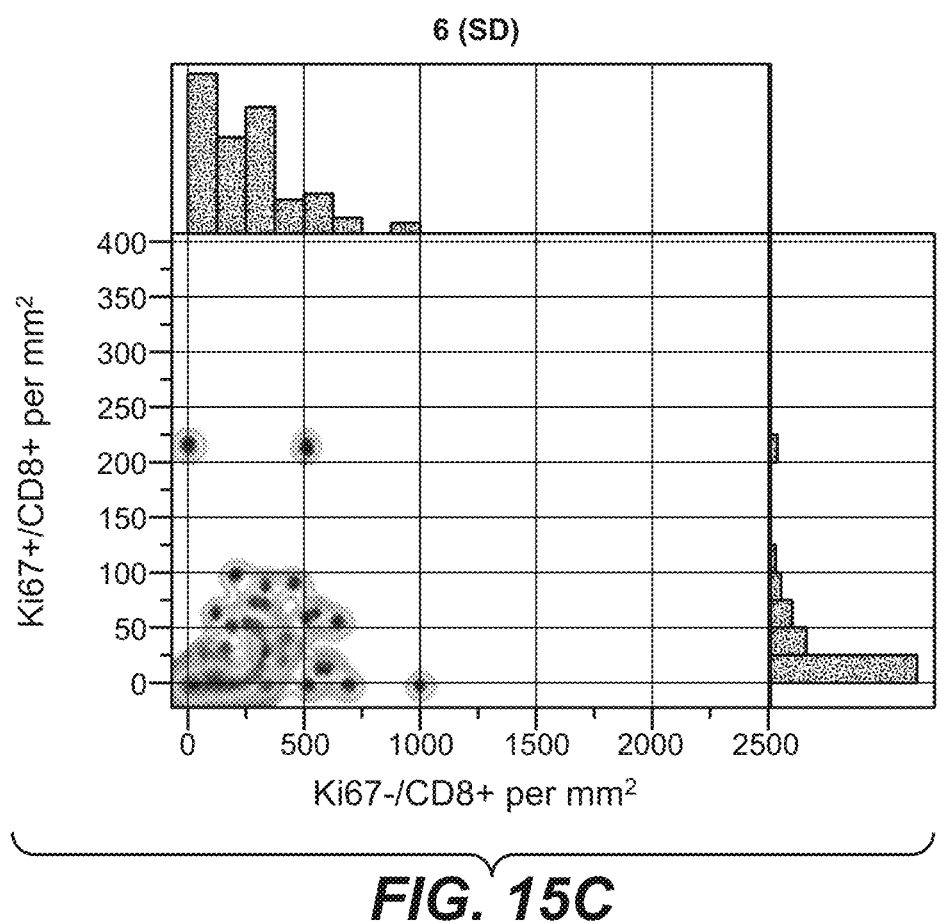
Figure 16A:
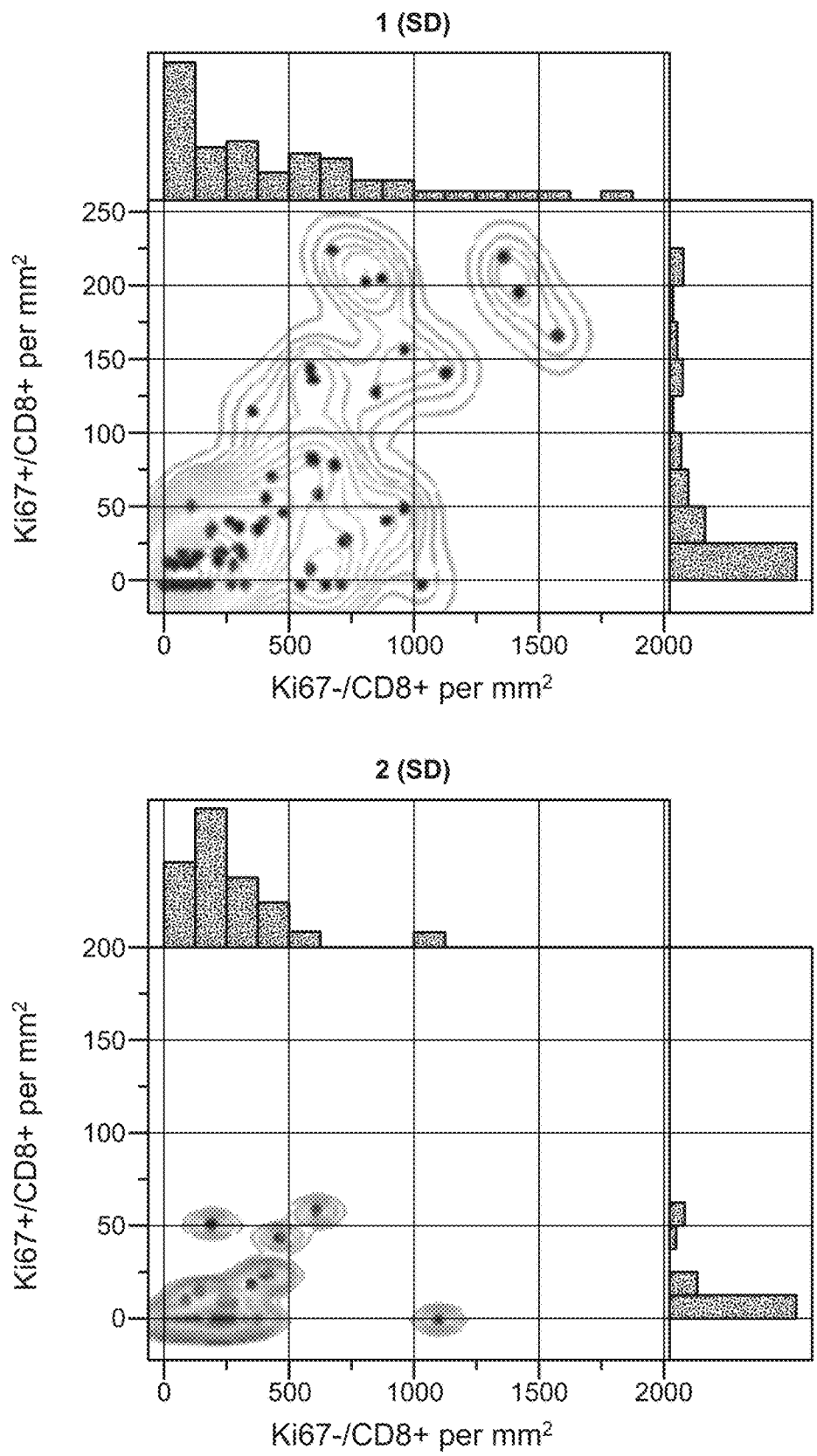
FIGS. 16A-16C are a series of graphs showing the number of cells expressing CD8 or both Ki67 and CD8 per $mm^2$ tumor area for each patient at the post-bevacizumab+atezolizumab time point.
Figure 16B:
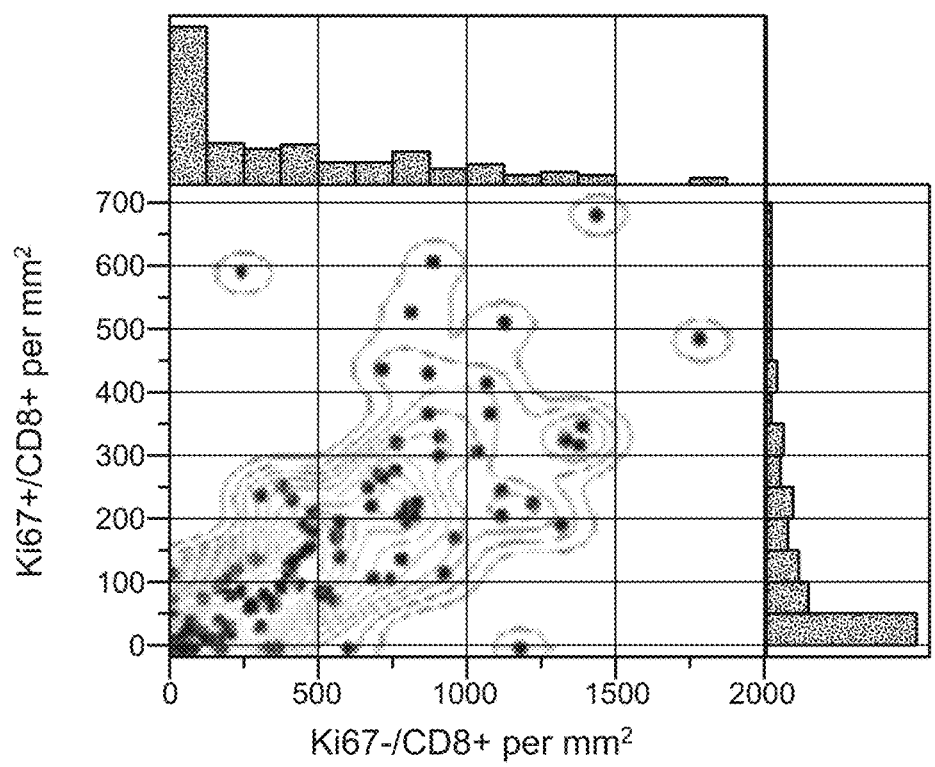
Figure 16B:
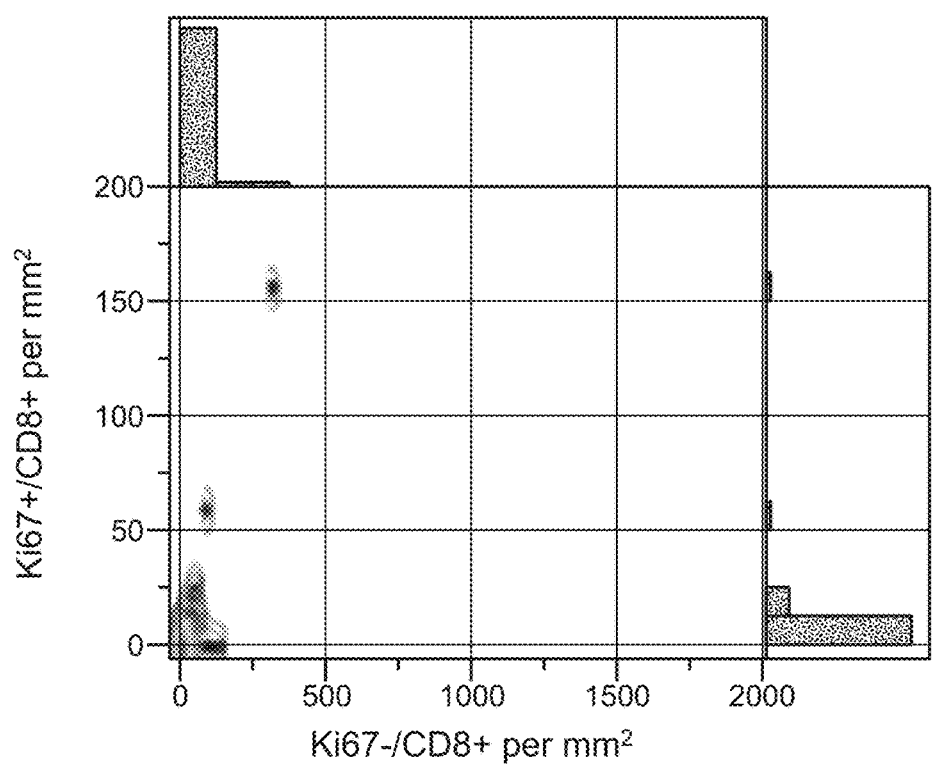
Figure 16C:
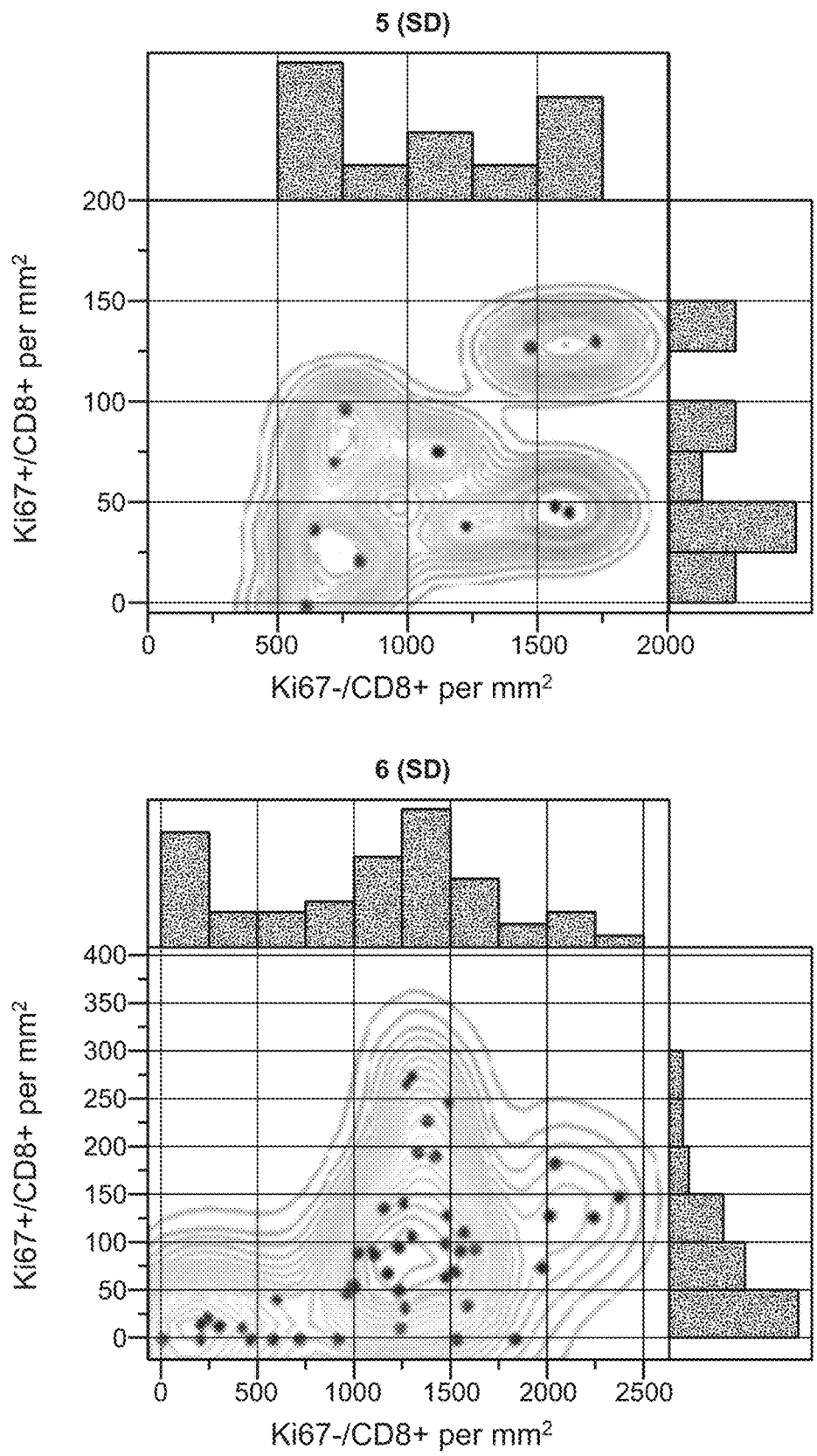
Figure 17A:
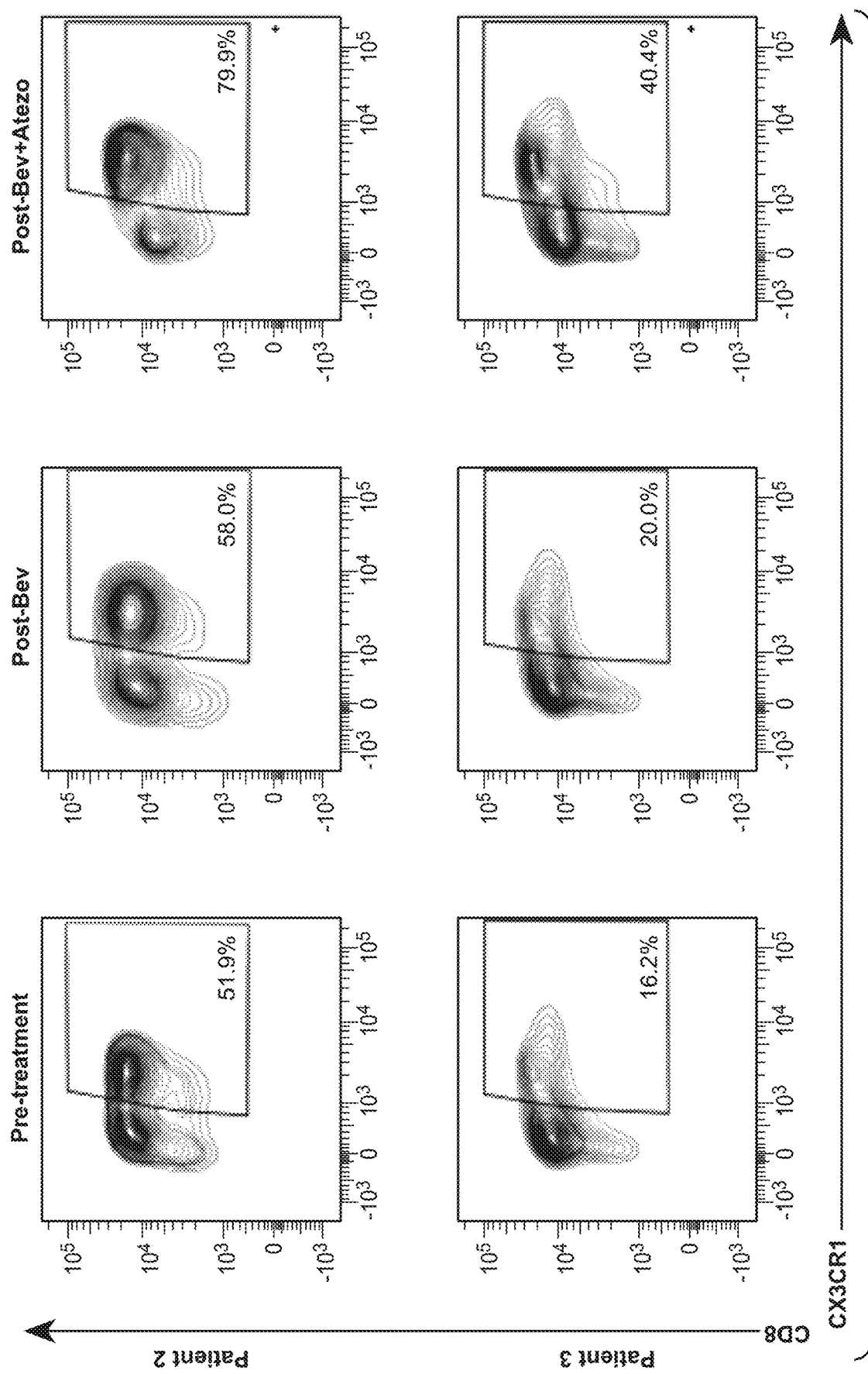
FIGS. 17A and 17B are a series of flow cytometry plots showing the percentage of CD8+ cells in tumor samples expressing CX3CR1. Pre-treatment samples are shown in the left-hand column, post-bevacizumab samples are shown in the middle column, and post-bevacizumab+atezolizumab samples are shown in the right-hand column. Each row shows the results from an individual patient.
Figure 17B:
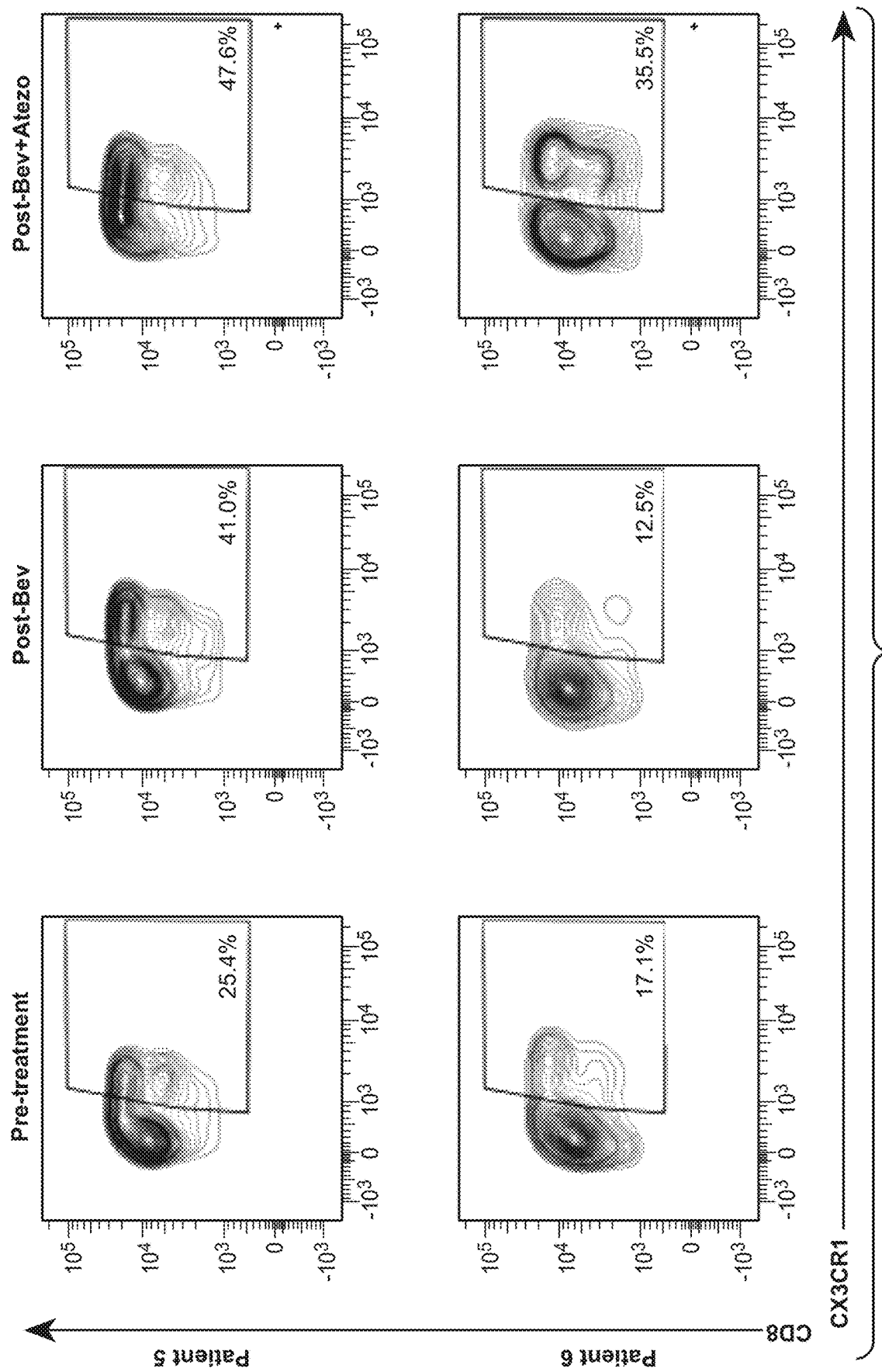
Figure 18:
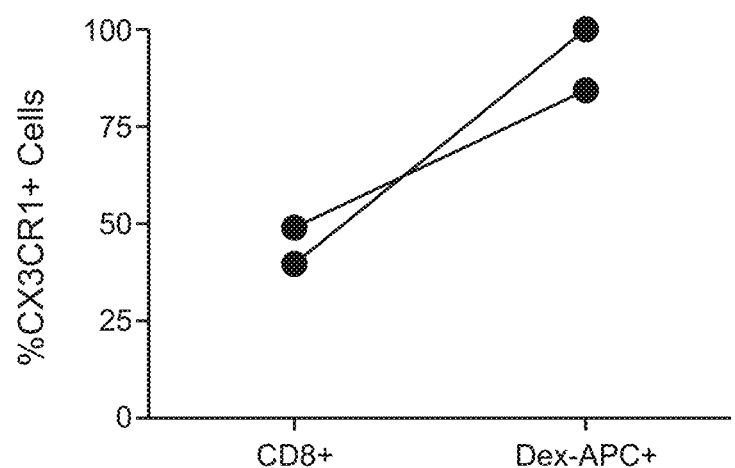
FIG. 18 is a graph showing the expression of CX3CR1 as a percentage of total CD8+ cells (left) and as a percentage of tumor antigen-specific (Dex-APC+) T cells (right), based on flow cytometry analysis.

The receptor for fractalkine, CX3CR1, has been shown to be expressed on armed CD8+ T cells (perforinggranzyme B+) (Nishimura et al. *J. Immunol.* 168:6173-6180, 2002). In the present study, CX3CR1 was upregulated on peripheral CD8+ T cells following combination treatment (FIG. 13). Furthermore, the majority of dextramer-positive cells (FIG. 19) also expressed CX3CR1 (84% and 100% for patients 2 and 6, respectively; FIG. 16). The concordant upregulation of fractalkine and other chemokines in the tumor and CX3CR1 on CD8+ T cells on-treatment suggest a mechanism for the increased tumor infiltration of CD8+ T cells.

T cell receptor (TCR) sequencing was performed on tumors and CD8+ T cells were sorted from matched PBMCs to investigate treatment-induced changes in T cell repertoire and trafficking of T cells into the tumor. Comparison of the top clones from pre-treatment and on-treatment TILs for patients 3 and 6 showed that some clones were retained on-treatment (FIGS. 21A-23C and 22). There were clones that appeared following bevacizumab alone while other clones emerged only after the combination therapy. There were also clones detected in pre-treatment but not on-treatment tumors. Altogether, these dynamic changes in intratumoral T cell composition suggest that the anti-tumor T cell response is evolving on-treatment.

Figure 23A:
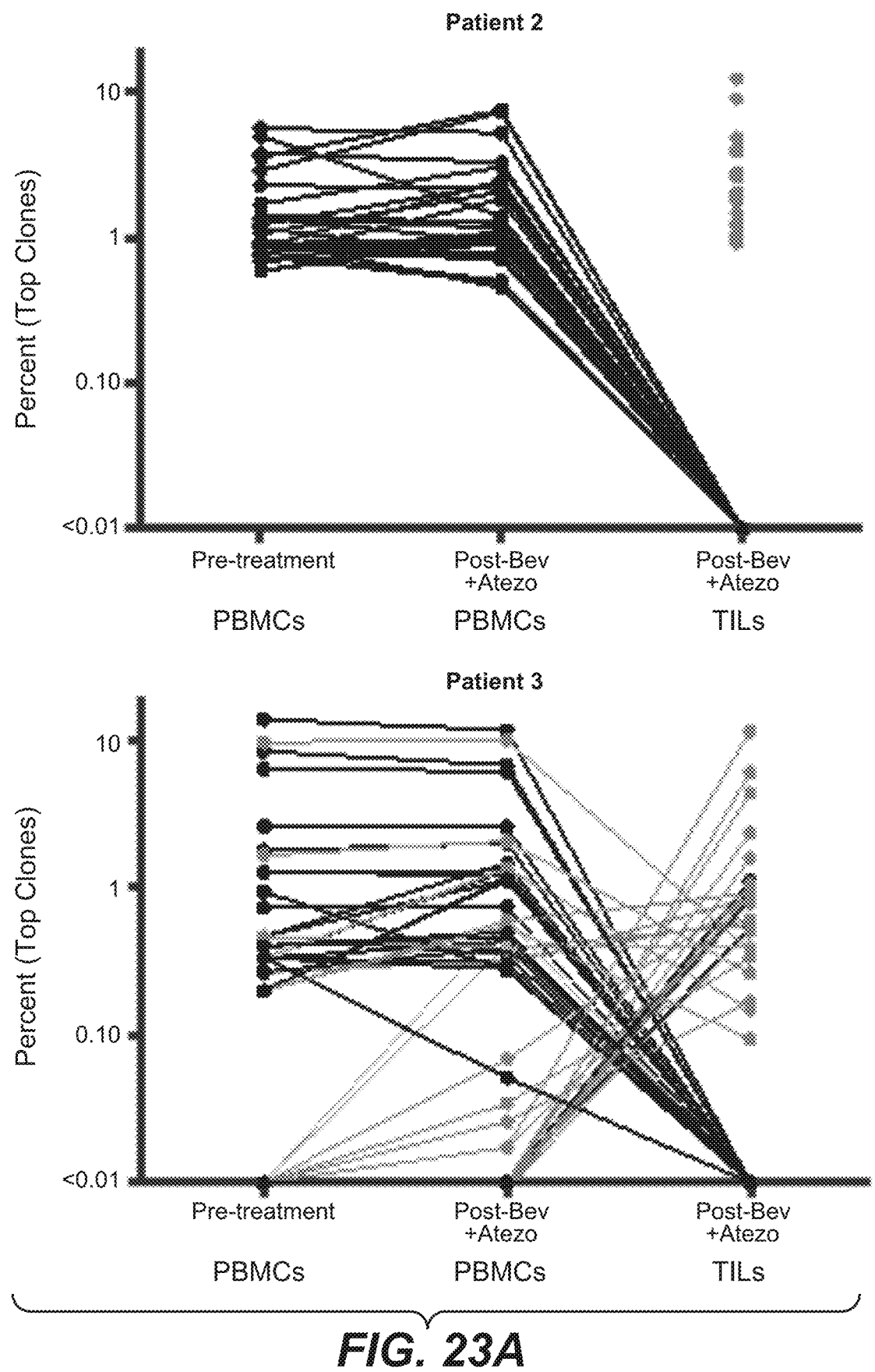
FIGS. 23A and 23B are a series of graphs showing the results of TCRβ sequencing of pre-treatment PBMCs, post-bevacizumab+atezolizumab peripheral blood mononuclear cells (PBMCs), and post-bevacizumab+atezolizumab TILs from patients 2, 3, and 6.
Figure 23B:
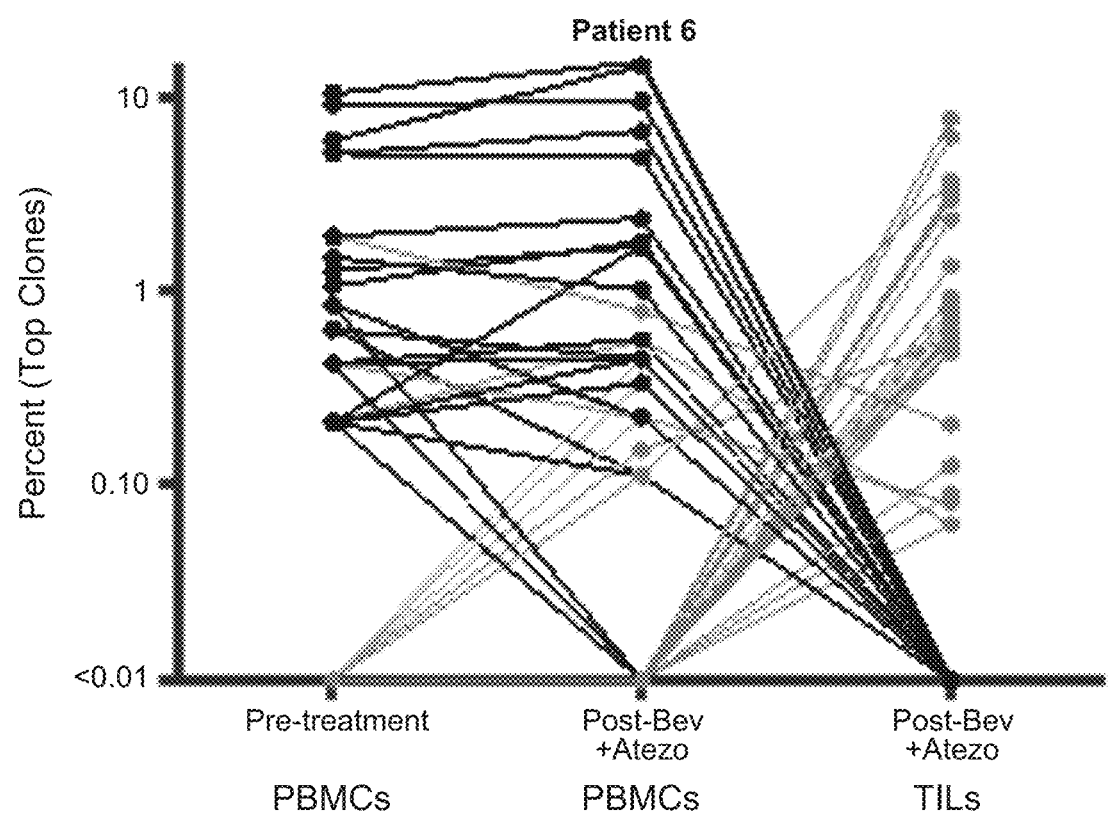
Figure 24:
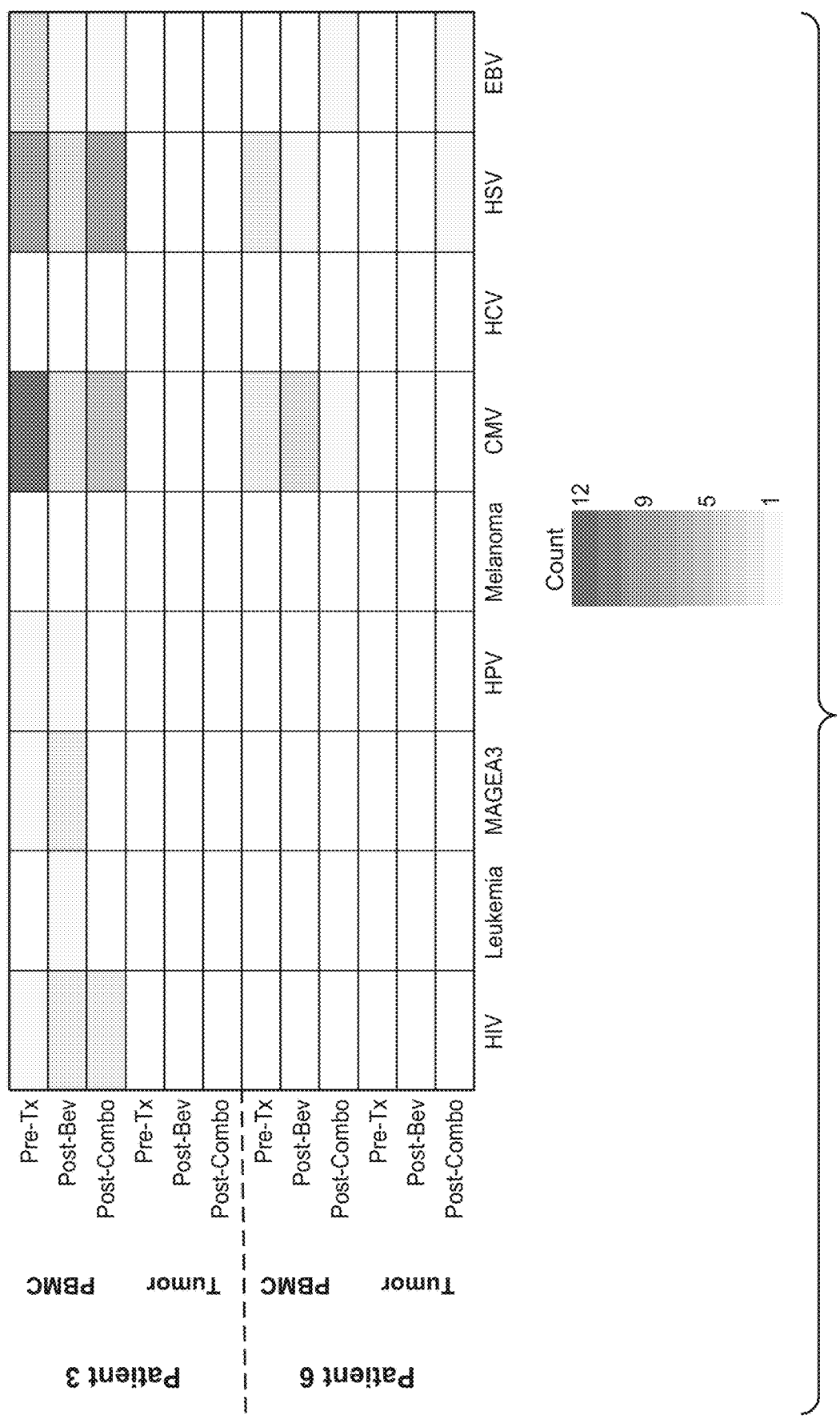
FIG. 24 is a heat map showing the number of viral antigen-specific clones in the PBMC pool versus the TIL pool at each treatment time point, for Patients 3 and 6.

Evaluation of TCR sequences from sorted peripheral CD8+ T cells showed that many of the top clones were maintained between pre-treatment and on-treatment samples, but there was also some overlap between clones found in PBMCs versus on-treatment TILs (FIGS. 23A and 23B). In particular, there were no shared clones between PBMCs and TILs of patient 2, the patient in which intratumoral CD8+ T cells did not increase on-treatment. For patients 3 and 6, there were some clones present at similar frequencies between PBMCs and TILs. A blast of the Adaptive Public Clone Database revealed that some of the top PBMC clones likely recognize viral antigens, but only some of these clones were detected in TILs, further suggesting that tumor antigen-specific T cells may be migrating into the tumor (FIG. 24). The majority of top clones in on-treatment TILs were present at much lower levels in the blood while the most dominant clones in the blood are not detected in the tumor. Because the relative proportions of top clones are not maintained in PBMCs compared to TILs, this may suggest that the increase in CD8+ T cells in the tumor induced by combination treatment occurs through a selective trafficking mechanism. It is also possible that the infiltration is non-biased and there is retention of antigen-specific T cells in the tumor.

Example 5

Molecular Correlates of Differential Response to Atezolizumab Monotherapy and Bevacizumab and Atezolizumab Combination Therapy Compared to Sunitinib Monotherapy A phase II clinical study, IMmotion150 (NCT01984242), was performed to evaluate the safety and tolerability of atezolizumab, alone or in combination with bevacizumab, as compared to sunitinib in patients with previously untreated metastatic renal cell carcinoma (mRCC). Integrated tumor genomic analyses were also performed to correlate molecular biomarkers with observed clinical outcomes in the phase II study.

PD-L1 status on tumor-infiltrating immune cells (IC) was assessed in the phase II IMmotion150 study by immunohistochemistry (IHC) using the anti-human PD-L1 rabbit monoclonal antibody, SP142, and scored using an identical IHC scoring criteria (IC1/2/3=≥1% of tumor-infiltrating lymphocytes are PD-L1-positive; IC2/3=≥5% of tumor-infiltrating lymphocytes are PD-L1-positive) (n=297). PD-L1 status can be assessed as described in International Patent Application Publication Nos. WO 2016/183326 and WO 2016/196298. Mutation evaluations by whole exome sequencing (WES) and gene expression analyses by RNA-Seq (n=263) were also performed. For the gene expression analyses, gene expression levels were evaluated for T effector and IFNγ response (Teff) genes (CD8A, IFNG, PRF1, EOMES, and PD-L1), as well as for angiogenesis-related (Ang) genes (VEGFA, KDR, ESM1, PECAM1, ANGPTL4, and CD34), and myeloid inflammation-related (Myeloid) genes (IL6, CXCL1, CXCL2, CXCL3, CXCL8, and PTGS2). The Teff genes at low expression levels (i.e., below the median expression levels of the evaluated Teff genes; "Teff low") and high expression levels (i.e., at or above the median expression levels of the evaluated Teff genes; "Teff high") were evaluated in relation to progress-free survival (PFS) per RECIST v.1.1 via Independent Review Facility (IRF) assessment. The Ang genes at low expression levels (i.e., below the median expression levels of the evaluated Ang genes; "Ang low") and high expression levels (i.e., at or above the median expression levels of the evaluated Ang genes; "Ang high") were also evaluated in relation to PFS per RECIST v.1.1 via IRF assessment. The Myeloid genes at low expression levels (i.e., below the median expression levels of the evaluated Myeloid genes; "Myeloid low") and high expression levels (i.e., at or above the median expression levels of the evaluated Myeloid genes; "Myeloid high") were also evaluated in relation to PFS per RECIST v.1.1 via IRF assessment. To determine the median expression levels, first a Z-score was calculated for the normalized expression of all of the genes in a group. The median level of all the Z-scores across the dataset was used as a reference level to identify biomarker high versus biomarker low subgroups.

Figure 25:
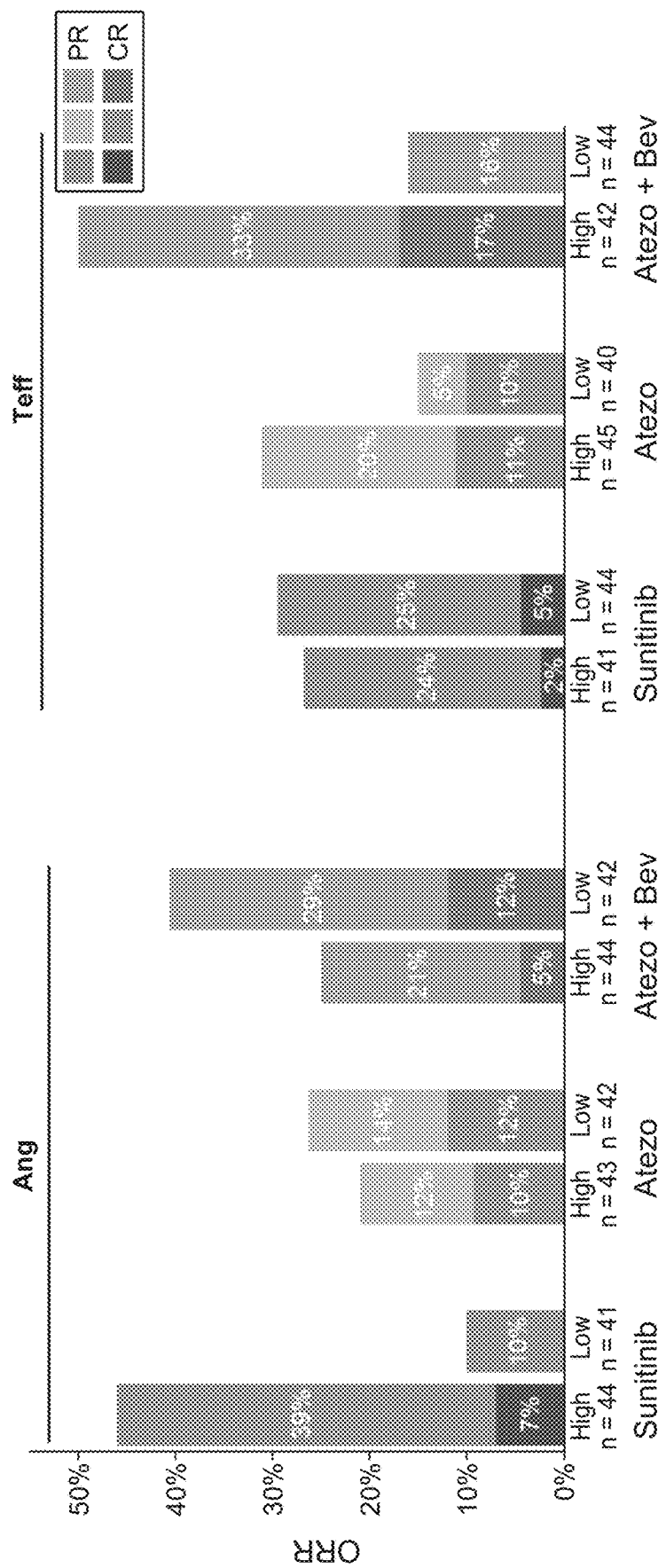
FIG. 25 is a graph showing the overall response rate (ORR) correlated with progression-free survival (PFS) in the indicated gene expression subgroups. Atezo, atezolizumab; atezo+bev; atezolizumab and bevacizumab. Ang indicates VEGFA, KDR, ESM1, PECAM1, ANGPTL4, and CD34; Teff indicates CD8A, EOMES, PRF1, IFNG, and PD-L1.
Figure 29A:
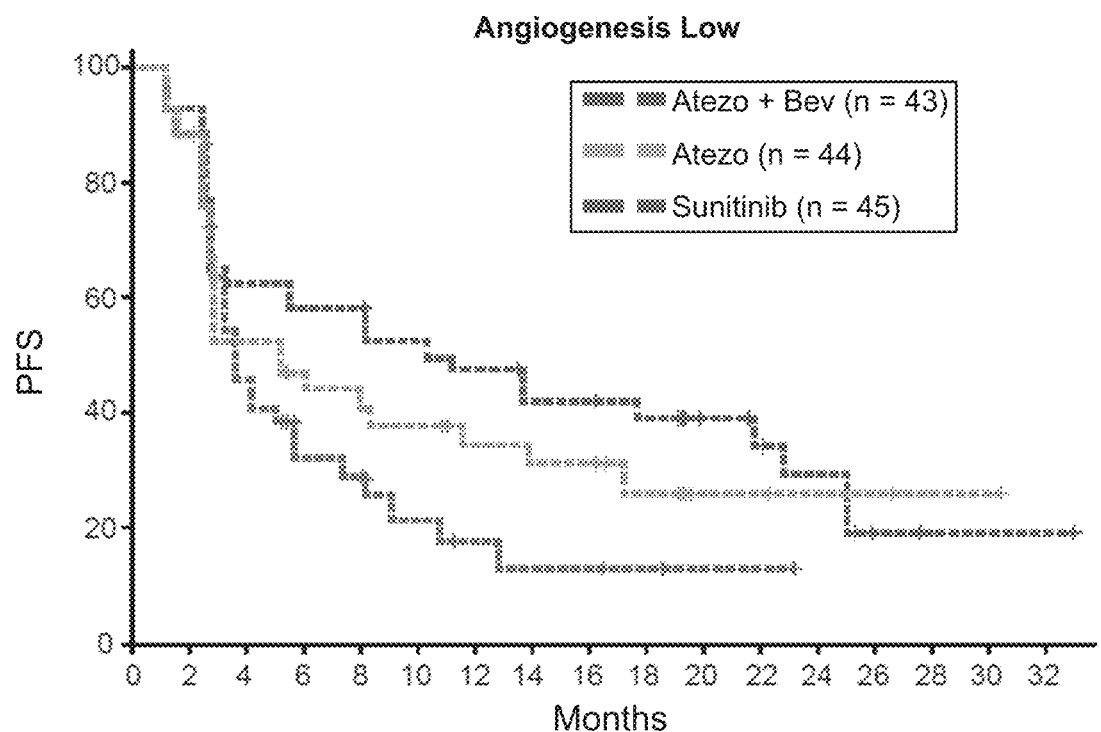
FIGS. 29A and 29B are a series of graphs showing that atezolizumab+bevacizumab demonstrated improved PFS compared to sunitinib in the Angiogenesis low subgroup (FIG. 29A), whereas sunitinib treatment demonstrated improved PFS in the Angiogenesis high subgroup (FIG. 29B). PFS for patients having high median expression) or low (<median expression) expression of Angiogenesis genes (VEGFA, KDR, ESM1, PECAM1, ANGPTL4, and CD34) is shown for the indicated treatment arms.
Figure 29B:
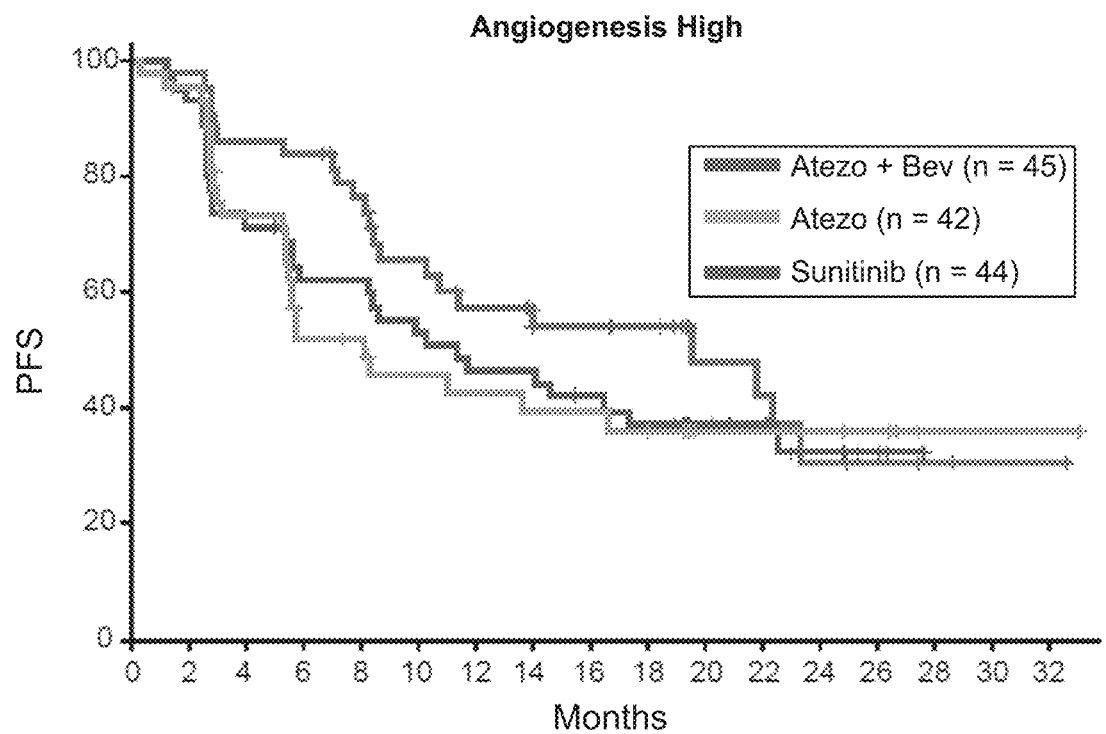
Figure 30A:
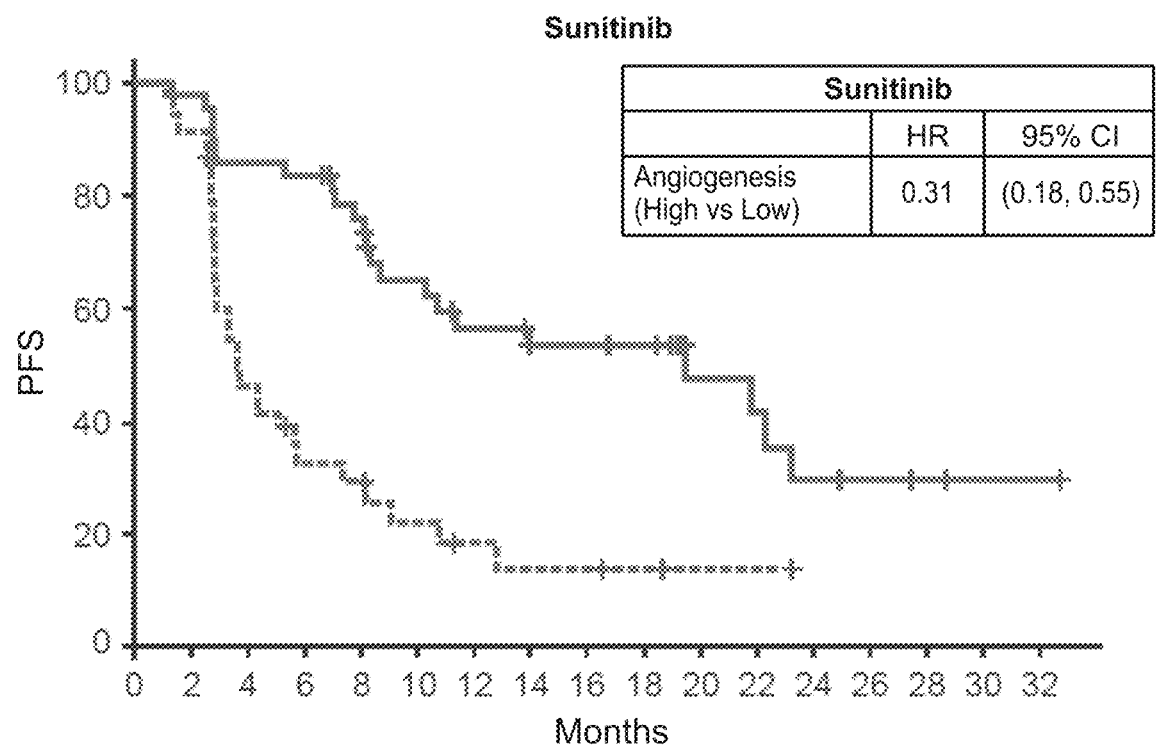
FIGS. 30A-30C are a series of graphs showing that sunitinib treatment demonstrated improved PFS in the Angiogenesis high subset compared to the Angiogenesis low subset. PFS for patients in the sunitinib (FIG. 30A), atezolizumab+bevacizumab (FIG. 30B), and atezolizumab (FIG. 30C) treatment arms was evaluated for the patient subgroups having high median expression) or low (<median expression) expression of Angiogenesis genes (VEGFA, KDR, ESM1, PECAM1, ANGPTL4, and CD34). The tables under the graph show hazard ratio (HR) and 95% confidence interval (95% CI).
Figure 30B:
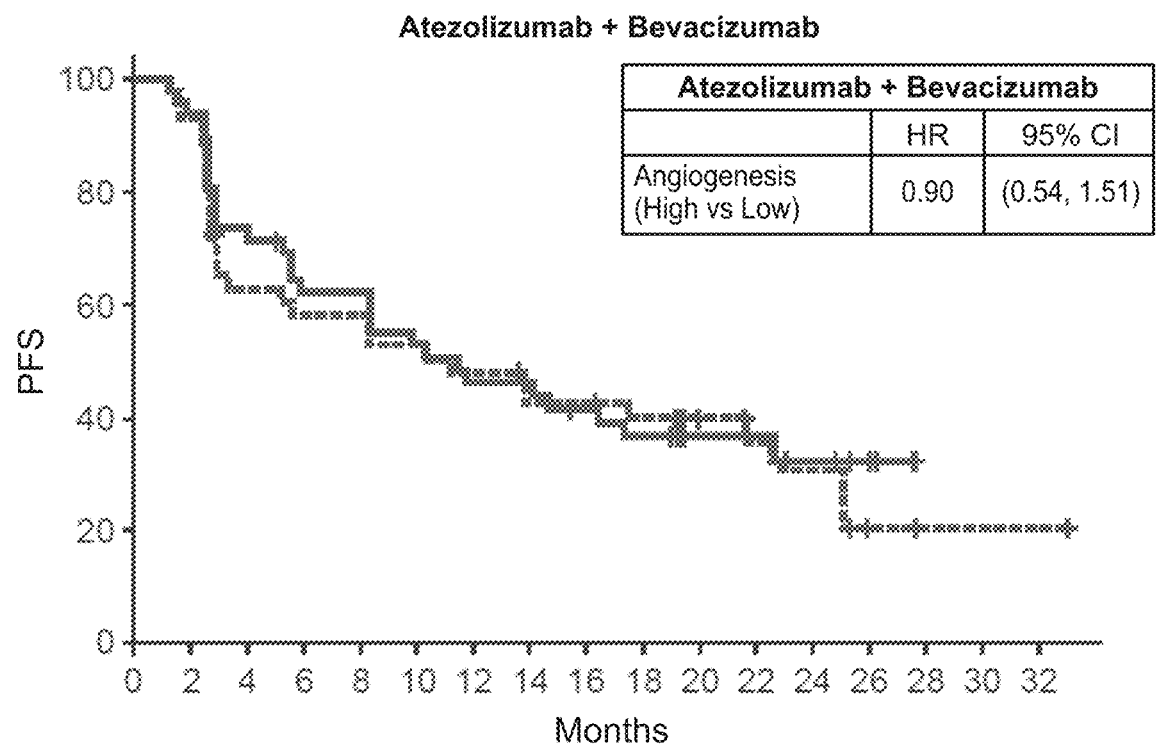
Figure 30C:
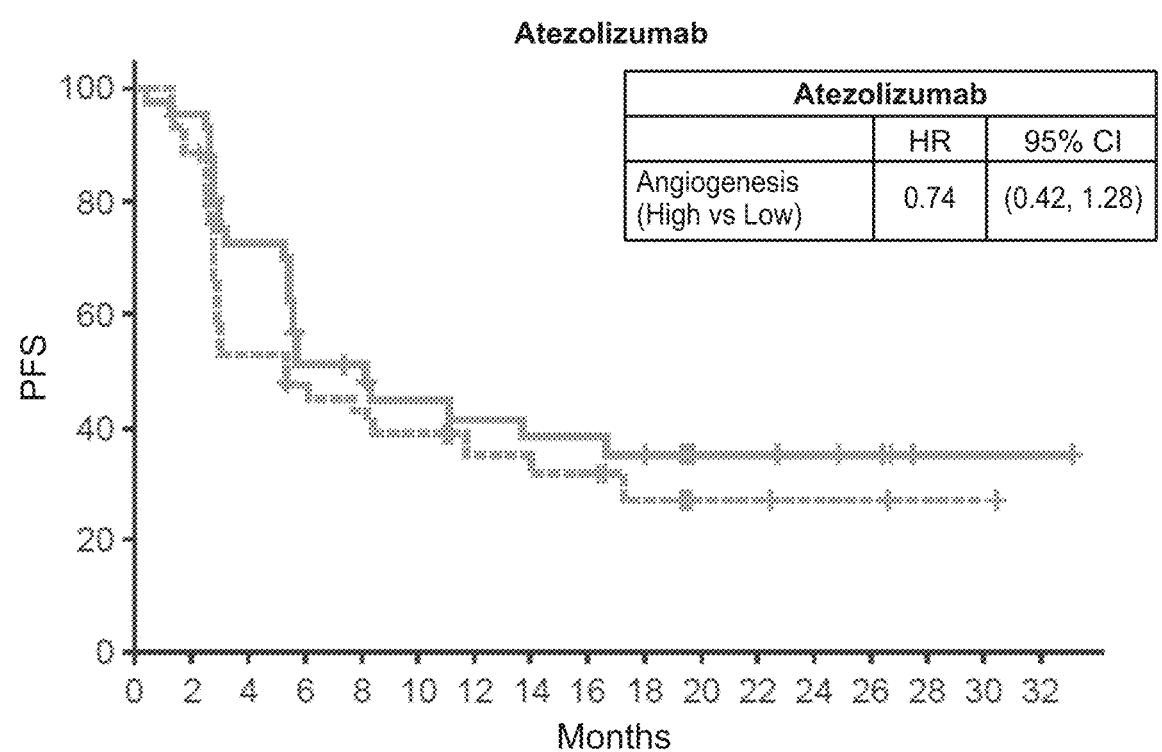
Figure 31A:
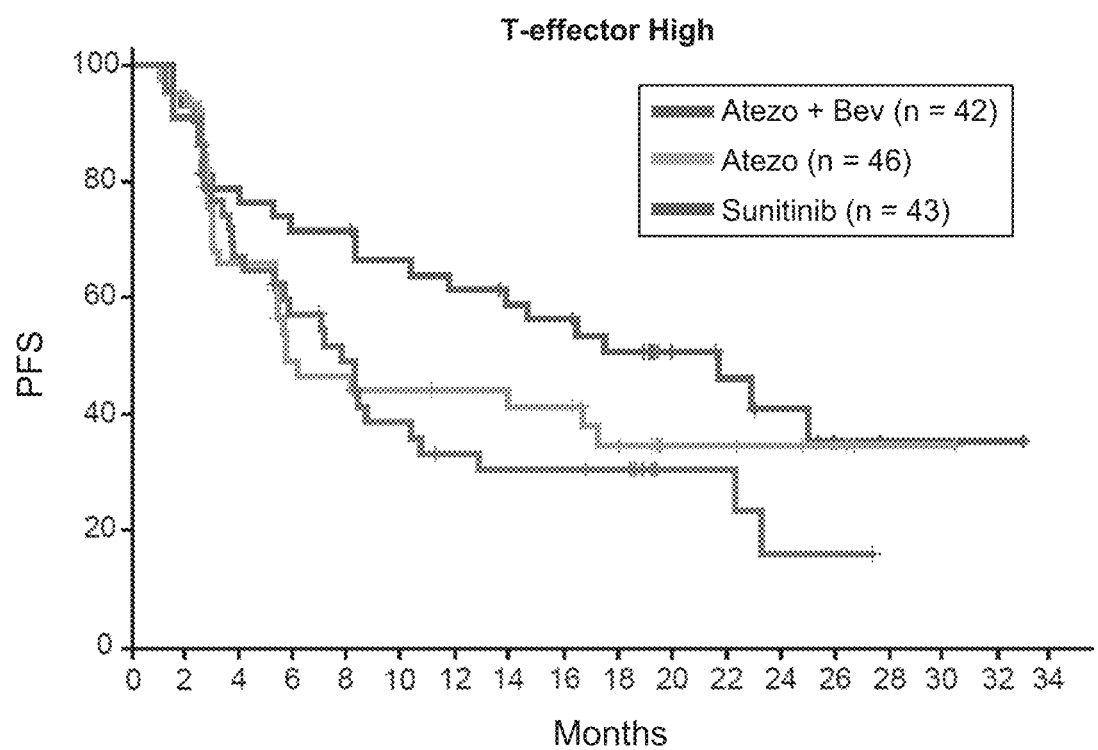
FIGS. 31A and 31B are a series of graphs showing that atezolizumab+bevacizumab demonstrated improved PFS compared to sunitinib in the Teff high subset. PFS for patients having high median expression) (FIG. 31A) or low (<median expression) (FIG. 31B) expression of Teff genes (CD8A, EOMES, PRF1, IFNG, and PD-L1) is shown for the indicated treatment arms.
Figure 31B:
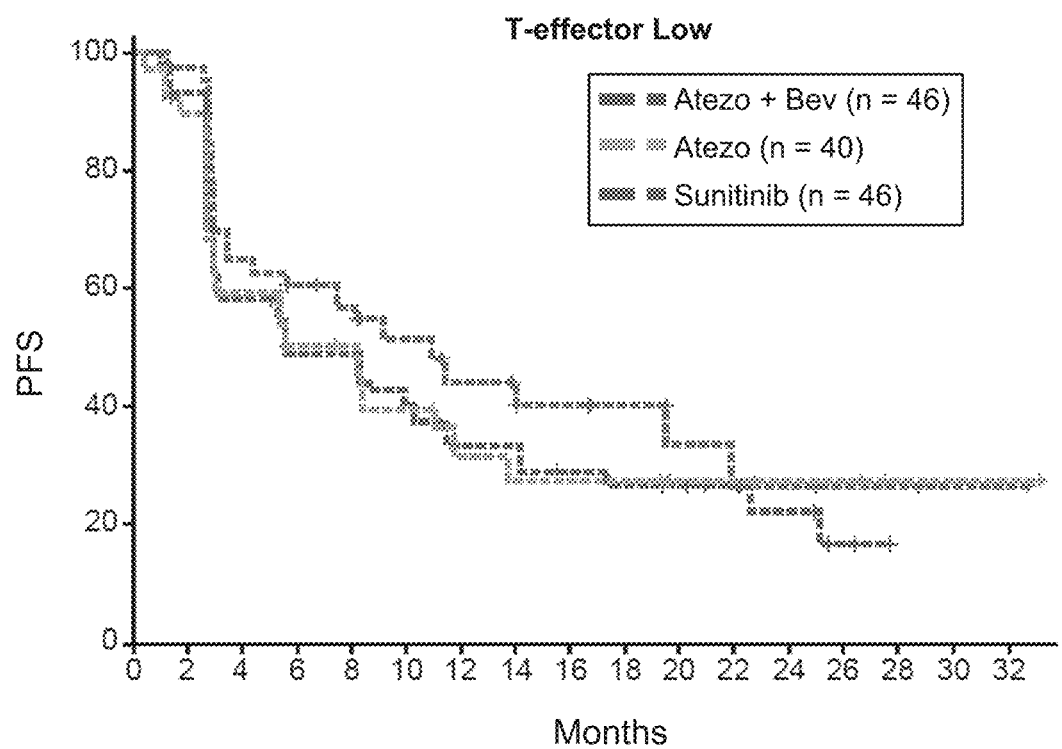
Figure 32A:
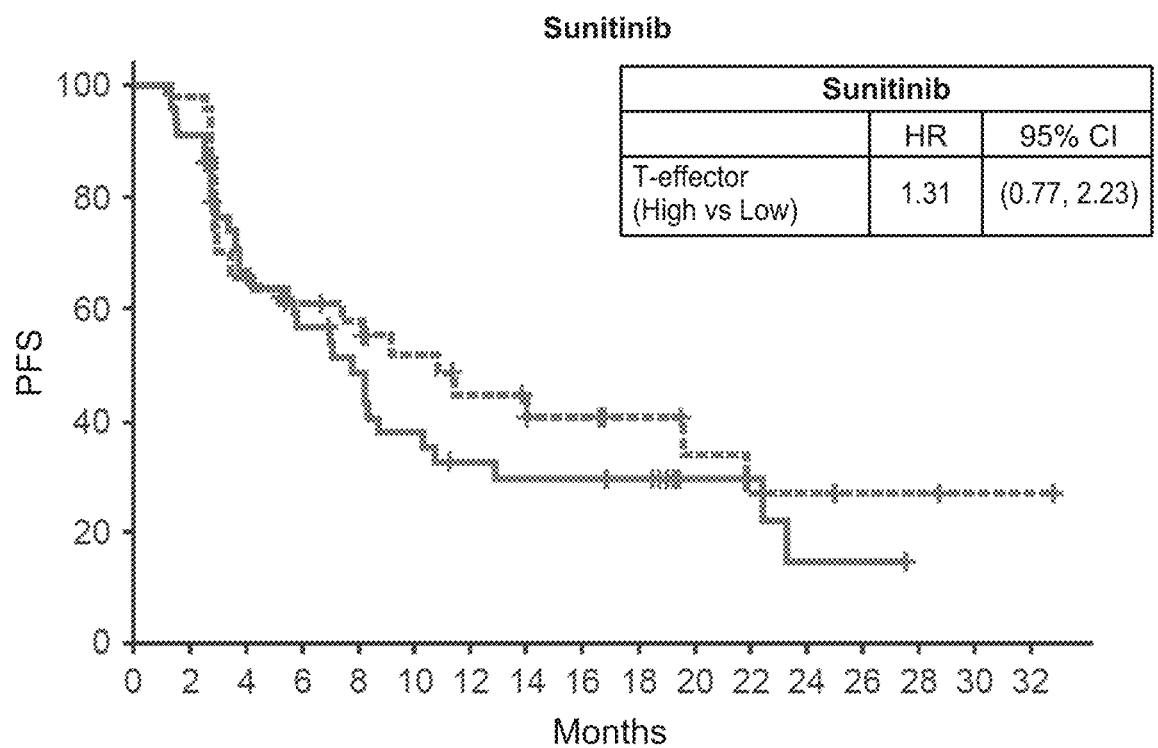
FIGS. 32A-32C are a series of graphs showing that atezolizumab+bevacizumab demonstrated improved PFS in the Teff high subgroup versus the Teff low subgroup. PFS for patients in the sunitinib (FIG. 32A), atezolizumab+bevacizumab (FIG. 32B), and atezolizumab (FIG. 32C) treatment arms was evaluated for the patient subgroups having high median expression) or low (<median expression) expression of Teff genes (CD8A, EOMES, PRF1, IFNG, and PD-L1). The tables under the graph show hazard ratio (HR) and 95% confidence interval (95% CI).
Figure 32B:
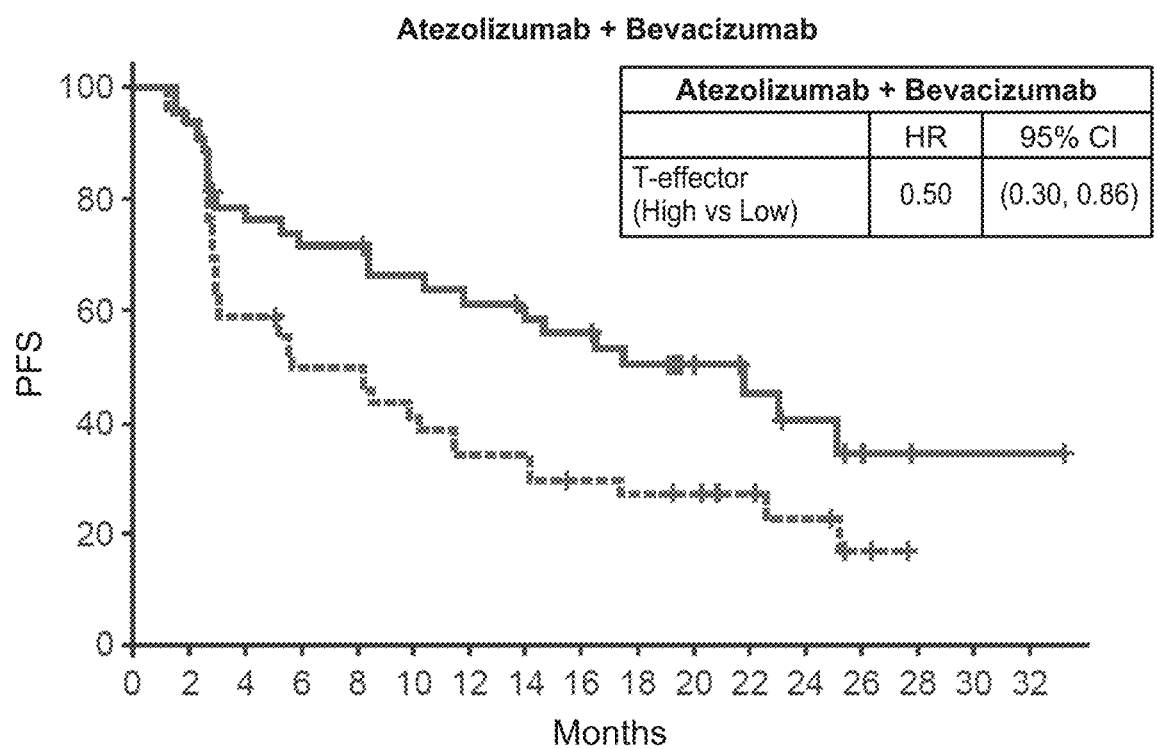
Figure 32C:
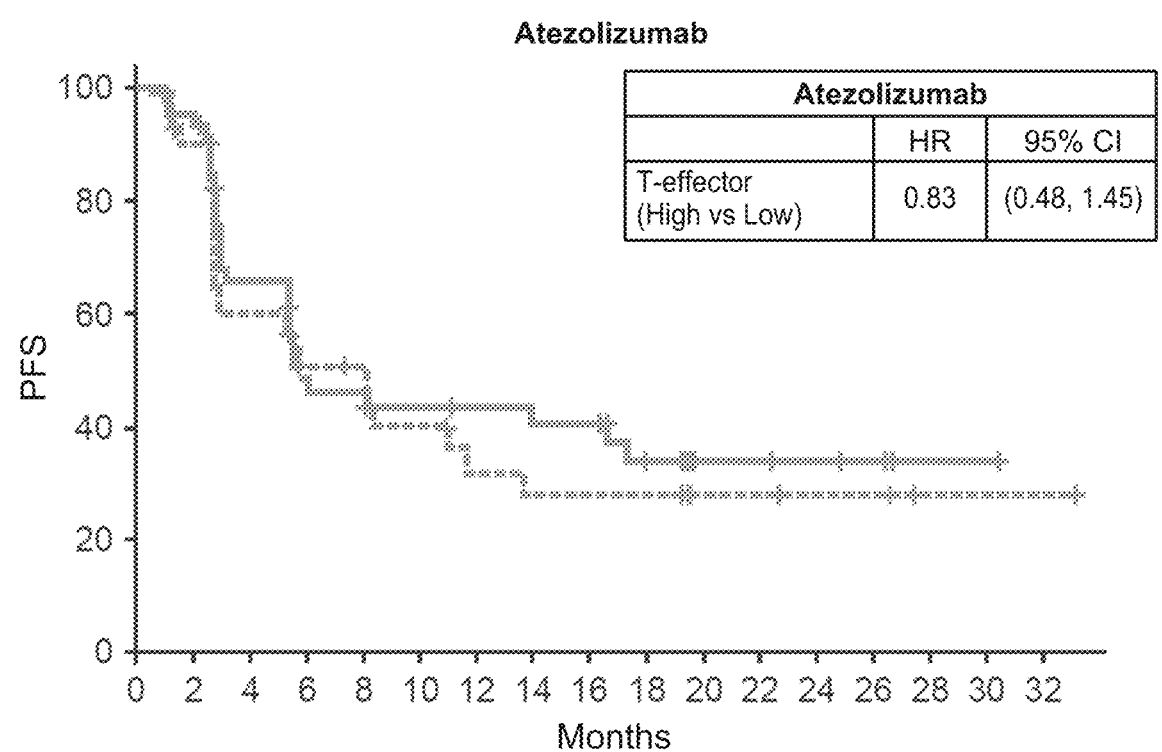

PFS was determined to be longer for PD-L1 IC2/3 and PD-L1 IC1/2/3 patients in the atezolizumab+bevacizumab treatment arm relative to PFS for patients in the sunitinib monotherapy arm. PFS was also determined to be longer for PD-L1 IC2/3 patients in the atezolizumab monotherapy arm relative to PFS for patients in the sunitinib monotherapy arm. When considering the evaluated gene expression levels, Teff high expression levels were found to be associated with PD-L1 IHC and longer PFS for patients in the atezolizumab+bevacizumab treatment arm compared to PFS for patients in the sunitinib monotherapy arm (FIGS. 31A, 31B, and 32A-32C). Ang low expression levels were also found to be associated with improved PFS for patients in the atezolizumab+bevacizumab treatment arm compared to PFS for patients in the sunitinib monotherapy arm (FIG. 29A). Ang high expression levels, on the other hand, were associated with improved clinical activity in the sunitinib monotherapy arm, but not the atezolizumab+bevacizumab treatment arm (FIGS. 29B and 30A-30C). PFS hazard ratios (HR) with 95% confidence intervals (95% CI) for both the atezolizumab+bevacizumab and atezolizumab treatment arms relative to the sunitinib treatment arm are provided in Table 20 for patients binned according to PD-L1 status, Teff gene expression levels, and Ang gene expression levels. The data in Table 20 with respect to PD-L1 IHC are unstratified HRs. The overall response rate (ORR) correlated with PFS in the gene expression subgroups (FIG. 25). Table 21 shows stratified PFS HRs with 95% CI for both the atezolizumab+bevacizumab and atezolizumab treatment arms relative to the sunitinib treatment arm for patients binned according to PD-L1 status and in the intent-to-treat (ITT) population.

TABLE 20

Molecular Correlates of PFS Responses to Atezolizumab + Bevacizumab Combination Therapy or Atezolizumab Monotherapy Compared to Sunitinib Monotherapy

| | PFS HR (95% CI) | |
|---|---|---|
| PFS HR (95 % CI) | Atezo + Bev vs Sun | Atezo vs Sun |
| PD-L1 IHC IC1/2/3 | 0.66 (0.41-1.07) | 0.97 (0.61-1.55) |
| PD-L1 IHC IC2/3 | 0.36 (0.14-0.88) | 0.54 (0.23-1.28) |
| Teff high | 0.55 (0.32-0.95) | 0.85 (0.50-1.43) |
| Teff low | 1.41 (0.84-2.03) | 1.33 (0.76-2.33) |
| Ang high | 1.36 (0.78-2.36) | 1.46 (0.81-2.60) |
| Ang low | 0.58 (0.35-0.98) | 0.75 (0.45-1.25) |

TABLE 21

Molecular Correlates of PFS Responses to Atezolizumab + Bevacizumab Combination Therapy or Atezolizumab Monotherapy Compared to Sunitinib Monotherapy

| | Stratified PFS HR (95% CI) | |
|---|---|---|
| PFS HR (95% CI) | Atezo + Bev vs Sun | Atezo vs Sun |
| ITT | 1.00 (0.69-1.45) | 1.19 (0.82-1.71) |
| PD-L1 IHC IC1/2/3 | 0.64 (0.38-1.08) | 1.03 (0.63-1.67) |
| PD-L1 IHC IC2/3 | 0.34 (0.13-0.91) | 0.64 (0.27-1.54) |

Figure 26:
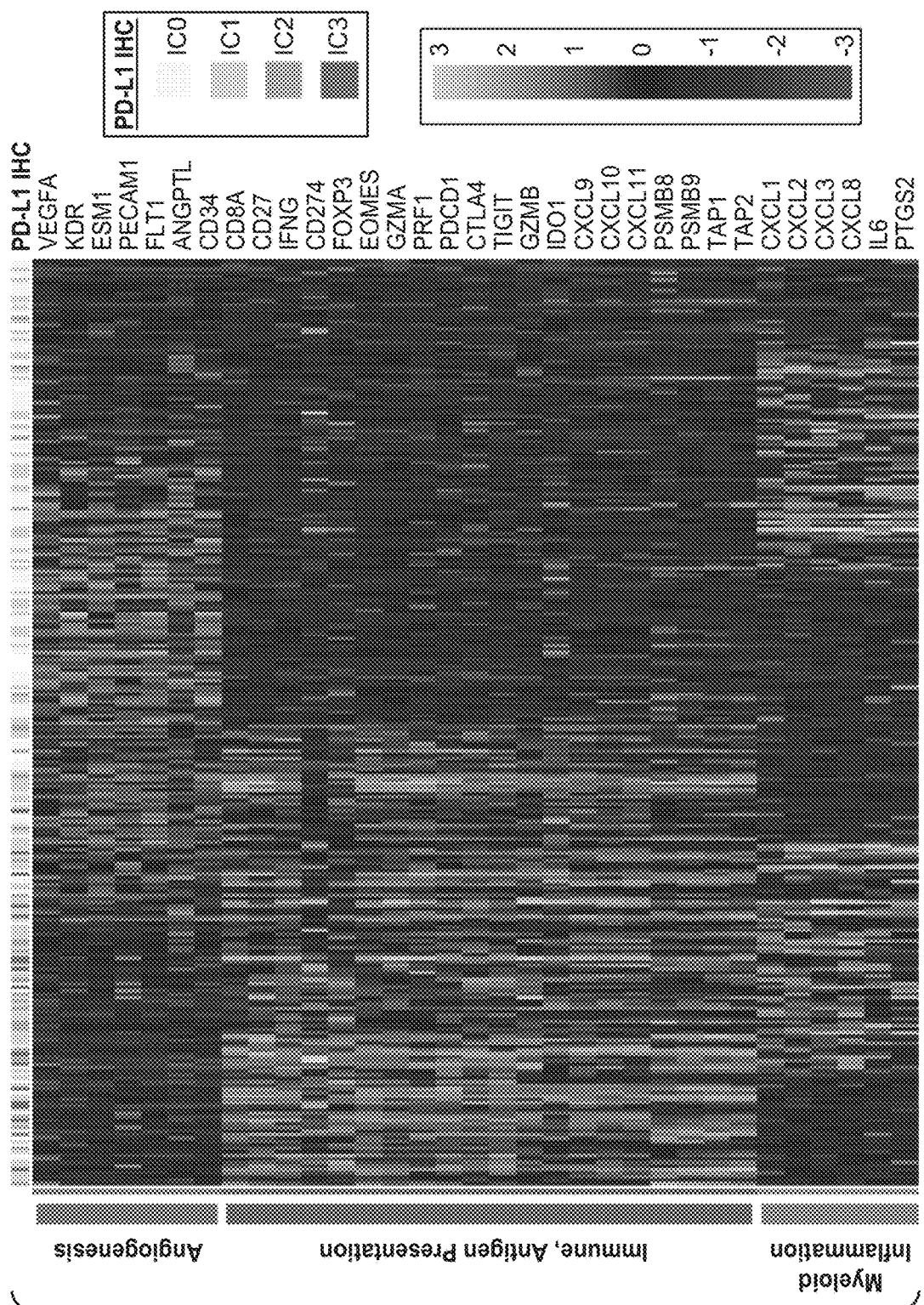
FIG. 26 is a heatmap showing a transcriptome map of angiogenesis, immune associated, and myeloid associated genes in RCC tumors.

FIG. 26 shows a transcriptome map of angiogenesis and immune-associated genes in RCC tumors. Expression levels of the genes shown in FIG. 26 can be used as predictive biomarkers for response to an anti-cancer therapy that includes a VEGF antagonist VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab) or a PD-1 binding antagonist (e.g., an anti-PD-1 antibody), or an anti-cancer therapy that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). In particular, genes associated with angiogenesis (e.g., VEGFA, KDR, ESM1, PECAM1, FLT1, ANGLT4, and/or CD34), immune/antigen presentation (e.g., CD8A, CD27, INFG, PD-L1 (CD274), FOXP3, EOMES, GZMA, PFR1, PD-1 (PDCD1), CLTA4, TIGIT, GZMB, IDO1, CXCL9, CXCL10, CXCL11, PSMB8, PSMB9, TAP1, and/or TAP2), and myeloid inflammation (e.g., CXCL1, CXCL2, CXCL3, CXCL8, IL6, PTGS2, CXCR1, CXCR2, S100A8, and/or S100A9) can be used to predict response to an anti-cancer therapy that includes a VEGF antagonist (e.g., an anti-VEGF antibody, (e.g., bevacizumab) or a VEGFR inhibitor (e.g., a multi-targeted tyrosine kinase inhibitor (e.g., sunitinib, axitinib, pazopanib, or cabozantinib))) and a PD-L1 axis binding antagonist (e.g., a PD-L1 binding antagonist (e.g., an anti-PD-L1 antibody, e.g., atezolizumab) or a PD-1 binding antagonist (e.g., an anti-PD-1 antibody), or an anti-cancer therapy that includes an angiogenesis inhibitor (e.g., a VEGF antagonist (e.g., a VEGFR inhibitor, (e.g., a multi-targeted tyrosine kinase inhibitor (e.g., sunitinib, axitinib, pazopanib, or cabozantinib)))). For example, an expression level of one or more of CD8A, CD27, INFG, PD-L1 (CD274), FOXP3, EOMES, GZMA, PFR1, PD-1 (PDCD1), CLTA4, TIGIT, GZMB, IDO1, CXCL9, CXCL10, CXCL11, PSMB8, PSMB9, TAP1, and/or TAP2 at or above a reference level of the one or more genes can indicate the patient may benefit from treatment with atezolizumab and bevacizumab (or other VEGF antagonists and PD-L1 axis binding antagonists). In some instances, such patients may have an expression level of one or more of CXCL1, CXCL2, CXCL3, CXCL8, IL6, PTGS2, CXCR1, CXCR2, S100A8, and/or S100A9 that is at or above a reference level of the one or more genes. In another example, an expression level of one or more of VEGFA, KDR, ESM1, PECAM1, FLT1, ANGLT4, and/or CD34 below a reference level of the one or more genes can indicate the patient may benefit from treatment with atezolizumab and bevacizumab (or other VEGF antagonists and PD-L1 axis binding antagonists). In a further example, an expression level of one or more of VEGFA, KDR, ESM1, PECAM1, FLT1, ANGLT4, and/or CD34 above a reference level can indicate the patient may benefit from treatment with sunitinib (or another angiogenesis inhibitor (e.g., a VEGF antagonist (e.g., a VEGFR inhibitor, (e.g., a multi-targeted tyrosine kinase inhibitor (e.g., axitinib, pazopanib, or cabozantinib))))). In another example, an expression level of one or more of CXCL1, CXCL2, CXCL3, CXCL8, IL6, PTGS2, CXCR1, CXCR2, S100A8, and/or S100A9 that is below a reference level of the one or more genes can indicate that the patient may benefit from treatment with atezolizumab and bevacizumab (or other VEGF antagonists and PD-L1 axis binding antagonists).

Figure 27A:
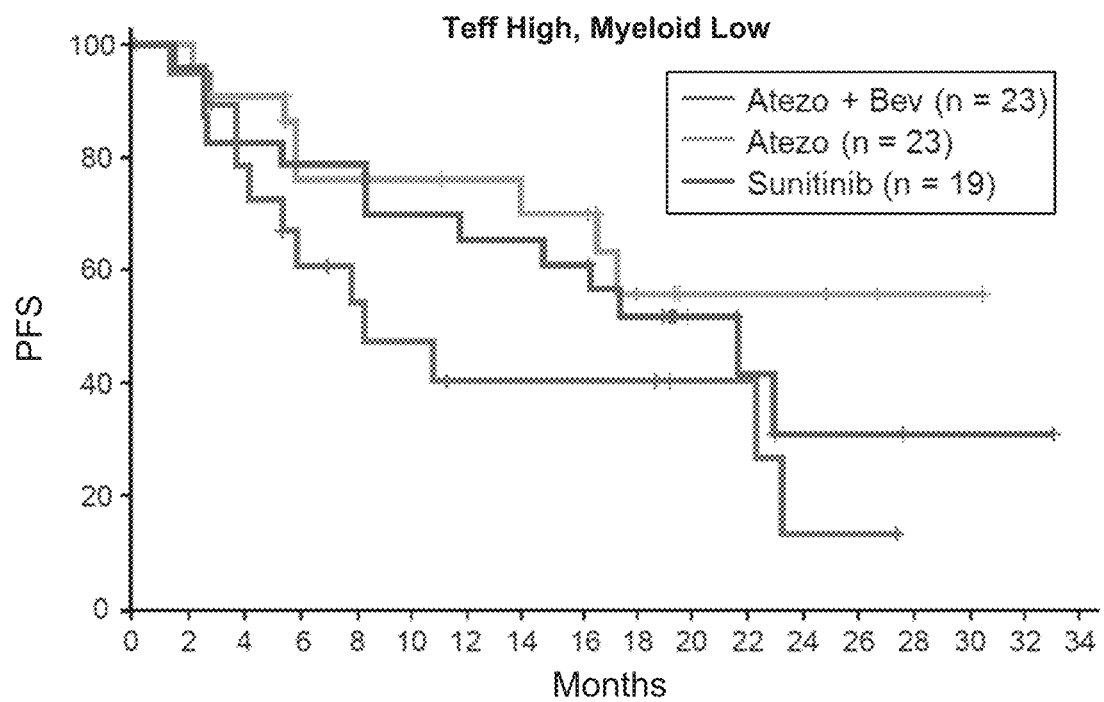
FIGS. 27A and 27B is a series of graphs showing that addition of bevacizumab to atezolizumab was associated with improved PFS benefit in the T-effector (Teff) high/myeloid inflammation (Myeloid) high subgroup (FIG. 27B), but not in the Teff high myeloid low subgroup (FIG. 27A). Teff indicates CD8A, EOMES, PRF1, IFNG, and PD-L1. Myeloid indicates IL6, CXCL1, CXCL2, CXCL3, CXCL8, and PTGS2. High: median expression, Low: <median expression.
Figure 27B:
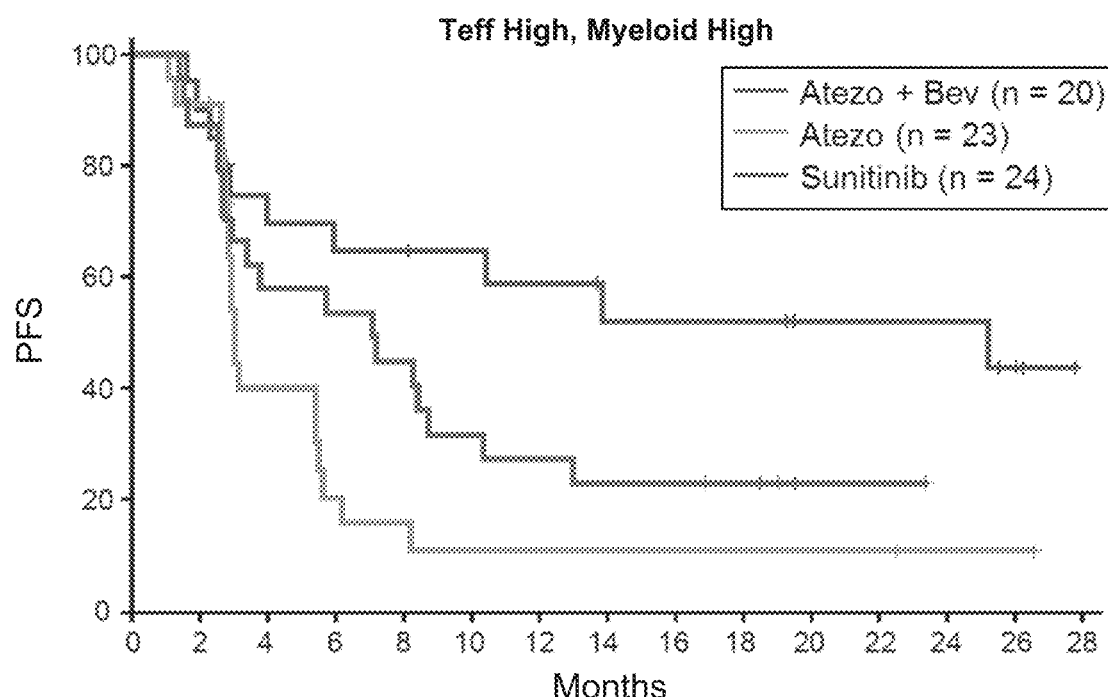
Figure 28:
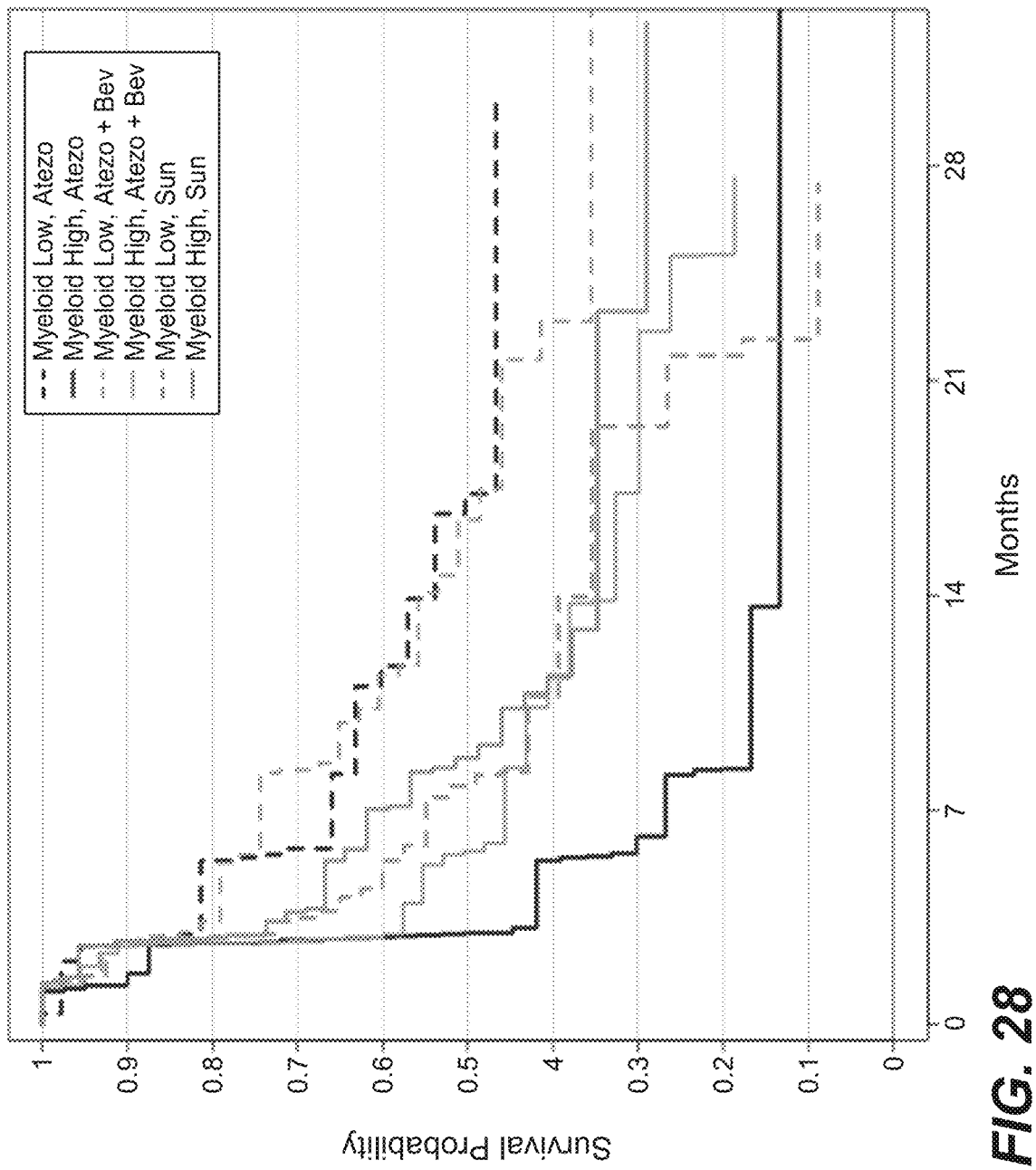
FIG. 28 is a graph showing that the Myeloid genes (IL6, CXCL1, CXCL2, CXCL3, CXCL8, and PTGS2), independently of the Teff genes, were associated with relatively worse PFS outcome when comparing Myeloid High versus Myeloid Low patients within the Atezo+Bev arm of the study described in Example 5. When compared to sunitinib (Sun), Atezo+Bev was not different from Sun in the Myeloid High population, but Atezo+Bev demonstrated improved PFS benefit in the Myeloid Low population. High: ≥median expression, Low: <median expression.

Addition of bevacizumab to atezolizumab (Atezo+Bev) was associated with improved PFS in the Teff high/Myeloid high subgroup (FIG. 27). Reduced atezolizumab monotherapy 1L activity in Teff high/Myeloid high patients suggests a potential mechanism of immune escape, which may be rescued by the addition bevacizumab. The Myeloid genes, independently of the Teff-related genes, were associated with relatively worse PFS outcome when comparing Myeloid high expression levels to Myeloid low expression levels within the atezolizumab+bevacizumab treatment arm (FIG. 28). Treatment benefit in terms of PFS from atezolizumab+bevacizumab was not different from sunitinib monotherapy in the Myeloid high population, but was improved in the Myeloid low population compared to sunitinib monotherapy (FIG. 28).

After progression on atezolizumab or sunitinib, crossover to atezolizumab+bevacizumab was allowed in the IMmotion150 trial design (except that crossover following atezolizumab monotherapy was not allowed in Europe). 77% and 75% of patients crossed over after 1L sunitinib or atezolizumab, respectively, among patients who progressed and were eligible based on geographic location. The crossover patients were also analyzed by baseline tumor microenvironment (TME) gene expression status. A trend of a similar result with respect to improved PFS in the Teff high/Myeloid high subgroup for addition of bevacizumab to atezolizumab (Atezo+Bev) was observed (n=8).

In summary, these studies demonstrate that biomarkers described herein can be used to predict patient response to anti-cancer therapies (e.g., anti-cancer therapy that includes a VEGF antagonist and a PD-L1 axis binding antagonist, or a multi-targeted tyrosine kinase), and to select patients for an anti-cancer therapy that is optimized for their cancer.

Example 6

Atezolizumab Alone or in Combination with Bevacizumab Versus Sunitinib: Efficacy, Safety and Molecular Correlates of Differential Response in a Randomized Phase 2 Trial in Renal Cell Carcinoma In this example, additional primary clinical results of the phase 2 IMmotion150 study are described along with the results of molecular analyses conducted to evaluate the predictive value of biomarkers described herein.

A. Results

Study Design and Efficacy

The primary objective of this phase 2 trial was to evaluate the efficacy of atezolizumab+bevacizumab and atezolizumab monotherapy compared with sunitinib. The sample size of 100 patients per arm and 70% events rate was deemed adequate for estimation of effect size (including median PFS and hazard ratio [HR]) in the intention-to-treat (ITT) as well as the PD-L1+ subgroup.

Tumor specimens from patients acquired <12 months prior to study treatment were required for enrollment in the study. Tissue was prospectively tested for PD-L1 expression on IC by a central laboratory using the SP142 IHC assay (VENTANA, Tucson, Ariz.). IC staining was defined as follows: any discernible PD-L1 staining of any intensity in IC covering <1% or absent, between ≥1% and <5%, between ≥5% and <10%, or ≥10% of tumor area.

Figure 33:
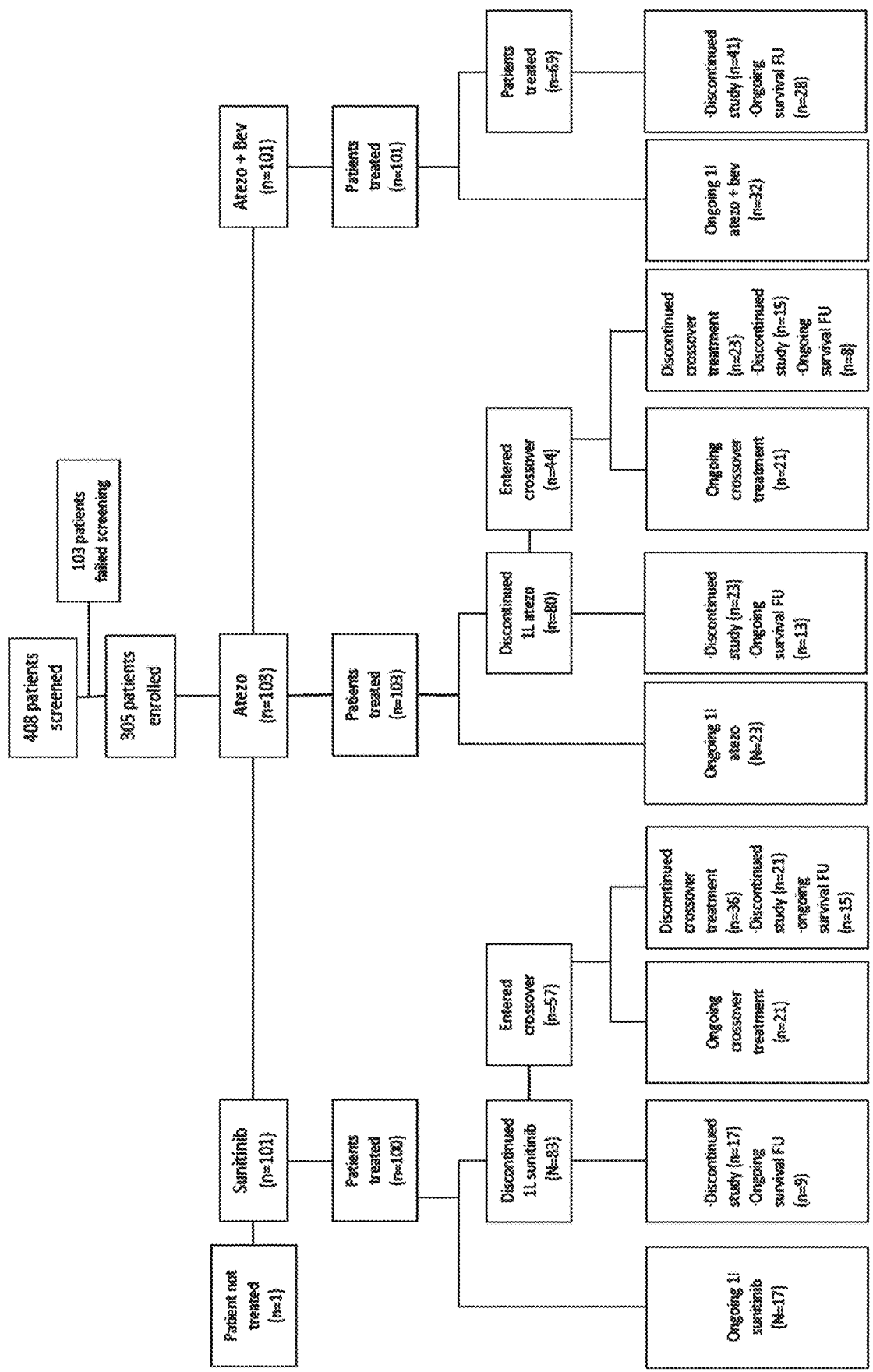
FIG. 33 is a schematic diagram showing a flow chart of patients randomized to one of three treatment arms in the IMmotion150 trial: sunitinib, atezolizumab monotherapy, or atezolizumab+bevacizumab in combination. One patient in the sunitinib arm did not receive study drug due to withdrawal of consent and was excluded from the safety analysis.

Patients were enrolled in the study from Jan. 8, 2014 to Mar. 16, 2015. This report reflects the results of data with a clinical cutoff date of Oct. 17, 2016 and a median survival follow-up of 20.7 months. All randomized patients were included in the ITT population (N=305) for all efficacy analyses. Patients in the safety analysis population (n=304) received more than one dose of study drug. One patient in the sunitinib arm was excluded from the safety analysis due to withdrawal of consent before receiving study drug (FIG. 33). Discontinuation of treatment was higher with atezolizumab (77.7%) and sunitinib (82.2%) than with atezolizumab+bevacizumab (68.3%), and disease progression was the most common reason for discontinuation among all treatment arms.

Patient demographics were comparable across treatment arms for the safety and ITT populations. (Table 22).

TABLE 22

| Baseline demographics/patient characteristics | | | |
|---|---|---|---|
| | Sunitinib n = 101 | Atezolizumab + Bevacizumab n = 101 | Atezolizumab n = 103 |
| Age, median (range), y | 61 (25-85) | 62 (32-88) | 61 (27-81) |
| Male, n (%) | 79 (78%) | 74 (73%) | 77 (75%) |
| Karnofsky performance status (KPS) ≥ 80, n (%) | 94 (93%) | 99 (99%) | 101 (99%) |
| Predominant clear cell histology, n (%) | 96 (96%) | 97 (96%) | 95 (92%) |
| Sarcomatoid component, n (%) | 14 (14%) | 15 (15%) | 16 (15%) |
| Prior nephrectomy, n (%) | 88 (87%) | 88 (87%) | 89 (86%) |
| Memorial Sloan Kettering Cancer Center (MSKCC) risk category, n (%) | | | |
| Favorable (0) | 21 (21%) | 30 (30%) | 26 (25%) |
| Intermediate (1 or 2) | 70 (69%) | 62 (61%) | 69 (67%) |
| Poor (≥3) | 10 (10%) | 9 (9%) | 8 (8%) |
| ≥1% PD-L1 expression on IC (PD-L1$_+$), n (%) | 60 (59%) | 50 (50%) | 54 (52%) |

Figure 34A:
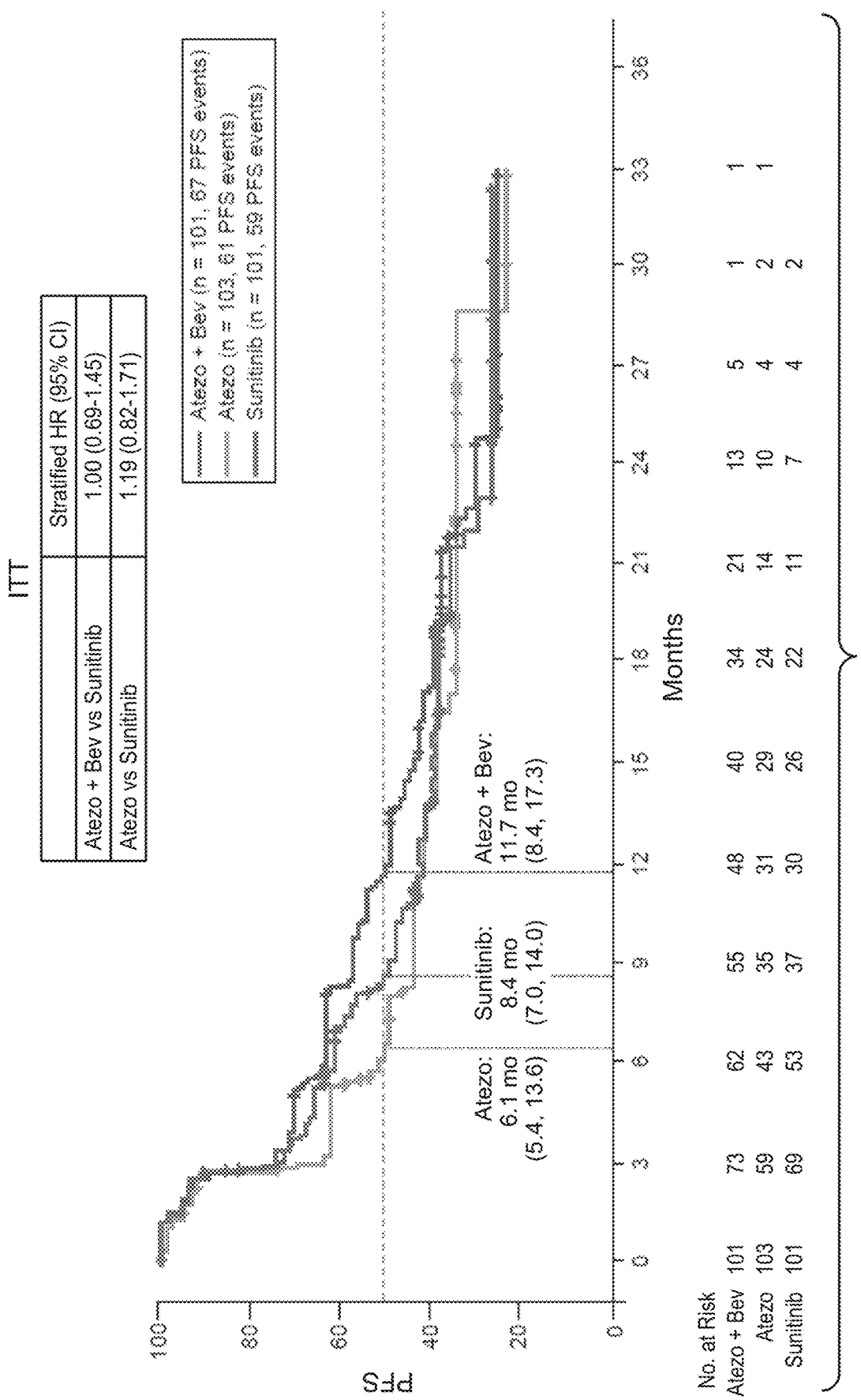
FIGS. 34A-34C are a series of graphs showing positive independent review facility (IRF)-assessed efficacy associated with atezolizumab+bevacizumab in mRCC patients with PD-L1+IC. Kaplan-Meier curves depict IRF-assessed median PFS in the atezolizumab bevacizumab, atezolizumab monotherapy, and sunitinib treatment arms in the ITT population (FIG. 34A) and PD-L1+(≥1% PD-L1 expression on IC by IHC) population (FIG. 34B) across 33 months. Censored data are indicated by vertical tick marks in Kaplan-Meier curves. Objective response rate (ORR) as depicted by partial response (PR) and complete response (CR) for the ITT and PD-L1+ populations for each treatment arm (FIG. 34C).
Figure 34B:
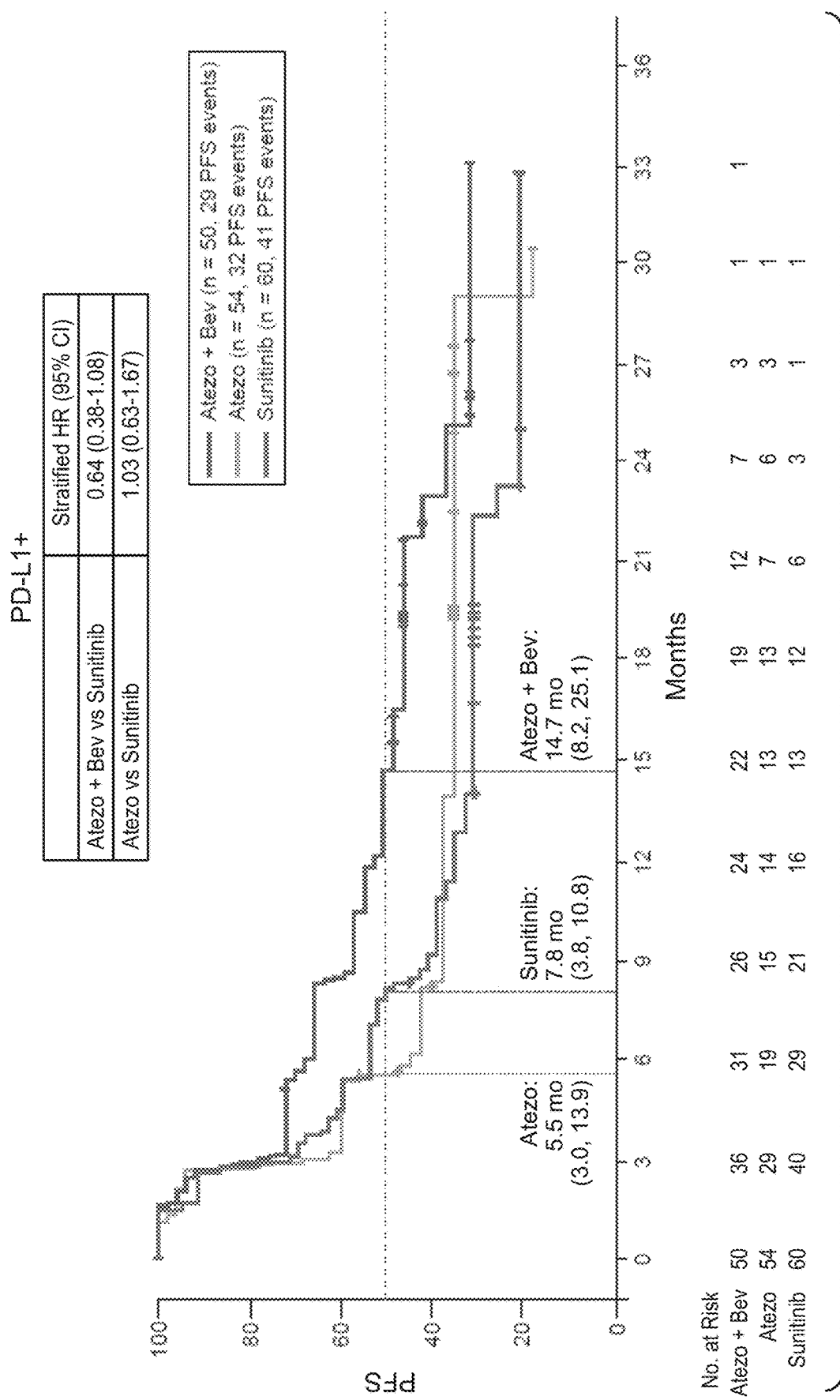
Figure 34C:
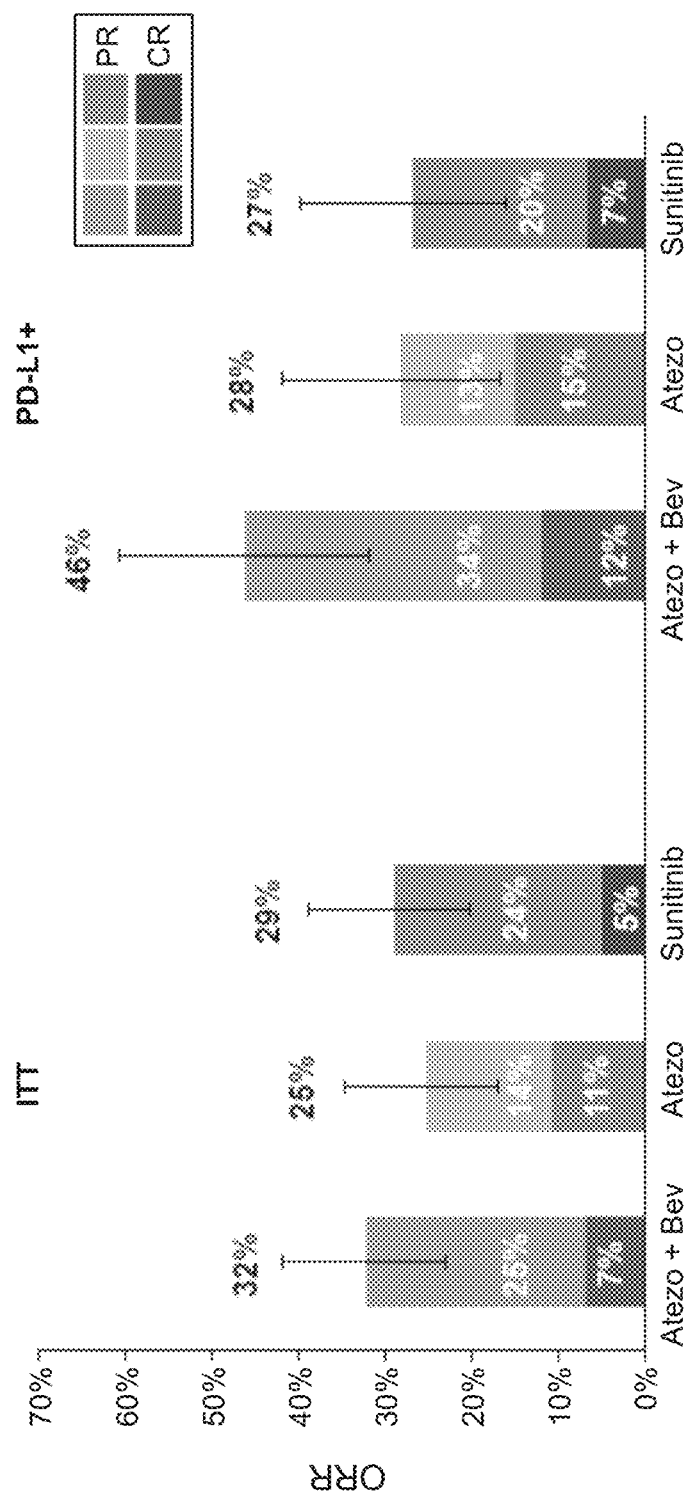
Figure 35A:
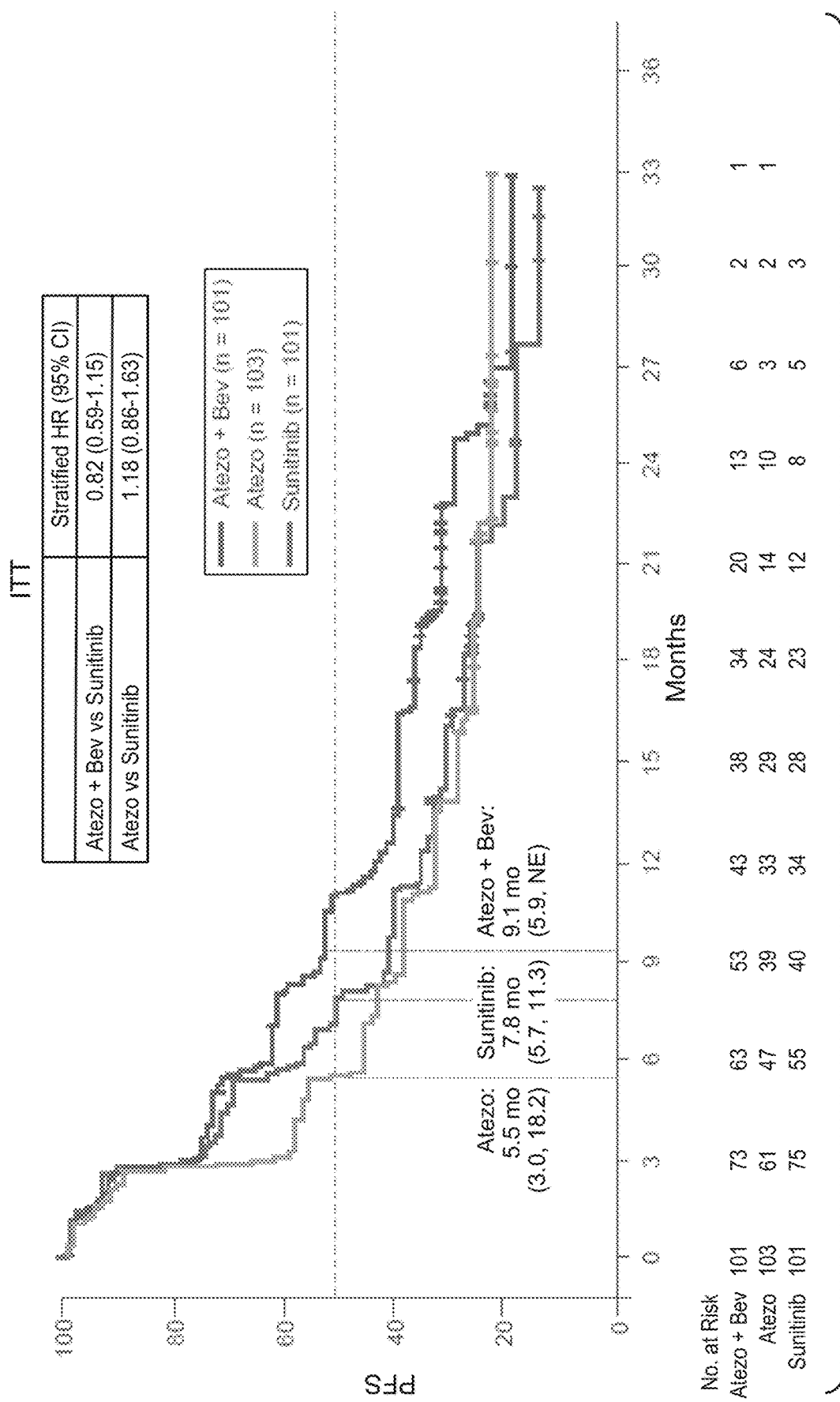
FIGS. 35A and 35B are a series of graphs showing investigator (INV)-assessed PFS associated with atezolizumab+bevacizumab in mRCC patients with PD-L1+IC. Kaplan-Meier curves depict INV-assessed median PFS in the atezolizumab+bevacizumab, atezolizumab monotherapy, and sunitinib treatment arms in the ITT population (FIG. 35A) and PD-L1+(≥1% PD-L1 expression on IC by IHC) population (FIG. 35B) across 33 months. Censored data are indicated by vertical tick marks in Kaplan-Meier curves.
Figure 35B:
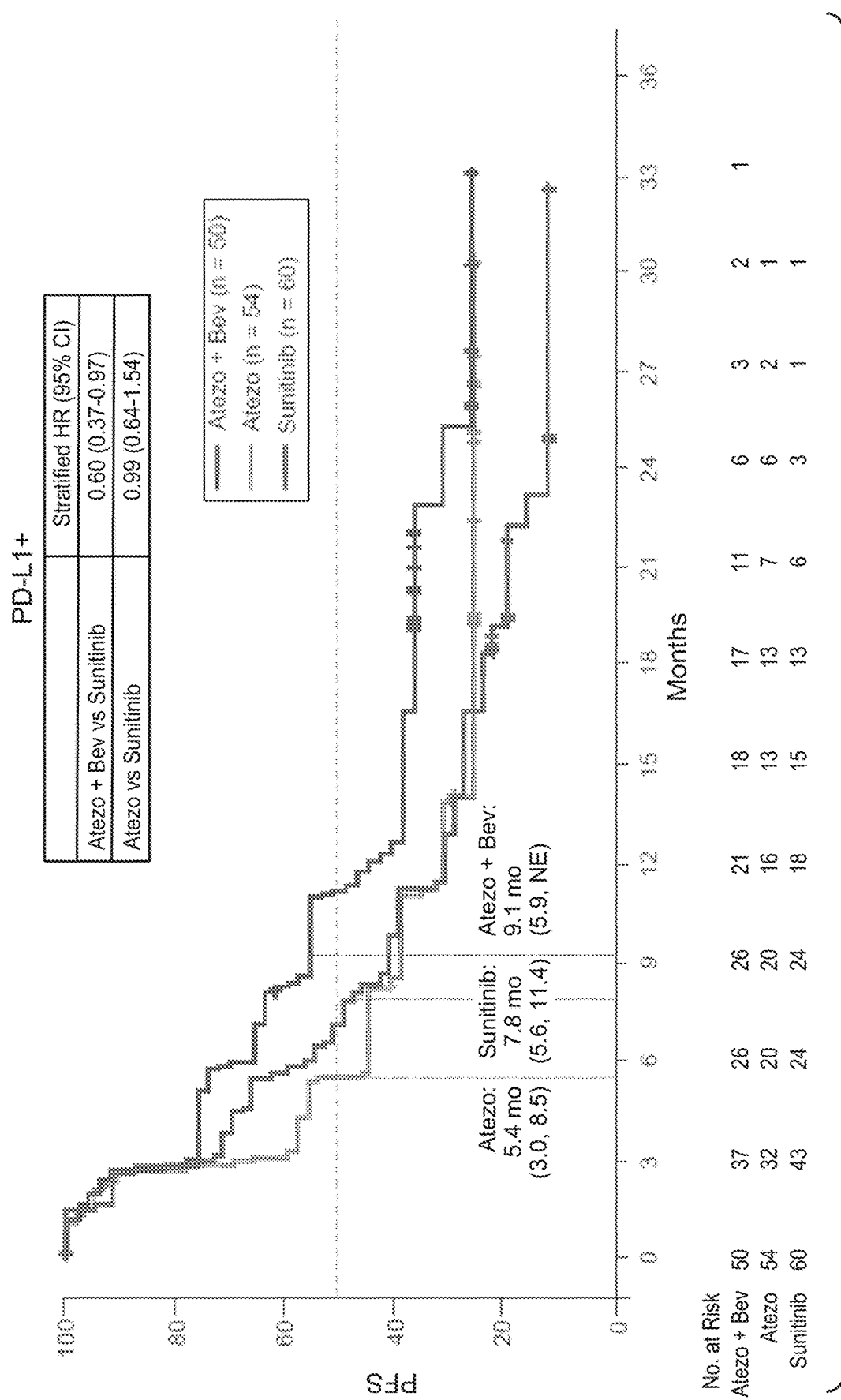
Figure 36A:
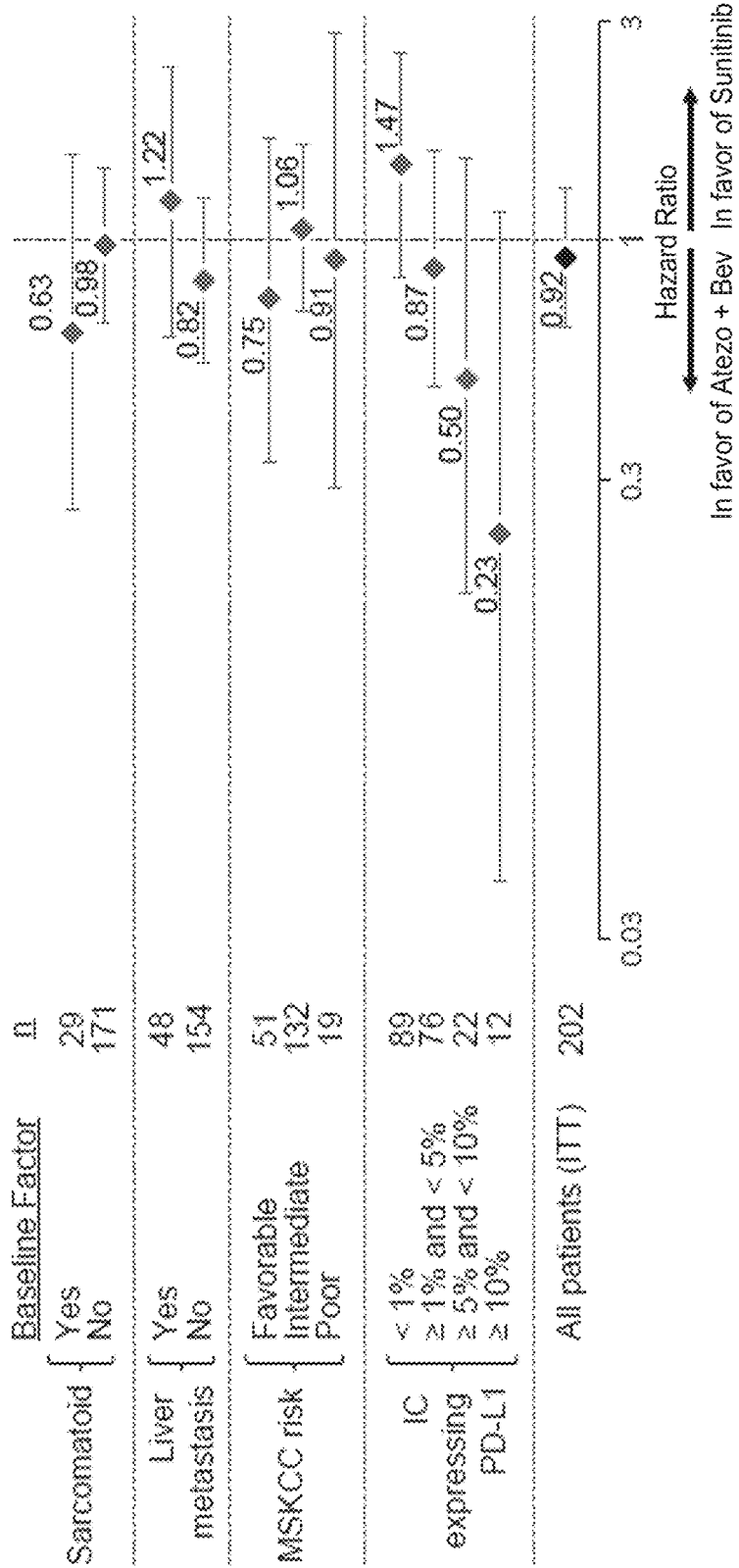
FIGS. 36A and 36B are a series of Forest plots showing IRF-assessed PFS hazard ratios (HRs) in key subgroups. The Forest plots are shown depicting median PFS versus sunitinib HRs in specific patient subgroups for atezolizumab+ bevacizumab (FIG. 36A) and atezolizumab monotherapy (FIG. 36B). The analyses were unstratified.
Figure 36B:
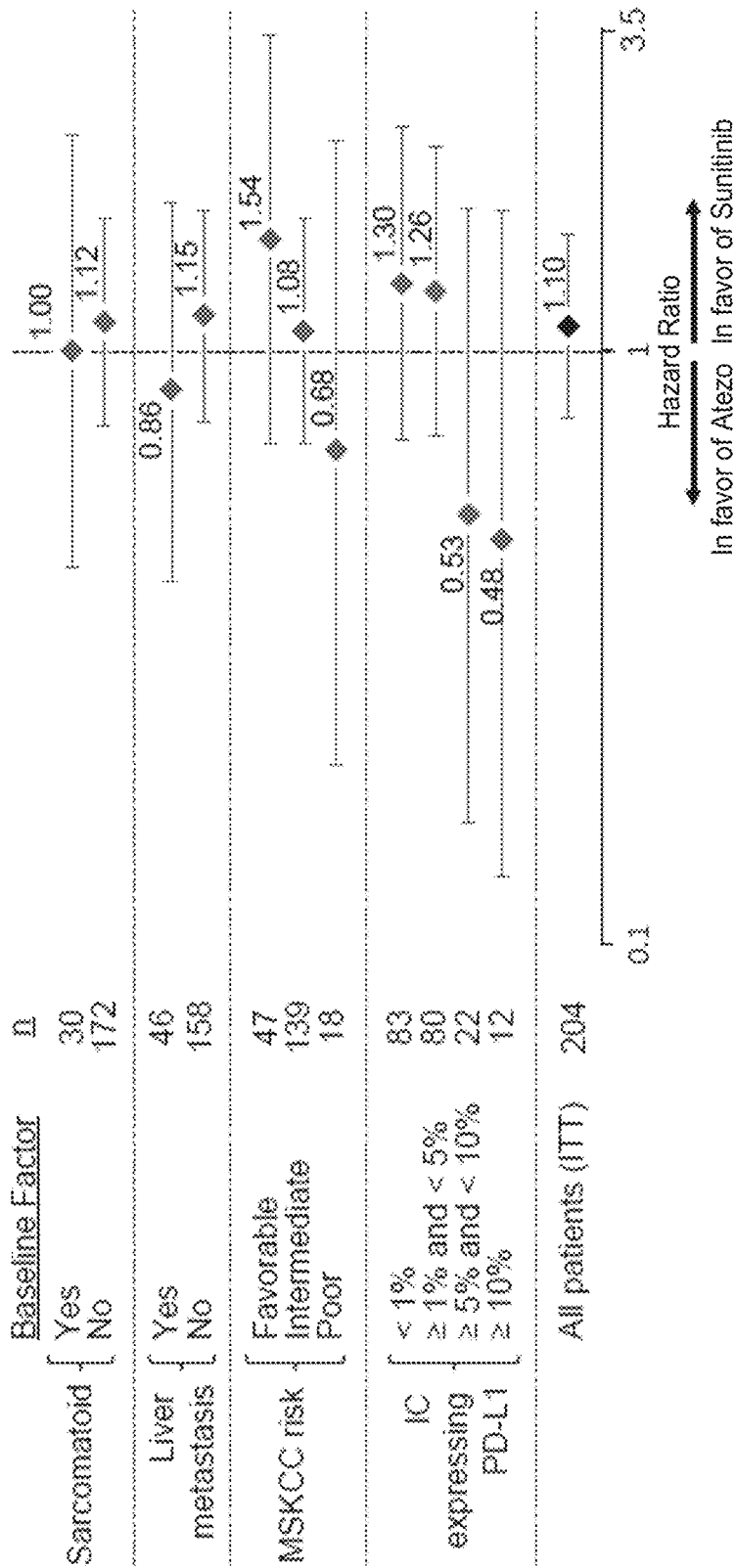

Independent review facility (IRF)-assessed efficacy endpoints are summarized as follows. Stratified analysis in the ITT population showed a median progression-free survival (PFS) of 11.7 months (95% CI, 8.4-17.3) with atezolizumab+bevacizumab versus 8.4 months (95% CI, 7.0-14.0) with sunitinib (HR 1.00; 95% CI, 0.69-1.45) and 6.1 months (95% CI, 5.4-13.6) with atezolizumab monotherapy (HR 1.19; 95% CI, 0.82-1.71 versus sunitinib; FIG. 34A). In the PD-L1+ population, the median PFS was 14.7 months (95% CI, 8.2-25.1) with atezolizumab+bevacizumab versus 7.8 months (95% CI, 3.8-10.8) with sunitinib (HR 0.64; 95% CI, 0.38-1.08) and 5.5 months (95% CI, 3.0-13.9) with atezolizumab monotherapy (HR 1.03; 95% CI, 0.63-1.67 versus sunitinib; FIG. 34B). The objective response rates (ORRs) were 32% (7% complete response [CR], 25% partial response [PR]), 25% (11% CR, 14% PR) and 29% (5% CR, 24% PR) with atezolizumab+bevacizumab, atezolizumab monotherapy, and sunitinib, respectively (FIG. 34C). In PD-L1+ patients, the ORRs were 46% (12% CR, 34% PR), 28% (15% CR, 13% PR), and 27% (7% CR, 20% PR) with atezolizumab+bevacizumab, atezolizumab monotherapy, and sunitinib, respectively (FIG. 34C). The concordance between investigator-assessed PFS (FIGS. 35A and 35B), and IRF-assessed PFS was 77% for all patients and was similar between study arms. PFS in key subgroups with atezolizumab+bevacizumab and atezolizumab monotherapy versus sunitinib is shown in FIGS. 36A and 36B. Of note, we observed a trend for improved efficacy (PFS) with higher expression of PD-L1 with atezolizumab+bevacizumab and for atezolizumab monotherapy versus sunitinib at a PD-L1 cutoff of ≥5% (unstratified analysis; FIGS. 36A and 36B).

Safety

Treatment-related adverse events (AEs) leading to discontinuation occurred in 9% of patients in the atezolizumab+bevacizumab arm, 3% in the atezolizumab monotherapy arm, and 9% in the sunitinib arm (Table 23).

TABLE 23

Toxicity profile/safety summary

| | Sunitinib n = 100 | Atezolizumab + Bevacizumab n = 101 | Atezolizumab n = 103 |
|---|---|---|---|
| Treatment duration, median (range), mo | 6.7 (0.1-33.1) | Atezolizumab: 11.8 (0.7-32.7) Bevacizumab: 10.3 (0.0-29.8) | 7.6 (0.0-33.1) |
| All-grade AEs, any cause, n (%) | 99 (99%) | 101 (100%) | 101 (98%) |
| Treatment-related AE | 96 (96%) | 91(90%) | 86 (83%) |
| Grade 3/4 AEs, any cause, n (%) | 69 (69%) | 64 (63%) | 41 (40%) |
| Treatment-related grade 3/4 AEs | 57 (57%) | 40 (40%) | 17 (17%) |
| AEs leading to death, n (%)$^a$ | 2 (2%) | 3 (3%) | 2 (2%) |
| Treatment-related AEs leading to death$^a$ | 2 (2%) | 1 (1%) | 0 |
| AEs leading to withdrawal from treatment, n (%) | 10 (10%) | 15(15%) | 7 (7%) |
| Treatment-related AEs leading to withdrawal from treatment | 9 (9%) | 9 (9%) | 3 (3%) |
| AEs leading to dose modification or interruption, n (%) | 70 (70%) | 61(60%) | 28 (27%) |

$^a$Sunitinib arm: sudden death (related), intestinal hemorrhage (related). Atezolizumab arm: hematophagic hitiocytosis, lower respiratory tract infection. Atezolizumab + Bevacizumab arm: intracranial hemorrheage (related), hemorrhage, pneumonia.

In the atezolizumab+bevacizumab group, proteinuria was the most common related AE leading to treatment discontinuation (5%). With sunitinib, the most common related AEs leading to treatment discontinuation were increased blood creatinine and palmar-plantar erythrodysesthesia syndrome (2% each). With atezolizumab monotherapy, nephritis, pancreatitis, and demyelination (1% each) were the treatment-related AEs leading to discontinuation of treatment. FIGS. 38A and 38B show all-cause AEs occurring at frequency of 20% in the atezolizumab+bevacizumab and sunitinib arms, or the atezolizumab monotherapy and sunitinib arms, with a difference in incidence between the two arms of ≥5%. Select AEs of special interest are shown below in Table 24, and all AEs occurring in ≥20% of patients in any of the three arms are shown in Table 25.

TABLE 24

Selected AEs of special interest

| n (%) | Sunitinib n = 100 | Atezo + Bev n = 101 | Atezo n = 103 | Sunitinib n = 100 | Atezo + Bev n = 101 | Atezo n = 103 |
|---|---|---|---|---|---|---|
| | | All Grade | | | Grade 3/4 | |
| Pneumonitis | 0 | 0 | 1 (1%) | 0 | 0 | 0 |
| Colitis | 1 (1%) | 1 (1%) | 0 | 0 | 0 | 0 |

TABLE 24-continued

Selected AEs of special interest

| n (%) | Sunitinib n = 100 All Grade | Atezo + Bev n = 101 All Grade | Atezo n = 103 All Grade | Sunitinib n = 100 Grade 3/4 | Atezo + Bev n = 101 Grade 3/4 | Atezo n = 103 Grade 3/4 |
|---|---|---|---|---|---|---|
| Elevated liver enzymes/hepatitis | 20 (20%) | 16 (16%) | 9 (9%) | 4 (4%) | 4 (4%) | 3 (3%) |
| TSH decreased/ hypothyroidism | 20 (20%) | 23 (23%) | 15 (15%) | 0 | 0 | 0 |
| TSH increased/ hyperthyroidism | 6 (6%) | 7 (7%) | 5 (5%) | 0 | 0 | 0 |
| Decreased blood cortisol/adrenal insufficiency | 0 | 3 (3%) | 0 | 0 | 1 (1%) | 0 |

TABLE 25

All AEs occurring in ≥20% of patients in any arm

| Preferred Term | Sunitinib (n = 100) | Atezo (n = 103) | Atezo +Bev (n = 101) |
|---|---|---|---|
| Any AE | 99 (99.0%) | 101 (98.1%) | 101 (100.0%) |
| Fatigue | 70 (70.0%) | 49 (47.6%) | 60 (59.4%) |
| Arthralgia | 18 (18.0%) | 15 (14.6%) | 38 (37.6%) |
| Hypertension | 35 (35.0%) | 6 (5.8%) | 37 (36.6%) |
| Proteinuria | 9 (9.0%) | 8 (7.8%) | 36 (35.6%) |
| Diarrhea | 59 (59.0%) | 17 (16.5%) | 34 (33.7%) |
| Nausea | 45 (45.0%) | 19 (18.4%) | 36 (35.6%) |
| Headache | 23 (23.0%) | 15 (14.6%) | 33 (32.7%) |
| Constipation | 30 (30.0%) | 14 (13.6%) | 28 (27.7%) |
| Epistaxis | 12 (12.0%) | 2 (1.9%) | 28 (27.7%) |
| Rash | 13 (13.0%) | 21 (20.4%) | 22 (21.8%) |
| Pruritus | 10 (10.0%) | 16 (15.5%) | 22 (21.8%) |
| Decreased appetite | 29 (29.0%) | 10 (9.7%) | 22 (21.8%) |
| Pyrexia | 12 (12.0%) | 25 (24.3%) | 21 (20.8%) |
| Vomiting | 20 (20.0%) | 9 (8.7%) | 19 (18.8%) |
| Cough | 25 (25.0%) | 23 (22.3%) | 19 (18.8%) |
| Mucosal inflammation | 33 (33.0%) | 4 (3.9%) | 15 (14.9%) |
| Stomatitis | 25 (25.0%) | 3 (2.9%) | 13 (12.9%) |
| Dysgeusia | 30 (30.0%) | 3 (2.9%) | 1 (11.9%) |
| Palmar-plantar erythrodysesthesia syndrome | 40 (40.0%) | — | 3 (3.0%) |
| Infections and infestations | 32 (32.0%) | 42 (40.8%) | 63 (62.4%) |

Molecular Correlates of Clinical Outcome

We conducted studies to evaluate molecular biomarkers relevant to the disease and tumor immune biology in RCC and their association with clinical outcomes within each treatment group and across treatment groups. Demographic and baseline characteristics in biomarker subgroups were generally consistent with those in the ITT population (Table 26).

TABLE 26

Demographic and baseline characteristics in ITT and biomarker evaluable populations

| Covariate | ITT (%) | RNAseq (%) | WES (%) |
|---|---|---|---|
| Male sex | 230 (75) | 201 (76) | 154 (74) |
| Prior nephrectomy | 265 (87) | 233 (89) | 189 (91) |
| Has liver metastasis | 73 (24) | 66 (25) | 47 (23) |
| PD-L1₊ | 172 (56) | 157 (60) | 128 (62) |

TABLE 26-continued

Demographic and baseline characteristics in ITT and biomarker evaluable populations

| Covariate | | ITT (%) | RNAseq (%) | WES (%) |
|---|---|---|---|---|
| MSKCC | Favorable | 77 (25) | 59 (22) | 47 (23) |
| | Intermediate | 201 (66) | 181 (69) | 148 (71) |
| | Poor | 27 (9) | 23 (9) | 13 (6) |
| Fuhrman grade | Grade 1 | 5 (2) | 5 (2) | 4 (2) |
| | Grade 2 | 38 (12) | 32 (12) | 30 (14) |
| | Grade 3 | 80 (26) | 72 (27) | 54 (26) |
| | Grade 4 | 73 (24) | 63 (24) | 51 (25) |
| | N/A | 109 (36) | 91 (35) | 69 (33) |

A heatmap of genes relevant to RCC and immune biology in 263 evaluable pretreatment tumors (FIG. 38A) shows distinct biological subgroups based on relative expression levels of angiogenesis (Angio), immune (including T-effector presence and function, IFN-γ response, checkpoint inhibitors, and antigen presentation), and myeloid inflammation-associated genes. The subgroup with high expression of the Angio gene signature (Angio$^{High}$) was characterized by relatively higher vascular density as evaluated by CD31 IHC (FIG. 38B), whereas the subgroup with high expression of the Teffector (Teff) gene signature (Teff$^{High}$) was positively associated with protein expression of PD-L1 on IC by IHC (FIG. 38C) and CD8 T-cell infiltration (FIG. 38D), indicative of pre-existing adaptive anti-tumor immunity. Additionally, differential expression of genes associated with myeloid inflammation within the Teff$^{High}$ and Teff$^{Low}$ subgroups was observed, suggesting further functional subcategories of these tumors (FIG. 38A). The association of clinical outcome in these biological subgroups within each treatment arm and across treatment arms is shown in Table 27. The following comparisons represent a subset of the larger analysis. Biomarker associations with clinical outcome are discussed if the 95% CI for HR did not cross 1 for PFS evaluation and if the 95% CI were non-overlapping for ORR comparisons.

TABLE 27

PFS HRs in biomarker subpopulations

| | PFS, HR (95% CI) | | | | | |
|---|---|---|---|---|---|---|
| | Across Arm Analysis | | | Within Arm Analysis | | |
| Subpopulation | Atezo + Bev vs Sunitinib | Atezo vs Sunitinib | Atezo + Bev vs Atezo | Atezo + Bev | Sunitinib | Atezo |
| $Angio^{High}$ | 1.36 (0.78-2.36) | 1.46 (0.81-2.60) | 0.93 (0.54-1.60) | $Angio^{High}$ vs $Angio^{Low}$ | | |
| $Angio^{Low}$ | 0.59 (0.35-0.98) | 0.75 (0.45-1.25) | 0.78 (0.46-1.33) | 0.90 (0.54-1.51) | 0.31 (0.18-0.55) | 0.74 (0.42-1.28) |
| $Teff^{High}$ | 0.55 (0.32-0.95) | 0.85 (0.50-1.43) | 0.65 (0.37-1.14) | $Teff^{High}$ vs $Teff^{Low}$ | | |
| $Teff^{Low}$ | 1.41 (0.85-2.36) | 1.33 (0.76-2.33) | 1.06 (0.63-1.79) | 0.50 (0.30-0.86) | 1.31 (0.77-2.23) | 0.83 (0.48-1.45) |
| $Myeloid^{High}$ | 1.31 (0.79-2.17) | 2.03 (1.21-3.40) | 0.64 (0.39-1.06) | $Myeloid^{High}$ vs $Myeloid^{Low}$ | | |
| $Myeloid^{Low}$ | 0.57 (0.33-0.99) | 0.53 (0.30-0.96) | 1.07 (0.59-1.93) | 1.71 (1.01-2.88) | 0.82 (0.48-1.39) | 2.98 (1.68-5.29) |
| $Teff^{High}$ $Myeloid^{High}$ | 0.45 (0.20-1.05) | 1.81 (0.92-3.58) | 0.25 (0.10-0.60) | $Teff^{High}Myeloid^{High}$ vs $Teff^{High}Myeloid^{Low}$ | | |
| $Teff^{High}$ $Myeloid^{Low}$ | 0.6 (0.28-1.31) | 0.47 (0.20-1.09) | 1.29 (0.57-2.90) | 0.80 (0.34-1.87) | 1.10 (0.53-2.29) | 3.82 (1.70-8.60) |

To determine if highly angiogenic tumors were more responsive to anti-angiogenic therapy, we investigated the association of the Angio gene signature with clinical outcome in each treatment arm. High expression of the Angio gene signature, based on median signature score, was associated with improved ORR (45% in $Angio^{High}$ versus 10% in $Angio^{Low}$, FIG. 38E) and PFS (HR 0.31; 95% CI, 0.18-0.55; FIG. 38E) within the sunitinib treatment arm. When evaluated across treatment arms, no apparent difference in PFS was observed in the $Angio^{High}$ subgroup between the atezolizumab+bevacizumab and sunitinib arms or between the atezolizumab monotherapy and sunitinib arms (FIG. 38H). In the $Angio^{Low}$ subgroup, atezolizumab+bevacizumab demonstrated improved PFS versus sunitinib (HR 0.59; 95% CI, 0.35-0.98; FIG. 38G).

We next asked if the presence of a pre-existing immune response, as identified by expression of the Teff gene signature, was associated with clinical benefit to immunotherapy containing regimens. High Teff gene signature expression, based on median signature score, was associated with improved ORR (50% in $Teff^{High}$ versus 16% in $Teff^{Low}$; FIG. 38I) and PFS (HR 0.50; 95% CI, 0.30-0.86; FIG. 38J) versus low Teff gene signature expression within the atezolizumab+bevacizumab arm (FIG. 38J). When compared across treatment arms, high Teff gene signature expression was associated with improved PFS with atezolizumab+bevacizumab versus sunitinib (HR 0.55; 95% CI: 0.32-0.95, FIG. 38L).

Because myeloid inflammation has been associated with suppression of the anti-tumor adaptive T cell response, we next investigated the contribution of the myeloid inflammation signature to clinical outcome. High myeloid inflammation gene signature expression ($Myeloid^{High}$), based on median signature score, was associated with reduced PFS in the atezolizumab monotherapy arm (HR 2.98; 95% CI, 1.68-5.29) and, to a lesser extent, in the atezolizumab +bevacizumab arm (HR 1.71; 95% CI, 1.01-2.88) but not in the sunitinib arm (Table 27). When compared across treatment arms, $Myeloid^{High}$ was associated with worse PFS with atezolizumab monotherapy versus sunitinib (HR 2.03; 95% CI, 1.21-3.40); however, this was not observed between atezolizumab+bevacizumab versus sunitinib (Table 27).

In addition to evaluation of gene expression signatures that distinguish between the clinical activity of atezolizumab+bevacizumab versus sunitinib, we investigated gene expression profiles that may differentiate the activity of atezolizumab+bevacizumab versus atezolizumab monotherapy. Teff, Angio, or Myeloid Inflammation (Myeloid) gene expression signatures did not differentiate activity of atezolizumab+bevacizumab versus atezolizumab monotherapy when evaluated across the respective dichotomized expression subgroups (Table 27). The heat map of the three gene signatures (FIG. 38A) showed a distinct population of $Myeloid^{High}$ tumors within the inflamed ($Teff^{High}$) category of mRCC tumors. We asked if the presence of myeloid inflammation within this subgroup of $Teff^{High}$ tumors impacted clinical outcome with the three therapies. Atezolizumab monotherapy had worse activity in the $Teff^{High}$ $Myeloid^{High}$ tumors compared with the $Teff^{High}Myeloid^{Low}$ tumors (HR 3.82; 95% CI, 1.70-8.60; Table 27). When compared across treatment arms, atezolizumab+bevacizumab showed improved PFS compared with atezolizumab monotherapy (HR 0.25; 95% CI, 0.10-0.60; FIG. 38N). No apparent difference in PFS was observed between atezolizumab+bevacizumab and atezolizumab monotherapy in the $Teff^{High}Myeloid^{Low}$ subgroup (FIG. 38M).

B. Discussion

To our knowledge, IMmotion150 is the first randomized study to evaluate the clinical activity of the combination of an anti-angiogenesis agent and an immune checkpoint inhibitor in treatment-naïve patients with mRCC. It is distinguished from other ongoing randomized trials investigating checkpoint inhibition in untreated mRCC by the inclusion of a PD-L1/PD-1 inhibitor monotherapy arm. The combination of atezolizumab+bevacizumab produced encouraging efficacy compared to the most commonly applied kidney cancer therapy, sunitinib, in the subgroup of patients with tumors expressing PD-L1 on ≥1% of IC (54% of enrolled patients). This finding will be further evaluated in a randomized phase 3 study (IMmotion151, NCT02420821). Atezolizumab also demonstrated anti-tumor activity when administered as a single agent and was well tolerated. Of note, the high response rate observed with atezolizumab monotherapy, including complete responses, supports its clinical efficacy, including in the adjuvant setting for patients with resected high-risk RCC (IMmotion010, NCT03024996). Safety in the atezolizumab+bevacizumab arm and the atezolizumab monotherapy arm was consistent with previous data for each drug alone, and AEs leading to treatment discontinuation were low.

A consistent trend of increasing efficacy with increasing levels of PD-L1 IC expression across both atezolizumab containing arms underscores the relevance of pre-existing immunity for differentiating the activity of atezolizumab and atezolizumab+bevacizumab from sunitinib in mRCC. This is particularly true in the atezolizumab+bevacizumab arm, in which bevacizumab appears to enhance anti-tumor activity in immunogenic tumors (FIG. 38N). The predictive relevance of PD-L1 expression on IC is further supported by the strong correlation of PD-L1 IC determined by IHC with the Teff immune gene signature (FIG. 38C). These data support a PD-L1 IHC and/or an immune gene expression signature-based diagnostic or enrichment strategy in treatment naïve patients with mRCC.

To further identify determinants of differential activity across the three treatment groups, we interrogated three biological axes that we hypothesized play a role in the response to the treatment regimens studied: tumor angiogenesis, pre-existing immunity, and immunosuppressive myeloid inflammation. Sunitinib efficacy was enriched in highly angiogenic tumors (Angio$^{high}$) (FIG. 38F). The combination of atezolizumab+bevacizumab improved clinical benefit compared with sunitinib in Teff$^{High}$ tumors (FIG. 38L). Atezolizumab monotherapy was effective in tumors with pre-existing immunity and a relatively lower expression of myeloid inflammation-associated genes (Teff$^{High}$Myeloid$^{Low}$), but less so in immunogenic tumors with concomitantly high myeloid inflammation (Teff$^{High}$Myeloid$^{High}$). Myeloid inflammation associated with high expression of IL-6, prostaglandins, and the CXCL8 family of chemokines has been implicated in accumulation of myeloid-derived suppressor cells (MDSCs) in tumors and suppression of anti-tumor immunity, and VEGF/VEGF receptor blockade has been shown to reduce MDSCs in tumors and blood in preclinical tumor models and human cancers. The improved clinical outcome associated with atezolizumab+bevacizumab compared with atezolizumab monotherapy in the immune-suppressed Teff$^{High}$Myeloid$^{High}$ subgroup (FIG. 38N, Table 27) suggests that the addition of bevacizumab to atezolizumab may overcome innate inflammation-mediated resistance in these tumors. The molecular subgroups identified in this study are expected to have discriminatory characteristics with potential broad relevance for application of anti-angiogenesis and checkpoint inhibitor based therapies across a spectrum of cancers, for which VEGF expression may contribute to tumor immunosuppression. Notably, a recent study investigating chemotherapy in combination with atezolizumab+bevacizumab in NSCLC reported improved efficacy versus chemotherapy and bevacizumab alone. The combination of atezolizumab+bevacizumab is also under evaluation in hepatocellular carcinoma, gastric, and ovarian cancer (NCT02715531, NCT02715531, and NCT03038100, respectively).

Overall, data from IMmotion150 indicate that atezolizumab+bevacizumab may particularly enhance PFS benefit in patients with pre-existing anti-tumor immunity (as determined by a high Teff score and PD-L1 IC expression) compared with sunitinib. In addition, comprehensive biomarker analyses that expand our understanding of the biology of kidney cancer and identify patient populations that derive benefit from sunitinib, atezolizumab, or the combination of atezolizumab+bevacizumab may enable personalized therapy in patients with mRCC. Furthermore, our findings identify myeloid inflammation as a potential mechanism of innate resistance to atezolizumab monotherapy in mRCC that may be overcome by the addition of bevacizumab.

C. Methods

Study Design and Outcomes

IMmotion150 is a phase 2, multicenter, randomized, open-label study conducted in 96 institutions that was designed to evaluate the safety and to provide preliminary evidence of activity of atezolizumab+bevacizumab versus sunitinib, and atezolizumab monotherapy versus sunitinib, as well as to inform the study design of the phase 3 trial (IMmotion151; NCT02420821). The sample size was approximately 100 patients per arm, and 70% events rate was deemed adequate for estimation of effect size (including median PFS and HR) in the ITT and PDL1+ subgroups. This trial, however, will not have sufficient power to detect clinically meaningful differences between treatment arms at a statistically significant α (type I) error level of 5%. For example, with 140 events in two comparator arms, there is only 56% power to detect HR=0.7 at 5% significance level.

The original primary endpoint was PFS per Response Evaluation Criteria In Solid Tumors version 1.1 (RECIST v1.1) via IRF in the ITT population. Although patients were stratified by ≥5% PD-L1 expression on IC, the definition of PD-L1 positivity was revised from ≥5% to ≥1% PD-L1 expression on IC, based on phase 1a data, and the study protocol was amended to create PD-L1 expression on IC as a coprimary endpoint of IRF-assessed PFS. This amendment likely contributed to the slight imbalance in the numbers of PD-L1+ patients between treatment arms (sunitinib, 59%; atezolizumab, 52%; atezolizumab+bevacizumab, 50%; Table 22). Secondary endpoints included investigator (INV)-assessed PFS, ORR, and duration of response (DOR) per RECIST v1.1, overall survival (OS), patient-reported outcomes, and safety. Key exploratory objectives included evaluation of the relationship between the expression of predictive and prognostic exploratory biomarkers and their association with disease status and efficacy as defined by ORR and PFS.

All data are reported per IRF assessment, unless otherwise stated.

Participants

Eligible patients were 18 years of age, had a Karnofsky performance score ≥70, and had unresectable advanced or mRCC with a component of clear cell histology and/or sarcomatoid histology not previously treated with any systemic agents for RCC. Patients were required to have adequate hematologic and end-organ function. Patients were excluded if they had known active brain or spinal cord metastases, uncontrolled pleural/pericardial effusion or ascites, or uncontrolled hypercalcemia.

Randomization and Masking

After written informed consent was obtained and eligibility determined, the study site obtained each patient's identification number and treatment assignment from the interactive voice/Web response system (IxRS). Stratification factors at the time of randomization included Memorial Sloan Kettering Cancer Center (MSKCC) risk category (low, intermediate, or high risk) (Motzer et al. *J. Clin. Oncol.* 17:2530-2540, 1999), prior nephrectomy (yes or no), and PD-L1 status (≥ or <5% PD-L1 expression on IC) as determined by IHC staining using the SP142 assay. Stratified permuted block randomization was used to assign patients in a 1:1:1 ratio to one of three treatment arms: atezolizumab+ bevacizumab, atezolizumab, or sunitinib. The study was open-label and allocation was unmasked.

Procedures

Study treatment consisted of atezolizumab 1200 mg fixed intravenous dose +bevacizumab 15 mg/kg every three weeks, atezolizumab 1200 mg fixed intravenous dose every three weeks, or sunitinib 50 mg/day orally for four weeks followed by two weeks of rest. On disease progression (as assessed by the investigator per RECIST v1.1), patients randomized to atezolizumab monotherapy or sunitinib had the option to cross over and receive the atezolizumab+ bevacizumab combination in some regions (option was not available in Europe). In the absence of unacceptable toxicity, treatment with the combination continued until evidence of progressive disease. Where permitted, patients in the atezolizumab-containing arms could continue to be treated beyond disease progression per RECIST v1.1 until lack of clinical benefit; those in non-European nations could cross over to atezolizumab+bevacizumab therapy at any time after disease progression per RECIST v1.1, provided all eligibility criteria were met.

During the study, each cycle was six weeks (42 days) in duration, and data on tumor measurement and survival status were collected for evaluation of PFS, milestone PFS (at 24, 52, and 76 weeks), OS, and ORR per RECIST v1.1. Tumor assessments occurred at baseline and every 12 weeks ±five business days after Cycle 1, Day 1, or more frequently if clinically indicated. Patients who discontinued first-line treatment or crossover treatment were followed up for survival approximately every three months until death, withdrawal of consent, loss to follow-up, or study termination. Patients who discontinued study treatment for reasons other than disease progression (e.g., toxicity) continued to undergo scheduled tumor assessments (every 12 weeks) until death, disease progression per RECIST v1.1, withdrawal of consent, or study termination, whichever occurred first.

Statistical Analysis

Kaplan-Meier methodology was used to estimate the median PFS for each treatment arm, and Kaplan-Meier curves were produced. The primary analysis was triggered when 140 INV-PFS events occurred among patients treated with atezolizumab+bevacizumab and with sunitinib or among patients treated with atezolizumab alone and with sunitinib, whichever occurred later. The HR estimates and their 95% CIs were determined by using the stratified Cox proportional hazards model. The stratification factors included prior nephrectomy, tumor PD-L1 status, and MSKCC score and were determined based on data from the electronic case report form; if such data were missing, data collected by the IxRS at the time of randomization were used. Tumor specimens were prospectively tested for PD-L1 expression on ICs by a central laboratory using the SP142 IHC assay (VENTANA, Tucson, Ariz.). IC staining was defined as follows: any discernible PD-L1 staining of any intensity in IC covering <1% or absent (IC0), between ≥1% and <5% (IC1), between ≥5% and <10% (IC2), or ≥10% (IC3) of tumor area occupied by tumor cells, associated intratumoral, and contiguous peri-tumoral desmoplastic stroma.

Gene Expression Analyses

Whole transcriptome profiles were generated for 263 patients using TRUSEQ® RNA Access technology (ILLUMINA®). RNAseq reads were first aligned to ribosomal RNA sequences to remove ribosomal reads. The remaining reads were aligned to the human reference genome (NCBI Build 38) using GSNAP version 2013-10-10 (Wu et al. Bioinformatics 26:873-881, 2010; Wu et al. *Methods Mol. Biol.* 1418:283-334, 2016), allowing a maximum of two mismatches per 75 base sequence (parameters: '-M 2-n 10-B 2-i 1'N 1-w 200000-E 1—pairmax-rna=200000— clip-overlap). To quantify gene expression levels, the number of reads mapped to the exons of each RefSeq gene was calculated using the functionality provided by the R/Bioconductor package GenomicAlignments (Lawrence et al. *PLoS Comput. Biol.* 9:e1003118, 2013).

Gene signatures were defined as follows: Angio: VEGFA, KDR, ESM1, PECAM1, ANGPTL4, and CD34; Teff: CD8A, EOMES, PRF1, IFNG, and CD274; Myeloid inflammation (Myeloid): IL-6, CXCL1, CXCL2, CXCL3, CXCL8, and PTGS2.

To calculate scores for each of these signatures, counts were first normalized using edgeR's normalization factors, followed by filtering out genes with low coverage (i.e., not reaching 0.25 CPM (counts per million) in at least one-tenth of available samples) and $\log_2$ transformation using limma's voom (Ritchie et al. Nucleic Acids Res. 43:e47, 2015). For each sample, the average expression of all genes in a given signature was then computed, which is reported as the sample's signature score. For each gene signature, patients were divided into two groups based on the median gene signature score of all tumors: high gene signature expression was defined as expression at or above median levels, and low gene signature expression was defined as expression below the median.

For the heatmap (FIG. 38A), each patient was placed into high or low groups for all three gene expression signatures: Angio, Teff and Myeloid (based on median expression, as described above). Subsequently, patients were sorted by the combination of these three groups: first $\text{Teff}^{High}$, $\text{Angio}^{Low}$ patients are shown, sorted by Myeloid low/high; then $\text{Teff}^{High}$, $\text{Angio}^{High}$ patients are shown, sorted by Myeloid high/low; then $\text{Teff}^{Low}$, $\text{Angio}^{High}$ patients are shown, sorted by Myeloid low/high; finally, $\text{Teff}^{Low}$, $\text{Angio}^{Low}$ patients are shown, sorted by Myeloid high/low. Also, the ordering of the genes was predetermined, based on biological function. Z-score transformed normalized counts are shown.

Biomarker Association Analyses

For testing associations between a continuous variable and a binary trait (e.g., FIGS. 38B and 38D), two-tailed t tests were used. Otherwise, for testing associations between a continuous variable and a categorical variable with more than two levels (e.g., FIG. 38C), likelihood ratio test P values were calculated using ANOVA. For testing association between two continuous variables, Pearson correlation coefficient was calculated.

All P values reported were for descriptive propose only and not adjusted for multiple testing. Biomarker associations with clinical outcome were further discussed above if the 95% CIs for HR did not cross 1 for PFS evaluation and if the 95% CKIs were non-overlapping for ORR comparisons.

VII. Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of identifying and treating an individual having a renal cell carcinoma (RCC) who may benefit from treatment with an anti-cancer therapy comprising bevacizumab and atezolizumab, the method comprising:
   (a) determining the expression levels of one or more of the following sets of genes in a tumor tissue sample from the individual prior to treatment with bevacizumab and atezolizumab:
   T effector and interferon gamma (IFNγ) response (Teff) genes comprising CD8A, EOMES, PRF1, IFNG, and PD-L1;
   Angiogenesis-related (Ang) genes comprising VEGFA, KDR, ESM1, PECAM1, ANGPTL4, and CD34; or
   Myeloid inflammation-related (Myeloid) genes comprising IL6, CXCL1, CXCL2, CXCL3, CXCL8, and PTGS2;
   wherein
   (i) the mRNA expression levels of CD8A, EOMES, PRF1, IFNG, and PD-L1 in the tumor tissue sample are at or above reference expression levels of the genes; or
   (ii) the mRNA expression levels of VEGFA, KDR, ESM1, PECAM1, ANGPTL4, and CD34; or IL6, CXCL1, CXCL2, CXCL3, CXCL8, and PTGS2 in the tumor tissue sample are below reference expression levels of the genes,
   thereby identifying the individual as one who may benefit from treatment with an anti-cancer therapy comprising bevacizumab and atezolizumab, wherein the reference expression levels of the genes are the median expression levels of the genes determined in a population of individuals having RCC; and
   (b) administering an effective amount of an anti-cancer therapy comprising bevacizumab and atezolizumab to the individual identified in step (a) as being one who may benefit from treatment with an anti-cancer therapy comprising bevacizumab and atezolizumab.

2. A method for selecting a therapy for, and treating, an individual having an RCC, the method comprising:
   (a) determining the expression levels of one or more of the following sets of genes in a tumor tissue sample from the individual prior to treatment with bevacizumab and atezolizumab:
   Teff genes comprising CD8A, EOMES, PRF1, IFNG, and PD-L1;
   Ang genes comprising VEGFA, KDR, ESM1, PECAM1, ANGPTL4, and CD34; or
   Myeloid genes comprising IL6, CXCL1, CXCL2, CXCL3, CXCL8, and PTGS2;
   wherein
   (i) the mRNA expression levels of CD8A, EOMES, PRF1, IFNG, and PD-L1 in the tumor tissue sample are at or above reference expression levels of the genes; or
   (ii) the mRNA expression levels of VEGFA, KDR, ESM1, PECAM1, ANGPTL4, and CD34; or IL6, CXCL1, CXCL2, CXCL3, CXCL8, and PTGS2 in the tumor tissue sample are below reference expression levels of the genes,
   thereby identifying the individual as one who may benefit from treatment with an anti-cancer therapy comprising bevacizumab and atezolizumab, wherein the reference expression levels of the genes are the median expression levels of the genes determined in a population of individuals having RCC;
   (b) selecting an anti-cancer therapy comprising bevacizumab and atezolizumab for the individual identified in step (a) as being one who may benefit from treatment with an anti-cancer therapy comprising bevacizumab and atezolizumab; and
   (c) administering an effective amount of an anti-cancer therapy comprising bevacizumab and atezolizumab to the individual selected in step (b).

3. A method of treating an individual having an RCC, the method comprising:
   (a) determining the expression levels of one or more of the following sets of genes in a tumor tissue sample from the individual prior to treatment with bevacizumab and atezolizumab:
   Teff genes comprising CD8A, EOMES, PRF1, IFNG, and PD-L1;
   Ang genes comprising VEGFA, KDR, ESM1, PECAM1, ANGPTL4, and CD34; or
   Myeloid genes comprising IL6, CXCL1, CXCL2, CXCL3, CXCL8, and PTGS2;
   wherein
   (i) the mRNA expression levels of CD8A, EOMES, PRF1, IFNG, and PD-L1 in the tumor tissue sample are determined to be at or above reference expression levels of the genes; or
   (ii) the mRNA expression levels of VEGFA, KDR, ESM1, PECAM1, ANGPTL4, and CD34; or IL6, CXCL1, CXCL2, CXCL3, CXCL8, and PTGS2 in the tumor tissue sample are determined to be below reference expression levels of the genes, wherein the reference expression levels of the genes are the median expression levels of the genes determined in a population of individuals having RCC; and (b) administering an effective amount of an anti-cancer therapy comprising bevacizumab and atezolizumab to the individual having (i) mRNA expression levels of CD8A, EOMES, PRF1, IFNG, and PD-L1 in the tumor tissue sample that are at or above the reference expression levels of the genes; or (ii) mRNA expression levels of VEGFA, KDR, ESM1, PECAM1, ANGPTL4, and CD34; or IL6, CXCL1, CXCL2, CXCL3, CXCL8, and PTGS2 in the tumor tissue sample that are below the reference expression levels of the genes.

4. A method of treating an individual having an RCC, the method comprising administering to the individual an effective amount of an anti-cancer therapy comprising bevacizumab and atezolizumab, wherein prior to treatment with bevacizumab and atezolizumab (i) the mRNA expression levels of CD8A, EOMES, PRF1, IFNG, and PD-L1 in a tumor tissue sample from the individual have been determined to be at or above reference expression levels of the genes; or (ii) the mRNA expression levels of VEGFA, KDR, ESM1, PECAM1, ANGPTL4, and CD34; or IL6, CXCL1, CXCL2, CXCL3, CXCL8, and PTGS2 in a tumor tissue sample from the individual have been determined to be below reference expression levels of the genes, and wherein the reference expression levels of the genes are the median expression levels of the genes determined in a population of individuals having RCC.

5. The method of claim 4, wherein the reference expression levels of the genes are the median level of Z-scores of the normalized expression levels of the genes determined from a population of individuals having an RCC.

6. The method of claim 4, wherein the individual has not been previously treated for the RCC.

7. The method of claim 4, wherein the RCC is metastatic RCC (mRCC).

8. The method of claim 4, further comprising administering an additional therapeutic agent to the individual.

9. A method of treating an individual with previously untreated metastatic RCC, the method comprising administering to the individual an effective amount of an anti-cancer therapy comprising bevacizumab and atezolizumab, wherein prior to treatment with bevacizumab and atezolizumab the mRNA expression levels of CD8A, EOMES, PRF1, IFNG, and PD-L1 in a tumor tissue sample from the individual have been determined to be at or above reference expression levels of the genes, wherein the reference expression levels of the genes are the median expression levels of the genes determined in a population of individuals having RCC.

* * * * *